United States Patent
Lee et al.

(10) Patent No.: US 12,303,129 B2
(45) Date of Patent: May 20, 2025

(54) END TOOL OF SURGICAL INSTRUMENT, AND SURGICAL INSTRUMENT COMPRISING SAME

(71) Applicant: LIVSMED INC., Seongnam-si (KR)

(72) Inventors: Jaeyeong Lee, Seongnam-si (KR); Junghwan Kim, Seongnam-si (KR); Jung Joo Lee, Seongnam-si (KR); Heejin Kim, Seongnam-si (KR); Dongkyu Jang, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 0 days.

(21) Appl. No.: 18/593,392

(22) Filed: Mar. 1, 2024

(65) Prior Publication Data
US 2024/0285275 A1 Aug. 29, 2024

Related U.S. Application Data

(63) Continuation of application No. PCT/KR2022/013250, filed on Sep. 5, 2022.

(30) Foreign Application Priority Data

Sep. 3, 2021 (KR) .......................... 10-2021-0117997

(51) Int. Cl.
*A61B 17/072* (2006.01)
*A61B 34/30* (2016.01)

(52) U.S. Cl.
CPC .. *A61B 17/07207* (2013.01); *A61B 2034/305* (2016.02)

(58) Field of Classification Search
CPC .................... A61B 17/07207; A61B 2034/305
USPC ............................................................ 606/1
See application file for complete search history.

(56) References Cited

U.S. PATENT DOCUMENTS

| | | |
|---|---|---|
| 10,758,298 B2 | 9/2020 | Felder et al. |
| 2014/0305987 A1 | 10/2014 | Parihar et al. |
| 2016/0192927 A1 | 7/2016 | Kostrzewski |
| 2017/0265954 A1 | 9/2017 | Burbank et al. |
| 2019/0167267 A1 | 6/2019 | Kobayashi et al. |

FOREIGN PATENT DOCUMENTS

| | | |
|---|---|---|
| CN | 111419310 A | 7/2020 |
| EP | 3205274 A1 | 8/2017 |
| EP | 4327756 A1 | 2/2024 |
| JP | 6046635 B2 | 12/2016 |
| JP | 6382235 B2 | 8/2018 |
| KR | 10-2122508 B1 | 6/2020 |
| WO | 2011/007351 A1 | 1/2011 |
| WO | 2018/096711 A1 | 5/2018 |
| WO | 2020/055705 A1 | 3/2020 |
| WO | 2021/085678 A1 | 5/2021 |

*Primary Examiner* — Aaron F Roane
(74) *Attorney, Agent, or Firm* — Bridgeway IP Law Group, PLLC; Sang Ho Lee; Hyun Woo Shin

(57) ABSTRACT

Provided is an end tool of a surgical instrument and a surgical instrument including the same, and more particularly, to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

23 Claims, 213 Drawing Sheets

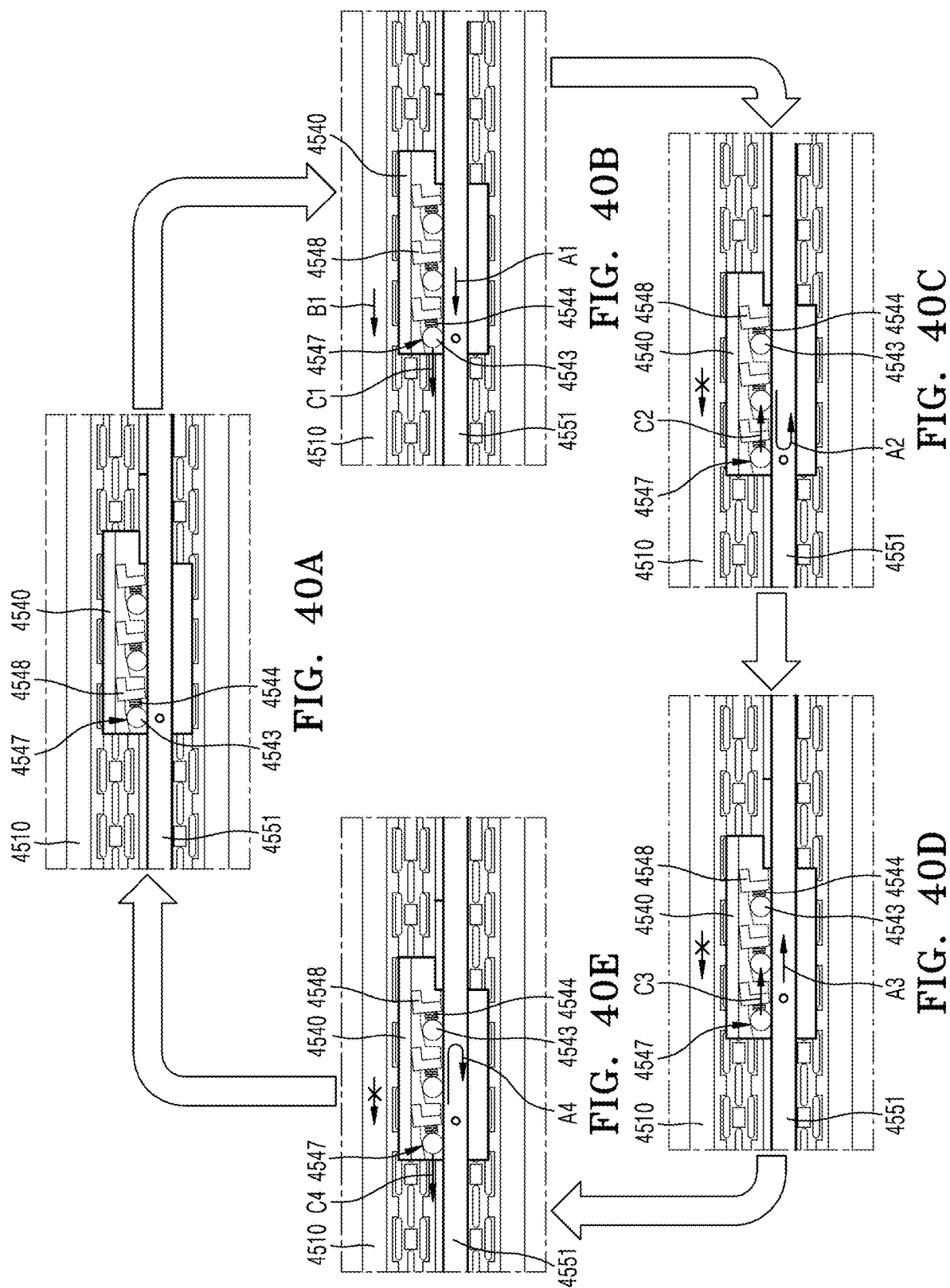

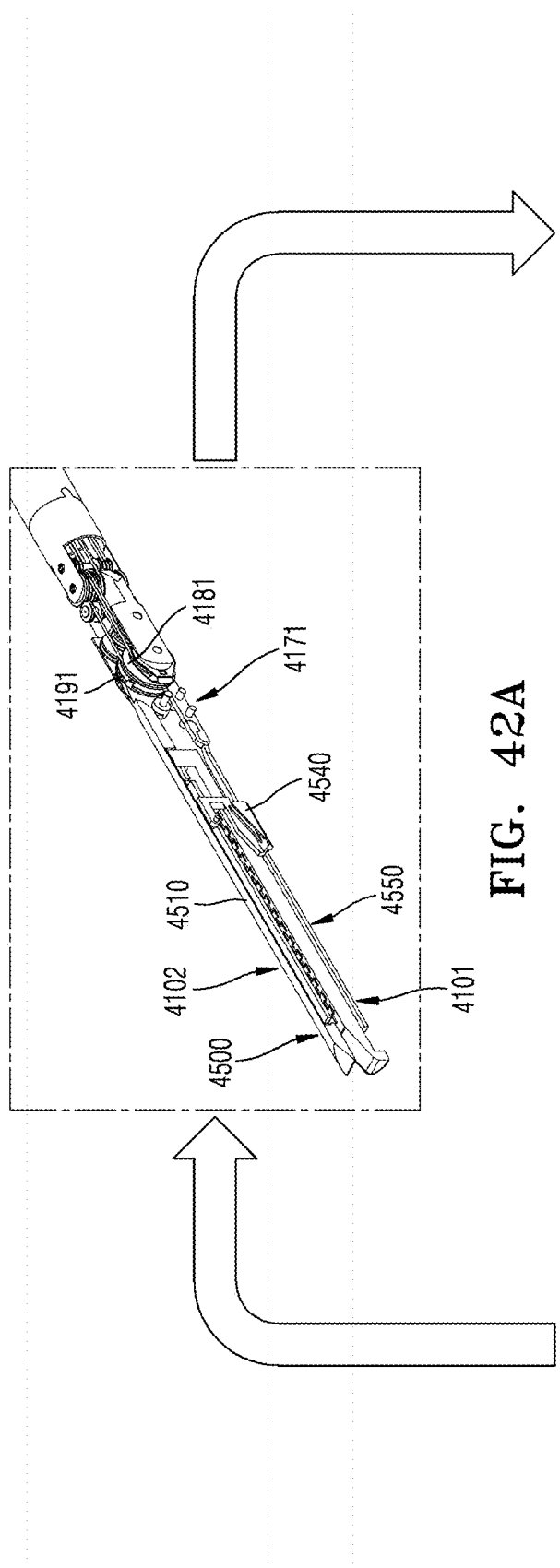
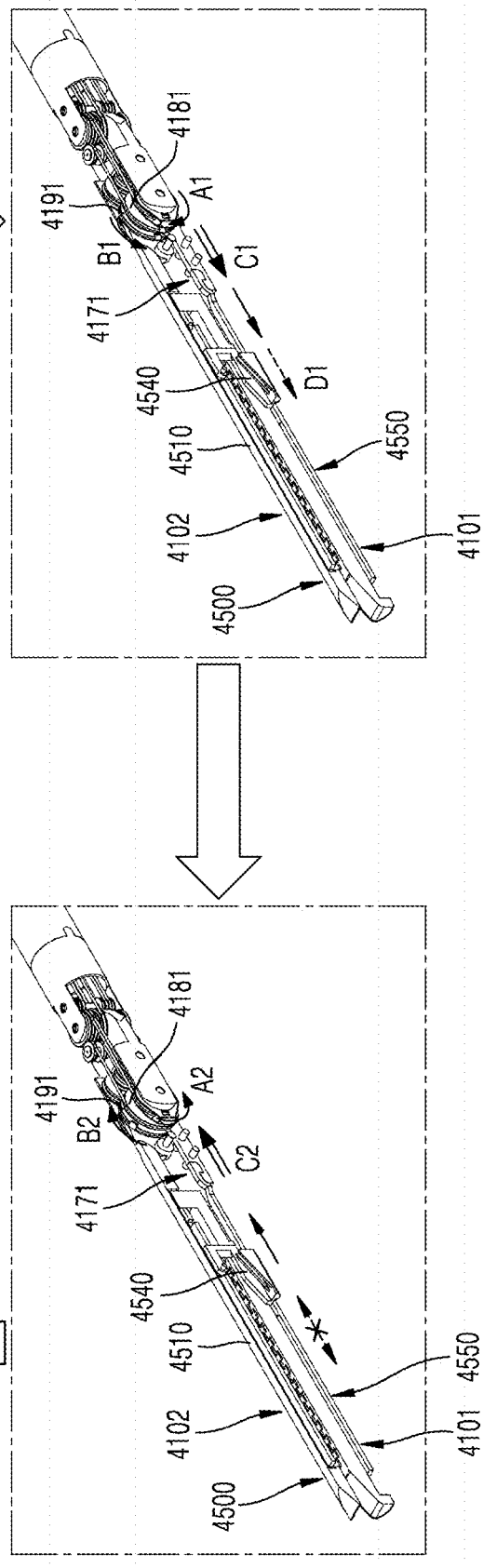
FIG. 42A
FIG. 42B
FIG. 42C

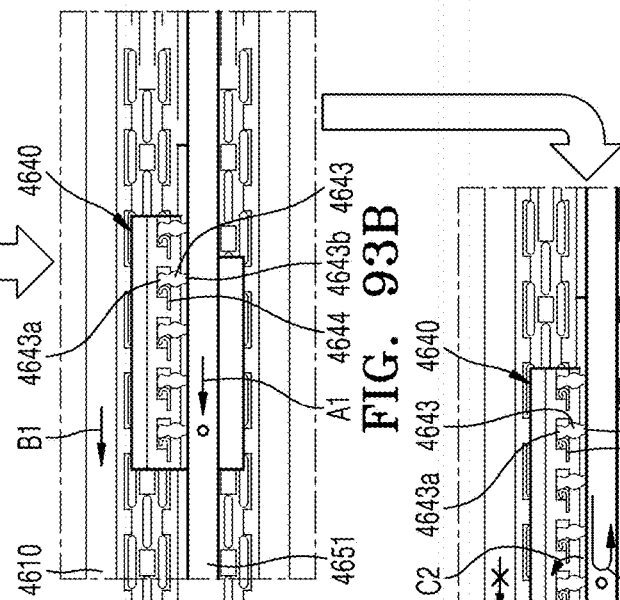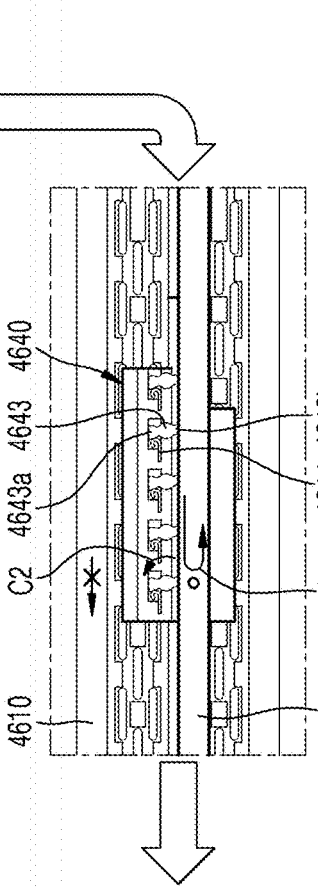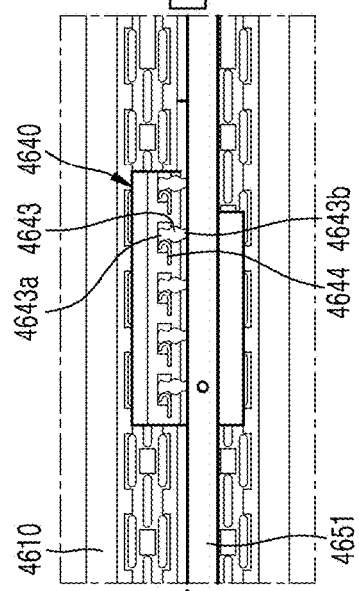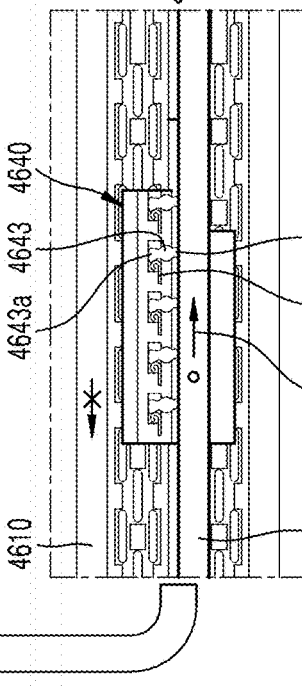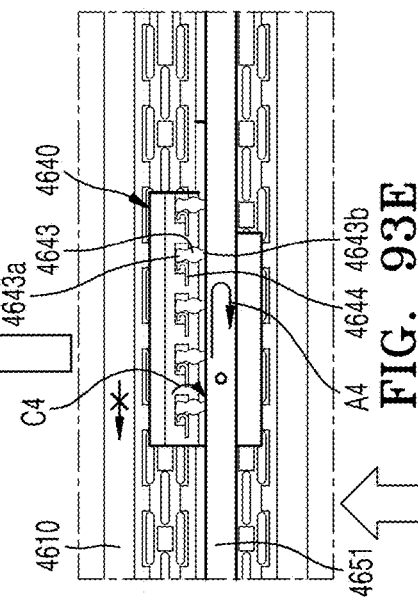

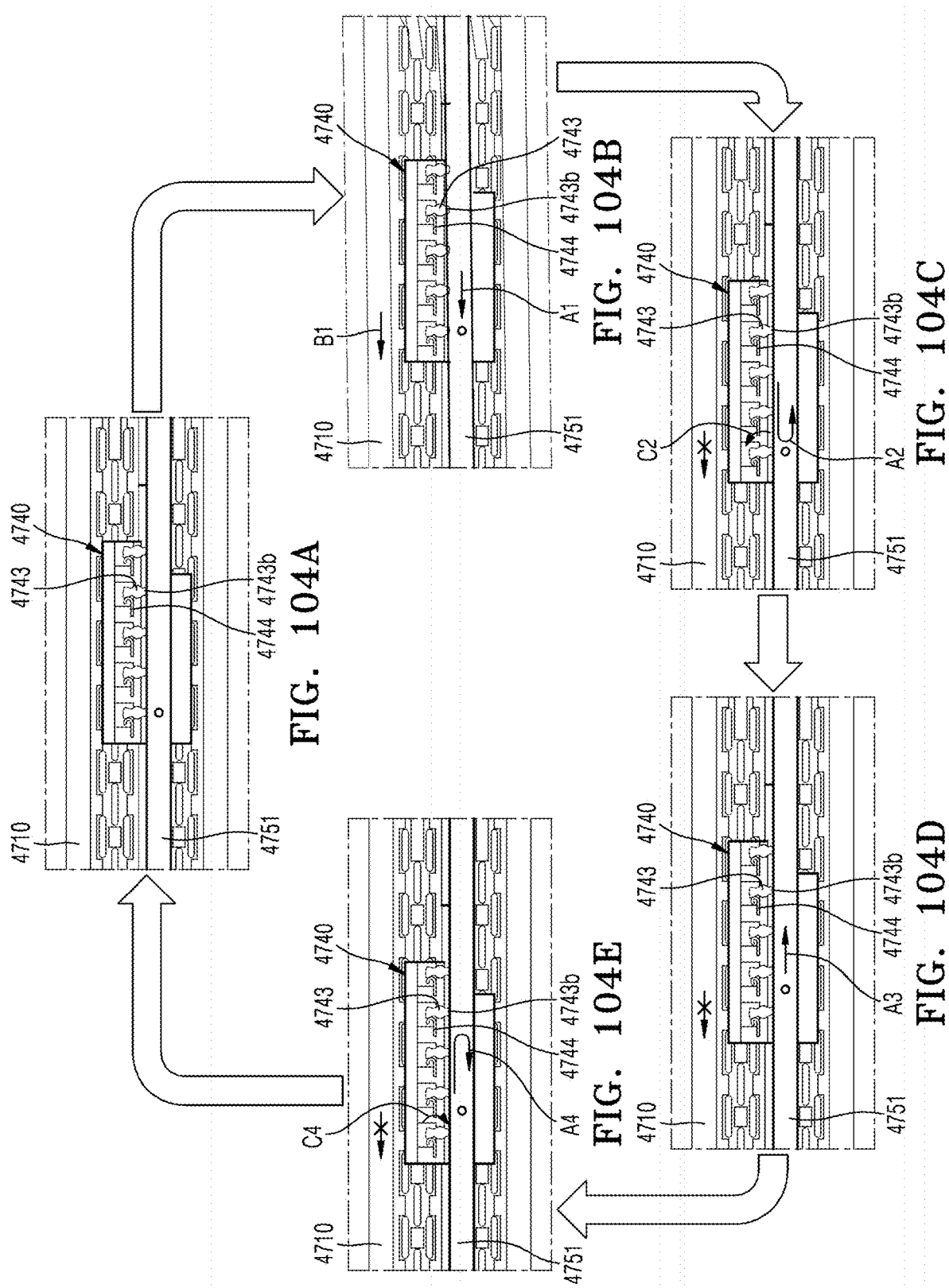

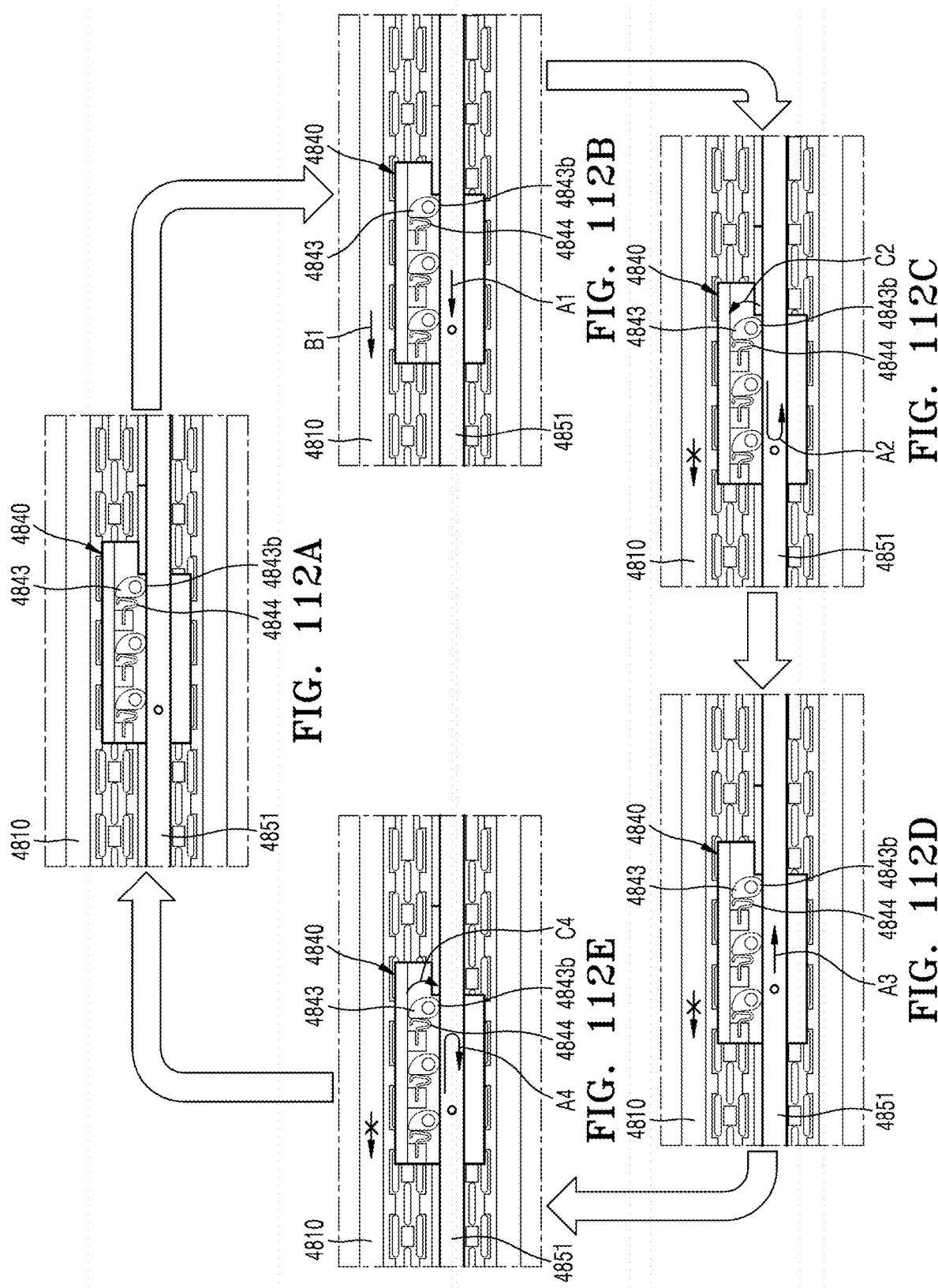

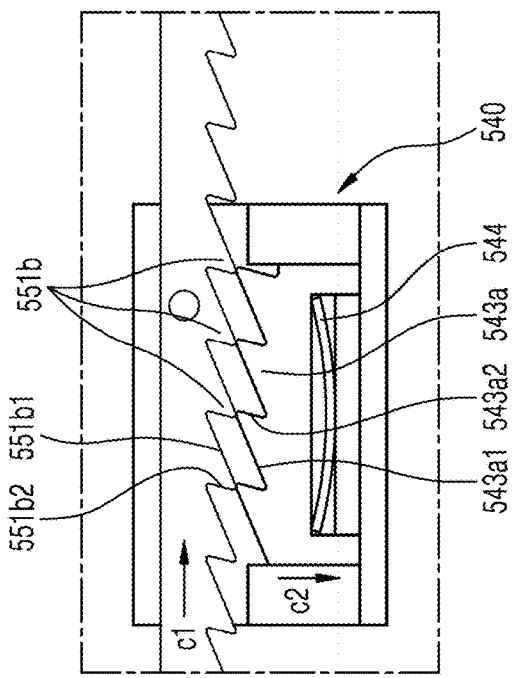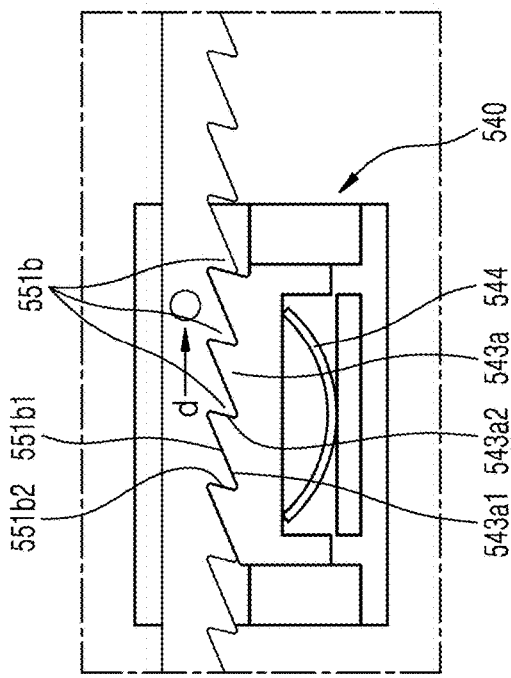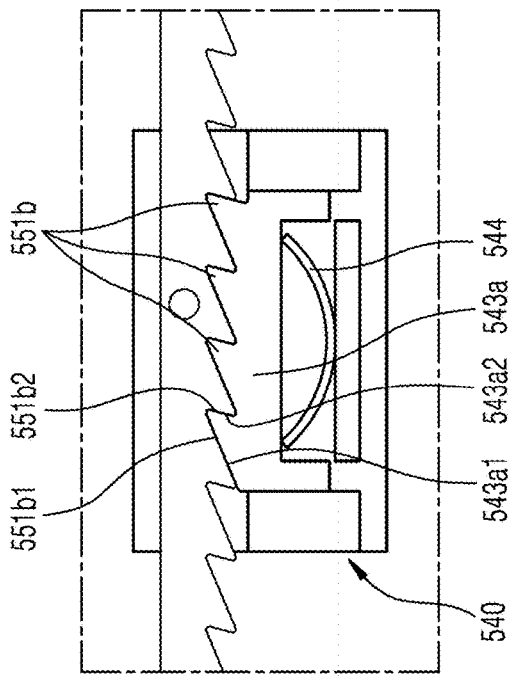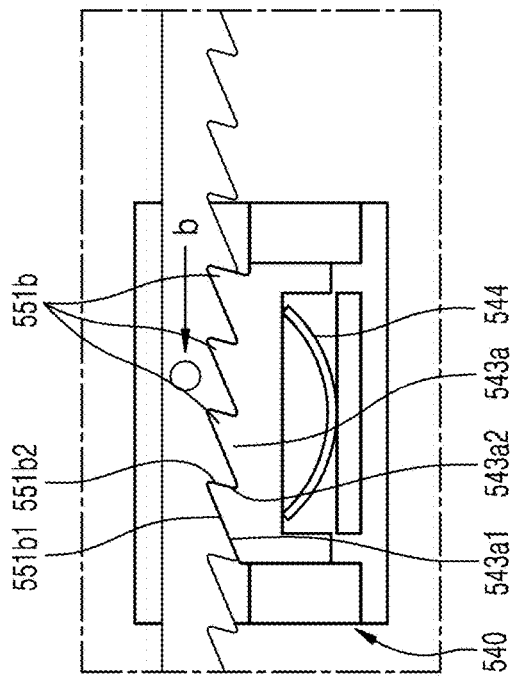

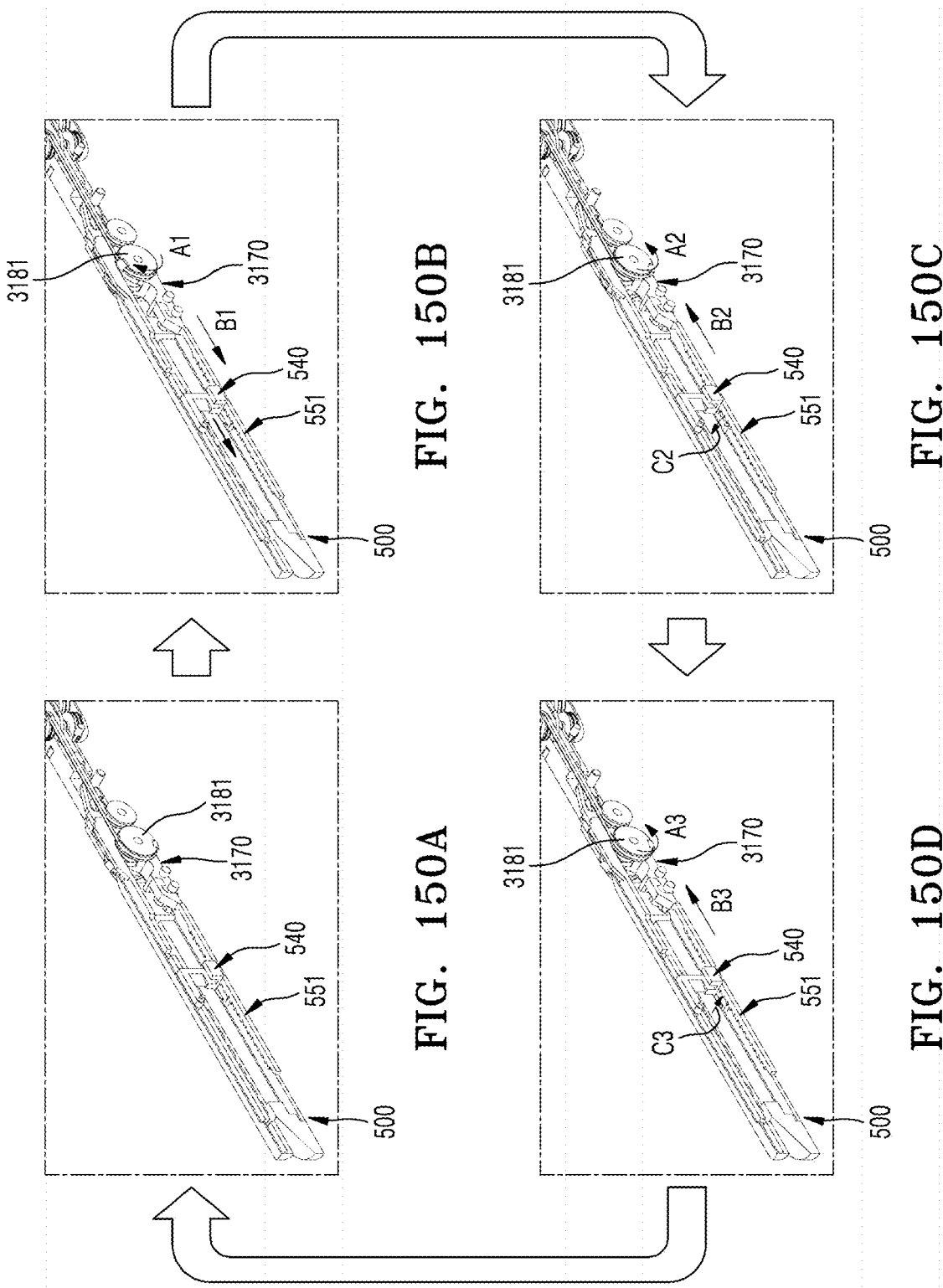

END TOOL OF SURGICAL INSTRUMENT, AND SURGICAL INSTRUMENT COMPRISING SAME

CROSS-REFERENCE TO RELATED APPLICATION(S)

This application is a continuation application of international application No. PCT/KR2022/013250, filed on Sep. 5, 2022, and claims priority to Korean Patent Application No. 10-2021-0117997, filed on Sep. 3, 2021, with the Korean Intellectual Property Office, the disclosures of which are incorporated herein in their entirety by reference.

TECHNICAL FIELD

The present disclosure relates to an end tool of a surgical instrument and a surgical instrument including the same, and more particularly, to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

BACKGROUND ART

In recent years, laparoscopic surgery has been actively utilized to reduce postoperative recovery time and complications through small incisions. The laparoscopic surgery is a surgical method in which a plurality of small holes are drilled in the abdomen of a patient and the inside of the abdominal cavity is observed through these holes, and is widely used in general surgery and the like.

In performing the laparoscopic surgery, a suturing instrument inserted into the body is used to suture a surgical site in the abdominal cavity, and a surgical stapler for suturing the surgical site using medical staples is used as the suturing instrument.

In general, a surgical stapler is a medical instrument that is often used for cutting and anastomosis of an organ in abdominal and thoracic surgery. The surgical stapler includes an open stapler used in thoracotomy and laparotomy and an endo stapler used in thoracoscopic surgery and celioscopic surgery.

The surgical stapler has advantages of not only shortening operation time since cutting of a surgical site and anastomosis of an organ are simultaneously performed, but also accurately stapling the surgical site. In addition, the surgical stapler has advantages of a faster recovery and a smaller scar than those when tissue is cut and stapled using a surgical stapling thread, and thus has been widely used in modern surgical operations. In particular, the surgical stapler has been widely used in cancer surgery to cut cancer tissue and suture a cut site.

The aforementioned background technology is technical information possessed by the inventor for derivation of the present disclosure or acquired by the inventor during the derivation of the present disclosure, and is not necessarily prior art disclosed to the public before the application of the present disclosure.

DESCRIPTION OF EMBODIMENTS

Technical Problem

The present disclosure is directed to providing a surgical instrument, which may be mounted on a robotic arm or operable manually to be used in laparoscopic surgery or other various surgeries and includes an end tool rotatable in one or more directions and moved in a way that intuitively matches a motion of a manipulation part, and a surgical instrument including the same.

Solution to Problem

According to an aspect of the present disclosure, there is provided a surgical instrument including an end tool having a first jaw, a second jaw formed to face the first jaw, a first jaw pulley coupled to the first jaw and formed to be rotatable around a first shaft, a second jaw pulley coupled to the second jaw, formed to be rotatable around a shaft substantially the same as or parallel to the first shaft, and formed to be spaced apart from the first jaw pulley by a certain extent, and a staple drive assembly including one or more staple pulleys at least partially formed between the first jaw pulley and the second jaw pulley, and a cartridge having a reciprocating member that is connected to the staple drive assembly, and linearly moved when the staple pulley is rotationally moved, and an operation member including a contact member formed to be in contact with the reciprocating member, and configured to move in one direction together with the reciprocating member when the reciprocating member is moved in the one direction, wherein, when the reciprocating member is moved toward a distal end of the cartridge, a relative movement between the operation member and the reciprocating member is restricted by the contact member, so that the reciprocating member and the operation member are moved together, and when the reciprocating member is moved toward a proximal end of the cartridge, the relative movement between the operation member and the reciprocating member is possible, so that only the reciprocating member is moved.

Advantageous Effects of Disclosure

According to the present disclosure, a direction in which a surgical operator manipulates the manipulation part and a direction in which an end tool is operated are intuitively the same, so that convenience of the surgical operator can be improved, and accuracy, reliability, and speed of surgery can be improved.

BRIEF DESCRIPTION OF DRAWINGS

FIGS. 40A to 41D are plan views illustrating a clutch drive operation of the end tool of FIG. 33.

FIGS. 42A to 42C are perspective views illustrating an entire clutch drive operation of the end tool of FIG. 33.

FIGS. 93A to 94D are plan views illustrating a clutch drive operation of the end tool of FIG. 87.

FIGS. 104A to 105D are plan views illustrating a clutch drive operation of the end tool of FIG. 98.

FIGS. 112A to 113D are plan views illustrating a clutch drive operation of the end tool of FIG. 106.

FIGS. 130A to 131C are side views illustrating operating states of the staple pulley in the end tool of the surgical instrument of FIG. 114.

FIGS. 149A to 149D are plan views illustrating a ratchet drive operation of the end tool of FIG. 145.

FIGS. 150A to 150D are perspective views illustrating an entire ratchet drive operation of the end tool of FIG. 145.

FIG. 206 is a side view illustrating the end tool of FIG. 202.

FIG. 207 is a plan view illustrating the end tool of FIG. 202.

FIG. 208 is an exploded perspective view of the end tool of FIG. 202.

FIG. 209 is an exploded perspective view of a staple pulley and a link member of the end tool of FIG. 199.

FIG. 210 is a perspective view of a second jaw of the end tool of FIG. 199.

FIGS. 211 and 212 are plan views illustrating motions of a jaw pulley of the end tool of FIG. 202.

BEST MODE

Figure 1A:
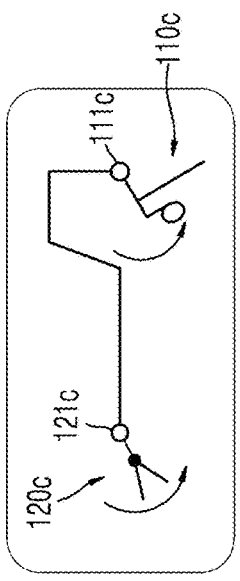
FIG. 1A is a conceptual diagram of a pitch motion of a conventional surgical instrument.

One aspect of the present disclosure provides a surgical instrument comprising: an end tool including: a first jaw; a second jaw formed to face the first jaw; a first jaw pulley coupled to the first jaw and formed to be rotatable around a first shaft; a second jaw pulley coupled to the second jaw, formed to be rotatable around a shaft substantially the same as or parallel to the first shaft, and formed to be spaced apart from the first jaw pulley by a certain extent; and a staple drive assembly including one or more staple pulleys at least partially formed between the first jaw pulley and the second jaw pulley; and a cartridge including: a reciprocating member that is connected to the staple drive assembly, and linearly moved when the staple pulley is rotationally moved; and an operation member including a contact member formed to be in contact with the reciprocating member, and configured to move in one direction together with the reciprocating member when the reciprocating member is moved in the one direction, wherein, when the reciprocating member is moved toward a distal end of the cartridge, a relative movement between the operation member and the reciprocating member is restricted by the contact member, so that the reciprocating member and the operation member are moved together, and when the reciprocating member is moved toward a proximal end of the cartridge, the relative movement between the operation member and the reciprocating member is possible, so that only the reciprocating member is moved.

In the present disclosure, when the reciprocating member is moved toward the distal end of the cartridge, the contact member and the reciprocating member are in a fitted state, so that the relative movement between the operation member and the reciprocating member is restricted, and when the reciprocating member is moved toward the proximal end of the cartridge, the fitted state between the contact member and the reciprocating member is released, so that the relative movement between the operation member and the reciprocating member is possible.

In the present disclosure, when the staple pulley is rotated, the reciprocating member connected to the staple drive assembly is moved toward the distal end or the proximal end of the cartridge.

In the present disclosure, when the staple pulley is alternately rotated in a clockwise direction and a counterclockwise direction, the reciprocating member connected to the staple drive assembly is alternately moved toward the distal end and the proximal end of the cartridge.

In the present disclosure, when the reciprocating member is moved toward the distal end of the cartridge, the operation member is moved toward the distal end of the cartridge by the reciprocating member.

In the present disclosure, wherein a bidirectional rotational motion of the staple pulley is converted into a reciprocating linear motion of the reciprocating member, which is connected to the staple drive assembly, by the staple drive assembly.

In the present disclosure, as the operation member is moved in the one direction, a wedge of the operation member sequentially pushes and raises a plurality of staples in the cartridge to perform a stapling motion, and simultaneously a blade formed at one side of the wedge of the operation member is moved in the one direction to perform a cutting motion.

In the present disclosure, when the reciprocating member is moved toward the distal end of the cartridge, the contact member and the reciprocating member are in a fitted state to allow the reciprocating member to push the operation member including the contact member, so that the operation member is moved toward the distal end of the cartridge.

In the present disclosure, when the reciprocating member is moved toward the proximal end of the cartridge, the operation member remains stationary with respect to the one direction.

In the present disclosure, wherein the contact member is formed to be spaced apart from the reciprocating member by a certain extent when the reciprocating member is moved toward the proximal end of the cartridge.

In the present disclosure, wherein the staple drive assembly includes a link member configured to connect the staple pulley and the reciprocating member.

In the present disclosure, when the staple pulley is rotated in a first direction between a clockwise direction and a counterclockwise direction, the link member connected to the staple pulley, the reciprocating member connected to the link member, and the operation member in contact with the reciprocating member are moved toward the distal end of the cartridge.

In the present disclosure, when the staple pulley is rotated in a direction opposite to the first direction between the clockwise and counterclockwise directions, the link member connected to the staple pulley and the reciprocating member connected to the link member are moved toward a proximal end of the end tool, and the operation member remains stationary with respect to the one direction.

In the present disclosure, the operation member of the cartridge includes: a body; one or more wedges formed at one side of the body and each including an inclined surface formed to have a greater height at a proximal end side of the cartridge than a distal end side of the cartridge; and a blade formed at one side of the wedge and including an edge formed to be sharp, wherein the contact member is disposed in an accommodation part formed on one surface of the body.

In the present disclosure, an inclined part is formed on a surface of the accommodation part, which is formed on the body, facing the reciprocating member, and a width of the accommodation part becomes narrower toward the distal end of the cartridge.

In the present disclosure, a spacing between the inclined part and the reciprocating member decreases toward the distal end of the cartridge.

In the present disclosure, when the contact member is pressed in a direction in which the spacing between the inclined part and the reciprocating member decreases, the contact member and the reciprocating member are in a fitted state, so that the relative movement between the reciprocating member and the operation member is blocked.

In the present disclosure, wherein the contact member is formed such that a center distance is different for each region, wherein the center distance is a distance from a center of rotation of the contact member to an end portion of the contact member.

In the present disclosure, when a region of the contact member, in which the center distance is relatively large, is in contact with the reciprocating member, the contact member and the reciprocating member are in a fitted state, so that the relative movement between the operation member and the reciprocating member is restricted, and when a region of the contact member, in which the center distance is relatively small, is in contact with the reciprocating member, the fitted state between the contact member and the reciprocating member is released, so that the relative movement between the operation member and the reciprocating member is possible.

In the present disclosure, further comprising a staple wire coupled to the staple pulley and configured to rotate the staple pulley.

In the present disclosure, further comprising: a pair of end tool first jaw pitch main pulleys formed at one side of the first jaw pulley, and formed to be rotatable around a second shaft forming a predetermined angle with the first shaft; and a pair of end tool second jaw pitch main pulleys formed at one side of the second jaw pulley, and formed to be rotatable around a shaft that is substantially the same as or parallel to the second shaft.

In the present disclosure, wherein the end tool is formed to be yaw-rotatable around the first shaft and simultaneously pitch-rotatable around the second shaft.

In the present disclosure, wherein the first jaw pulley, the one or more staple pulleys, and the second jaw pulley are sequentially stacked.

Another aspect of the present disclosure provides a cartridge of a surgical instrument having an end tool rotatable in at least one direction, the cartridge comprising: a housing; a cover configured to cover one surface of the housing and having a slit formed in a first direction that is a length direction of the housing; a plurality of staples disposed in the first direction inside the housing; a reciprocating member disposed inside the housing and formed to be relatively movable in the first direction with respect to the housing; and an operation member formed at one side of the reciprocating member, including a contact member formed to be in contact with the reciprocating member, and formed to be movable in the first direction by the reciprocating member, wherein, when the reciprocating member is moved toward a distal end of the cartridge, a relative movement between the operation member and the reciprocating member is restricted by the contact member, so that the reciprocating member and the operation member are moved together, and when the reciprocating member is moved toward a proximal end of the cartridge, the relative movement between the operation member and the reciprocating member is possible, so that only the reciprocating member is moved.

In the present disclosure, wherein the reciprocating member is connected to a staple drive assembly formed on the end tool, and is moved in the first direction when a staple pulley of the staple drive assembly is rotated.

In the present disclosure, when the staple pulley is alternately rotated in a clockwise direction and a counterclockwise direction, the reciprocating member connected to the staple drive assembly is alternately moved toward the distal end and the proximal end of the cartridge. In the present disclosure, when the reciprocating member is moved toward the distal end of the cartridge, the contact member and the reciprocating member are in a fitted state, so that the relative movement between the operation member and the reciprocating member is restricted, and when the reciprocating member is moved toward the proximal end of the cartridge, the fitted state between the contact member and the reciprocating member is released, so that the relative movement between the operation member and the reciprocating member is possible.

In the present disclosure, wherein the operation member is movable only toward the distal end of the cartridge, and restricted in movement toward the proximal end of the cartridge.

In the present disclosure, wherein the operation member and the reciprocating member form a one-way clutch that allows movement in one direction but restricts movement in a direction opposite to the one direction.

In the present disclosure, the operation member includes: a body; one or more wedges formed at one side of the body and each including an inclined surface formed to have a greater height at a proximal end side of the cartridge than a distal end side of the cartridge; and a blade formed at one side of the wedge and including an edge formed to be sharp, wherein the contact member is disposed in an accommodation part formed on one surface of the body.

In the present disclosure, when the reciprocating member is moved toward the distal end of the cartridge, the contact member and the reciprocating member are in a fitted state to allow the reciprocating member to push the operation member including the contact member, so that the operation member is moved toward the distal end of the cartridge.

In the present disclosure, when the reciprocating member is moved toward the proximal end of the cartridge, the operation member remains stationary with respect to the one direction.

In the present disclosure, wherein the contact member is formed to be spaced apart from the reciprocating member by a certain extent when the reciprocating member is moved toward the proximal end of the cartridge.

In the present disclosure, further comprising an elastic member formed between the body and the contact member and configured to provide an elastic force to press the contact member in one direction.

In the present disclosure, an inclined part is formed on a surface of the accommodation part, which is formed on the body, facing the reciprocating member, and a width of the accommodation part becomes narrower toward the distal end of the cartridge.

In the present disclosure, a spacing between the inclined part and the reciprocating member decreases toward the distal end of the cartridge.

In the present disclosure, when the contact member is pressed in a direction in which the spacing between the inclined part and the reciprocating member decreases, the contact member and the reciprocating member are in a fitted state, so that the relative movement between the reciprocating member and the operation member is blocked.

In the present disclosure, when the contact member is in a fitted state by being simultaneously in contact with the operation member and the reciprocating member, a locked state is entered in which the relative movement between the operation member and the reciprocating member is blocked, and when the contact member is separated from at least one side of the operation member and the reciprocating member and thus the fitted state is released, an unlocked state is entered in which the relative movement between the operation member and the reciprocating member is possible.

In the present disclosure, wherein the elastic member presses the contact member in a direction in which a spacing between the inclined part and the reciprocating member decreases.

In the present disclosure, wherein the contact member is formed such that a center distance is different for each region, wherein the center distance is a distance from a center of rotation of the contact member to an end portion of the contact member.

In the present disclosure, when a region of the contact member, in which the center distance is relatively large, is in contact with the reciprocating member, the contact member and the reciprocating member are in a fitted state, so that the relative movement between the operation member and the reciprocating member is restricted, and when a region of the contact member, in which the center distance is relatively small, is in contact with the reciprocating member, the fitted state between the contact member and the reciprocating member is released, so that the relative movement between the operation member and the reciprocating member is possible.

In the present disclosure, wherein the contact member includes a body, and a protrusion protruding from the body and formed to be in contact with the reciprocating member, wherein the protrusion includes a long axis part in which the center distance is relatively large, and a short axis part in which the center distance is relatively small.

In the present disclosure, when a torque is applied to the contact member in a direction in which the long axis part is in contact with the reciprocating member, the contact member and the reciprocating member are in a fitted state, and when a torque is applied to the contact member in a direction in which the short axis part is in contact with the reciprocating member, the fitted state between the contact member and the reciprocating member is released.

In the present disclosure, wherein the contact member is formed such that the center distance from the center of the body to an end portion of the protrusion increases toward the proximal end of the cartridge.

In the present disclosure, wherein the elastic member presses the contact member in a direction in which the long axis part is in contact with the reciprocating member.

In the present disclosure, wherein the cartridge is a sprag.

In the present disclosure, wherein the contact member is a cam that is rotated around a predetermined rotation axis.

Another aspect of the present disclosure provides a method of driving a surgical instrument, the method comprising operations: (a) in which, when a staple pulley of a staple drive assembly is rotated in a first direction around a first shaft, a staple link assembly connected to the staple pulley and a reciprocating member of a cartridge connected to the staple link assembly are moved along a second shaft toward a distal end of the cartridge; (b) in which, when the reciprocating member is moved toward the distal end of the cartridge, the reciprocating member and an operation member in contact with the reciprocating member are in a fitted state, so that the operation member is moved toward the distal end of the cartridge together with the reciprocating member; (c) in which, as the operation member is moved toward the distal end of the cartridge, the operation member ejects staples in the cartridge to the outside of the cartridge, and simultaneously, a blade of the operation member is moved toward the distal end of the cartridge; and (d) in which, when the staple pulley is rotated in a second direction opposite to the first direction around the first shaft, the staple link assembly, which is connected to the staple pulley, and the reciprocating member of the cartridge, which is connected to the staple link assembly, are moved toward a proximal end of the cartridge.

In the present disclosure, when the staple pulley is rotated in the first direction or the second direction, the reciprocating member is moved toward the distal end or the proximal end of the cartridge.

In the present disclosure, a bidirectional rotational motion of the staple pulley around the first shaft is converted into a reciprocating linear motion of the reciprocating member, which is connected to the staple pulley, with respect to the second shaft.

In the present disclosure, the operation member is moved toward the distal end of the cartridge by the reciprocating linear motion of the reciprocating member.

In the present disclosure, the operation member includes a contact member formed at one side of the reciprocating member to be in contact with the reciprocating member, and in operation (b), when the reciprocating member is moved toward the distal end of the cartridge, the contact member and the reciprocating member are in a fitted state, and a relative movement between the operation member and the reciprocating member is restricted, so that the operation member is moved toward the distal end of the cartridge together with the reciprocating member.

In the present disclosure, in operation (d), when the reciprocating member is moved toward the proximal end of the cartridge, the fitted state of the contact member and the reciprocating member is released, and the relative movement between the operation member and the reciprocating member is possible, so that only the reciprocating member is moved toward the proximal end of the cartridge while the operation member remains stationary.

In the present disclosure, in operation (d), the operation member remains stationary with respect to a direction of the second shaft.

In the present disclosure, the operation member is moved toward the distal end of the cartridge together with the reciprocating member only when the reciprocating member is moved toward the distal end of the cartridge.

In the present disclosure, the surgical instrument further includes a staple wire coupled to the staple pulley to rotate the staple pulley, wherein a bidirectional rotation of the staple pulley is converted into a reciprocating linear motion of the reciprocating member by the staple wire.

In the present disclosure, as the operation member is moved toward the distal end of the cartridge, a wedge of the operation member sequentially pushes and raises a plurality of staples in the cartridge to perform a stapling motion, and simultaneously a blade formed at one side of the wedge of the operation member is moved toward the distal end of the cartridge to perform a cutting motion.

In the present disclosure, operations (a) to (d) are repeatedly performed.

Another aspect of the present disclosure provides a surgical instrument comprising: an end tool including: a first jaw; a second jaw formed to face the first jaw and formed to be rotatable around a first shaft with respect to the first jaw; a staple drive assembly having at least a portion formed in the first jaw or the second jaw and including one or more staple pulleys formed to be rotatable around a shaft substantially the same as or parallel to the first shaft; and a cartridge including: a reciprocating assembly that is connected to the staple drive assembly, and linearly moved when the one or more staple pulleys are rotationally moved; and an operation member that is in contact with the reciprocating assembly, and is moved in one direction by the reciprocating assembly when the reciprocating assembly is moved in the one direction.

In the present disclosure, the end tool further includes: a pair of first pitch main pulleys formed at one side of the staple drive assembly and formed to be rotatable around a second shaft; and a pair of second pitch main pulleys formed at one side of the staple drive assembly and formed to be rotatable around a shaft substantially the same as or parallel to the second shaft.

In the present disclosure, the end tool further includes: a pair of first pitch sub-pulleys formed at one side of the first pitch main pulley and formed to be rotatable around a shaft substantially the same as or parallel to the second shaft; and a pair of second pitch sub-pulleys formed at one side of the second pitch main pulley and formed to be rotatable around a shaft substantially the same as or parallel to the second shaft.

In the present disclosure, wherein the end tool is formed to be pitch-rotatable around the second shaft.

In the present disclosure, the end tool includes a first pulley and a second pulley formed to face each other in the first jaw or the second jaw and formed to be rotatable around a shaft substantially the same as or parallel to the first shaft, wherein at least one of the first pulley and the second pulley is the staple pulley of the staple drive assembly.

In the present disclosure, further comprising: a first wire coupled to the first pulley to rotate the first pulley and wound around at least a portion of the pair of first pitch main pulleys; and a second wire coupled to the second pulley to rotate the second pulley and wound on at least a portion of the pair of second pitch main pulleys.

In the present disclosure, the first pulley is a first staple pulley of the staple drive assembly, and the second pulley is a second staple pulley of the staple drive assembly.

In the present disclosure, the end tool further includes an actuation wire connected to the second jaw and configured to rotate the second jaw with respect to the first jaw by pushing or pulling the second jaw.

In the present disclosure, the first pulley is a jaw pulley connected to the first jaw or the second jaw to rotate the first jaw or the second jaw, and the second pulley is the staple pulley of the staple drive assembly.

In the present disclosure, when the staple pulley is rotated, the reciprocating assembly connected to the staple drive assembly is moved toward a distal end or a proximal end of the cartridge.

In the present disclosure, when the staple pulley is alternately rotated in a clockwise direction and a counterclockwise direction, the reciprocating assembly connected to the staple drive assembly is alternately moved toward the distal end and the proximal end of the cartridge.

In the present disclosure, when the reciprocating assembly is moved toward the distal end of the cartridge, the operation member is moved toward the distal end of the cartridge by the reciprocating assembly.

In the present disclosure, a bidirectional rotational motion of the staple pulley is converted into a reciprocating linear motion of the reciprocating assembly, which is connected to the staple drive assembly, by the staple drive assembly.

In the present disclosure, as the operation member is moved in the one direction, a wedge of the operation member sequentially pushes and raises a plurality of staples in the cartridge to perform a stapling motion, and simultaneously a blade formed at one side of the wedge of the operation member is moved in the one direction to perform a cutting motion.

In the present disclosure, the staple drive assembly includes a link member configured to connect the staple pulley and the reciprocating assembly.

In the present disclosure, the operation member includes a ratchet member having a ratchet formed on at least one surface thereof, wherein the ratchet of the ratchet member is formed to be in contact with the reciprocating assembly.

In the present disclosure, the operation member is moved toward a distal end of the cartridge together with the reciprocating assembly only when the reciprocating assembly is moved toward the distal end of the cartridge.

In the present disclosure, when the staple pulley is rotated in a first direction between a clockwise direction and a counterclockwise direction, the link member connected to the staple pulley, the reciprocating assembly connected to the link member, and the operation member in contact with the reciprocating assembly are moved toward a distal end of the cartridge.

In the present disclosure, when the staple pulley is rotated in a direction opposite to the first direction between the clockwise and counterclockwise directions, the link member connected to the staple pulley and the reciprocating assembly connected to the link member are moved toward a proximal end of the end tool, and the operation member remains stationary with respect to the one direction.

Another aspect of the present disclosure provides an end tool of a surgical instrument, the end tool comprising: a first jaw capable of accommodating a cartridge; a second jaw formed to face the first jaw and formed to be rotatable around a first shaft with respect to the first jaw; a staple drive assembly having at least a portion formed in the first jaw and including one or more staple pulleys formed to be rotatable around a shaft substantially the same as or parallel to the first shaft; a staple wire at least partially in contact with the staple pulley and configured to transmit, to the staple pulley, a driving force necessary for rotating the staple pulley; a pair of first pitch main pulleys formed at one side of the staple drive assembly and formed to be rotatable around a second shaft; and a pair of second pitch main pulleys formed at one side of the staple drive assembly and formed to be rotatable around a shaft substantially the same as or parallel to the second shaft, wherein the staple drive assembly is connected to a reciprocating assembly of the cartridge and configured to convert a rotational motion of the staple pulley into a linear motion of the reciprocating assembly.

In the present disclosure, the staple drive assembly further includes a staple link assembly that connects the staple pulley and the reciprocating assembly and reciprocates in response to bidirectional rotation of the staple pulley.

In the present disclosure, wherein the staple link assembly is coupled to the reciprocating assembly of the cartridge accommodated in the first jaw and reciprocates the reciprocating assembly.

In the present disclosure, when the staple pulley is alternately rotated in a clockwise direction and a counterclockwise direction, the staple link assembly connected to the staple pulley is alternately moved toward a distal end and a proximal end of the end tool.

In the present disclosure, a bidirectional rotational motion of the staple pulley is converted into a reciprocating linear motion of the reciprocating assembly, which is connected to the staple link assembly, by the staple link assembly.

In the present disclosure, a protruding member is formed on the staple pulley, a slot is formed in the staple link assembly, and when the staple pulley is rotated, the protruding member is moved in the slot while coming into contact with the slot.

In the present disclosure, the protruding member is formed in the form of a cam, and the protruding member presses the slot of the staple link assembly while rotating so that the staple link assembly is moved.

In the present disclosure, a center of the protruding member does not coincide with a center of the staple pulley, and the protruding member is formed to be eccentric to a certain extent with respect to the staple pulley.

In the present disclosure, when the staple pulley is rotated in a first direction between a clockwise direction and a counterclockwise direction, the staple link assembly connected to the staple pulley, and the reciprocating assembly connected to the staple link assembly are moved toward a distal end of the cartridge.

In the present disclosure, when the staple pulley is rotated in a direction opposite to the first direction between the clockwise and counterclockwise directions, the staple link assembly connected to the staple pulley is moved toward a proximal end of the end tool.

In the present disclosure, the end tool further includes: a pair of first pitch sub-pulleys formed at one side of the first pitch main pulley and formed to be rotatable around a shaft substantially the same as or parallel to the second shaft; and a pair of second pitch sub-pulleys formed at one side of the second pitch main pulley and formed to be rotatable around a shaft substantially the same as or parallel to the second shaft.

In the present disclosure, the end tool is formed to be pitch-rotatable around the second shaft.

In the present disclosure, the end tool further includes a first pulley and a second pulley formed to face each other in the first jaw or the second jaw and formed to be rotatable around a shaft substantially the same as or parallel to the first shaft, wherein at least one of the first pulley and the second pulley is the staple pulley of the staple drive assembly.

In the present disclosure, a first wire coupled to the first pulley to rotate the first pulley and wound around at least a portion of the pair of first pitch main pulleys; and a second wire coupled to the second pulley to rotate the second pulley and wound on at least a portion of the pair of second pitch main pulleys.

In the present disclosure, further comprising a staple auxiliary pulley disposed between the staple pulley and the pair of first pitch main pulleys or the pair of second pitch main pulleys.

In the present disclosure, the staple wire is located on a common internal tangent of the staple pulley and the staple auxiliary pulley, and a rotation angle of the staple pulley is increased by the staple auxiliary pulley.

In the present disclosure, when the first jaw pulley and the second jaw pulley are rotated in the same direction around the second shaft, the staple pulley is rotated together with the first jaw pulley and the second jaw pulley.

In the present disclosure, while the staple pulley is rotated by the staple wire, the first jaw and the second jaw are either rotated or not rotated.

In the present disclosure, a cartridge accommodation part in which the cartridge is accommodated is formed in the first jaw, and an anvil with which a staple of the cartridge is in contact is formed in the second jaw.

Another aspect of the present disclosure provides an end tool of a surgical instrument, the end tool comprising: a first jaw capable of accommodating a cartridge;

a second jaw formed to face the first jaw and formed to be rotatable around a first shaft with respect to the first jaw; an actuation wire connected to the second jaw and configured to rotate the second jaw with respect to the first jaw by pushing or pulling the second jaw; a staple pulley assembly having at least a portion formed in the first jaw and including a first staple pulley and a second staple pulley that are formed to be rotatable around a shaft substantially the same as or parallel to the first shaft; a staple link assembly connected to the first staple pulley or the second staple pulley and configured to reciprocate in response to rotation of the first staple pulley or the second staple pulley; a first staple wire of which at least a portion is wound around the first staple pulley; a second staple wire of which at least a portion is wound around the second staple pulley; a pair of first pitch main pulleys formed at one side of the first staple pulley and formed to be rotatable around a second shaft; and a pair of second pitch main pulleys formed at one side of the second staple pulley, and formed to be rotatable around a shaft that is substantially the same as or parallel to the second shaft.

In the present disclosure, a bidirectional rotational motion of the staple pulley assembly is converted into a reciprocating linear motion of the staple link assembly.

In the present disclosure, the staple link assembly is coupled to a reciprocating assembly of the cartridge accommodated in the first jaw, and a rotational motion of the staple pulley assembly is transmitted to an operation member of the cartridge via the staple link assembly and the reciprocating assembly.

In the present disclosure, the staple link assembly is moved toward a distal end or a proximal end of the end tool according to a rotation direction of the first staple pulley or the second staple pulley.

In the present disclosure, the staple link assembly includes a link member coupled to each of the first staple pulley, the second staple pulley, and the reciprocating assembly.

In the present disclosure, a first protruding member is formed in the first staple pulley, a second protruding member is formed in the second staple pulley, and a first slot to which the first protruding member is coupled and a second slot to which the second protruding member is coupled are formed in the link member, wherein, when the first staple pulley is rotated, the first protruding member is moved in the first slot while coming into contact with the first slot, and when the second staple pulley is rotated, the second protruding member is moved in the second slot while coming into contact with the second slot.

In the present disclosure, the first slot and the second slot are formed in the link member to be symmetrical with respect to each other, when the first staple pulley and the second staple pulley are rotated in opposite directions, the link member is moved in one direction, and when the first staple pulley and the second staple pulley are rotated in the same direction, the link member remains stationary with respect to the one direction.

In the present disclosure, the first protruding member and the second protruding member are formed in the form of a cam, and as the first protruding member presses the first slot while rotating and the second protruding member presses the second slot while rotating, the staple link assembly is moved.

In the present disclosure, a center of the first protruding member does not coincide with a center of the first staple pulley, the first protruding member is formed to be eccentric to a certain extent with respect to the first staple pulley, a center of the second protruding member does not coincide with a center of the second staple pulley, and the second protruding member is formed to be eccentric to a certain extent with respect to the second staple pulley.

In the present disclosure, when the first staple pulley or the second staple pulley is alternately rotated in a clockwise direction and a counterclockwise direction, the staple link assembly connected to the first staple pulley or the second staple pulley is alternately moved toward a distal end and a proximal end of the end tool.

In the present disclosure, a guide groove is formed in the first jaw in a length direction of the first jaw, and the staple link assembly is moved along the guide groove.

In the present disclosure, the end tool further includes a guide tube that internally accommodates at least a portion of the actuation wire and is formed to be bendable to a certain extent.

In the present disclosure, the actuation wire passes through an inside of the guide tube and is connected to the second jaw.

In the present disclosure, when the guide tube is bent to a certain extent, the actuation wire inside the guide tube is also bent together with the guide tube.

In the present disclosure, the actuation wire is formed to be movable along the guide tube in the guide tube.

In the present disclosure, the first jaw includes a cartridge accommodation part formed on one end portion of the first jaw, and a first pitch pulley part and a second pitch pulley part that are formed at the other end portion of the first jaw to face each other.

In the present disclosure, at least a portion of the guide tube is disposed between the first pitch pulley part and the second pitch pulley part.

In the present disclosure, a pitch slit through which the guide tube does pass is formed between the first pitch pulley part and the second pitch pulley part.

In the present disclosure, the second shaft includes a first sub-shaft formed at a side of the first pitch pulley part and a second sub-shaft formed at a side of the second pitch pulley part, and the pitch slit is formed between the first sub-shaft and the second sub-shaft of the second shaft.

In the present disclosure, a guide pin is formed at one end portion of the actuation wire, a pin guide groove through which the guide pin does move is formed in the first jaw, and a pin guide groove through which the guide pin does move is formed in the second jaw.

In the present disclosure, the second jaw is rotated with respect to the first jaw as the guide pin pushes the pin guide groove of the second jaw while being moved along the pin guide groove of the first jaw in a state in which the guide pin is fitted into the pin guide groove of the first jaw and the pin guide groove of the second jaw.

In the present disclosure, the end tool further includes a pair of first pitch sub-pulleys formed at one side of the first pitch main pulley and formed to be rotatable around a shaft substantially the same as or parallel to the second shaft; and a pair of second pitch sub-pulleys formed at one side of the second pitch main pulley and formed to be rotatable around a shaft substantially the same as or parallel to the second shaft.

In the present disclosure, the end tool is formed to be pitch-rotatable around the second shaft.

Another aspect of the present disclosure provides an end tool of a surgical instrument, the end tool comprising: a first jaw capable of accommodating a cartridge; a second jaw formed to face the first jaw; a jaw pulley coupled to the first jaw or the second jaw and formed to be rotatable around a first shaft; a staple pulley assembly having at least a portion formed in the first jaw or the second jaw and including a staple pulley formed to be rotatable around a shaft substantially the same as or parallel to the first shaft; a staple link assembly connected to the staple pulley and reciprocating in response to rotation of the staple pulley; and a jaw wire of which at least a portion is wound around the jaw pulley; a staple wire of which at least a portion is wound around the staple pulley; a pair of first pitch main pulleys formed at one side of the jaw pulley and formed to be rotatable around a second shaft; and a pair of second pitch main pulleys formed at one side of the staple pulley, and formed to be rotatable around a shaft that is substantially the same as or parallel to the second shaft.

In the present disclosure, a bidirectional rotational motion of the staple pulley assembly is converted into a reciprocating linear motion of the staple link assembly.

In the present disclosure, when the staple pulley is alternately rotated in a clockwise direction and a counterclockwise direction, the staple link assembly connected to the staple pulley is alternately moved toward a distal end and a proximal end of the end tool.

In the present disclosure, the staple link assembly is coupled to a reciprocating assembly of the cartridge accommodated in the first jaw, and a rotational motion of the staple pulley assembly is transmitted to an operation member of the cartridge via the staple link assembly and the reciprocating assembly.

In the present disclosure, a bidirectional rotational motion of the staple pulley is converted into a reciprocating linear motion of the reciprocating assembly, which is connected to the staple link assembly, by the staple link assembly.

In the present disclosure, the staple link assembly includes a link member coupled to each of the staple pulley and the reciprocating assembly.

In the present disclosure, a protruding member is formed in the staple pulley, a slot to which the protruding member is coupled is formed in the link member, and when the staple pulley is rotated, the protruding member is moved in the slot while coming into contact with the slot.

In the present disclosure, the protruding member is formed in the form of a cam, and the staple link assembly is moved as the protruding member presses the slot while rotating.

In the present disclosure, a center of the protruding member does not coincide with a center of the staple pulley, and the protruding member is formed to be eccentric to a certain extent with respect to the staple pulley.

In the present disclosure, a protruding member is formed in the jaw pulley, a slot to which the protruding member is coupled is formed in the second jaw, and when the jaw pulley is rotated, the protruding member is moved in the slot while coming into contact with the slot.

In the present disclosure, the protruding member is formed in the form of a cam, and the second jaw is moved as the protruding member presses the slot while rotating.

In the present disclosure, a center of the protruding member does not coincide with a center of the jaw pulley, and the protruding member is formed to be eccentric to a certain extent with respect to the jaw pulley.

In the present disclosure, further comprising a jaw-pulley connection link configured to connect the jaw pulley and the second jaw.

In the present disclosure, when the jaw pulley is rotated, the rotation of the jaw pulley is transmitted to the second jaw through the jaw-pulley connection link, so that the second jaw is rotated with respect to the first jaw.

In the present disclosure, the jaw pulley is integrally formed with the second jaw as one body.

In the present disclosure, when the jaw pulley is rotated as the jaw wire coupled to the jaw pulley is pushed or pulled, the second jaw integrally formed with the jaw pulley as one body is rotated together with the jaw pulley.

In the present disclosure, the end tool further includes: a pair of first pitch sub-pulleys formed at one side of the first pitch main pulley and formed to be rotatable around a shaft substantially the same as or parallel to the second shaft; and a pair of second pitch sub-pulleys formed at one side of the second pitch main pulley and formed to be rotatable around a shaft substantially the same as or parallel to the second shaft.

In the present disclosure, the end tool is formed to be pitch-rotatable around the second shaft.

In the present disclosure, wherein the jaw pulley and the staple pulley are formed to be rotatable independently of each other.

Other aspects, features, and advantages in addition to the aforementioned will become apparent from the following drawings, claims, and detailed description of the disclosure.

MODE OF DISCLOSURE

While the present disclosure is susceptible to various modifications and alternative forms, specific embodiments thereof are shown by way of example in the drawings and will herein be described in detail. However, it should be understood that there is no intent to limit the present disclosure to the particular forms disclosed herein, rather, the present disclosure should be construed to cover various modifications, equivalents, and alternatives of embodiments of the present disclosure. In describing the present disclosure, detailed description of known related arts will be omitted when it is determined that the gist of the present disclosure may be unnecessarily obscured Although terms such as "first," "second," and the like may be used to describe various components, such components should not be limited to the above terms The terms are only used to distinguish one component from another.

The terms used herein are for the purpose of describing particular embodiments only and are not intended to be limiting to the present disclosure. Singular forms are intended to include plural forms as well, unless the context clearly indicates otherwise. In the present application, it will be further understood that the terms "comprise," "comprising," "include," and/or "including", when used in this specification, specify the presence of stated features, integers, steps, operations, elements, components and/or groups thereof but do not preclude the presence or addition of one or more other features, integers, steps, operations, elements, components and/or groups thereof.

Hereinafter, the embodiments of the present disclosure will be described below in detail with reference to the accompanying drawings, and when the embodiments of the present disclosure are described with reference to the drawings, the same or corresponding components are given the same reference numerals, and repetitive descriptions thereof will be omitted.

Further, in describing the various embodiments of the present disclosure, it is to be understood that each embodiment is not intended to be interpreted or implemented independently, and that the technical ideas described in each embodiment may be interpreted or implemented in combination with other embodiments described separately.

In a surgical instrument according to the present disclosure, when a manipulation part is rotated in one direction for at least any one of pitch, yaw, and actuation motions, an end tool is rotated in intuitively the same direction as a direction in which the manipulation part is moved.

Figure 1C:
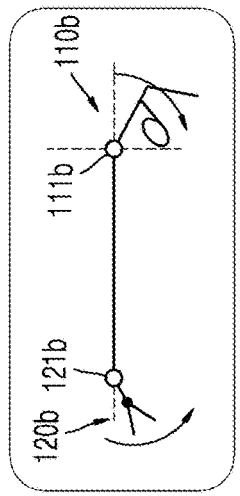
FIG. 1C is a conceptual diagram of a pitch motion of another conventional surgical instrument.
Figure 1E:
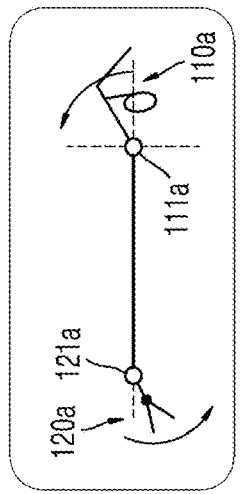
FIG. 1E is a conceptual diagram of a pitch motion of a surgical instrument according to the present disclosure.
Figure 1B:
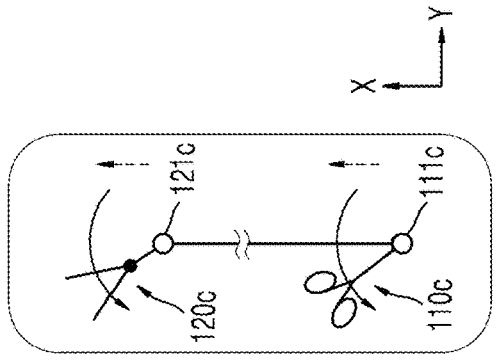
FIG. 1B is a conceptual diagram of a yaw motion thereof.

FIG. 1A is a conceptual diagram of a pitch motion of a conventional surgical instrument, and FIG. 1B is a conceptual diagram of a yaw motion thereof.

Referring to FIG. 1A, in performing a pitch motion of a conventional surgical instrument, in a state in which an end tool 120a is formed in front of a rotation center 121a of the end tool, and a manipulation part 110a is formed at the rear of a rotation center 111a of the manipulation part, when the manipulation part 110a is rotated in a clockwise direction, the end tool 120a is also rotated in the clockwise direction, and when the manipulation part 120a is rotated in a counterclockwise direction, the end tool 120a is also rotated in the counterclockwise direction. Referring to FIG. 1B, in performing a yaw motion of the conventional surgical instrument, in a state in which the end tool 120a is formed in front of the rotation center 121a of the end tool, and the manipulation part 110a is formed at the rear of the rotation center 111a of the manipulation part, when the manipulation part 110a is rotated in the clockwise direction, the end tool 120a is also rotated in the clockwise direction, and when the manipulation part 120a is rotated in the counterclockwise direction, the end tool 120a is also rotated in the counterclockwise direction. In this case, in view of left and right directions of a user, when the user moves the manipulation part 110a to the left, the end tool 120a is moved to the right, and when the user moves the manipulation part 110a to the right, the end tool 120a is moved to the left. As a result, a manipulation direction of the user and an operation direction of the end tool are opposite to each other, which may cause the user to make a mistake, and user's manipulation may not be easy.

Figure 1D:
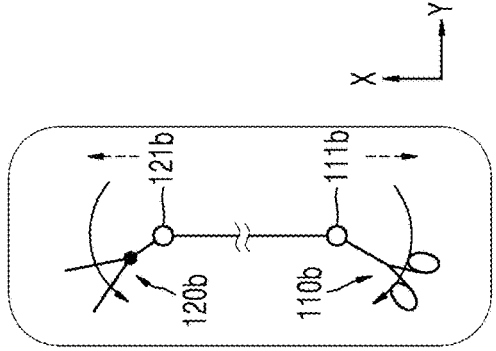
FIG. 1D is a conceptual diagram of a yaw motion thereof.

FIG. 1C is a conceptual diagram of a pitch motion of another conventional surgical instrument, and FIG. 1D is a conceptual diagram of a yaw motion thereof.

Figure 1F:
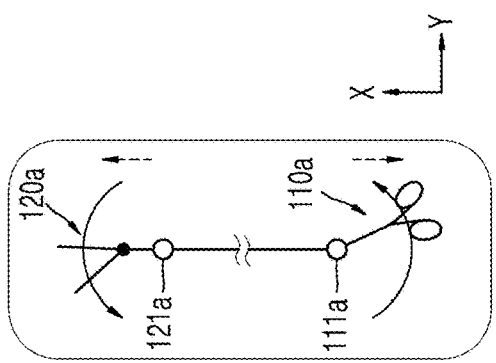
FIG. 1F is a conceptual diagram of a yaw motion thereof.

Referring to FIG. 1C, in the conventional surgical instrument, which is partially formed in a mirror symmetrical shape, in performing a pitch motion, in a state in which an end tool 120b is formed in front of a rotation center 121b of the end tool, and a manipulation part 110b is formed at the rear of a rotation center 111b of the manipulation part, when the manipulation part 110b is rotated in the clockwise direction, the end tool 120b is rotated in the counterclockwise direction, and when the manipulation part 110b is rotated in the counterclockwise direction, the end tool 120b is rotated in the clockwise direction. In this case, in view of rotation directions of the manipulation part and the end tool, a rotation direction in which the user rotates the manipulation part 110b and a rotation direction of the end tool 120b according thereto are opposite to each other. As a result, the user may be confused with the manipulation direction, and as the operation of a joint is not intuitive, the user may make an error. Further, referring to FIG. 1D, in performing a yaw motion, in a state in which the end tool 120b is formed in front of the rotation center 121b of the end tool, and the manipulation part 110b is formed at the rear of the rotation center 111b of the manipulation part, when the manipulation part 110b is rotated in the clockwise direction, the end tool 120b is rotated in the counterclockwise direction, and when the manipulation part 110b is rotated in the counterclockwise direction, the end tool 120b is rotated in the clockwise direction. In this case, in view of rotation directions of the manipulation part and the end tool, a rotation direction in which the user rotates the manipulation part 110b and a rotation direction of the end tool 120b according thereto are opposite to each other. As a result, the user may be confused with the manipulation direction, and as the operation of the joint is not intuitive, the user may make an error. In the user's pitch or yaw manipulation of the conventional surgical instrument, the user's manipulation direction and the end tool's operation direction do not match each other in view of one of the rotation direction and the left and right directions. This is because the configurations of the end tool and the manipulation part are different from each other in the joint configuration of the conventional surgical instrument. That is, this is because the manipulation part is formed at the rear of the rotation center of the manipulation part, while the end tool is formed in front of the rotation center of the end tool. In order to address the above problems, in a surgical instrument according to an embodiment of the present disclosure, which is illustrated in FIGS. 1E and 1F, an end tool 120c is formed in front of a rotation center 121c of the end tool and a manipulation part 110c is also formed in front of a rotation center 111c of the manipulation part, so that the operations of the manipulation part 110c and the end tool 120c are intuitively matched with each other. In other words, unlike existing examples such as those shown in FIGS. 1A, 1B, 1C, and 1D, in which the manipulation part is close to a user with respect to the joint thereof (that is, away from the end tool), the surgical instrument according to an embodiment of the present disclosure, which is illustrated in FIGS. 1E and 1F, is formed such that at least a portion of the manipulation part is closer (than a joint thereof) to the end tool with respect to the joint thereof at any one moment or more in a manipulation process.

In other words, in the conventional surgical instrument as illustrated in FIGS. 1A, 1B, 1C, and 1D, the manipulation part is formed at the rear of the rotation center thereof, while the end tool is located in front of the rotation center thereof, and thus the end tool is moved at a front side thereof with a rear side fixed through a motion of the manipulation part that is moved at a rear side thereof with a front side thereof fixed, which is not an intuitively matching structure. Accordingly, a mismatch may occur between the manipulation of the manipulation part and the motion of the end tool in view of the left and right directions or in view of the rotation direction, which may cause confusion to the user, and the manipulation of the manipulation part may be difficult to perform intuitively and quickly and may cause mistakes. In contrast, in the surgical instrument according to an embodiment of the present disclosure, since both the end tool and the manipulation part are moved with respect to the rotation center formed at the rear side thereof, it may be said that the motions are intuitively matched with each other in terms of structure. In other words, moving portions of the manipulation part are moved with respect to the rotation center formed at the rear side thereof just as moving portions of the end tool are moved with respect to the rotation center formed at the rear side thereof, and thus it may be said that the motions are intuitively matched with each other in terms of structure. This allows the user to intuitively and quickly perform a control in a direction toward the end tool, and a possibility of making a mistake may be significantly reduced. Hereinafter, a detailed mechanism enabling the above-described function will be described below.

First Embodiment of Surgical Instrument

Figure 2:
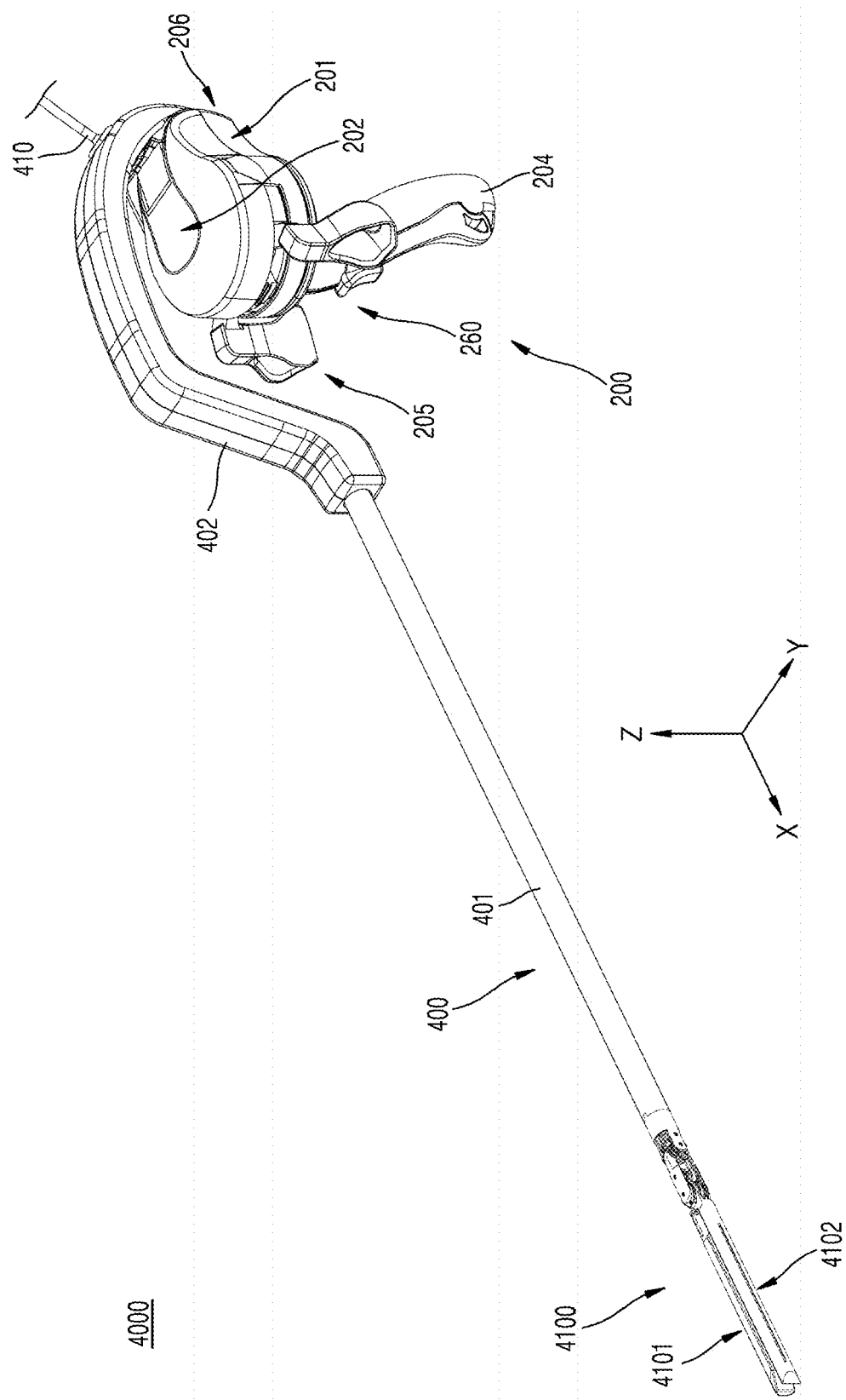
FIG. 2 is a perspective view illustrating a surgical instrument according to a first embodiment of the present disclosure.
Figure 3:
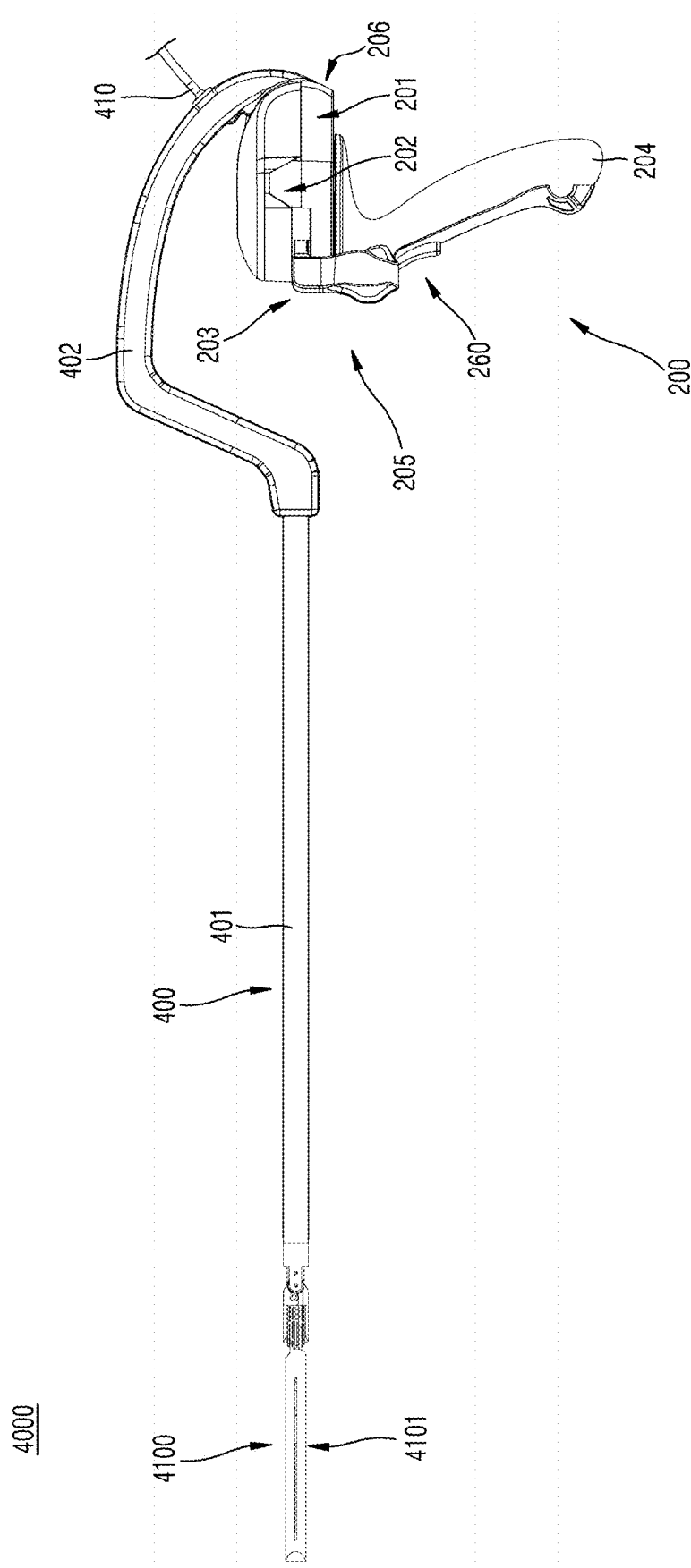
FIG. 3 is a side view of the surgical instrument of FIG. 2.
Figure 4:
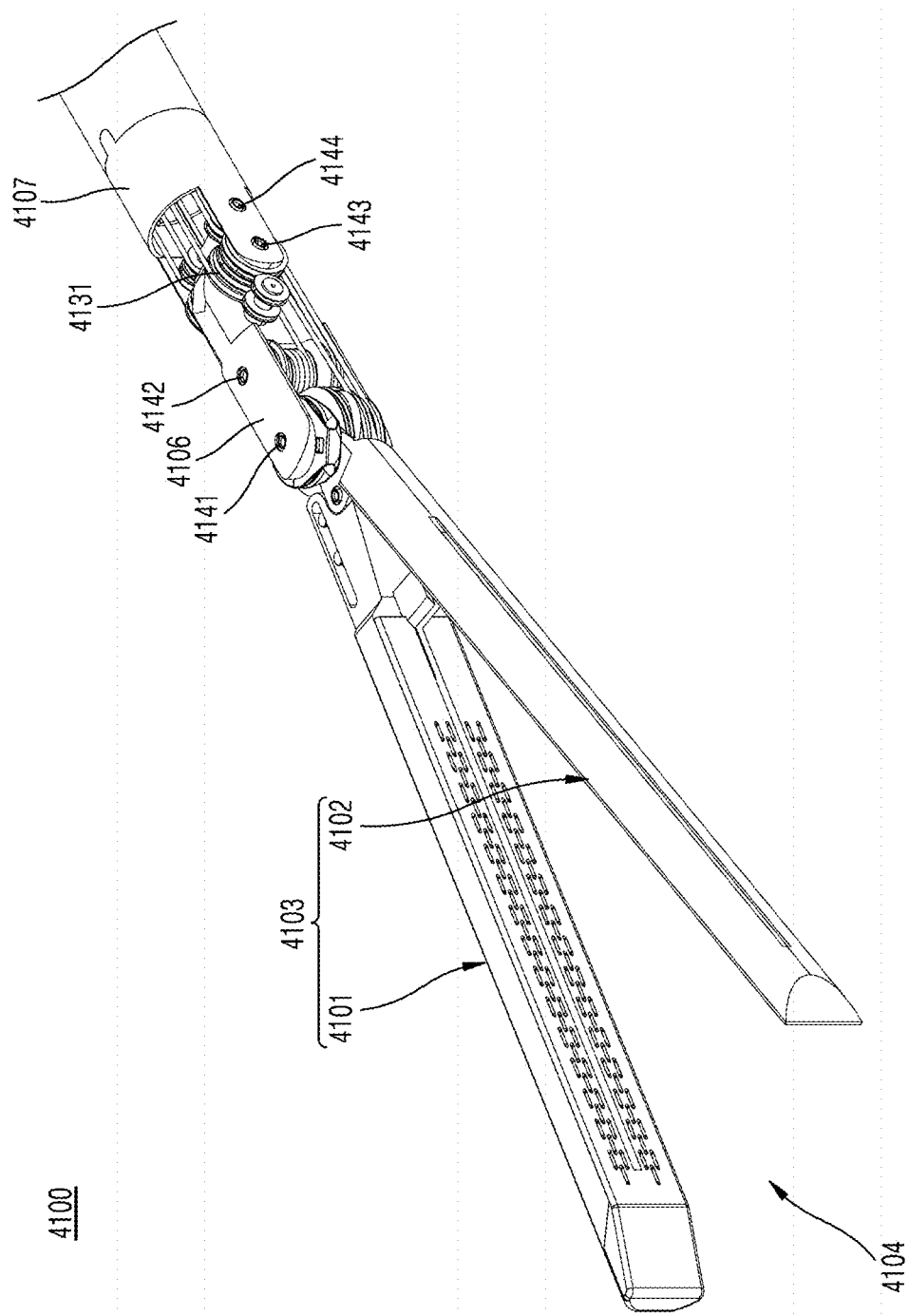
FIGS. 4 and 5 are perspective views illustrating an end tool of the surgical instrument of FIG. 2.
Figure 5:
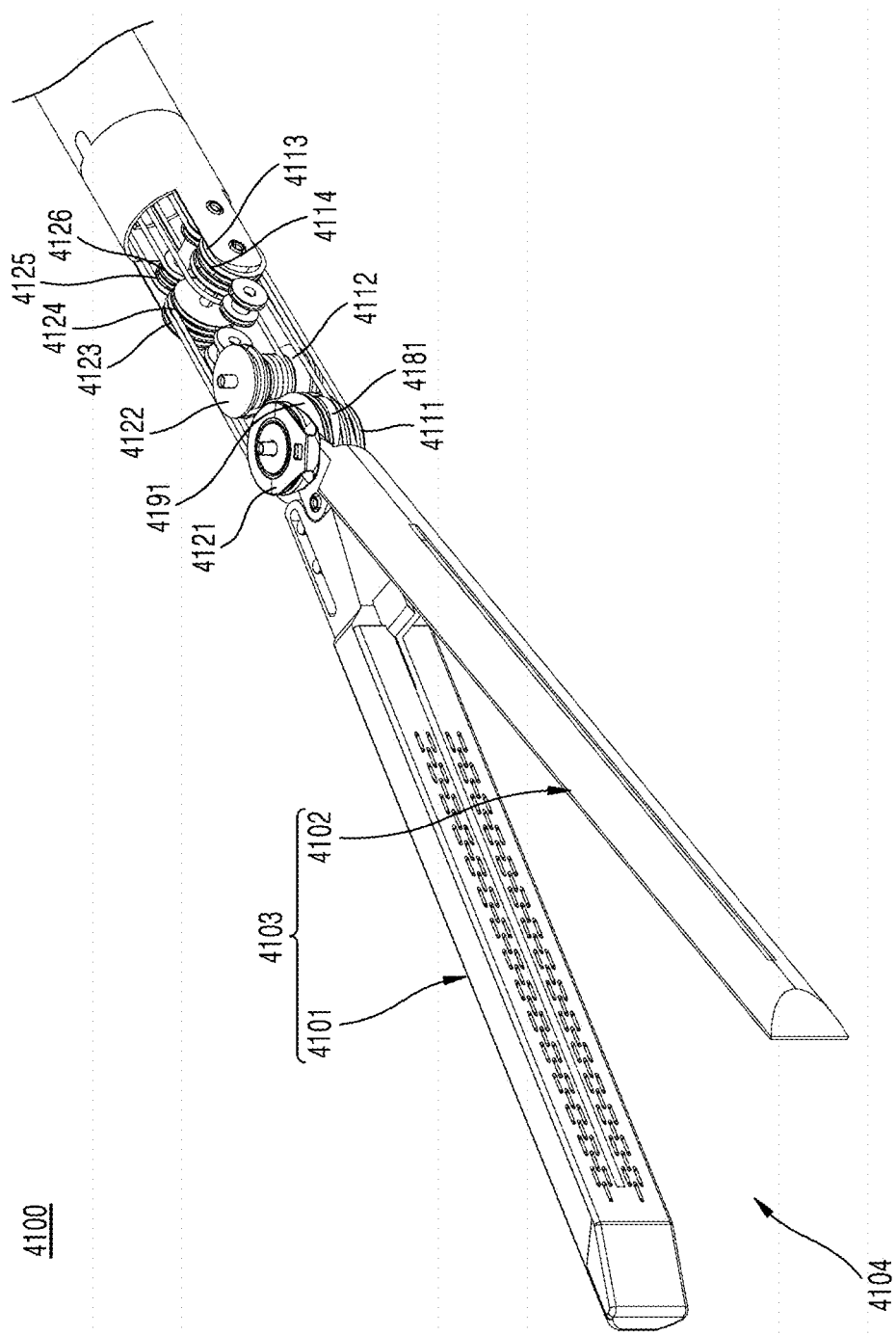
Figure 6:
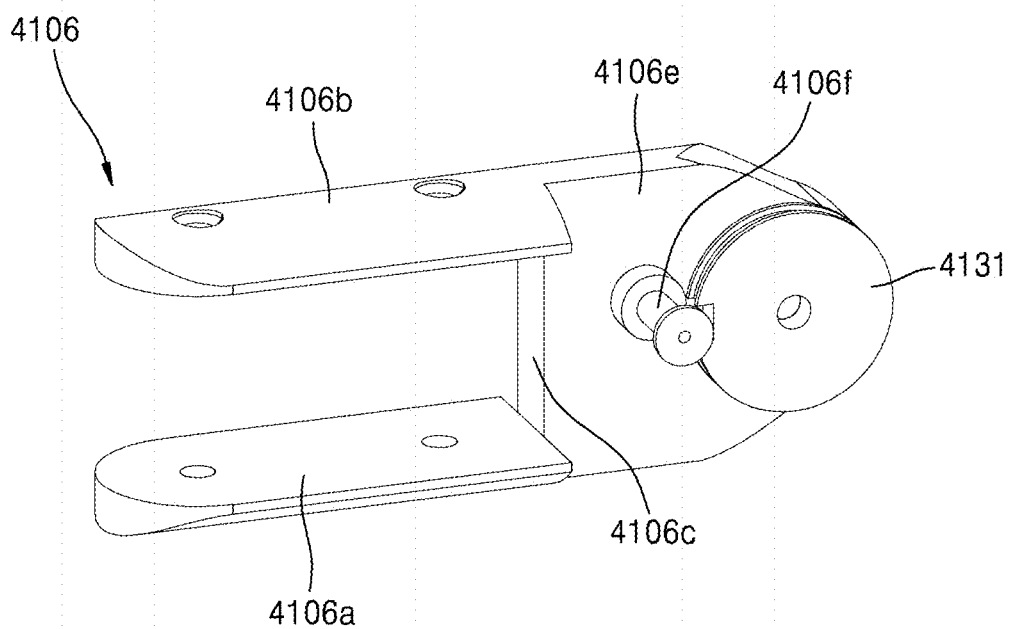
FIG. 6 is a perspective view illustrating an end tool hub of the end tool of the surgical instrument of FIG. 2.
Figure 7:
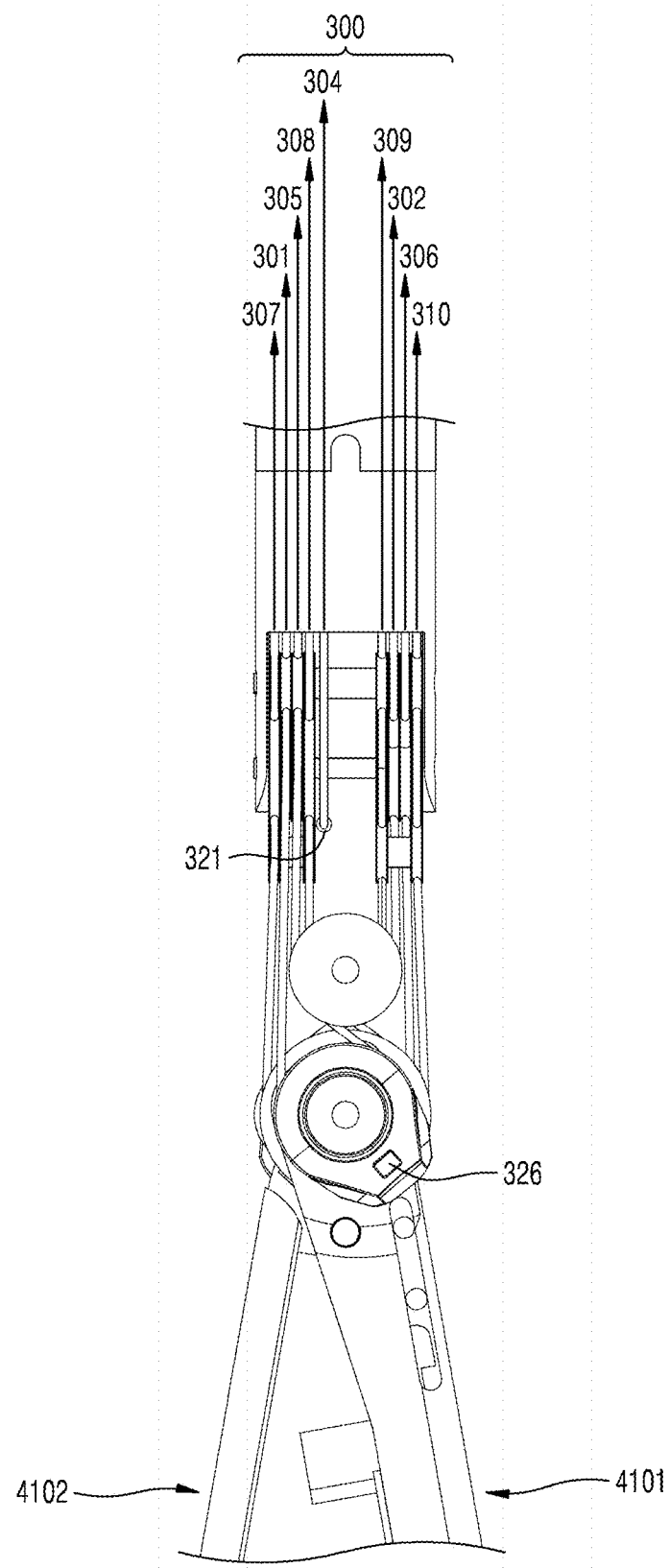
FIGS. 7 and 8 are plan views illustrating the end tool of the surgical instrument of FIG. 2.
Figure 8:
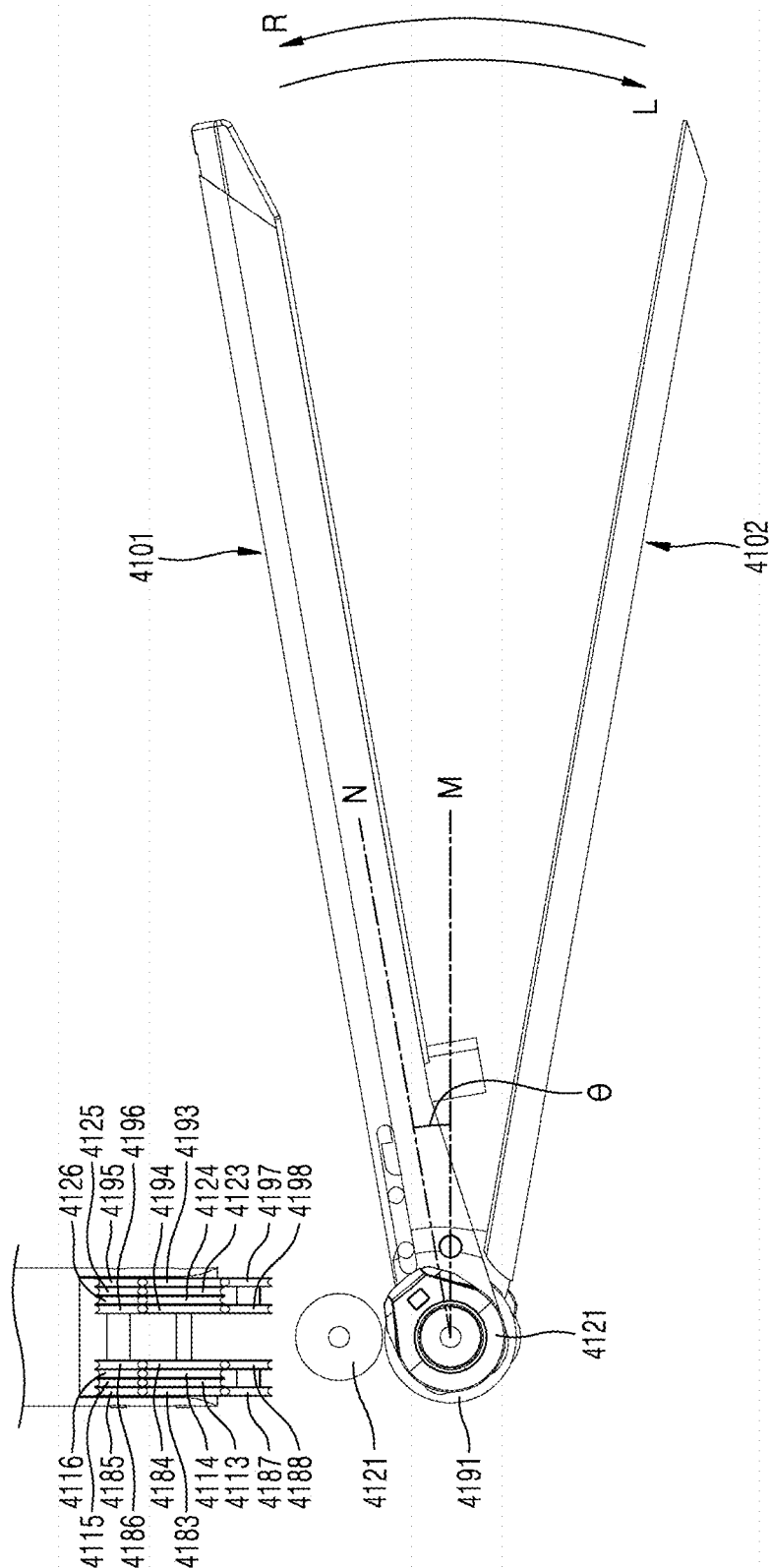
Figure 9:
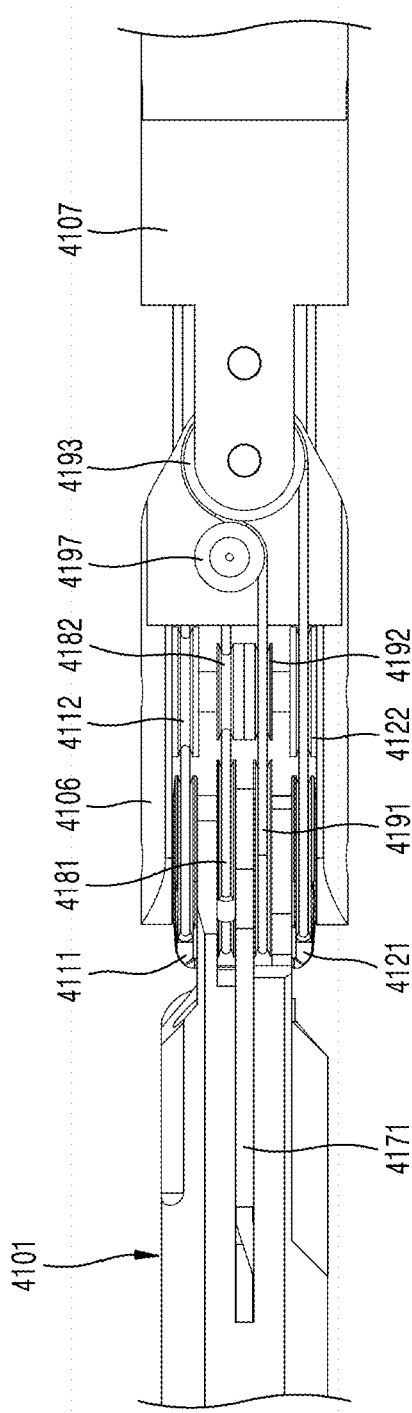
FIG. 9 is a side view illustrating the end tool of the surgical instrument of FIG. 2.
Figure 10:
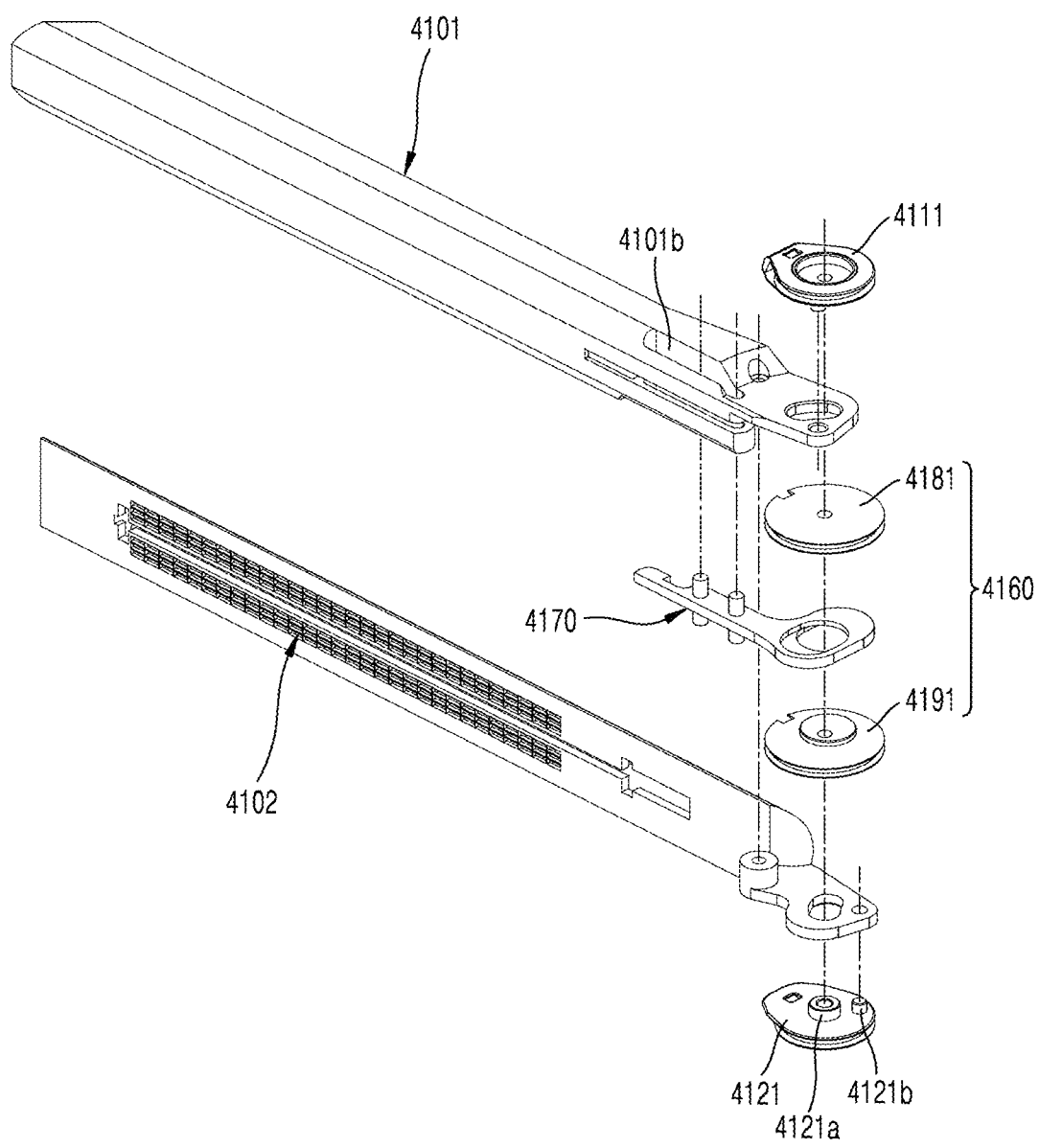
FIGS. 10 and 11 are exploded perspective views of the end tool of the surgical instrument of FIG. 2.
Figure 11:
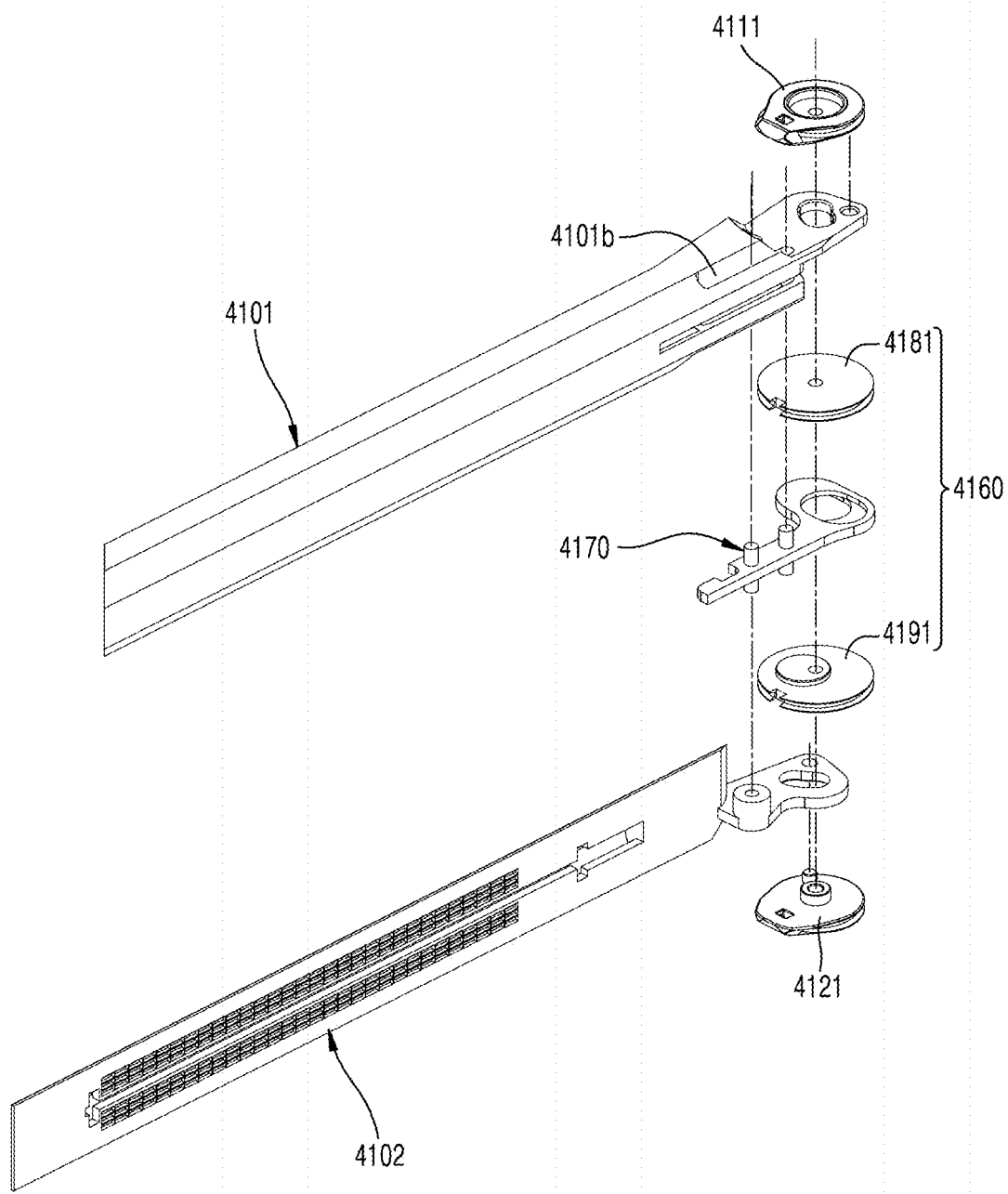
Figure 12:
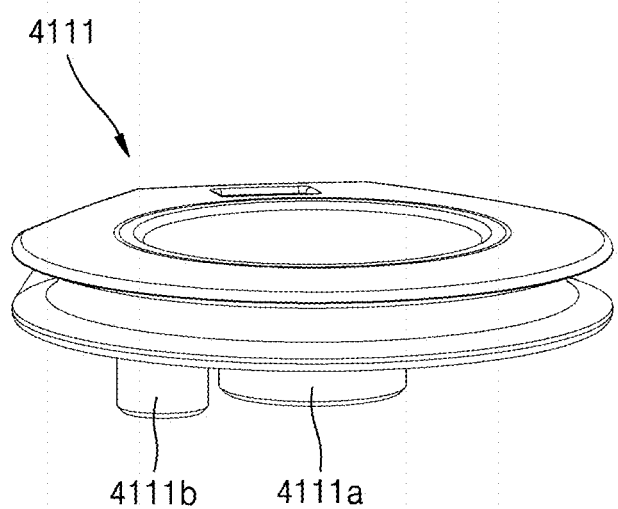
FIG. 12 is a perspective view illustrating a first jaw pulley of the surgical instrument of FIG. 2.
Figure 13:
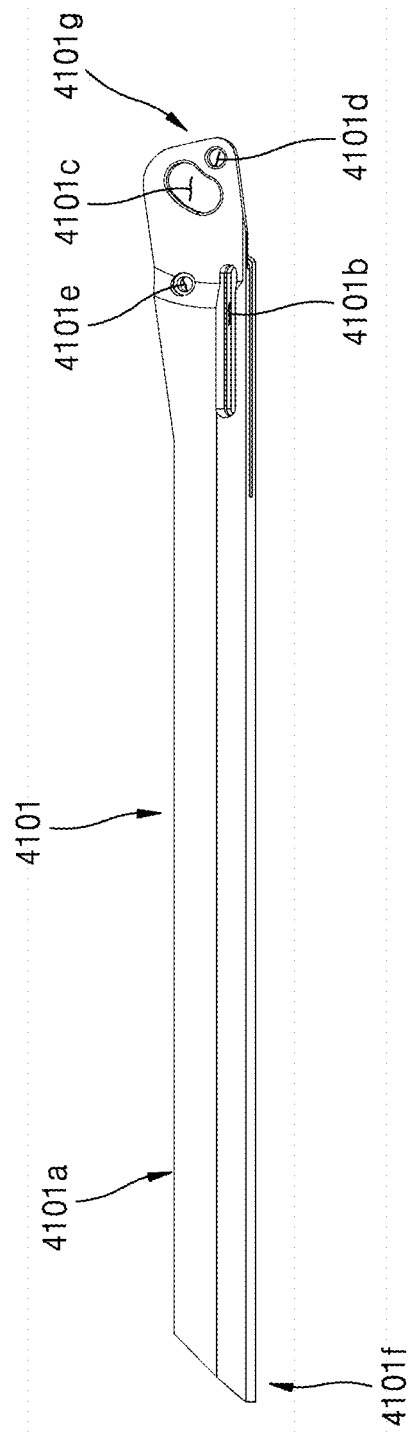
FIG. 13 is a plan view illustrating a first jaw of the surgical instrument of FIG. 2.
Figure 14:
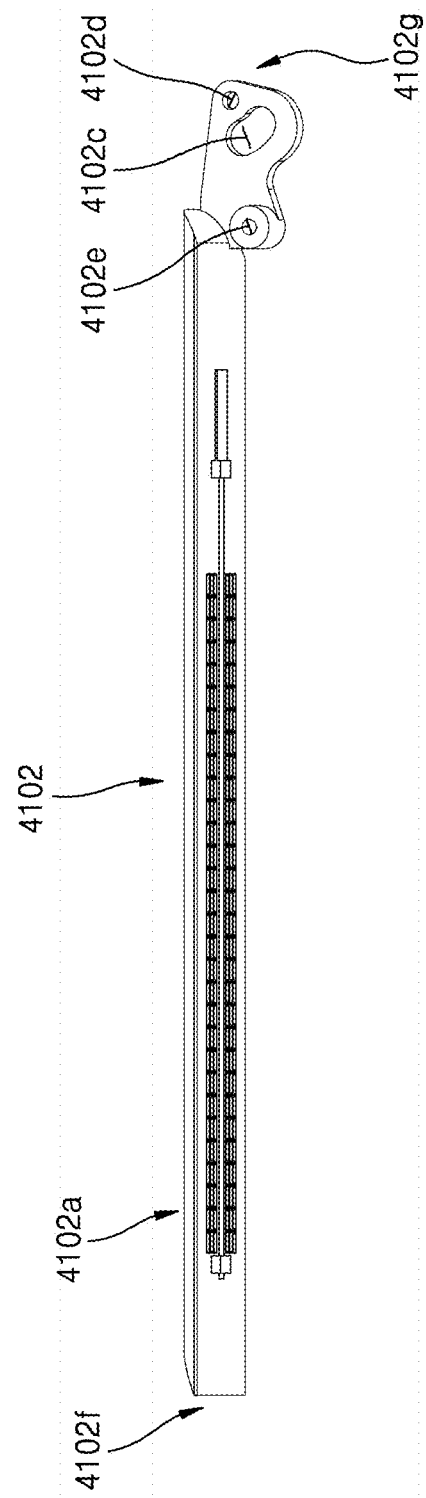
FIG. 14 is a plan view illustrating a second jaw of the surgical instrument of FIG. 2.
Figure 15:
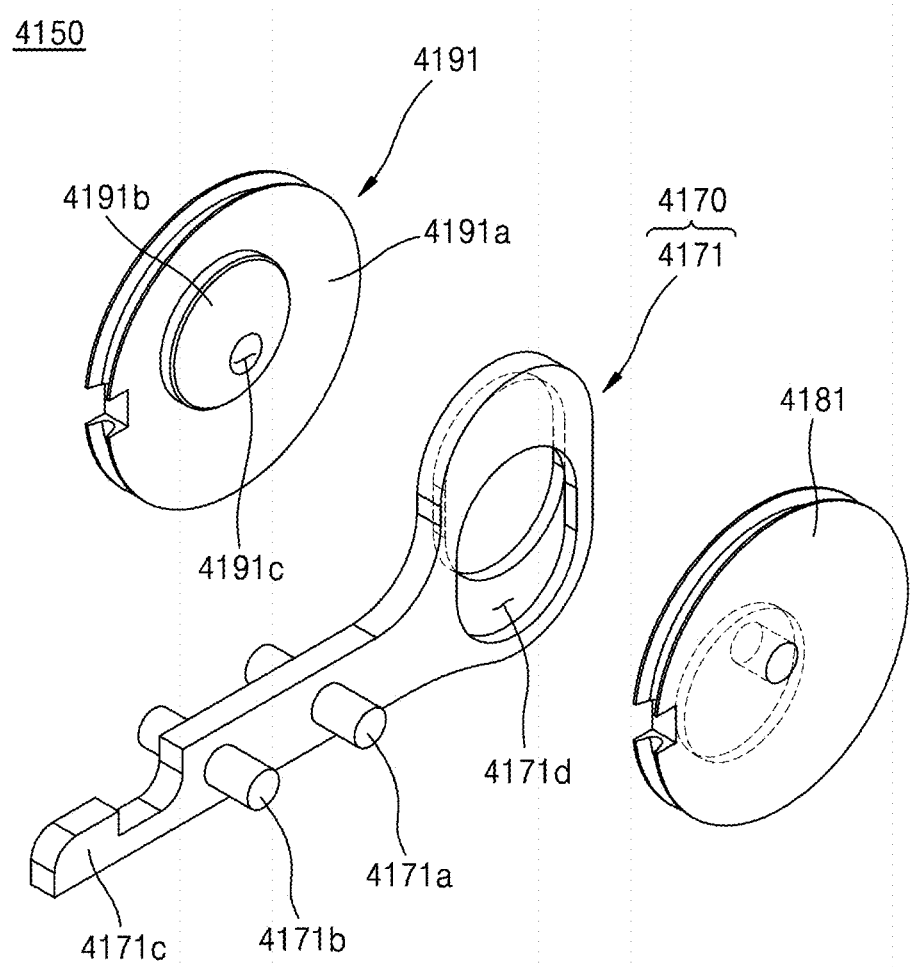
FIGS. 15 and 16 are exploded perspective views illustrating a staple pulley and a staple link of the surgical instrument of FIG. 2.
Figure 16:
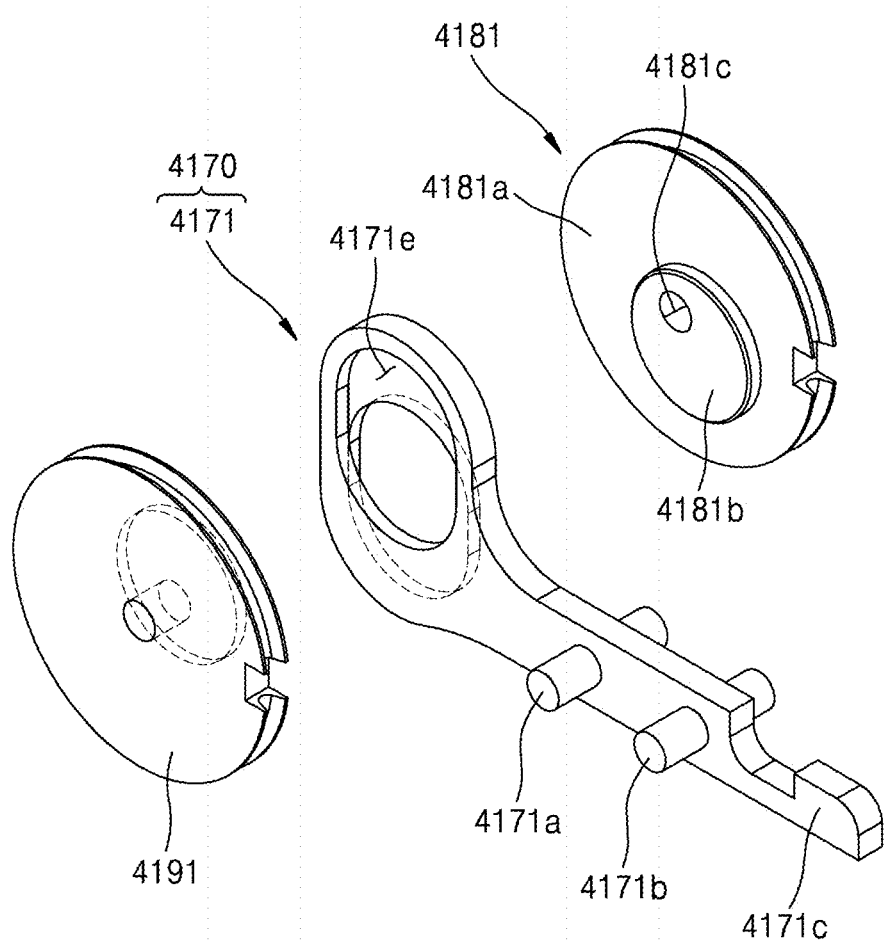
Figure 17:
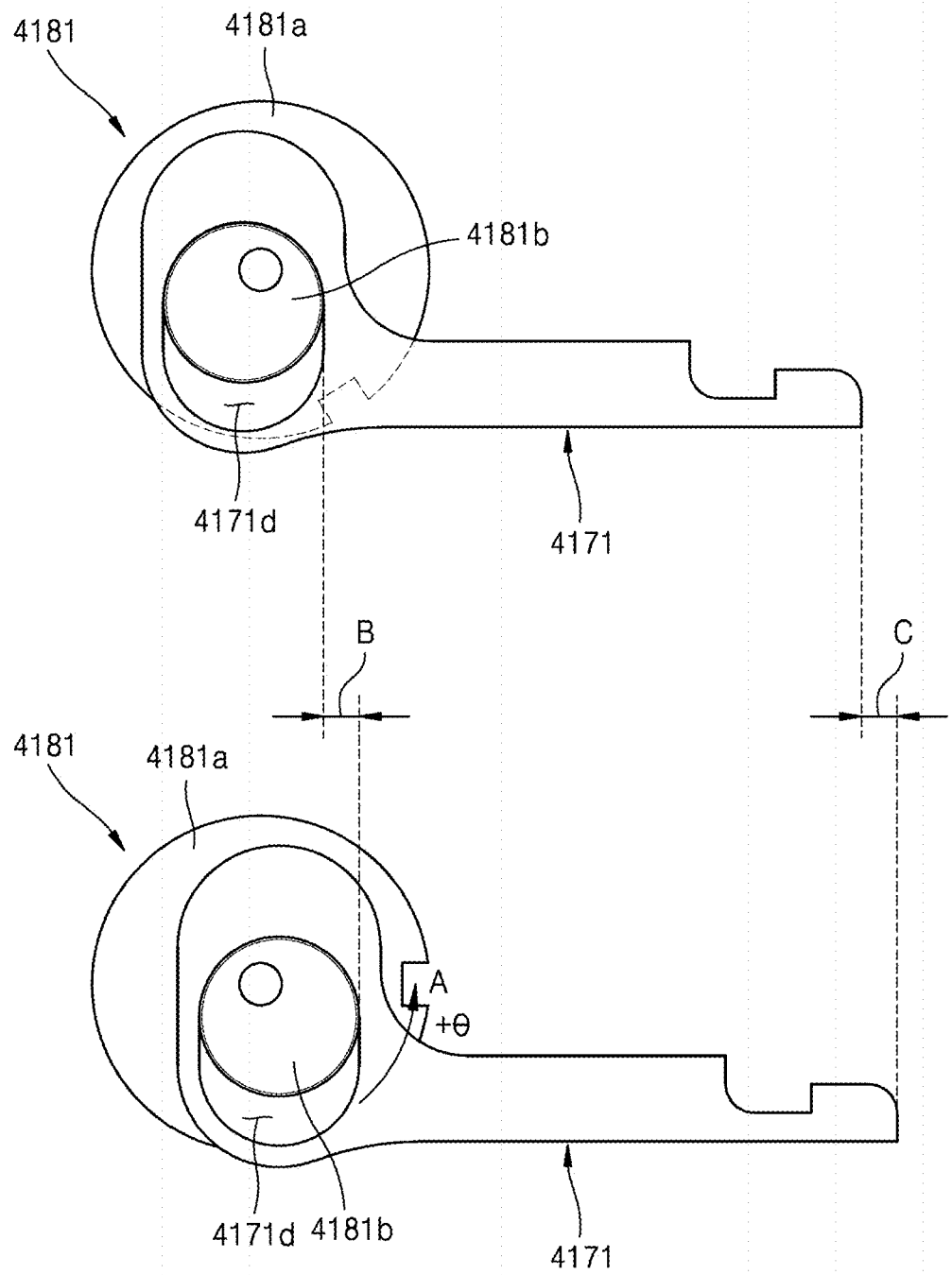
FIGS. 17 and 18 are side views illustrating operating states of the staple pulley in the end tool of the surgical instrument of FIG. 2.
Figure 18:
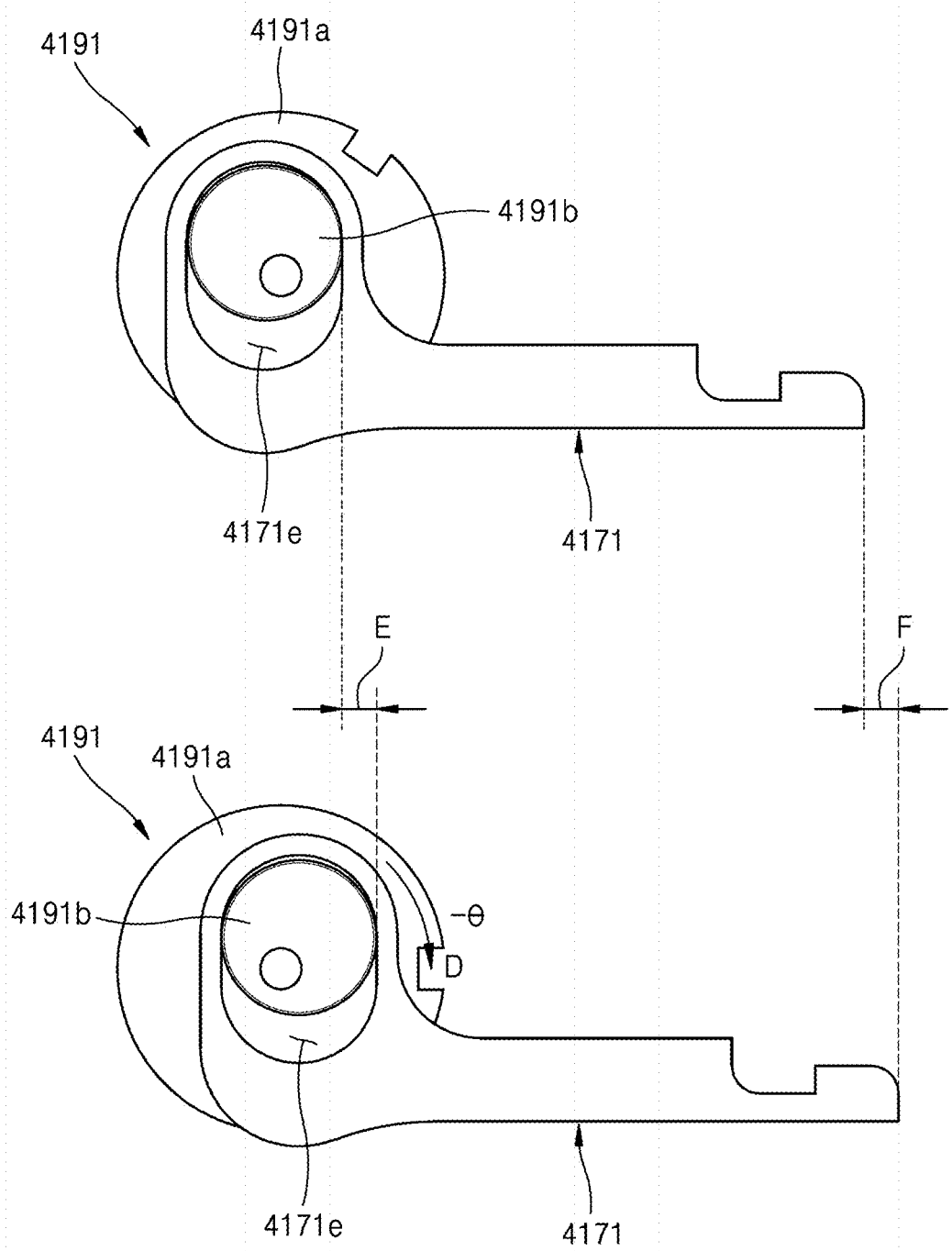
Figure 19:
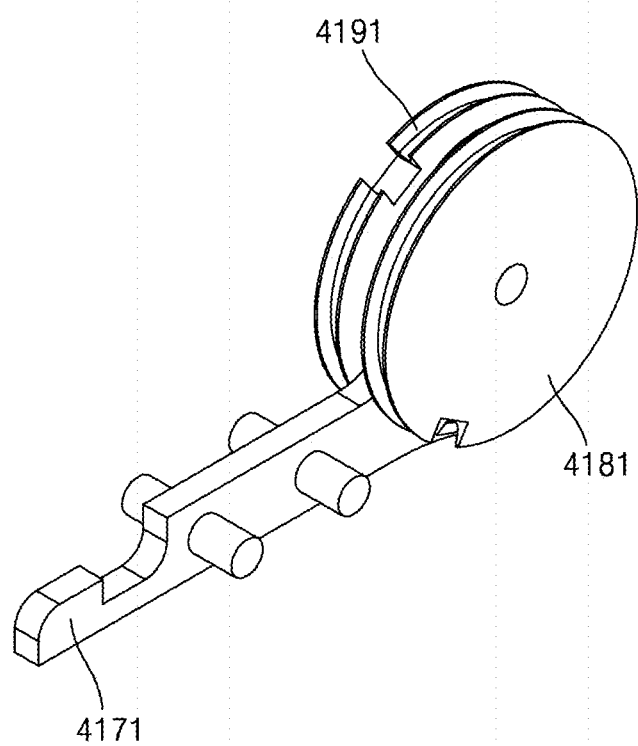
FIGS. 19 and 20 are perspective views illustrating operating states of the staple pulley in the end tool of the surgical instrument of FIG. 2.
Figure 20:
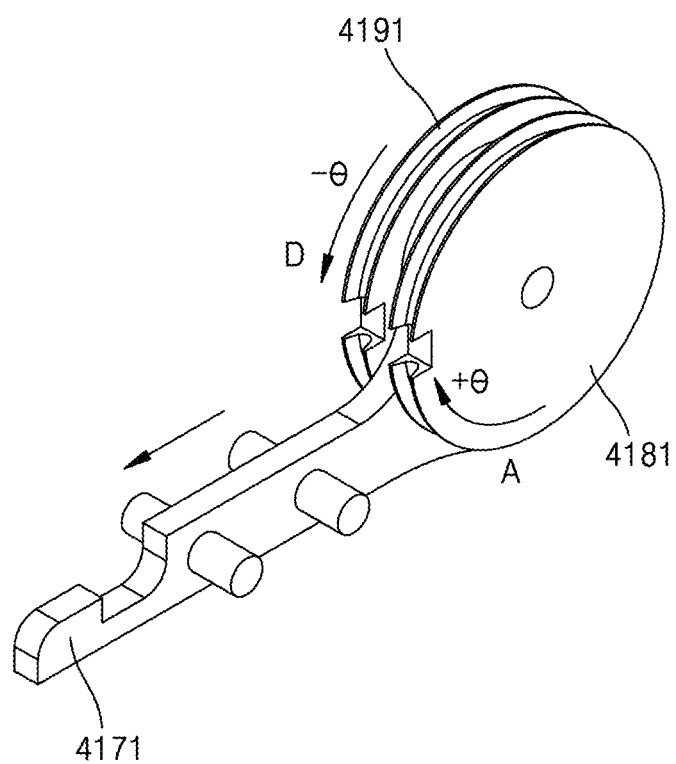
Figure 23:
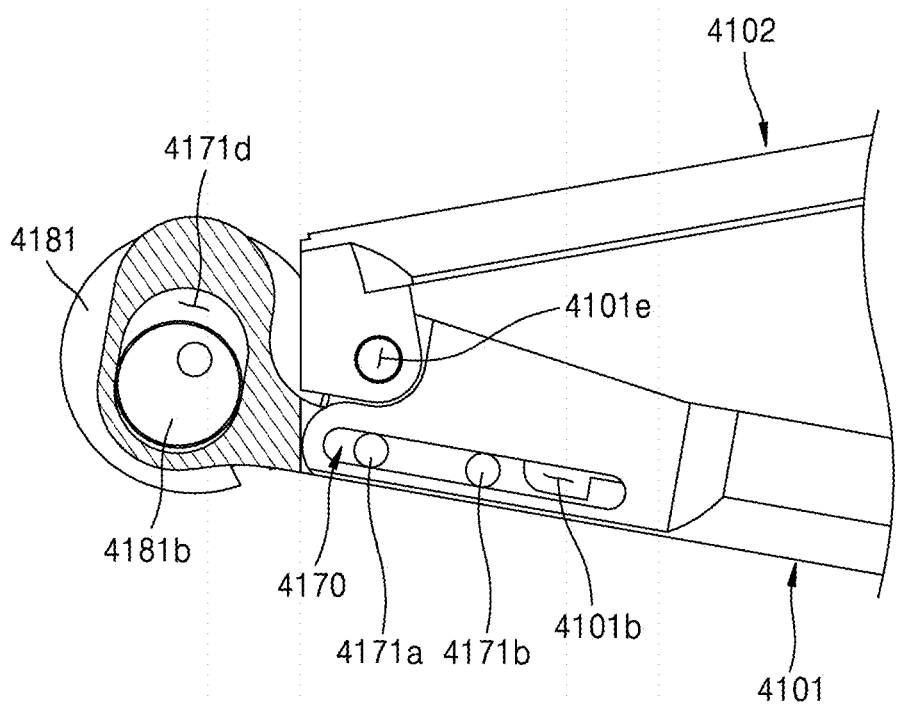
Figure 24:
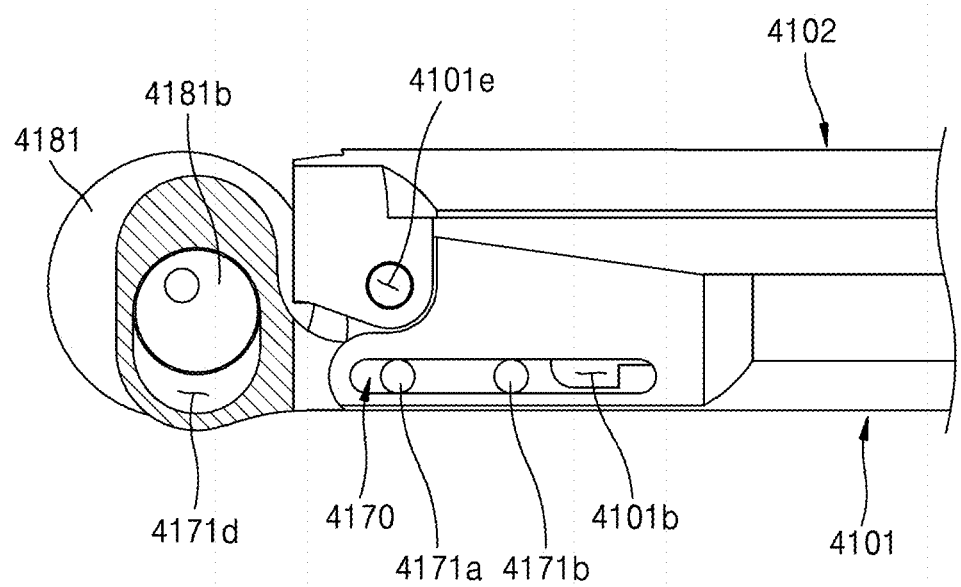
Figure 25:
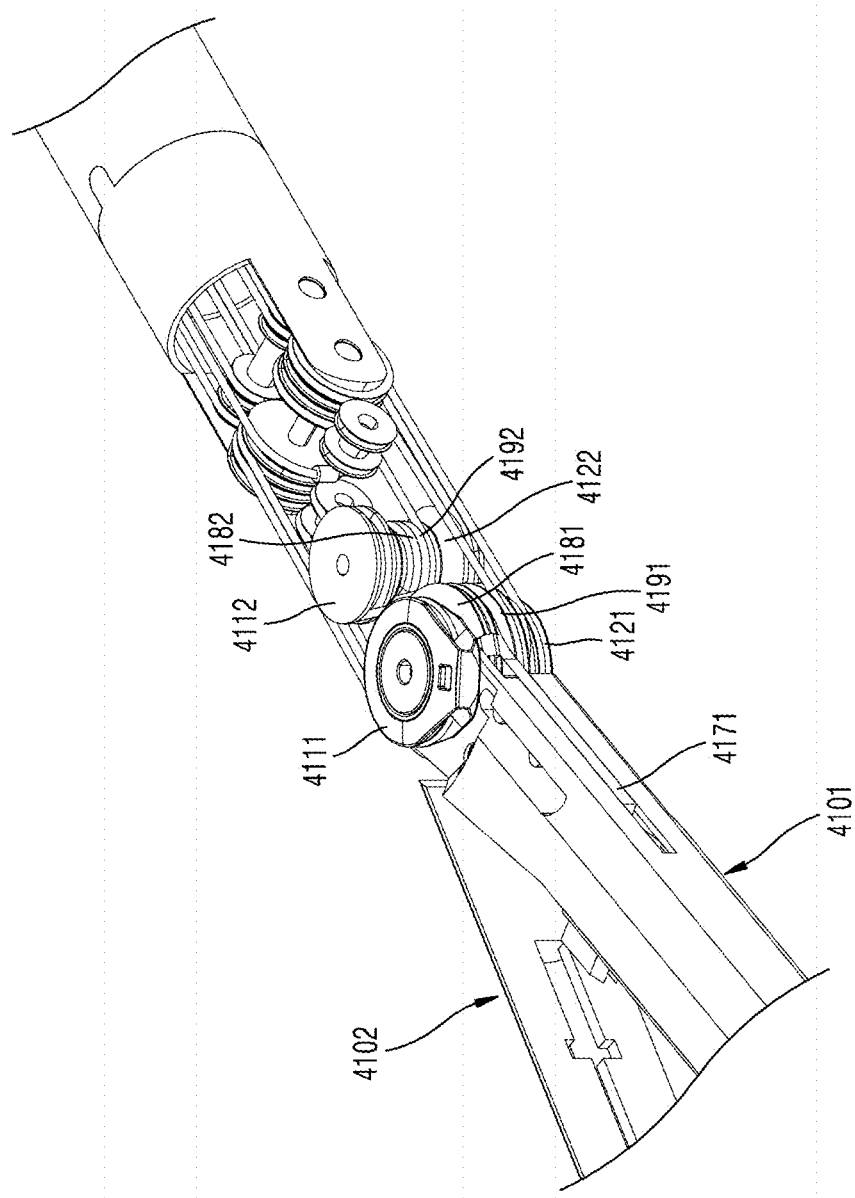
FIGS. 25 and 26 are perspective views illustrating opening and closing motions of the end tool of the surgical instrument of FIG. 2.
Figure 26:
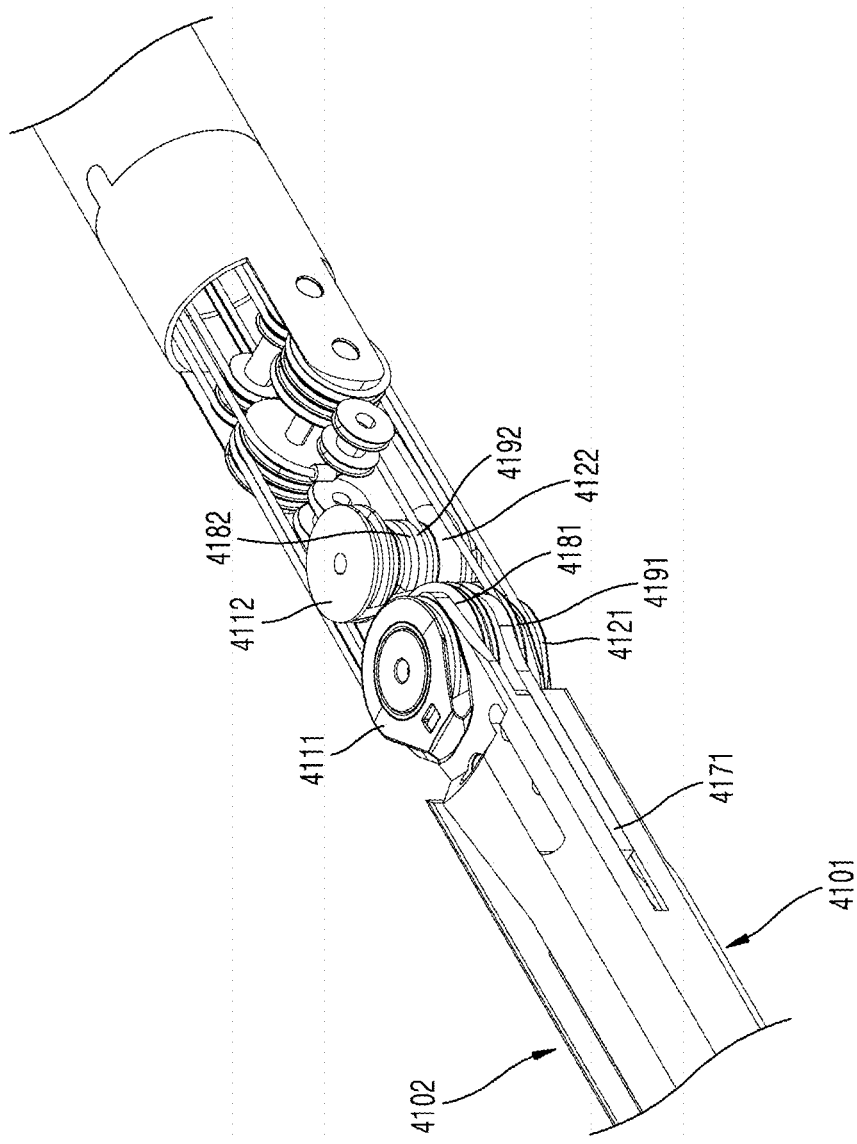

FIG. 2 is a perspective view illustrating a surgical instrument according to a first embodiment of the present disclosure. FIG. 3 is a side view of the surgical instrument of FIG. 2. FIGS. 4 and 5 are perspective views illustrating an end tool of the surgical instrument of FIG. 2. FIG. 6 is a perspective view illustrating an end tool hub of the end tool of the surgical instrument of FIG. 2. FIGS. 7 and 8 are plan views illustrating the end tool of the surgical instrument of FIG. 2. FIG. 9 is a side view illustrating the end tool of the surgical instrument of FIG. 2. FIGS. 10 and 11 are exploded perspective views of the end tool of the surgical instrument of FIG. 2. FIG. 12 is a perspective view illustrating a first jaw pulley of the surgical instrument of FIG. 2. FIG. 13 is a plan view illustrating a first jaw of the surgical instrument of FIG. 2. FIG. 14 is a plan view illustrating a second jaw of the surgical instrument of FIG. 2. FIGS. 15 and 16 are exploded perspective views illustrating a staple pulley and a staple link of the surgical instrument of FIG. 2. FIGS. 17 and 18 are side views illustrating operating states of a staple pulley in the end tool of the surgical instrument of FIG. 2. FIGS. 19 and 20 are perspective views illustrating operating states of the staple pulley in the end tool of the surgical instrument of FIG. 2. FIGS. 21, 22, 23, and 24 are plan views illustrating opening and closing motions of the first jaw and the second jaw of the surgical instrument of FIG. 2. FIGS. 25 and 26 are perspective views illustrating opening and closing motions of the end tool of the surgical instrument of FIG. 2.

First, referring to FIGS. 2 and 3, a surgical instrument 4000 according to a first embodiment of the present disclosure includes an end tool 4100, a manipulation part 200, a power transmission part 300, and a connection part 400.

Here, the connection part 400 is formed in the shape of a hollow shaft, and one or more wires and electric wires may be accommodated therein. The manipulation part 200 is coupled to one end portion of the connection part 400, the end tool 4100 is coupled to the other end portion thereof, and the connection part 400 may serve to connect the manipulation part 200 and the end tool 4100. Here, the connection part 400 of the surgical instrument 4000 according to the first embodiment of the present disclosure includes a straight part 401 and a bent part 402, wherein the straight part 401 is formed at a side coupled to the end tool 4100, and the bent part 402 is formed at a side to which the manipulation part 200 is coupled. As such, since the end portion of the connection part 400 at the side of the manipulation part 200 is formed to be bent, a pitch manipulation part 201, a yaw manipulation part 202, and an actuation manipulation part 203 may be formed along an extension line of the end tool 4100 or adjacent to the extension line. From another perspective, it may be said that the pitch manipulation part 201 and the yaw manipulation part 202 are at least partially accommodated in a concave portion formed by the bent part 402. Due to the above-described shape of the bent part 402, the shapes and motions of the manipulation part 200 and the end tool 4100 may be further intuitively matched with each other.

Meanwhile, a plane on which the bent part 402 is formed may be substantially the same plane as a pitch plane, that is, an XZ plane of FIG. 2. As such, as the bent part 402 is formed on substantially the same plane as the XZ plane, interference with the manipulation part may be reduced. Of course, for intuitive motions of the end tool and the manipulation part, any form other than the XZ plane may be possible.

Meanwhile, a connector 410 may be formed on the bent part 402. The connector 410 may be connected to an external power source (not shown), and the connector 410 may also be connected to the end tool 4100 via an electric wire, and may transmit, to the end tool 4100, electric energy supplied from the external power source (not shown). In addition, the electric energy transmitted to the end tool 4100 as described above may produce a driving force for rotating a staple pulley (see 4160 of FIG. 10) to be described later in the clockwise or counterclockwise direction.

The manipulation part 200 is formed at the one end portion of the connection part 400 and provided as an interface to be directly controlled by a medical doctor, for example, a tongs shape, a stick shape, a lever shape, or the like, and when the medical doctor controls the manipulation part 200, the end tool 4100, which is connected to the interface and inserted into the body of a surgical patient, performs a certain motion, thereby performing surgery. Here, the manipulation part 200 is illustrated in FIG. 2 as being formed in a handle shape that is rotatable while the finger is inserted therein, the concept of the present disclosure is not limited thereto, and various types of manipulation parts that are connected to the end tool 4100 and manipulate the end tool 4100 may be possible.

The end tool 4100 is formed on the other end portion of the connection part 400, and performs necessary motions for surgery by being inserted into a surgical site. In an example of the end tool 4100, as illustrated in FIG. 2, a pair of jaws 103 for performing a grip motion may be used. However, the concept of the present disclosure is not limited thereto, and various devices for performing surgery may be used as the end tool 4100. For example, a configuration of a cantilever cautery may also be used as the end tool. The end tool 4100 is connected to the manipulation part 200 by the power transmission part 300, and receives a driving force of the manipulation part 200 through the power transmission part 300 to perform a motion necessary for surgery, such as gripping, cutting, suturing, or the like.

Here, the end tool 4100 of the surgical instrument 4000 according to the first embodiment of the present disclosure is formed to be rotatable in at least one direction, for example, the end tool 4100 may perform a pitch motion around a Y-axis of FIG. 2 and simultaneously perform a yaw motion and an actuation motion around a Z-axis of FIG. 2.

Here, each of the pitch, yaw, and actuation motions used in the present disclosure are defined as follows.

First, the pitch motion means a motion of the end tool 4100 rotating in a vertical direction with respect to an extension direction of the connection part 400 (an X-axis direction of FIG. 2), that is, a motion rotating around the Y-axis of FIG. 2. In other words, the pitch motion means a motion of the end tool 4100, which is formed to extend from the connection part 400 in the extension direction of the connection part 400 (the X-axis direction of FIG. 2), rotating vertically around the Y-axis with respect to the connection part 400.

Next, the yaw motion means a motion of the end tool 4100 rotating in the left and right directions, that is, a motion rotating around the Z-axis of FIG. 2, with respect to the extension direction of the connection part 400 (the X-axis direction of FIG. 2). In other words, the yaw motion means a motion of the end tool 4100, which extends from the connection part 400 in the extension direction of the connection part 400 (the X-axis direction of FIG. 2), rotating horizontally around the Z-axis with respect to the connection part 400. That is, the yaw motion means a motion of the two jaws 103, which are formed on the end tool 4100, rotating around the Z-axis in the same direction.

Meanwhile, the actuation motion may mean a motion of the end tool 4100 rotating around the same shaft of rotation as that of the yaw motion, while the two jaws 103 rotating in the opposite directions so as to be closed or opened. That is, the actuation motion means rotating motions of the two jaws 103, which are formed on the end tool 4100, in the opposite directions around the Z-axis.

The power transmission part 300 may connect the manipulation part 200 to the end tool 4100, transmit the driving force of the manipulation part 200 to the end tool 4100, and include a plurality of wires, pulleys, links, sections, gears, or the like.

The end tool 4100, the manipulation part 200, and the power transmission part 300 of the surgical instrument 4000 of FIG. 2 will be described in detail later.

(Intuitive Driving)

Hereinafter, intuitive driving of the surgical instrument 4000 of the present disclosure will be described.

First, while holding a first handle 204 with the palm of the hand, the user may rotate a first handle 204 around the Y-axis (i.e., a rotation shaft 246 of FIG. 47) to perform a pitch motion, and rotate the first handle 204 around the Z-axis (i.e., a rotation shaft 243 of FIG. 47) to perform a yaw motion. In addition, the user may perform an actuation motion by manipulating the actuation manipulation part 203 while inserting the thumb and the index finger into a first actuation extension part 252 and/or a second actuation extension part 257 in the form of a hand ring formed at one end portion of the actuation manipulation part 203.

Here, in the surgical instrument 4000 according to the first embodiment of the present disclosure, when the manipulation part 200 is rotated in one direction with respect to the connection part 400, the end tool 4100 is rotated in a direction that is intuitively the same as a manipulation direction of the manipulation part 200. In other words, when the first handle 204 of the manipulation part 200 is rotated in one direction, the end tool 4100 is also rotated in a direction intuitively the same as the one direction, so that a pitch motion or a yaw motion is performed. Here, the phrase "intuitively the same direction" may be further explained as meaning that a direction of movement of the user's finger gripping the manipulation part 200 and a direction of movement of a distal end of the end tool 4100 form substantially the same direction. Of course, "the same direction" as used herein may not be a perfectly matching direction on a three-dimensional coordinate, and may be understood to be equivalent to the extent that, for example, when the user's finger moves to the left, the distal end of the end tool 4100 is moved to the left, and when the user's finger moves down, the end portion of the end tool 4100 is moved down.

In addition, to this end, in the surgical instrument 4000 according to the first embodiment of the present disclosure, the manipulation part 200 and the end tool 4100 are formed in the same direction with respect to a plane perpendicular to the extension axis (X-axis) of the connection part 400. That is, when viewed based on a YZ plane of FIG. 2, the manipulation part 200 is formed to extend in a positive (+) X-axis direction, and the end tool 4100 is also formed to extend in the positive (+) X-axis direction. In other words, it may be said that a formation direction of the end tool 4100 on one end portion of the connection part 400 is the same as a formation direction of the manipulation part 200 on the other end portion of the connection part 400 on the basis of the YZ plane. Further, in other words, it may be said that the manipulation part 200 may be formed in a direction away from the body of a user holding the manipulation part 200, that is, in a direction in which the end tool 4100 is formed. That is, in the parts such as the first handle 204, a first actuation manipulation part 251, a second actuation manipulation part 256, and the like, which are moved by the user's grip for actuation motion, yaw motion, and pitch motions, a corresponding portion that is moved for the motion is formed to extend in the positive (+) X-axis direction from the rotation center of a corresponding joint for the motion. In this manner, the manipulation part 200 may be configured in the same manner as the end tool 4100 in which each moving portion is formed to extend in the positive (+) X-axis direction from the rotation center of a corresponding joint for the motion, and as described with reference to FIG. 1, the manipulation direction of the user may be identical to the operation direction of the end tool from the viewpoint of the rotation directions and the left and right directions. As a result, intuitively the same manipulation may be achieved.

In detail, in the case of the conventional surgical instrument, a direction in which a user manipulates the manipulation part is different from a direction in which the end tool is actually operated, that is, intuitively different from the direction in which the end tool is actually operated, and thus, a surgical operator may not easily intuitively manipulate the surgical instrument and may spend a long time to learn a skill of operating the end tool in desired directions, and in some cases, malfunctions may occur, which may cause damage to patients.

In order to address such problems, the surgical instrument 4000 according to the first embodiment of the present disclosure is configured such that the manipulation direction of the manipulation part 200 and the operation direction of the end tool 4100 are intuitively identical to each other. To this end, the manipulation part 200 is configured like the end tool 4100, that is, in the manipulation part 200, portions that are actually moved for actuation, yaw, and pitch motions extend respectively from rotation centers of corresponding joints in the positive (+) X-axis direction.

Hereinafter, the end tool 4100, the manipulation part 200, the power transmission part 300, and the like of the surgical instrument 4000 of FIG. 2 will be described in more detail.

(Power Transmission Part)

Hereinafter, the power transmission part 300 of the surgical instrument 4000 of FIG. 2 will be described in more detail.

Referring to FIGS. 2 to 20, 47, and the like, the power transmission part 300 of the surgical instrument 4000 according to an embodiment of the present disclosure may include a wire 301, a wire 302, a wire 303, a wire 304, a wire 305, a wire 306, a wire 307, a wire 308, a wire 309, and a wire 310.

Here, the wire 301 and the wire 305 may form a pair to serve as a first jaw wire. The wire 302 and the wire 306 may form a pair to serve as a second jaw wire. Here, a component encompassing the wire 301 and the wire 305, which are the first jaw wire, and the wire 302 and the wire 306, which are the second jaw wire, may be referred to as a jaw wire. The wire 303 and the wire 304 may form a pair to serve as a pitch wire. In addition, the wire 307 and the wire 308 may form a pair to serve as a first staple wire. In addition, the wire 309 and the wire 310 may form a pair to serve as a second staple wire. Here, a component encompassing the wire 307 and the wire 308, which are the first staple wire, and the wire 309 and the wire 310, which are the second staple wire, may be referred to as a staple wire.

In addition, the power transmission part 300 of the surgical instrument 4000 according to an embodiment of the present disclosure may include a fastening member 321 a fastening member 323, a fastening member 324, a fastening member 326, a fastening member 327, a fastening member 329, and a fastening member 330 that are coupled to respective ends of the wires to respectively combine the wires with the pulleys. Here, each of the fastening members may have various shapes as necessary, such as a ball shape, a tube shape, and the like.

Here, on the side of the end tool 4100, the fastening member 321 may serve as a pitch wire-end tool fastening member, the fastening member 323 may serve as a first jaw wire-end tool fastening member, the fastening member 326 may serve as a second jaw wire-end tool fastening member, and the fastening member 329 may serve as a staple wire-end tool fastening member.

In addition, on the side of the manipulation portion 200, the fastening member 324 may serve as a first jaw wire-manipulation portion fastening member, and the fastening member 327 may serve as a second jaw wire-manipulation portion fastening member. In addition, although not illustrated in the drawings, a pitch wire-manipulation portion fastening member and a staple wire-manipulation portion fastening member may be further formed on the side of the manipulation portion 200.

The coupling relationship between the wires, the fastening members, and each pulley will be described as follows.

First, the wire 301 and the wire 305, which are the first jaw wire, may be a single wire. The fastening member 323, which is the first jaw wire-end tool fastening member, may be fit into a middle point of the first jaw wire and when the fastening member 323 is fixed through crimping, two strands of the first jaw wire on either side of the fastening member 323 may be referred to as the wire 301 and the wire 305, respectively.

Alternatively, the wire 301 and the wire 305, which are the first jaw wire, may be formed as separate wires, and the wire 301 and the wire 305 may be connected to each other by the fastening member 323.

In addition, as the fastening member 323 is coupled to a pulley 4111, the wire 301 and the wire 305 may be fixedly coupled to the pulley 4111. This allows the pulley 4111 to rotate as the wire 301 and the wire 305 are pulled and unwound.

In the wire 301 and the wire 305, the first jaw wire-manipulation portion fastening member (see 324 of FIG. 47) may be coupled to an end opposite to the end to which the fastening member 323 is coupled.

In addition, as the first jaw wire-manipulation portion fastening member (see 324 of FIG. 47) is coupled to a pulley 210, the wire 301 and the wire 305 may be fixedly coupled to the pulley 210. As a result, when the pulley 210 is rotated by a motor or human force, the pulley 4111 of the end tool 4100 may rotate as the wire 301 and the wire 305 are pulled and unwound.

In the same manner, the wire 302 and the wire 306, which are the second jaw wire, are coupled to the fastening member (see 326 of FIG. 47), which is the second jaw wire-end tool, and the second jaw wire-manipulation portion fastening member (see 327 of FIG. 47), respectively. In addition, the fastening member (see 326 of FIG. 47) is coupled to a pulley 4121, and the second jaw wire-manipulation portion fastening member (see 327 of FIG. 47) is coupled to a pulley 220. As a result, when the pulley 220 is rotated by a motor or human force, the pulley 4121 of the end tool 4100 may rotate as the wire 302 and the wire 306 are pulled and unwound.

In the same manner, the wire 303 and the wire 304, which are the pitch wire, are coupled to the fastening member 321, which is the pitch wire-end tool fastening member, and the pitch wire-manipulation portion fastening member (not shown), respectively. In addition, the fastening member 321 is coupled to a pulley 4131, and the pitch wire-manipulation portion fastening member (not shown) is coupled to a pulley 231. As a result, when the pulley 231 is rotated by a motor or a human force, the pulley 4131 of the end tool 4100 may be rotated as the wire 303 and the wire 304 are pulled and unwound.

In the same manner, the wire 307 and the wire 308, which are first staple wires, are coupled to the fastening member (see 329 of FIG. 66), which is the staple wire-end tool fastening member, and the staple wire-manipulation portion fastening member (not shown), respectively. In addition, the fastening member (see 329 of FIG. 66) is coupled to a first staple pulley 4181, and the staple wire-manipulation portion fastening member (not shown) is coupled to a pulley (see 269 of FIG. 51). As a result, when the pulley 269 is rotated by a motor or a human force, the first staple pulley 4181 of the end tool 4100 may be rotated as the wire 307 and the wire 308 are pulled and unwound.

In the same manner, the wire 309 and the wire 310, which are second staple wires, are coupled to the fastening member (see 330 of FIG. 67), which is the staple wire-end tool fastening member, and the staple wire-manipulation portion fastening member (not shown), respectively. In addition, the fastening member (see 330 of FIG. 67) is coupled to a second staple pulley 4191, and the staple wire-manipulation portion fastening member (not shown) is coupled to a pulley (see 270 of FIG. 51). As a result, when the pulley 270 is rotated by a motor or a human force, the second staple pulley 4191 of the end tool 4100 may be rotated as the wire 309 and the wire 310 are pulled and unwound.

(End Tool)

Hereinafter, the end tool 4100 of the surgical instrument 4000 of FIG. 2 will be described in more detail.

FIGS. 4 and 5 are perspective views illustrating the end tool of the surgical instrument of FIG. 2, FIG. 6 is a perspective view illustrating an end tool hub of the end tool of the surgical instrument of FIG. 2, and FIGS. 7 and 8 are plan views illustrating the end tool of the surgical instrument of FIG. 2.

Here, FIG. 4 illustrates a state in which an end tool hub 4106 and a pitch hub 4107 are coupled to each other, and FIG. 5 illustrates a state in which the end tool hub 4106 is removed. Meanwhile, FIG. 7 is a diagram mainly illustrating the wires, and FIG. 8 is a diagram mainly illustrating the pulleys.

Referring to FIGS. 4 to 8 and the like, the end tool 4100 of the first embodiment of the present disclosure includes a pair of jaws for performing a grip motion, that is, a first jaw 4101 and a second jaw 4102. Here, a component encompassing each of the first jaw 4101 and the second jaw 4102 or both the first jaw 4101 and the second jaw 4102 may be referred to as a jaw 4103.

In addition, the end tool 4100 may include the pulley 4111, a pulley 4112, a pulley 4113, a pulley 4114, a pulley 4115, and a pulley 4116, which are associated with the rotational motion of the first jaw 4101. In addition, the end tool 4100 may include the pulley 4121, a pulley 4122, a pulley 4123, a pulley 4124, a pulley 4125, and a pulley 4126, which are associated with the rotational motion of the second jaw 4102.

Here, although the drawings illustrate that the pulleys facing each other are arranged in parallel with each other, the technical concepts of the present disclosure are not limited thereto, and the pulleys may be formed in various positions and sizes suitable for the configuration of the end tool.

In addition, the end tool 4100 of the first embodiment of the present disclosure may include the end tool hub 4106 and the pitch hub 4107.

A rotation shaft 4141 and a rotation shaft 4142 to be described below may be inserted through the end tool hub 4106, and the end tool hub 4106 may accommodate therein at least portions of the pulley 4111 and the pulley 4121, which are axially coupled to the rotation shaft 4141. In addition, the end tool hub 4106 may accommodate therein at least portions of the pulley 4112 and the pulley 4122, which are axially coupled to the rotation shaft 4142.

In detail, referring to FIG. 6, the end tool hub 4106 includes a first jaw pulley coupling portion 4106a, a second jaw pulley coupling portion 4106b, a guide portion 4106c, a pitch pulley coupling portion 4106e, and a separation prevention pulley coupling portion 4106f.

In detail, the first jaw pulley coupling portion 4106a and the second jaw pulley coupling portion 4106b are formed to face each other, and the pulley 4111, the pulley 4121, the first staple pulley 4181, and the second staple pulley 4191 are accommodated inside the first jaw pulley coupling portion 4106a and the second jaw pulley coupling portion 4106b. In addition, a through hole is formed in each of the first jaw pulley coupling portion 4106a and the second jaw pulley coupling portion 4106b such that the rotation shaft 4141 passes through and axially couples the first jaw pulley coupling portion 4106a, the pulley 4111, the first staple pulley 4181, the second staple pulley 4191, the pulley 4121, and the second jaw pulley coupling portion 4106b.

The first jaw pulley coupling portion 4106a and the second jaw pulley coupling portion 4106b are connected to each other by the guide portion 4106c. That is, the first jaw pulley coupling portion 4106a and the second jaw pulley coupling portion 4106b, which are parallel to each other, are coupled to each other by the guide portion 4106c formed in a direction approximately perpendicular to the first jaw pulley coupling portion 4106a and the second jaw pulley coupling portion 4106b, such that the first jaw pulley coupling portion 4106*a*, the second jaw pulley coupling portion 4106*b*, and the guide portion 4106*c* form an approximately C-shape, and the pulley 4111, the pulley 4121, the first staple pulley 4181, and the second staple pulley 4191 are accommodated therein.

Here, the pulley 4111, which is a first jaw pulley, is arranged adjacent to the first jaw pulley coupling portion 4106*a* of the end tool hub 4106, and the pulley 4121, which is a second jaw pulley, is arranged adjacent to the second jaw pulley coupling portion 4106*b* of the end tool hub 4106, such that a staple assembly accommodation portion may be formed between the first jaw pulley coupling portion 4106*a* and the second jaw pulley coupling portion 4106*b*. In addition, at least portions of a staple pulley assembly (see 4160 of FIG. 13) and a staple link assembly (see 4170 of FIG. 13) to be described below may be formed in the staple assembly accommodation portion. In other words, it may be said that at least portions of the first staple pulley 4181, the second staple pulley 4191, and a link member 4171 are arranged between the first jaw pulley coupling portion 4106*a* and the second jaw pulley coupling portion 4106*b*. As such, according to the present disclosure, by arranging at least portions of the staple pulley assembly (see 4160 of FIG. 13) and the staple link assembly (see 4170 of FIG. 13) between the pulley 4111, which is a first jaw pulley, and the pulley 4121, which is a second jaw pulley, the end tool 4100 is allowed to perform pitch and yaw motions, as well as stapling and cutting motions using the first staple pulley 4181 and the second staple pulley 4191. This will be described below in more detail.

Meanwhile, the pulley 4131 serving as an end tool pitch pulley may be formed at one end of the end tool hub 4106. As illustrated in FIG. 6, the pulley 4131 may be integrally formed with the end tool hub 4106 as one body. That is, a disk-shaped pulley may be formed at one end of the end tool hub 4106, and a groove around which a wire may be wound may be formed on an outer circumferential surface of the end tool hub 4106. Alternatively, the pulley 4131 may be formed as a separate member from the end tool hub 4106 and coupled to the end tool hub 4106. The wire 303 and the wire 304 described above are coupled to the pulley 4131 serving as an end tool pitch pulley, and a pitch motion is performed as the pulley 4131 rotates around a rotation shaft 4143.

Meanwhile, the separation prevention pulley coupling portion 4106*f* may be further formed on one side of the pulley 4131. The separation prevention pulley coupling portion 4106*f* may be formed parallel to the rotation shaft 4143, which is an end tool pitch rotation shaft, such that a pulley 4187, a pulley 4188, a pulley 4197, and a pulley 4198 to be described below are coupled thereto. Here, the pulley 4187 and the pulley 4188 may function as first staple wire separation prevention pulleys, and the pulley 4197 and pulley 4198 may function as second staple wire separation prevention pulleys. This will be described below in more detail.

The rotation shaft 4143 and a rotation shaft 4144 to be described below may be inserted through the pitch hub 4107, and the pitch hub 4107 and the end tool hub 4106 may be axially coupled to the pitch hub 4107 by the rotation shaft 4143. Thus, the end tool hub 4106 and the pulley 4131 may be formed to be rotatable around the rotation shaft 4143 with respect to the pitch hub 4107.

In addition, the pitch hub 4107 may accommodate therein at least portions of the pulley 4113, the pulley 4114, the pulley 4123, and the pulley 4124 that are axially coupled to the rotation shaft 4143. In addition, the pitch hub 4107 may accommodate therein at least portions of the pulley 4115, the pulley 4116, the pulley 4125, and the pulley 4126 that are axially coupled to the rotation shaft 4144.

Meanwhile, the end tool 4100 of the first embodiment of the present disclosure may include the rotation shaft 4141, the rotation shaft 4142, the rotation shaft 4143, and the rotation shaft 4144. As described above, the rotation shaft 4141 and the rotation shaft 4142 may be inserted through the end tool hub 4106, and the rotation shaft 4143 and the rotation shaft 4144 may be inserted through the pitch hub 4107.

The rotation shaft 4141, the rotation shaft 4142, the rotation shaft 4143, and the rotation shaft 4144 may be arranged sequentially from a distal end 4104 of the end tool 4100 toward a proximal end 4105. Accordingly, in the direction from the distal end 4104, the rotation shaft 4141 may be referred to as a first pin, the rotation shaft 4142 may be referred to as a second pin, the rotation shaft 4143 may be referred to as a third pin, and the rotation shaft 4144 may be referred to as a fourth pin.

Here, the rotation shaft 4141 may function as an end tool jaw pulley rotation shaft, the rotation shaft 4142 may function as an end tool jaw auxiliary pulley rotation shaft, the rotation shaft 4143 may function as an end tool pitch rotation shaft, and the rotation shaft 4144 may function as an end tool pitch auxiliary rotation shaft of the end tool 4100.

One or more pulleys may be fit into each of the rotation shafts 4141, 4142, 4143, and 4144, which will be described below in detail.

Meanwhile, a rotation shaft 4145 may be further formed on one side of the rotation shaft 4141, specifically, on the side of the distal end 4104 of the rotation shaft 4141. The rotation shaft 4145 may be inserted through the first jaw 4101 and the second jaw 4102 to function as a jaw rotation shaft. This will be described in detail below.

The pulley 4111 functions as an end tool first jaw pulley, and the pulley 4121 functions as an end tool second jaw pulley. The pulley 4111 may be referred to as a first jaw pulley, the pulley 4121 may be referred to as a second jaw pulley, and the two components may be collectively referred to as an end tool jaw pulley or simply as a jaw pulley.

The pulley 4111 and the pulley 4121, which are end tool jaw pulleys, are formed to face each other, and are formed to be rotatable independently of each other around the rotation shaft 4141, which is an end tool jaw pulley rotation shaft. In this case, the pulley 4111 and the pulley 4121 are formed to be spaced apart from each other by a certain extent, and a staple assembly accommodation portion may be formed therebetween. In addition, at least portions of the staple pulley assembly 4160 and the staple link assembly 4170 to be described below may be arranged in the staple assembly accommodation portion.

Here, although the drawings illustrate that the pulley 4111 and the pulley 4121 are formed to rotate around one rotation shaft 4141, it is also possible that each end tool jaw pulley may be formed to be rotatable around a separate shaft. Here, the first jaw 4101 may be fixedly coupled to the pulley 4111 to rotate together with the pulley 4111, and the second jaw 4102 may be fixedly coupled to the pulley 4121 to rotate together with the pulley 4121. Yaw and actuation motions of the end tool 4100 are performed according to the rotation of the pulley 4111 and the pulley 4121. That is, when the pulley 4111 and the pulley 4121 rotate in the same direction around the rotation shaft 4141, the yaw motion is performed, and when the pulley 4111 and the pulley 4121 rotate in opposite directions around the rotation shaft 4141, the actuation motion is performed.

Here, the first jaw 4101 and the pulley 4111 may be formed as separate members and coupled to each other, or the first jaw 4101 and the pulley 4111 may be integrally formed as one body. Similarly, the second jaw 4102 and the pulley 4121 may be formed as separate members and coupled to each other, or the second jaw 4102 and the pulley 4121 may be integrally formed as one body.

The pulley 4112 functions as an end tool first jaw auxiliary pulley, the pulley 4122 functions as an end tool second jaw auxiliary pulley, and the two components may be collectively referred to as an end tool jaw auxiliary pulley or simply as an auxiliary pulley.

In detail, the pulley 4112 and the pulley 4122, which are the end tool jaw auxiliary pulley, may be additionally provided on one side of the pulley 4111 and the pulley 4121. In other words, the pulley 4112, which is an auxiliary pulley, may be arranged between the pulley 4111 and the pulley 4113/the pulley 4114. In addition, the pulley 4122, which is an auxiliary pulley, may be arranged between the pulley 4121 and the pulley 4123/the pulley 4124. The pulley 4112 and the pulley 4122 may be formed to be rotatable independently of each other around the rotation shaft 4142. Here, although the drawings illustrate that the pulley 4112 and the pulley 4122 are formed to rotate around one rotation shaft 4142, it is also possible that each of the pulley 4112 and the pulley 4122 may be formed to be rotatable around a separate shaft. Such an auxiliary pulley will be described below in more detail.

The pulley 4113 and the pulley 4114 function as end tool first jaw pitch main pulleys, the pulley 4123 and the pulley 4124 function as end tool second jaw pitch main pulleys, and the two components may collectively be referred to as an end tool jaw pitch main pulley.

The pulley 4115 and the pulley 4116 function as end tool first jaw pitch subsidiary pulleys, the pulley 4125 and the pulley 4126 function as end tool second jaw pitch subsidiary pulleys, and the two components may collectively be referred to as an end tool jaw pitch subsidiary pulley.

Hereinafter, components associated with the rotation of the pulley 4111 will be described.

The pulley 4113 and the pulley 4114 function as end tool first jaw pitch main pulleys. That is, the pulley 4113 and the pulley 4114 function as main rotation pulleys of the pitch motion of the first jaw 4101. Here, the wire 301, which is the first jaw wire, is wound around the pulley 4113, and the wire 305, which is the first jaw wire, is wound around the pulley 4114.

The pulley 4115 and the pulley 4116 function as end tool first jaw pitch subsidiary pulleys. That is, the pulley 4115 and the pulley 4116 function as subsidiary rotation pulleys of the pitch motion of the first jaw 4101. Here, the wire 301, which is the first jaw wire, is wound around the pulley 4115, and the wire 305, which is the first jaw wire, is wound around the pulley 4116.

Here, the pulley 4113 and the pulley 4114 are arranged on one side of the pulley 4111 and the pulley 4112 to face each other. Here, the pulley 4113 and the pulley 4114 are formed to be rotatable independently of each other around the rotation shaft 4143, which is an end tool pitch rotating shaft. In addition, the pulley 4115 and the pulley 4116 are arranged on one side of each of the pulley 4113 and the pulley 4114 to face each other. Here, the pulley 4115 and the pulley 4116 are formed to be rotatable independently of each other around the rotation shaft 4144, which is an end tool pitch auxiliary rotating shaft. Here, although the drawings illustrate that the pulley 4113, the pulley 4115, the pulley 4114, and the pulley 4116 are formed to be rotatable around a Y-axis direction, the technical concepts of the present disclosure are not limited thereto, and the rotation shafts of each pulley may be formed in various directions suitable for their respective configurations.

The wire 301, which is the first jaw wire, is wound sequentially such that at least a portion thereof is in contact with the pulley 4115, the pulley 4113, and the pulley 4111. In addition, the wire 305 connected to the wire 301 by the fastening member 323 is sequentially wound such that at least a portion thereof is in contact with the pulley 4111, the pulley 4112, the pulley 4114, and the pulley 4116.

In other words, the wire 301 and wire 305, which are the first jaw wire, are be sequentially wound such that at least portions thereof are in contact with the pulley 4115, the pulley 4113, the pulley 4111, the pulley 4112, the pulley 4114, and the pulley 4116, and the wire 301 and the wire 305 are formed to move along the pulleys while rotating the pulleys.

Accordingly, when the wire 301 is pulled toward an arrow 301 of FIG. 7, the fastening member 323 coupled to the wire 301 and the pulley 4111 coupled to the fastening member 323 rotate in the direction of an arrow L of FIG. 7. On the contrary, when the wire 305 is pulled toward the arrow 305 of FIG. 7, the fastening member 323 coupled to the wire 305 and the pulley 4111 coupled to the fastening member 323 rotate in the direction of the arrow R of FIG. 7.

Next, components associated with the rotation of the pulley 4121 will be described.

The pulley 4123 and the pulley 4124 function as end tool second jaw pitch main pulleys. That is, the pulley 4123 and the pulley 4124 function as main rotation pulleys of the pitch motion of the second jaw 4102. Here, the wire 306, which is the second jaw wire, is wound around the pulley 4123, and the wire 302, which is the second jaw wire, is wound around the pulley 4124.

The pulley 4125 and the pulley 4126 function as end tool second jaw pitch subsidiary pulleys. That is, the pulley 4125 and the pulley 4126 function as subsidiary rotation pulleys of the pitch motion of the second jaw 4102. Here, the wire 306, which is the second jaw wire, is wound around the pulley 4125, and the wire 302, which is the second jaw wire, is wound around the pulley 4126.

The pulley 4123 and the pulley 4124 are arranged on one side of the pulley 4121 to face each other. Here, the pulley 4123 and the pulley 4124 are formed to be rotatable independently of each other around the rotation shaft 4143, which is an end tool pitch rotating shaft. In addition, the pulley 4125 and the pulley 4126 may be arranged on one side of each of the pulley 4123 and the pulley 4124 to face each other. Here, the pulley 4125 and the J15 pulley 4123J25 are formed to be rotatable independently of each other around the rotation shaft 4144, which is an end tool pitch auxiliary rotating shaft. Here, although the drawings illustrate that the pulley 4123, the pulley 4125, the pulley 4124, and the pulley 4126 are formed to be rotatable around the Y-axis direction, the technical concepts of the present disclosure are not limited thereto, and the rotation shafts of each pulley may be formed in various directions suitable for their respective configurations.

The wire 306, which is the second jaw wire, is wound sequentially such that at least a portion thereof is in contact with the pulley 4125, the pulley 4123, and the pulley 4121. In addition, the wire 302 connected to the wire 306 by the fastening member 326 is sequentially wound such that at least a portion thereof is in contact with the pulley 4121, the pulley 4122, the pulley 4124, and the pulley 4126.

In other words, the wire 306 and wire 302, which are the second jaw wire, are sequentially wound such that at least portions thereof are in contact with the pulley 4125, the pulley 4123, the pulley 4121, the pulley 4122, the pulley 4124, and the pulley 4126, and the wire 306 and the wire 302 are formed to move along the pulleys while rotating the pulleys.

Accordingly, when the wire 306 is pulled in the direction of an arrow 306 of FIG. 7, the fastening member 322 to which the wire 306 is coupled, and the pulley 4121 coupled to the fastening member 322 rotate in the direction of the arrow R of FIG. 7. On the contrary, when the wire 302 is pulled in the direction of the arrow 302 of FIG. 7, the fastening member 326 to which the wire 302 is coupled, and the pulley 4121 coupled to the fastening member 326 rotate in the direction of the arrow L of FIG. 7.

Hereinafter, the pulley 4112 and the pulley 4122 serving as auxiliary pulleys will be described in more detail.

As the pulley 4112 and the pulley 4122 are in contact with the wire 305, which is the first jaw wire, and the wire 302, which is the second jaw wire, to change an arrangement path of the wire 305 and the wire 302 to a certain extent, the pulley 4112 and the pulley 4122 may serve to enlarge a rotation angle of each of the first jaw 4101 and the second jaw 4102.

That is, when no auxiliary pulley is arranged, each of first jaw and the second jaw may rotate up to the right angle, however, in an embodiment of the present disclosure, by additionally arranging the pulley 4112 and the pulley 4122, which are auxiliary pulleys, the maximum rotation angle may be increased by θ as illustrated in FIG. 8. This enables the opening motion of the two jaws of the end tool 4100 for the actuation motion when the two jaws are yaw-rotated by 90° in the L direction. This is because the second jaw 4102 may rotate by the additional angle θ as illustrated in FIG. 8. Similarly, the actuation motion may be performed even when the two jaws are yaw-rotated in the L direction. In other words, through the pulley 4112 and the pulley 4122, a range of yaw rotation allowing the actuation motion may be expanded.

This will be described in more detail as follows.

When no auxiliary pulley is arranged, as the first jaw wire is fixedly coupled to the end tool first jaw pulley, and the second jaw wire is fixedly coupled to the end tool second jaw pulley, each of the end tool first jaw pulley and the end tool second jaw pulley may rotate only up to 90°. In this case, when the actuation motion is performed in a state where the first jaw and the second jaw are placed on the 90° line, the first jaw may be opened, but the second jaw may not be able to rotate over 90°. Accordingly, in a state where the first jaw and the second jaw perform the yaw motion over a certain angle, the actuation motion may not be performed smoothly.

In order to address such a problem, in the surgical instrument 4000 of the present disclosure, the pulley 4112 and the pulley 4122, which are auxiliary pulleys, are additionally arranged at one sides of the pulley 4111 and the pulley 4121, respectively. By arranging the pulley 4112 and the pulley 4122, the arrangement path of the wire 305, which is the first jaw wire, and the wire 302, which is the second jaw wire, is changed to a certain extent, and a tangential direction of the wire 305 and the wire 302 are changed, which allows rotation of the fastening member 323 coupling the wire 302 to the pulley 4111 up to the N line of FIG. 8. That is, the fastening member 323, which is a coupling portion between the wire 301 and the pulley 4111, is rotatable until it is positioned on a common internal tangent of the pulley 4111 and the pulley 4112. Similarly, the fastening member 326, which is a coupling portion of the wire 302 and the pulley 4121, is rotatable until it is positioned on a common internal tangent of the pulley 4121 and the pulley 4122, which allows expansion of the rotation range in the R direction.

In other words, by the pulley 4112, the wire 301 and the wire 305, which are two strands of the first jaw wire wound around the pulley 4111, are arranged on one side with respect to a plane perpendicular to the Y-axis and passing through the X-axis. At the same time, by the pulley 4122, the wire 302 and the wire 306, which are two strands of the second jaw wire wound around the pulley 4121, are arranged on another side with respect to the plane perpendicular to the Y-axis and passing through the X-axis.

In other words, the pulley 4113 and the pulley 4114 are arranged on one side with respect to the plane perpendicular to the Y-axis and passing through the X-axis, and the pulley 4123 and the pulley 4124 are arranged on another side with respect to the plane perpendicular to the Y-axis and passing through the X-axis.

In other words, the wire 305 is arranged on an internal tangent of the pulley 4111 and the pulley 4112, and the rotation angle of the pulley 4111 may be expanded by the pulley 4112. In addition, the wire 302 is arranged on an internal tangent of the pulley 4121 and the pulley 4122, and the rotation angle of the pulley 4121 is expanded by the pulley 4122.

According to the present disclosure, as the rotational radius of the jaw 4101 and the jaw 4102 is widened, the range of yaw motion allowing a normal open-and-shut actuation motion may be expanded.

Figure 47:
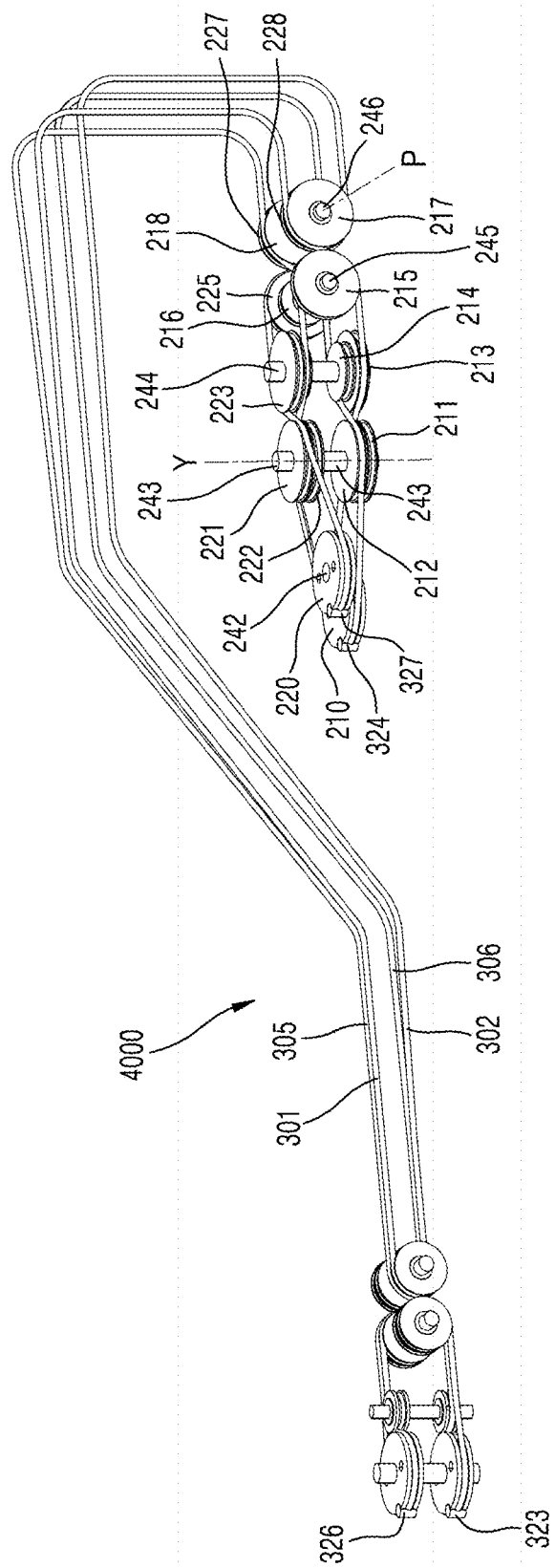
FIG. 47 is a view schematically illustrating only a configuration of pulleys and wires constituting joints of the surgical instrument illustrated in FIG. 2.

Hereinafter, the pitch motion of the present disclosure will be described in more detail. Meanwhile, when the wire 301 is pulled in the direction of the arrow 301 of FIG. 7, and simultaneously the wire 305 is pulled in the direction of the arrow 305 of FIG. 7 (i.e., both strands of the first jaw wire are pulled), as the wire 301 and the wire 305 are wound downward around the pulley 4113 and the pulley 4114, which are rotatable around the rotation shaft 4143 which is the end tool pitch rotation shaft, as illustrated in FIG. 47, the pulley 4111 fixedly coupled to the wire 301 and the wire 305 and the end tool hub 4106 coupled to the pulley 4111 rotate in the counterclockwise direction around the rotation shaft 4143, and as a result, the end tool 4100 rotates downward to perform the pitch motion. In this case, as the second jaw 4102 and the wire 302 and the wire 306 fixedly coupled to the second jaw 4102 are wound upward around the pulley 4123 and the pulley 4124, which are rotatable around the rotation shaft 4143, the wire 302 and the wire 306 are unwound in directions opposite to the directions 302 and 306, respectively.

On the contrary, when the wire 302 is pulled in the direction of the arrow 302 of FIG. 7, and simultaneously the wire 306 is pulled in the direction of the arrow 306 of FIG. 7, as the wire 302 and the wire 306 are wound upward around the pulley 4123 and the pulley 4124, which are rotatable around the rotation shaft 4143, which is the end tool pitch rotation shaft, as illustrated in FIG. 47, the pulley 4121 fixedly coupled to the wire 302 and the wire 306 and the end tool hub 4106 coupled to the pulley 4121 rotate around the rotation shaft 4143 in the clockwise direction, and as a result, the end tool 4100 rotates upward to perform the pitch motion. In this case, as the first jaw 4101 and the wire 301 and the wire 305 fixedly coupled to the first jaw 4101 are wound downward around the pulley 4113 and the pulley 4114, which are rotatable around the rotation shaft 4143, the wire 302 and the wire 306 are moved in directions opposite to the directions 301 and 305, respectively.

Meanwhile, the end tool 4100 of the surgical instrument 4000 of the present disclosure may further include the pulley 4131, which is an end tool pitch pulley, the manipulation portion 200 may further include the pulley 231 and a pulley 232, which are manipulation portion pitch pulleys, and the power transmission part 300 may further include the wire 303 and the wire 304, which are pitch wires. In detail, the pulley 4131 of the end tool 4100 is rotatable around the rotation shaft 4143, which is an end tool pitch rotation shaft, and may be integrally formed with the end tool hub 4106 as one body (or to be fixedly coupled to the end tool hub 4106). In addition, the wire 303 and the wire 304 may serve to connect the pulley 4131 of the end tool 4100 to the pulley 231 and the pulley 232 of the manipulation portion 200.

Thus, when the pulley 231 and the pulley 232 of the manipulation portion 200 rotate, the rotation of the pulley 231 and the pulley 232 is transmitted to the pulley 4131 of the end tool 4100 through the wire 303 and the wire 304 such that the pulley 4131 rotates together therewith, and as a result, the end tool 4100 performs a pitch motion while rotating.

That is, in the surgical instrument 4000 according to the first embodiment of the present disclosure, by providing the pulley 4131 of the end tool 4100, the pulley 231 and the pulley 232 of the manipulation portion 200, and the wire 303 and the wire 304 of the power transmission part 300, the driving force for the pitch motion of the manipulation portion 200 may be perfectly transmitted to the end tool 4100, thereby improving operation reliability.

Here, a diameter of the pulley 4113, the pulley 4114, the pulley 4123, and the pulley 4124, which are end tool jaw pitch main pulleys, and a diameter of the pulley 4131, which is an end tool pitch pulley, may be equal to or different from each other. Here, a ratio of the diameter of the end tool jaw pitch main pulley to the diameter of the end tool pitch pulley may be equal to a ratio of a diameter of the manipulation portion pitch pulley of the manipulation portion 200 to a diameter of a manipulation portion pitch main pulley to be described below.

This will be described in detail below.

(Components Associated with Staple Pulley)

Hereinafter, the first staple pulley 4181 and the second staple pulley 4191 of the staple pulley assembly 4160 of the end tool 4100 of the surgical instrument 4000 of FIG. 2 will be described in more detail.

FIG. 9 is a side view illustrating the end tool of the surgical instrument of FIG. 2, and FIGS. 10 and 11 are perspective views illustrating the first jaw of the surgical instrument of FIG. 2. FIG. 12 is a perspective view illustrating the first jaw pulley of the surgical instrument of FIG. 2, FIG. 13 is a plan view illustrating the first jaw of the surgical instrument of FIG. 2, FIG. 14 is a plan view illustrating the second jaw of the surgical instrument of FIG. 2, and FIGS. 15 and 16 are exploded perspective views illustrating the staple pulley and the staple link of the surgical instrument of FIG. 2.

Referring to FIGS. 4 to 16 and the like, the end tool 4100 of the first embodiment of the present disclosure may include the first staple pulley 4181, a first staple auxiliary pulley 4182, a pulley 4183, a pulley 4184, a pulley 4185, and a pulley 4186 that are associated with linear/rotational motions of respective pulleys and links for stapling and cutting. In addition, the end tool 4100 of the first embodiment of the present disclosure may further include the pulley 4187 and the pulley 4188.

In addition, the end tool 4100 of the first embodiment of the present disclosure may include the second staple pulley 4191, a second staple auxiliary pulley 4192, a pulley 4193, a pulley 4194, a pulley 4195, and a pulley 4196 that are associated with linear/rotational motions of respective pulleys and links for stapling and cutting. In addition, the end tool 4100 of the first embodiment of the present disclosure may further include the pulley 4197 and the pulley 4198.

The first staple pulley 4181 and the second staple pulley 4191 are formed to face the pulley 4111 and the pulley 4121, which are end tool jaw pulleys, and are formed to be rotatable independently of each other around the rotation shaft 4141, which is an end tool jaw pulley rotation shaft. Here, although the drawings illustrate that the first staple pulley 4181 and the second staple pulley 4191 are arranged between the pulley 4111 and the pulley 4121, the technical concepts of the present disclosure is not limited thereto, and the first staple pulley 4181 and the second staple pulley 4191 may be arranged at various positions adjacent to the pulley 4111 or the pulley 4121.

Here, according to the present disclosure, the first staple pulley 4181, the second staple pulley 4191, the pulley 4111, and the pulley 4121 are formed to rotate around substantially the same shaft. As such, as the first staple pulley 4181, the second staple pulley 4191, the pulley 4111, and the pulley 4121 are formed to rotate around the same shaft, it is possible to perform a pitch motion/yaw motion/actuation motion as well as stapling and cutting motions. This will be described below in more detail. However, although the drawings illustrate that the first staple pulley 4181, the second staple pulley 4191, the pulley 4111, and the pulley 4121 are formed to rotate around one rotation shaft 4141, the pulleys may also be formed to be rotatable around separate shafts that are concentric with each other.

In other words, it may also be described that the pulley 4111, which is the first jaw pulley, the first staple pulley 4181, the second staple pulley 4191, and the pulley 4121, which is the second jaw pulley, are sequentially stacked along the rotation shaft 4141. Alternatively, it may also be described that the first staple pulley 4181 and the second staple pulley 4191 are arranged between the pulley 4111 and the pulley 4121 facing each other. Here, the pulley 4111, which is the first jaw pulley, the first staple pulley 4181, the second staple pulley 4191, and the pulley 4121, which is the second jaw pulley, may be formed to rotate independently of each other.

The first staple auxiliary pulley 4182 may be additionally provided on one side of the first staple pulley 4181. In other words, the first staple auxiliary pulley 4182 may be arranged between the first staple pulley 4181 and the pulley 4183/the pulley 4184. The first staple auxiliary pulley 4182 may be formed to be rotatable independently of the pulley 4112 and the pulley 4122 around the rotation shaft 4142.

Meanwhile, the pulley 4187 and the pulley 4188 may be additionally arranged between the first staple auxiliary pulley 4182 and the pulley 4183/the pulley 4184. The pulley 4187 and the pulley 4188 may be formed to be rotatable around the separation prevention pulley coupling portion 4106f of the end tool hub 4106. Here, the separation prevention pulley coupling portion 4106f may be formed parallel to the rotation shaft 4143, which is the central axis of the pulley 4183 and the pulley 4184. Here, the pulley 4187 and the pulley 4188 may function as first staple wire separation prevention pulleys.

Meanwhile, the pulley 4183 and the pulley 4184 may function as staple pitch main pulleys, and the pulley 4185 and the pulley 4186 may function as staple pitch subsidiary pulleys.

The second staple auxiliary pulley 4192 may be additionally provided on one side of the second staple pulley 4191. In other words, the second staple auxiliary pulley 4192 may be arranged between the second staple pulley 4191 and the pulley 4193/the pulley 4194. The second staple auxiliary pulley 4192 may be formed to be rotatable independently of the pulley 4112 and the pulley 4122 around the rotation shaft 4142.

Here, although the drawings illustrate that the first staple auxiliary pulley 4182, the second staple auxiliary pulley 4192, the pulley 4112, and the pulley 4122 are formed to rotate around one rotation shaft 4142, the first staple auxiliary pulley 4182, the second staple auxiliary pulley 4192, the pulley 4112, and the pulley 4122 may also be formed to be rotatable around separate shafts. Such a staple auxiliary pulley will be described in more detail below.

Meanwhile, the pulley 4197 and the pulley 4198 may be additionally arranged between the second staple auxiliary pulley 4192 and the pulley 4193/the pulley 4194. The pulley 4197 and the pulley 4198 may be formed to be rotatable around the separation prevention pulley coupling portion 4106*f* of the end tool hub 4106. Here, the separation prevention pulley coupling portion 4106*f* may be formed parallel to the rotation shaft 4143, which is the central axis of the pulley 4183 and the pulley 4184. Here, the pulley 4197 and the pulley 4198 may function as second staple wire separation prevention pulleys.

Meanwhile, the pulley 4193 and the pulley 4194 may function as staple pitch main pulleys, and the pulley 4195 and the pulley 4196 may function as staple pitch subsidiary pulleys.

Hereinafter, the first staple auxiliary pulley 4182 will be described in more detail.

The first staple auxiliary pulley 4182 may serve to increase the rotation angle of the first staple pulley 4181 by coming into contact with the wire 308, which is a first staple wire, to change the arrangement path of the wire 308 to a certain extent.

That is, when no staple auxiliary pulley is arranged, the staple pulley is rotatable only up to a right angle, but in an embodiment of the present disclosure, by additionally providing the first staple auxiliary pulley 4182, which is an auxiliary pulley, the maximum rotation angle may be increased by 0. This allows the first staple pulley 4181 to rotate for the stapling and cutting motions while the two jaws of the end tool 4100 are yaw-rotated together by 90°, thus enabling a linear motion of an operation member 540 to be described below. In other words, a feature of increasing the range of yaw rotation in which stapling and cutting motions are possible may be obtained through the first staple auxiliary pulley 4182.

This will be described in more detail as follows.

In the surgical instrument 4000 of the present disclosure, the first staple auxiliary pulley 4182 is further arranged on one side of the first staple pulley 4181. As such, by arranging the first staple auxiliary pulley 4182 to change the arrangement path of the wire 308, which is the first staple wire, to a certain extent, the tangential direction of the wire 308 is changed, and thus the rotation angle of the fastening member (see 329 of FIG. 62) that couple the wire 308 to the first staple pulley 4181 is increased. That is, the fastening member (see 329 of FIG. 62), which is a coupling portion of the wire 308 and the first staple pulley 4181, is rotatable until the fastening member 329 is located on the common internal tangent of the first staple pulley 4181 and the staple auxiliary pulley 4122.

In other words, the wire 308 is located on the internal tangent of the first staple pulley 4181 and the first staple auxiliary pulley 4182, and the rotation angle of the first staple pulley 4181 is increased by the first staple auxiliary pulley 4182.

According to the present disclosure, as the rotation radius of the first staple pulley 4181 increases, a yaw motion range in which normal stapling and cutting motions may be performed may be increased.

Hereinafter, the pulley 4187 and the pulley 4188, which are first staple wire separation prevention pulleys, will be described in more detail.

The end tool 4100 of the surgical instrument according to the first embodiment of the present disclosure may further include the pulley 4187 and the pulley 4188, which are the first staple wire separation prevention pulleys, and thus may serve to prevent separation of the wire 307 and the wire 308, which are the first staple wires.

That is, the pulley 4187/the pulley 4188 are arranged between the first staple auxiliary pulley 4182 and the pulley 4183/the pulley 4184 so as to change the path of the wire 307 to the first staple pulley 4181 via the pulley 4183 and the path of the wire 308 to the first staple auxiliary pulley 4182 via the pulley 4184, to a certain extent. In more detail, the path of the wire 307/the wire 308 is changed to a certain extent such that the wire 307 toward the first staple pulley 4181 via the pulley 4183 and the wire 308 toward the first staple auxiliary pulley 4182 via the pulley 4184 are parallel to the X-axis.

In detail, the height of the wire 307 wound around the pulley 4183 in the Z-axis direction is different from the height of the wire 307 toward the first staple pulley 4181 in the Z-axis direction. Similarly, the height of the wire 308 wound around the pulley 4184 in the Z-axis direction is different from the height of the wire 308 toward the first staple auxiliary pulley 4182 in the Z-axis direction. Thus, when the pulley 4187/the pulley 4188, which are the first staple wire separation prevention pulleys, do not exist, the path of the wire 307/the wire 308 becomes oblique (i.e., the fleet angle of the wire relative to the pulley increases), and thus, there is a risk that the wire 307/the wire 308 are separated from the pulley, and there is also a risk that the wire 307/the wire 308 are damaged.

Thus, in the present embodiment, the pulley 4187/the pulley 4188, which are the first staple wire separation prevention pulleys, are arranged between the first staple auxiliary pulley 4182 and the pulley 4183/the pulley 4184, to serve to change the path of the wire 307/the wire 308 to a certain extent such that the wire 307/the wire 308 toward the distal end 4104 of the end tool 4100 after being wound around the pulley 4183/the pulley 4184 are parallel to the X-axis.

According to the present disclosure, the wire 307 and the wire 308, which are the first staple wires, are prevented from being separated from the pulleys, thereby more smoothly performing the cutting motion.

Hereinafter, components associated with the rotation of the first staple pulley 4181 will be described.

The pulley 4183 and the pulley 4184 function as staple pitch main pulleys. Here, the wire 307, which is a first staple wire, is wound around the pulley 4183, and the wire 308, which is a first staple wire, is wound around the pulley 4184.

The pulley 4185 and the pulley 4186 function as staple pitch subsidiary pulleys. Here, the wire 307, which is a first staple wire, is wound around the pulley 4185, and the wire 308, which is a first staple wire, is wound around the pulley 4186.

Here, the pulley 4183 and the pulley 4184 are arranged on one side of the first staple pulley 4181, the first staple auxiliary pulley 4182, and the pulley 4187/the pulley 4188, to face each other. Here, the pulley 4183 and the pulley 4184 are formed to be rotatable independently of each other around the rotation shaft 4143, which is an end tool pitch rotation shaft. In addition, the pulley 4185 and the pulley 4186 are arranged on one sides of the pulley 4183 and the pulley 4184, respectively, to face each other. Here, the pulley 4185 and the pulley 4186 are formed to be rotatable independently of each other around the rotation shaft 4144, which is an end tool pitch auxiliary rotating shaft. Although the drawings illustrate that the pulley 4183, the pulley 4185, the pulley 4184, and the pulley 4186 are formed to be rotatable around the Y-axis direction, the technical concepts of the present disclosure are not limited thereto, and the rotation shafts of each pulley may be formed in various directions suitable for their respective configurations.

As described above, the rotation shaft 4141, the rotation shaft 4142, the rotation shaft 4143, and the rotation shaft 4144 may be arranged sequentially from the distal end 4104 of the end tool 4100 toward the proximal end 4105. Accordingly, the first staple pulley 4181, the first staple auxiliary pulley 4182, the pulley 4187/the pulley 4188, the pulley 4183/the pulley 4184, and the pulley 4185/the pulley 4186 may be arranged sequentially from the distal end 4104 of the end tool 4100 to the proximal end 4105.

The wire 307, which is the first staple wire, is sequentially wound such that at least a portion thereof is in contact with the pulley 4185, the pulley 4183, the pulley 4187, and the first staple pulley 4181. In addition, the wire 308 connected to the wire 307 by the fastening member (see 329 of FIG. 62) is sequentially wound such that at least a portion thereof is in contact with the first staple pulley 4181, the first staple auxiliary pulley 4182, the pulley 4188, the pulley 4184, and the pulley 4186.

In other words, the wire 307 and the wire 308, which are first staple wires, are sequentially wound such that at least portions thereof are in contact with the pulley 4185, the pulley 4183, the first staple pulley 4181, the first staple auxiliary pulley 4182, the pulley 4188, the pulley 4184, and the pulley 4186, and the wire 307 and the wire 308 are formed to move along the pulleys while rotating above pulleys.

Accordingly, when the wire 307 is pulled, the fastening member (see 329 of FIG. 62) to which the wire 307 is coupled and the first staple pulley 4181 coupled to the fastening member 329 rotate in one direction. On the contrary, when the wire 308 is pulled, the fastening member (see 329 of FIG. 62) to which the wire 308 is coupled and the first staple pulley 4181 coupled to the fastening member 329 rotate in the opposite direction.

Meanwhile, the second staple pulley 4191, the second staple auxiliary pulley 4192, and the pulley 4193, the pulley 4194, the pulley 4195, the pulley 4196, the pulley 4197, the pulley 4198, the wire 309, the wire 310, and the like, which are associated with the second staple pulley 4191, the second staple auxiliary pulley 4192, may have the same or similar configurations as those of the components associated with the first staple pulley 4181 described above.

In detail, the pulley 4193 and the pulley 4194 function as staple pitch main pulleys. Here, the wire 310, which is a second staple wire, is wound around the pulley 4193, and the wire 309, which is a second staple wire, is wound around the pulley 4194.

The pulley 4195 and the pulley 4196 function as staple pitch subsidiary pulleys. Here, the wire 310, which is a second staple wire, is wound around the pulley 4195, and the wire 309, which is a second staple wire, is wound around the pulley 4196.

Here, the pulley 4193 and the pulley 4194 are arranged on one side of the second staple pulley 4191, the second staple auxiliary pulley 4192, and the pulley 4197/the pulley 4198, to face each other. Here, the pulley 4193 and the pulley 4194 are formed to be rotatable independently of each other around the rotation shaft 4143, which is an end tool pitch rotation shaft. In addition, the pulley 4195 and the pulley 4196 are arranged on one sides of the pulley 4193 and the pulley 4194, respectively, to face each other. Here, the pulley 4195 and the pulley 4196 are formed to be rotatable independently of each other around the rotation shaft 4144, which is an end tool pitch auxiliary rotating shaft. Although the drawings illustrate that the pulley 4193, the pulley 4195, the pulley 4194, and the pulley 4196 are formed to be rotatable around the Y-axis direction, the technical concepts of the present disclosure are not limited thereto, and the rotation shafts of each pulley may be formed in various directions suitable for their respective configurations.

As described above, the rotation shaft 4141, the rotation shaft 4142, the rotation shaft 4143, and the rotation shaft 4144 may be arranged sequentially from the distal end 4104 of the end tool 4100 toward the proximal end 4105. Accordingly, the second staple pulley 4191, the second staple auxiliary pulley 4192, the pulley 4197/the pulley 4198, the pulley 4193/the pulley 4194, and the pulley 4195/the pulley 4196 may be arranged sequentially from the distal end 4104 of the end tool 4100 to the proximal end 4105.

The wire 310, which is the second staple wire, is sequentially wound such that at least a portion thereof is in contact with the pulley 4195, the pulley 4193, the pulley 4197, and the first staple pulley 4191. In addition, the wire 309 connected to the wire 310 by the fastening member (see 330 of FIG. 62) is sequentially wound such that at least a portion thereof is in contact with the first staple pulley 4191, the first staple auxiliary pulley 4192, the pulley 4198, the pulley 4194, and the pulley 4196.

In other words, the wire 310 and the wire 309, which are second staple wires, are sequentially wound such that at least portions thereof are in contact with the pulley 4195, the pulley 4193, the first staple pulley 4191, the first staple auxiliary pulley 4192, the pulley 4198, the pulley 4194, and the pulley 4196, and the wire 310 and the wire 309 are formed to move along the pulleys while rotating above pulleys.

Accordingly, when the wire 310 is pulled, the fastening member (see 330 of FIG. 62) to which the wire 310 is coupled and the first staple pulley 4191 coupled to the fastening member 330 rotate in one direction. On the contrary, when the wire 309 is pulled, the fastening member (see 330 of FIG. 62) to which the wire 309 is coupled and the first staple pulley 4191 coupled to the fastening member 330 rotate in the opposite direction.

(Staple Drive Assembly)

Hereinafter, a staple drive assembly 4150 will be described in detail.

Referring to FIGS. 15 to 20 and the like, the staple drive assembly 4150 may include the staple pulley assembly 4160 and the staple link assembly 4170. Here, the staple drive assembly 4150 is connected to a reciprocating assembly 550 of a cartridge 500 to be described below, to convert a rotational motion of the staple pulley assembly 4160 into a linear motion of the reciprocating assembly 550. In other embodiments of the present disclosure to be described below, the staple drive assembly may be understood as a concept including the staple pulley assembly and the staple link assembly.

The staple pulley assembly 4160 may include one or more staple pulleys. The staple pulley assembly 4160 may be formed between the pulley 4111 and the pulley 4121 to be adjacent to the pulley 4111 and the pulley 4121. In the present embodiment, it is assumed that the staple pulley assembly 4160 includes two staple pulleys, which are the first staple pulley 4181 and the second staple pulley 4191.

The staple link assembly 4170 may include one or more link members 4171. In addition, the link member 4171 may include one or more links. In the first embodiment of the present disclosure, it is assumed that the staple link assembly 4170 includes one link member 4171 and the link member 4171 includes one link.

In the end tool 4100 of the surgical instrument according to the present disclosure, the staple pulley assembly 4160 and the staple link assembly 4170 form a cam/slot structure. In addition, with such a structure, a force for moving the reciprocating assembly 550 forward may be amplified.

In detail, the staple pulley assembly 4160 may include the first staple pulley 4181 and the second staple pulley 4191.

The first staple pulley 4181 may include a body 4181*a*, a protruding member 4181*b*, and a shaft pass-through part 4181*c*.

The body 4181*a* is formed in a disk shape.

The shaft pass-through part 4181*c* may be formed in a central portion of the body 4181*a*. The shaft pass-through part 4181*c* may be formed in the form of a hole, and the rotation shaft 4141, which is an end tool jaw pulley rotation shaft, may be inserted through the shaft pass-through part 4181*c*.

In addition, the protruding member 4181*b* may be formed on the body part 4181*a* of the first staple pulley 4181. The protruding member 4181*b* may be coupled to the link member 4171 of the staple link assembly 4170. Here, the center of the protruding member 4181*b* may not coincide with the center of the first staple pulley 4181, and the protruding member 4181*b* may be formed to be eccentric to a certain extent with respect to the first staple pulley 4181. The protruding member 4181*b* may be fitted into a first slot 4171*d* of the link member 4171 to be described below.

The second staple pulley 4191 may include a body 4191*a*, a protruding member 4191*b*, and a shaft pass-through part 4191*c*.

The body 4191*a* is formed in a disk shape.

the shaft pass-through part 4191*c* may be formed in a central portion of the body 4191*a*. The shaft pass-through part 4191*c* may be formed in the form of a hole, and the rotation shaft 4141, which is an end tool jaw pulley rotation shaft, may be inserted through the shaft pass-through part 4191*c*.

In addition, the protruding member 4191*b* may be formed on the body part 4191*a* of the second staple pulley 4191. The protruding member 4191*b* may be coupled to the link member 4171 of the staple link assembly 4170. Here, the center of the protruding member 4191*b* may not coincide with the center of the second staple pulley 4191, and the protruding member 4191*b* may be formed to be eccentric to a certain extent with respect to the first staple pulley 4191. The protruding member 4191*b* may be fitted into a second slot 4171*e* of the link member 4171 to be described below.

Meanwhile, the end tool 4100 of the present disclosure may further include the staple link assembly 4170 connected to the staple pulley assembly 4160, and the staple link assembly 4170 may include the link member 4171. Here, the staple link assembly 4170 may serve to connect the staple pulley assembly 4160 to a reciprocating assembly 4150 of a cartridge 4110 to be described below.

In the present embodiment, the staple link assembly 4170 includes one link member 4171, and the link member 4171 includes only one link. That is, by coupling the staple pulley assembly 4160 to the staple link assembly 4170 by a cam/slot structure, it is possible to convert a rotational motion of the staple pulley assembly 4160 into a linear motion of the staple link assembly 4170 even when the staple link assembly 4170 includes only one link.

In detail, the link member 4171 may be formed as a single link.

The link member 4171 is formed in a shape of a combination of an elongated bar with an elliptical flat plate, and may be formed in an approximately 'L' shape. Here, the link member 4171 may include a first protrusion 4171*a*, a second protrusion 4171*b*, a fastening portion 4171*c*, the first slot 4171*d*, and the second slot 4171*e*.

the first protrusion 4171*a* and the second protrusion 4171*b* may be formed in one region of a central portion of the link member 4171. The first protrusion 4171*a* and the second protrusion 4171*b* may be fitted into a guide groove 4101*b* of the first jaw 4101.

As such, as the first protrusion 4171*a* and the second protrusion 4171*b* are moved along the guide groove 4101*b* in a state in which the first protrusion 4171*a* and the second protrusion 4171*b* of the link member 4171 formed in a protruding shape are fitted into the groove-shaped guide groove 4101*b*, the link member 4171 is moved with respect to the first jaw 4101 (and the cartridge 500 therein). This will be described below in more detail.

Meanwhile, the fastening portion 4171*c* may be formed at one end of the link member 4171. The fastening portion 4171*c* may be coupled to a fastening portion 551*a* of a reciprocating member 551 of the cartridge 500.

Meanwhile, the first slot 4171*d* and the second slot 4171*e* may be formed at an end opposite to the end of the link member 4171 at which the fastening portion 4171*c* is formed.

In detail, the first slot 4171*d* may be formed on a surface of the link member 4171 facing the first staple pulley 4181. Here, the first slot 4171*d* may be formed in the shape of an elongated hole, and the protruding member 4181*b* of the first staple pulley 4181 may be inserted into the first slot 4171*d*. The first slot 4171*d* may be formed to have a predetermined curvature, and may be formed in an approximately elliptical shape. Here, the first slot 4171*d* may be formed to be greater than the protruding member 4181*b* by a certain extent. Accordingly, the protruding member 4181*b* is formed to be movable to a certain extent in the first slot 4171*d* in a state in which the protruding member 4181*b* of the first staple pulley 4181 is fitted into the first slot 4171*d* of the link member 4171.

As described above, the protruding member 4181*b* may be formed to be eccentric with respect to the center of the first staple pulley 4181 by a certain extent. Accordingly, when the first staple pulley 4181 rotates, the protruding member 4181*b* in contact with the first slot 4171*d* may push the first slot 4171*d* to move the link member 4171. That is, when the first staple pulley 4181 rotates, the protruding member 4181*b* may move while being in contact with the first slot 4171*d* within the first slot 4171*d*, and accordingly, the link member 4171 may linearly move along the guide groove 4101*b* of the first jaw 4101.

Here, the first slot 4171*d* may be formed not to pass through the entire thickness of the link member 4171, but to pass through about half of the entire thickness of the link member 4171. In other words, the first slot 4171*d* may be formed to have substantially the same thickness as the thickness of the protruding member 4181*b* of the first staple pulley 4181.

Meanwhile, the second slot 4171*e* may be formed in the link member 4171. In detail, the second slot 4171*e* may be formed on a surface of the link member 4171 facing the second staple pulley 4191. Here, the second slot 4171*e* may be formed in the shape of an elongated hole, and the protruding member 4191*b* of the second staple pulley 4191 may be inserted into the second slot 4171*e*. The second slot 4171*e* may be formed to have a predetermined curvature, and may be formed in an approximately elliptical shape. Here, the second slot 4171*e* may be formed to be greater than the protruding member 4191*b* by a certain extent. Accordingly, the protruding member 4191*b* is formed to be movable to a certain extent in the second slot 4171*e* in a state in which the protruding member 4191*b* of the second staple pulley 4191 is fitted into the second slot 4171*e* of the link member 4171.

As described above, the protruding member 4191*b* may be formed to be eccentric with respect to the center of the second staple pulley 4191 by a certain extent. Accordingly, when the second staple pulley 4191 rotates, the protruding member 4191*b* in contact with the second slot 4171*e* may push the second slot 4171*e* to move the link member 4171. That is, when the second staple pulley 4191 rotates, the protruding member 4191*b* may move while being in contact with the second slot 4171*e* within the second slot 4171*e*, and accordingly, the link member 4171 may linearly move along the guide groove 4101*b* of the first jaw 4101.

Here, the second slot 4171*e* may be formed not to pass through the entire thickness of the link member 4171, but to pass through about half of the entire thickness of the link member 4171. In other words, the second slot 4171*e* may be formed to have substantially the same thickness as the thickness of the protruding member 4191*b* of the second staple pulley 4191. Here, the first slot 4171*d* and the second slot 4171*e* may be formed to at least partially overlap each other. In addition, the sum of the thicknesses of the first slot 4171*d* and the second slot 4171*e* in the Y-axis direction may be substantially equal to the thickness of the link member 4171 in the Y-axis direction.

Here, the first slot 4171*d* and the second slot 4171*e* may be formed to be vertically symmetrical with respect to the rotation shaft 4141. As such, as the first slot 4171*d* and the second slot 4171*e* are vertically symmetrical with respect to the rotation shaft 4141, the protruding member 4181*b* of the first staple pulley 4181 and the protruding member 4191*b* of the second staple pulley 4191, which are coupled to the link member 4171, may be arranged to be symmetrical with each other. This will be described below in more detail.

(Displacement and Operation of Staple Link Assembly According to Rotation of Staple Pulley)

Hereinafter, displacement of the staple link assembly 4170 according to rotation of the first staple pulley 4181 and the second staple pulley 4191 will be described.

Referring to FIG. 17, in the first embodiment of the present disclosure, the first staple pulley 4181 and the staple link assembly 4170 are coupled to each other in a cam/slot form. That is, the cam-shaped protruding member 4181*b* formed on the first staple pulley 4181 is coupled to the first slot 4171*d* formed in the link member 4171. Thus, when the first staple pulley 4181 rotates in the direction of an arrow A, the displacement of the protruding member 4181*b* of the first staple pulley 4181 in the X-axis direction becomes B. In addition, the displacement of the staple link assembly 4170 in the X-axis direction becomes C.

Similarly, referring to FIG. 18, in the first embodiment of the present disclosure, the second staple pulley 4191 and the staple link assembly 4170 are coupled to each other in a cam/slot form. That is, the cam-shaped protruding member 4191*b* formed on the second staple pulley 4191 is coupled to the second slot 4171*e* formed in the link member 4171. Thus, when the second staple pulley 4191 rotates in the direction of an arrow D, the displacement of the protruding member 4191*b* of the second staple pulley 4191 in the X-axis direction becomes E. In addition, the displacement of the staple link assembly 4170 in the X-axis direction becomes F.

In comparison with the above case, when a staple pulley and a staple link assembly are coupled to each other in a link-shaft manner rather than the cam/slot manner, the displacement of the staple link assembly in the X-axis direction becomes much longer than that in the first embodiment of the present disclosure.

In other words, compared to when the staple pulley and the staple link assembly are axially coupled to each other, when the staple pulley and the staple link assembly are coupled to each other in the cam/slot manner as in the present embodiment, the displacement of the staple link assembly displacement in the X-axis direction decreases even when the staple pulley rotates by the same amount.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the first embodiment of the present disclosure, because the first staple pulley 4181 and the second staple pulley 4191 are each coupled to the staple link assembly 4170 in the cam/slot form, and the displacement of the staple link assembly 4170 in the X-axis direction due to the rotation of the first staple pulley 4181 and the second staple pulley 4191 is relatively reduced compared to other embodiments, the force received by the staple link assembly 4170 in the X-axis direction relatively increases compared to a simple link structure.

According to the first embodiment of the present disclosure described above, a force for moving forward the staple link assembly 4170 and the reciprocating assembly 550 connected thereto is amplified, and thus, a stapling motion may be performed more robustly.

In particular, in the first embodiment of the present disclosure, because two staple pulleys (i.e., the first staple pulley 4181 and the second staple pulley 4191) symmetrical to each other are provided, the force with which the staple pulley assembly 4160 pushes the staple link assembly 4170 may be amplified by approximately two times compared to a case in which only one staple pulley is provided.

In addition, because the first staple pulley 4181 and the second staple pulley 4191 are arranged to be horizontally symmetrical with each other with respect to an XZ plane, the horizontal balance is achieved in performing a stapling motion, such that the end tool 4100 may perform the motion stably with respect to the rotation shaft 4141, which a yaw rotation shaft, without shaking left and right. In addition, when the winding directions of the wire 307/the wire 308, which are first staple wires, and the wire 309/the wire 310, which are second staple wires, are changed to be opposite to each other with respect to the rotation shaft 4143, which is a pitch rotation shaft, shaking with respect to the rotation shaft 4143 may be mutually offset.

Hereinafter, rotation directions of the first staple pulley 4181 and the second staple pulley 4191 will be described.

Referring to FIGS. 17, 18, 19, 20, and the like, the first staple pulley 4181 moves forward the staple link assembly 4170 when rotating in the direction of an arrow A of FIG. 20 (i.e., the clockwise direction), and the second staple pulley 4191 moves forward the staple link assembly 4170 when rotating in the direction of an arrow D of FIG. 20 (i.e., the counterclockwise direction).

On the contrary, the first staple pulley 4181 moves backward the staple link assembly 4170 when rotating in the counterclockwise direction, and the second staple pulley 4191 moves backward the staple link assembly 4170 when rotating in the clockwise direction.

Accordingly, when the first staple pulley 4181 and the second staple pulley 4191 rotate in opposite directions, the staple link assembly 4170 is moved (forward or backward). On the contrary, when the first staple pulley 4181 and the second staple pulley 4191 rotate in the same direction, the rotation of the two pulleys is offset, and thus, the staple link assembly 4170 is not moved.

Accordingly, in a state illustrated in FIG. 19, when the first staple pulley 4181 rotates in the clockwise direction and the second staple pulley 4191 rotates in the counterclockwise direction at the same time, the link member 4171 connected to the first staple pulley 4181 and the second staple pulley 4191 may move toward a distal end (see 4101$f$ of FIG. 13) of the first jaw 4101.

On the contrary, when the first staple pulley 4181 rotates in the counterclockwise direction and the second staple pulley 4191 rotates in the clockwise direction at the same time, the link member 4171 connected to the first staple pulley 4181 and the second staple pulley 4191 may move toward a proximal end (see 101$g$ of FIG. 13) of the first jaw 4101.

Thus, a bidirectional rotational motion of the staple pulley assembly 4160 causes a reciprocating linear motion of the reciprocating assembly 550 of the cartridge 500 through the staple link assembly 4170. This will be described below in more detail.

(First and second jaws and actuation motion)

Hereinafter, the coupling structure of the first jaw 4101 and the second jaw 4102 of the end tool 4100 of the surgical instrument 4000 of FIG. 2 will be described in more detail.

Figure 21:
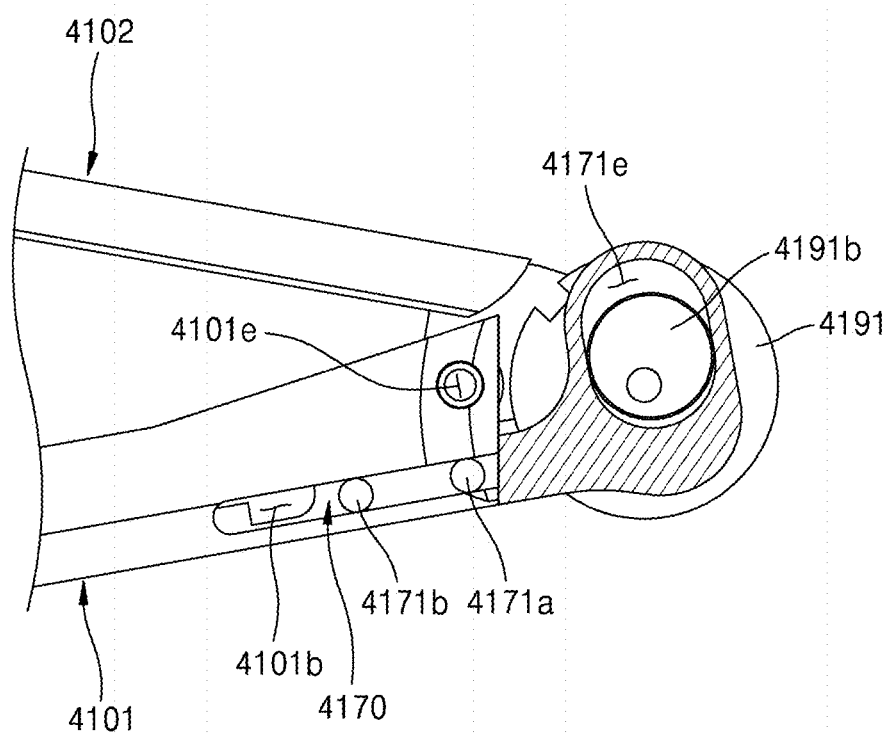
FIGS. 21 to 24 are plan views illustrating opening and closing motions of the first jaw and the second jaw of the surgical instrument of FIG. 2.
Figure 22:
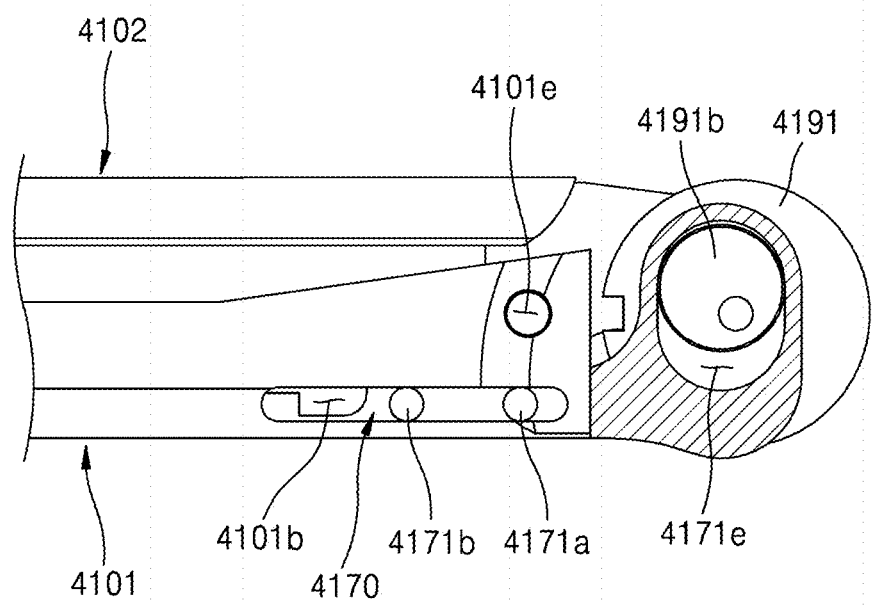

FIG. 13 is a plan view illustrating a first jaw of the surgical instrument of FIG. 2, and FIG. 14 is a plan view illustrating a second jaw of the surgical instrument of FIG. 2. FIGS. 21 and 22 are plan views illustrating opening and closing motions of the first jaw and the second jaw of the surgical instrument of FIG. 2. FIGS. 23 and 24 are plan views illustrating opening and closing motions of the first jaw and the second jaw of the surgical instrument of FIG. 2. FIGS. 25 and 26 are perspective views illustrating opening and closing motions of the end tool of the surgical instrument of FIG. 2.

Referring to FIGS. 9 to 26 and the like, the first jaw 4101 includes a cartridge accommodation portion 4101$a$, the guide groove 4101$b$, a movable-coupling hole 4101$c$, a jaw pulley coupling hole 4101$d$, and a shaft pass-through part 4101$c$.

The first jaw 4101 is formed entirely in the shape of an elongated bar, the cartridge 500 is accommodated in the side of the distal end 4101$f$, and the pulley 4111 is coupled to the proximal end 4101$g$, such that the first jaw 4101 is formed to be rotatable around the rotation shaft 4141. In other words, the first jaw 4101 may be formed entirely in the form of a hollow box whose one surface (upper surface) is removed, such that the cartridge accommodation portion 4101$a$ capable of accommodating the cartridge 500 may be formed inside the first jaw 4101. That is, the first jaw 4101 may be formed in an approximately 'U' shape in cross section.

The guide groove 4101$b$ to guide the movement of the staple link assembly 4170 to be described below may be formed on one side of the cartridge accommodation portion 4101$a$ of the first jaw 4101, for example, on the side of the proximal end 4101$g$. The guide groove 4101$b$ may be formed in the shape of a groove formed along a moving path of the staple link assembly 4170. In addition, as the first protrusion 4171$a$ and the second protrusion 4171$b$ move along the guide groove 4101$b$ in a state in which the first protrusion 4171$a$ and the second protrusion 4171$b$ of the link member 4171 formed in a protruding shape are fitted into the groove-shaped guide groove 4101$b$, the staple link assembly 4170 moves with respect to the first jaw 4101 (and the cartridge 500 therein). That is, the staple link assembly 4170 may move along the guide groove 4101$b$ of the first jaw 4101.

Meanwhile, the movable-coupling hole 4101$c$, the jaw pulley coupling hole 4101$d$, and the shaft pass-through part 4101$e$ may be formed on the side of the proximal end of the first jaw 4101.

Here, the movable-coupling hole 4101$c$ may be formed to have a predetermined curvature, and may be formed in an approximately elliptical shape. A shaft coupling portion 4111$a$ of the pulley 4111 to be described below may be fitted into the movable-coupling hole 4101$c$. Here, a short radius of the movable-coupling hole 4101$c$ may be substantially equal to or slightly greater than a radius of the shaft coupling portion 4111$a$. Meanwhile, a long radius of the movable-coupling hole 4101$c$ may be greater than the radius of the shaft coupling portion 4111$a$. Thus, the shaft coupling portion 4111$a$ is formed to be movable to a certain extent within the movable-coupling hole 4101$c$ in a state in which the shaft coupling portion 4111$a$ of the pulley 4111 is fitted into the movable-coupling hole 4101$c$ of the first jaw 4101. This will be described in more detail below.

Meanwhile, the jaw pulley coupling hole 4101$d$ is formed in the form of a cylindrical hole, and a jaw coupling portion 4111$b$ of the pulley 4111 to be described below may be fitted into the jaw pulley coupling hole 4101$d$. Here, a radius of the jaw pulley coupling hole 4101$d$ may be substantially equal to or slightly greater than a radius of the jaw coupling portion 4111$b$. Thus, the jaw coupling portion 4111$b$ of the pulley 4111 may be formed to be rotatably coupled to the jaw pulley coupling hole 4101$d$ of the first jaw 4101. This will be described in more detail below.

The shaft pass-through part 4101$e$ may be formed closer to the distal end 4101$f$ of the first jaw 4101 compared to the movable-coupling hole 4101$c$ and the jaw pulley coupling hole 4101$d$. The shaft pass-through part 4101$e$ may be formed in the form of a hole, and the rotation shaft 4145, which is a jaw rotation shaft, may be inserted through the shaft pass-through part 4101$c$.

The second jaw 4102 includes an anvil 4102$a$, a movable-coupling hole 4102$c$, a jaw pulley coupling hole 4102$d$, and a shaft pass-through part 4102$e$.

The second jaw 4102 is formed entirely in the shape of an elongated bar, the anvil 4102$a$ is formed on the side of a distal end 4102f, and the pulley 4112 is coupled to a proximal end 4102g, such that the second jaw 4102 is formed to be rotatable around the rotation shaft 4141.

In detail, the anvil 4102a is formed in the form of a flat plane, shapes corresponding to the shapes of staples 530 to be described below may be formed on one surface of the anvil 4102a. The anvil 4102a may serve as a support for supporting the staple 530 on the opposite side of the operation member 540 when the operation member 540 pushes and raises the staple 530 during a stapling motion, such that the staple 530 is bent.

Meanwhile, the movable-coupling hole 4102c, the jaw pulley coupling hole 4102d, and the shaft pass-through part 4102e may be formed on the side of the proximal end of the second jaw 4102.

Here, the movable-coupling hole 4102c may be formed to have a predetermined curvature, and may be formed in an approximately elliptical shape. A shaft coupling portion 4121a of the pulley 4121 to be described below may be fitted into the movable-coupling hole 4102c. Here, a short radius of the movable-coupling hole 4102c may be substantially equal to or slightly greater than a radius of the shaft coupling portion 4121a. Meanwhile, a long radius of the movable-coupling hole 4102c may be greater than the radius of the shaft coupling portion 4121a. Thus, the shaft coupling portion 4121a is formed to be movable to a certain extent within the movable-coupling hole 4102c in a state in which the shaft coupling portion 4121a of the pulley 4121 is fitted into the movable-coupling hole 4102c of the second jaw 4102. This will be described in more detail below.

Meanwhile, the jaw pulley coupling hole 4102d is formed in the form of a cylindrical hole, and a jaw coupling portion 4121b of the pulley 4121 to be described below may be fitted into the jaw pulley coupling hole 4102d. Here, a radius of the jaw pulley coupling hole 4102d may be substantially equal to or slightly greater than a radius of the jaw coupling portion 4121b. Thus, the jaw coupling portion 4121b of the pulley 4121 may be formed to be rotatably coupled to the jaw pulley coupling hole 4102d of the second jaw 4102. This will be described in more detail below.

Meanwhile, the shaft pass-through part 4102e may be formed on the side of the distal end 4102g of the second jaw 4102 compared to the movable-coupling hole 4102c and the jaw pulley coupling hole 4102d. The shaft pass-through part 4102e may be formed in the form of a hole, and the rotation shaft 4145, which is a jaw rotation shaft, may be inserted through the shaft pass-through part 4102c.

The pulley 4111, which is a first jaw pulley, may include the shaft coupling portion 4111a and the jaw coupling portion 4111b. The pulley 4111 is formed entirely in the form of a rotatable disk, and the shaft coupling portion 4111a and the jaw coupling portion 4111b may be formed to protrude to a certain extent from one surface of the pulley 4111. As described above, the shaft coupling portion 4111a of the pulley 4111 may be fitted into the movable-coupling hole 4101c of the first jaw 4101, and the jaw coupling portion 4111b of the pulley 4111 may be fitted into the jaw pulley coupling hole 4101d of the first jaw 4101. The pulley 4111 may be formed to be rotatable around the center of the rotation shaft 4141, which is an end tool jaw pulley rotation shaft.

Meanwhile, the pulley 4121, which is a second jaw pulley, may include the shaft coupling portion 4121a and the jaw coupling portion 4121b. The pulley 4121 is formed entirely in the form of a rotatable disk, and the shaft coupling portion 4121a and the jaw coupling portion 4121b may be formed to protrude to a certain extent from one surface of the pulley 4121. As described above, the shaft coupling portion 4112a of the pulley 4112 may be fitted into the movable-coupling hole 4102c of the second jaw 4102, and the jaw coupling portion 4112b of the pulley 4112 may be fitted into the jaw pulley coupling hole 4102d of the second jaw 4102. The pulley 4121 may be formed to be rotatable around the center of the rotation shaft 4141, which is an end tool jaw pulley rotation shaft.

The coupling relationship between the components described above is as follows.

The rotation shaft 4141, which is an end tool jaw pulley rotation shaft, is sequentially inserted through the shaft coupling portion 4111a of the pulley 4111, the movable-coupling hole 4101c of the first jaw 4101, the shaft pass-through part 4181c of the first staple pulley 4181, the movable-coupling hole 4102c of the second jaw 4102, and the shaft coupling portion 4121a of the pulley 4121.

The rotation shaft 4145, which is a jaw rotation shaft, is sequentially inserted through the shaft pass-through part 4101e of the first jaw 4101 and the shaft pass-through part 4102c of the second jaw 4102.

The shaft coupling portion 4111a of the pulley 4111 is fitted into the movable-coupling hole 4101c of the first jaw 4101, and the jaw coupling portion 4111b of the pulley 4111 is fitted into the jaw pulley coupling hole 4101d of the first jaw 4101.

Here, the jaw pulley coupling hole 4101d of the first jaw 4101 and the jaw coupling portion 4111b of the pulley 4111 are axially coupled to each other to be rotatable, and the movable-coupling hole 4101c of the first jaw 4101 and the shaft coupling portion 4111a of the pulley 4111 are movably coupled to each other.

The shaft coupling portion 4121a of the pulley 4121 is fitted into the movable-coupling hole 4102c of the second jaw 4102, and the jaw coupling portion 4121b of the pulley 4121 is fitted into the jaw pulley coupling hole 4102d of the second jaw 4102.

Here, the jaw pulley coupling hole 4102d of the second jaw 4101 and the jaw coupling portion 4121b of the pulley 4121 are axially coupled to each other to be rotatable, and the movable-coupling hole 4102c of the second jaw 4102 and the shaft coupling portion 4121a of the pulley 4121 are movably coupled to each other.

Here, the pulley 4111 and the pulley 4121 rotate around the rotation shaft 4141, which is an end tool jaw pulley rotation shaft. The first jaw 4101 and the second jaw 4102 rotate around the rotation shaft 4145, which is a jaw rotation shaft. That is, the pulley 4111 and the first jaw 4101 differ from each other in rotation shaft. Similarly, the pulley 4121 and the second jaw 4102 differ from each other in rotation shaft.

That is, the rotation angle of the first jaw 4101 is limited to a certain extent by the movable-coupling hole 4101c, but is basically rotate around the rotation shaft 4145, which is a jaw rotation shaft. Similarly, the rotation angle of the second jaw 4102 is limited to a certain extent by the movable-coupling hole 4102c, but is basically rotate around the rotation shaft 4145, which is a jaw rotation shaft.

Amplification of grip force due to the coupling relationship between the above-described components will be described.

In the surgical instrument 4000 according to an embodiment of the present disclosure, the coupling structure of the first jaw 4101 and the second jaw 4102 forms an X-shaped structure, and thus, when the first jaw 4101 and the second jaw 4102 rotate in directions in which they approach to each other close (i.e., when the first jaw 4101 and the second jaw 4102 are closed), the grip force becomes stronger in a direction in which the first jaw 4101 and the second jaw 4102 are closed. This will be described in more detail as follows.

As described above, in motions of opening and closing the first jaw 4101 and the second jaw 4102, there are two shafts that are the center of rotation of the jaws. That is, the first jaw 4101 and the second jaw 4102 perform opening and closing motions around two shafts, which are the rotation shaft 4141 and the rotation shaft 4145. Here, the center of rotation of the first jaw 4101 and the second jaw 4102 is the rotation shaft 4145, and the center of rotation of the pulley 4111 and the pulley 4121 is the rotation shaft 4141. Here, the rotation shaft 4141 is a shaft whose position is relatively fixed, and the rotation shaft 4145 is a shaft whose position linearly moves. In other words, when the pulley 4111 and the pulley 4121 rotate in a state in which the position of the rotation shaft 4141 is fixed, the first jaw 4101 and the second jaw 4102 are opened/closed as the rotation shaft 4145, which is the rotation shaft of the first jaw 4101 and the second jaw 4102, moves backward and forward.

With this configuration, the grip force becomes stronger when the first jaw 4101 and the second jaw 4102 are closed, thereby enabling a surgical operator to perform the actuation motion powerfully even with a weak force.

(Cartridge)

Hereinafter, the cartridge 4500 of the surgical instrument 4000 of FIG. 2 will be described in more detail.

Figure 27:
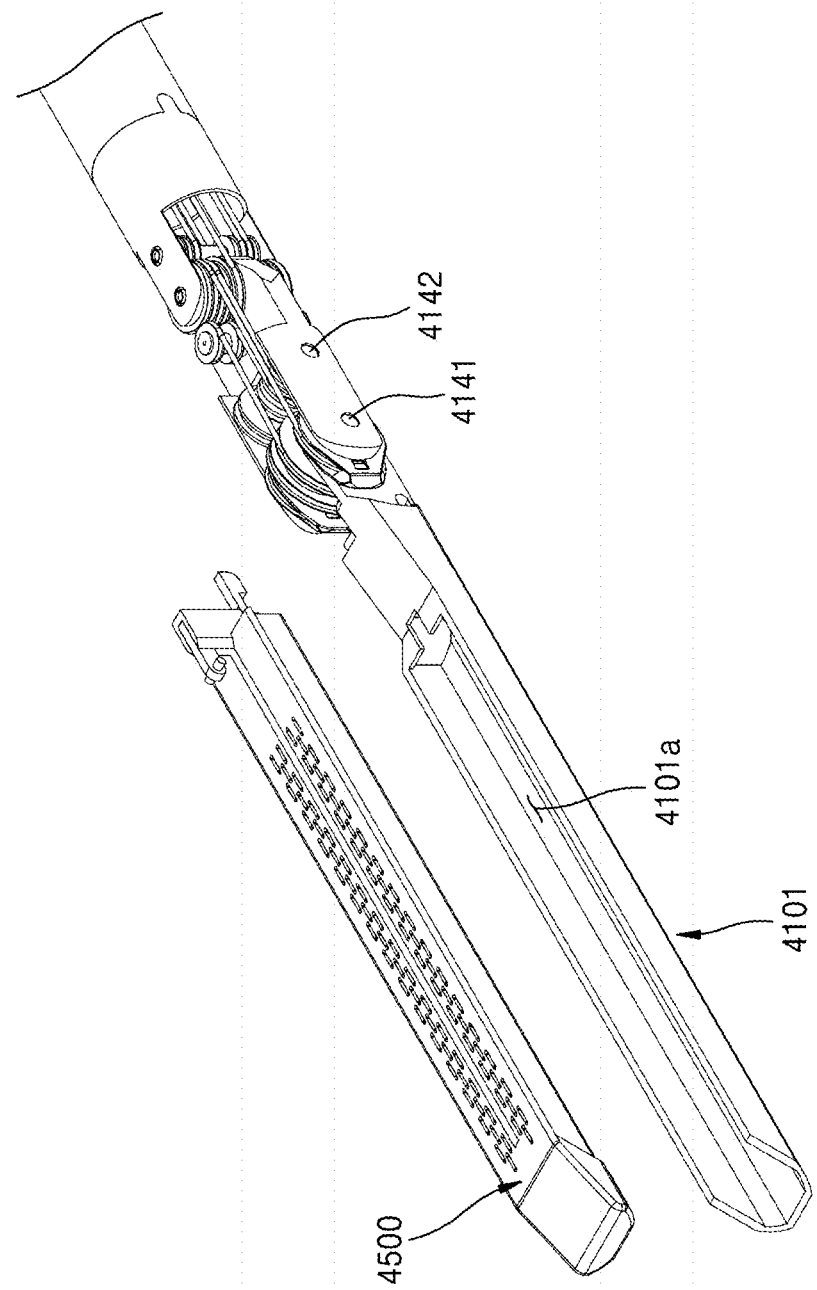
FIG. 27 is a perspective view illustrating the first jaw and a cartridge of the surgical instrument of FIG. 2.
Figure 28:
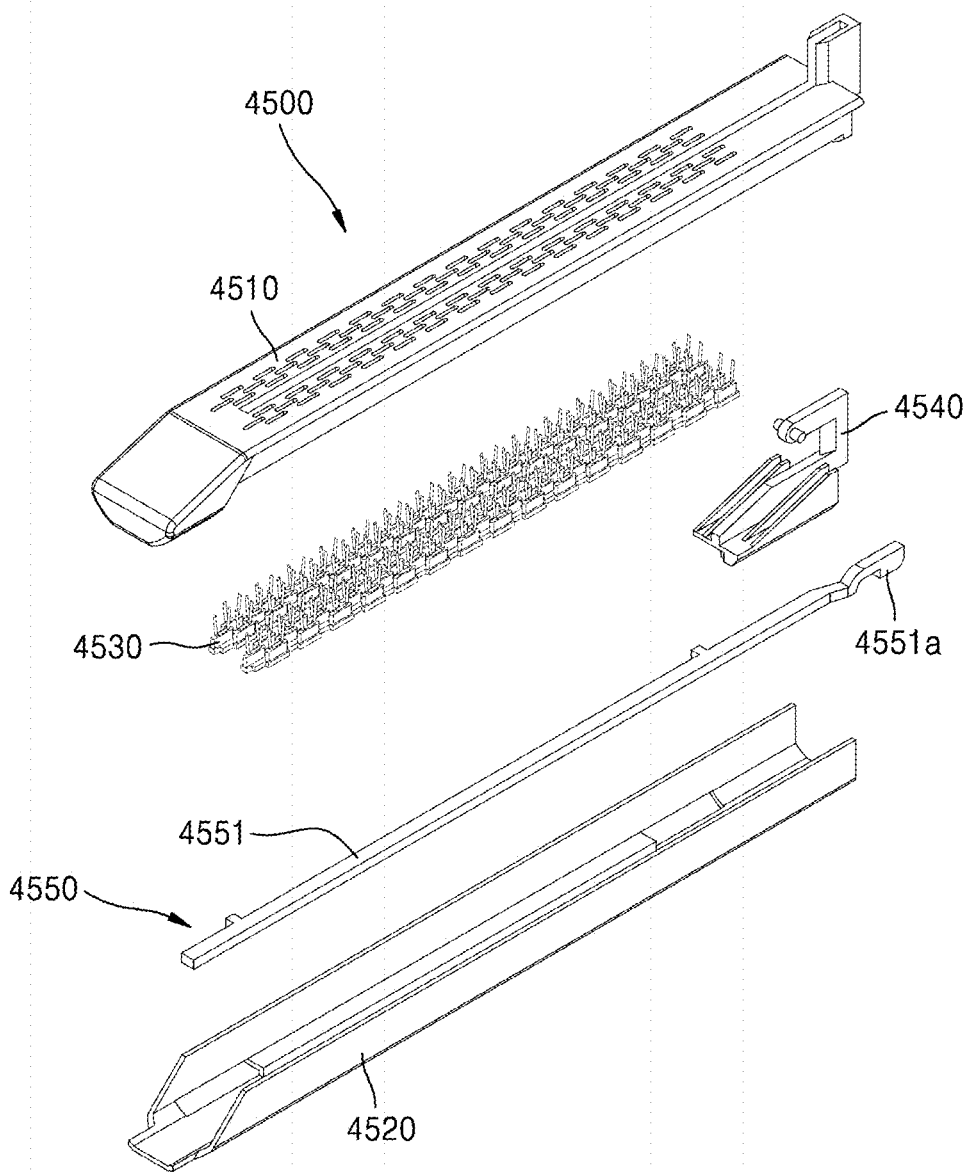
FIG. 28 is an exploded perspective view illustrating the cartridge of FIG. 27.
Figure 29:
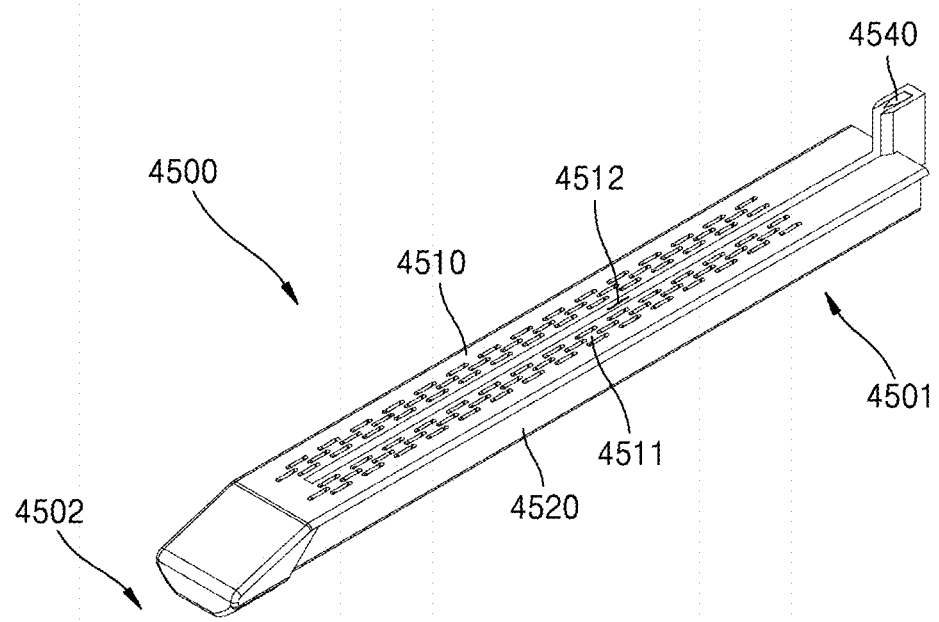
FIG. 29 is an assembled perspective view illustrating the cartridge of FIG. 27.
Figure 30:
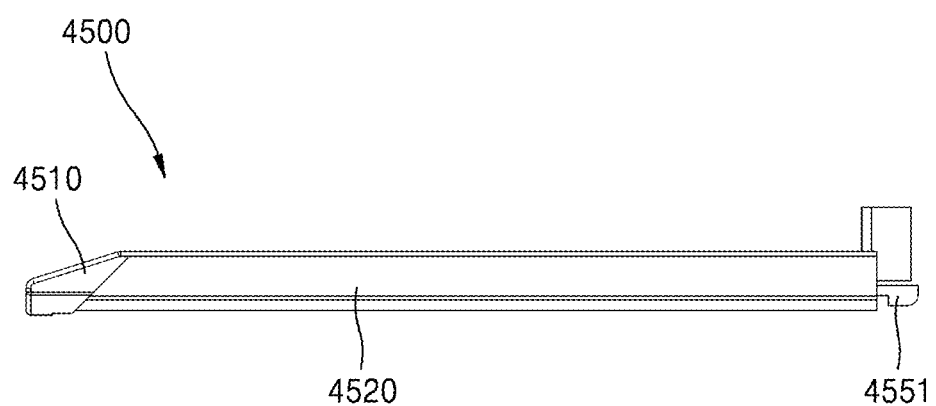
FIG. 30 is a side view illustrating the cartridge of FIG. 27.
Figure 31:
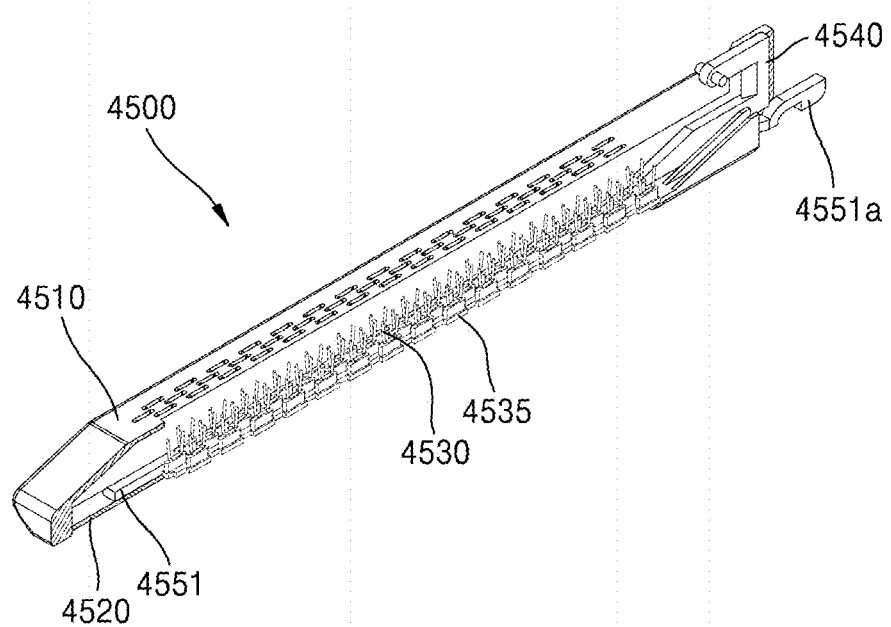
FIG. 31 is a perspective cross-sectional view illustrating the cartridge of FIG. 27.
Figure 32:
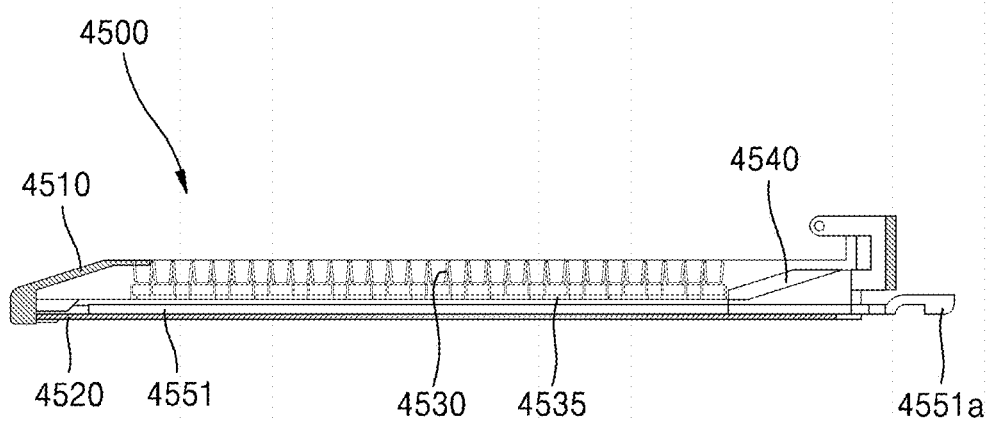
FIG. 32 is a side cross-sectional view illustrating the cartridge of FIG. 27.
Figure 33:
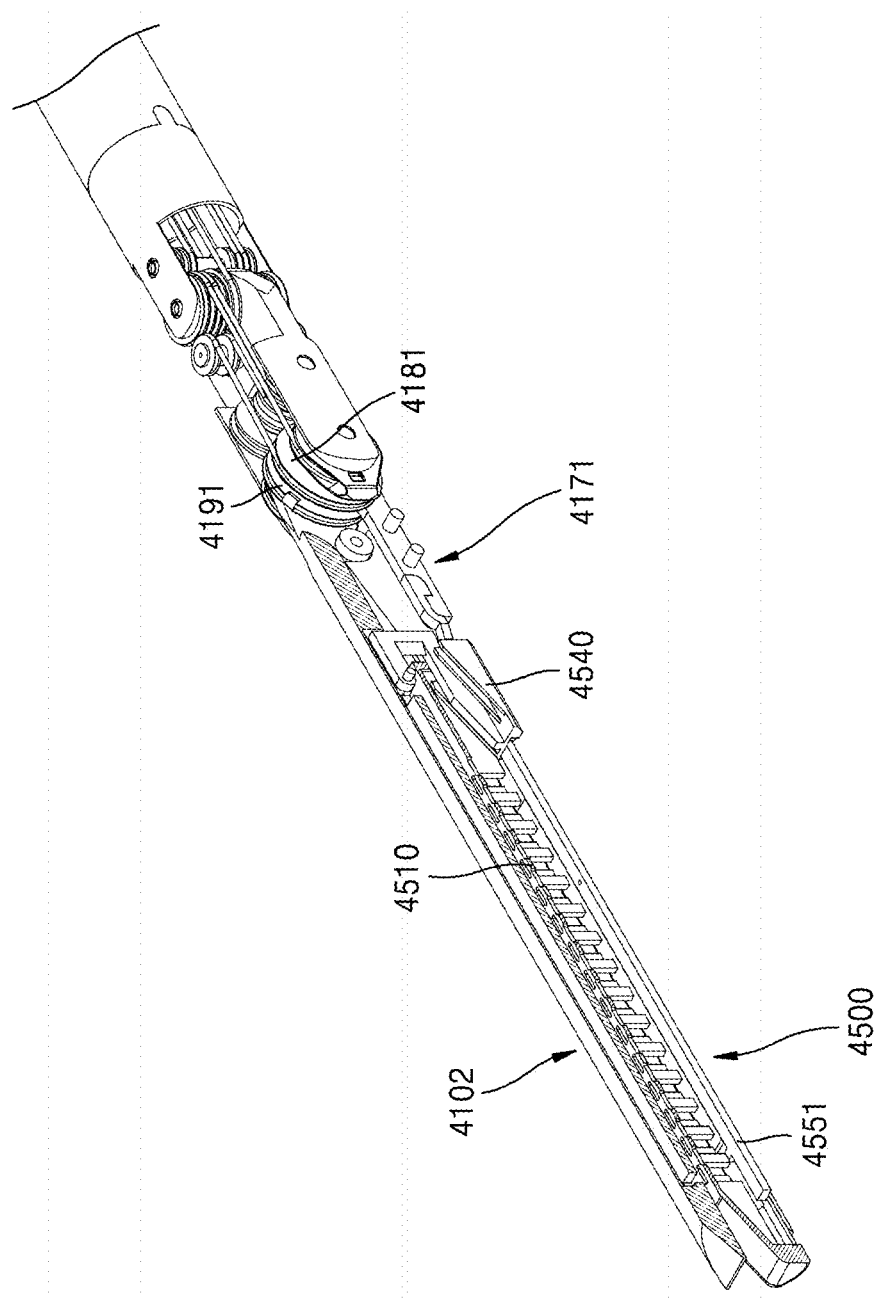
FIGS. 33 and 34 are perspective cross-sectional views illustrating a stapling structure of the end tool of the surgical instrument of FIG. 2.
Figure 34:
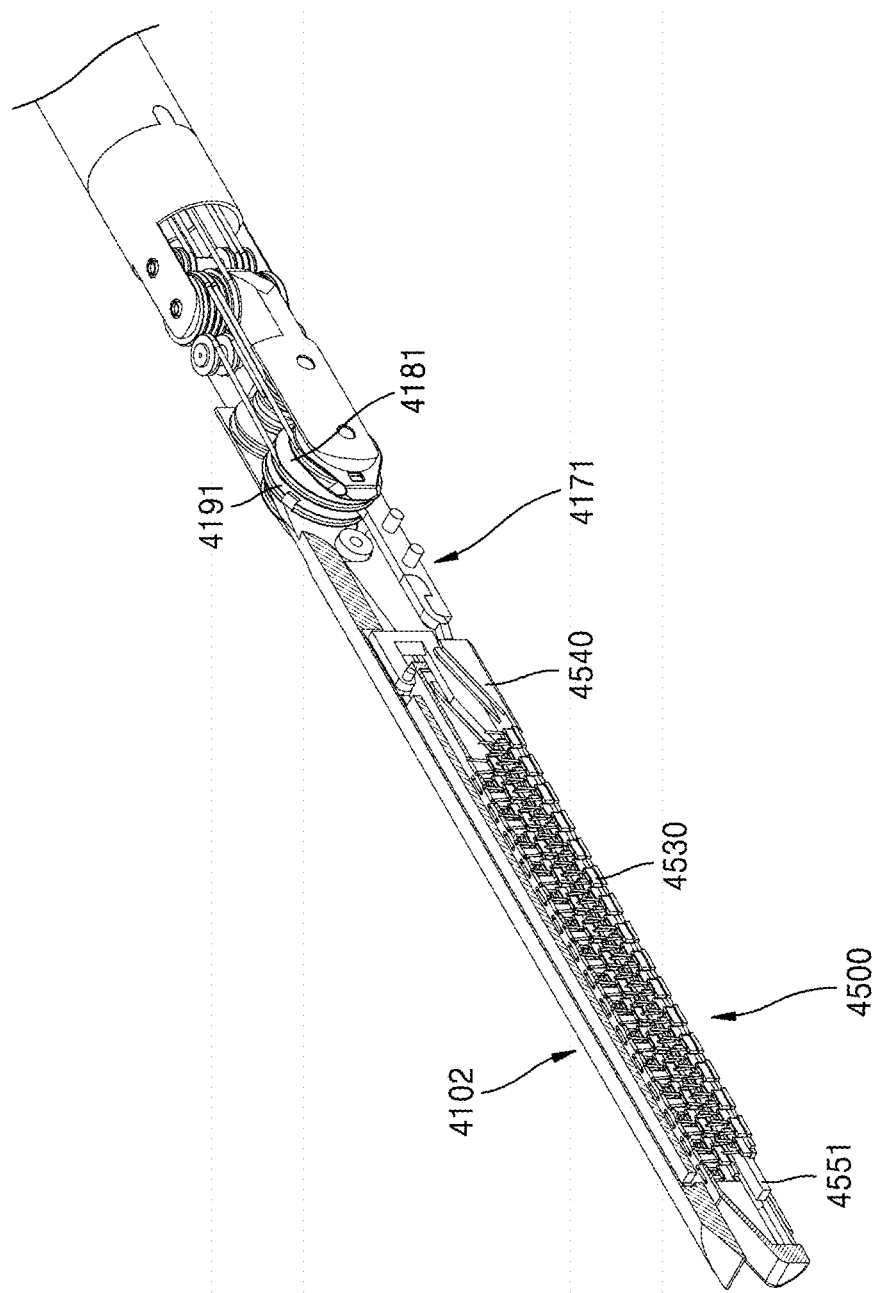
Figure 35:
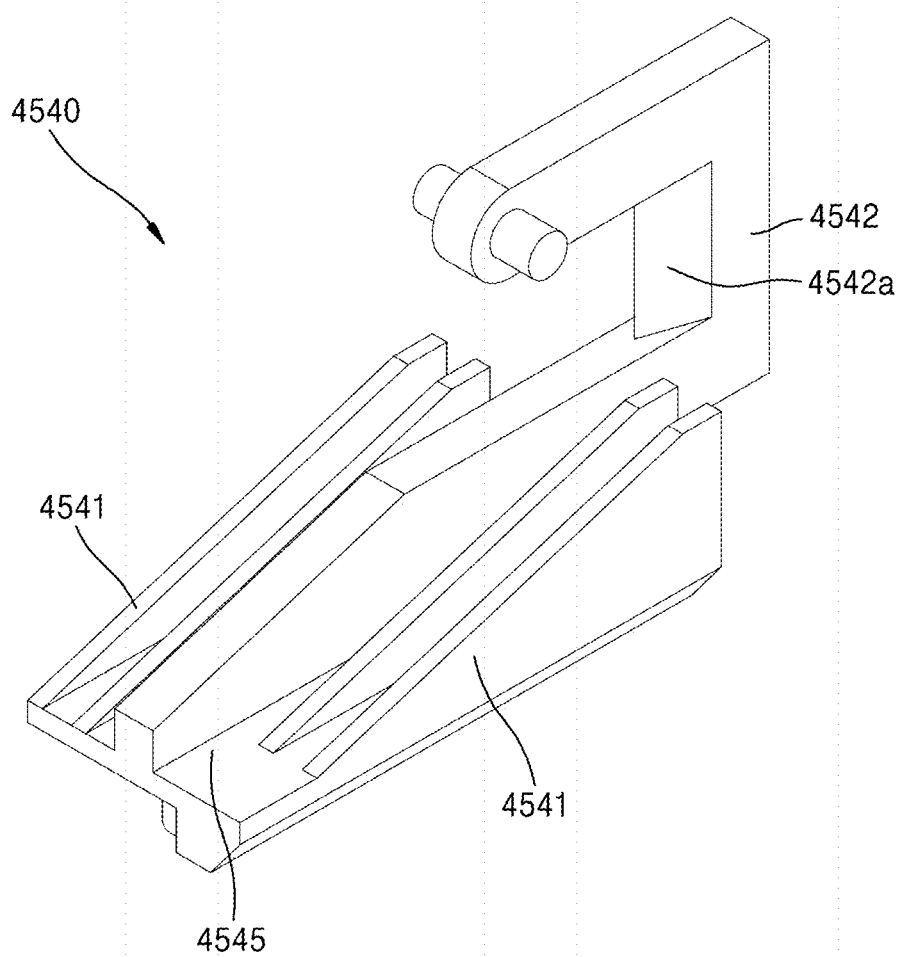
FIGS. 35 to 37 are perspective views illustrating an operation member of the cartridge of FIG. 27.
Figure 36:
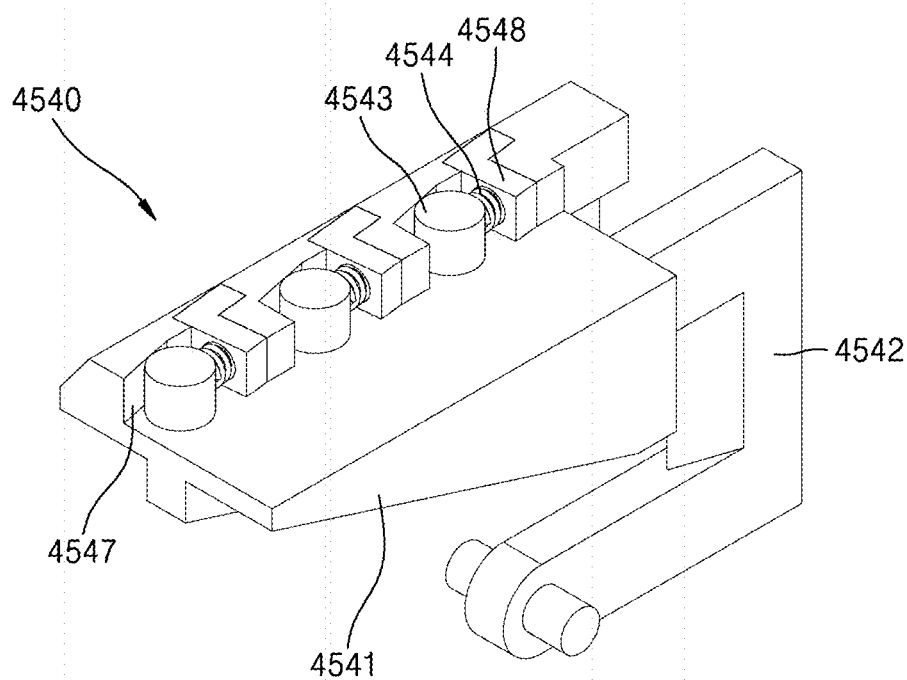
Figure 37:
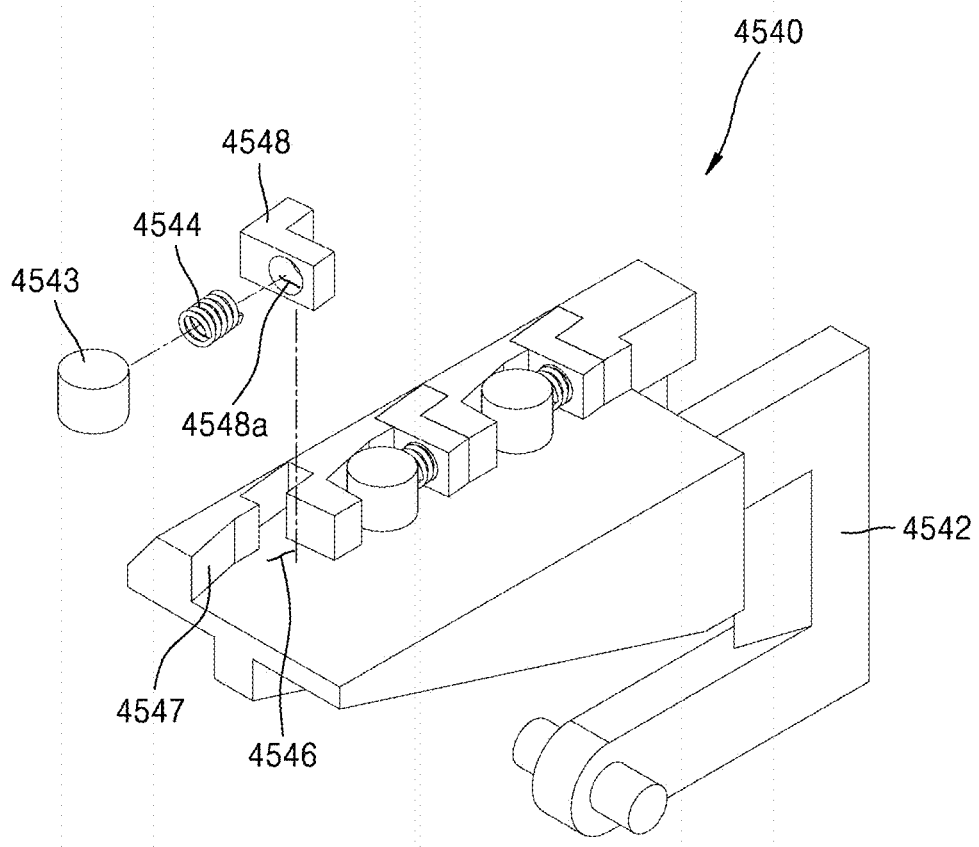
Figure 38:
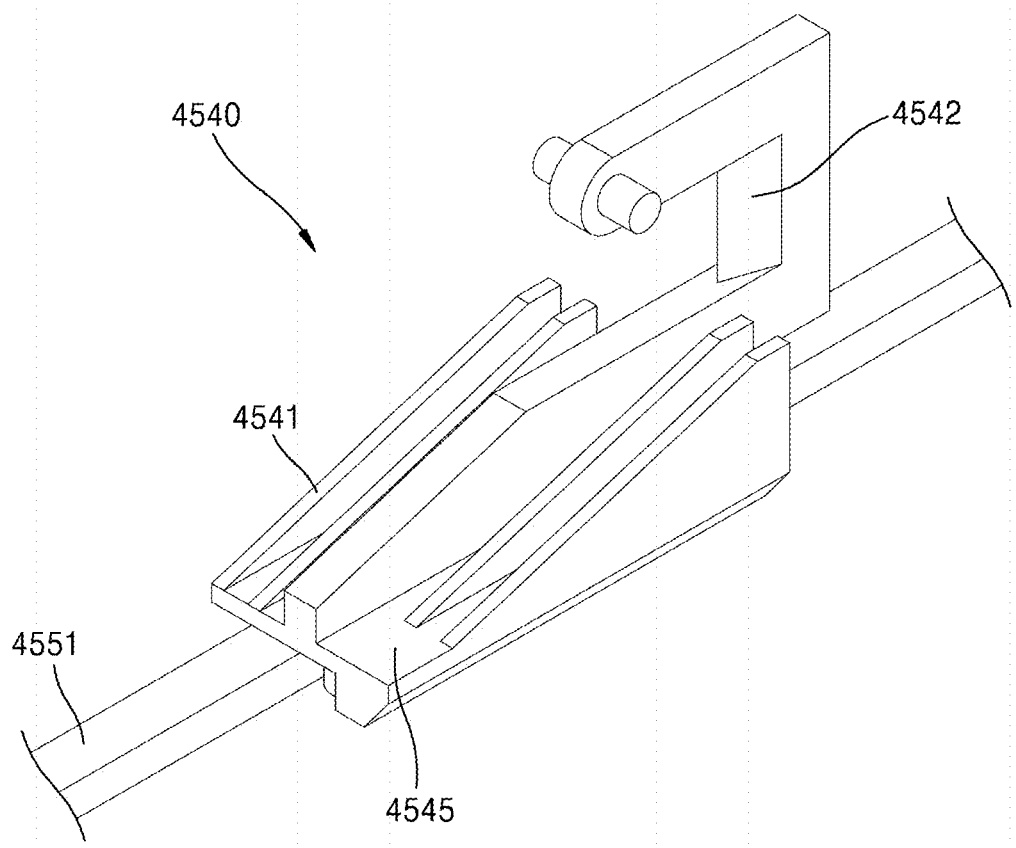
FIGS. 38 and 39 are perspective views illustrating a state in which the operation member of FIG. 35 is coupled to the reciprocating member.
Figure 39:
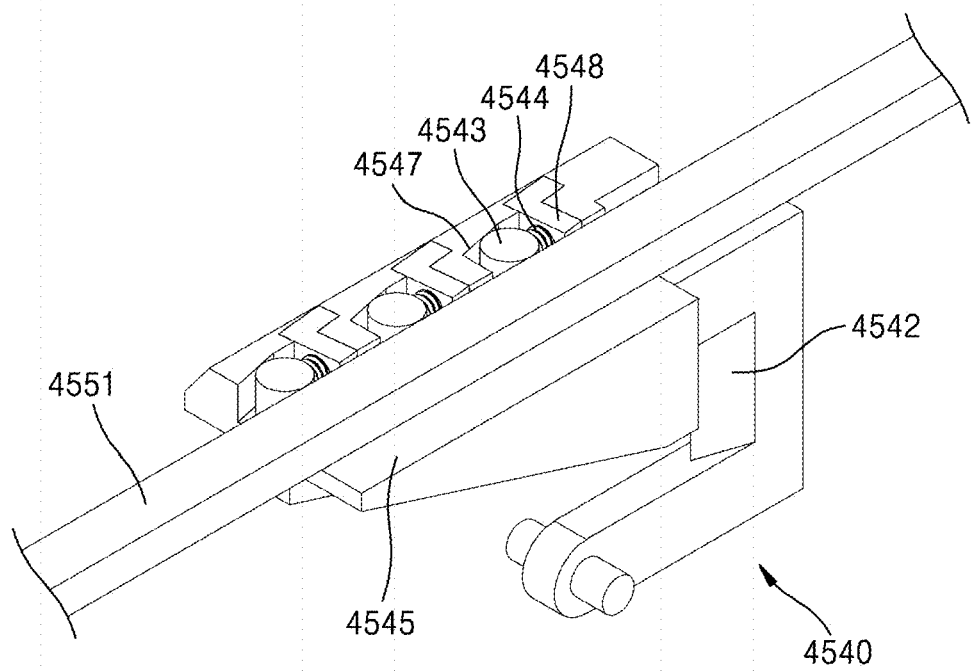
Figure 41A:
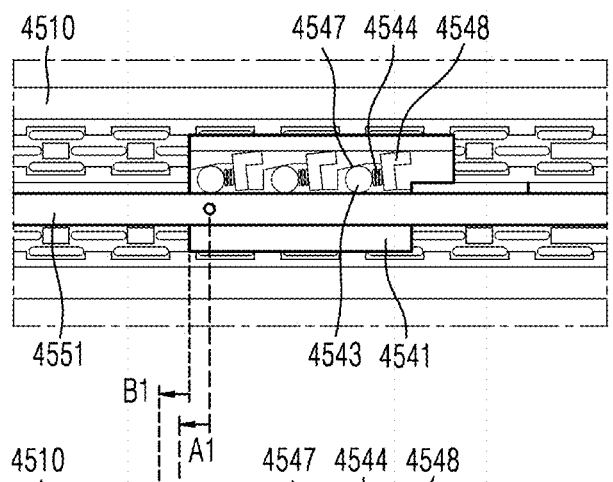
Figure 41B:
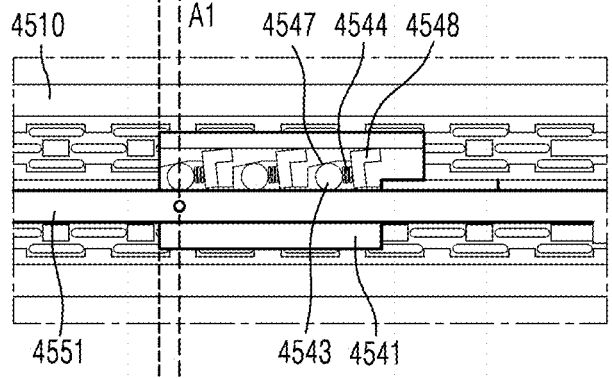
Figure 41C:
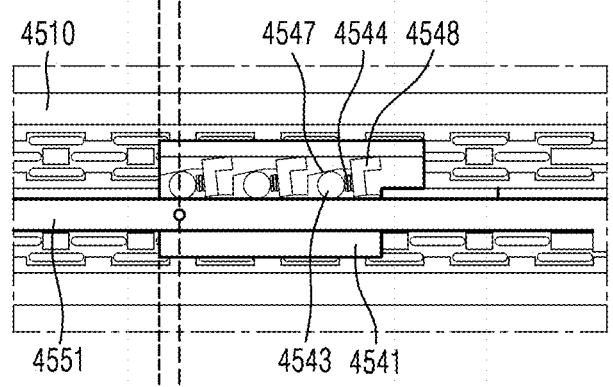
Figure 41D:
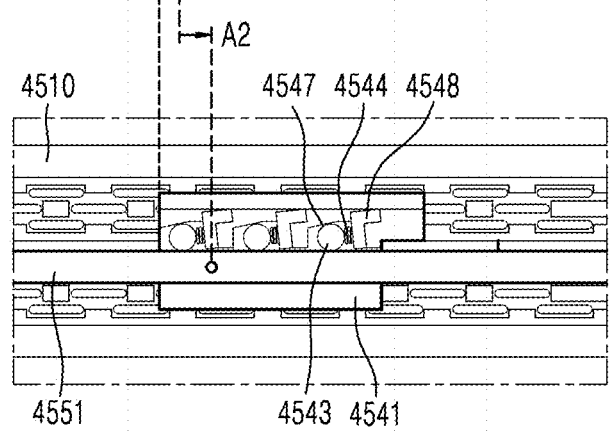
Figure 43A:
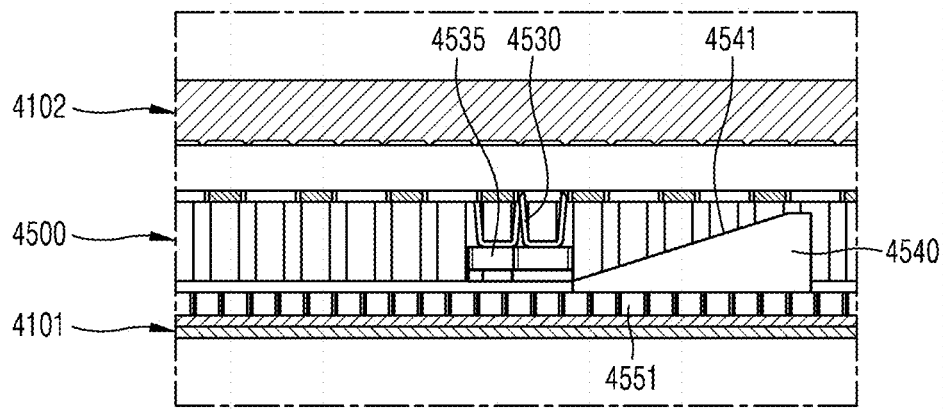
FIGS. 43A to 44 are perspective views illustrating an entire stapling motion of the end tool of FIG. 33.

FIG. 27 is a perspective view illustrating the first jaw and the cartridge of the surgical instrument of FIG. 2. FIG. 28 is an exploded perspective view illustrating the cartridge of FIG. 27. FIG. 29 is an assembled perspective view illustrating the cartridge of FIG. 27. FIG. 30 is a side view illustrating the cartridge of FIG. 27. FIG. 31 is a perspective cross-sectional view illustrating the cartridge of FIG. 27. FIG. 32 is a side cross-sectional view illustrating the cartridge of FIG. 27. FIGS. 33 and 34 are perspective cross-sectional views illustrating a stapling structure of the end tool of the surgical instrument of FIG. 2. FIGS. 35 to 37 are perspective views illustrating the operation member of the cartridge of FIG. 27. FIGS. 38 and 39 are perspective views illustrating a state in which the operation member of FIG. 35 is coupled to the reciprocating member. FIGS. 40A to 41D are plan views illustrating a clutch drive operation of the end tool of FIG. 33. FIGS. 42A to 42C are perspective views illustrating an entire clutch drive operation of the end tool of FIG. 33. FIGS. 43A to 44 are perspective views illustrating an entire stapling motion of the end tool of FIG. 33.

Referring to FIGS. 27 to 44 and the like, the cartridge 4500 is formed to be mountable to and dismountable from the first jaw 4101, and includes a plurality of staples 4530 and a blade 4542 therein to perform suturing and cutting of tissue. Here, the cartridge 4500 may include a cover 4510, a housing 4520, the staples 4530, withdrawal members 4535, the operation member 4540, and the reciprocating assembly 4550.

The housing 4520 forms an outer shape of the cartridge 4500, and may be formed entirely in the form of a hollow box with one surface (upper surface) thereof is removed to accommodate the reciprocating assembly 4550, the operation member 4540, and the staple 4530 therein. Here, the housing 4520 may be formed in an approximately "U" shape in cross section.

The cover 4510 is formed to cover the upper portion of the housing 4520. Staple holes 4511 through which the plurality of staples 4530 may be ejected to the outside may be formed in the cover 4510. As the staples 4530, which are accommodated inside the housing 4520 before a stapling operation, are pushed and raised upward by the operation member 4540 during a stapling motion, and pass through the staple holes 4511 of the cover 4510 to be withdrawn to the outside of the cartridge 4500, stapling is performed.

Meanwhile, a slit 4512 may be formed in the cover 4510 along a length direction of the cover 4510. The blade 4542 of the operation member 4540 may protrude out of the cartridge 4500 through the slit 4512. As the blade 4542 of the operation member 4540 passes along the slit 4512, staple-completed tissue may be cut.

The plurality of staples 4530 may be disposed inside the housing 4520. As the operation member 4540, which will be described later, is linearly moved in one direction, the plurality of staples 4530 are sequentially pushed and raised from the inside of the housing 4520 to the outside, thereby performing suturing, that is, stapling. Here, the staples 4530 may be made of a material that may include titanium, stainless steel, or the like.

Meanwhile, the withdrawal member 4535 may be further disposed between the housing 4520 and the staple 4530. In other words, it may be said that the staple 4530 is disposed above the withdrawal member 4535. In this case, the operation member 4540 is linearly moved in one direction to push and raise the withdrawal member 4535, and the withdrawal member 4535 may push and raise the staple 4530.

As such, the operation member 4540 may be described as pushing and raising the staples 4530 in both the case in which the operation member 4540 directly pushes and raises the staples 4530 and the case in which the operation member 4540 pushes and raises the withdrawal members 4535 and the withdrawal members 4535 pushes and raises the staples 4530 (i.e., the operation member 4540 indirectly pushes and raises the staples 4530).

The reciprocating assembly 4550 may be disposed at an inner lower side of the housing 4520. The reciprocating assembly 4550 may include one or more reciprocating members 4551. In the present embodiment, it is illustrated that one reciprocating member 4551 is provided, but in other embodiments, a plurality of reciprocating members 4551 may be provided.

In the present embodiment, the reciprocating member 4551 may be a bar. In detail, the reciprocating member 4551 may be formed in the form of a substantially elongated hexahedron whose surface is formed in a smooth shape in which recesses or saw teeth are not formed. The bar-shaped reciprocating member 4551 may be formed to be in contact with the operation member 4540, which will be described later, and specifically, with a contact member 4543 of the operation member 4540.

Meanwhile, although not shown in the drawings, in addition to a bar shape, the reciprocating member 4551 may be provided as various shapes of members, which are directly or indirectly connected to the staple pulley assembly 4160 and may perform a linear reciprocating motion according to a rotational motion of the staple pulley assembly 4160. For example, the reciprocating member 4551 may be in the form of a ratchet in which recesses are formed.

Here, the reciprocating member 4551 is not fixedly coupled to the other components of the cartridge 4500, and may be formed to be movable relative to the other components of the cartridge 4500. That is, the reciprocating member 4551 may perform a reciprocating linear motion with respect to the housing 4520 and the cover 4510 coupled to the housing 4520.

Meanwhile, in the reciprocating member 4551, the coupling part 4551a may be formed at a proximal end 4501 side adjacent to the pulley 4111, and the coupling part 4551*a* may be fastened and coupled to the staple link assembly 4170 of the end tool 4100. Thus, when the staple link assembly 4170 performs a reciprocating linear motion in the extension direction (i.e., the Y-axis direction) of the connection part 400, the reciprocating member 4551 coupled thereto may also perform a reciprocating linear motion in the extension direction (i.e., the Y-axis direction) of the connection part 400. This will be described in more detail later.

The operation member 4540 may be disposed inside the housing 4520. The operation member 4540 is formed to be in contact with the reciprocating member 4551, and may be formed to linearly move in one direction according to a reciprocating linear motion of the reciprocating member 4551. In other words, the operation member 4540 interacts with the reciprocating member 4551 to perform stapling and cutting motions while moving in the extension direction of the connection part 400.

The operation member 4540 may include a wedge 4541, the blade 4542, the contact member 4543, an elastic member 4544, and a body 4545. In addition, the operation member 4540 may further include a holder 4548.

The body 4545 may be formed in the shape of an elongated square column, and forms a base of the operation member 4540.

An accommodation part 4546 and an inclined part 4547 may be formed on the body 4545.

In detail, a plurality of accommodation parts 4546 may be formed on a lower surface of the body 4545, and the contact member 4543, the elastic member 4544, and the holder 4548, which will be described later, may be accommodated in each of the accommodation parts 4546.

Here, at least a portion of the accommodation part 4546 is formed in a shape substantially the same as or similar to that of the holder 4548, so that the position of the holder 4548 may be fixed once the holder 4548 is fitted into the accommodation part 4546. In addition, a through hole 4548*a* may be formed in the holder 4548, and the elastic member 4544 may be fitted into the through hole 4548*a*.

In addition, the inclined part 4547 may be formed on one surface of each of the accommodation parts 4546. The inclined part 4547 may be formed such that a width of the accommodation part 4546 becomes narrower toward a distal end 4502 of the cartridge 4500. That is, the inclined part 4547 may be formed to be closer to the reciprocating member 4551 as it approaches the distal end 4502 of the cartridge 4500. In addition, the contact member 4543 may be formed to be moved by a certain extent in the accommodation part 4546, and may be formed to be in contact with the inclined part 4547 depending on the position thereof.

The accommodation part 4546 and the inclined part 4547 will be described in more detail below.

The wedge 4541 is formed on at least one side of the body 4545, and may be formed to have a predetermined inclined surface. That is, the wedge 4541 may be formed to be inclined to a certain extent in the extension direction of the connection part 400. In other words, the wedge 4541 may be formed to have a greater height at a proximal end 4501 side of the cartridge 4500 than the distal end 4502 side of the cartridge 4500. In the drawing, it is illustrated that two wedges 4541 are formed on each side of the body 4545, but the concept of the present disclosure is not limited thereto, and the wedge 4541 may be formed in various numbers and shapes depending on the shape of the staple 4530 or the withdrawal member 4535 that is in contact with the wedge 4541.

Figure 49:
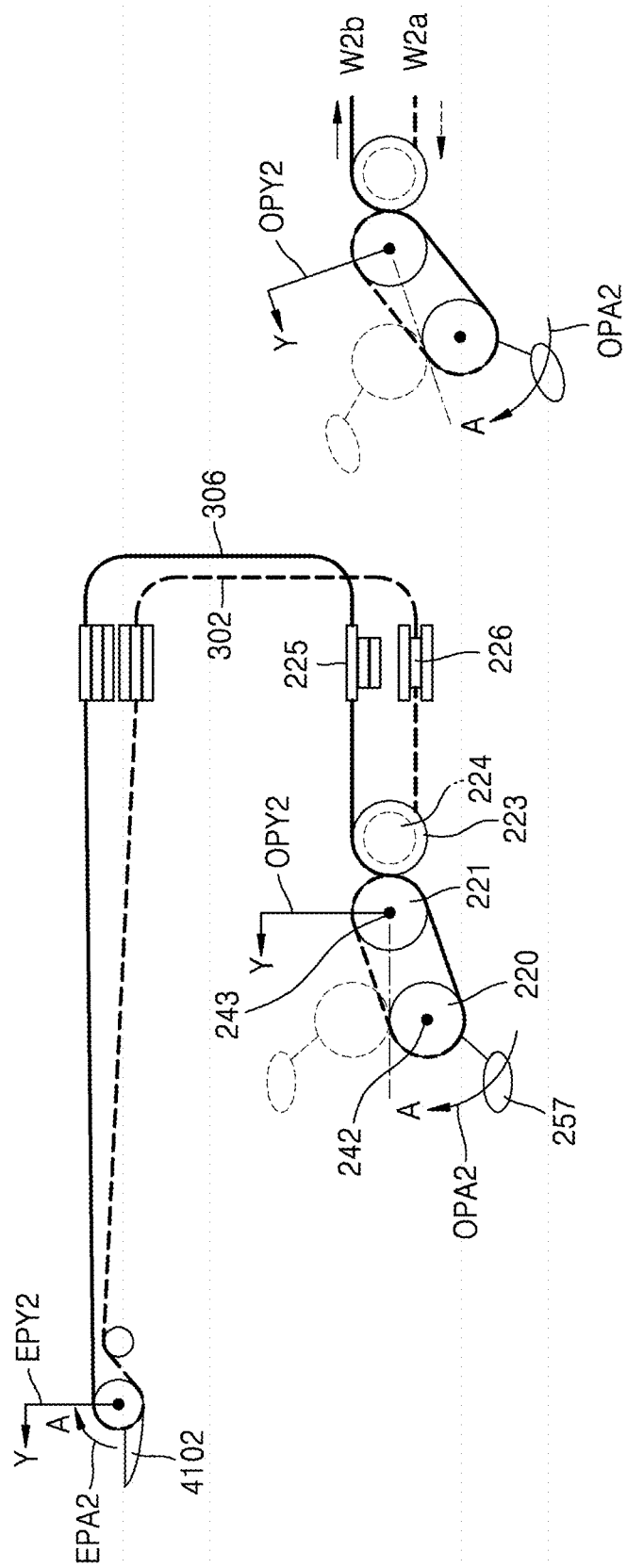
FIGS. 49 and 50 are diagrams illustrating a configuration of pulleys and wires, which are related to an actuation motion and a yaw motion of the surgical instrument illustrated in FIG. 2, in detail for each of the first jaw and the second jaw.

The wedge 4541 may be formed to be in contact with the withdrawal members 4535 or the plurality of staples 4530 in turn and may serve to sequentially push and raise the staples 4530. As shown in FIG. 49 to be described later and elsewhere herein, the operation member 4540 may serve to withdraw the staples 4530 to the outside of the cartridge 4500 by sequentially pushing and raising the staples 4530 while moving toward the distal end 4502.

The blade 4542 may be formed at one side of the wedge 4541, more specifically, at one side of the wedge 4541 at the proximal end 4501 side. An edge 4542*a* formed to be sharp to cut tissue is formed in one region of the blade 4542. As at least a portion of the edge 4542*a* is withdrawn to the outside of the first jaw 4101 and the cartridge 4500, tissue disposed between the first jaw 4101 and the second jaw 4102 may be cut. The edge 4542*a* of the blade 4542 may be always withdrawn to the outside of the first jaw 4101. Alternatively, the edge 4542*a* of the blade 4542 may normally be accommodated inside the first jaw 4101 or inside the cartridge 4500, and may be withdrawn to the outside of the first jaw 4101 only when the operation member 4540 is moved in a length direction.

The contact member 4543 is formed at one side of the body 4545, more specifically, under the body 4545, and may be formed to face the reciprocating member 4551 to be described later. The contact member 4543 may be formed in the form of a roller, and may be formed to be in contact with the inclined part 4547 of the body 4545 and the reciprocating member 4551. In more detail, the contact member 4543 may be formed to be always in contact with the reciprocating member 4551 by being pressed by the elastic member 4544 to be described later. Meanwhile, the contact member 4543 may be formed to be in contact with or spaced apart from the inclined part 4547 of the body 4545.

Here, in a state in which the contact member 4543 is simultaneously in contact with the inclined part 4547 of the body 4545 and the reciprocating member 4551, the state becomes a kind of locked state, and thus when the reciprocating member 4551 is moved in one direction, the moving member 4540 including the contact member 4543 entirely moves in the one direction together with the reciprocating member 4551.

On the other hand, in a state in which the contact member 4543 is in contact with only the reciprocating member 4551 and is spaced apart from the inclined part 4547 of the body 4545 by a certain extent, the state becomes a kind of unlocked state, and thus, even when the reciprocating member 4551 is moved in the opposite direction, the moving member 4540 remains stationary without moving.

The elastic member 4544 is formed between the body 4545 and the contact member 4543 and serves to apply a predetermined elastic force to the contact member 4543. In an example, the elastic member 4544 may be formed such that one region is in contact with the accommodation part 4546 of the body 4545, and another region is in contact with the contact member 4543. In this case, in order to guide the position of the elastic member 4544, the holder 4548 may be disposed in the accommodation part 4546, and the elastic member 4544 may be fitted into the holder 4548. Here, the elastic member 4544 may apply an elastic force in a direction in which the contact member 4543 comes into close contact with the inclined part 4547. To this end, the elastic member 4544 may be formed in the form of a coil spring, and may also be provided in various forms capable of providing a predetermined elastic force to the contact member 4543, such as a leaf spring, a dish spring, and the like.

In the first embodiment of the present disclosure, the reciprocating assembly 4550 and the operation member 4540 configure a kind of one-way clutch, in particular, a roller clutch.

In detail, when the reciprocating member 4551 is moved forward toward the distal end 4502 of the cartridge 4500, the movement of the reciprocating member 4551 is transmitted to the operation member 4540 due to a frictional force caused by the fitting, so that the reciprocating member 4551 and the operation member 4540 are moved together toward the distal end 4502 of the cartridge 4500.

On the other hand, when the reciprocating member 4551 is moved backward toward the proximal end 4501 of the cartridge 4500, the contact member 4543 rolls with respect to the inclined part 4547 of the operation member 4540 or is spaced apart from the inclined part 4547 by a certain extent, so that the movement of the reciprocating member 4551 is not transmitted to the operation member 4540, and only the reciprocating member 4551 is alone moved toward the proximal end 4501 of the cartridge 4500, and the operation member 4540 does not move. This will be described below in more detail.

The body 4545 of the operation member 4540 and the reciprocating member 4551 are formed to be movable relative to each other. That is, the reciprocating member 4551 is formed to be movable along a length direction of the shaft relative to the body 4545.

The contact member 4543 is disposed between the inclined part 4547 of the body 4545 and the reciprocating member 4551, and depending on the position of the contact member 4543, the reciprocating member 4551 may be in a state of movable relative to the operation member 4540, or in a state in which relative movement is blocked.

Here, a spacing between the inclined part 4547 of the body 4545 and the reciprocating member 4551 may decrease in one direction. In detail, the inclined part 4547 of the body 4545 is disposed to face the reciprocating member 4551 with the contact member 4543 interposed therebetween.

Here, the inclined part 4547, which is an upper inner surface of the accommodation part 4546 formed inside the body 4545, is formed to be inclined to a certain extent so that the spacing between the inclined part 4547 and the reciprocating member 4551 is changed in a predetermined section.

Accordingly, in the predetermined section, the contact member 4543 disposed between the inclined part 4547 and the reciprocating member 4551 may be formed to be simultaneously in contact with the inclined part 4547 and the reciprocating member 4551.

In addition, except for the section in which the contact member 4543 is simultaneously in contact with the inclined part 4547 and the reciprocating member 4551, the contact member 4543 may be disposed to be in contact with only one of the inclined part 4547 and the reciprocating member 4551. In addition, the reciprocating member 4551 is formed to be movable relative to the body 4545 unless the contact member 4543 is not in contact with the inclined part 4547 and the reciprocating member 4551 at the same time.

Alternatively, even when the contact member 4543 is simultaneously in contact with the inclined part 4547 and the reciprocating member 4551, the reciprocating member 4551 may be formed to be movable relative to the body 4545 since the contact member 4543 is in contact with the inclined part 4547 of the operation member 4540 just enough to roll with respect to the inclined part 4547.

Referring to FIG. 37 or the like, in the surgical instrument 4000 according to the first embodiment of the present disclosure, a spacing between one surface of the inclined part 4547 and one surface of the reciprocating member 4551 may decrease toward the distal end 4502 of the cartridge 4500.

Specifically, based on a right end portion (based on FIG. 37) of the inclined part 4547, the spacing between one surfaces of the inclined part 4547 and the reciprocating member 4551, which are facing each other, may decrease toward (in a direction from right to left based on FIG. 37 seen from a paper side) the distal end 4502. That is, a spacing between an upper surface of the reciprocating member 4551, which is formed to be flat, and an inner surface of the inclined part 4547 facing the upper surface may decrease from one end portion of the reciprocating member 4551 toward the other end portion thereof.

Meanwhile, the elastic member 4544 may be formed to press the contact member 4543 in a direction in which the spacing between the inclined part 4547 and the reciprocating member 4551 decreases.

Here, in the present disclosure, the contact member 4543 is disposed between the inclined part 4547 and the reciprocating member 4551, and when the reciprocating member 4551 is moved toward the distal end 4502 of the cartridge 4500, the contact member 4543 may be simultaneously brought into contact with the inclined part 4547 and the reciprocating member 4551.

In the first embodiment of the present disclosure, the reciprocating member 4551 is formed to be flat, and the inclined part 4547 facing the reciprocating member 4551 may be formed to form an acute angle with an axis of the reciprocating member 4551 in a horizontal direction that is a moving direction of the reciprocating member 4551.

In an example, referring to FIG. 37 or the like, the inclined part 4547 facing the reciprocating member 4551 may be formed to be inclined downward from the right to the left based on one end portion (a right end portion based on FIG. 37) of the accommodation part 4546 on which the holder 4548 is disposed.

That is, when the spacing between the inclined part 4547 and the reciprocating member 4551 decreases toward the left based on one end portion (the right end portion) of the accommodation part 4546, and the contact member 4543 moving between the inclined part 4547 and the reciprocating member 4551 is moved toward the distal end 4502 of the cartridge 4500, the contact member 4543 is simultaneously brought into contact with the inclined part 4547 and the reciprocating member 4551.

At this time, a frictional force is generated between the contact member 4543 and the inclined part 4547, and the reciprocating member 4551. At this time, when the reciprocating member 4551 is moved toward the distal end 4502 of the cartridge 4500 by an external force, the contact member 4543 is also moved toward the distal end 4502 of the cartridge 4500 together with the reciprocating member 4551 by the frictional force between the contact member 4543 and the reciprocating member 4551.

In addition, as the contact member 4543 is moved toward the distal end 4502, the frictional force between the contact member 4543 and the inclined part 4547, and the reciprocating member 4551 may be increased to a greater extent by the inner surface of the inclined part 4547 inclined downward at a predetermined angle. As a result, the force by which the reciprocating member 4551 is moved toward the distal end 4502 of the cartridge 4500 is efficiently transmitted to the operation member 4540 through the contact member 4543.

That is, when the contact member 4543 is simultaneously in contact with the inclined part 4547 of the operation member 4540 and the reciprocating member 4551, as the reciprocating member 4551 is moved toward the distal end 4502, the operation member 4540 is sandwiched between the inclined part 4547 and the reciprocating member 4551, and as a result, the force by which the reciprocating member 4551 is moved toward the distal end 4502 of the cartridge 4500 is efficiently transmitted to the operation member 4540.

Meanwhile, even when the contact member 4543 is simultaneously in contact with the inclined part 4547 and the reciprocating member 4551, when the reciprocating member 4551 is moved toward the proximal end 4501 of the cartridge 4500, the contact member 4543 is also moved toward the proximal end 4501 of the cartridge 4500 by the frictional force between the contact member 4543 and the reciprocating member 4551.

In addition, as the contact member 4543 is moved toward the proximal end 4501, the contact member 4543 is spaced apart from the inner surface of the inclined part 4547, which is further inclined to the left, so that, unlike the previous case, the force by which the reciprocating member 4551 is moved toward the distal end 4502 is not efficiently transmitted to the operation member 4540.

That is, when the reciprocating member 4551 is moved toward the distal end 4502 of the cartridge 4500, the movement of the reciprocating member 4551 is transmitted to the operation member 4540 due to the frictional force caused by the fitting, so that the reciprocating member 4551 and the operation member 4540 are moved together toward the distal end 4502 of the cartridge 4500.

On the other hand, when the reciprocating member 4551 is moved toward the proximal end 4501 of the cartridge 4500, the contact member 4543 rolls with respect to the inclined part 4547 of the operation member 4540 or is spaced apart from the inclined part 4547 by a certain extent, so that the movement of the reciprocating member 4551 is not transmitted to the operation member 4540, and only the reciprocating member 4551 is alone moved toward the proximal end 4501 of the cartridge 4500, and the operation member 4540 does not move.

With this configuration, the operation member 4540 including the contact member 4543 and the inclined part 4547, and the reciprocating member 4545 constitute a kind of one-way clutch, allowing movement in only one direction.

In an example, when the reciprocating member 4551 is moved toward the distal end 4502 in a state in which the contact member 4543 is in contact with the reciprocating member 4551 and the inclined part 4547, the operation member 4540 including the contact member 4543 is moved toward the distal end 4502 together with the reciprocating member 4551 by the reciprocating member 4551. That is, the reciprocating member 4551 pushes the contact member 4543 and the operation member 4540 together such that the operation member 4540 is moved in the direction of the distal end 4502.

In contrast, in a state in which the contact member 4543 is in contact with the reciprocating member 4551 and the inclined part 4547, when the reciprocating member 4551 is moved toward the proximal end 4501, only the reciprocating member 4551 is alone moved toward the proximal end 4501 while the contact member 4543 remains stationary. That is, when the reciprocating member 4551 is moved toward the proximal end 4501, the contact member 4543 rolls with respect to the inclined part 4547 of the operation member 4540 or is spaced apart from the inclined part 4547 by a certain extent, so that the movement of the reciprocating member 4551 is not transmitted to the operation member 4540, and only the reciprocating member 4551 is alone moved toward the proximal end 4501 of the cartridge 4500, and the operation member 4540 does not move.

From another perspective, when the reciprocating member 4551 is moved toward the distal end 4502 of the cartridge 4500, it may be said that the contact member 4543 is in a fitted state between the reciprocating member 4551 and the operation member 4540, and the relative movement between the reciprocating member 4551 and the operation member 4540 is blocked.

In contrast, when the reciprocating member 4551 is moved toward the proximal end 4501 of the cartridge 4500, it may be said that the contact member 4543 is released from the fitted state between the reciprocating member 4551 and the operation member 4540, and the relative movement between the reciprocating member 4551 and the operation member 4540 is possible.

As a result, the cartridge 4500 is accommodated in the cartridge accommodation part 4101a of the first jaw 4101, and in this case, the reciprocating member 4551 of the cartridge 4500 is coupled to the staple link assembly 4170 of the end tool 4100. Thus, a rotational motion of the first staple pulley 4181 and the second staple pulley 4191 of the end tool 4100 is converted into a linear motion of the reciprocating member 4551 through the staple link assembly 4170.

In this case, when the coupling part 4551a of the reciprocating member 4551 is connected to the staple pulley assembly 4160 through the staple link assembly 4170, and the first staple pulley 4181 and the second staple pulley 4191 of the staple pulley assembly 4160 are alternately rotated in the clockwise/counterclockwise directions, the reciprocating member 4551 may be repeatedly moved forward and backward. In addition, when the reciprocating member 4551 is moved forward, the operation member 4540 may be moved forward together with the reciprocating member 4551, and when the reciprocating member 4551 is moved backward, only the reciprocating member 4551 may be moved backward and the operation member 4540 may remain stationary in place. As the operation member 4540 is moved forward while repeating this process, the staple 4530 may be stapled by the wedge 4541 while the blade 4542 cuts stapled tissue.

This will be described in more detail as follows.
(Stapling and Cutting Motions)

Referring to FIGS. 42A to 42C, a method of driving the surgical instrument according to an embodiment of the present disclosure is described as follows.

First, when the first staple pulley 4181 is rotated in the clockwise direction and the second staple pulley 4191 is rotated in the counterclockwise direction, the staple link assembly 4170 connected to the staple pulley assembly 4160 and the reciprocating assembly 4550 of the cartridge 4500 connected to the staple link assembly 4170 are moved toward the distal end 4502 of the cartridge 4500.

In addition, when the reciprocating assembly 4550 is moved toward the distal end 4502 of the cartridge 4500, the operation member 4540 in contact with the reciprocating assembly 4550 is moved toward the distal end 4502 of the cartridge 4500 together with the reciprocating assembly 4550.

In addition, as the operation member 4540 is moved toward the distal end 4502 of the cartridge 4500, the blade 4542 of the operation member 4540 is moved toward the distal end 4502 of the cartridge 4500 while the operation member 4540 ejects the staples 4530 out of the cartridge 4500.

Meanwhile, when the first staple pulley 4181 is rotated in the counterclockwise direction and the second staple pulley 4191 is rotated in the clockwise direction, the reciprocating assembly 4550 of the staple link assembly 4170 connected to the staple pulley assembly 4160 and the cartridge 4500 connected to the staple link assembly 4170 are moved toward the proximal end 4501 of the cartridge 4500, and at this time, the operation member 4540 remains stationary.

In addition, as the above operations are repeatedly performed, a stapling motion by the wedge 4541 and a cutting motion by the blade 4542 are simultaneously performed.

This will be described in more detail as follows.

First, in the state as shown in FIG. 42A, as shown in FIG. 42B, when the first staple pulley 4181 is rotated in the direction of an arrow A1 (i.e., in the clockwise direction) and the second staple pulley 4191 is rotated in the direction of an arrow B1 (i.e., in the counterclockwise direction), the staple link assembly 4170 connected to the first and second staple pulleys 4181 and 4191 and the reciprocating member 4551 coupled to the staple link assembly 4170 are moved in the direction of an arrow C1 (i.e., toward the distal end) In this state, since the reciprocating member 4551 and the contact member 4543 of the operation member 4540 are in close contact with each other by the elastic member (see 4544 of FIGS. 40A to 40E), when the reciprocating member 4551 is moved in the direction of the arrow C1, the operation member 4540 is moved in the direction of an arrow D1 together with the reciprocating member 4551.

On the other hand, as shown in FIG. 42C, when the first staple pulley 4181 is rotated in the direction of an arrow A2 (i.e., in the counterclockwise direction) and the second staple pulley 4191 is rotated in the direction of an arrow B2 (i.e., in the clockwise direction), the staple link assembly 4170 connected to the first and second staple pulleys 4181 and 4191 and the reciprocating member 4551 coupled to the staple link assembly 4170 are moved in the direction of an arrow C2 (i.e., toward the proximal end). In this state, due to the structure of the contact member 4543 and the reciprocating member 4551, even when the reciprocating member 4551 is moved in the direction of the arrow C2, only the contact member 4543 is spaced apart from the reciprocating member 4551 by a certain extent while the overall position of the operation member 4540 remains unchanged (referring to FIGS. 41 and 43). That is, even when the reciprocating member 4551 is moved in the direction of the arrow C2, the operation member 4540 remains stationary in place when viewed in the X-axis direction.

In this state, when the first staple pulley 4181 stops rotating, as shown in FIG. 42A, the staple link assembly 4170, the reciprocating member 4551, and the operation member 4540 also stop moving.

When the first staple pulley 4181 and the second staple pulley 4191 are alternately rotated in the clockwise and counterclockwise directions while repeating the above process, the reciprocating member 4551 is repeatedly moved forward and backward, and the operation member 4540 repeats moving forward and stopping, and as a result, the operation member 4540 is moved toward the distal end 4502. In addition, as the operation member 4540 is moved toward the distal end 4502, a stapling motion by the wedge 4541 and a cutting motion by the blade 4542 are simultaneously performed.

Hereinafter, a stapling motion of the surgical instrument according to an embodiment of the present disclosure will be described.

Figure 43B:
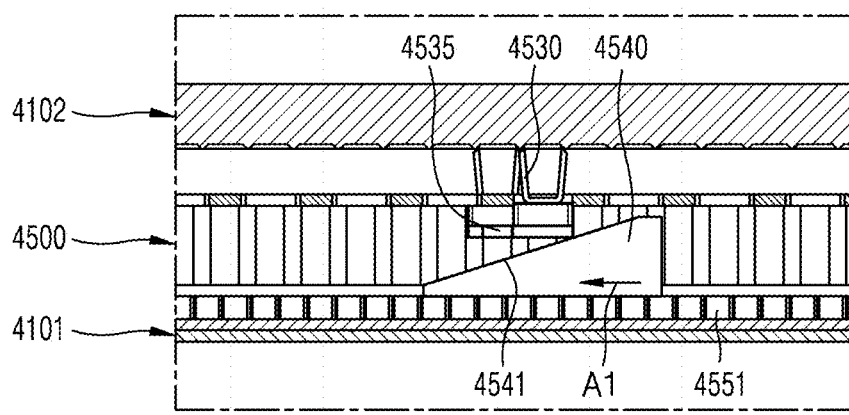
Figure 43C:
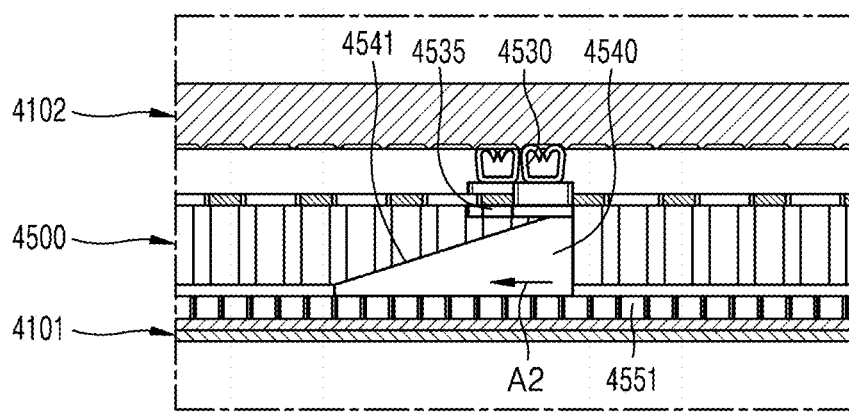
Figure 44:
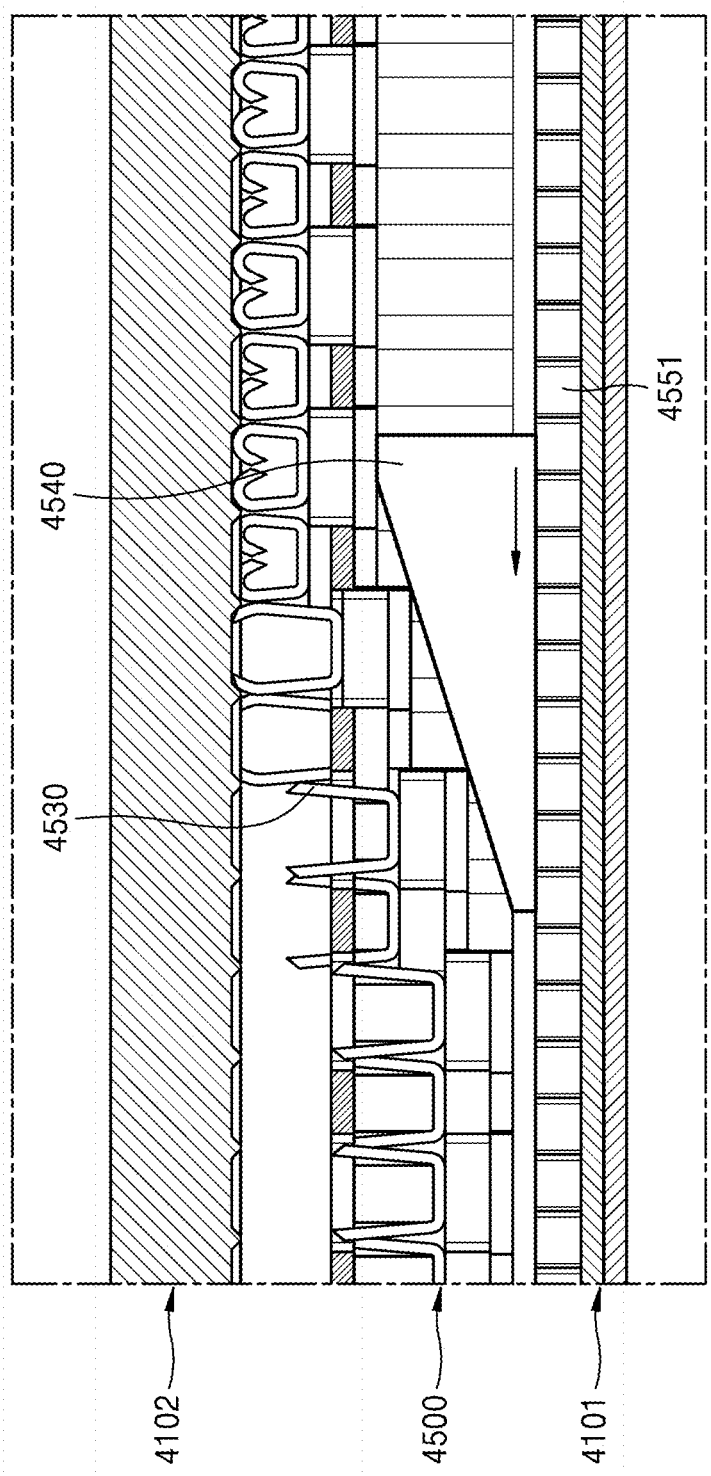

FIGS. 43A to 43C are perspective views illustrating a stapling motion of the end tool of FIG. 36 for each section, and FIG. 44 is a perspective view illustrating an entire stapling motion of the end tool of FIG. 36.

Referring to FIGS. 43 and 44, in the state as shown in FIG. 43A, as the operation member 4540 is moved in the direction of an arrow A1 of FIG. 43B, the wedge 4541 of the operation member 4540 pushes and raises the withdrawal member 4535, and the withdrawal member 4535 pushes and raises one side of a lower portion of the staple 4530. In addition, due thereto, the staple 4530 is ejected to the outside of the first jaw 4101 and the cartridge 4500.

In this state, when the operation member 4540 is further moved in the direction of an arrow A2 of FIG. 43C, the ejected staple 4530 is continuously pushed and raised by the operation member 4540 while in contact with the anvil 4102a of the second jaw 4102, so that stapling is performed while both end portions of the staple 4530 are bent.

As such motions are continuously performed, stapling is sequentially performed from the staple 4530 at the proximal end 4501 side to the staple 4530 at the distal end 4502 side among the plurality of staples 4530, as illustrated in FIG. 44.

(Manipulation Part)

Figure 45:
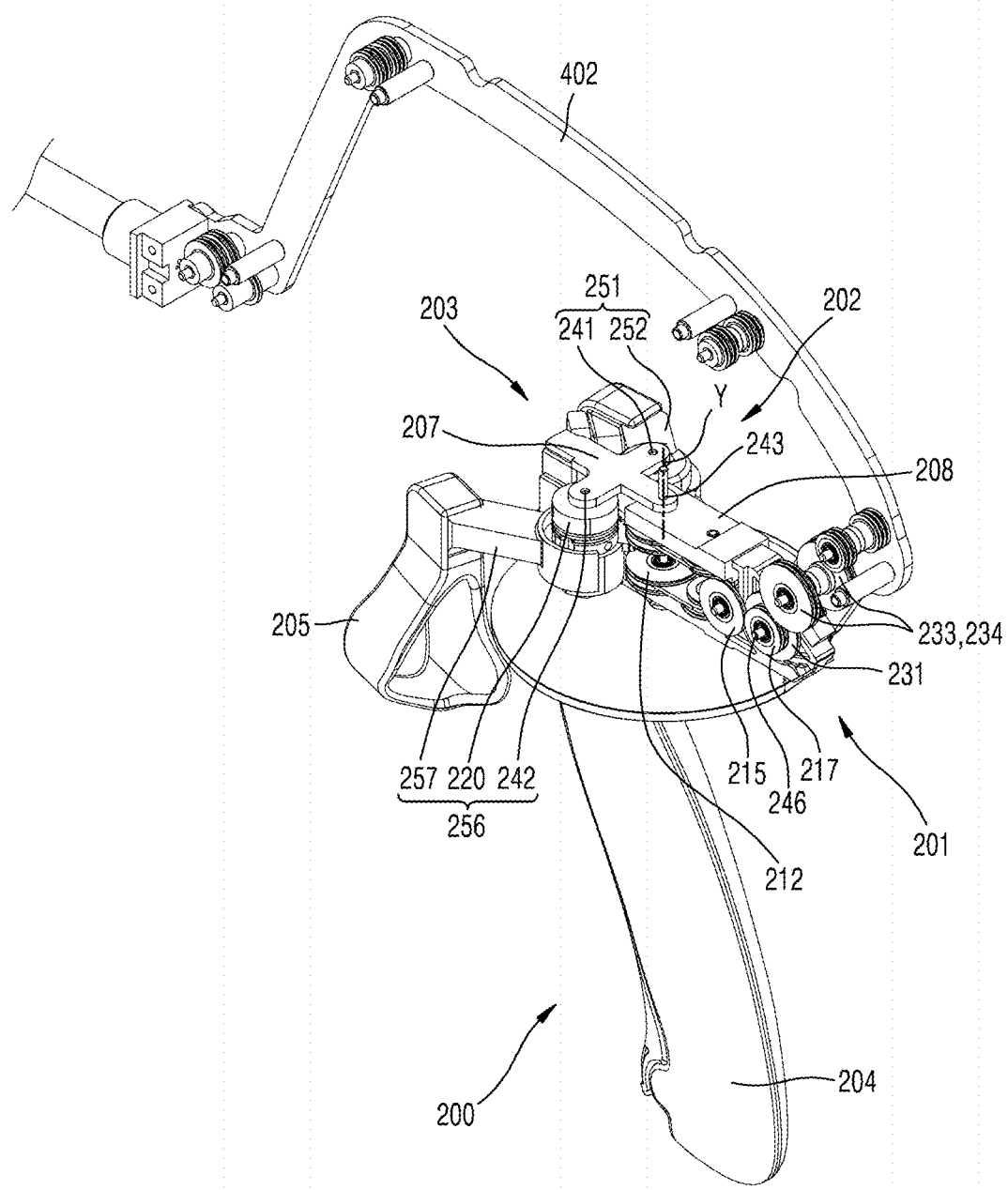
FIGS. 45 and 46 are perspective views illustrating a manipulation part of the surgical instrument of FIG. 2.
Figure 46:
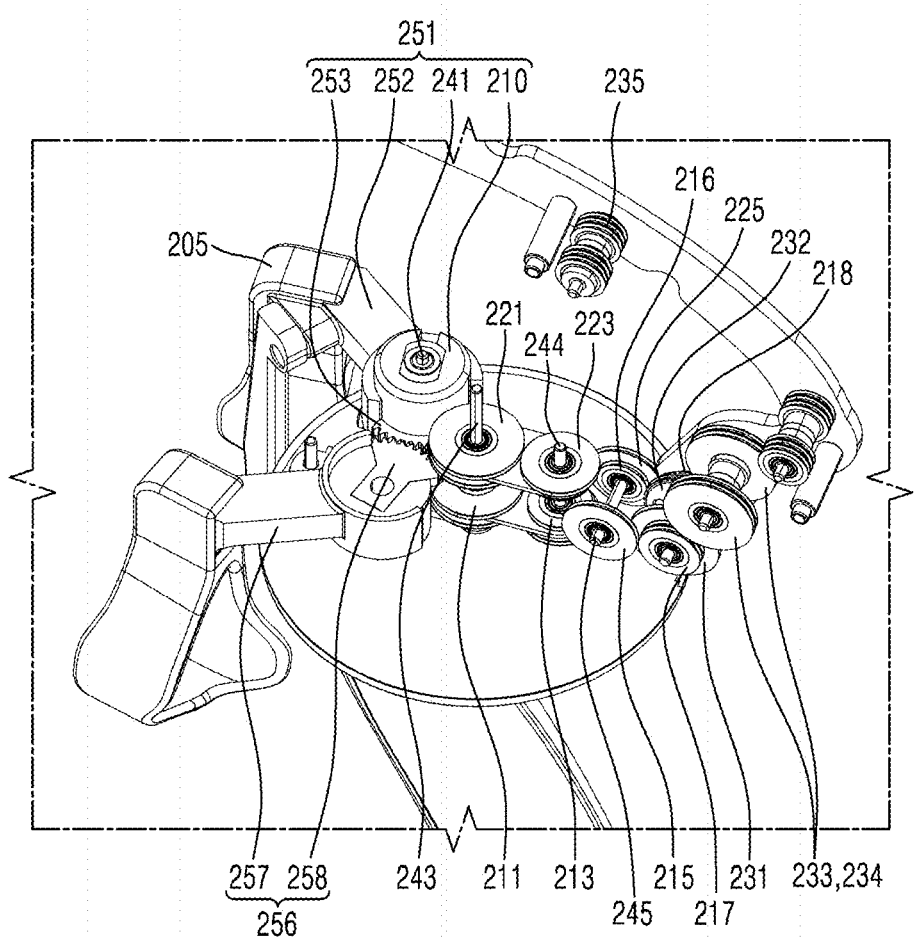

FIGS. 45 and 46 are perspective views illustrating the manipulation part of the surgical instrument of FIG. 2. FIG. 47 is a view schematically illustrating only a configuration of pulleys and wires constituting joints of the surgical instrument illustrated in FIG. 2.

Referring to FIGS. 2 to 47, the manipulation part 200 of the surgical instrument 4000 according to the first embodiment of the present disclosure includes a first handle 204 that a user can grip, the actuation manipulation part 203 configured to control an actuation motion of the end tool 4100, the yaw manipulation part 202 configured to control a yaw motion of the end tool 4100, and the pitch manipulation part 201 configured to control a pitch motion of the end tool 4100. Here, it is understood that only the components related to the pitch/yaw/actuation motions of the surgical instrument 4000 are illustrated in FIGS. 41 and 42.

In addition, the manipulation part 200 of the surgical instrument 4000 may further include a staple manipulation part 260 configured to control the motion of the staple pulley assembly 4160 of the end tool 4100 to perform stapling and cutting motions.

The manipulation part 200 may include the pulley 210, a pulley 211, a pulley 212, a pulley 213, a pulley 214, a pulley 215, a pulley 216, a pulley 217, and a pulley 218 that are related to a rotational motion of the first jaw 4101. In addition, the manipulation part 200 may include the pulley 220, a pulley 221, a pulley 222, a pulley 223, a pulley 224, a pulley 225, a pulley 226, a pulley 227, and a pulley 228 that are related to a rotational motion of the second jaw 4102. In addition, the manipulation part 200 may include the pulley 231, the pulley 232, a pulley 233, and a pulley 234 that are related to a pitch motion thereof. In addition, the manipulation part 200 may include a pulley 235, which is a relay pulley disposed at some places along the bent part 402 of the connection part 400.

Here, the pulleys facing each other are illustrated in the drawings as being formed parallel to each other, but the concept of the present disclosure is not limited thereto, and each of the pulleys may be variously formed with a position and a size suitable for the configuration of the manipulation part.

Further, the manipulation part 200 of the first embodiment of the present disclosure may include a rotation shaft 241, a rotation shaft 242, the rotation shaft 243, a rotation shaft 244, a rotation shaft 245, and the rotation shaft 246. Here, the rotation shaft 241 may function as a manipulation part first jaw actuation rotation shaft, and the rotation shaft 242 may function as a manipulation part second jaw actuation rotation shaft. In addition, the rotation shaft 243 may function as a manipulation part yaw main rotation shaft, and the rotation shaft 244 may function as a manipulation part yaw sub-rotation shaft. In addition, the rotation shaft 245 may function as a manipulation part pitch sub-rotation shaft, and the rotation shaft 246 may function as a manipulation part pitch main rotation shaft.

The rotation shaft 241/rotation shaft 242, the rotation shaft 243, the rotation shaft 244, the rotation shaft 245, and the rotation shaft 246 may be sequentially disposed from a distal end 205 of the manipulation part 200 toward a proximal end 206.

Each of the rotation shafts 241, 242, 243, 244, 245, and 246 may be fitted into one or more pulleys, which will be described in detail later.

The pulley 210 functions as a manipulation part first jaw actuation pulley, the pulley 220 functions as a manipulation part second jaw actuation pulley, and these components may also be collectively referred to as a manipulation part actuation pulley.

The pulley 211 and the pulley 212 function as manipulation part first jaw yaw main pulleys, the pulley 221 and the pulley 222 function as manipulation part second jaw yaw main pulleys, and these components may also be collectively referred to as a manipulation part yaw main pulley.

The pulley 213 and the pulley 214 function as manipulation part first jaw yaw sub-pulleys, the pulley 223 and the pulley 224 function as manipulation part second jaw yaw sub-pulleys, and these components may also be collectively referred to as a manipulation part yaw sub-pulley.

The pulley 215 and the pulley 216 function as manipulation part first jaw pitch sub-pulleys, the pulley 225 and the pulley 226 function as manipulation part second jaw pitch sub-pulleys, and these components may also be collectively referred to as a manipulation part pitch sub-pulley.

The pulley 217 and the pulley 218 function as manipulation part first jaw pitch main pulleys, and the pulley 227 and the pulley 228 function as manipulation part second jaw pitch main pulleys, and these components may also be collectively referred to as the manipulation part pitch main pulley.

The pulley 231 and the pulley 232 function as manipulation part pitch wire main pulleys, and the pulley 233 and the pulley 234 function as manipulation part pitch wire sub-pulleys.

The above components are categorized from the perspective of the manipulation part for each motion (pitch/yaw/actuation) as follows.

The pitch manipulation part 201 configured to control a pitch motion of the end tool 4100 may include the pulley 215, the pulley 216, the pulley 217, the pulley 218, the pulley 225, the pulley 226, the pulley 227, the pulley 228, the pulley 231, the pulley 232, and the pulley 234. In addition, the pitch manipulation part 201 may include the rotation shaft 245 and the rotation shaft 246. In addition, the pitch manipulation part 201 may further include a pitch frame 208.

The yaw manipulation part 202 configured to control a yaw motion of the end tool 4100 may include the pulley 211, the pulley 212, the pulley 213, the pulley 214, the pulley 221, the pulley 222, the pulley 223, and the pulley 224. In addition, the yaw manipulation part 202 may include the rotation shaft 243 and the rotation shaft 244. In addition, the yaw manipulation part 202 may further include a yaw frame 207.

The actuation manipulation part 203 configured to control an actuation motion of the end tool 4100 may include the pulley 210, the pulley 220, the rotation shaft 241, and the rotation shaft 242. In addition, the actuation manipulation part 203 may further include the first actuation manipulation part 251 and the second actuation manipulation part 256.

Hereinafter, each component of the manipulation part 200 will be described in more detail.

The first handle 204 may be formed to be gripped by a user with the hand, and in particular, may be formed to be grasped by the user by wrapping the first handle 204 with his/her palm. In addition, the actuation manipulation part 203 and the yaw manipulation part 202 are formed on the first handle 204, and the pitch manipulation part 201 is formed on one side of the yaw manipulation part 202. In addition, the other end portion of the pitch manipulation part 201 is connected to the bent part 402 of the connection part 400.

The actuation manipulation part 203 includes the first actuation manipulation part 251 and the second actuation manipulation part 256. The first actuation manipulation part 251 includes the rotation shaft 241, the pulley 210, the first actuation extension part 252, and a first actuation gear 253. The second actuation manipulation part 256 includes the rotation shaft 242, the pulley 220, the second actuation extension part 257, and a second actuation gear 258. Here, end portions of the first actuation extension part 252 and the second actuation extension part 257 are formed in the shape of a hand ring, which may act as a second handle.

Here, the rotation shaft 241 and the rotation shaft 242, which are actuation rotation axes, may be formed to form a predetermined angle with an XY plane on which the connection part 400 is formed. For example, the rotation shaft 241 and the rotation shaft 242 may be formed in a direction parallel to the Z-axis, and in this state, when the pitch manipulation part 201 or the yaw manipulation part 202 is rotated, the coordinate system of the actuation manipulation part 203 may change relatively. Of course, the concept of the present disclosure is not limited thereto, and the rotation shaft 241 and the rotation shaft 242 may be formed in various directions so as to be suitable for a structure of the hand of the user gripping the actuation manipulation part 203 according to an ergonomic design.

Meanwhile, the pulley 210, the first actuation extension part 252, and the first actuation gear 253 are fixedly coupled to each other to be rotatable together around the rotation shaft 241. Here, the pulley 210 may be configured to be a single pulley or two pulleys fixedly coupled to each other.

Similarly, the pulley 220, the second actuation extension part 257, and the second actuation gear 258 are fixedly coupled to each other to be rotatable together around the rotation shaft 242. Here, the pulley 220 may be configured to be a single pulley or two pulleys fixedly coupled to each other.

Here, the first actuation gear 253 and the second actuation gear 258 are formed to be engaged with each other such that, when any one gear is rotated in one direction, the other gear is rotated together in a direction opposite to the one direction.

The yaw manipulation part 202 may include the rotation shaft 243, the pulleys 211 and 212, which are manipulation part first jaw yaw main pulleys, the pulleys 221 and 222, which are manipulation part second jaw yaw main pulleys, and the yaw frame 207. In addition, the yaw manipulation part 202 may further include the pulleys 213 and 214, which are manipulation part first jaw yaw sub-pulleys formed on one side of the pulleys 211 and 212, and the pulleys 223 and 224 that are manipulation part second jaw yaw sub-pulleys formed on one side of the pulleys 221 and 222. Here, the pulleys 213 and 214 and the pulleys 223 and 224 may be coupled to the pitch frame 208 to be described later.

Here, it is illustrated in the drawings that the yaw manipulation part 202 includes the pulleys 211 and 212 and the pulleys 221 and 222, wherein the pulleys 211 and 212 and the pulleys 221 and 222 are each provided with two pulleys formed to face each other and independently rotatable, but the concept of the present disclosure is not limited thereto. That is, one or more pulleys having the same diameter or different diameters may be provided according to the configuration of the yaw manipulation part 202.

In detail, the rotation shaft 243, which is a manipulation part yaw main rotation shaft, is formed on one side of the actuation manipulation part 203 on the first handle 204. At this time, the first handle 204 is formed to be rotatable around the rotation shaft 243.

Here, the rotation shaft 243 may be formed to form a predetermined angle with the XY plane on which the connection part 400 is formed. For example, the rotation shaft 243 may be formed in a direction parallel to the Z-axis, and in this state, when the pitch manipulation part 201 is rotated, the coordinate system of the rotation shaft 243 may change relatively as described above. Of course, the concept of the present disclosure is not limited thereto, and the rotation shaft 243 may be formed in various directions so as to be suitable for a structure of the hand of the user gripping the manipulation part 200 according to an ergonomic design.

Meanwhile, the pulleys 211 and 212 and the pulleys 221 and 222 are coupled to the rotation shaft 243 so as to be rotatable around the rotation shaft 243. In addition, the wire 301 or the wire 305, which is a first jaw wire, is wound around the pulleys 211 and 212, and the wire 302 or the wire 306, which is a second jaw wire, may be wound around the pulleys 221 and 222. In this case, the pulleys 211 and 212 and the pulleys 221 and 222 may each be configured as two pulleys formed to face each other and independently rotatable. Accordingly, a wire being wound and a wire being released may be wound around respective separate pulleys so that the wires may perform motions without interference with each other.

The yaw frame 207 rigidly connects the first handle 204, the rotation shaft 241, the rotation shaft 242, and the rotation shaft 243, so that the first handle 204, the yaw manipulation part 202, and the actuation manipulation part 203 are integrally yaw-rotated around the rotation shaft 243.

The pitch manipulation part 201 may include the rotation shaft 246, the pulley 217 and the pulley 218, which are manipulation part first jaw pitch main pulleys, the pulleys 227 and 228, which are manipulation part second jaw pitch main pulleys, and the pitch frame 208. In addition, the pitch manipulation part 201 may further include the rotation shaft 245, the pulleys 215 and 216, which are manipulation part first jaw pitch sub-pulleys formed on one side of the pulley 217 and the pulley 218, and the pulleys 225 and 226, which are manipulation part second jaw pitch sub-pulleys formed on one side of the pulley 227 and the pulley 228. The pitch manipulation part 201 may be connected to the bent part 402 of the connection part 400 through the rotation shaft 246.

In detail, the pitch frame 208 is a base frame of the pitch manipulation part 201, and the rotation shaft 243 is rotatably coupled to one end portion thereof. That is, the yaw frame 207 is formed to be rotatable around the rotation shaft 243 with respect to the pitch frame 208.

As described above, since the yaw frame 207 connects the first handle 204, the rotation shaft 243, the rotation shaft 241, and the rotation shaft 242, and the yaw frame 207 is also axially coupled to the pitch frame 208, when the pitch frame 208 is pitch-rotated around the rotation shaft 246, the yaw frame 207 connected to the pitch frame 208, the first handle 204, the rotation shaft 241, the rotation shaft 242, and the rotation shaft 243 are pitch-rotated together. That is, when the pitch manipulation part 201 is rotated around the rotation shaft 246, the actuation manipulation part 203 and the yaw manipulation part 202 are rotated together with the pitch manipulation part 201. In other words, when a user pitch-rotates the first handle 204 around the rotation shaft 246, the actuation manipulation part 203, the yaw manipulation part 202, and the pitch manipulation part 201 are moved together.

The pulleys 217 and 218 and the pulleys 227 and 228 are coupled to the rotation shaft 246 so as to be rotatable around the rotation shaft 246 of the pitch frame 208.

Here, the pulley 217 and the pulley 218 may be formed to face each other so as to be independently rotatable. Accordingly, a wire being wound and a wire being released may be wound around respective separate pulleys so that the wires may perform motions without interference with each other. Similarly, the pulley 227 and the pulley 228 may also be formed to face each other so as to be independently rotatable. Accordingly, a wire being wound and a wire being released may be wound around respective separate pulleys so that the wires may perform motions without interference with each other.

Next, a motion of each of the wires 303 and 304, which are pitch wires, is described as follows.

The pulley 4131, which is an end tool pitch pulley, is fixedly coupled to the end tool hub 4106 in the end tool 4100, and the pulley 231 and the pulley 232, which are manipulation part pitch pulleys, are fixedly coupled to the pitch frame 208 in the manipulation part 200. In addition, these pulleys are connected to each other by the wires 303 and 304, which are pitch wires, so that a pitch motion of the end tool 4100 may be performed more easily according to the pitch manipulation of the manipulation part 200. Here, the wire 303 is fixedly coupled to the pitch frame 208 via the pulley 231 and the pulley 233, and the wire 304 is fixedly coupled to the pitch frame 208 via the pulley 232 and the pulley 234. That is, the pitch frame 208 and the pulleys 231 and 232 are rotated together around the rotation shaft 246 by the pitch rotation of the manipulation part 200, and as a result, the wires 303 and 304 are also moved, and thus, a driving force of additional pitch rotation may be transmitted separately from the pitch motion of the end tool by the wire 301, the wire 302, the wire 305, and the wire 306, which are jaw wires.

A connection relationship of each of the first handle 204, the pitch manipulation part 201, the yaw manipulation part 202, and the actuation manipulation part 203 is summarized as follows. The rotation shafts 241 and 242, the rotation shaft 243, the rotation shaft 244, the rotation shaft 245, and the rotation shaft 246 may be formed on the first handle 204. In this case, since the rotation shafts 241 and 242 are directly formed on the first handle 204, the first handle 204 and the actuation manipulation part 203 may be directly connected to each other. Meanwhile, since the rotation shaft 243 is directly formed on the first handle 204, the first handle 204 and the yaw manipulation part 202 may be directly connected to each other. On the other hand, since the pitch manipulation part 201 is formed on one side of the yaw manipulation part 202 so as to be connected to the yaw manipulation part 202, the pitch manipulation part 201 is not directly connected to the first handle 204, and the pitch manipulation part 201 and the first handle 204 may be formed to be indirectly connected to each other via the yaw manipulation part 202.

Continuing to refer to the drawings, in the surgical instrument 4000 according to the first embodiment of the present disclosure, the pitch manipulation part 201 and the end tool 4100 may be formed on the same or parallel axis (X-axis). That is, the rotation shaft 246 of the pitch manipulation part 201 is formed at one end portion of the bent part 402 of the connection part 400, and the end tool 4100 is formed at the other end portion of the connection part 400.

In addition, one or more relay pulleys 235 configured to change or guide paths of the wires may be disposed at some places along the connection part 400, particularly in the bent part 402. As at least some of the wires are wound around the relay pulleys 235 to guide the paths of the wires, these wires may be disposed along a bent shape of the bent part 402.

Here, in the drawings, it is illustrated that the connection part 400 is formed to be curved with a predetermined curvature by having the bent part 402, but the concept of the present disclosure is not limited thereto, and the connection part 400 may be formed linearly or to be bent one or more times as necessary, and even in this case, it may be said that the pitch manipulation part 201 and the end tool 4100 are formed on substantially the same axis or parallel axes. In addition, although FIG. 3 illustrates that each of the pitch manipulation part 201 and the end tool 4100 is formed on an axis parallel to the X-axis, the concept of the present disclosure is not limited thereto, and the pitch manipulation part 201 and the end tool 4100 may be formed on different axes.

The staple manipulation part 260 is connected to the first staple pulley 4181 of the end tool 4100 by the wires 307 and 308, which are first staple wires, and serves to alternately rotate the first staple pulley 4181 in the clockwise or counterclockwise direction. The staple manipulation part 260 is connected to the second staple pulley 4191 of the end tool 4100 by the wires 309 and 310, which are second staple wires, and serves to alternately rotate the second staple pulley 4191 in the counterclockwise or clockwise direction.

To this end, although not shown in the drawings, the staple manipulation part 260 may include a motor (not shown). That is, the motor (not shown) is driven while the user presses the staple manipulation part 260 formed in the form of a button to alternately rotate the manipulation part staple pulley (see 269 of FIG. 47) in the clockwise or counterclockwise direction. In addition, due thereto, the first staple pulley 4181 and the second staple pulley 4191 of the end tool 4100 may be alternately rotated in the clockwise or counterclockwise direction.

(Actuation, Yaw, and Pitch Motions)

Actuation, yaw, and pitch motions in the present embodiment will be described as follows.

First, the actuation motion will be described below.

In a state in which a user inserts his/her index finger in the hand ring formed on the first actuation extension part 252 and his/her thumb in the hand ring formed on the second actuation extension part 257, when the user rotates the actuation rotation parts 252 and 257 using one or both of his/her index finger and thumb, the pulley 210 and the first actuation gear 253 fixedly coupled to the first actuation extension part 252 are rotated around the rotation shaft 241, and the pulley 220 and the second actuation gear 258 fixedly coupled to the second actuation extension part 257 are rotated around the rotation shaft 242. At this time, the pulley 210 and the pulley 220 are rotated in opposite directions, and thus the wires 301 and 305 fixedly coupled to the pulley 210 at one end portion thereof and the wires 302 and 306 fixedly coupled to the pulley 220 at one end portion thereof are also moved in opposite directions. In addition, a rotating force is transmitted to the end tool 4100 through the power transmission part 300, and two jaws 4103 of the end tool 4100 perform an actuation motion.

Here, as described above, the actuation motion refers to a motion in which the two jaws 4101 and 4102 are splayed or closed while being rotated in opposite directions. That is, when the actuation rotation parts 252 and 257 of the actuation manipulation part 203 are rotated in directions close to each other, the first jaw 4101 is rotated in the counterclockwise direction, and the second jaw 4102 is rotated in the clockwise direction, thereby closing the end tool 4100. That is, when the actuation rotation parts 252 and 257 of the actuation manipulation part 203 are rotated in directions away from each other, the first jaw 121 is rotated in the counterclockwise direction, and the second jaw 122 is rotated in the clockwise direction, thereby opening the end tool 4100.

In the present embodiment, for the actuation manipulation described above, the first actuation extension part 252 and the second actuation extension part 257 are provided to configure the second handle and manipulated by gripping the second handle with two fingers. However, for the actuation manipulation in which the two jaws of the end tool 4100 are opened or closed, the actuation manipulation part 203 may be configured in a manner different from the above-described manner, such as configuring the two actuation pulleys (the pulley 210 and the pulley 220) to act in opposition to each other with an actuation rotation part.

Next, the yaw motion will be described below.

When a user rotates the first handle 204 around the rotation shaft 243 while holding the first handle 204, the actuation manipulation part 203 and the yaw manipulation part 202 are yaw-rotated around the rotation shaft 243. That is, when the pulley 210 of the first actuation manipulation part 251 to which the wires 301 and 305 are fixedly coupled is rotated around the rotation shaft 243, the wires 301 and 305 wound around the pulleys 211 and 212 are moved. Similarly, when the pulley 220 of the second actuation manipulation part 256, to which the wires 302 and 306 are fixedly coupled, is rotated around the rotation shaft 243, the wires 302 and 306 wound around the pulleys 221 and 222 are moved. At this time, the wires 301 and 305 connected to the first jaw 4101 and the wires 302 and 306 connected to the second jaw 4102 are wound around the pulleys 211 and 212 and the pulleys 221 and 222, so that the first jaw 4101 and the second jaw 4102 are rotated in the same direction during yaw rotation. In addition, a rotating force is transmitted to the end tool 4100 through the power transmission part 300, and thus a yaw motion in which two jaws 4103 of the end tool 4100 are rotated in the same direction is performed.

At this time, since the yaw frame 207 connects the first handle 204, the rotation shaft 241, the rotation shaft 242, and the rotation shaft 243, the first handle 204, the yaw manipulation part 202, and the actuation manipulation part 203 are rotated together around the rotation shaft 243.

Next, the pitch motion will be described below.

When a user rotates the first handle 204 around the rotation shaft 246 while holding the first handle 204, the actuation manipulation part 203, the yaw manipulation part 202, and the pitch manipulation part 201 are pitch-rotated around the rotation shaft 246. That is, when the pulley 210 of the first actuation manipulation part 251 to which the wires 301 and 305 are fixedly coupled is rotated around the rotation shaft 246, the wires 301 and 305 wound around the pulley 217 and the pulley 218 are moved. Similarly, when the pulley 220 of the second actuation manipulation part 256, to which the wires 302 and 306 are fixedly coupled, is rotated around the rotation shaft 246, the wires 302 and 306 wound around the pulley 227 and the pulley 228 are moved. At this time, as described with reference to FIG. 5, in order to allow the first jaw 4101 and the second jaw 4102 to pitch-rotate, the wires 301 and 305, which are first jaw wires, are moved in the same direction and respectively wound around the pulley 217 and the pulley 218, which are manipulation part pitch main pulleys, and the wires 302 and 306, which are second jaw wires, are moved in the same direction and respectively wound around the pulley 227 and the pulley 228, which are manipulation part pitch main pulleys. In addition, a rotating force is transmitted to the end tool 4100 through the power transmission part 300, and two jaws 103 of the end tool 4100 perform a pitch motion.

At this time, since the pitch frame 208 is connected to the yaw frame 207, and the yaw frame 207 connects the first handle 204, the rotation shaft 241, the rotation shaft 242, and the rotation shaft 243, when the pitch frame 208 is rotated around the rotation shaft 246, the yaw frame 207, the first handle 204, the rotation shaft 241, the rotation shaft 242, and the rotation shaft 243 connected to the pitch frame 208 are rotated together. That is, when the pitch manipulation part 201 is rotated around the rotation shaft 246, the actuation manipulation part 203 and the yaw manipulation part 202 are rotated together with the pitch manipulation part 201.

In summary, in the surgical instrument 4000 according to an embodiment of the present disclosure, the pulleys are formed on respective joint points (an actuation joint, a yaw joint, and a pitch joint), the wires (the first jaw wire or the second jaw wire) are wound around the pulleys, the rotational manipulations (actuation rotation, yaw rotation, and pitch rotation) of the manipulation part cause the movement of each wire, which in turn induces the desired motion of the end tool 4100. Furthermore, the auxiliary pulley may be formed on one side of each of the pulleys, and the wire may not be wound several times around one pulley due to the auxiliary pulley.

FIG. 47 is a view schematically illustrating only a configuration of pulleys and wires constituting joints of the surgical instrument 4000 according to an embodiment of the present disclosure illustrated in FIG. 2. In FIG. 47, the relay pulleys for changing paths of the wires and not related to the operation of joints are omitted.

Referring to FIG. 47, the manipulation part 200 may include the pulley 210, the pulley 211, the pulley 212, the pulley 213, the pulley 214, the pulley 215, the pulley 216, the pulley 217, and the pulley 218 that are related to a rotational motion of the first jaw 4101.

In addition, the manipulation part 200 may include the pulley 220, the pulley 221, the pulley 222, the pulley 223, the pulley 224, the pulley 225, the pulley 226, the pulley 227, and the pulley 228 that are related to a rotational motion of the second jaw 4102 (the arrangement and structure of each of the pulleys of the manipulation part 200 are the same in principle as the arrangement and structure of each of the pulleys of the end tool 4100, and thus specific designations of some reference numerals are omitted in the drawings).

The pulleys 211 and 212 and the pulleys 221 and 222 may be formed to be rotatable independently of each other around the same shaft, that is the rotation shaft 243. In this case, the pulleys 211 and 212 and the pulleys 221 and 222 may each be formed as two pulleys formed to face each other and formed to be independently rotatable.

The pulleys 213 and 214 and the pulleys 223 and 224 may be formed to be rotatable independently of each other around the same shaft, that is the rotation shaft 244. Here, the pulleys 213 and 214 may be formed as two pulleys formed to face each other and formed to be independently rotatable, and in this case, the two pulleys may be formed to have different diameters. Similarly, the pulleys 223 and 224 may be formed as two pulleys formed to face each other and formed to be independently rotatable, and in this case, the two pulleys may be formed to have different diameters.

The pulleys 215 and 216 and the pulleys 225 and 226 may be formed to be rotatable independently of each other around the same shaft, that is the rotation shaft 245. In this case, the pulleys 215 and 216 may be formed to have different diameters. In addition, the pulleys 225 and 226 may be formed to have different diameters.

The pulleys 217 and 218 and the pulleys 227 and 228 may be formed to be rotatable independently of each other around the same shaft, that is the rotation shaft 246.

The wire 301 is wound around the pulley 210 after sequentially passing through the pulley 217, the pulley 215, the pulley 213, and the pulley 211 of the manipulation part 200, and then is coupled to the pulley 210 by the coupling member 324. Meanwhile, the wire 305 sequentially passes through the pulley 218, the pulley 216, the pulley 214, and the pulley 212 of the manipulation part 200 and is coupled to the pulley 210 by the coupling member 324. Thus, when the pulley 210 is rotated, the wires 301 and 305 are wound around or released from the pulley 210, and accordingly, the first jaw 4101 is rotated.

The wire 306 is wound around the pulley 220 after sequentially passing through the pulley 227, the pulley 225, the pulley 223, and the pulley 221 of the manipulation part 200, and then is coupled to the pulley 220 by the coupling member 327. Meanwhile, the wire 302 sequentially passes through the pulley 228, the pulley 226, the pulley 224, and the pulley 222 of the manipulation part 200 and is coupled to the pulley 220 by the coupling member 327. Thus, when the pulley 220 is rotated, the wire 302 and the wire 306 are wound around or released from the pulley 220, and accordingly, the second jaw 4102 is rotated.

(Conceptual Diagram of Pulleys and Wires)

Figure 48:
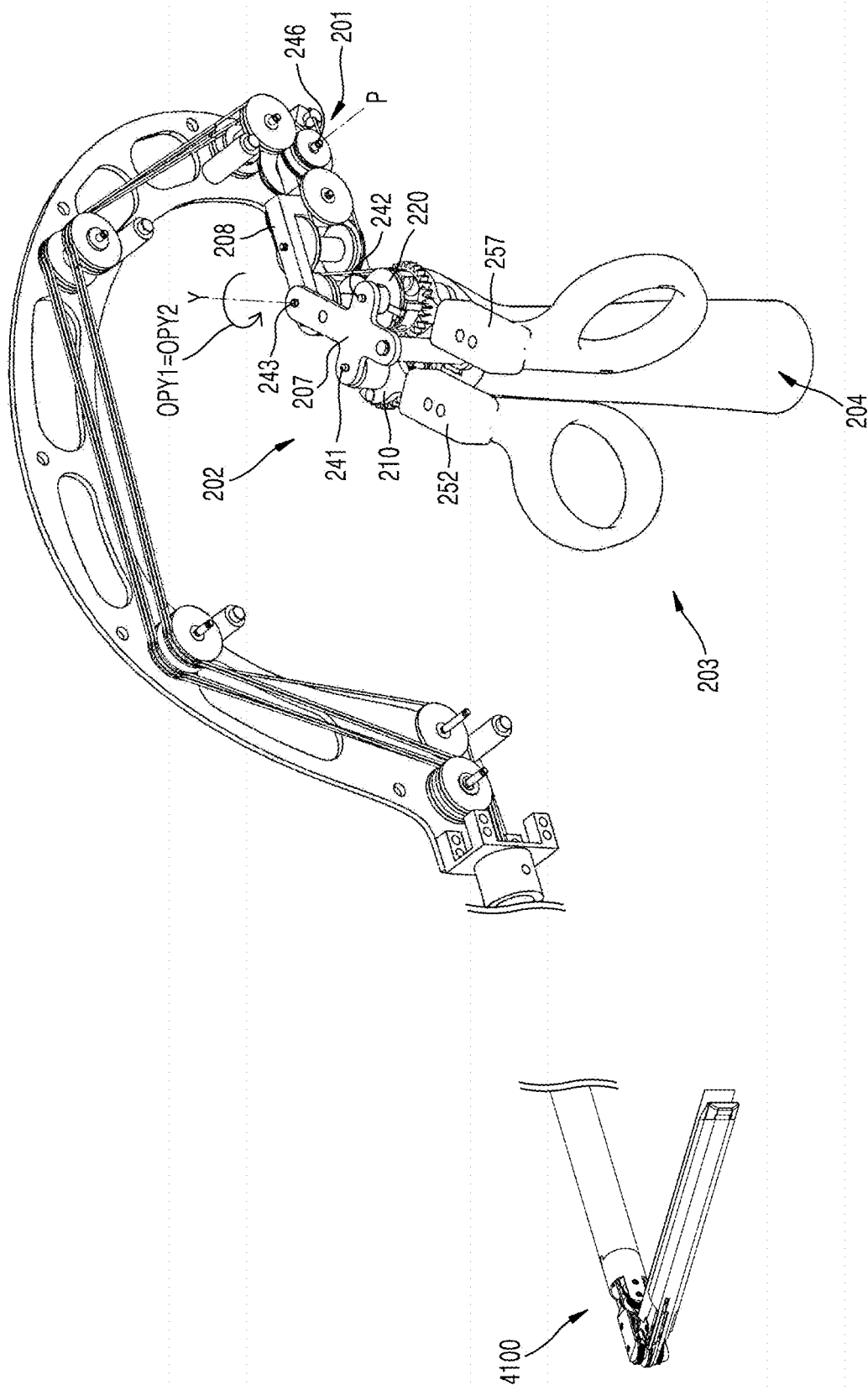
FIG. 48 is a perspective view illustrating a yaw motion of the surgical instrument of FIG. 2.
Figure 50:
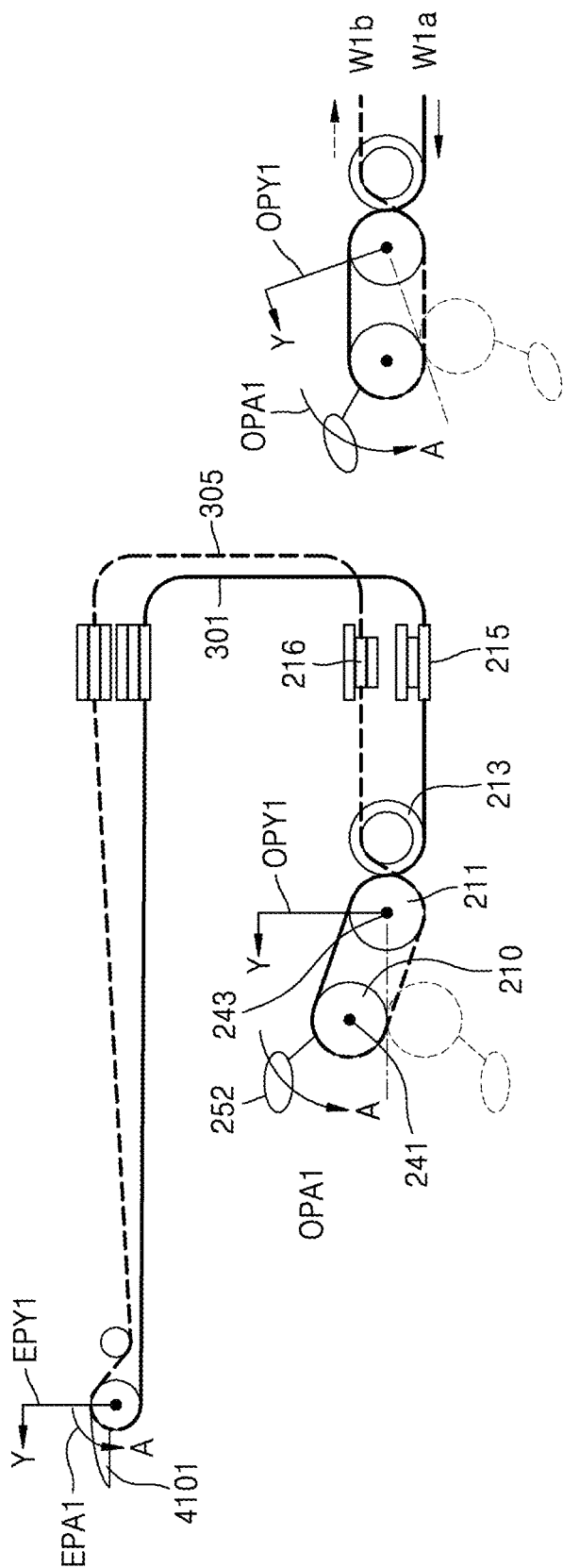

FIGS. 49 and 50 are diagrams illustrating a configuration of pulleys and wires, which are related to an actuation motion and a yaw motion of the surgical instrument 4000 according to an embodiment of the present disclosure illustrated in FIG. 2, in detail for each of the first jaw and the second jaw. FIG. 49 is a diagram illustrating only pulleys and wires related to the second jaw, and FIG. 50 is a diagram illustrating only pulleys and wires related to the first jaw. In addition, FIG. 48 is a perspective view illustrating a yaw motion of the surgical instrument of FIG. 2. Here, in FIG. 48, components related to stapling and cutting motions are omitted.

First, a wire motion of the actuation motion will be described.

Referring to FIG. 50, when the first actuation extension part 252 is rotated around the rotation shaft 241 in the direction of an arrow OPA 1, the pulley 210 connected to the first actuation extension part 252 is rotated, and the wire 301 and the wire 305 wound around the pulley 210 are moved in directions W1a and W1b, respectively, and as a result, the first jaw 4101 of the end tool 4100 is rotated in the direction of an arrow EPA1.

Referring to FIG. 49, when the second actuation extension part 257 is rotated around the rotation shaft 242 in the direction of an arrow OPA2, the pulley 220 connected to the second actuation extension part 257 is rotated, and thus both strands of the wires 302 and 306 wound around the pulley 220 are moved in directions W2a and W2b, respectively, and as a result, the second jaw 4102 of the end tool 4100 is rotated in the direction of an arrow EPA2. Accordingly, when a user manipulates the first actuation extension part 252 and the second actuation extension part 257 in directions close to each other, a motion of the first jaw 4101 and the second jaw 4102 of the end tool being close to each other is performed.

Next, a wire motion of the yaw motion will be described.

First, since the rotation shaft 243 is connected to the rotation shafts 241 and 242 by the yaw frame (see 207 of FIG. 30), the rotation shaft 243 and the rotation shafts 241 and 242 are integrally rotated together.

Referring to FIG. 50, when the first handle 204 is rotated around the rotation shaft 243 in the direction of an arrow OPY1, the pulley 210 and the pulleys 211 and 212 and the wires 301 and 305 wound therearound are rotated as a whole around the rotation shaft 243, and as a result, the wires 301 and 305 wound around the pulleys 211 and 212 are moved in the directions W1a and W1b, respectively, which in turn causes the first jaw 4101 of the end tool 4100 to rotate in the direction of an arrow EPY1.

Referring to FIG. 49, when the first handle 204 is rotated around the rotation shaft 243 in the direction of an arrow OPY2, the pulley 220 and the pulleys 221 and 222 and the wires 302 and 306 wound therearound are rotated as a whole around the rotation shaft 243, and as a result, the wires 302 and 306 wound around the pulleys 221 and 222 are respectively moved in a direction opposite to a direction W1a and a direction opposite to a direction W1b, which in turn causes the first jaw 4101 of the end tool 4100 to rotate in the direction of an arrow EPY2.

FIGS. 51 to 53B are diagrams illustrating a configuration of pulleys and wires, which are related to stapling and cutting motions of the surgical instrument 4000 according to an embodiment of the present disclosure illustrated in FIG. 2, in detail for each of the first jaw and the second jaw. Here, FIGS. 51 to 53B are drawings mainly illustrating pulleys and wires related to the second jaw.

Figure 51:
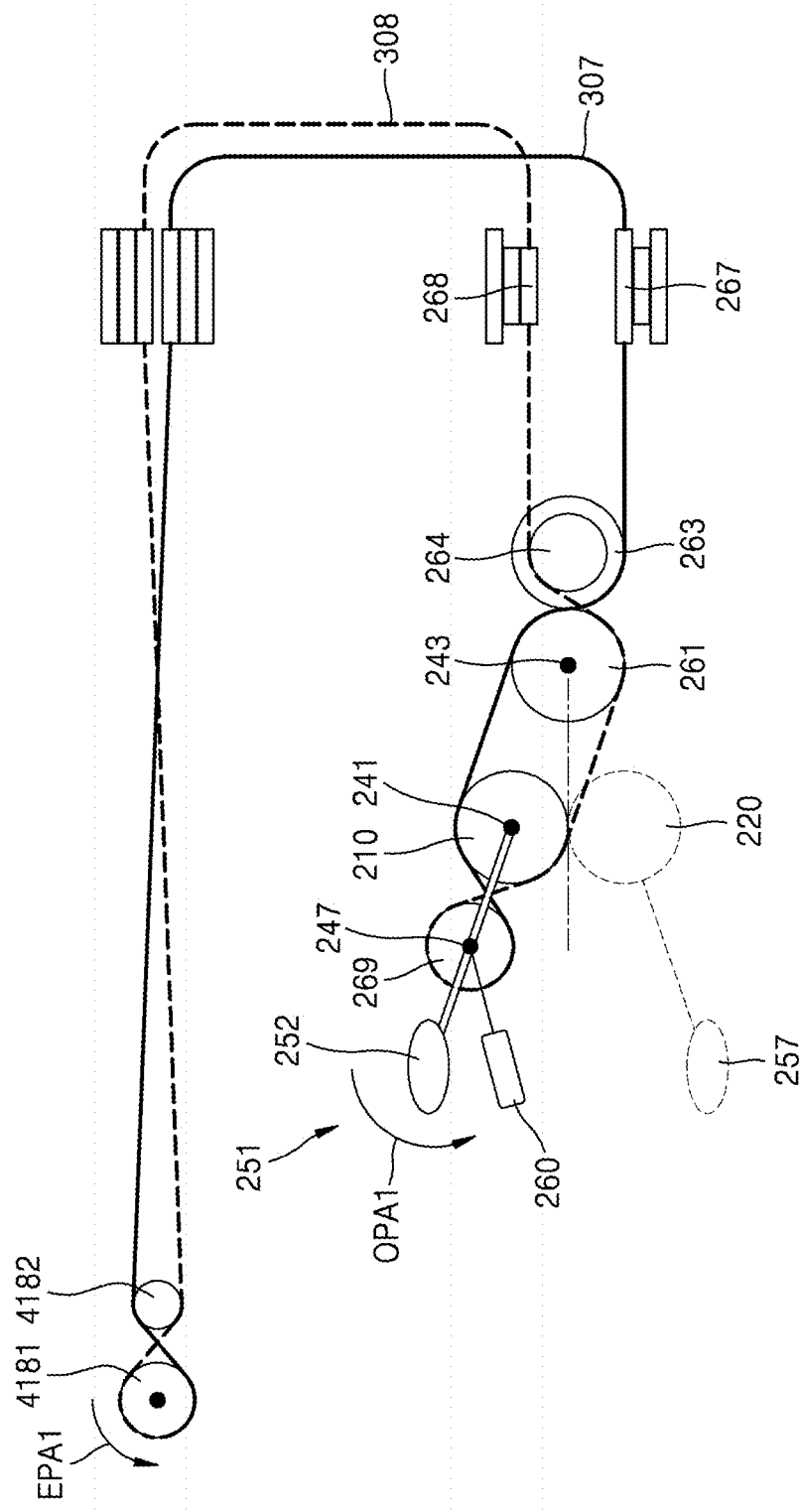
FIGS. 51 to 53B are diagrams illustrating a configuration of pulleys and wires, which are related to stapling and cutting motions of the surgical instrument illustrated in FIG. 2, in detail for each of the first jaw and the second jaw.
Figure 52:
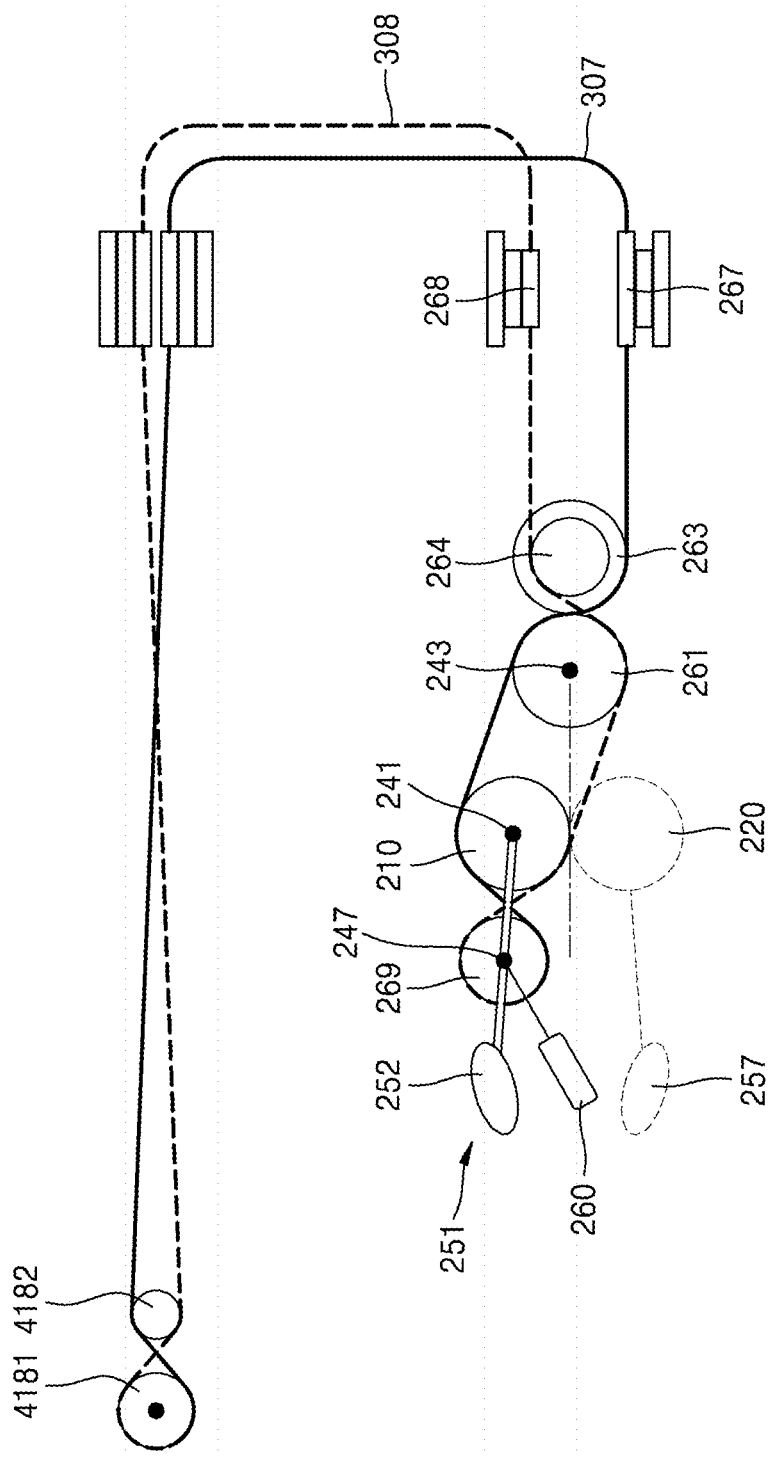
Figure 54:
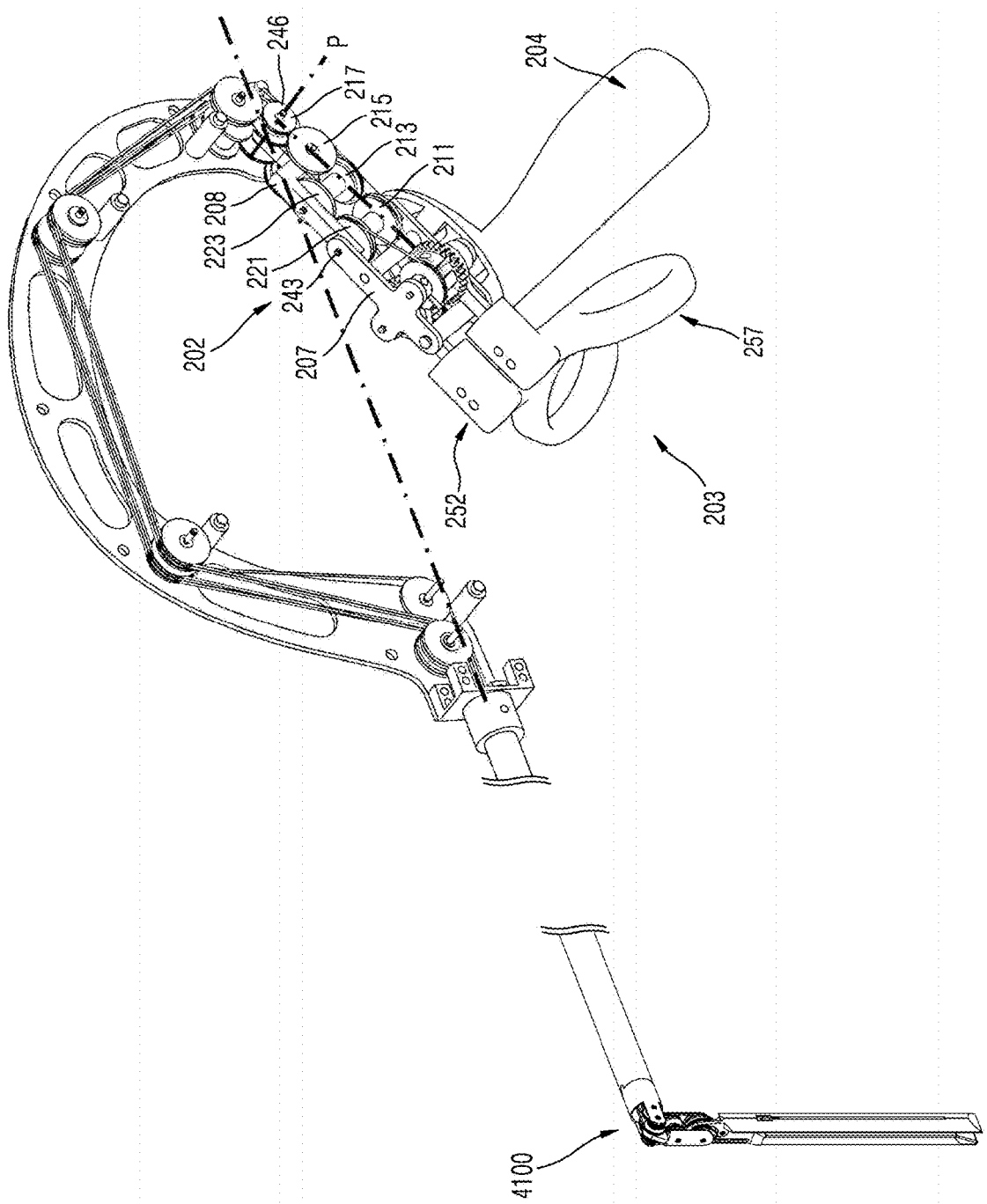
FIG. 54 is a perspective view illustrating a pitch motion of the surgical instrument of FIG. 2.
Figure 55:
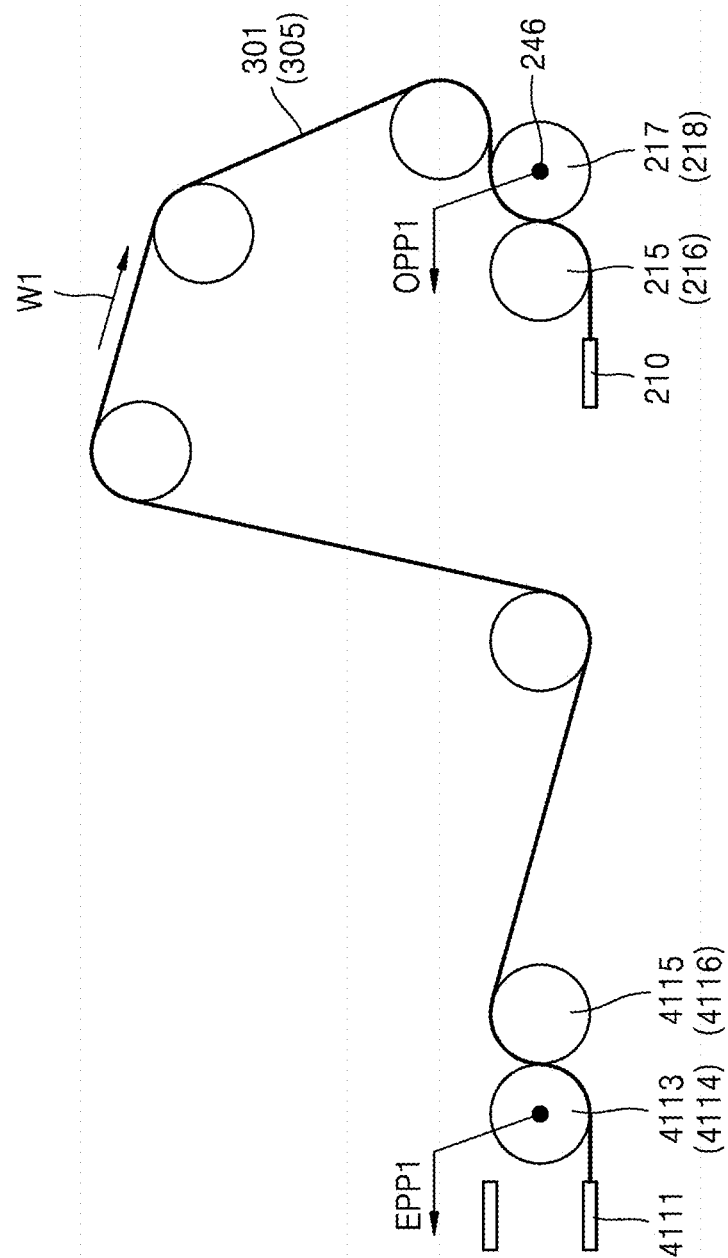
FIGS. 55 to 57 are diagrams illustrating a configuration of pulleys and wires, which are related to a pitch motion of the surgical instrument illustrated in FIG. 2, in detail for each of the first jaw and the second jaw.

Here, FIGS. 51 and 52 illustrate the process of actuation motion of closing two jaws, and FIGS. 54 and 55 illustrate the process of motion of stapling and cutting of tissue interposed between two jaws.

First, a wire motion of the actuation motion will be described.

Referring to FIGS. 51 and 52, when the first actuation extension part 252 of the first actuation manipulation part 251 is rotated in the direction of an arrow OPA1 around the rotation shaft 241, the pulley 210 connected to the first actuation extension part 252 is rotated, and each of the wire (see 301 of FIG. 49) and the wire (see 305 of FIG. 49) wound around the pulley 210 is moved, which in turn causes the first jaw 4101 of the end tool 4100 to rotate in the direction of an arrow EPA1.

At this time, the manipulation part staple pulley 269 of the staple manipulation part 260 is formed to be rotatable around the rotation shaft 241 together with the first actuation manipulation part 251. Thus, when the first actuation extension part 252 is rotated around the rotation shaft 241, the staple manipulation part 260 is also rotated around the rotation shaft 241 together with the first actuation manipulation part 251.

As a result, in the actuation motion, when the pulley 2111 is rotated in the end tool 4100, the first staple pulley 4181 is also rotated together with the pulley 2111.

Next, a wire operation of the stapling and cutting motions will be described.

Figure 53A:
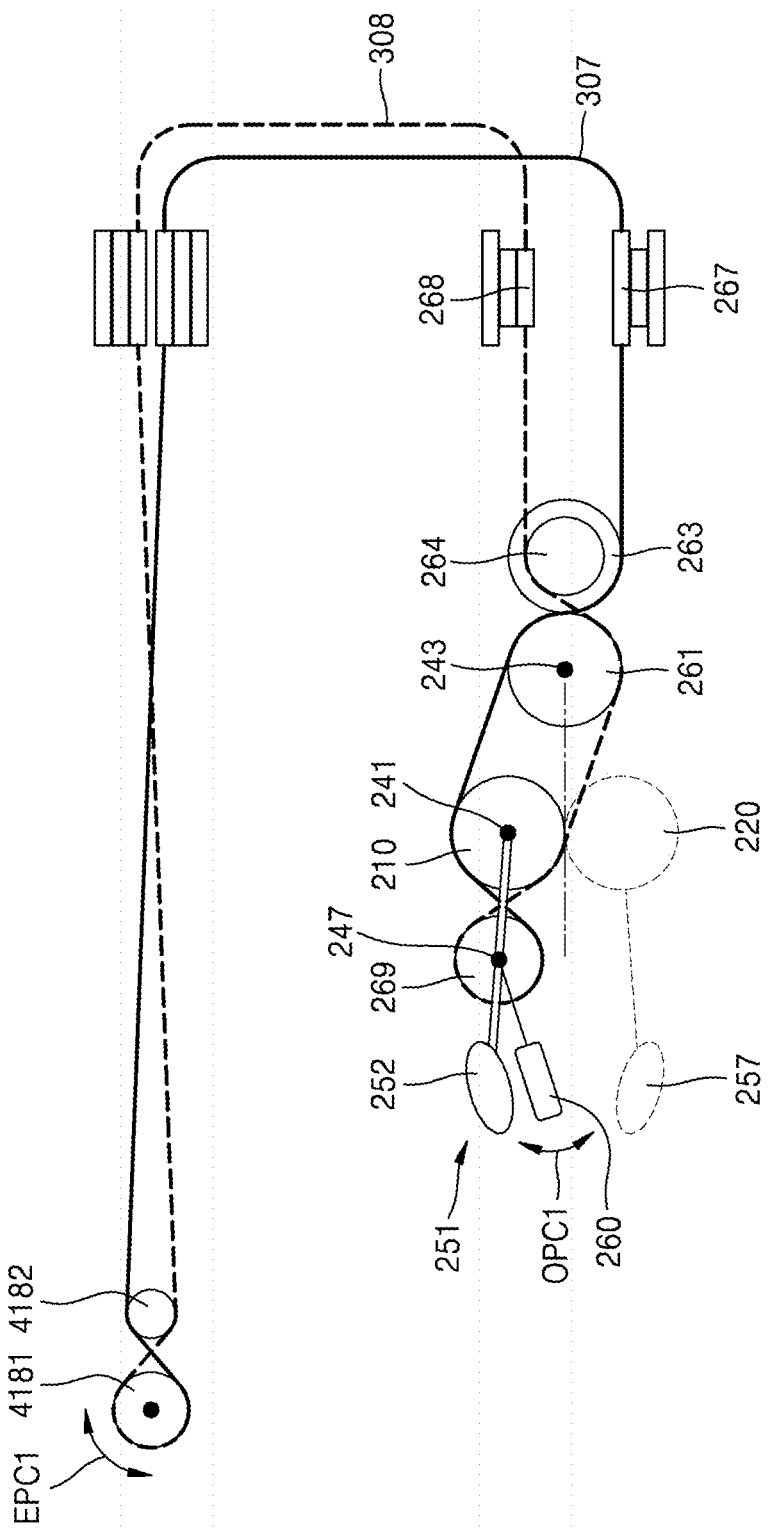

Referring to FIG. 53A, when the staple manipulation portion 260 is rotated in the direction of an arrow OPC1 around a rotation shaft 247, which is a manipulation portion cutting rotation shaft, the manipulation portion staple pulley 269, and the wire 307 and the wire 308, which are staple wires wound around the manipulation portion staple pulley 269, rotate around the rotation shaft 247, and as a result, each of the wire 307 and the wire 308 wound around the manipulation portion staple pulley 269 moves, which in turn causes the first staple pulley 4181 of the end tool 4100 to rotate in the direction of an arrow EPC1.

Figure 53B:
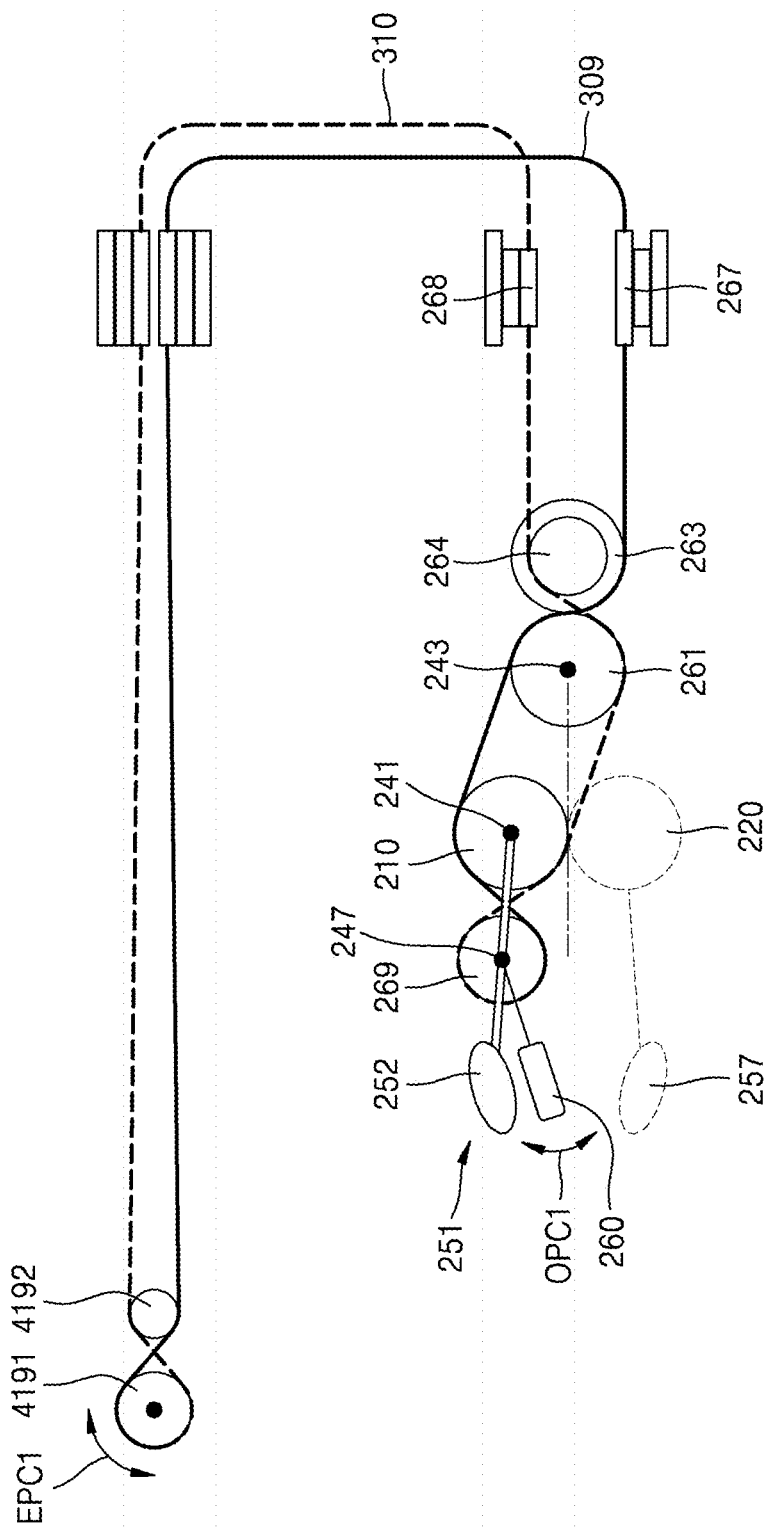

Referring to FIG. 53B, when the staple manipulation portion 260 is rotated in the direction of an arrow OPC1 around the rotation shaft 247, which is a manipulation portion cutting rotation shaft, the manipulation portion staple pulley 269, and the wire 309 and the wire 310, which are staple wires wound around the manipulation portion staple pulley 269, rotate around the rotation shaft 247, and as a result, each of the wire 309 and the wire 310 wound around the manipulation portion staple pulley 269 moves, which in turn causes the second staple pulley 4191 of the end tool 4100 to rotate in the direction of an arrow EPC1.

Meanwhile, when the staple manipulation portion 260 rotates, the manipulation portion staple pulley 269 rotates around the rotation shaft 247, and at this time, the rotation of the staple manipulation portion 260 does not affect the first actuation manipulation portion 251.

As a result, when the manipulation portion staple pulley 269 rotates, the first staple pulley 4181 and the second staple pulley 4191 of the end tool 4100 rotate independently of the first jaw 4101. In addition, when the first staple pulley 4181 and the second staple pulley 4191 rotate alternately in the clockwise/counterclockwise directions, the staple link assembly 2170 connected to the first staple pulley 4181 and the second staple pulley 4191, and the reciprocating assembly 4550 of the cartridge 4500 connected thereto perform a reciprocating linear motion, and accordingly, as the operation member 4540 of the cartridge 4500 moves toward the distal end 502, stapling and cutting motions are performed.

Here, as described above, the first staple pulley 4181 and the second staple pulley 4191 may rotate in opposite directions. For example, when the staple manipulation portion 260 rotates in any one direction, the first staple pulley 4181 rotates in the clockwise direction and the second staple pulley 4191 rotates in the counterclockwise direction, such that the staple link assembly 2170 may move toward the distal end 4104 of the end tool 4100. On the contrary, when the staple manipulation portion 260 rotates in the opposite direction, the first staple pulley 4181 rotates in the counterclockwise direction and the second staple pulley 4191 rotates in the clockwise direction, such that the staple link assembly 2170 may move toward the proximal end 4105 of the end tool 4100.

Here, although the drawings illustrate that the staple manipulation portion 260 is formed in a bar shape and a user manually rotates the staple manipulation portion 260, but the technical concepts of the present disclosure is not limited thereto. That is, as described above, the staple manipulation portion 260 may include a motor (not shown), and while the user presses the staple manipulation portion 260 formed in a button shape, the motor (not shown) may be driven to alternately rotate the manipulation portion staple pulley 269 in the clockwise or counterclockwise direction. In addition, accordingly, the first staple pulley 4181 of the end tool 4100 may alternately rotate in the clockwise or counterclockwise direction.

Figure 56:
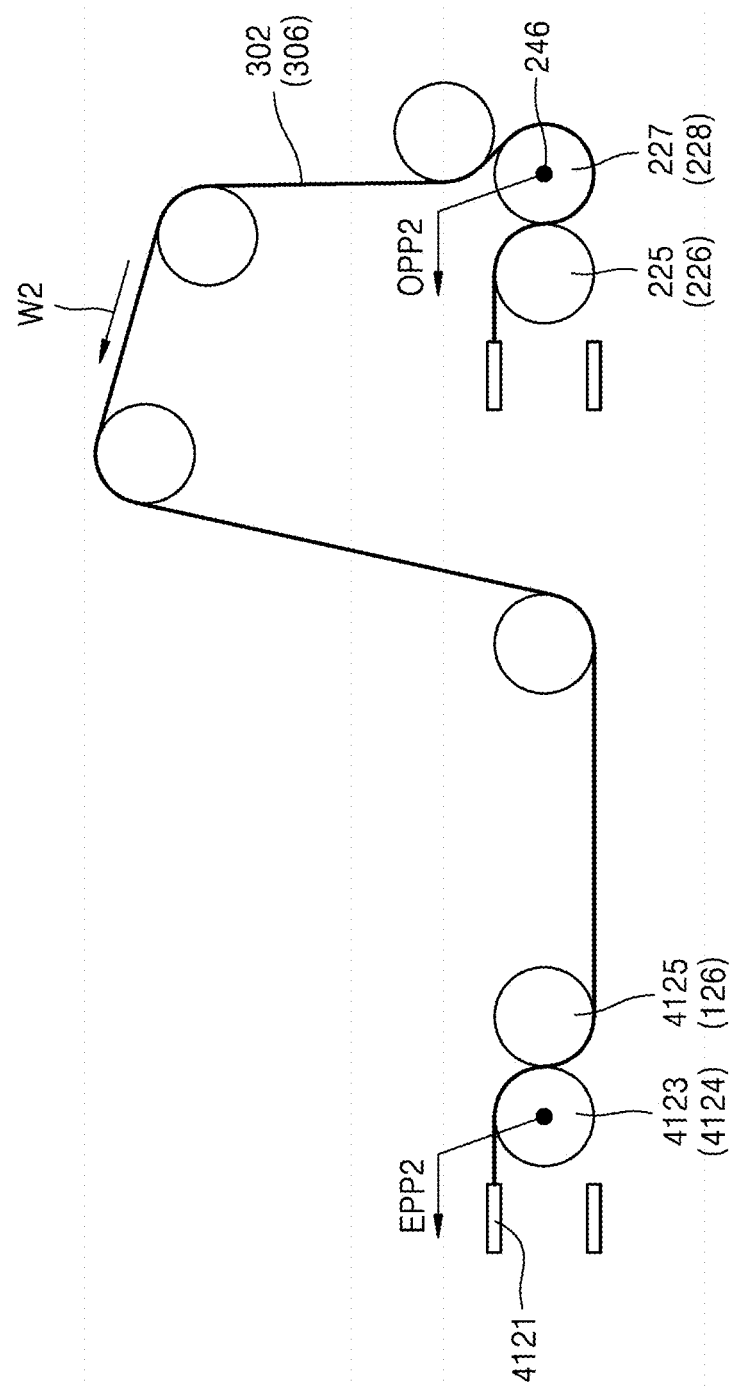
Figure 57:
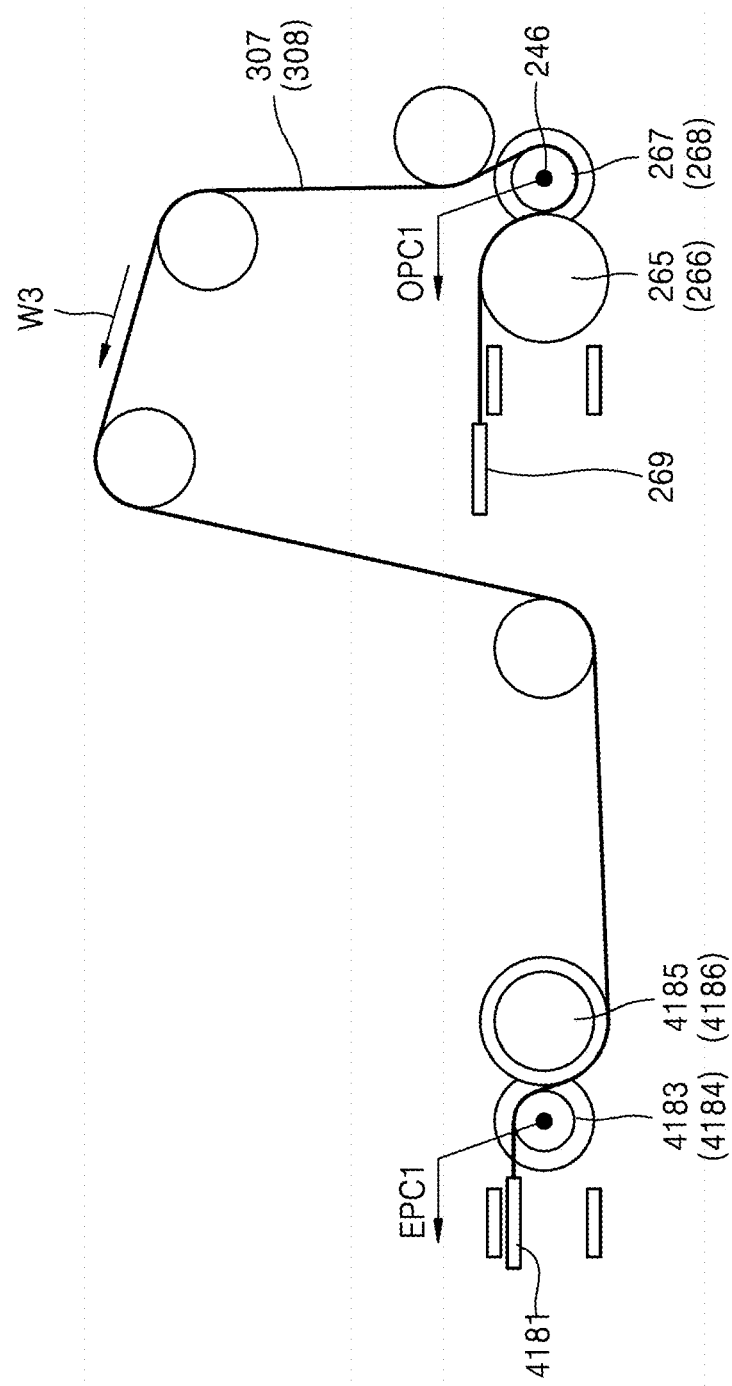

FIGS. 55 to 57 are diagrams illustrating a configuration of pulleys and wires, which are related to a pitch motion of the surgical instrument 4000 according to an embodiment of the present disclosure illustrated in FIG. 2, in detail for each of the first jaw and the second jaw. FIG. 55 is a diagram illustrating only pulleys and wires related to the second jaw, and FIG. 56 is a diagram illustrating only pulleys and wires related to the first jaw. FIG. 57 is a diagram illustrating only pulleys and wires related to the staple pulley. As shown in FIG. 9 and elsewhere herein, there are two pulleys related to the pitch motion, and both strands of each wire are wound in the same path, which is illustrated with one line in FIGS. 55 and 57. In addition, FIG. 56 is a perspective view illustrating a pitch motion of the surgical instrument of FIG. 2. Here, in FIG. 56, components related to stapling and cutting motions are omitted.

Referring to FIG. 55, when the first handle 204 is rotated around the rotation shaft 246 in the direction of an arrow OPP1, the pulley 210, the pulley 215, the pulley 217, and the like, and the wire 301 and the like wound therearound are rotated as a whole around the rotation shaft 246. At this time, since the wires 301 and 305, which are first jaw wires, are wound around upper portions of the pulley 217 and the pulley 218 as shown in FIG. 55, the wires 301 and 305 are moved in the direction of an arrow W1. As a result, as described with reference to FIG. 5, the first jaw 4101 of the end tool 4100 is rotated in the direction of an arrow EPP1.

Referring to FIG. 56, when the first handle 204 is rotated around the rotation shaft 246 in the direction of an arrow OPP2, the pulley 220, the pulley 225, the pulley 227, and the like, and the wire 302 and the like wound therearound are rotated as a whole around the rotation shaft 246. At this time, since the wires 302 and 306, which are second jaw wires, are wound around lower portions of the pulley 227 and the pulley 228 as shown in FIG. 56, the wires 302 and 306 are moved in the direction of an arrow W2. As a result, as described with reference to FIG. 5, the second jaw 4102 of the end tool 4100 is rotated in the direction of an arrow EPP2.

Referring to FIG. 57, when the first handle 204 is rotated around the rotation shaft 246 in the direction of an arrow OPC1, the manipulation part staple pulley 269, a pulley 265, a pulley 267, and the like, and the wires 307 and 308 and the like wound therearound are rotated as a whole around the rotation shaft 246. At this time, since the wires 307 and 308, which are first staple wires, are wound around lower portions of the pulley 267 and a pulley 268, the wires 307 and 308 are moved in the direction of an arrow W3. As a result, as described with reference to FIG. 5, the first staple pulley 4181 of the end tool 4100 is rotated in the direction of an arrow EPC1.

As a result, in the pitch motion, when the pulley 2111 is rotated around the rotation shaft 2143 in the end tool 4100, the first staple pulley 4181 is also rotated around the rotation shaft 2143 together with the pulley 2111.

Thus, the actuation, yaw, and pitch manipulations are manipulatable independent of each other.

As described with reference to FIG. 1, the actuation manipulation part 203, the yaw manipulation part 202, and the pitch manipulation part 201 are configured such that the respective rotation shafts are located at the rear thereof to be identical to the joint configuration of the end tool, so that a user may intuitively perform matching manipulations.

In particular, in the surgical instrument 4000 according to an embodiment of the present disclosure, the pulleys are formed on respective joint points (an actuation joint, a yaw joint, and a pitch joint), the wires (the first jaw wire or the second jaw wire) are formed to be wound around the pulleys, the rotational manipulations (actuation rotation, yaw rotation, and pitch rotation) of the manipulation part cause the movement of each wire, which in turn induces the desired motion of the end tool 4100. Furthermore, the auxiliary pulleys may be formed on one side of the respective pulleys, and these auxiliary pulleys may prevent the wire from being wound on one pulley multiple times, so that the wires wound on the pulley do not come into contact with each other, and paths of the wire being wound around the pulley and the wire being released from the pulley are safely formed, so that safety and efficiency in the transmission of driving force of a wire may be improved.

Meanwhile, as described above, the yaw manipulation part 202 and the actuation manipulation part 203 are directly formed on the first handle 204. Thus, when the first handle 204 is rotated around the rotation shaft 246, the yaw manipulation part 202 and the actuation manipulation part 203 are also rotated together with the first handle 204. Accordingly, the coordinate systems of the yaw manipulation part 202 and the actuation manipulation part 203 are not fixed, but are continuously changed relative to the rotation of the first handle 204. That is, in FIG. 2 or the like, the yaw manipulation part 202 and the actuation manipulation part 203 are illustrated as being parallel to the z-axis. However, when the first handle 204 is rotated, the yaw manipulation part 202 and the actuation manipulation part 203 are not parallel to the Z-axis any longer. That is, the coordinate systems of the yaw manipulation part 202 and the actuation manipulation part 203 are changed according to the rotation of the first handle 204. However, in the present specification, for convenience of description, unless described otherwise, the coordinate systems of the yaw manipulation part 202 and the actuation manipulation part 203 are described on the basis of a state in which the first handle 204 is located perpendicular to the connection part 400 as illustrated in FIG. 2.

(Correlation Between Stapling and Cutting Motions and Other Motions)

Hereinafter, a correlation between stapling and cutting motions and other motions (pitch, yaw, and actuation motions) will be described.

First, when the end tool 4100 performs a pitch motion, the first staple pulley 4181 and the second staple pulley 4191 also perform a pitch motion. That is, when the pulley 2111 and the pulley 2121 perform a pitch motion of rotating in the same direction around the rotation shaft 2143, the first staple pulley 4181 and the second staple pulley 4191 need to rotate in the same direction together with the pulley 2111 and the pulley 2121. If the first staple pulley 4181 and the second staple pulley 4191 do not rotate together when the pulley 2111 and the pulley 2121 rotate around the rotation shaft 2143, there is a risk that the cartridge 4500 connected to the first staple pulley 4181 and the second staple pulley 4191 moves relative to the first jaw 4101 and is separated from the first jaw 4101. In addition, rotation of the first staple pulley 4181 and the second staple pulley 4191 that is not synchronized with the pulley 2111 may cause the reciprocating member 4551 to unintentionally move forward, which in turn may cause an unintended stapling motion.

Next, when the end tool 4100 performs a yaw motion, the first staple pulley 4181 and the second staple pulley 4191 also perform a yaw motion. That is, when the pulley 2111 and the pulley 2121 perform a yaw motion of rotating in the same direction around the rotation shaft 2141, the first staple pulley 4181 and the second staple pulley 4191 need to rotate in the same direction together with the pulley 2111 and the pulley 2121. If the first staple pulley 4181 and the second staple pulley 4191 do not rotate together when the pulley 2111 and the pulley 2121 rotate around the rotation shaft 2141, there is a risk that the cartridge 4500 connected to the first staple pulley 4181 and the second staple pulley 4191 moves relative to the first jaw 4101 and is separated from the first jaw 4101. In addition, rotation of the first staple pulley 4181 and the second staple pulley 4191 that is not synchronized with the pulley 2111 may cause the reciprocating member 4551 to unintentionally move forward, which in turn may cause an unintended stapling motion.

Next, when the end tool 4100 performs an actuation motion, the first staple pulley 4181 and the second staple pulley 4191 rotate together with the pulley 2111. That is, when the pulley 2111 and the pulley 2121 perform an actuation motion of rotating in opposite directions around the rotation shaft 2141, the first staple pulley 4181 and the second staple pulley 4191 need to rotate together with the pulley 2111. If the first staple pulley 4181 and the second staple pulley 4191 do not rotate together with the pulley 2111 when the pulley 2111 rotates around the rotation shaft 2143, there is a risk that the cartridge 4500 connected to the first staple pulley 4181 and the second staple pulley 4191 moves relative to the first jaw 4101 and is separated from the first jaw 4101. In addition, rotation of the first staple pulley 4181 and the second staple pulley 4191 that is not synchronized with the pulley 2111 may cause the reciprocating member 4551 to unintentionally move forward, which in turn may cause an unintended stapling motion.

Meanwhile, when the end tool 4100 performs stapling and cutting motions, the pulley 2111 and the pulley 2121 do not rotate. That is, when the first staple pulley 4181 and the second staple pulley 4191 rotate around the rotation shaft 2141, and the link member 2171 and the reciprocating member 4551 of the cartridge 4500 connected thereto perform a linear reciprocating motion, the pulley 2111 and the pulley 2121 need not to rotate. Otherwise, the first jaw 4101 or the second jaw 4102 rotate during the stapling and cutting motions, and thus, the stapling and cutting motions will not be performed normally.

As a result, when the pulley 2111, which is a first jaw pulley, rotates, the first staple pulley 4181 and the second staple pulley 4191 accommodated in the first jaw 4101 need to rotate together with the pulley 2111. On the contrary, when the first staple pulley 4181 and the second staple pulley 4191 rotate for stapling and cutting, the pulley 2111 and the pulley 2121 need to maintain their positions without rotating. As such, the correlation between the stapling and cutting motions and other motions (the yaw and actuation motions) are discussed above.

In other words, it may be said that the pulley 2111 and the pulley 2121 are independent of the rotation of the first staple pulley 4181 and the second staple pulley 4191. That is, even when the first staple pulley 4181 and the second staple pulley 4191 rotate by staple wires, the pulley 2111 and the pulley 2121 may not rotate. On the contrary, it may be said that the first staple pulley 4181 and the second staple pulley 4191 are dependent on rotation of the pulley 2111. That is, when the pulley 2111 rotates by a jaw wire, the first staple pulley 4181 and the second staple pulley 4191 may also rotate together with the pulley 2111.

Figure 58:
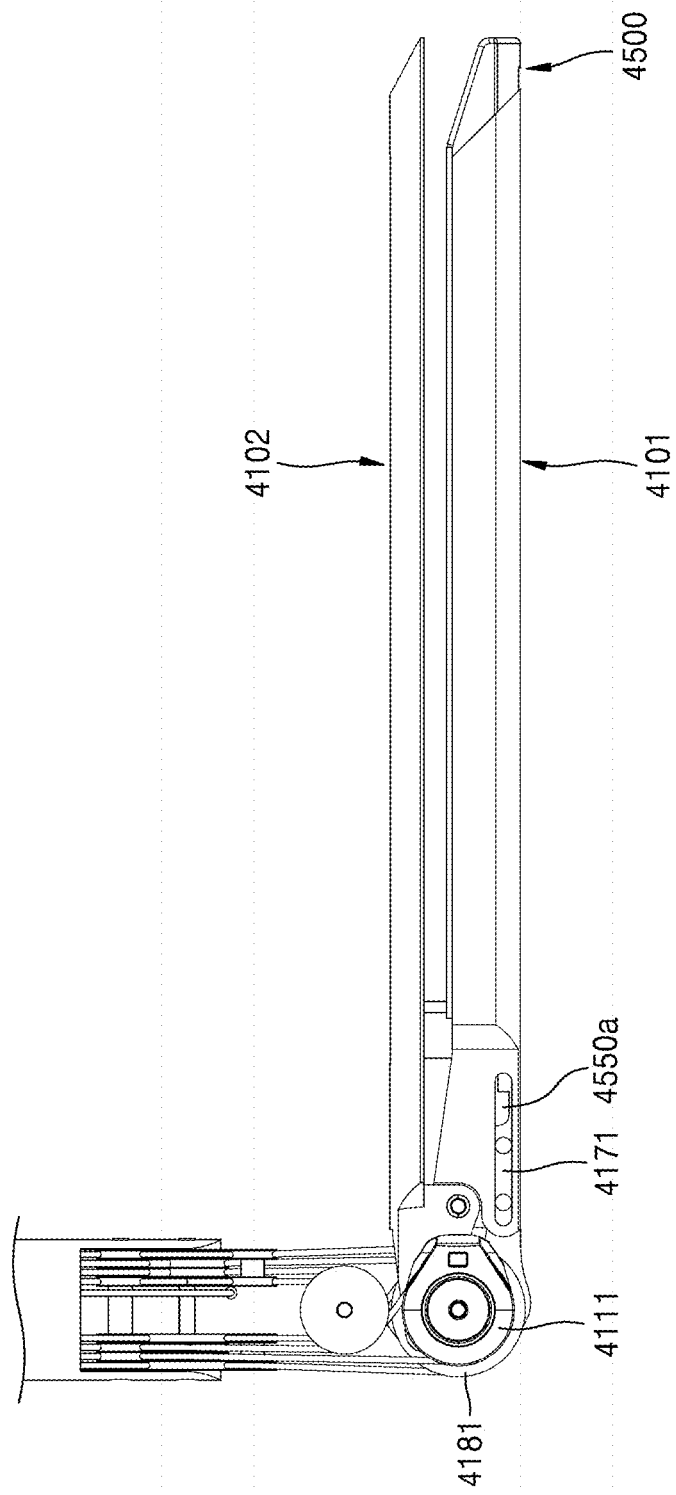
FIGS. 58 to 61 are plan views illustrating an actuation motion of the end tool of the surgical instrument of FIG. 2, and are views illustrating a process of performing an actuation motion in a state in which the jaws are yaw-rotated by −90°.
Figure 59:
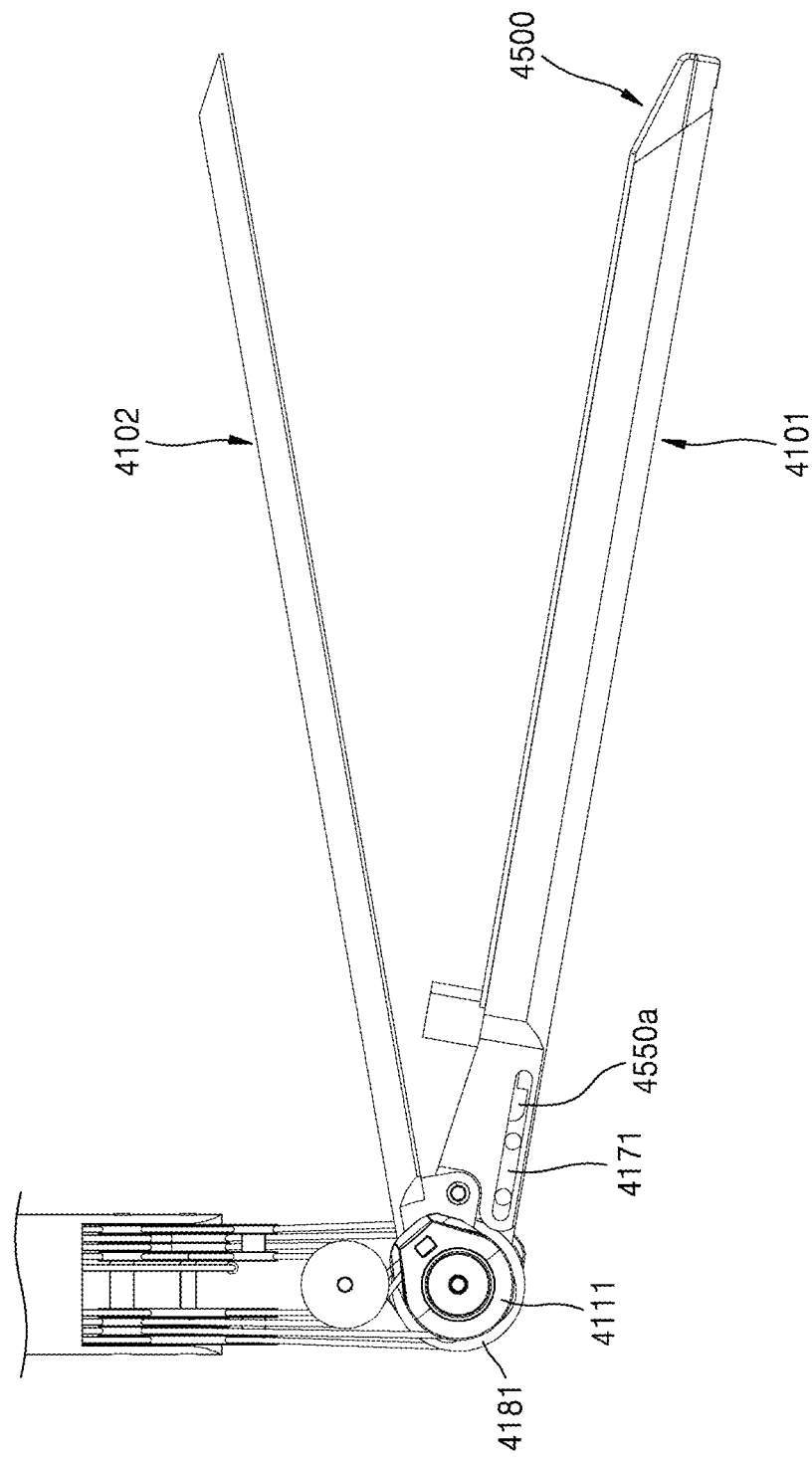
Figure 60:
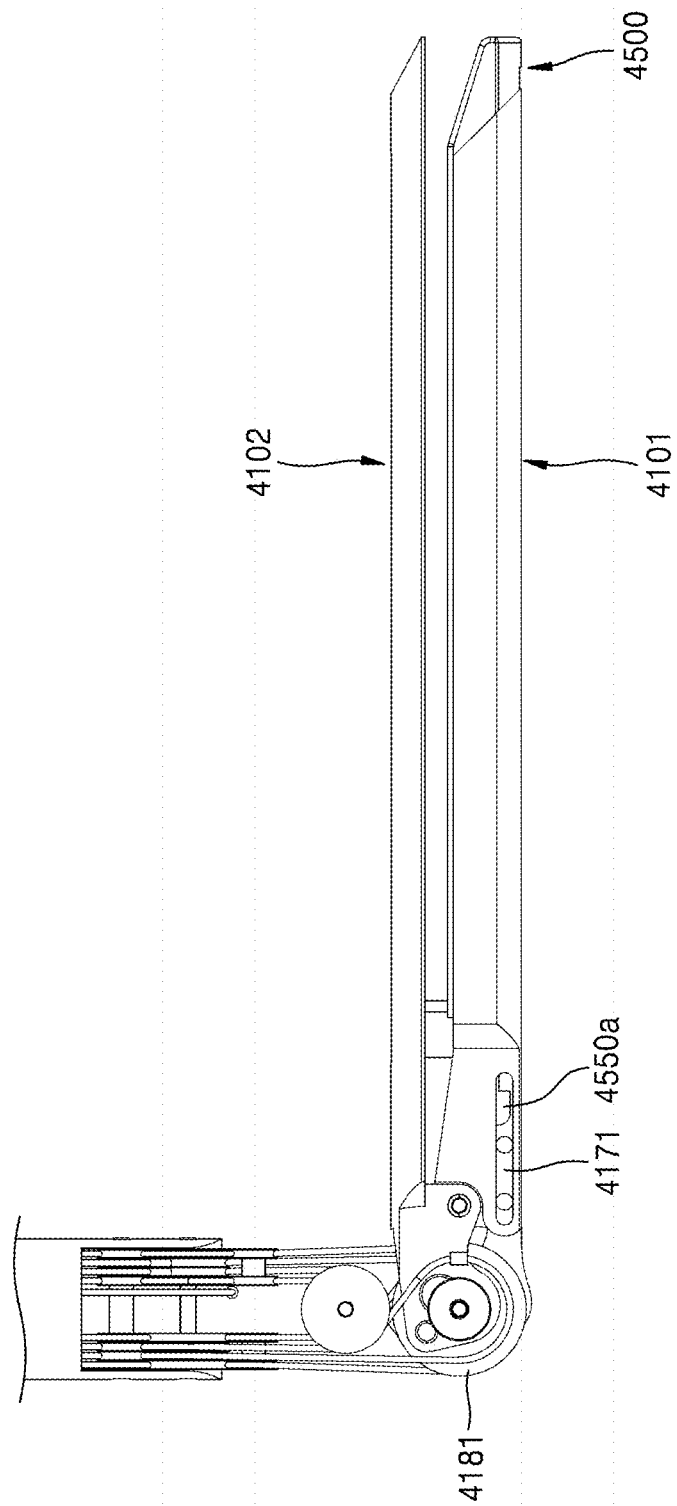
Figure 61:
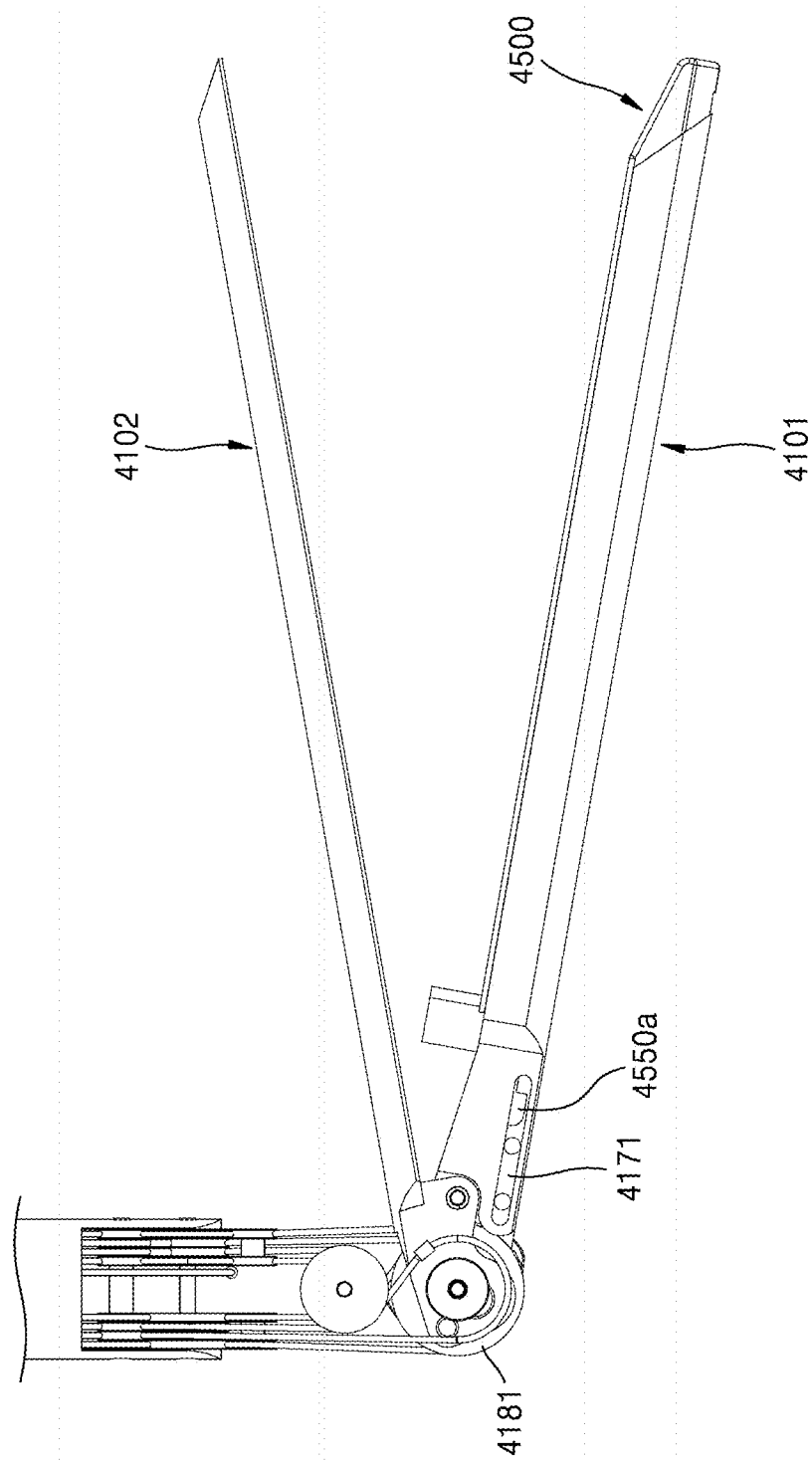

FIGS. 58 and 60 are diagrams illustrating a state in which jaws are yaw-rotated by −90°, and FIGS. 59 and 61 are diagrams illustrating a process of performing an actuation motion in a state in which jaws are yaw-rotated by −90°. Here, FIGS. 60 and 61 are diagrams in which the pulley 2111 is illustrated, and FIGS. 62 and 63 are diagrams in which the pulley 2111 is omitted.

Figure 62:
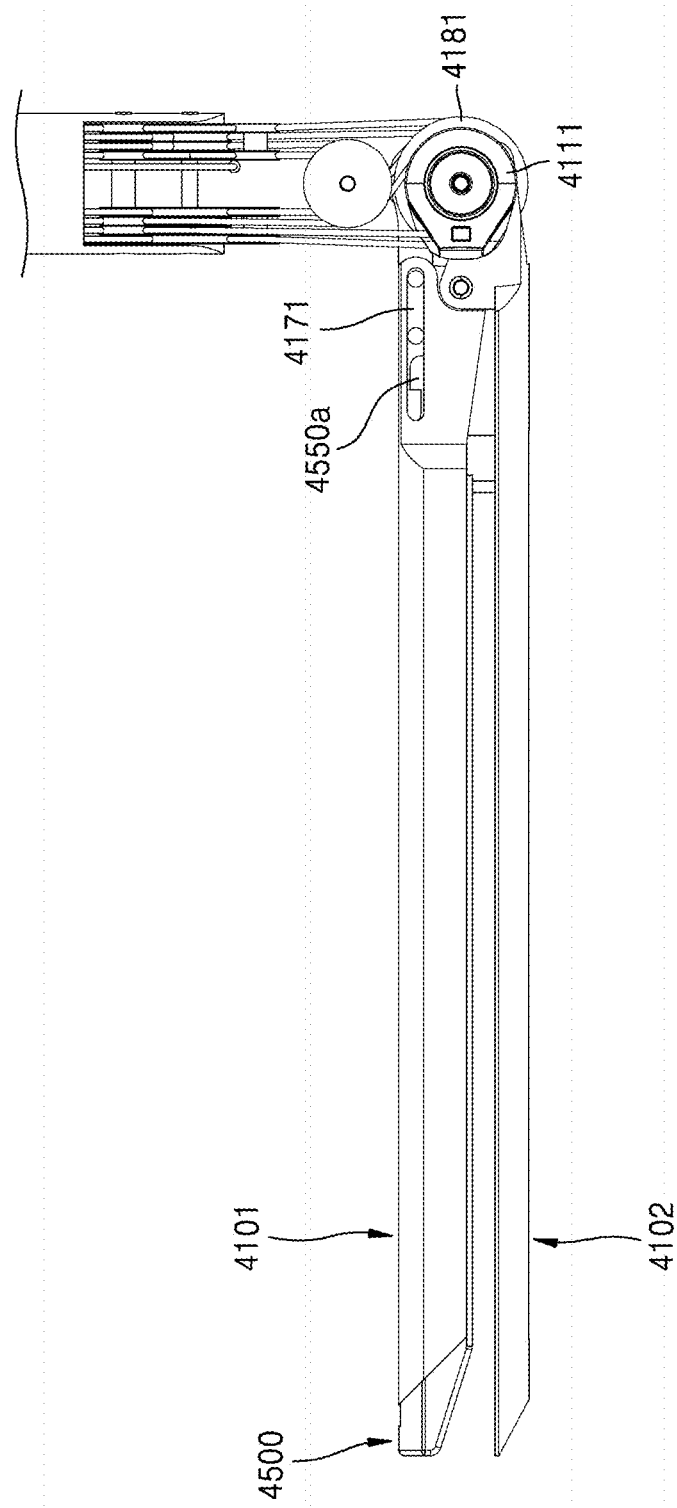
FIGS. 62 to 65 are plan views illustrating an actuation motion of the end tool of the surgical instrument of FIG. 2, and are views illustrating a process of performing an actuation motion in a state in which the jaws are yaw-rotated by +90°.
Figure 63:
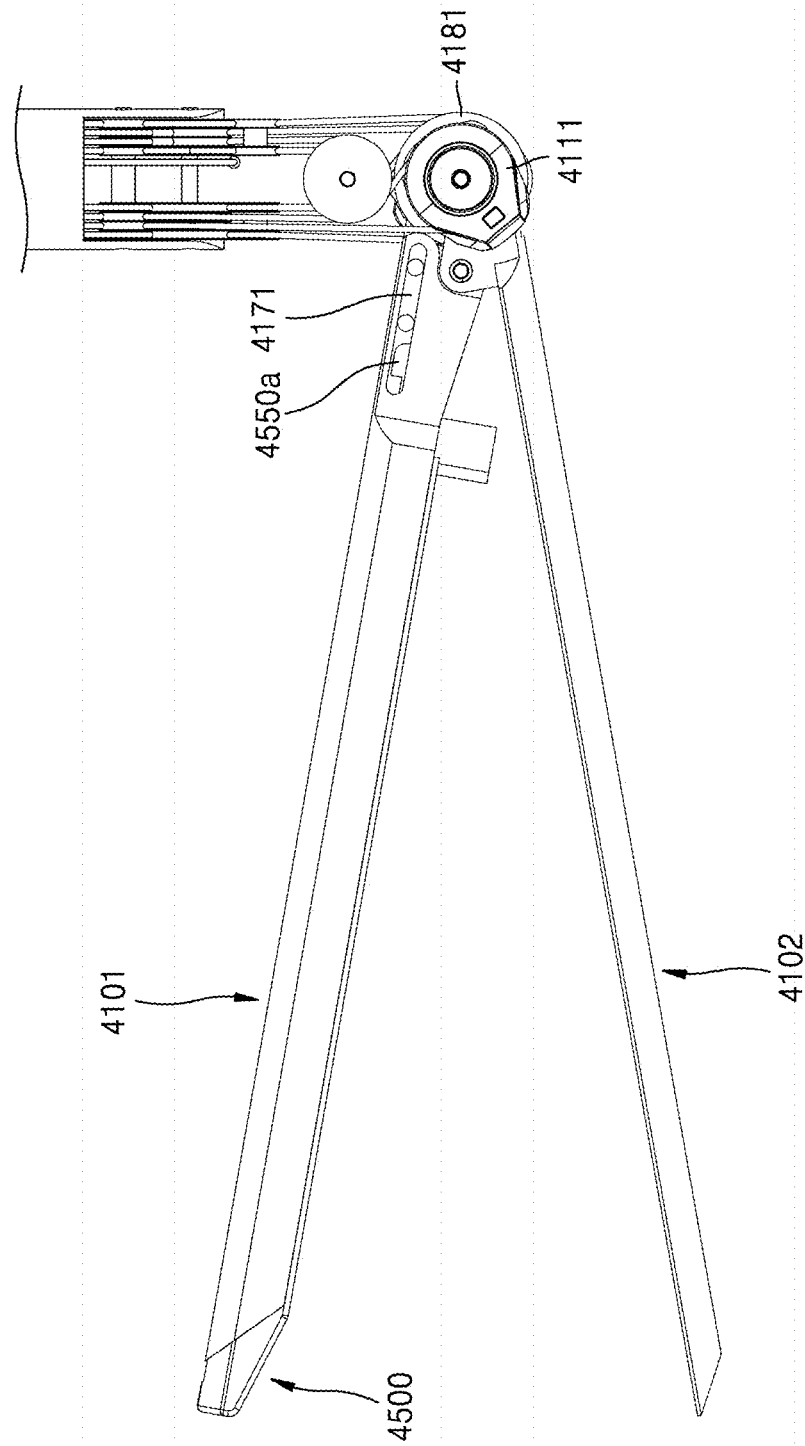
Figure 64:
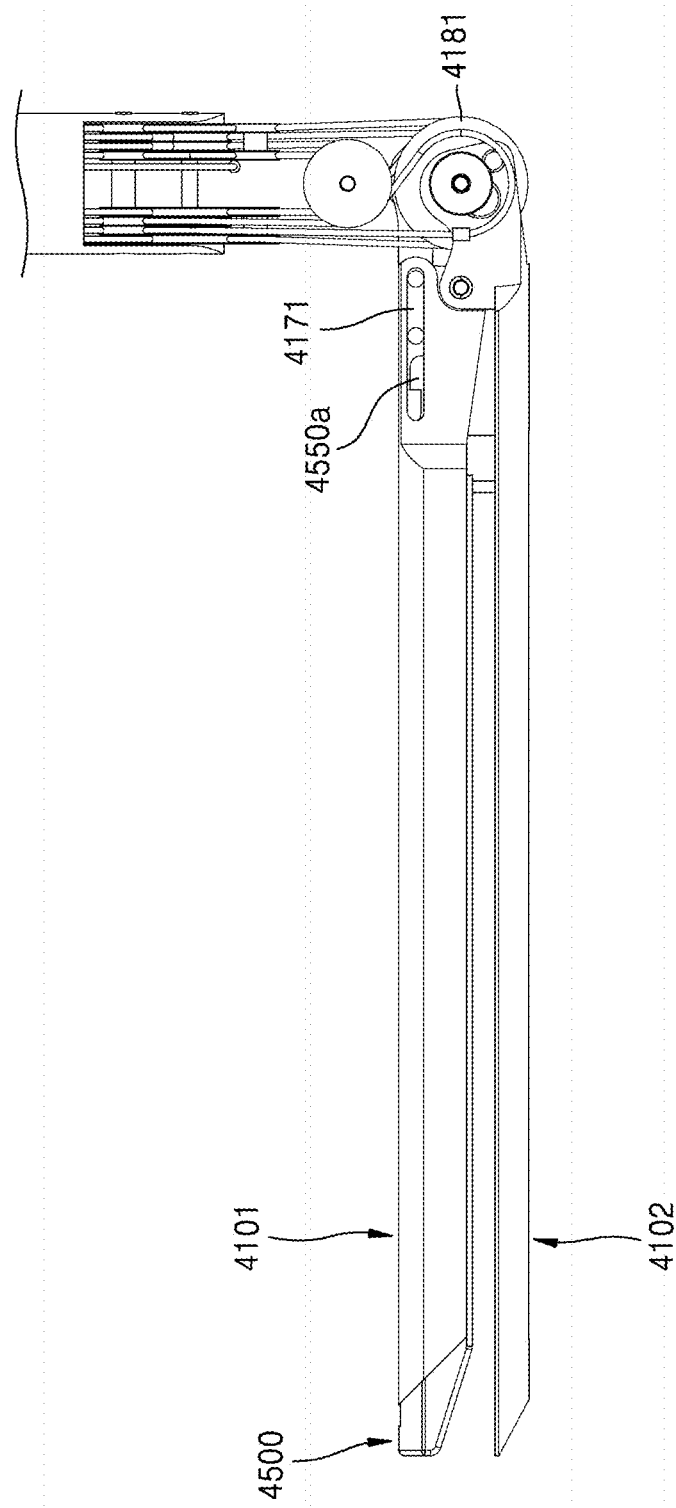
Figure 65:
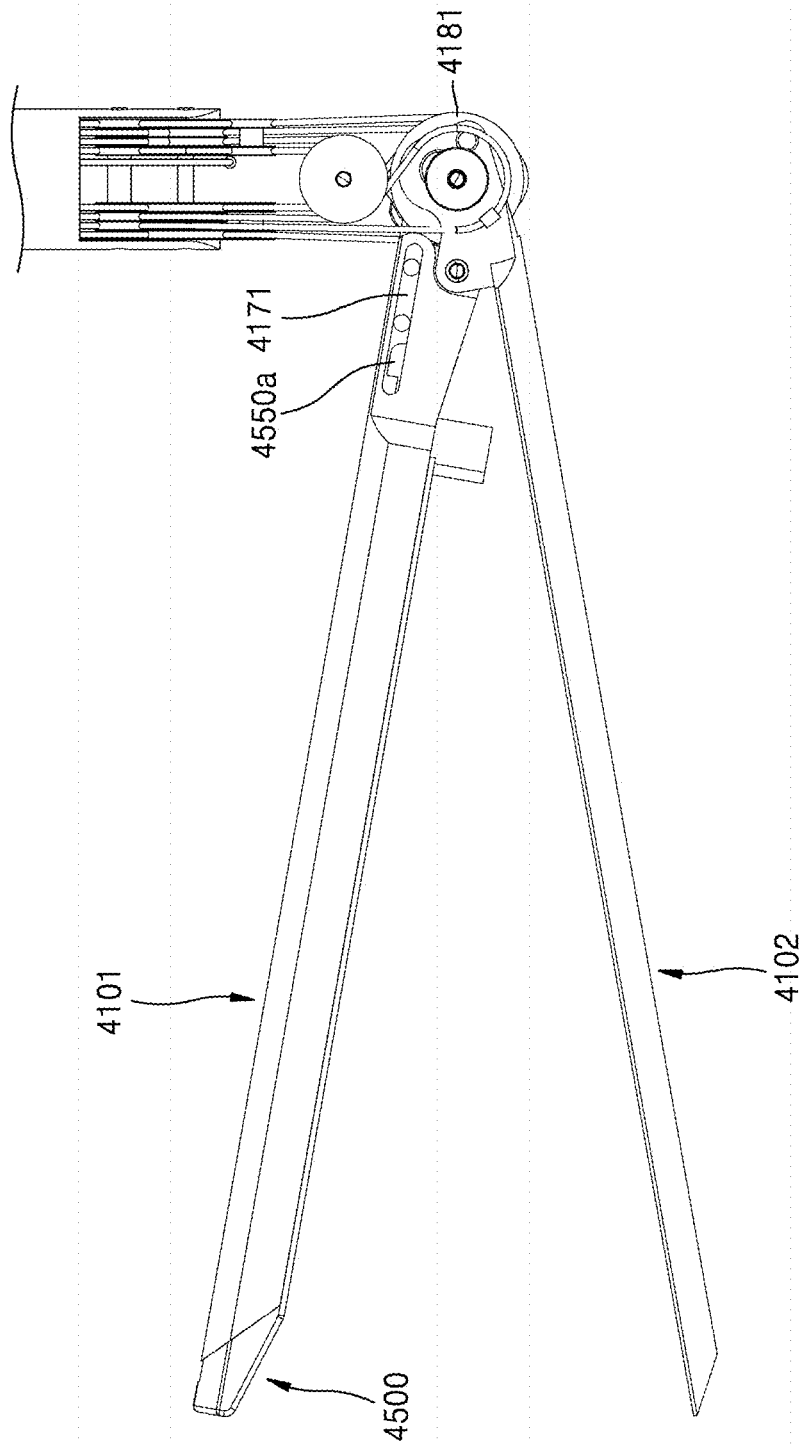

FIGS. 62 and 64 are diagrams illustrating a state in which jaws are yaw-rotated by −90°, and FIGS. 63 and 65 are diagrams illustrating a process of performing an actuation motion in a state in which jaws are yaw-rotated by −90°. Here, FIGS. 62 and 63 are diagrams in which the pulley 2111 is illustrated, and FIGS. 64 and 65 are diagrams in which the pulley 2111 is omitted.

As illustrated in FIGS. 58 to 65, the end tool of the surgical instrument according to the first embodiment of the present disclosure is formed to be able to normally perform an actuation motion even when the jaws are yaw-rotated by +90° or −90°.

Figure 66:
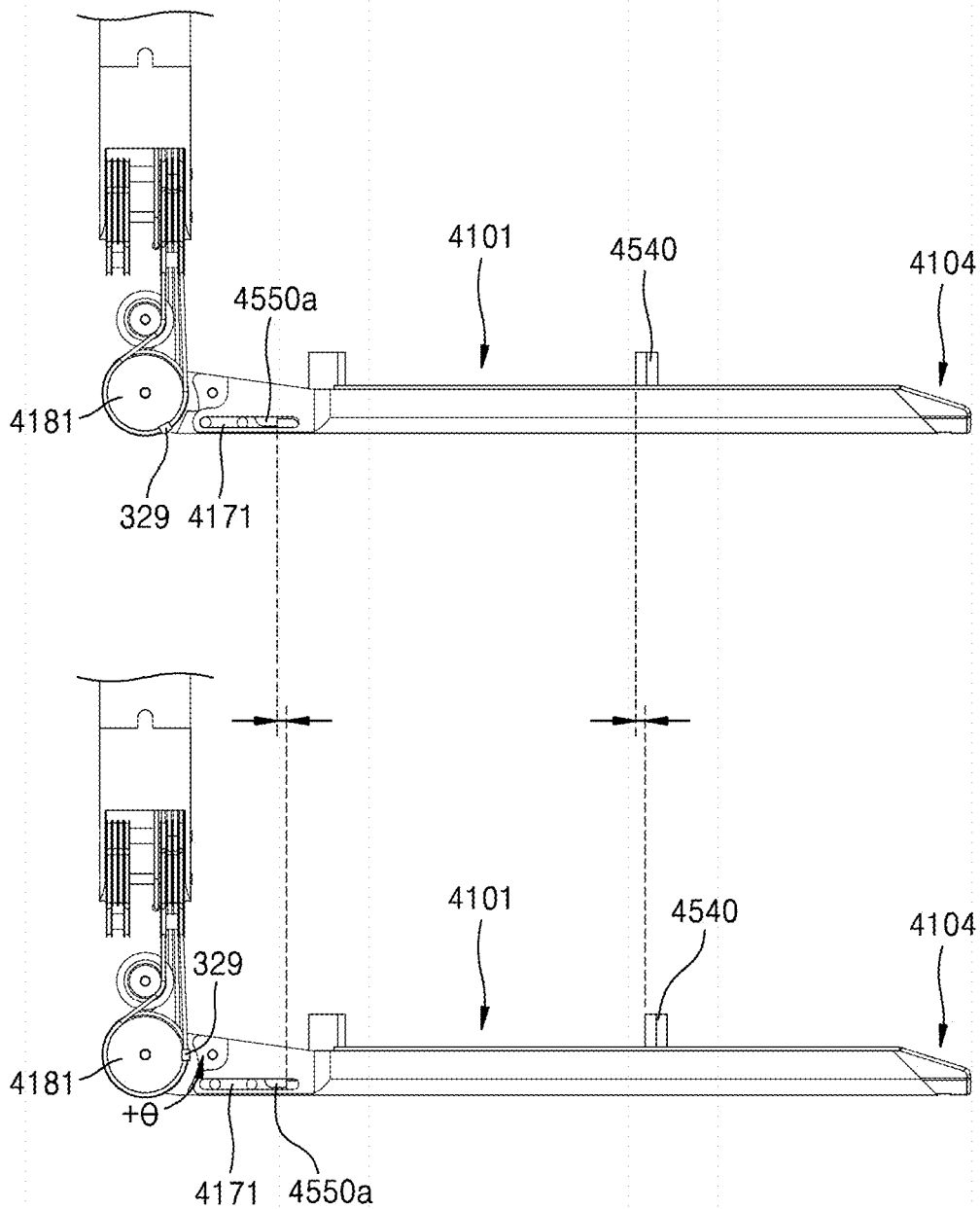
FIGS. 66 and 67 are plan views illustrating a stapling motion of the end tool of the surgical instrument of FIG. 2, and is a view illustrating a process of performing a stapling motion in a state in which the jaws are yaw-rotated by +90°.
Figure 67:
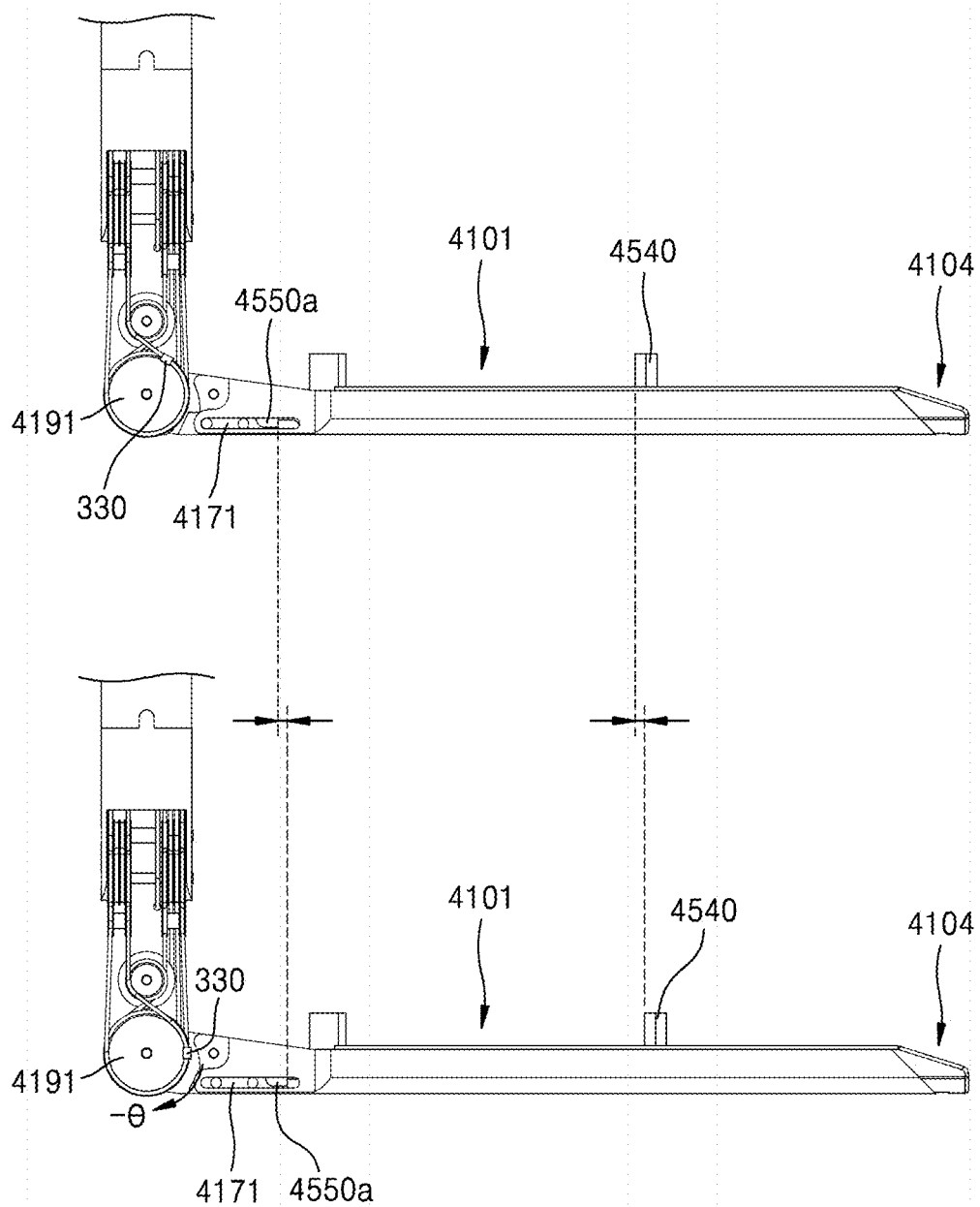

FIGS. 66 and 67 are plan views illustrating stapling and cutting motions of the end tool of the surgical instrument of FIG. 2, and illustrating a process of performing the stapling and cutting motions in a state in which jaws are yaw-rotated by +90°. As illustrated in FIG. 66, the end tool of the surgical instrument according to the first embodiment of the present disclosure is formed to be able to normally perform the stapling and cutting motions even when the jaws are yaw-rotated by +90°.

In detail, in a state in which the pulley 2111, the pulley 2121, the first staple pulley 4181, and the second staple pulley 4191 rotate by +90° around the rotation shaft 2141, when the first staple pulley 4181 and the second staple pulley 4191 rotate alternately in the clockwise/counterclockwise directions, the link member 2171 and the reciprocating member 4551 connected thereto repeatedly move forward and backward. In addition, when the reciprocating member 4551 moves forward, the operation member 4540 moves forward together with the reciprocating member 4551, and when the reciprocating member 4551 moves backward, only the reciprocating member 4551 moves backward and the operation member 4540 remains stationary in place. By repeating this process, the stapling and cutting motions are performed as the operation member 4540 moves toward the distal end 4502.

Figure 68:
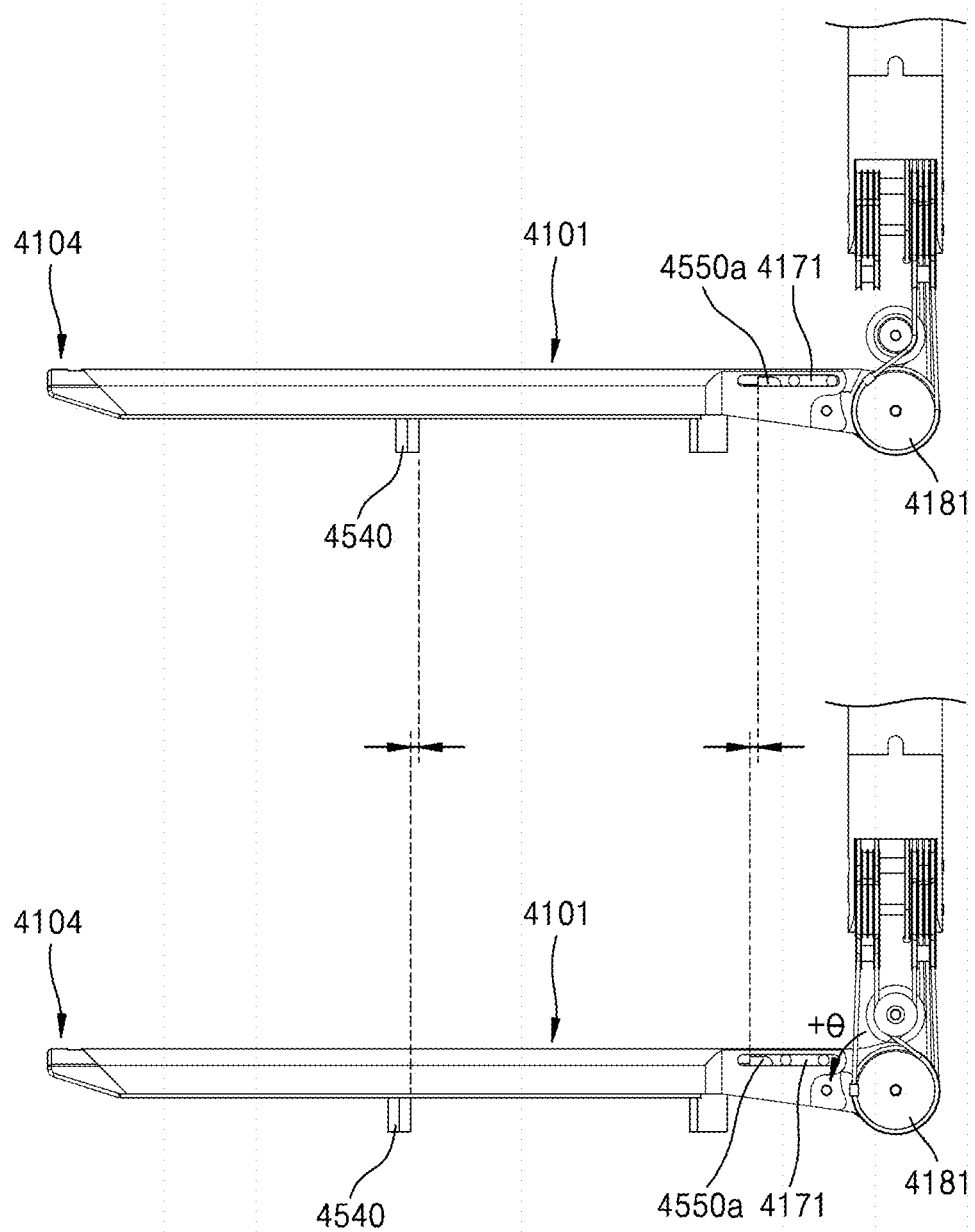
FIGS. 68 and 69 are plan views illustrating a stapling motion of the end tool of the surgical instrument of FIG. 2, and is a view illustrating a process of performing a stapling motion in a state in which the jaws are yaw-rotated by −90°.
Figure 69:
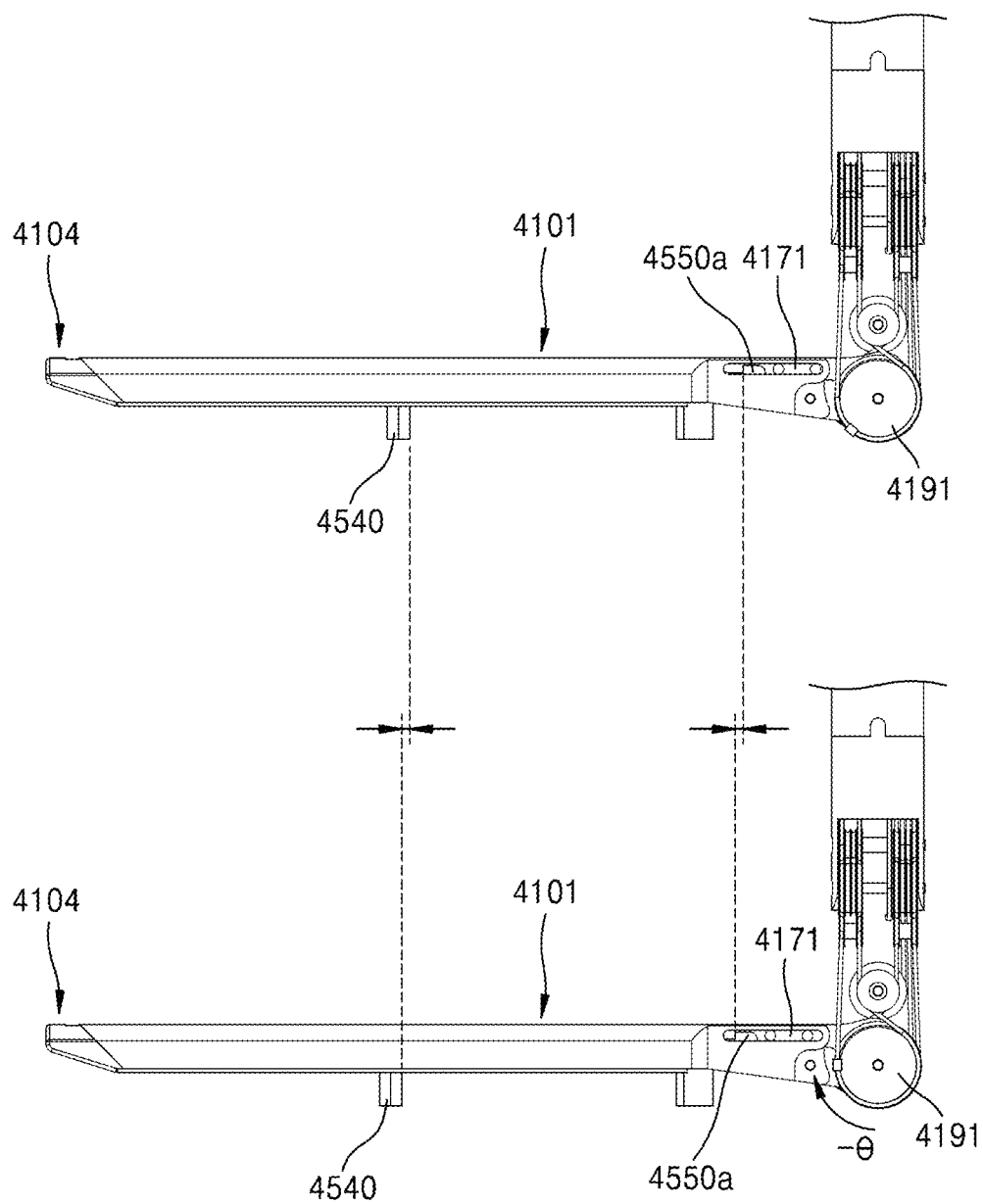

FIGS. 68 and 69 are plan views illustrating stapling and cutting motions of the end tool of the surgical instrument of FIG. 2, and illustrating a process of performing the stapling and cutting motions in a state in which jaws are yaw-rotated by −90°. As illustrated in FIG. 68, the end tool of the surgical instrument according to the first embodiment of the present disclosure is formed to be able to normally perform the stapling and cutting motions even when the jaws are yaw-rotated by −90°.

In detail, in a state in which the pulley 2111, the pulley 2121, the first staple pulley 4181, and the second staple pulley 4191 rotate by −90° around the rotation shaft 2141, when the first staple pulley 4181 and the second staple pulley 4191 rotate alternately in the clockwise/counterclockwise directions, the link member 2171 and the reciprocating member 4551 connected thereto repeatedly move forward and backward. In addition, when the reciprocating member 4551 moves forward, the operation member 4540 moves forward together with the reciprocating member 4551, and when the reciprocating member 4551 moves backward, only the reciprocating member 4551 moves backward and the operation member 4540 remains stationary in place. By repeating this process, the stapling and cutting motions are performed as the operation member 4540 moves toward the distal end 502.

Figure 70:
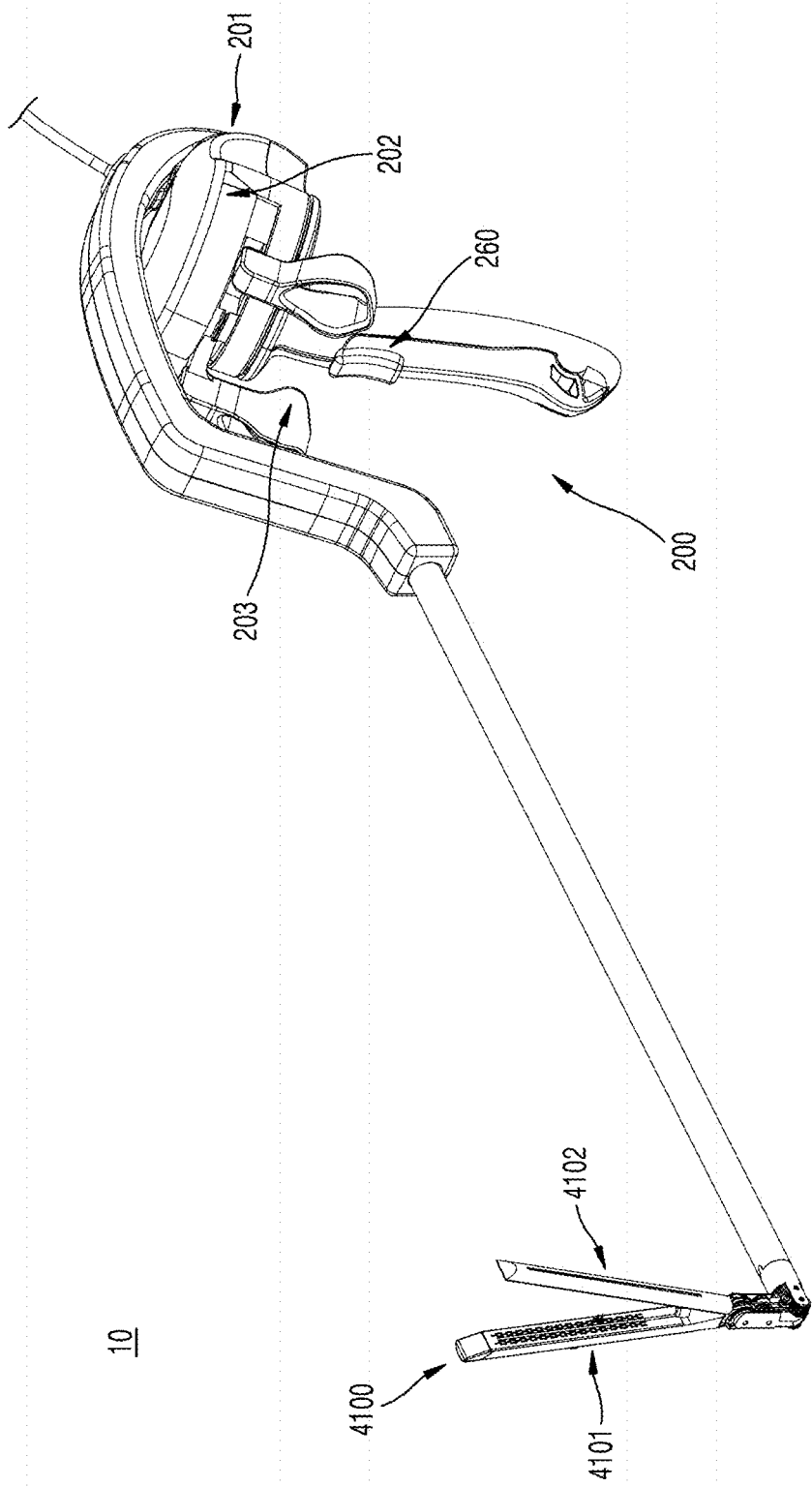
FIGS. 70 to 73 are perspective views illustrating a pitch motion of the surgical instrument of FIG. 2.
Figure 71:
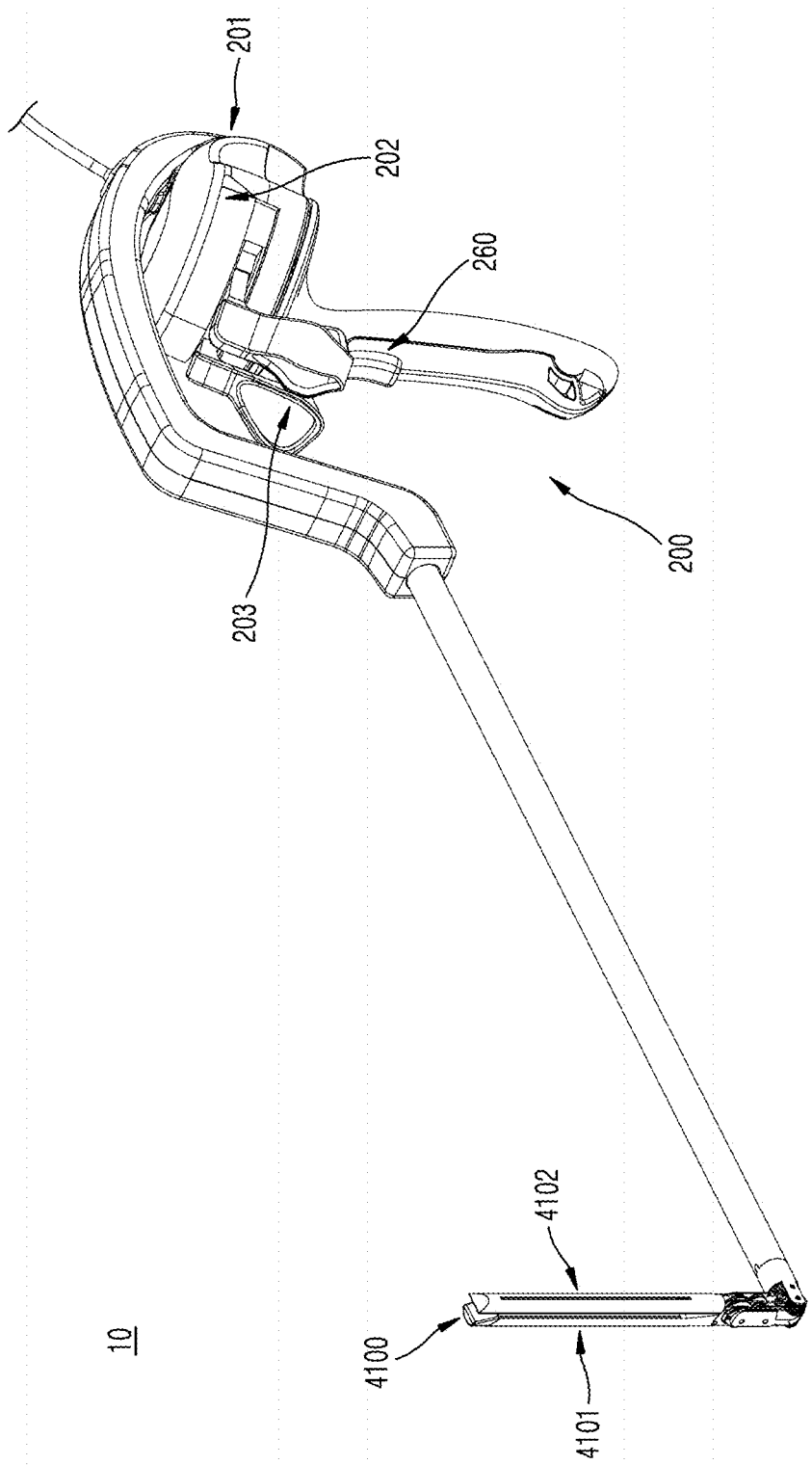
Figure 72:
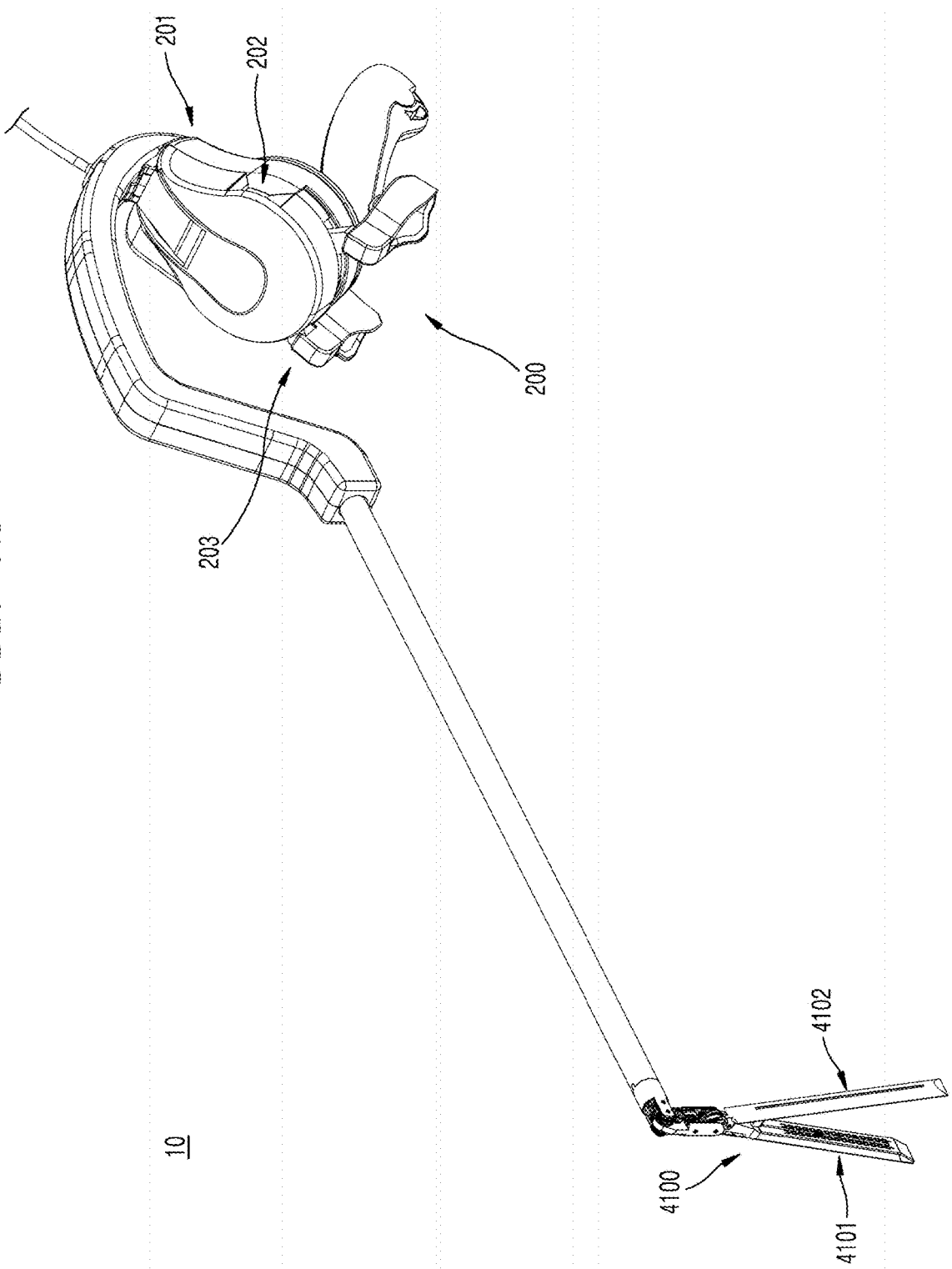
Figure 73:
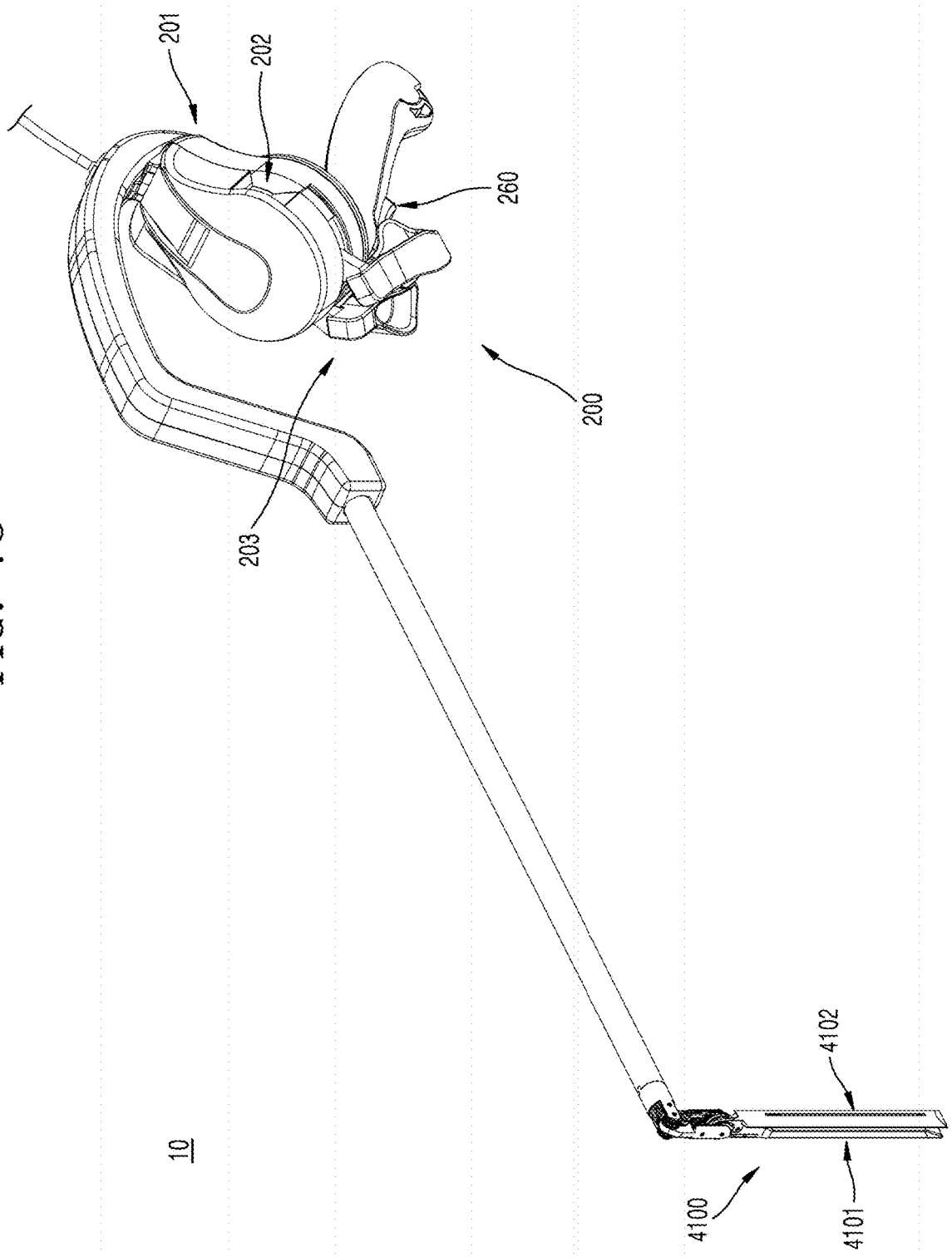

FIG. 70 is a diagram illustrating a state in which jaws are pitch-rotated by −90°, and FIG. 71 is a diagram illustrating a process of performing an actuation motion in a state in which jaws are pitch-rotated by −90°. FIG. 72 is a diagram illustrating a state in which jaws are pitch-rotated by +90°, and FIG. 73 is a diagram illustrating a process of performing an actuation motion in a state in which jaws are pitch-rotated by +90°.

Referring to FIGS. 70 to 73, it may be seen that, in performing a pitch motion, the motions of the manipulation portion 200 and the end tool 4100 are intuitively matched. That is, when the manipulation portion 200 rotates in a positive (+) direction with respect to the pitch rotation shaft (Y-axis), the end tool 4100 also rotates in the positive (+) direction with respect to the pitch rotation shaft (Y-axis). In addition, when the manipulation portion 200 is rotated in a negative (−) direction with respect to the pitch rotation shaft (Y-axis), the end tool 4100 also rotates in the negative (−) direction with respect to the pitch rotation shaft (Y-axis). Here, the rotation angle of the manipulation portion 200 and the rotation angle of the end tool 4100 may be variously set according to the proportions of the pulleys.

Figure 74:
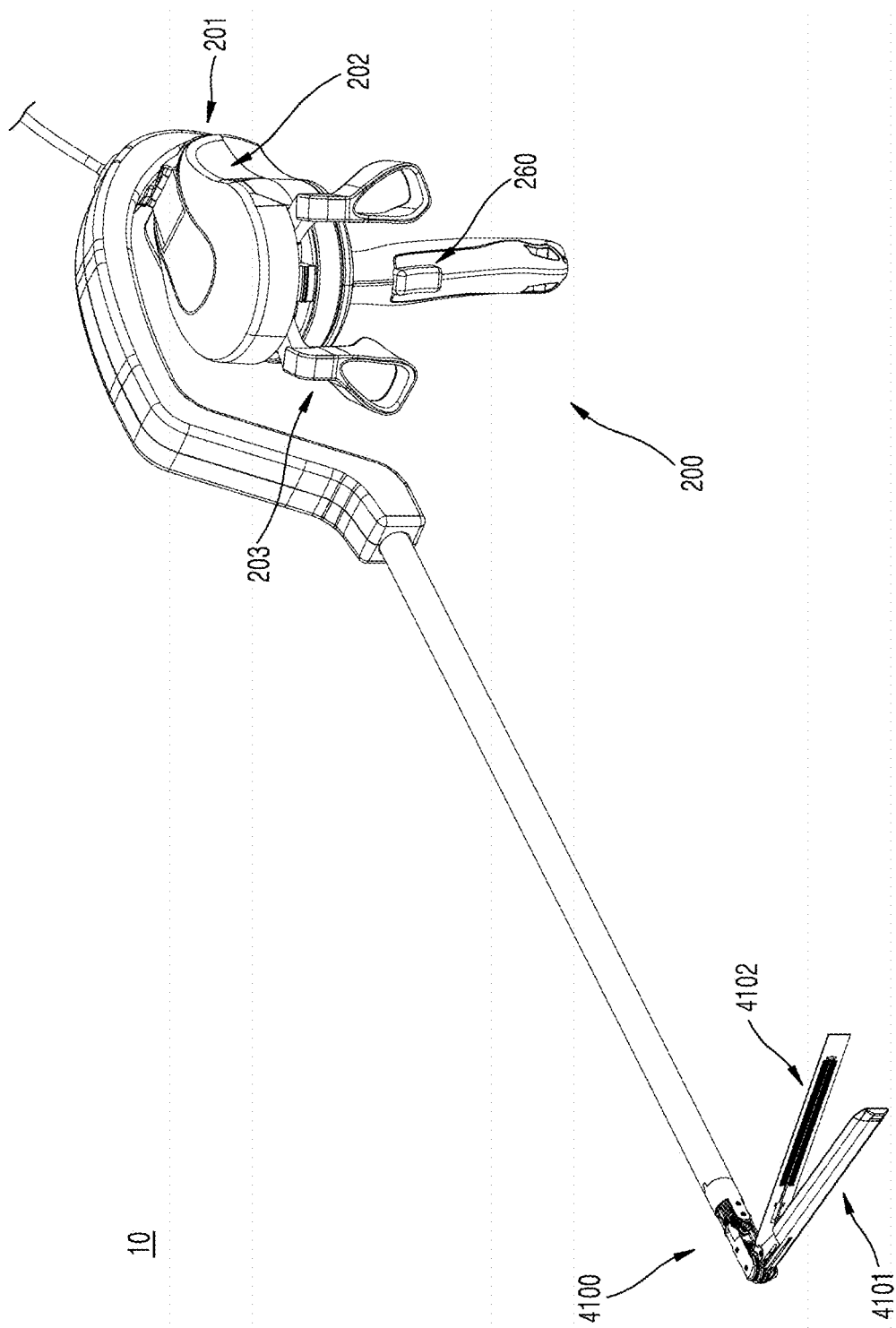
FIGS. 74 to 77 are perspective views illustrating a yaw motion of the surgical instrument of FIG. 2.
Figure 75:
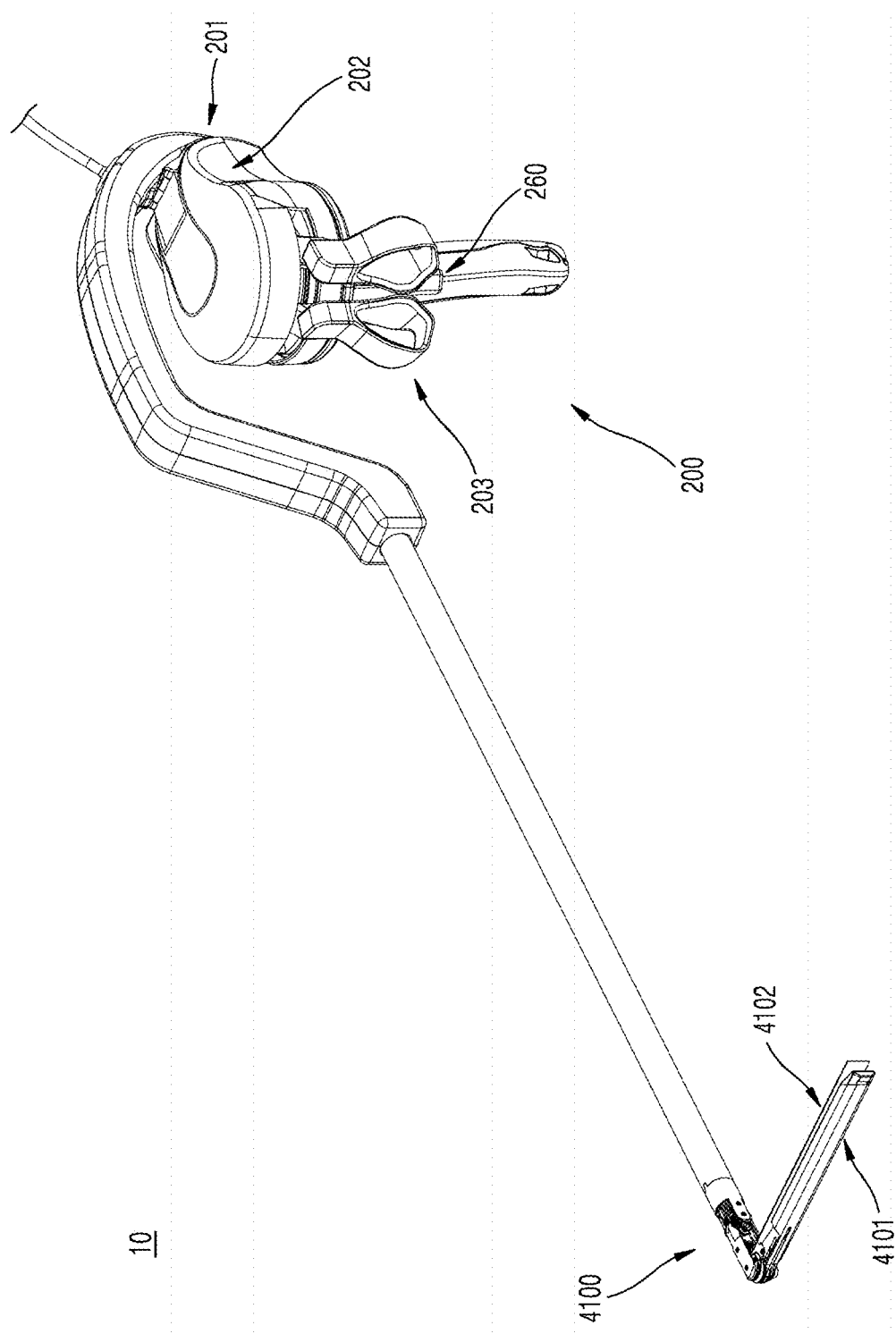
Figure 76:
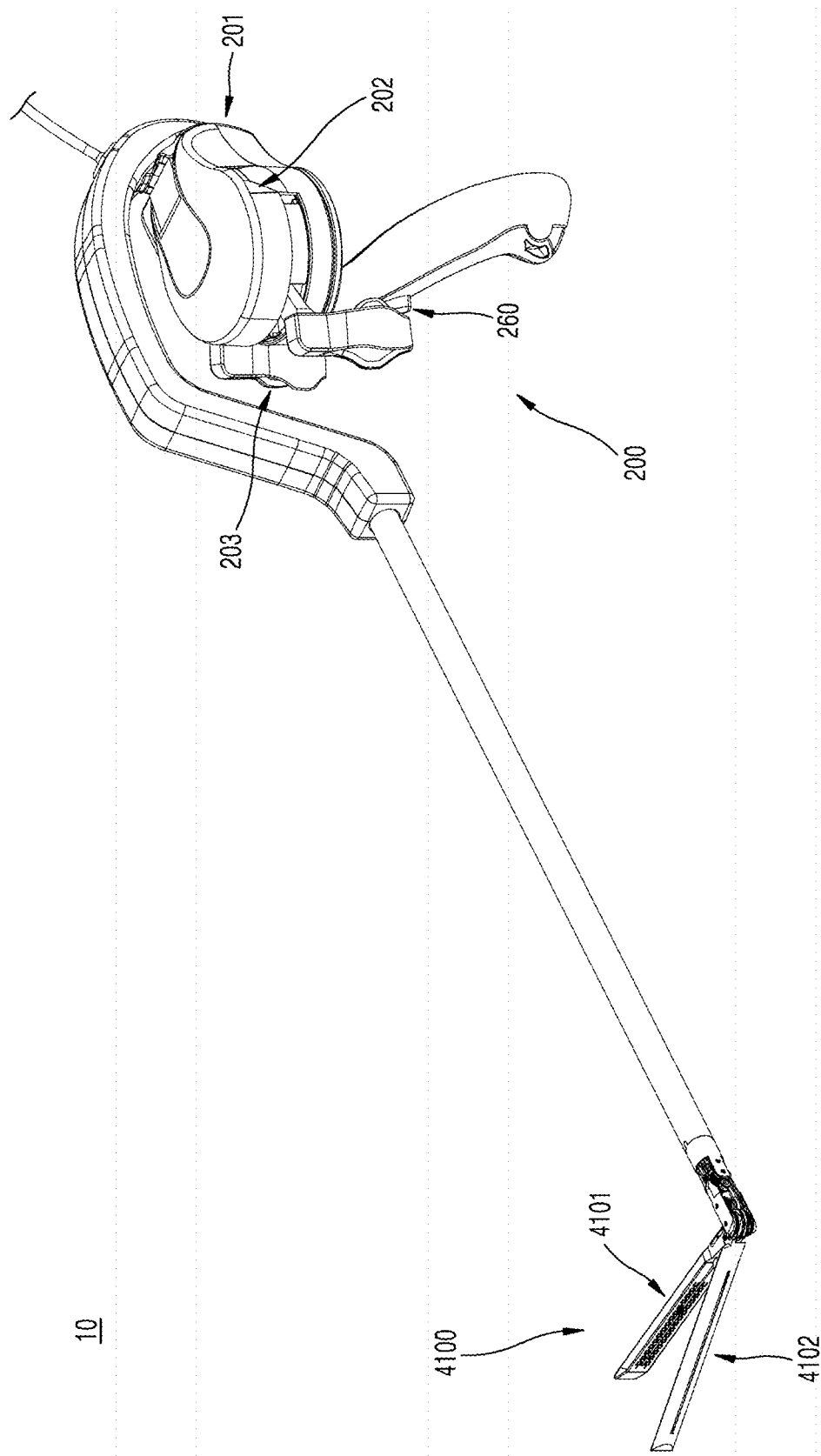
Figure 77:
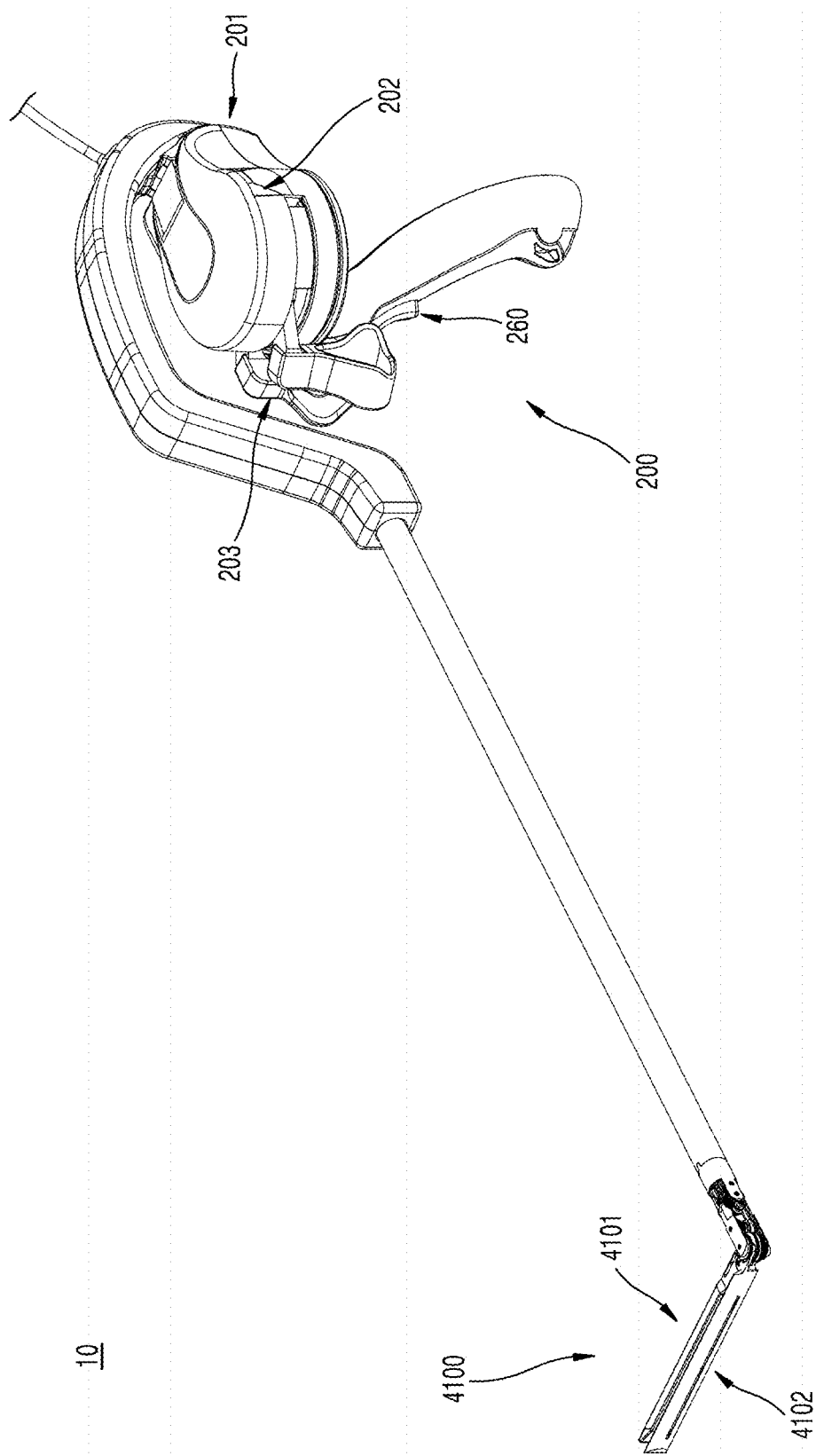

FIG. 74 is a diagram illustrating a state in which jaws are yaw-rotated by +90°, and FIG. 75 is a diagram illustrating a process of performing an actuation motion in a state in which jaws are yaw-rotated by +90°. FIG. 76 is a diagram illustrating a state in which jaws are yaw-rotated by −90°, and FIG. 77 is a diagram illustrating a process of performing an actuation motion in a state in which jaws are yaw-rotated by −90°.

Referring to FIGS. 74 to 77, it may be seen that, in performing a yaw motion, the motions of the manipulation portion 200 and the end tool 4100 are intuitively matched. That is, when the manipulation portion 200 rotates in a positive (+) direction with respect to the yaw rotation shaft (Z-axis), the end tool 4100 also rotates in the positive (+) direction with respect to the yaw rotation shaft (Z-axis). In addition, when the manipulation portion 200 rotates in a negative (−) direction with respect to the yaw rotation shaft (Z-axis), the end tool 4100 also rotates in the negative (−) direction with respect to the yaw rotation shaft (Z-axis). Here, the rotation angle of the manipulation portion 200 and the rotation angle of the end tool 4100 may be variously set according to the proportions of the pulleys.

Figure 78:
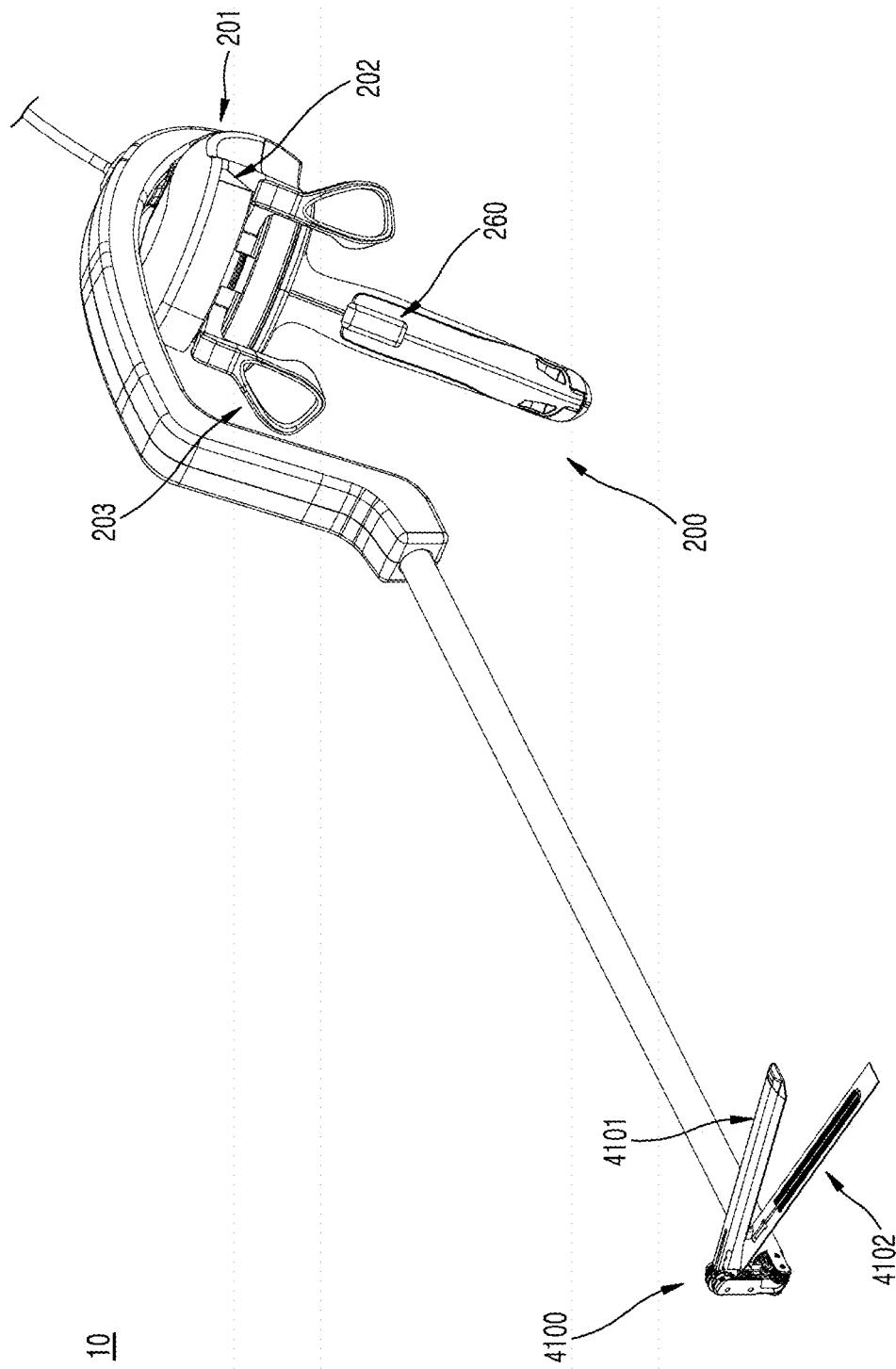
FIGS. 78 to 81 are plan views illustrating a state in which the end tool of the surgical instrument of FIG. 2 is pitch-rotated and yaw-rotated.
Figure 79:
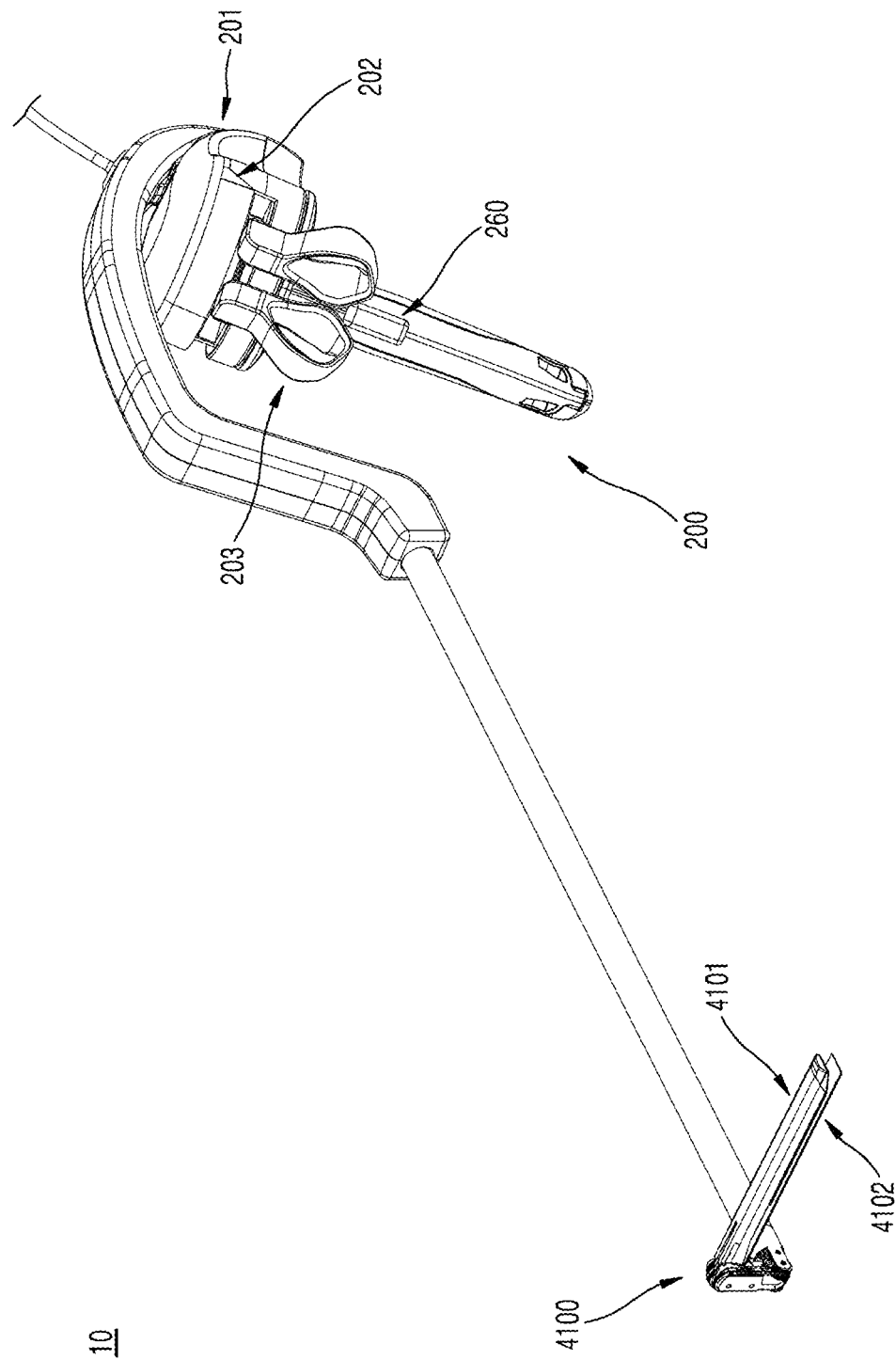
Figure 80:
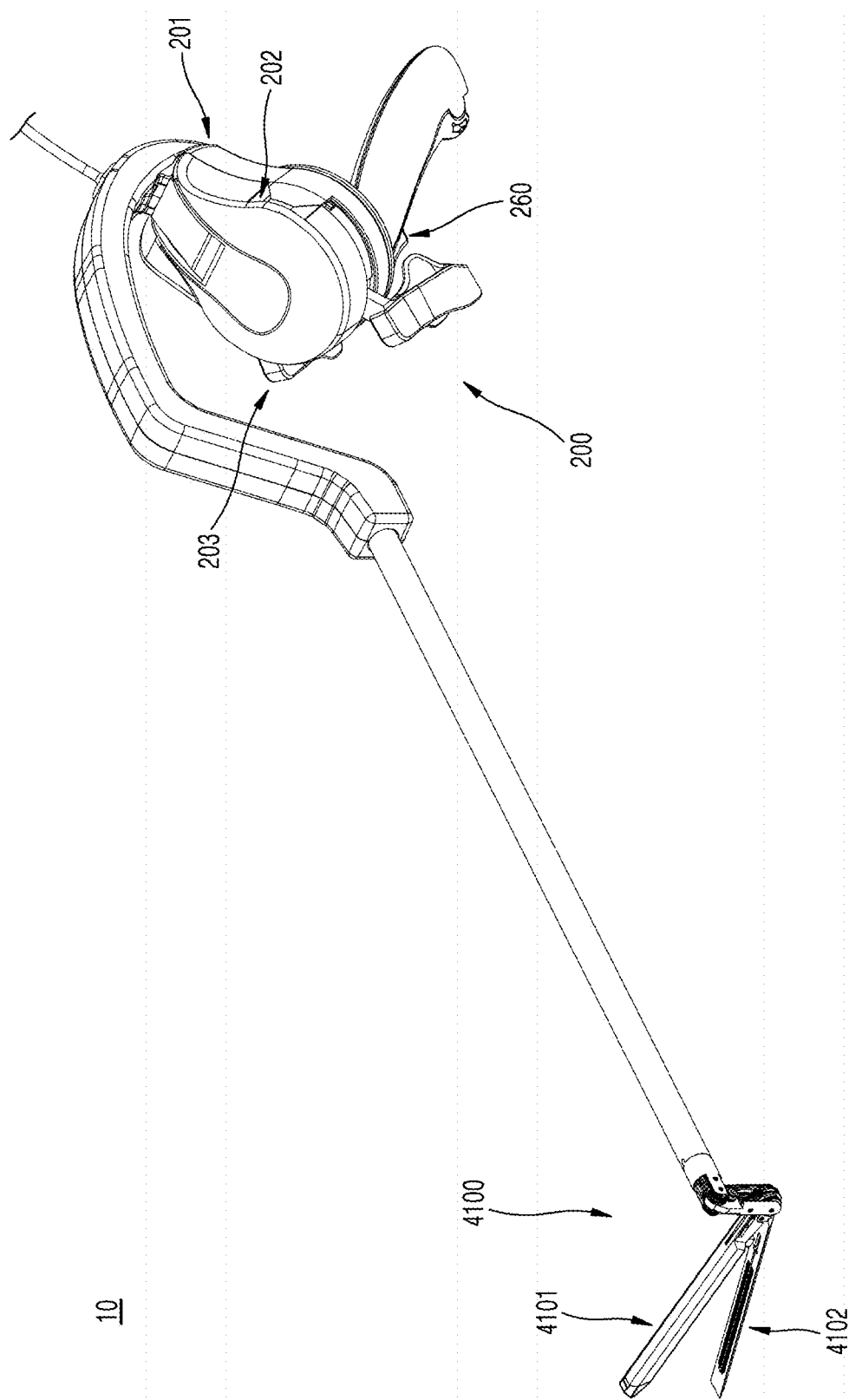
Figure 81:
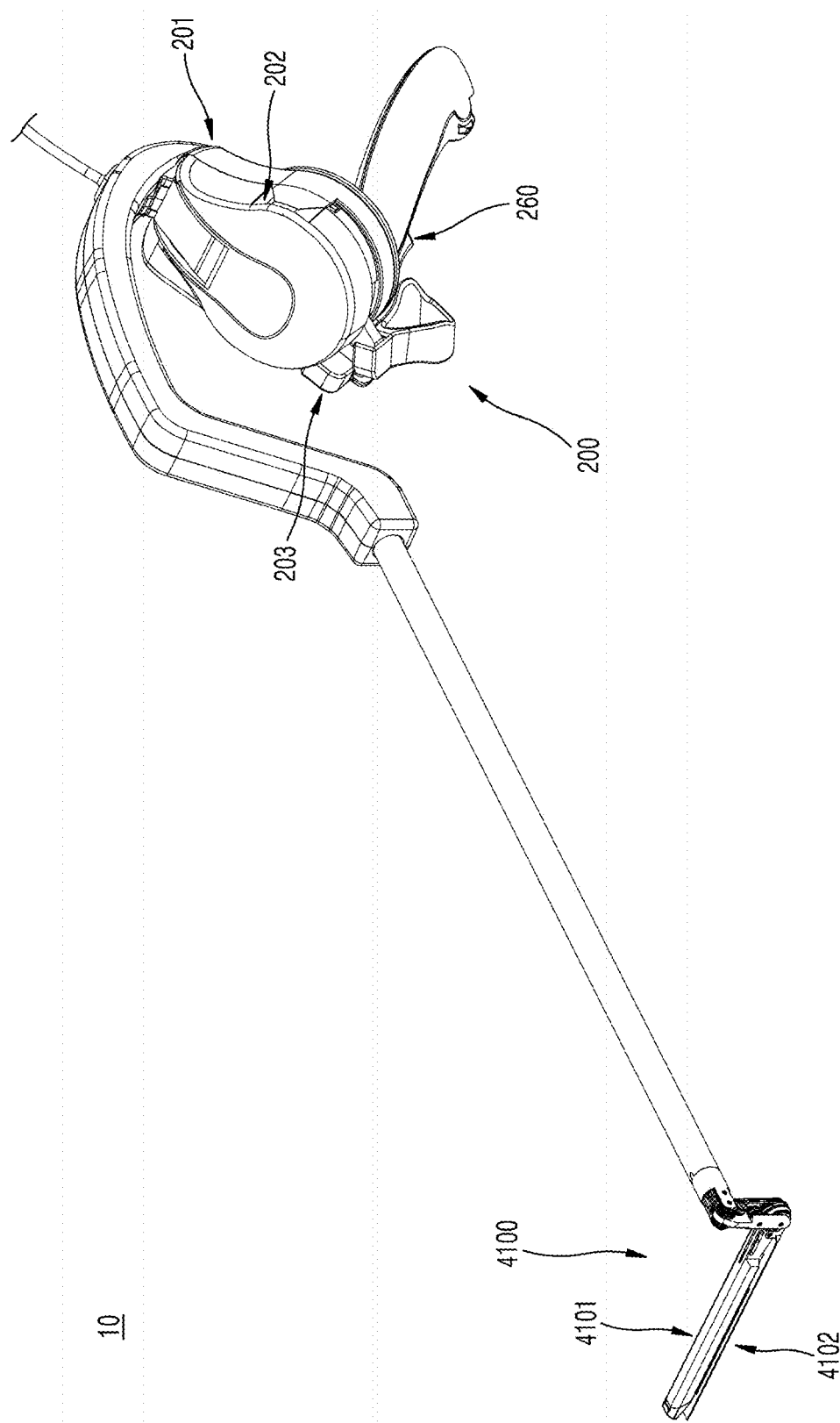

FIG. 78 is a diagram illustrating a state in which jaws are pitch-rotated by −90° and simultaneously yaw-rotated by +90°, and FIG. 79 is a diagram illustrating a process of performing an actuation motion in the state in which jaws are pitch-rotated by −90° and simultaneously yaw-rotated by +90°. FIG. 80 is a diagram illustrating a state in which jaws are pitch-rotated by +90° and simultaneously yaw-rotated by −90°, and FIG. 81 is a diagram illustrating a process of performing an actuation motion in the state in which jaws are pitch-rotated by +90° and simultaneously yaw-rotated by −90°.

Referring to FIGS. 78 to 81, it may be seen that the motions of the manipulation portion 200 and the end tool 4100 are intuitively matched, even when performing the pitch and yaw motions simultaneously.

First Modified Example of First Embodiment

Hereinafter, an operation member 4540 of a surgical instrument according to a first modified example of the first embodiment of the present disclosure will be described. Here, the operation member 4540 of the surgical instrument according to the first modified example of the first embodiment of the present disclosure is different from the above-described operation member (see 4540 of FIG. 35 or the like) of the surgical instrument according to the first embodiment of the present disclosure in that a sidewall 4549 is further provided. Hereinafter, the configuration that is different from that of the first embodiment will be described in detail.

Figure 82:
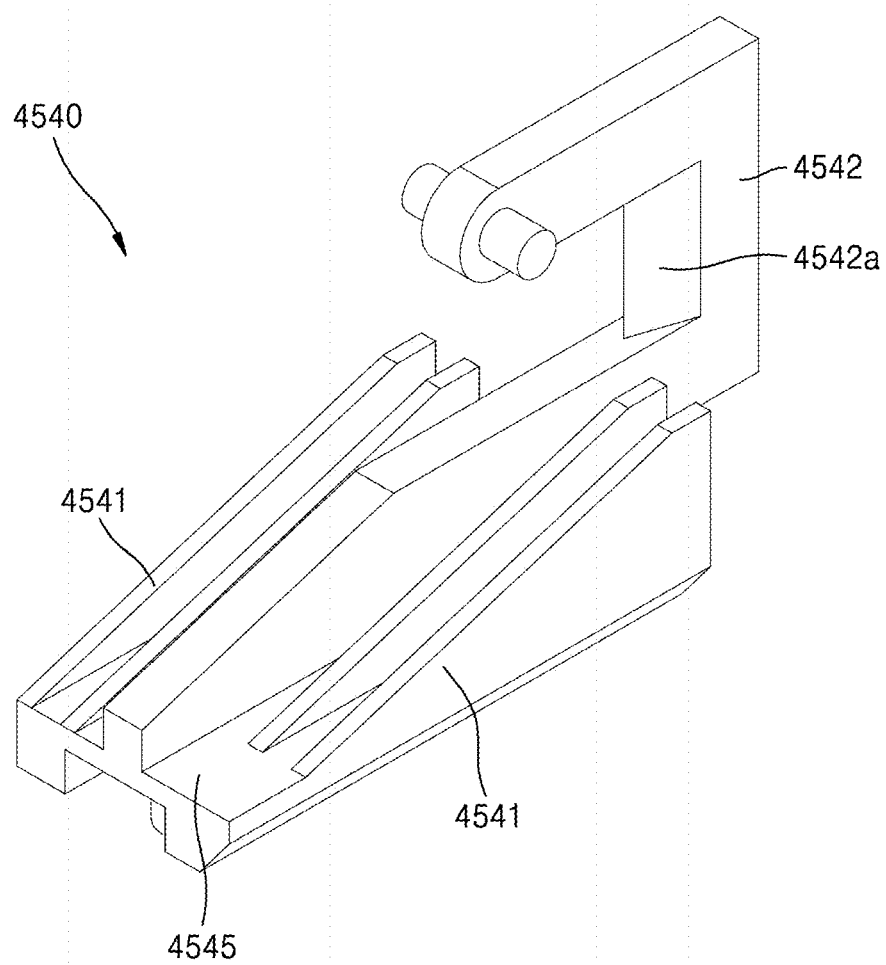
FIGS. 82 to 84 are perspective views illustrating an operation member of a surgical instrument according to a first modified example of the first embodiment of the present disclosure.
Figure 83:
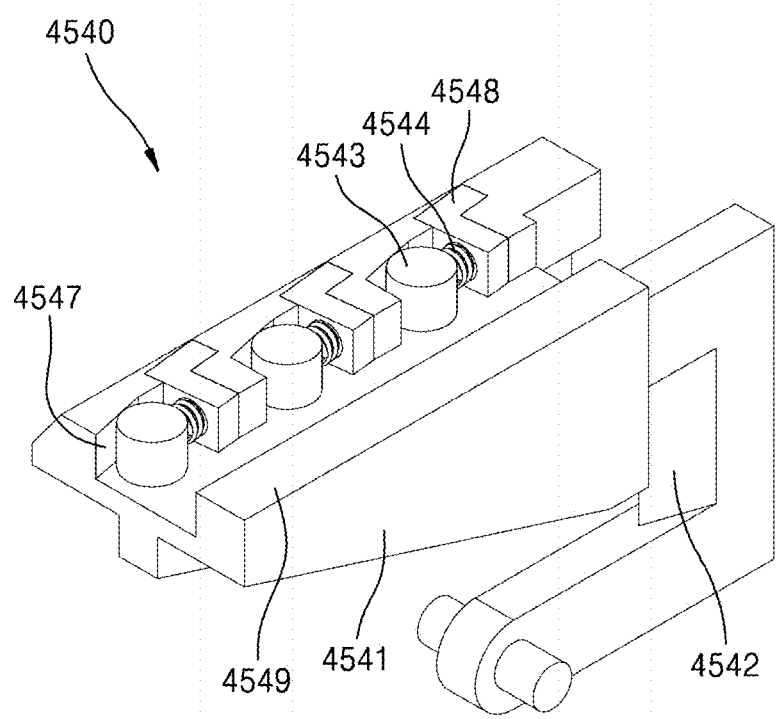
Figure 84:
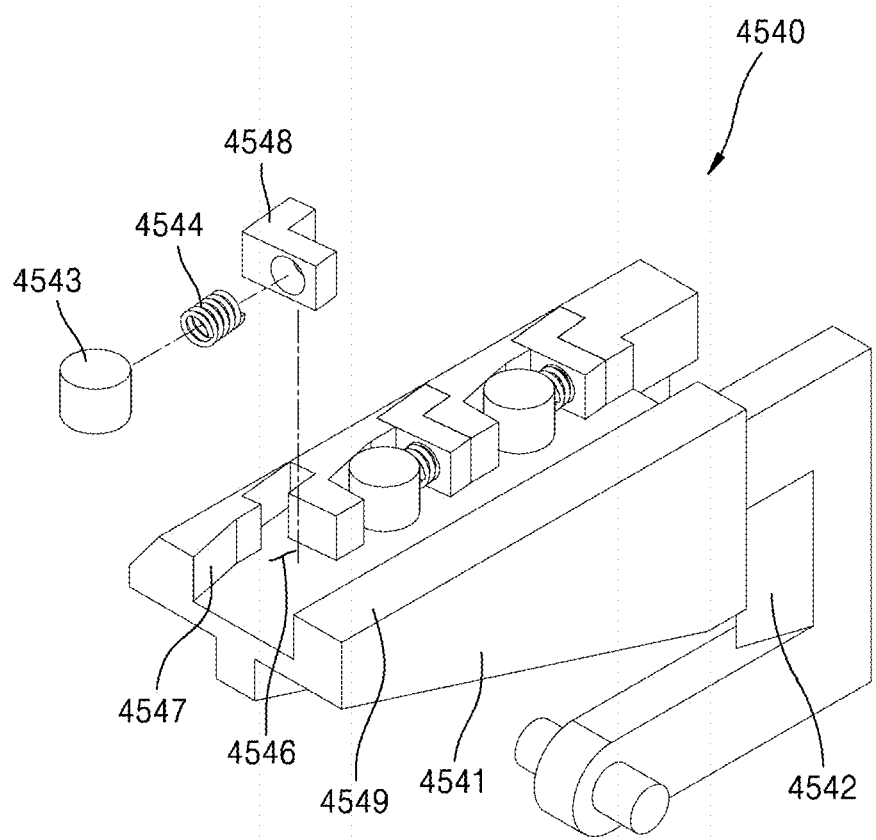
Figure 85:
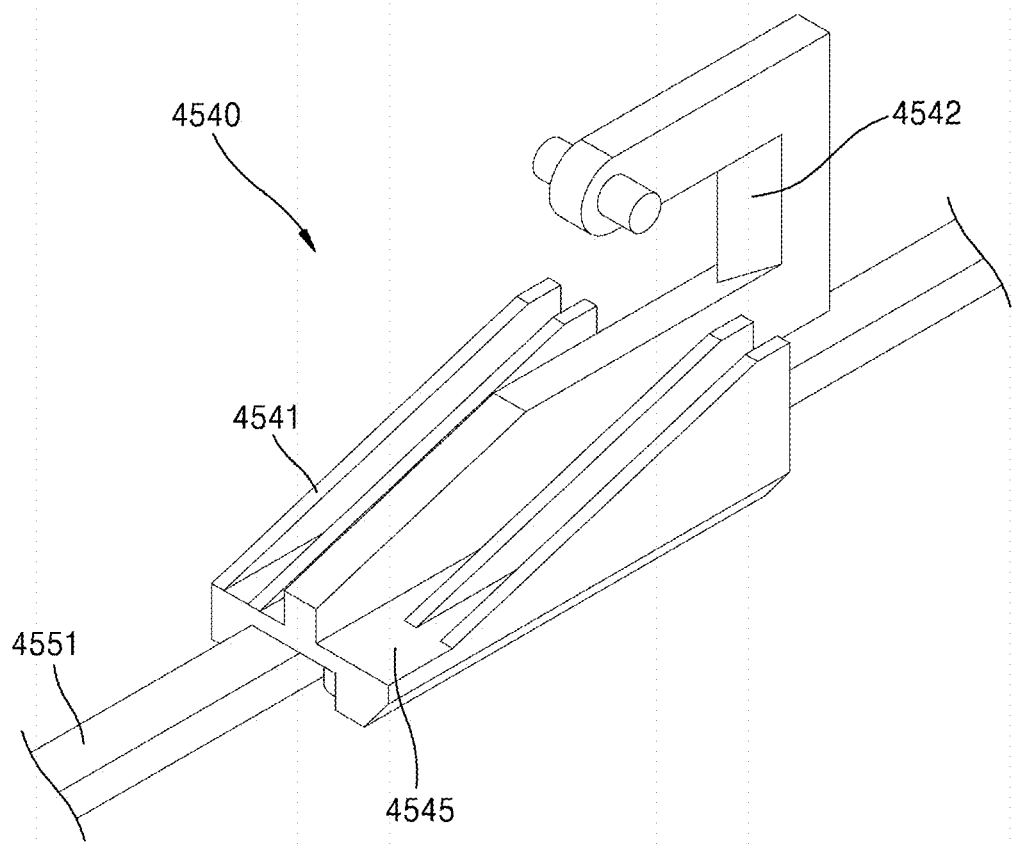
FIGS. 85 and 86 are perspective views illustrating a state in which the operation member of FIG. 82 is coupled to a reciprocating member.
Figure 86:
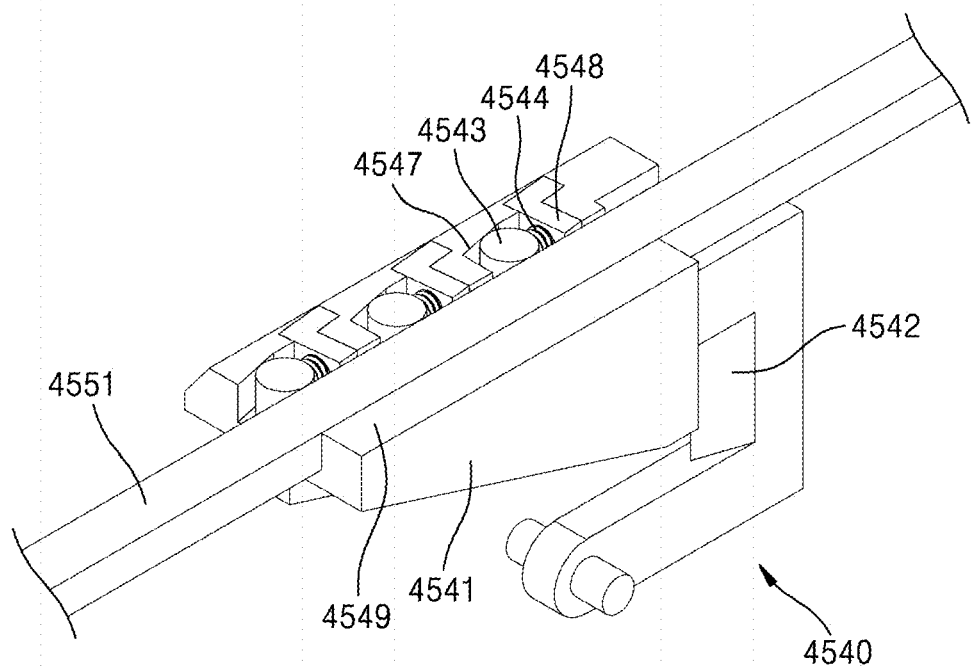

FIGS. 82 to 84 are perspective views illustrating the operation member of the surgical instrument according to the first modified example of the first embodiment of the present disclosure. FIGS. 85 and 86 are perspective views illustrating a state in which the operation member of FIG. 82 is coupled to the reciprocating member.

Referring to FIGS. 82 to 86, the operation member 4540 according to the first modified example of the first embodiment of the present disclosure may include a wedge 4541, a blade 4542, a contact member 4543, an elastic member 4544, a body 4545, and a holder 4548. An accommodation part 4546 and an inclined part 4547 may be formed in the body 4545. Furthermore, the operation member 454 of the present modified example may further include a sidewall 4549.

In detail, the sidewall 4549 may be further formed on a lower surface of the body 4545 at a side opposite to a side at which the accommodation part 4546 and the inclined part 4547 are formed. The sidewall 4549 may be formed to be in contact with a reciprocating member 4551.

From another perspective, the reciprocating member 4551 may be formed such that a first surface is in contact with the contact member 4543 and a second surface opposite to the first surface is in contact with the sidewall 4549.

As such, by further providing the sidewall 4549 in contact with the second surface of the reciprocating member 4551, an effect of preventing separation of the reciprocating member 4551 or the contact member 4543 may be obtained.

Second Modified Example of First Embodiment

Hereinafter, an operation member 4640 of a surgical instrument according to a second modified example of the first embodiment of the present disclosure will be described. Here, the operation member 4640 of the surgical instrument according to the second modified example of the first embodiment of the present disclosure is different from the above-described operation member (see 4540 of FIG. 35 or the like) of the surgical instrument according to the first embodiment of the present disclosure in that the configuration of a contact member 4643 and an elastic member 4644 is different. Hereinafter, the configuration that is different from that of the first embodiment will be described in detail.

Figure 87:
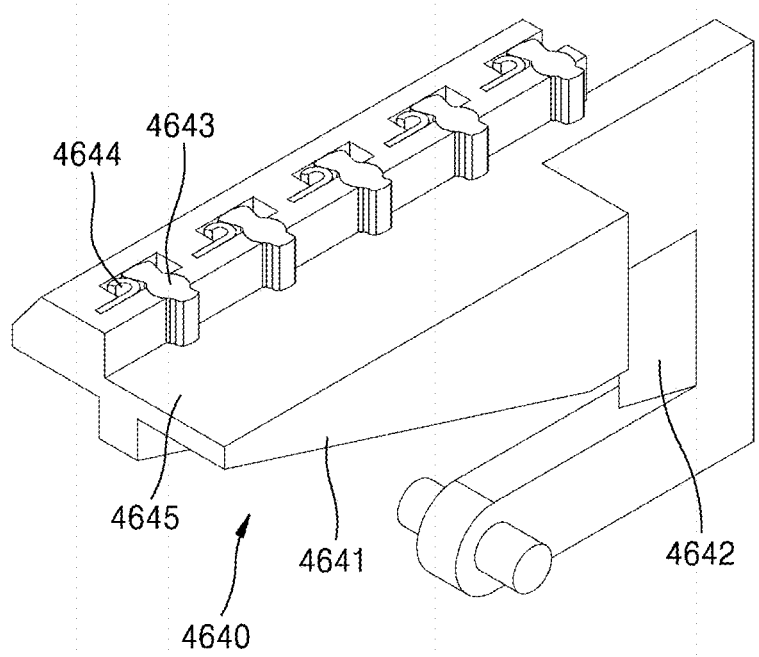
FIGS. 87 to 89 are perspective views illustrating an operation member of a surgical instrument according to a second modified example of the first embodiment of the present disclosure.
Figure 88:
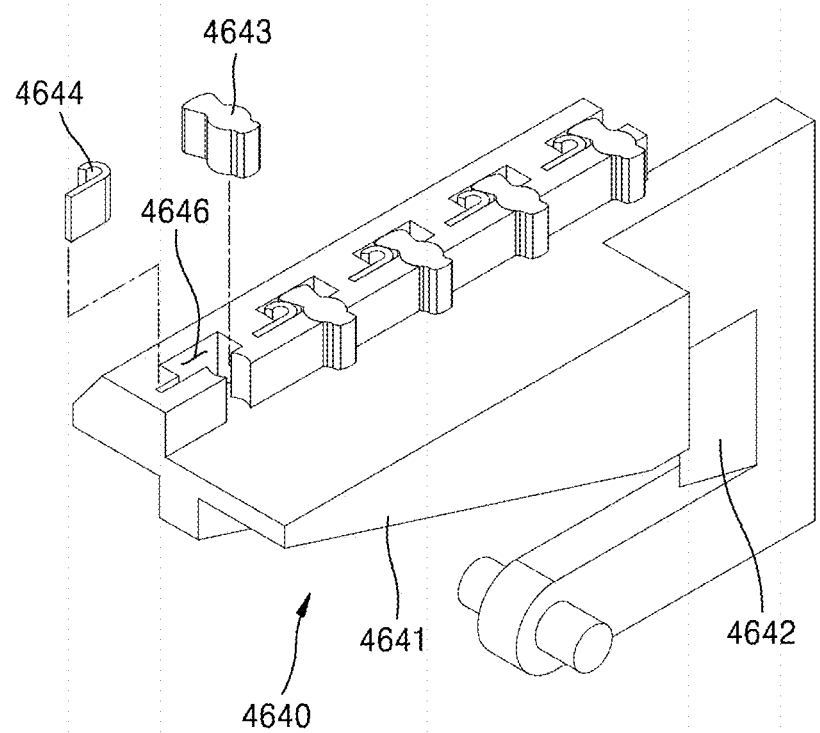
Figure 89:
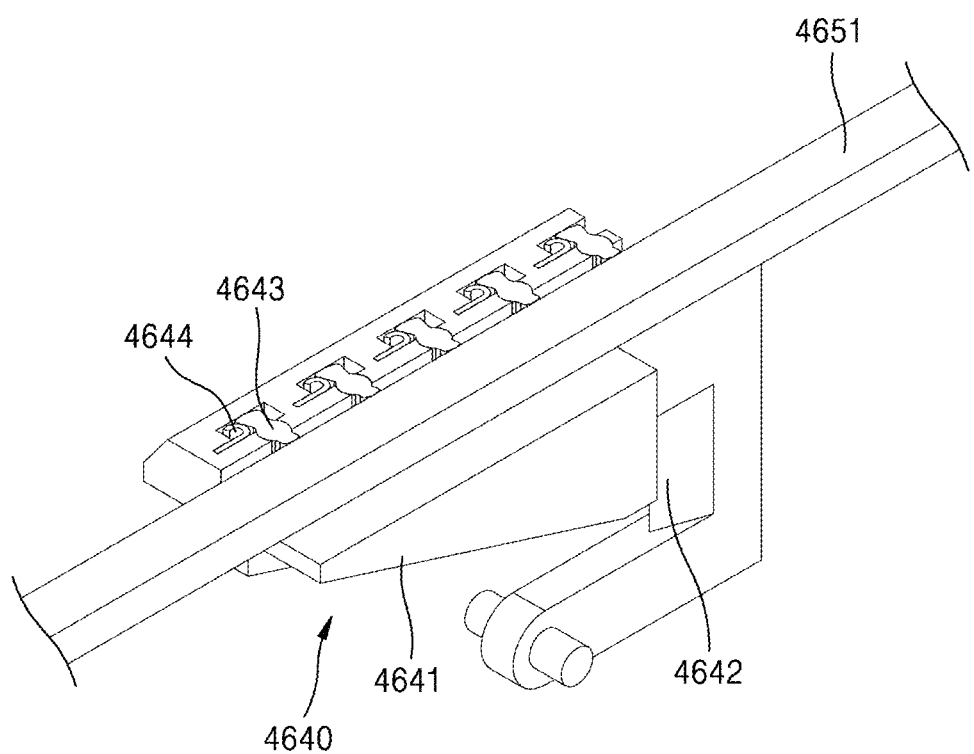
Figure 90:
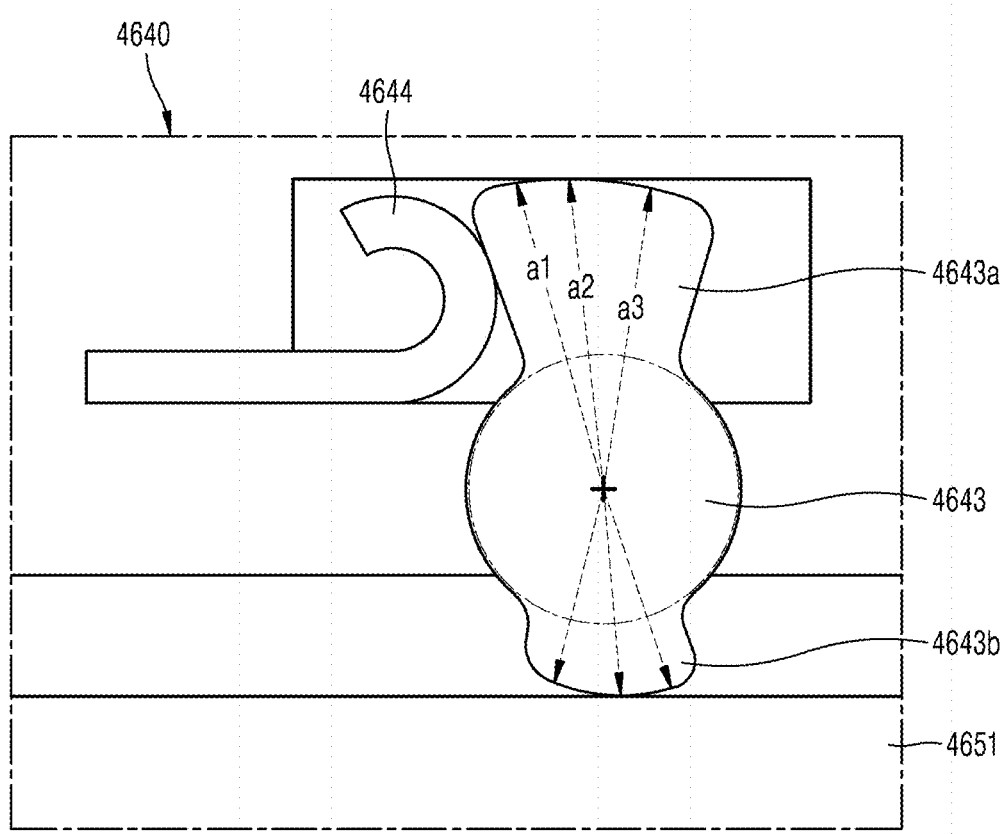
FIG. 90 is a plan view illustrating an elastic member and a contact member of the operation member of FIG. 87 in more detail.
Figure 91:
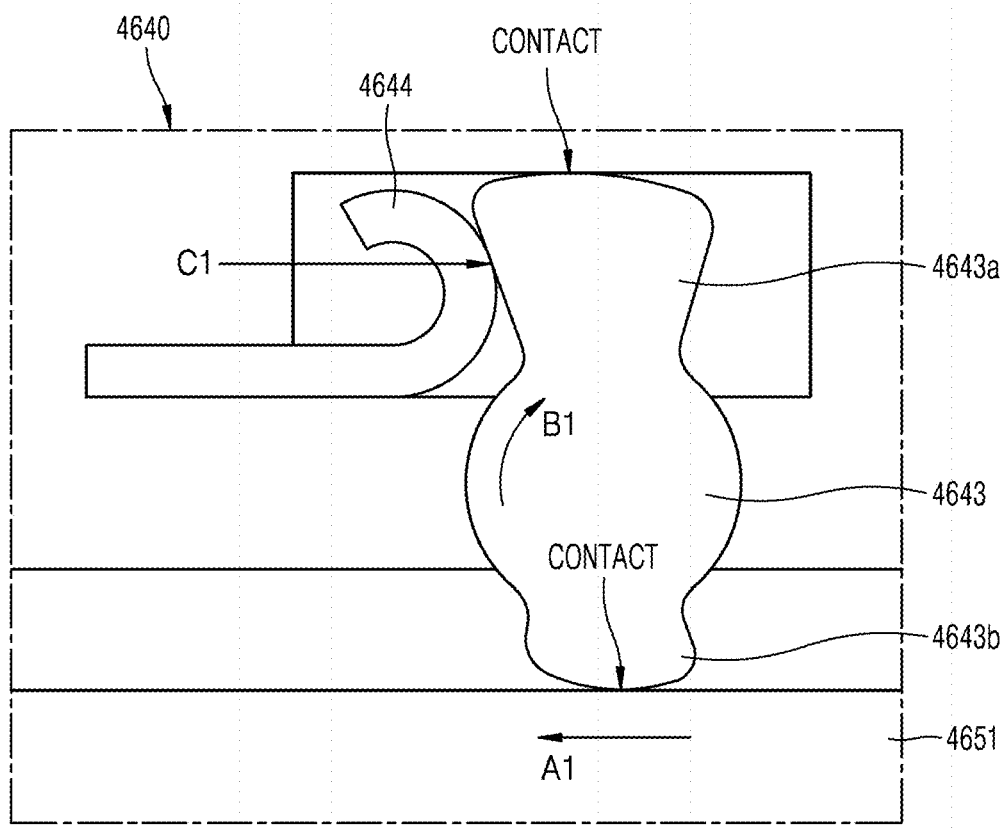
FIGS. 91 and 92 are plan views illustrating operating states of the elastic member and the contact member of the operation member of FIG. 87.
Figure 92:
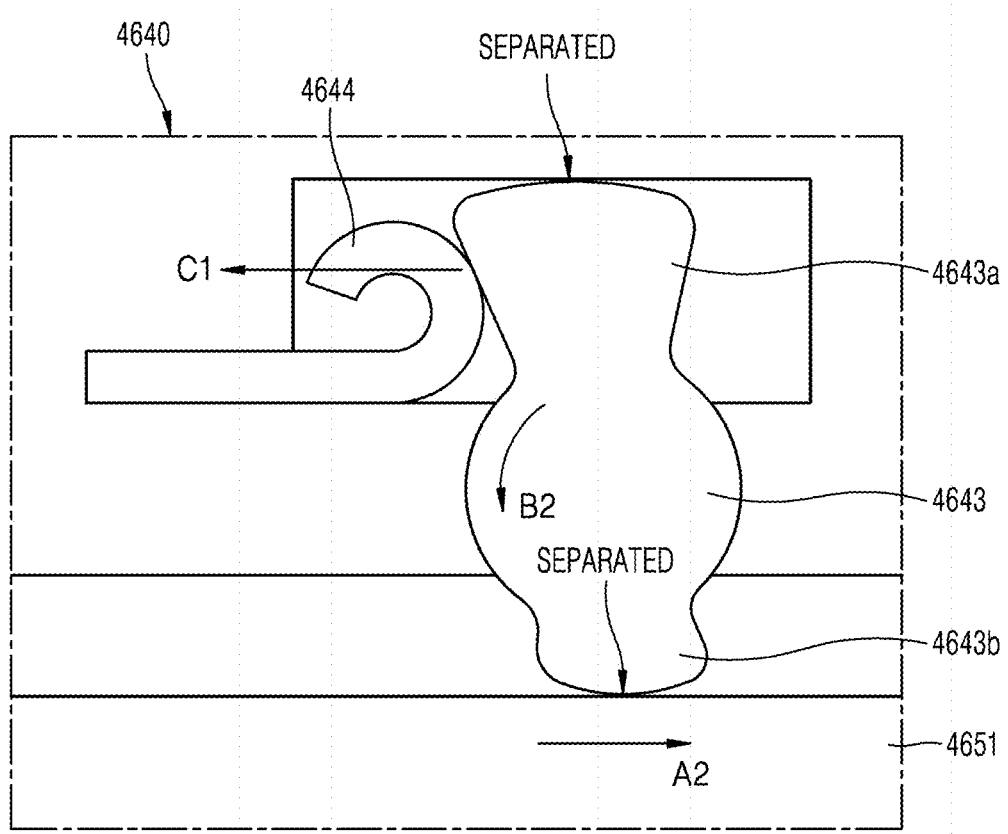

FIGS. 87 to 89 are perspective views illustrating the operation member of the surgical instrument according to the second modified example of the first embodiment of the present disclosure. FIG. 90 is a plan view illustrating the elastic member and the contact member of the operation member of FIG. 87 in more detail. FIGS. 91 and 92 are plan views illustrating operating states of the elastic member and the contact member of the operation member of FIG. 87. FIGS. 93A to 94D are plan views illustrating a clutch drive operation of the end tool of FIG. 87.

Referring to FIGS. 87 to 94D, the operation member 4640 according to the second modified example of the first embodiment of the present disclosure may include a wedge 4641, a blade 4642, the contact member 4643, the elastic member 4644, and a body 4645. In addition, an accommodation part 4646 may be formed in the body 4645.

The body 4645 may be formed in the shape of an elongated square column, and forms a base of the operation member 4640.

An accommodation part 4646 may be formed in the body 4645. In detail, a plurality of accommodation parts 4646 may be formed on a lower surface of the body 4645, and the contact member 4643 and the elastic member 4644, which will be described later, may be accommodated in each of the accommodation parts 4646.

Here, at least a portion of the accommodation part 4646 is formed in a shape substantially the same as or similar to at least a portion of the contact member 4643, so that the position of the contact member 4643 may be fixed once the contact member 4643 is fitted into the accommodation part 4646. In detail, a portion of the accommodation part 4646 is formed in a shape substantially the same as or similar to that of a body 4643*c* of the contact member 4643 to be described later, and the body 4643*c* of the contact member 4643 may be fitted into the accommodation part 4646. As such, the contact member 4643 may be formed to be rotatable without a separate rotation shaft in a state in which a portion thereof is fitted into the accommodation part 4646.

The wedge 4641 is formed on at least one side of the body 4645, and may be formed to have a predetermined inclined surface.

A blade 4642 may be formed at one side of the wedge 4641, more specifically, at a proximal end 4601 side of the wedge 4641.

The contact member 4643 is formed at one side of the body 4645, more specifically, under the body 4645, and may be formed to face a reciprocating member 4651. Here, in the present modified example, the contact member 4643 may be formed in the form of a sprag, and the contact member 4643 may be formed to be in contact with an inner side surface of the body 4645 that forms the accommodation part 4646 and the reciprocating member 4651.

In more detail, the contact member 4643 may be formed to be in contact with or spaced apart from each of the reciprocating member 4651 and the body 4645.

Here, in a state in which the contact member 4643 is simultaneously in contact with the body 4645 and the reciprocating member 4651, the state becomes a kind of locked state in which the movement of the reciprocating member 4651 with respect to the operation member 4540 is restricted, and thus, when the reciprocating member 4651 is moved in one direction, the moving member 4640 including the contact member 4643 is entirely moved in the one direction together with the reciprocating member 4651.

On the other hand, in a state in which the contact member 4643 is spaced apart from the reciprocating member 4651 and/or the body 4645 by a certain extent, the state becomes a kind of unlocked state, and thus, the reciprocating member 4651 is movable with respect to the operation member 4540. Thus, even when the reciprocating member 4651 is moved in one direction, the moving member 4640 remains stationary without moving.

The elastic member 4644 is formed between the body 4645 and the contact member 4643 and serves to apply a predetermined elastic force to the contact member 4643. In an example, the elastic member 4644 may be formed such that one region is in contact with the body 4645, and another region is in contact with the contact member 4643. Here, the elastic member 4644 may apply an elastic force in the direction of pushing the contact member 4643. To this end, the elastic member 4644 may be provided in various forms capable of providing a predetermined elastic force to the contact member 4643, such as a leaf spring, a coil spring, and a dish spring.

In the second modified example of the first embodiment of the present disclosure, a reciprocating assembly 4650 and the operation member 4640 configure a kind of one-way clutch, in particular, a sprag clutch.

In detail, when the reciprocating member 4651 is moved forward toward a distal end 4602 of the cartridge 4600, the movement of the reciprocating member 4651 is transmitted to the operation member 4640 due to a frictional force caused by the fitting, so that the reciprocating member 4651 and the operation member 4640 are moved together toward the distal end 4602 of the cartridge 4600.

On the other hand, when the reciprocating member 4651 is moved backward toward the proximal end 4601 of the cartridge 4600, since the contact member 4643 is spaced apart from the body 4645 and the reciprocating member 4651 by a certain extent, the movement of the reciprocating member 4651 is not transmitted to the operation member 4640, and only the reciprocating member 4651 is alone moved toward the proximal end 4601 of the cartridge 4600, and the operation member 4640 does not move.

This will be described below in more detail.

The body 4645 of the operation member 4640 and the reciprocating member 4651 are formed to be movable relative to each other. That is, the reciprocating member 4651 is formed to be movable along a length direction of the shaft relative to the body 4645.

The sprag-shaped contact member 4643 includes the body 4643*c*, a first protrusion 4643*a*, and a second protrusion 4643*b*.

The body 4643*c* is formed in an approximately circular shape when viewed in a cross section. The body 4643*c* may be formed to be fitted into the accommodation part 4646 and rotatable in the accommodation part 4646.

The first protrusion 4643*a* is formed to protrude in one direction from the body 4643*c*. Here, the first protrusion 4643*a* may be formed to be in contact with the inner side surface of the body 4645 that forms the accommodation part 4646. Meanwhile, the first protrusion 4643*a* may be formed such that a distance from the center of the body 4643*c* increases in the counterclockwise direction. That is, the first protrusion 4643*a* may be formed in an asymmetric shape. From another perspective, it may be expressed that the first protrusion 4643*a* is formed such that a distance from the center of the body 4643*c* to an end portion of the first protrusion 4643*a* increases toward the distal end (see 4502 of FIG. 29) of the cartridge 4640.

The second protrusion 4643*b* is formed to protrude in the other direction from the body 4643*c*. Here, the second protrusion 4643*b* may be formed to be in contact with the reciprocating member 4651. Meanwhile, the second protrusion 4643*b* may be formed such that a distance from the center of the body 4643*c* increases in the counterclockwise direction. That is, the second protrusion 4643*b* may be formed in an asymmetric shape. From another perspective, it may be expressed that a distance from the center of the body 4643*c* to an end portion of the second protrusion 4643*b* increases toward the proximal end (see 4501 of FIG. 29) of the cartridge 4640.

Here, when a transverse line connecting from one end portion of the first protrusion 4643*a* to one end portion of the second protrusion 4643*c* through the center of the body 4643*c* is drawn, the transverse line may be formed to be longer in the counterclockwise direction when viewed from FIG. 90. Here, a length of the transverse line may be defined as a center distance.

Here, a region having a relatively long center distance may be defined as a long axis part, and a region having a relatively short center distance may be defined as a short axis part. That is, in FIG. 90, a region with a center distance of a1 may be referred to as the long axis part, and a region with a center distance of a3 may be referred to as the short axis part.

At this time, the contact member 4643 has a shape whose center distance becomes longer in the counterclockwise direction. That is, the relationship of a1>a2>a3 is established.

Accordingly, when the contact member 4643 is rotated in the clockwise direction by a certain extent, the contact member 4643 is brought into contact with the operation member 4640 and the reciprocating member 4651. In other words, the contact member 4643 is sandwiched between the operation member 4640 and the reciprocating member 4651. In addition, in this state, when the contact member 4643 is further rotated in the clockwise direction, the state becomes a kind of locked state in which the relative movement between the operation member 4640 and the reciprocating member 4651 is restricted by the contact member 4643.

In contrast, when the contact member 4643 is rotated in the counterclockwise direction by a certain extent, the contact member 4643 is spaced apart from the operation member 4640 and the reciprocating member 4651. This state becomes an unlocked state in which the relative movement between the operation member 4640 and the reciprocating member 4651 is restricted by the contact member 4643.

Here, the elastic member 4644 applies a predetermined elastic force to the contact member 4643 in a direction in which the contact member 4643 is rotated in the clockwise direction. Accordingly, when there is no external force, the contact member 4643 is rotated by a certain extent in the clockwise direction by the elastic member 4644, the state becomes the locked state in which the relative movement between the operation member 4640 and the reciprocating member 4651 is restricted by the contact member 4643.

FIGS. 91 and 92 are plan views illustrating operating states of the elastic member and the sprag of the operation member of FIG. 87.

When the reciprocating member 4651 is moved in the direction of an arrow A1 of FIG. 91 (i.e., toward the distal end (see 4502 of FIG. 29) of the cartridge 4640), the contact member 4643 is rotated in the direction of an arrow B1 (i.e., in the clockwise direction) of FIG. 91 by the elastic force applied to the contact member 4643 by the elastic member 4644 and the frictional force between the reciprocating member 4651 and the contact member 4643. In addition, when the contact member 4643 is rotated in the direction of an arrow B1 of FIG. 91 (i.e., in the clockwise direction), the long axis part (i.e., the region with the center distance of a1) of the contact member 4643 is located in a vertical direction, and the state becomes a kind of locked state in which the relative movement between the operation member 4640 and the reciprocating member 4651 is restricted by the contact member 4643. That is, since the relative movement between the operation member 4640 and the reciprocating member 4651 is restricted by the contact member 4643, the reciprocating member 4651 does not move alone, and the operation member 4640 and the reciprocating member 4651 are moved together as one body, and thus, when the reciprocating member 4651 is moved in the direction of the arrow A1 of FIG. 91, the operation member 4540 is also moved in the direction of the arrow A1.

Meanwhile, when the reciprocating member 4651 is moved in the direction of an arrow A2 of FIG. 92 (i.e., toward the proximal end (see 4501 of FIG. 29) of the cartridge 4640), the contact member 4643 is rotated in the direction of an arrow B2 of FIG. 92 (i.e., in the counterclockwise direction) by the frictional force between the reciprocating member 4651 and the contact member 4643. In addition, when the contact member 4643 is rotated in the direction of the arrow B2 (i.e., in the counterclockwise direction) of FIG. 92, the short axis part (i.e., the region with the center distance of a3) of the contact member 4643 is located in the vertical direction, and the contact member 4643 is spaced apart from the operation member 4640 and the reciprocating member 4651 by a certain extent. That is, the state becomes the unlocked state in which the relative movement between the operation member 4640 and the reciprocating member 4651 is possible. Thus, even when the reciprocating member 4651 is moved in the direction of the arrow A2 of FIG. 92, the operation member 4540 does not move together with the reciprocating member 4651 and remains stationary.

From another perspective, when the reciprocating member 4651 is moved toward the distal end 4602 of the cartridge 4600, it may be said that the contact member 4643 is in a fitted state between the reciprocating member 4651 and the operation member 4640, and the relative movement between the reciprocating member 4651 and the operation member 4640 is blocked.

In contrast, when the reciprocating member 4651 is moved toward the proximal end 4601 of the cartridge 4600, it may be said that the contact member 4643 is released from the fitted state between the reciprocating member 4651 and the operation member 4640, and the relative movement between the reciprocating member 4651 and the operation member 4640 is possible.

FIGS. 93A to 94D are Plan Views Illustrating a Clutch Drive Operation of the End Tool of FIG. 87.

In the state as shown in FIG. 93A, when the reciprocating member 4651 is moved in the direction of an arrow A1 (i.e., toward the distal end) of FIG. 93B, the contact member 4643 is rotated in the clockwise direction, and the state becomes a kind of locked state in which the relative movement between the operation member 4640 and the reciprocating member 4651 is restricted by the contact member 4643. That is, since the operation member 4640 and the reciprocating member 4651 are in a state of moving together, when the reciprocating member 4651 is moved in the direction of the arrow A1, the operation member 4640 is moved in the direction of an arrow B1.

In this state, when the moving direction of the reciprocating member 4651 is switched to the direction of an arrow A2 of FIG. 93C (i.e., when the movement toward the distal end is switched to the movement toward the proximal end), the contact member 4643 is rotated in the direction of an arrow C2 (i.e., in the counterclockwise direction) of FIG. 93C, and the state becomes the unlocked state in which the relative movement between the operation member 4640 and the reciprocating member 4651 is possible. Thus, even when the reciprocating member 4651 is moved in the direction of the arrow A2 of FIG. 93C, the operation member 4640 remains stationary.

In this state, when the reciprocating member 4651 continues to move in the direction of an arrow A3 (i.e., toward the proximal end) of FIG. 93D, the contact member 4643 remains spaced apart from the reciprocating member 4651 and the operation member 4640. That is, the unlocked state in which the relative movement between the operation member 4640 and the reciprocating member 4651 is possible is maintained. Accordingly, even when the reciprocating member 4651 is moved in the direction of the arrow A3 of FIG. 93D, the operation member 4640 remains stationary.

In this state, when the moving direction of the reciprocating member 4651 is switched to the direction of an arrow A4 of FIG. 93E (i.e., when the movement toward the proximal end is switched to the movement toward the distal end), the contact member 4643 is rotated in the direction of an arrow C4 (i.e., in the clockwise direction) of FIG. 93E, and the state becomes a kind of locked state in which the relative movement between the operation member 4640 and the reciprocating member 4651 is restricted by the contact member 4643. In this state, when the reciprocating member 4651 is moved toward the distal end, the operation member 4640 is also moved toward the distal end.

While repeating this process, the operation member 4640 is moved forward toward the distal end, and in this process, cutting and stapling are performed.

Figure 94A:
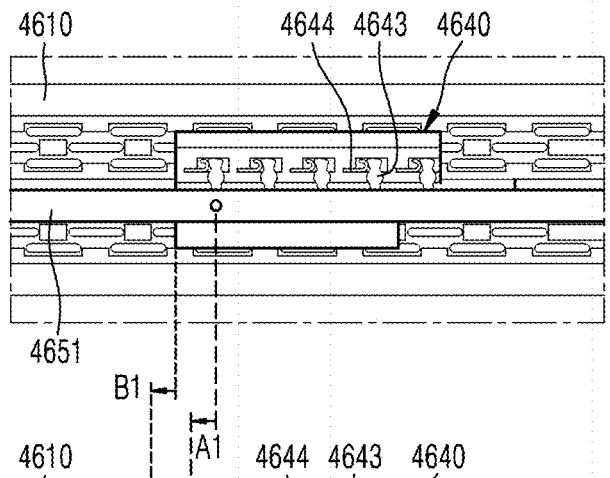
Figure 94B:
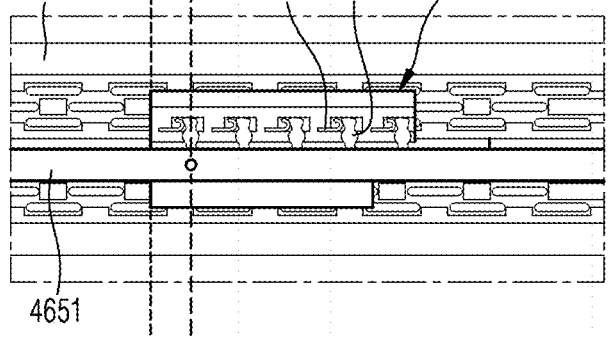
Figure 94C:
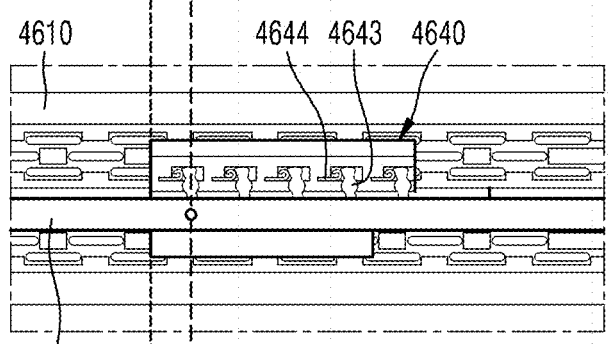
Figure 94D:
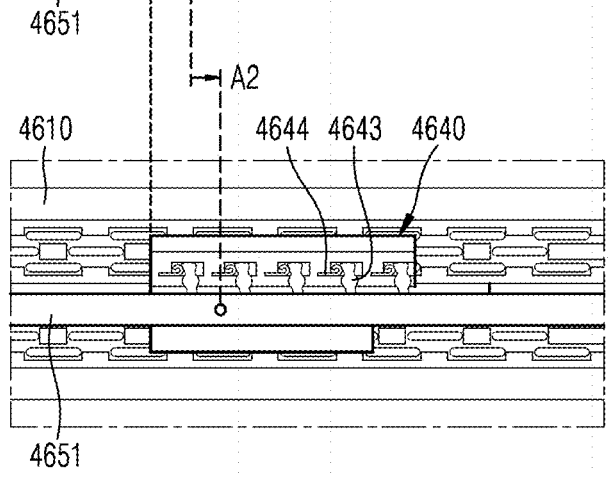

From another perspective, as shown in FIG. 94, when the reciprocating member 4640 is moved in the direction of an arrow A1 (i.e., toward the distal end) of FIG. 94B, the operation member 4640 is moved together with the reciprocating member 4640 in the direction of an arrow B1 (i.e., toward the distal end) of FIG. 94B. On the other hand, when the reciprocating member 4640 is moved in the direction of an arrow A2 (i.e., toward the proximal end) of FIG. 94D, the operation member 4640 remains stationary in place without moving. As a result, while the reciprocating member 4641 repeatedly moved forward and backward, the operation member 4640 is moved toward the distal end while repeating moving forward and stopping.

Third Modified Example of First Embodiment

Hereinafter, an operation member 4640 of a surgical instrument according to a third modified example of the first embodiment of the present disclosure will be described. Here, the operation member 4640 of the surgical instrument according to the third modified example of the first embodiment of the present disclosure is different from the above-described operation member (see 4640 of FIG. 87 or the like) of the surgical instrument according to the second modified example of the first embodiment of the present disclosure in that a sidewall 4649 is further provided. Hereinafter, the configuration that is different from that of the second modified example will be described in detail.

Figure 95:
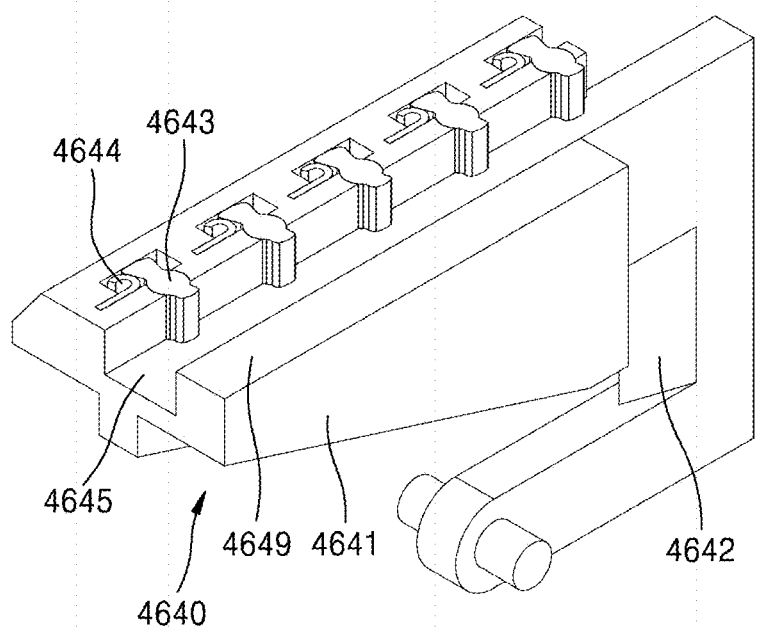
FIGS. 95 and 96 are perspective views illustrating an operation member of a surgical instrument according to a third modified example of the first embodiment of the present disclosure.
Figure 96:
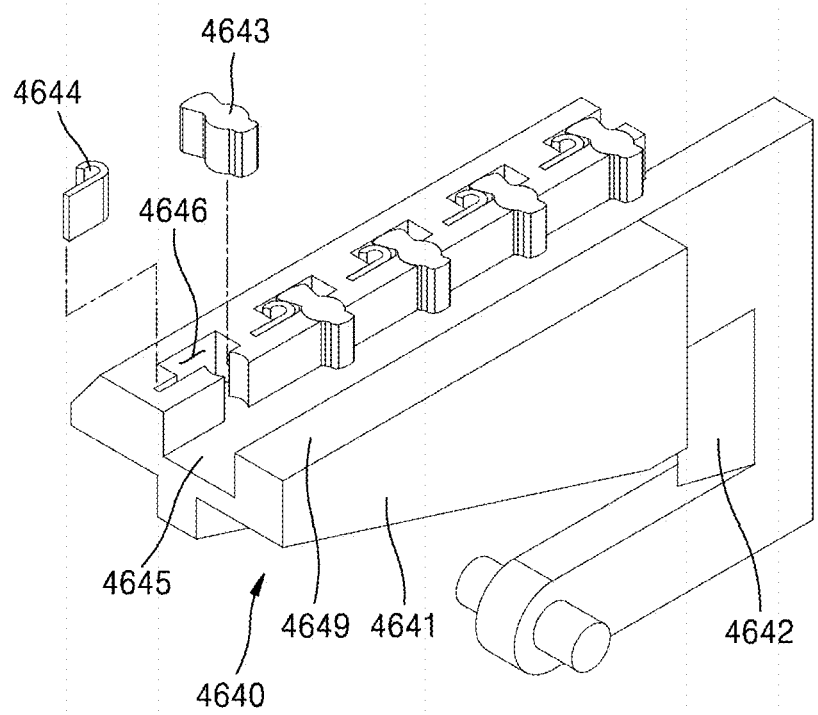
Figure 97:
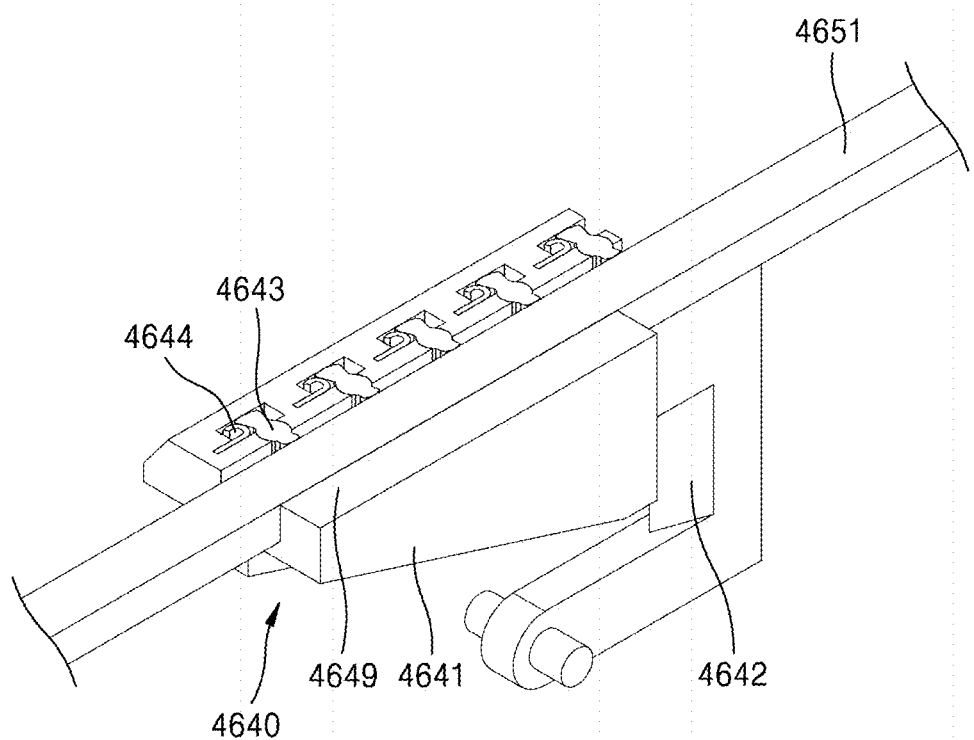
FIG. 97 is a perspective view illustrating a state in which the operation member of FIG. 95 is coupled to the reciprocating member.

FIGS. 95 and 96 are perspective views illustrating the operation member of the surgical instrument according to the third modified example of the first embodiment of the present disclosure, and FIG. 97 is a perspective view illustrating a state in which the operation member of FIG. 95 is coupled to a reciprocating member.

Referring to FIGS. 95 to 97, the operation member 4640 according to the third modified example of the first embodiment of the present disclosure may include a wedge 4641, a blade 4642, a contact member 4643, an elastic member 4644, and a body 4645. An accommodation part 4646 may be formed in the body 4645. Furthermore, the operation member 464 of the present modified example may further include the sidewall 4649.

In detail, the sidewall 4649 may be further formed on a lower surface of the body 4645 at a side opposite to a side at which the accommodation part 4646 is formed. The sidewall 4649 may be formed to be in contact with a reciprocating member 4651.

From another perspective, the reciprocating member 4651 may be formed such that a first surface is in contact with the contact member 4643 and a second surface opposite to the first surface is in contact with the sidewall 4649.

As such, by further providing the sidewall 4649 in contact with the second surface of the reciprocating member 4651, an effect of preventing separation of the reciprocating member 4651 or the contact member 4643 may be obtained.

Fourth Modified Example of First Embodiment

Hereinafter, an operation member 4740 of a surgical instrument according to a fourth modified example of the first embodiment of the present disclosure will be described. Here, the operation member 4740 of the surgical instrument according to the fourth modified example of the first embodiment of the present disclosure is different from the above-described operation member (see 4640 of FIG. 87 or the like) of the surgical instrument according to the second modified example of the first embodiment of the present disclosure in that the configuration of a contact member 4743 is different. Hereinafter, the configuration that is different from that of the second modified example will be described in detail.

Figure 98:
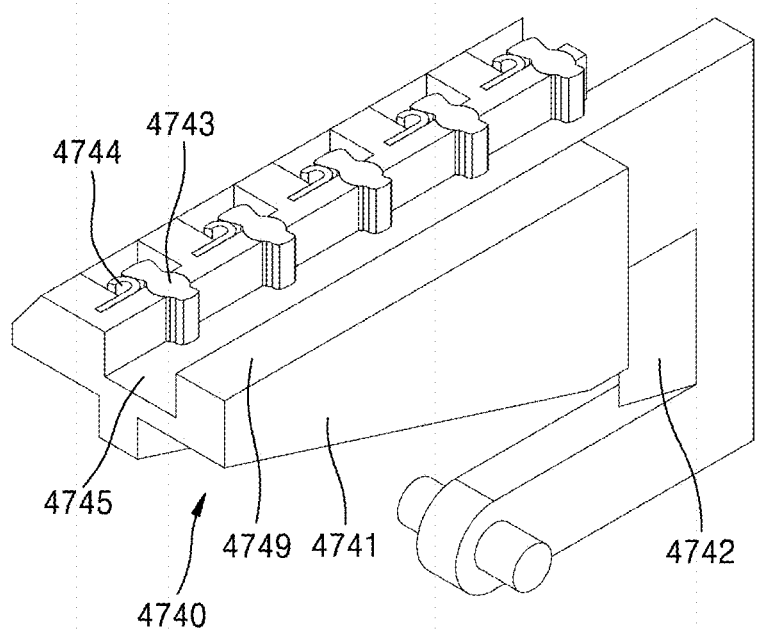
FIGS. 98 to 100 are perspective views illustrating an operation member of a surgical instrument according to a fourth modified example of the first embodiment of the present disclosure.
Figure 99:
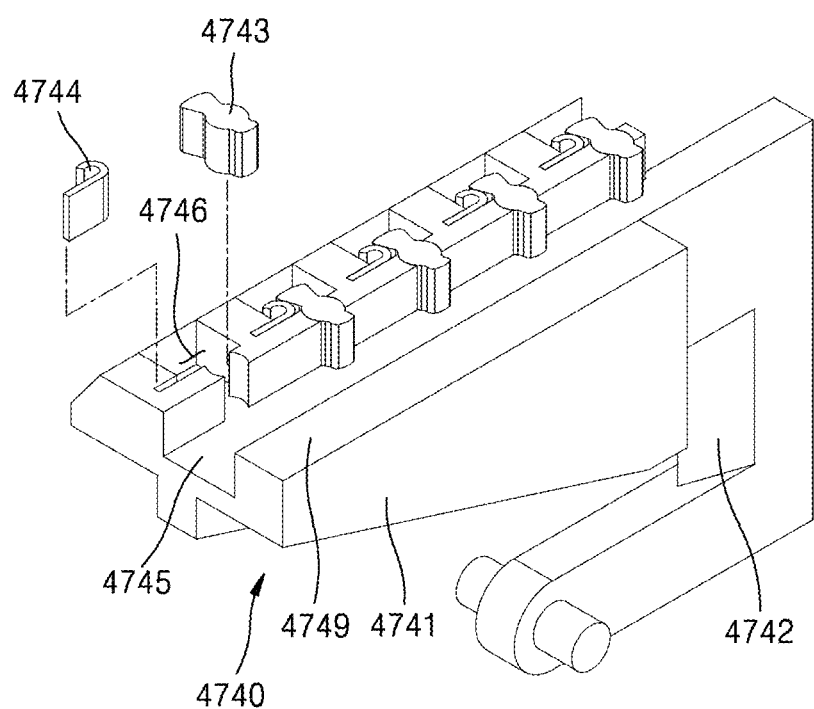
Figure 100:
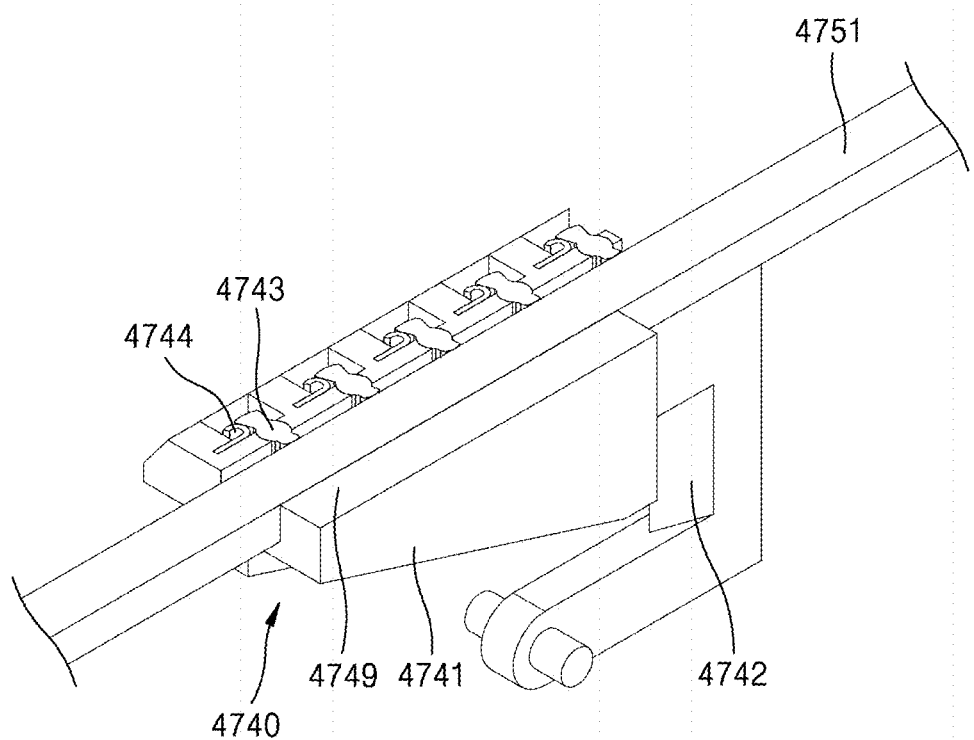
Figure 101:
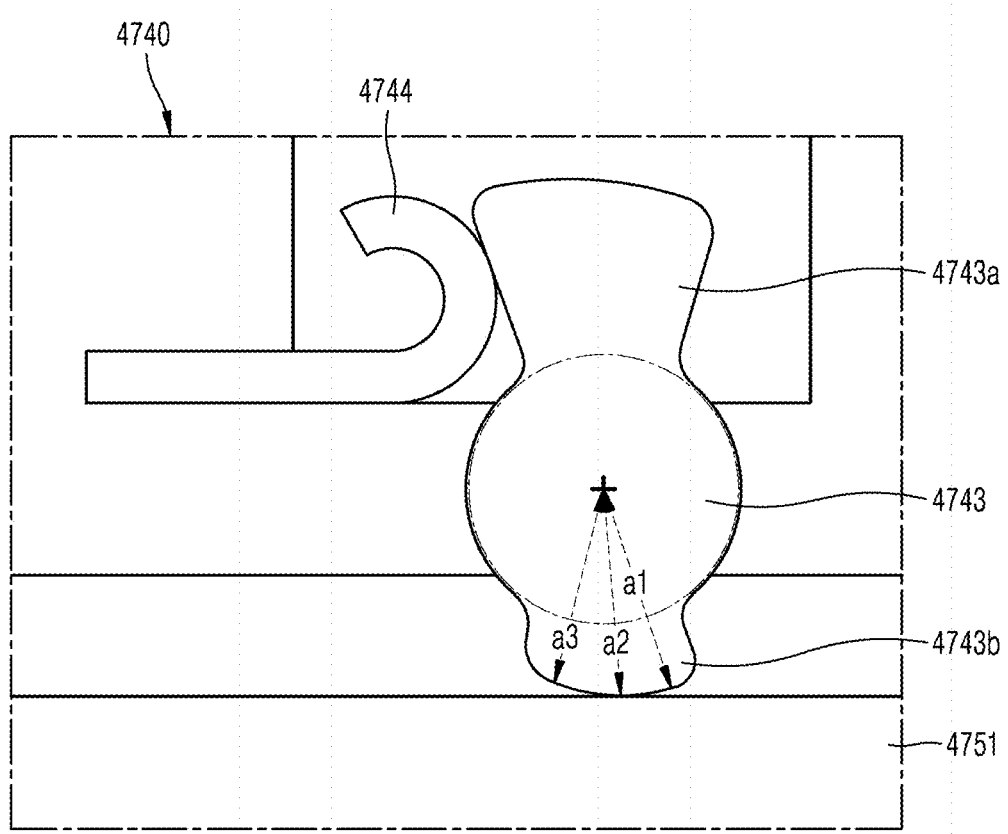
FIG. 101 is a plan view illustrating an elastic member and a contact member of the operation member of FIG. 98 in more detail.
Figure 102:

FIGS. 102 and 103 are plan views illustrating operating states of the elastic member and the contact member of the operation member of FIG. 98.
Figure 103:

FIGS. 98 to 100 are perspective views illustrating the operation member of the surgical instrument according to the fourth modified example of the first embodiment of the present disclosure. FIG. 101 is a plan view illustrating an elastic member and the contact member of the operation member of FIG. 98 in more detail. FIGS. 102 and 103 are plan views illustrating operating states of the elastic member and the contact member of the operation member of FIG. 98. FIGS. 104A to 105D are plan views illustrating a clutch drive operation of the end tool of FIG. 98.

Referring to FIGS. 98 to 105, the operation member 4740 according to the fourth modified example of the first embodiment of the present disclosure may include a wedge 4741, a blade 4742, the contact member 4743, an elastic member 4744, and a body 4745. In addition, an accommodation part 4746 may be formed in the body 4745. Here, the other components except for the contact member 4743 are the same as the operation member (see 4640 of FIG. 87 or the like) of the surgical instrument according to the second modified example of the first embodiment, and thus detailed descriptions thereof will be omitted.

The contact member 4743 is formed at one side of the body 4745, more specifically, under the body 4745, and may be formed to face a reciprocating member 4751. Here, in the present modified example, the contact member 4743 may be formed in the form of a sprag, and the contact member 4743 may be formed to be in contact with the reciprocating member 4751.

That is, in the modified example illustrated in FIG. 87 or the like, the contact member 4643 is formed to be simultaneously in contact with the inner side surface of the body 4645, which forms the accommodation part 4646, and the reciprocating member 4651, whereas in the present modified example illustrated in FIG. 98 or the like, the contact member 4743 is formed to be in contact with only the reciprocating member 4751.

In more detail, the contact member 4743 may be formed to be in contact with or spaced apart from the reciprocating member 4751.

Here, in a state in which the contact member 4743 is in contact with the reciprocating member 4751, the state becomes a kind of locked state in which the movement of the reciprocating member 4751 with respect to the operation member 4540 is restricted, and thus, when the reciprocating member 4751 is moved in one direction, the moving member 4740 including the contact member 4743 is entirely moved in the one direction together with the reciprocating member 4751.

On the other hand, in a state in which the contact member 4743 is spaced apart from the reciprocating member 4751 by a certain extent, the state becomes a kind of unlocked state, and thus, the reciprocating member 4751 is movable with respect to the operation member 4540. Accordingly, even when the reciprocating member 4751 is moved in one direction, the moving member 4740 remains stationary without moving.

In the fourth modified example of the first embodiment of the present disclosure, a reciprocating assembly 4750 and the operation member 4740 configure a kind of one-way clutch, in particular, a sprag clutch.

In detail, the body 4745 of the operation member 4740 and the reciprocating member 4751 are formed to be movable relative to each other. That is, the reciprocating member 4751 is formed to be movable along a length direction of the shaft relative to the body 4745.

The sprag-shaped contact member 4743 includes a body 4743c, a first protrusion 4743a, and a second protrusion 4743b.

The body 4743c is formed in an approximately circular shape when viewed from a cross section. The body 4743c may be formed to be fitted into the accommodation part 4746 and rotatable in the accommodation part 4746.

The first protrusion 4743a is formed to protrude in one direction from the body 4743c. Here, the first protrusion 4743a may be formed not to be in contact with an inner side surface of the body 4745 that forms the accommodation part 4746.

The second protrusion 4743b is formed to protrude in the other direction from the body 4743c. Here, the second protrusion 4743b may be formed to be in contact with the reciprocating member 4751. Meanwhile, the second protrusion 4743b may be formed such that a distance from the center of the body 4743c increases in the counterclockwise direction. That is, the second protrusion 4743b may be formed in an asymmetric shape. From another perspective, it may be expressed that a distance from the center of the body 4743c to an end portion of the second protrusion 4743b increases toward the proximal end (see 4501 of FIG. 29) of a cartridge 4740.

Here, when a transverse line connecting from the center of the body 4743c to one end portion of the second protrusion 4743c is drawn, the transverse line may be formed to be longer in the counterclockwise direction when viewed from FIG. 101. Here, a length of the transverse line may be defined as a center distance.

Here, a region having a relatively long center distance may be defined as a long axis part, and a region having a relatively short center distance may be defined as a short axis part. That is, in FIG. 101, a region with a center distance of a1 may be referred to as the long axis part, and a region with a center distance of a3 may be referred to as the short axis part.

At this time, the contact member 4743 has a shape whose center distance becomes longer in the counterclockwise direction. That is, the relationship of a1>a2>a3 is established.

Accordingly, when the contact member 4743 is rotated in the clockwise direction by a certain extent, the contact member 4743 is brought into contact with the reciprocating member 4751. In addition, in this state, when the contact member 4743 is further rotated in the clockwise direction, the state becomes a kind of locked state in which the relative movement between the operation member 4740 and the reciprocating member 4751 is restricted by the contact member 4743.

In contrast, when the contact member 4743 is rotated in the counterclockwise direction by a certain extent, the contact member 4743 is spaced apart from the reciprocating member 4751. This state becomes an unlocked state in which the relative movement between the operation member 4740 and the reciprocating member 4751 is restricted by the contact member 4743.

Here, the elastic member 4744 applies a predetermined elastic force to the contact member 4743 in a direction in which the contact member 4743 is rotated in the clockwise direction. Accordingly, when there is no external force, the contact member 4743 is rotated by a certain extent in the clockwise direction by the elastic member 4744, the state becomes the locked state in which the relative movement between the operation member 4740 and the reciprocating member 4751 is restricted by the contact member 4743.

FIGS. 102 and 103 are plan views illustrating operating states of the elastic member and the sprag of the operation member of FIG. 98.

When the reciprocating member 4751 is moved in the direction of an arrow A1 of FIG. 102 (i.e., toward the distal end (see 4502 of FIG. 29) of the cartridge 4740), the contact member 4743 is rotated in the direction of an arrow B1 (i.e., in the clockwise direction) of FIG. 102 by the elastic force applied to the contact member 4743 by the elastic member 4744 and a frictional force between the reciprocating member 4751 and the contact member 4743. In addition, when the contact member 4743 is rotated in the direction of the arrow B1 of FIG. 102 (i.e., in the clockwise direction), the long axis part (i.e., the region with the center distance of a1) of the contact member 4743 is located in a vertical direction, and the state becomes a kind of locked state in which the relative movement between the operation member 4740 and the reciprocating member 4751 is restricted by the contact member 4743. That is, since the relative movement between the operation member 4740 and the reciprocating member 4751 is restricted by the contact member 4743, the reciprocating member 4751 does not move alone, and the operation member 4740 and the reciprocating member 4751 are moved together as one body, and thus, when the reciprocating member 4751 is moved in the direction of the arrow A1 of FIG. 102, the operation member 4540 is also moved in the direction of the arrow A1.

Meanwhile, when the reciprocating member 4751 is moved in the direction of an arrow A2 of FIG. 103 (i.e., toward the proximal end (see 4501 of FIG. 29) of the cartridge 4740), the contact member 4743 is rotated in the direction of an arrow B2 of FIG. 103 (i.e., in the counterclockwise direction) by the frictional force between the reciprocating member 4751 and the contact member 4743. In addition, when the contact member 4743 is rotated in the direction of the arrow B2 (i.e., in the counterclockwise direction) of FIG. 103, the short axis part (i.e., the region with the center distance of a3) of the contact member 4743 is located in the vertical direction, and the contact member 4743 is spaced apart from the reciprocating member 4751 by a certain extent. That is, the state becomes the unlocked state in which the relative movement between the operation member 4740 and the reciprocating member 4751 is possible. Thus, even when the reciprocating member 4751 is moved in the direction of the arrow A2 of FIG. 103, the operation member 4540 does not move together with the reciprocating member 4751 and remains stationary.

From another perspective, when the reciprocating member 4751 is moved to the distal end 4702 of the cartridge 4700, it may be said that the contact member 4743 is in a fitted state between the reciprocating member 4751 and the operation member 4740, and the relative movement between the reciprocating member 4751 and the operation member 4740 is blocked.

In contrast, when the reciprocating member 4751 is moved toward the proximal end 4701 of the cartridge 4700, it may be said that the contact member 4743 is released from the fitted state between the reciprocating member 4751 and the operation member 4740, and the relative movement between the reciprocating member 4751 and the operation member 4740 is possible.

FIGS. 104A to 105D are Plan Views Illustrating a Clutch Drive Operation of the End Tool of FIG. 98.

In the state as shown in FIG. 104A, when the reciprocating member 4751 is moved in the direction of an arrow A1 (i.e., toward the distal end) of FIG. 104B, the contact member 4743 is rotated in the clockwise direction, and the state becomes a kind of locked state in which the relative movement between the operation member 4740 and the reciprocating member 4751 is restricted by the contact member 4743. That is, since the operation member 4740 and the reciprocating member 4751 are in a state of moving together, when the reciprocating member 4751 is moved in the direction of the arrow A1, the operation member 4740 is moved in the direction of an arrow B1.

In this state, when the moving direction of the reciprocating member 4751 is switched to the direction of an arrow A2 of FIG. 104C (i.e., when the movement toward the distal end is switched to the movement toward the proximal end), the contact member 4743 is rotated in the direction of an arrow C2 (i.e., in the counterclockwise direction) of FIG. 104C, and the state becomes the unlocked state in which the relative movement between the operation member 4740 and the reciprocating member 4751 is possible. Thus, even when the reciprocating member 4751 is moved in the direction of the arrow A2 of FIG. 104C, the operation member 4740 remains stationary.

In this state, when the reciprocating member 4751 continues to move in the direction of an arrow A3 (i.e., toward the proximal end) of FIG. 104D, the contact member 4743 remains spaced apart from the reciprocating member 4751 and the operation member 4740. That is, the unlocked state in which the relative movement between the operation member 4740 and the reciprocating member 4751 is possible is maintained. Thus, even when the reciprocating member 4751 is moved in the direction of the arrow A3 of FIG. 104D, the operation member 4740 remains stationary.

In this state, when the moving direction of the reciprocating member 4751 is switched to the direction of an arrow A4 of FIG. 104E (i.e., when the movement toward the proximal end is switched to the movement toward the distal end), the contact member 4743 is rotated in the direction of an arrow C4 (i.e., in the clockwise direction) of FIG. 104E, and the state becomes a kind of locked state in which the relative movement between the operation member 4740 and the reciprocating member 4751 is restricted by the contact member 4743 In this state, when the reciprocating member 4751 is moved toward the distal end, the operation member 4740 is also moved toward the distal end.

While repeating this process, the operation member 4740 is moved forward toward the distal end, and in this process, cutting and stapling are performed.

Figure 105A:
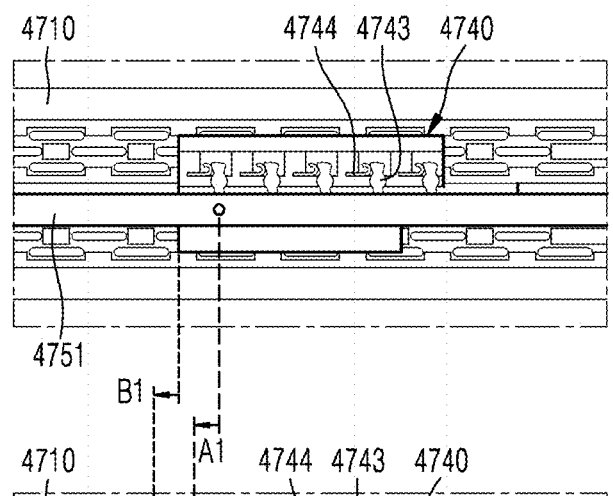
Figure 105B:
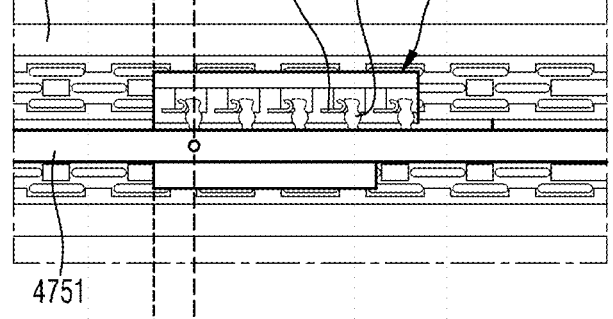
Figure 105C:
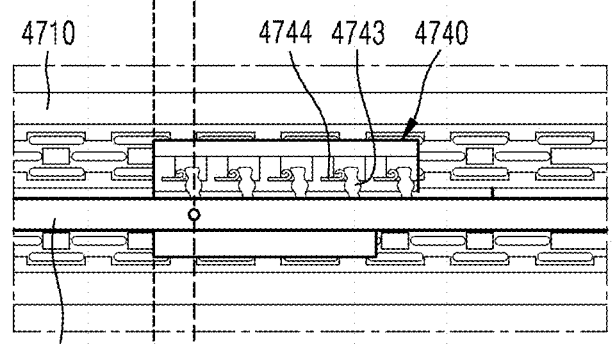
Figure 105D:
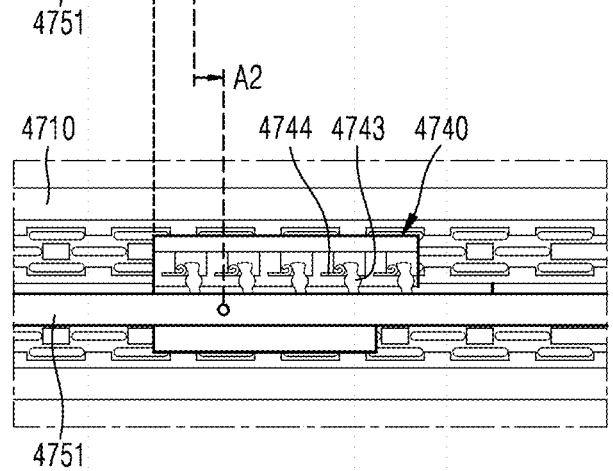

From another perspective, as shown in FIG. 105, when the reciprocating member 4740 is moved in the direction of an arrow A1 (i.e., toward the distal end) of FIG. 105B, the operation member 4740 is moved together with the reciprocating member 4740 in the direction of an arrow B1 (i.e., toward the distal end) of FIG. 105B. On the other hand, when the reciprocating member 4740 is moved in the direction of an arrow A2 (i.e., toward the proximal end) of FIG. 105D, the operation member 4740 remains stationary in place without moving. As a result, while the reciprocating member 4741 repeatedly moved forward and backward, the operation member 4740 is moved toward the distal end while repeating moving forward and stopping.

Fifth Modified Example of First Embodiment

Hereinafter, an operation member 4840 of a surgical instrument according to a fifth modified example of the first embodiment of the present disclosure will be described. Here, the operation member 4840 of the surgical instrument according to the fifth modified example of the first embodiment of the present disclosure is different from the above-described operation member (see 4640 of FIG. 87 or the like) of the surgical instrument according to the second modified example of the first embodiment of the present disclosure in that the configuration of a contact member 4843 and an elastic member 4844 is different. Hereinafter, the configuration that is different from that of the second modified example will be described in detail.

Figure 106:
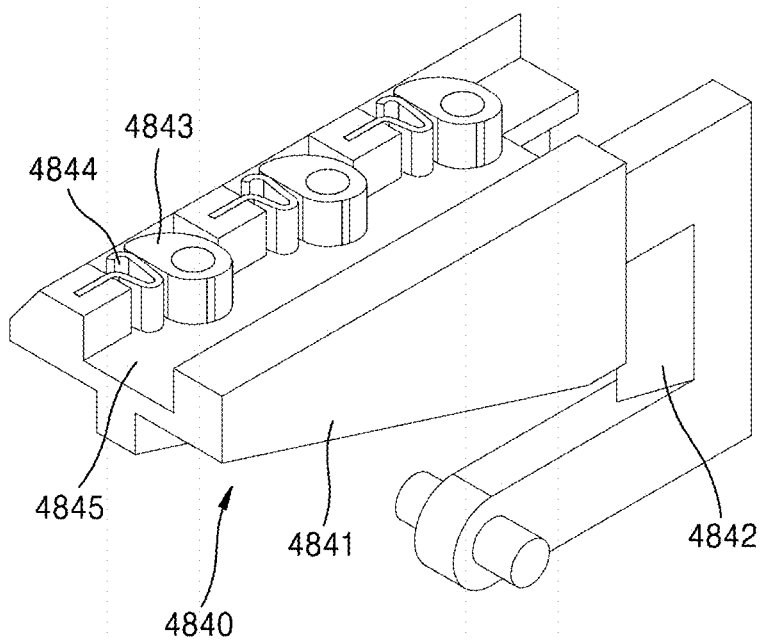
FIGS. 106 to 108 are perspective views illustrating an operation member of a surgical instrument according to a fifth modified example of the first embodiment of the present disclosure.
Figure 107:
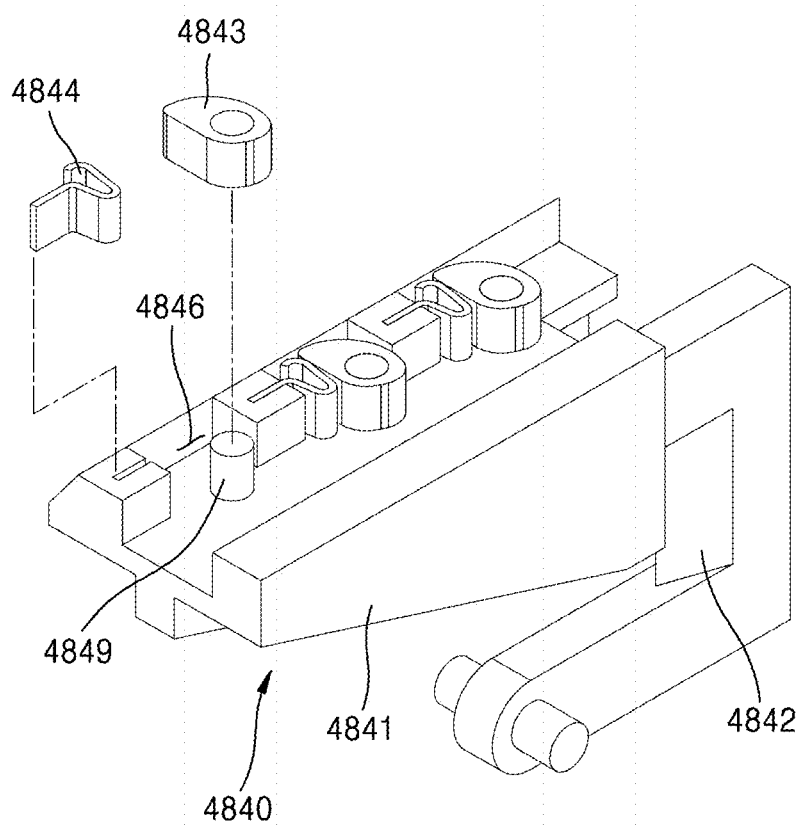
Figure 108:
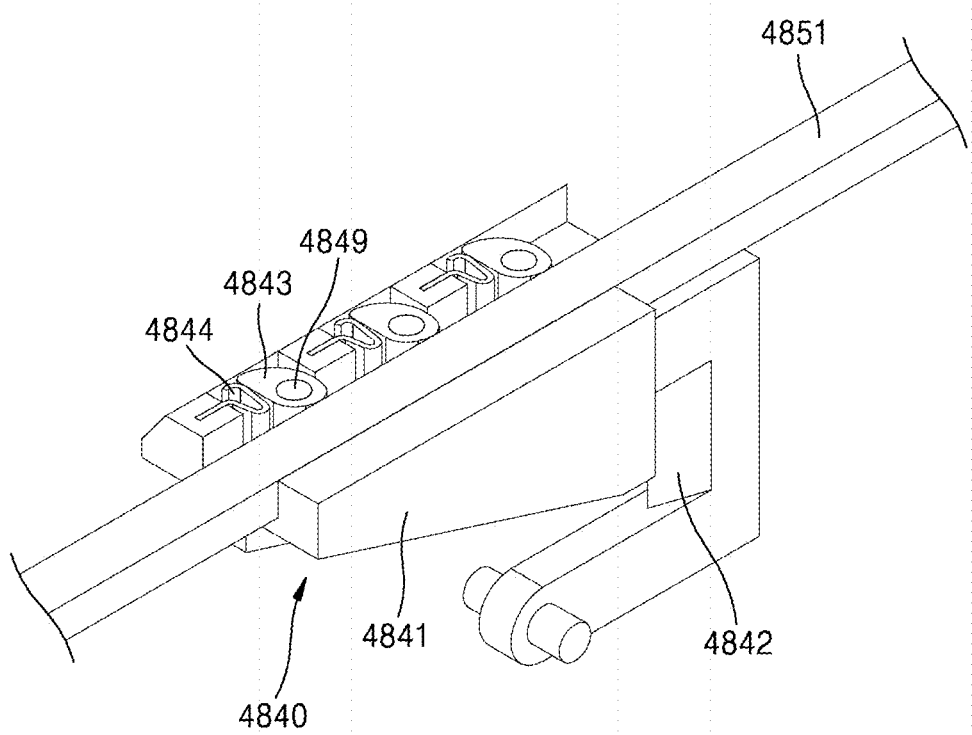
Figure 109:
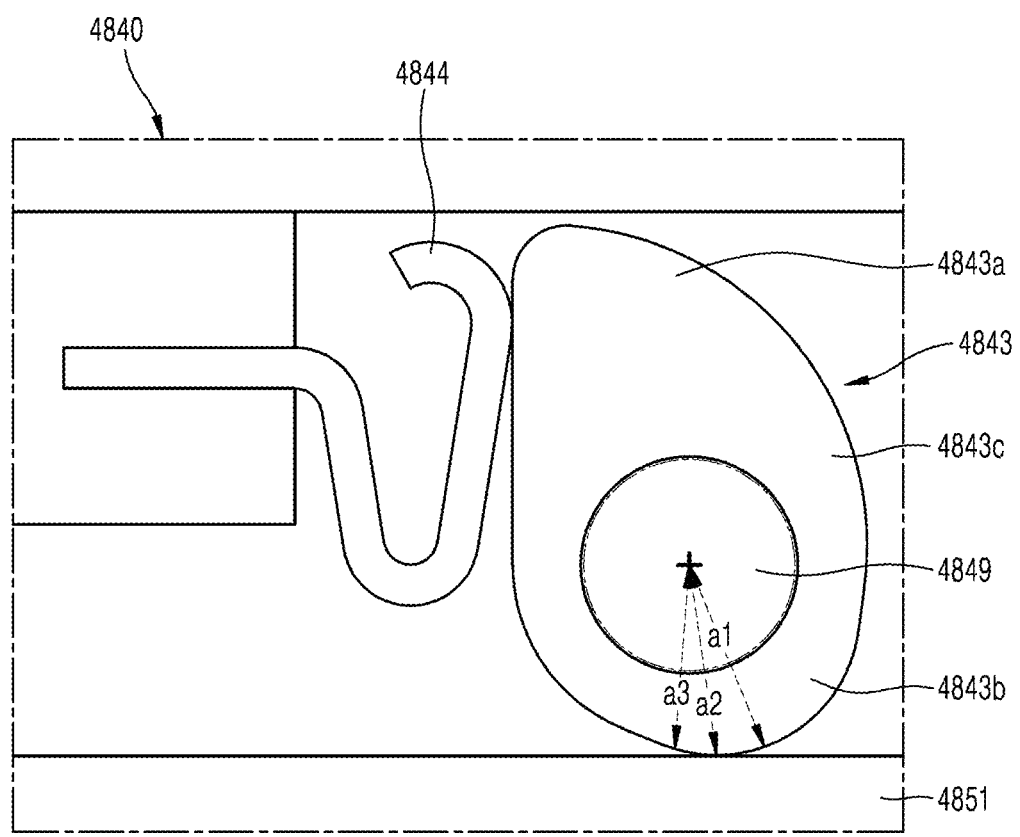
FIG. 109 is a plan view illustrating an elastic member and a contact member of the operation member of FIG. 106 in more detail.
Figure 110:
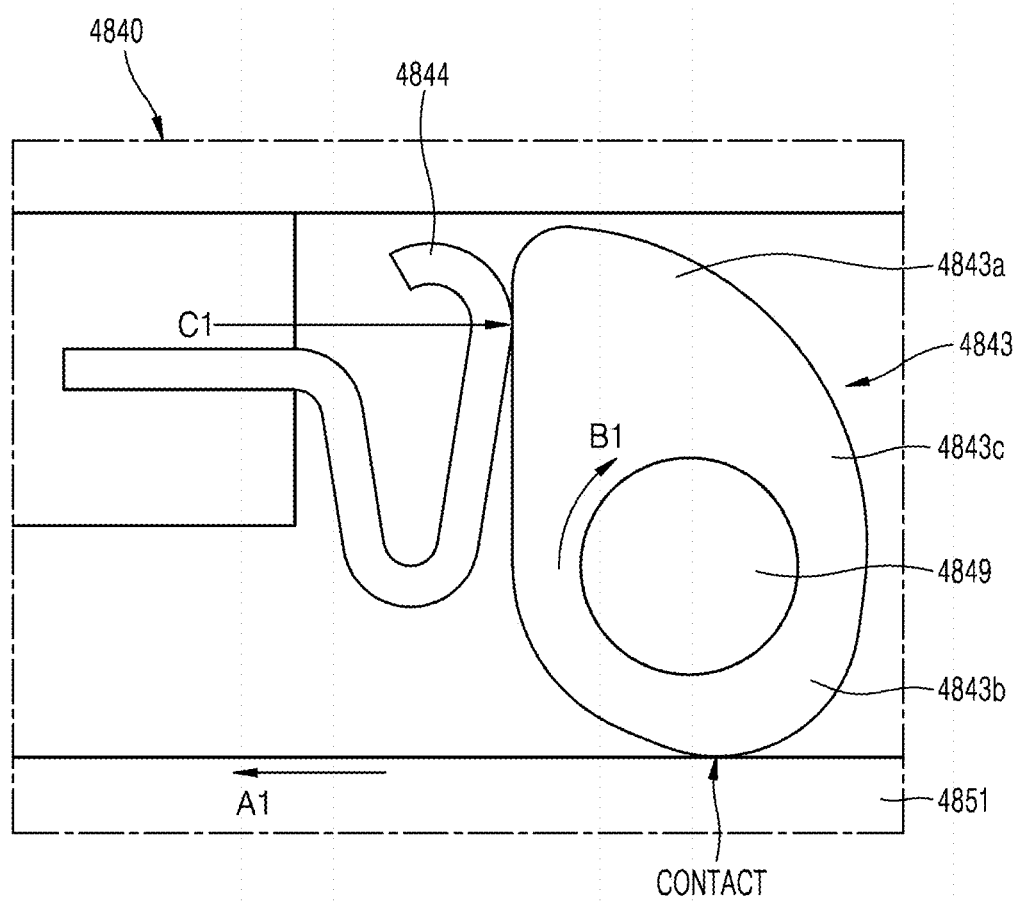
FIGS. 110 and 111 are plan views illustrating operating states of the elastic member and the contact member of the operation member of FIG. 106.
Figure 111:
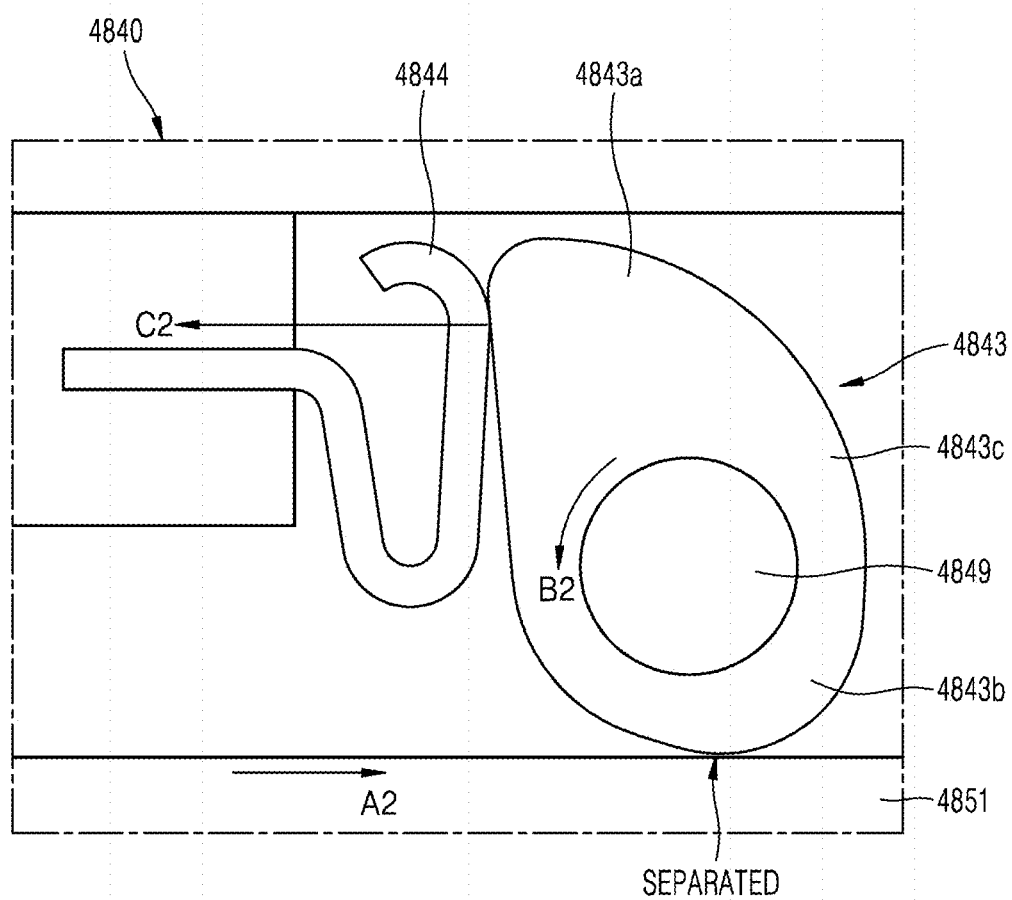
Figure 113A:
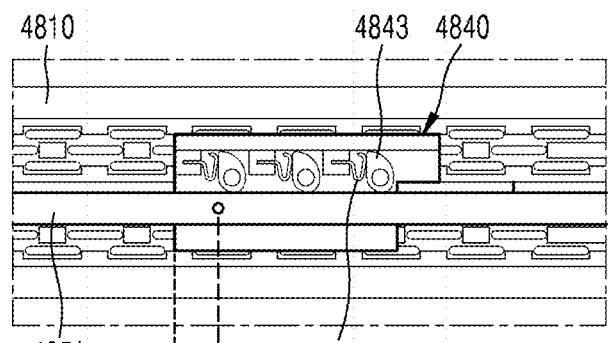
Figure 113B:
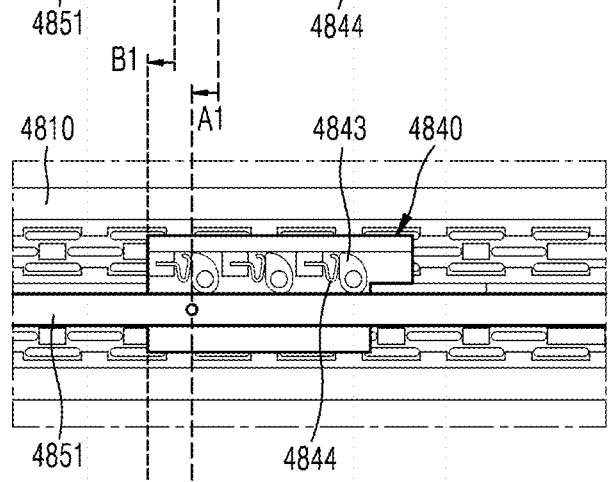
Figure 113C:
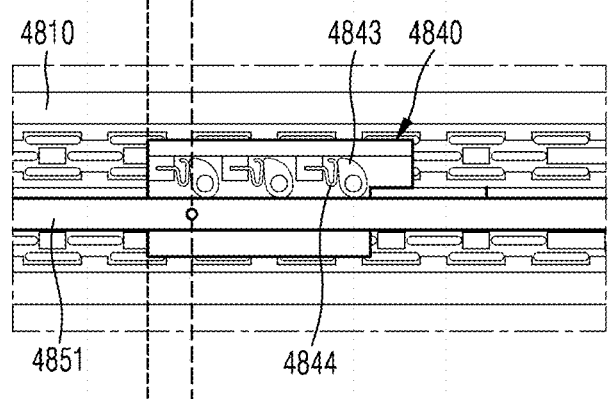
Figure 113D:
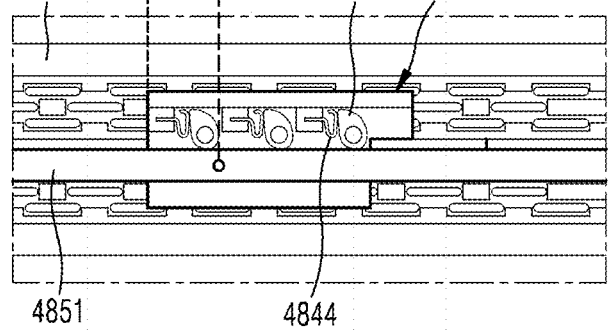

FIGS. 106 to 108 are perspective views illustrating the operation member of the surgical instrument according to the fifth modified example of the first embodiment of the present disclosure. FIG. 109 is a plan view illustrating the elastic member and the contact member of the operation member of FIG. 106 in more detail. FIGS. 110 and 111 are plan views illustrating operating states of the elastic member and the contact member of the operation member of FIG. 106. FIGS. 112A to 113D are plan views illustrating a clutch drive operation of the end tool of FIG. 106.

Referring to FIGS. 106 to 113D, the operation member 4840 according to the fifth modified example of the first embodiment of the present disclosure may include a wedge 4841, a blade 4842, the contact member 4843, the clastic member 4844, and a body 4845. In addition, an accommodation part 4846 may be formed in the body 4845, and a protrusion 4849 serving as a rotation shaft of the elastic member 4844 may be formed in the accommodation part 4846.

Here, the other components except for the contact member 4843 and the elastic member 4844 are the same as the operation member (see 4640 of FIG. 87 or the like) of the surgical instrument according to the second modified example of the first embodiment, and thus detailed descriptions thereof will be omitted.

The contact member 4843 is formed at one side of the body 4845, more specifically, under the body 4845, and may be formed to face a reciprocating member 4851. Here, in the present modified example, the contact member 4843 may be formed in the form of a cam, and the contact member 4843 may be formed to be in contact with the reciprocating member 4851.

That is, in the modified example illustrated in FIG. 87 or the like, the contact member 4643 is formed to be simultaneously in contact with the inner side surface of the body 4645, which forms the accommodation part 4646, and the reciprocating member 4651, whereas in the present modified example illustrated in FIG. 106 or the like, the contact member 4843 is formed to be in contact with only the reciprocating member 4851.

In more detail, the contact member 4843 may be formed to be in contact with or spaced apart from the reciprocating member 4851.

Here, in a state in which the contact member 4843 is in contact with the reciprocating member 4851, the state becomes a kind of a locked state in which the movement of the reciprocating member 4851 with respect to the operation member 4540 is restricted, and thus, when the reciprocating member 4851 is moved in one direction, the moving member 4840 including the contact member 4843 is entirely moved in the one direction together with the reciprocating member 4851.

On the other hand, in a state in which the contact member 4843 is spaced apart from the reciprocating member 4851 by a certain extent, the state becomes a kind of unlocked state, and thus, the reciprocating member 4851 is movable with respect to the operation member 4540. Accordingly, even when the reciprocating member 4851 is moved in one direction, the moving member 4840 remains stationary without moving.

In the fifth modified example of the first embodiment of the present disclosure, a reciprocating assembly 4850 and the operation member 4840 configure a kind of one-way clutch, in particular, a cam clutch.

In detail, the body 4845 of the operation member 4840 and the reciprocating member 4851 are formed to be movable relative to each other. That is, the reciprocating member 4851 is formed to be movable along a length direction of the shaft relative to the body 4845.

The cam-shaped contact member 4843 includes a body 4843c, a first protrusion 4843a, and a second protrusion 4843b.

The body 4843c may be formed to be rotatable in the accommodation part 4846 by being fitted into the protrusion 4849 that serves as a rotation shaft.

The first protrusion 4843a is formed to protrude in one direction from the body 4843c. Here, the first protrusion 4843a may be formed not to be in contact with an inner side surface of the body 4845 that forms the accommodation part 4846.

The second protrusion 4843b is formed to protrude in the other direction from the body 4843c. Here, the second protrusion 4843b may be formed to be in contact with the reciprocating member 4851. Meanwhile, the second protrusion 4843b may be formed such that a distance from the center of the protrusion 4849 serving as a rotation shaft increases in the counterclockwise direction. That is, the second protrusion 4843b may be formed in an asymmetric shape. From another perspective, it may be expressed that a distance from the center of the protrusion 4849 to an end portion of the second protrusion 4843b increases toward the proximal end (see 4501 of FIG. 29) of a cartridge 4840.

Here, when a transverse line connecting from the center of the protrusion 4849 to one end portion of the second protrusion 4843c is drawn, the transverse line may be formed to be longer in the counterclockwise direction when viewed from FIG. 109. Here, a length of the transverse line may be defined as a center distance.

Here, a region having a relatively long center distance may be defined as a long axis part, and a region having a relatively short center distance may be defined as a short axis part. That is, in FIG. 109, a region with a center distance of a1 may be referred to as the long axis part, and a region with a center distance of a3 may be referred to as the short axis part.

At this time, the contact member 4843 has a shape whose center distance becomes longer in the counterclockwise direction. That is, the relationship of a1>a2>a3 is established.

Accordingly, when the contact member 4843 is rotated in the clockwise direction by a certain extent, the contact member 4843 is brought into contact with the reciprocating member 4851. In addition, in this state, when the contact member 4843 is further rotated in the clockwise direction, the state becomes a kind of locked state in which the relative movement between the operation member 4840 and the reciprocating member 4851 is restricted by the contact member 4843.

In contrast, when the contact member 4843 is rotated in the counterclockwise direction by a certain extent, the contact member 4843 is spaced apart from the reciprocating member 4851. This state becomes an unlocked state in which the relative movement between the operation member 4840 and the reciprocating member 4851 is restricted by the contact member 4843.

Here, the elastic member 4844 applies a predetermined elastic force to the contact member 4843 in a direction in which the contact member 4843 is rotated in the clockwise direction. Accordingly, when there is no external force, the contact member 4843 is rotated by a certain extent in the clockwise direction by the elastic member 4844, the state becomes the locked state in which the relative movement between the operation member 4840 and the reciprocating member 4851 is restricted by the contact member 4843.

FIGS. 110 and 111 are plan views illustrating operating states of the elastic member and the contact member of the operation member of FIG. 106.

When the reciprocating member 4851 is moved in the direction of an arrow A1 of FIG. 110 (i.e., toward the distal end (see 4502 of FIG. 29) of the cartridge 4840), the contact member 4843 is rotated in the direction of an arrow B1 (i.e., in the clockwise direction) of FIG. 110 by the elastic force applied to the contact member 4843 by the elastic member 4844 and a frictional force between the reciprocating member 4851 and the contact member 4843. In addition, when the contact member 4843 is rotated in the direction of the arrow B1 of FIG. 110 (i.e., in the clockwise direction), the long axis part (i.e., the region with the center distance of a1) of the contact member 4843 is located in a vertical direction, and the state becomes a kind of locked state in which the relative movement between the operation member 4840 and the reciprocating member 4851 is restricted by the contact member 4843. That is, since the relative movement between the operation member 4840 and the reciprocating member 4851 is restricted by the contact member 4843, the reciprocating member 4851 does not move alone, and the operation member 4840 and the reciprocating member 4851 are moved together as one body, and thus, when the reciprocating member 4851 is moved in the direction of the arrow A1 of FIG. 110, the operation member 4540 is also moved in the direction of the arrow A1.

Meanwhile, when the reciprocating member 4851 is moved in the direction of an arrow A2 of FIG. 111 (i.e., toward the proximal end (see 4501 of FIG. 29) of the cartridge 4840), the contact member 4843 is rotated in the direction of an arrow B2 of FIG. 111 (i.e., in the counterclockwise direction) by the frictional force between the reciprocating member 4851 and the contact member 4843. In addition, when the contact member 4843 is rotated in the direction of the arrow B2 (i.e., in the counterclockwise direction) of FIG. 111, the short axis part (i.e., the region with the center distance of a3) of the contact member 4843 is located in the vertical direction, and the contact member 4843 is spaced apart from the reciprocating member 4851 by a certain extent. That is, the state becomes the unlocked state in which the relative movement between the operation member 4840 and the reciprocating member 4851 is possible. Thus, even when the reciprocating member 4851 is moved in the direction of the arrow A2 of FIG. 111, the operation member 4540 does not move together with the reciprocating member 4851 and remains stationary.

From another perspective, when the reciprocating member 4851 is moved toward the distal end 4802 of the cartridge 4800, it may be said that the contact member 4843 is in a fitted state between the reciprocating member 4851 and the operation member 4840, and the relative movement between the reciprocating member 4851 and the operation member 4840 is blocked.

In contrast, when the reciprocating member 4851 is moved toward the proximal end 4801 of the cartridge 4800, it may be said that the contact member 4843 is released from the fitted state between the reciprocating member 4851 and the operation member 4840, and the relative movement between the reciprocating member 4851 and the operation member 4840 is possible.

FIGS. 112A to 112E and FIGS. 105A to 105D are Plan Views Illustrating a Clutch Drive Operation of the End Tool of FIG. 98.

In the state as shown in FIG. 112A, when the reciprocating member 4851 is moved in the direction of an arrow A1 (i.e., toward the distal end) of FIG. 112B, the contact member 4843 is rotated in the clockwise direction, and the state becomes a kind of locked state in which the relative movement between the operation member 4840 and the reciprocating member 4851 is restricted by the contact member 4843. That is, since the operation member 4840 and the reciprocating member 4851 are in a state of moving together, when the reciprocating member 4851 is moved in the direction of the arrow A1, the operation member 4840 is moved in the direction of an arrow B1.

In this state, when the moving direction of the reciprocating member 4851 is switched to the direction of an arrow A2 of FIG. 112C (i.e., when the movement toward the distal end is switched to the movement toward the proximal end), the contact member 4843 is rotated in the direction of an arrow C2 (i.e., in the counterclockwise direction) of FIG. 112C, and the state becomes the unlocked state in which the relative movement between the operation member 4840 and the reciprocating member 4851 is possible. Thus, even when the reciprocating member 4851 is moved in the direction of the arrow A2 of FIG. 112C, the operation member 4840 remains stationary.

In this state, when the reciprocating member 4851 continues to move in the direction of an arrow A3 (i.e., toward the proximal end) of FIG. 112D, the contact member 4843 remains spaced apart from the reciprocating member 4851 and the operation member 4840. That is, the unlocked state in which the relative movement between the operation member 4840 and the reciprocating member 4851 is possible is maintained. Thus, even when the reciprocating member 4851 is moved in the direction of the arrow A3 of FIG. 112D, the operation member 4840 remains stationary.

In this state, when the moving direction of the reciprocating member 4851 is switched to the direction of an arrow A4 of FIG. 112E (i.e., when the movement toward the proximal end is switched to the movement toward the distal end), the contact member 4843 is rotated in the direction of an arrow C4 (i.e., in the clockwise direction) of FIG. 112E, and the state becomes a kind of locked state in which the relative movement between the operation member 4840 and the reciprocating member 4851 is restricted by the contact member 4843 In this state, when the reciprocating member 4851 is moved toward the distal end, the operation member 4840 is also moved toward the distal end.

While repeating this process, the operation member 4840 is moved forward toward the distal end, and in this process, cutting and stapling are performed.

From another perspective, as shown in FIG. 105, when the reciprocating member 4840 is moved in the direction of an arrow A1 (i.e., toward the distal end) of FIG. 105B, the operation member 4840 is moved together with the reciprocating member 4840 in the direction of an arrow B1 (i.e., toward the distal end) of FIG. 105B. On the other hand, when the reciprocating member 4840 is moved in the direction of an arrow A2 (i.e., toward the proximal end) of FIG. 105D, the operation member 4840 remains stationary in place without moving. As a result, while the reciprocating member 4841 repeatedly moved forward and backward, the operation member 4840 is moved toward the distal end while repeating moving forward and stopping.

Second Embodiment of Surgical Instrument

Figure 114:
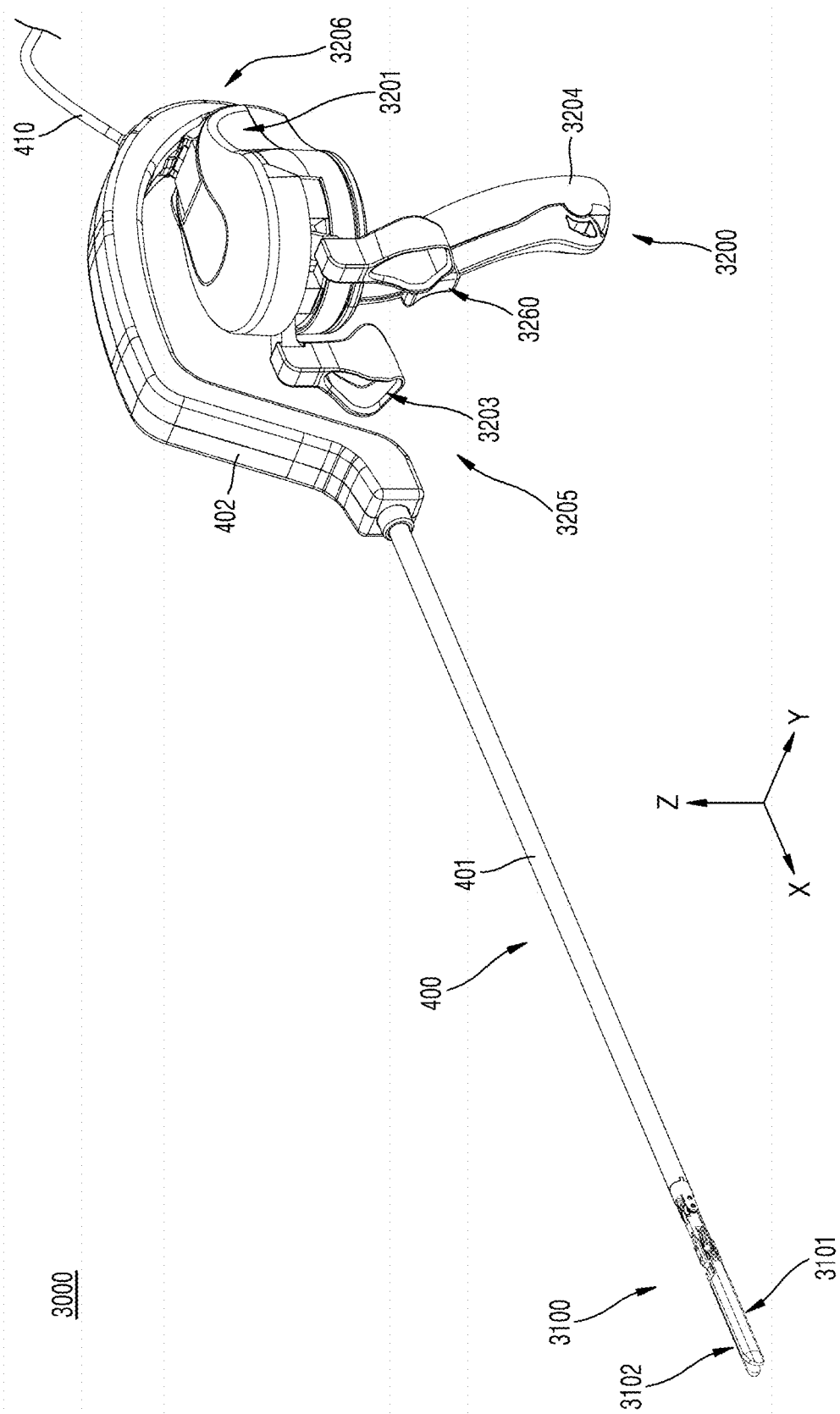
FIG. 114 is a perspective view illustrating a surgical instrument according to a second embodiment of the present disclosure.
Figure 115:
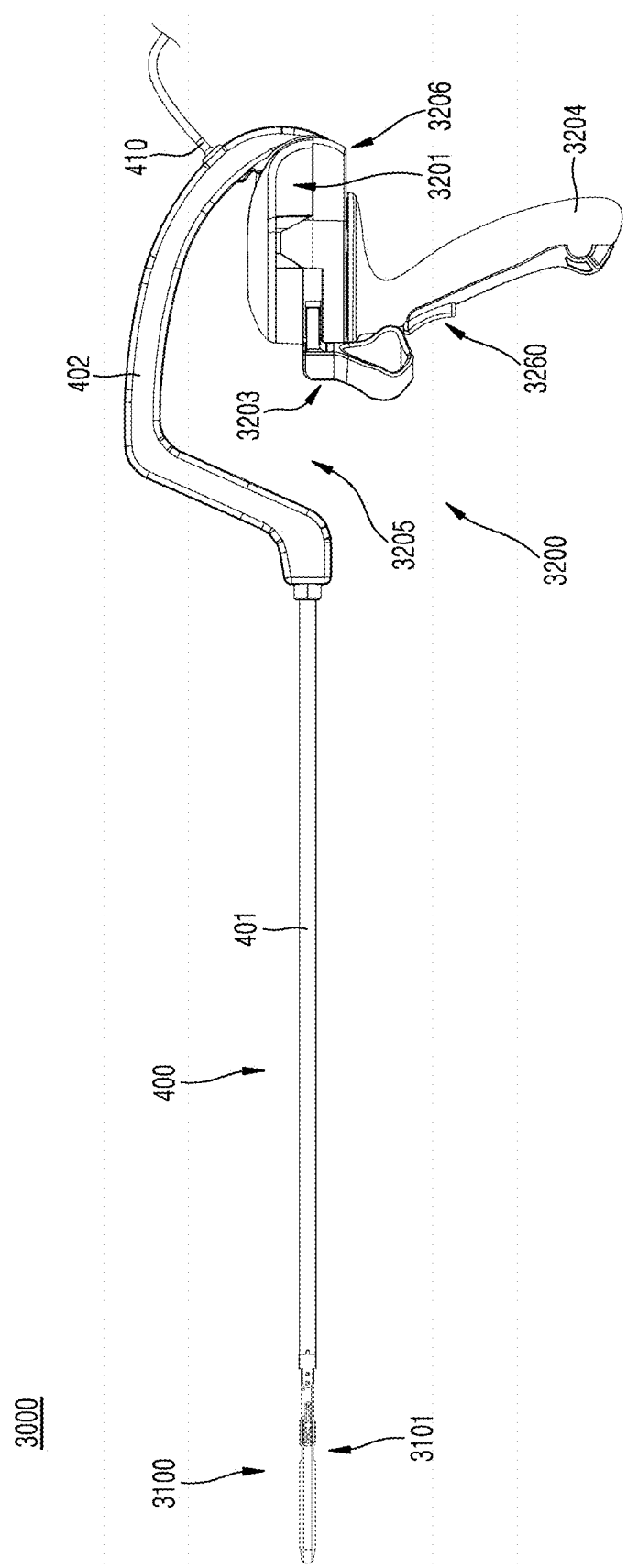
FIG. 115 is a side view of the surgical instrument of FIG. 114.
Figure 118:
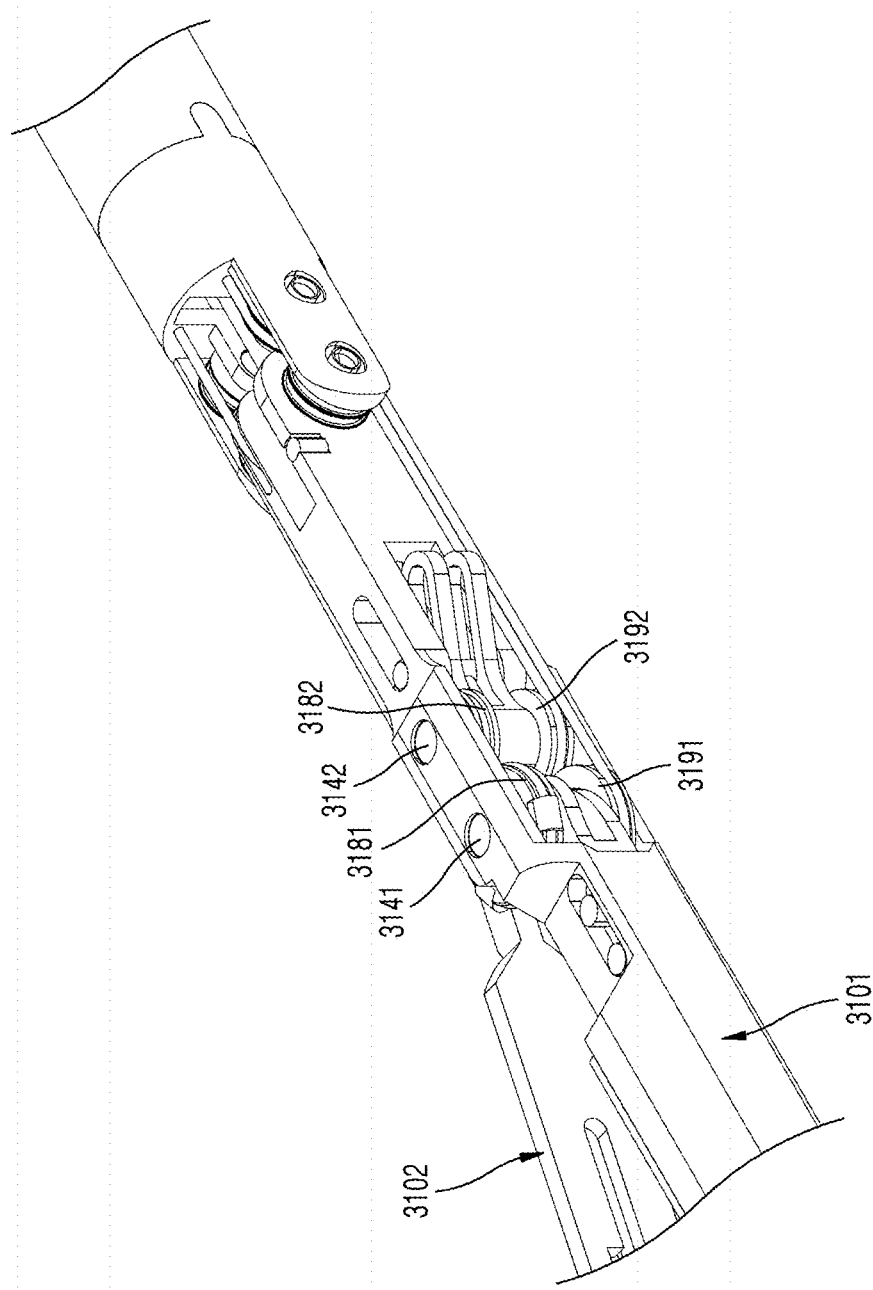
Figure 119:
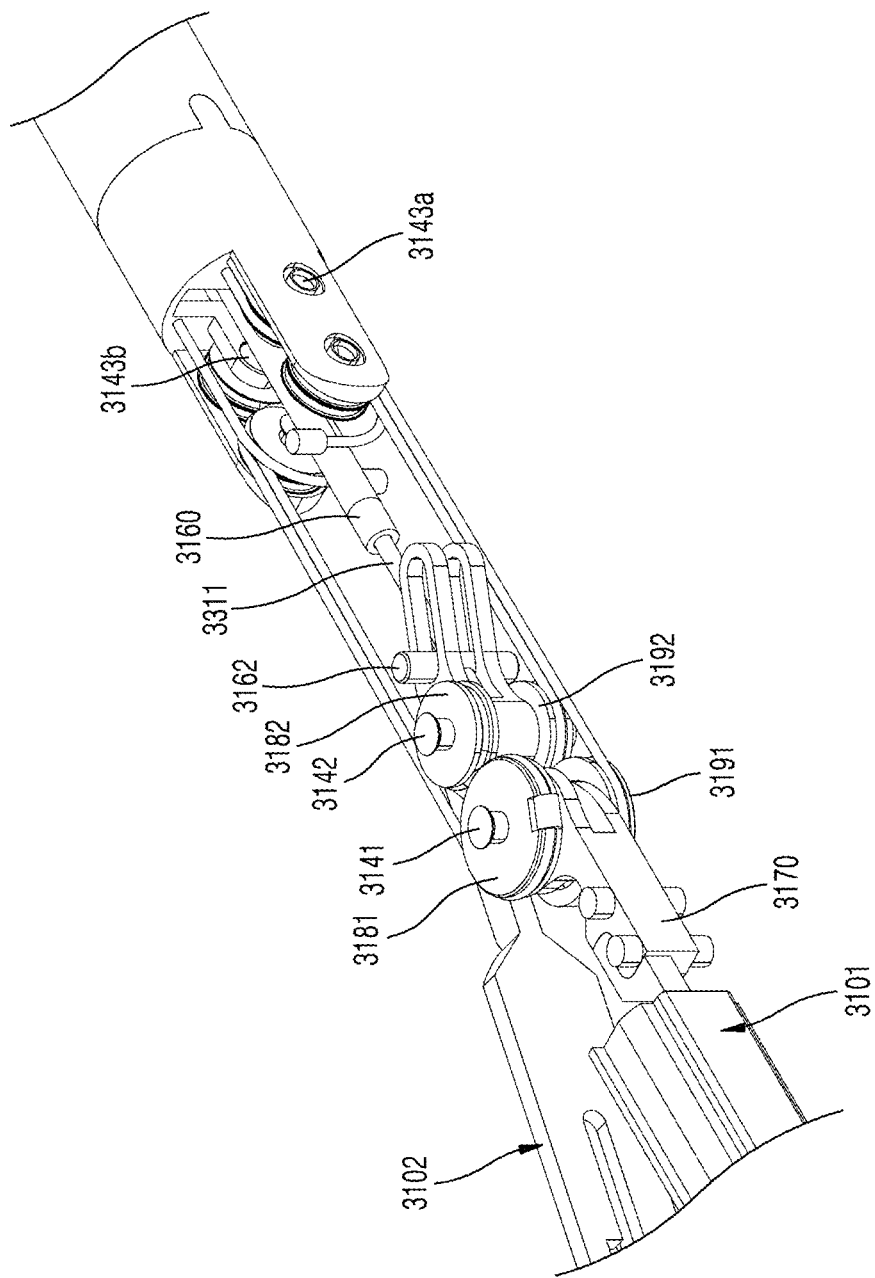
Figure 120:
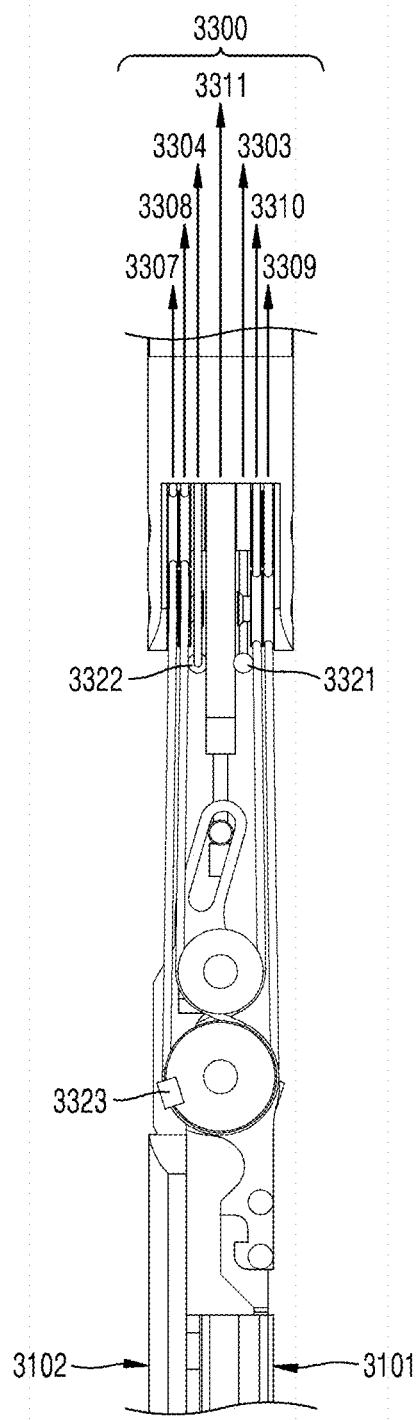
FIGS. 120 and 121 are plan views illustrating the end tool of the surgical instrument of FIG. 114.
Figure 121:
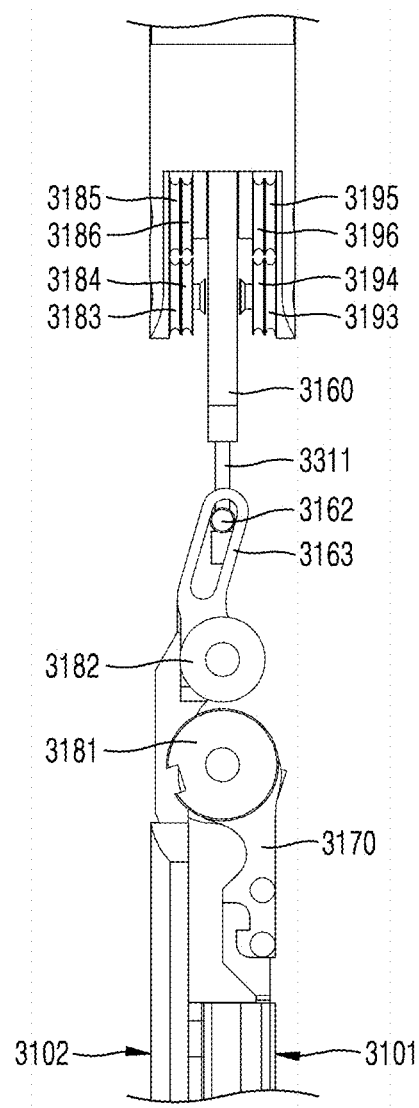
Figure 122:
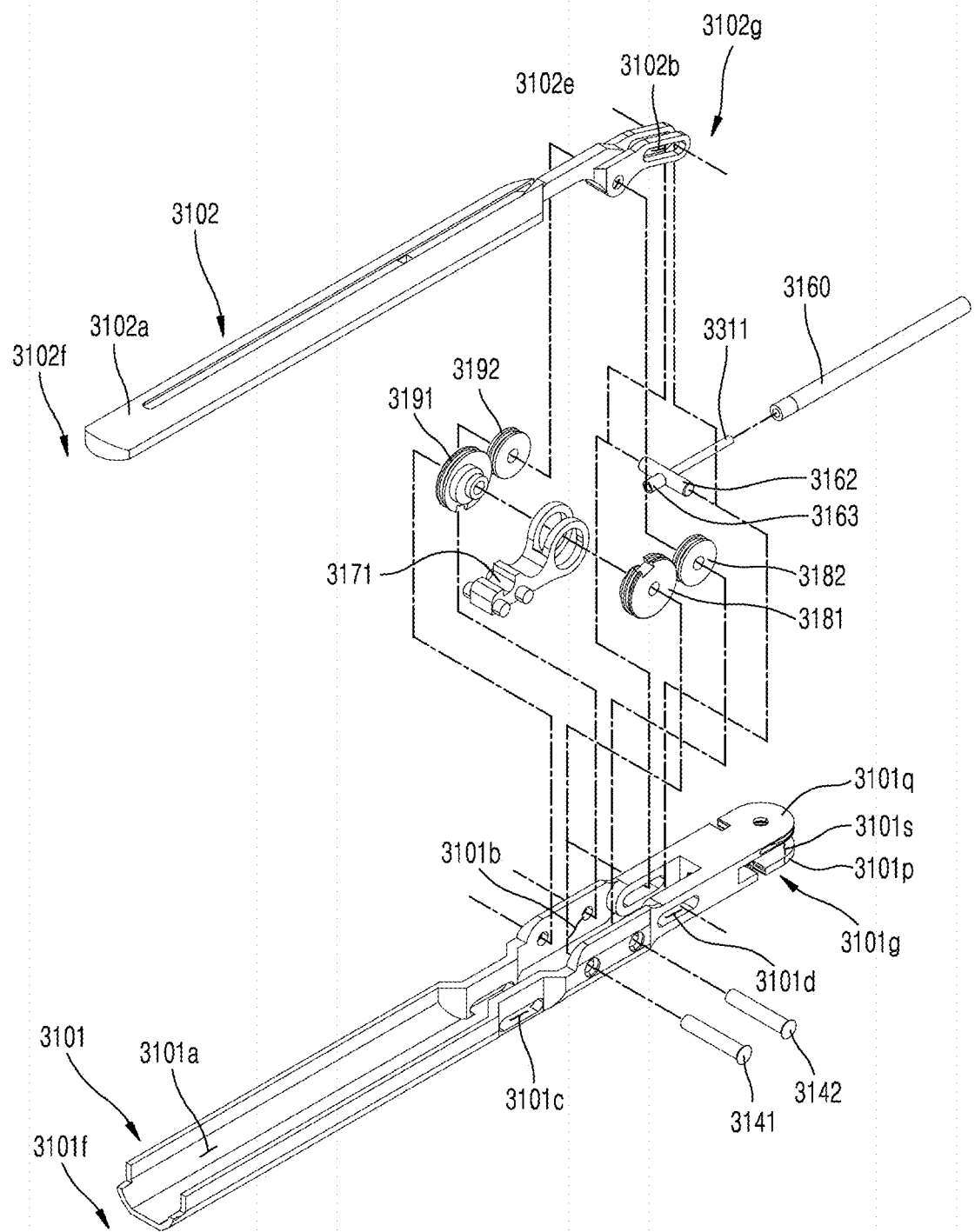
FIG. 122 is an exploded perspective view of the end tool of the surgical instrument of FIG. 114.
Figure 127:
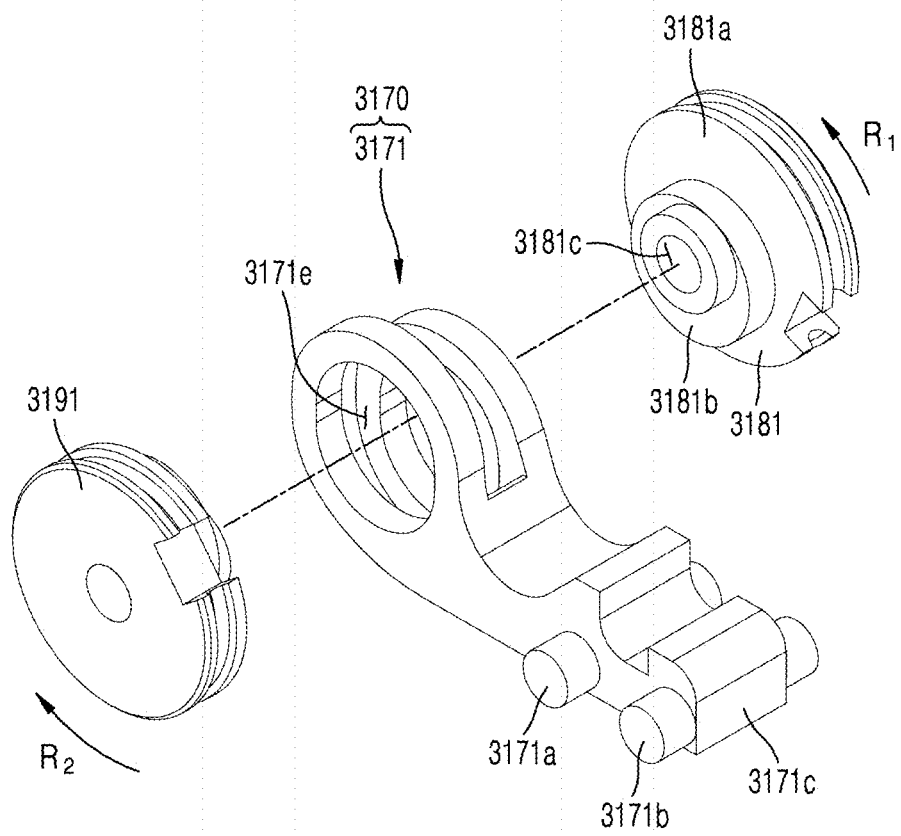
FIGS. 127 and 128 are exploded perspective views illustrating a staple pulley and a staple link of the surgical instrument of FIG. 114.
Figure 128:
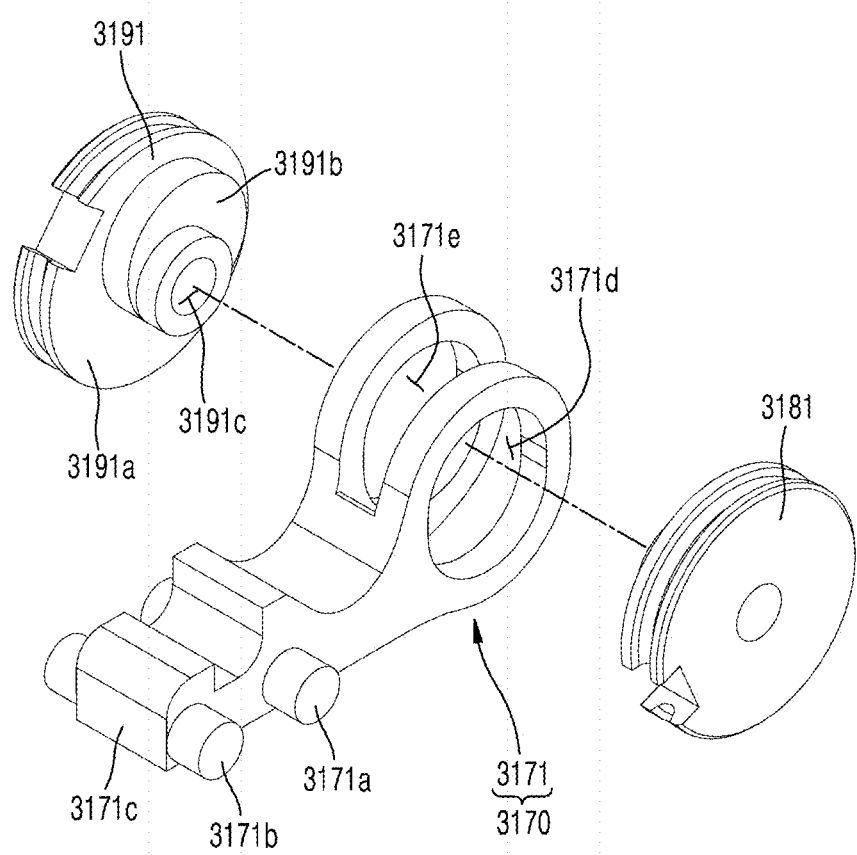
Figure 129:
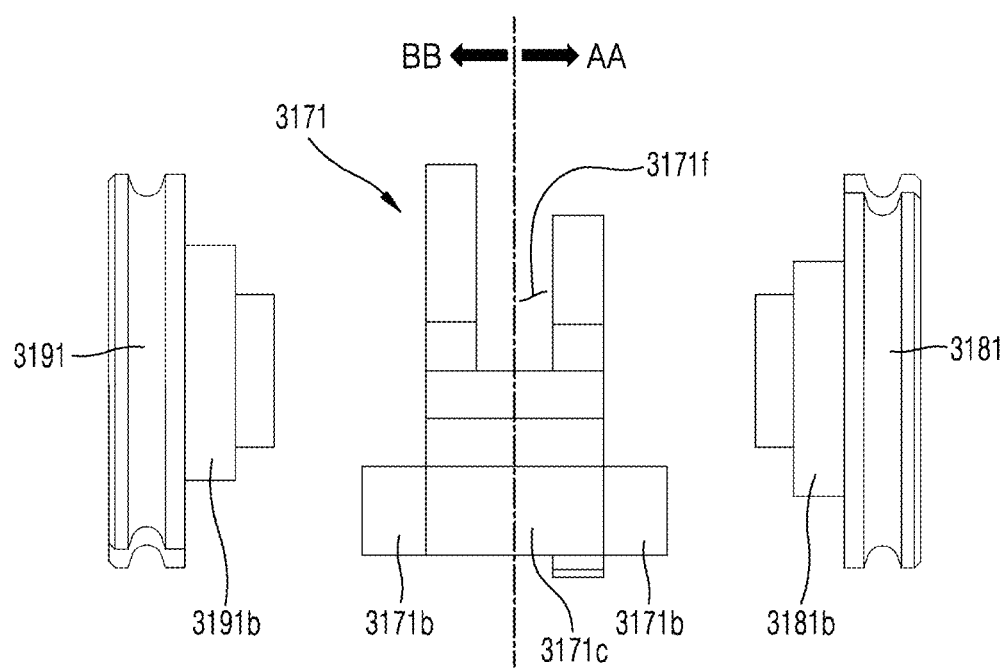
FIG. 129 is a front view illustrating the staple pulley and the staple link of the surgical instrument of FIG. 114.
Figure 132:
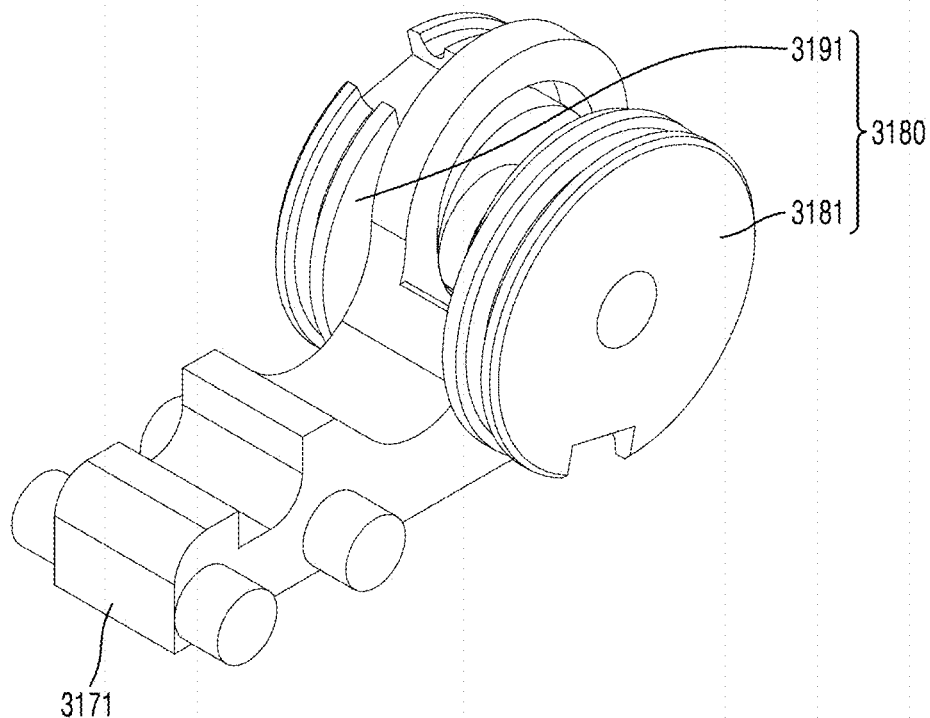
FIGS. 132 and 133 are perspective views illustrating operating states of the staple pulley in the end tool of the surgical instrument of FIG. 114.
Figure 133:
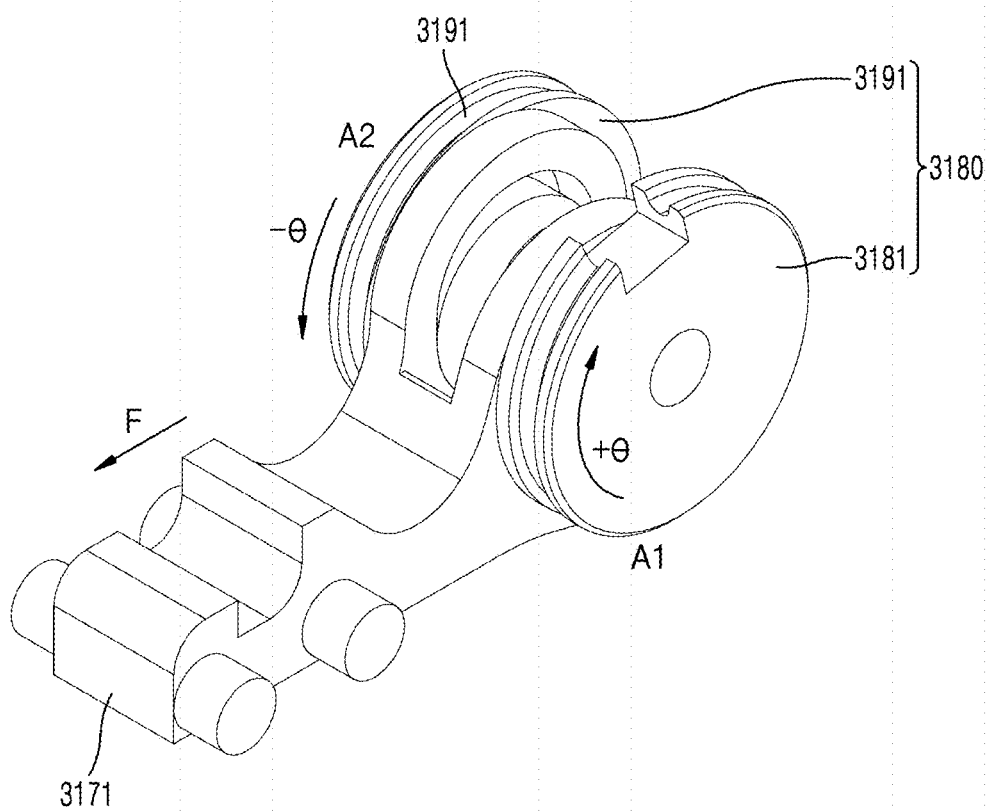

FIG. 114 is a perspective view illustrating a surgical instrument according to a second embodiment of the present disclosure. FIG. 115 is a side view of the surgical instrument of FIG. 114. FIGS. 116 to 119 are perspective views illustrating an end tool of the surgical instrument of FIG. 114. FIGS. 120 and 121 are plan views illustrating the end tool of the surgical instrument of FIG. 114. FIG. 122 is an exploded perspective view of the end tool of the surgical instrument of FIG. 114. FIGS. 123 to 126 are plan views illustrating opening and closing motions of a first jaw and a second jaw of the surgical instrument of FIG. 114. FIGS. 127 and 128 are exploded perspective views illustrating a staple pulley and a staple link of the surgical instrument of FIG. 114. FIG. 129 is a front view illustrating the staple pulley and the staple link of the surgical instrument of FIG. 114. FIGS. 130A to 131C are side views illustrating operating states of the staple pulley in the end tool of the surgical instrument of FIG. 114. FIGS. 132 and 133 are perspective views illustrating operating states of the staple pulley in the end tool of the surgical instrument of FIG. 114.

First, referring to FIGS. 114 to 121, a surgical instrument 3000 according to the second embodiment of the present disclosure includes an end tool 3100, a manipulation part 3200, a power transmission part 3300, and a connection part 400.

Here, the connection part 400 is formed in the shape of a hollow shaft, and one or more wires and electric wires may be accommodated therein. The manipulation part 3200 is coupled to one end portion of the connection part 400, the end tool 3100 is coupled to the other end portion thereof, and the connection part 400 may serve to connect the manipulation part 3200 and the end tool 3100. Here, the connection part 400 of the surgical instrument 3000 according to the second embodiment of the present disclosure includes a straight part 401 and a bent part 402, the straight part 401 is formed at a side of the connection part 400 coupled to the end tool 3100, and the bent part 402 is formed at a side of the connection part 400, to which the manipulation part 3200 is coupled. As such, since the end portion of the connection part 400 at the side of the manipulation part 3200 is formed to be bent, a pitch manipulation part 3201 and an actuation manipulation part 3203 may be formed along an extension line of the end tool 3100 or adjacent to the extension line. From another perspective, it may be said that the pitch manipulation part 3201 is at least partially accommodated in a concave portion formed by the bent part 402. Due to the above-described shape of the bent part 402, the shapes and motions of the manipulation part 3200 and the end tool 3100 may be further intuitively matched with each other.

Meanwhile, a plane on which the bent part 402 is formed may be substantially the same as a pitch plane, that is, an XZ plane of FIG. 114. As such, as the bent part 402 is formed on substantially the same plane as the XZ plane, interference with the manipulation part may be reduced. Of course, for the intuitively matched motions of the end tool and the manipulation part, any configuration formed on a plane other than the XZ plane may be possible.

Meanwhile, a connector 410 may be formed on the bent part 402. The connector 410 may be connected to an external power source (not shown), and the connector 410 may also be connected to the end tool 3100 via an electric wire, and may transmit, to the end tool 3100, electric energy supplied from the external power source (not shown). In addition, the electric energy transmitted to the end tool 3100 as described above may produce a driving force for rotating a staple pulley assembly (see 3180 of FIG. 132) to be described later in the clockwise or counterclockwise direction.

The manipulation part 3200 is formed at the one end portion of the connection part 400 and provided as an interface to be directly controlled by a medical doctor, for example, a tongs shape, a stick shape, a lever shape, or the like, and when the medical doctor controls the manipulation part 3200, the end tool 3100, which is connected to the interface and inserted into the body of a surgical patient, performs a certain motion, thereby performing surgery. Here, the manipulation part 3200 is illustrated in FIG. 114 as being formed in a handle shape that is rotatable while the finger is inserted therein, but the concept of the present disclosure is not limited thereto, and various types of manipulation parts that can be connected to the end tool 3100 and manipulate the end tool 3100 may be possible.

The end tool 3100 is formed on the other end portion of the connection part 400, and performs necessary motions for surgery by being inserted into a surgical site. As an example of the end tool 3100 described above, a pair of jaws 3103 for performing a grip motion may be used as illustrated in FIG. 114. However, the concept of the present disclosure is not limited thereto, and various devices for performing surgery may be used as the end tool 3100. For example, a configuration of a cantilever cautery may also be used as the end tool. The end tool 3100 is connected to the manipulation part 3200 by the power transmission part 3300, and receives a driving force of the manipulation part 3200 through the power transmission part 3300 to perform a motion necessary for surgery, such as gripping, cutting, suturing, or the like.

Here, the end tool 3100 of the surgical instrument 3000 according to the second embodiment of the present disclosure is formed to be rotatable in one or more directions, for example, the end tool 3100 may be formed to perform a pitch motion around a Y-axis of FIG. 114 and simultaneously perform an actuation motion around a Z-axis of FIG. 114.

Here, each of the pitch and actuation motions used in the present disclosure are defined as follows.

First, the pitch motion means a motion of the end tool 3100 rotating in a vertical direction with respect to an extension direction of the connection part 400 (an X-axis direction of FIG. 114), that is, a motion rotating around the Y-axis of FIG. 114. In other words, the pitch motion means a motion of the end tool 3100, which is formed to extend from the connection part 400 in the extension direction of the connection part 400 (the X-axis direction of FIG. 114), rotating vertically around the Y-axis with respect to the connection part 400.

Next, the actuation motion means a motion in which the end tool 3100 is rotated in left and right directions with respect to the extension direction (the X-axis direction of FIG. 114) of the connection part 400, that is, a motion in which the two jaws 3103 are closed or opened while rotating around the Z-axis of FIG. 114 but in opposite directions. In other words, the actuation motion means a motion of the end tool 3100, which is formed to extend from the connection part 400 in the extension direction (the X-axis direction of FIG. 114) of the connection part 400, rotating left and right around the Z-axis with respect to the connection part 400, and in this case, the two jaws 3103 formed on the end tool 3100 are rotated in opposite directions around the Z-axis.

Alternatively, the actuation motion may mean a motion in which one jaw remains stationary and the other jaw is rotated with respect to the stationary jaw. That is, the actuation motion may mean a motion in which one jaw is rotated relative to the other jaw. Hereinafter, a motion in which a second jaw 3102 is rotated with respect to a first jaw 3101 is referred to as an actuation motion.

The power transmission part 3300 serves to connect the manipulation part 3200 to the end tool 3100 and transmit the driving force of the manipulation part 3200 to the end tool 3100, and may include a plurality of wires, pulleys, links, sections, gears, or the like.

The end tool 3100, the manipulation part 3200, the power transmission part 3300, and the like of the surgical instrument 3000 of FIG. 114 will be described in detail later.

(Intuitive Driving)

Hereinafter, intuitive driving of the surgical instrument 3000 of the present disclosure will be described.

First, a user may perform a pitch motion by rotating a first handle 3204 around the Y-axis while holding the first handle 3204 with the palm. In addition, the user may perform an actuation motion by manipulating the actuation manipulation part 3203 while inserting the thumb and the index finger into a first actuation extension part and/or a second actuation extension part in the form of a ring formed at one end portion of the actuation manipulation part 3203.

Here, in the surgical instrument 3000 according to the second embodiment of the present disclosure, when the manipulation part 3200 is rotated in one direction with respect to the connection part 400, the end tool 3100 is rotated in a direction that is intuitively the same as a manipulation direction of the manipulation part 3200. In other words, when the first handle 3204 of the manipulation part 3200 is rotated in one direction, the end tool 3100 is also rotated in a direction intuitively the same as the one direction, so that the pitch motion is performed. Here, the phrase "intuitively the same direction" may be further explained as meaning that a direction of movement of the user's finger gripping the manipulation part 3200 and a direction of movement of a distal end of the end tool 3100 form substantially the same direction. Of course, "the same direction" as used herein may not be a perfectly matching direction on a three-dimensional coordinate, and may be understood to be equivalent to the extent that, for example, when the user's finger moves to the left, the distal end of the end tool 3100 is moved to the left, and when the user's finger moves down, the end portion of the end tool 3100 is moved down.

In addition, to this end, in the surgical instrument 3000 according to the second embodiment of the present disclosure, the manipulation part 3200 and the end tool 3100 are formed in the same direction with respect to a plane perpendicular to the extension axis (X-axis) of the connection part 400. That is, when viewed based on a YZ plane of FIG. 114, the manipulation part 3200 is formed to extend in a positive (+) X-axis direction, and the end tool 3100 is also formed to extend in the positive (+) X-axis direction. In other words, it may be said that a formation direction of the end tool 3100 on one end portion of the connection part 400 is the same as a formation direction of the manipulation part 3200 on the other end portion of the connection part 400 on the basis of the YZ plane. Further, in other words, it may be said that the manipulation part 3200 may be formed in a direction away from the body of a user holding the manipulation part 3200, that is, in a direction in which the end tool 3100 is formed. That is, in the parts such as the first handle 3204, a first actuation manipulation part, a second actuation manipulation part, and the like, which are moved by the user's grip for actuation and pitch motions, a corresponding portion that is moved for the motion is formed to extend in the positive (+) X-axis direction from the rotation center of a corresponding joint for the motion. In this manner, the manipulation part 3200 may be configured in the same manner as the end tool 3100 in which each moving portion is formed to extend in the positive (+) X-axis direction from the rotation center of a corresponding joint for the motion, and as described with reference to FIG. 1, the manipulation direction of the user may be identical to an operation direction of the end tool from the viewpoint of the rotation directions and the left and right directions. As a result, intuitively the same manipulation may be achieved.

That is, in the surgical instrument 3000 according to the second embodiment of the present disclosure, the manipulation direction of the manipulation part 3200 is ensured to be intuitively the same as the operation direction of the end tool 3100, and to this end, portions of the manipulation part 3200, which actually move for the actuation and pitch motions, are formed to extend in the positive (+) X-axis direction from the rotation center of the corresponding joint of each motion, like the end tool 3100.

Hereinafter, the end tool 3100, the manipulation part 3200, the power transmission part 3300, and the like of the surgical instrument 3000 of FIG. 114 will be described in more detail.

(Power Transmission Part)

Hereinafter, the power transmission part 3300 of the surgical instrument 3000 of FIG. 114 will be described in more detail.

Referring to FIGS. 114 to 133 and the like, the power transmission part 3300 of the surgical instrument 3000 according to the second embodiment of the present disclosure may include a wire 3303, a wire 3304, a wire 3307, a wire 3308, a wire 3309, and a wire 3310. In addition, the power transmission part 3300 may further include an actuation wire 3311.

Here, the wires 3303 and 3304 may be paired to serve as pitch wires. In addition, the wires 3307 and 3308, may be paired to serve as first staple wires. In addition, the wires 309 and 310, may be paired to serve as second staple wires. Here, a component encompassing the wires 307 and 308, which are first staple wires, and the wires 309 and 310, which are second staple wires, may be referred to as a staple wire.

In addition, the power transmission part 3300 of the surgical instrument 3000 according to an embodiment of the present disclosure may include a coupling member 3321, a coupling member 3322, a coupling member 3323, and a coupling member 3324 coupled to end portions of the wires to couple the wires and the pulleys, respectively. Here, each of the coupling members may have various shapes as necessary, such as a ball shape, a tube shape, and the like.

Here, at the end tool 3100 side, the coupling member 3321/coupling member 3322 serve as pitch wire-end tool coupling members, the coupling member 3323 serves as a first staple wire-end tool coupling member, and the coupling member 3324 may serve as a second staple wire-end tool coupling member.

In addition, although not shown in the drawings, a first staple wire-manipulation part coupling member, a second staple wire-manipulation part coupling member, a pitch wire-manipulation part coupling member, and an actuation wire-manipulation part coupling member may be further formed at the manipulation part 3200 side.

The coupling relationship between the wires and the coupling members, and the respectively pulleys will be described in detail as follows.

First, the wires 3307 and 3308, which are first staple wires, may be a single wire. The coupling member 3323, which is a first staple wire-end tool coupling member, is inserted at an intermediate point of the first staple wire, which is a single wire, and is crimped and fixed, and then, both strands of the first staple wire centered on the coupling member 3323 may be referred to as the wire 3307 and the wire 3308, respectively.

Alternatively, the wire 3307 and the wire 3308, which are first staple wires, may also be formed as separate wires, and connected by the coupling member 3323.

In addition, by coupling the coupling member 3323 to a first staple pulley 3181, the wire 3307 and the wire 3308 may be fixedly coupled to the first staple pulley 3181. This allows the first staple pulley 3181 to rotate as the wire 3307 and the wire 3308 are pulled and released.

Meanwhile, the first staple wire-manipulation part coupling member (not shown) may be coupled to end portions of the wires 3307 and 3308, which are opposite to one end portions to which the coupling member 3323 is coupled.

In addition, by coupling the first staple wire-manipulation part coupling member (not shown) to a first staple drive pulley (not shown) of the manipulation part 3200, the wires 3307 and 3308 may be fixedly coupled to the first staple drive pulley (not shown). As a result, the first staple pulley 3181 of the end tool 3100 may be rotated as the wire 3307 and the wire 3308 are pulled and released when the first staple drive pulley (not shown) is rotated by a motor or a human force.

In the same manner, the wire 3309 and the wire 3310, which are second staple wires, are respectively coupled to the coupling member 3324, which is a second staple wire-end tool coupling member, and the second staple wire-manipulation part coupling member (not shown). In addition, the coupling member 3324 is coupled to a second staple pulley 3191, and the second staple wire-manipulation part coupling member (not shown) is coupled to a second staple drive pulley (not shown). As a result, the second staple pulley 3191 of the end tool 3100 may be rotated as the wire 3309 and the wire 3310 are pulled and released when the second staple drive pulley (not shown) is rotated by a motor or a human force.

The coupling member 3321 may be coupled to the wire 3303 that is a pitch wire, and the coupling member 3321 may be coupled to a first pitch pulley part 3101*p* of the first jaw 3101, which will be described later. In the same manner, the coupling member 3322 may be coupled to the wire 3304 that is a pitch wire, and the coupling member 3322 may be coupled to a second pitch pulley part 3101*q* of the first jaw 3101, which will be described later. This allows the first jaw 3101 to rotate as the wires 3303 and 3304 are pulled and released.

Meanwhile, one end portion of the actuation wire 3311 is coupled to a guide pin 3162 to be described later, and the other end portion thereof is coupled to the actuation manipulation part 3203 of the manipulation part 3200. Through the manipulation of the actuation manipulation part 3203, the actuation wire 3311 is moved from a proximal end 3105 of the end tool 3100 toward a distal end 3104 so that an open motion of the jaw 3103 is performed, or the actuation wire 3311 is returned from the distal end 3104 toward the proximal end 3105 of the end tool 3100 so that a close motion of the jaw 3103 is performed.

At this time, at least a portion of the actuation wire 3311 may be accommodated inside a guide tube 3160 to be described later. Accordingly, when the guide tube 3160 is bent according to a pitch motion of the end tool 3100, the actuation wire 3311 accommodated inside the guide tube 3160 may also be bent together with the guide tube 3160. The guide tube 3160 will be described in more detail later.

In addition, the actuation wire 3311 is formed to be linearly moved in the connection part 400 along a length direction of the connection part 400. In addition, since one end portion of the actuation wire 3311 is coupled to the guide pin 3162, when the actuation wire 3311 is linearly moved along the length direction of the connection part 400, the guide pin 3162 connected thereto performs a linear motion. That is, when the actuation wire 3311 is linearly moved along the length direction of the connection part 400, the guide pin 3162 connected thereto is moved toward the distal end 3104 or the proximal end 3105 of the end tool 3100 while performing an actuation motion. This will be described in more detail later.

(Manipulation Part)

Referring to FIGS. 114 and 115 and the like, the manipulation part 3200 of the surgical instrument 3000 according to the second embodiment of the present disclosure includes the first handle 3204 that a user can grip, the actuation manipulation part 3203 configure to control an actuation motion of the end tool 3100, and the pitch manipulation part 3201 configured to control a pitch motion of the end tool 3100.

In addition, the manipulation part 3200 of the surgical instrument 3000 may further include a staple manipulation part 3260 configured to control the motion of the staple pulley assembly 3180 of the end tool 3100 to perform stapling and cutting motions.

Hereinafter, each component of the manipulation part 3200 will be described in more detail.

The first handle 3204 may be formed to be gripped by a user with the hand, and specifically, may be formed to be gripped by the user by wrapping the first handle 3204 with his/her palm. In addition, the actuation manipulation part 3203 is formed on the first handle 3204, and the pitch manipulation part 3201 is formed at one side of the actuation manipulation part 3203. In addition, the other end portion of the pitch manipulation part 3201 is connected to the bent part 402 of the connection part 400.

The actuation manipulation part 3203 may include a first actuation manipulation part and a second actuation manipulation part that are formed in a ring shape and operate as a second handle.

The pitch manipulation part 3201 may further include a rotation shaft, a manipulation part first jaw pitch main pulley, a manipulation part second jaw pitch main pulley, a manipulation part first jaw pitch sub-pulley, and a manipulation part second jaw pitch sub-pulley. The pitch manipulation part 3201 may be connected to the bent part 402 of the connection part 400 through a pitch rotation shaft (not shown). A pitch motion is performed as the pitch manipulation part 3201 is rotated around the pitch rotation shaft (not shown) with respect to the bent part 402 of the connection part 400.

A connection relationship of each of the first handle 3204, the pitch manipulation part 3201, and the actuation manipulation part 3203 is summarized as follows. First, the first handle 3204 may be directly connected to the actuation manipulation part 3203. On the other hand, the pitch manipulation part 3201 is formed to be connected to the actuation manipulation part 3203 at one side of the actuation manipulation part 3203, and thus, the pitch manipulation part 3201 may be formed to be indirectly connected to the first handle 3204 through the actuation manipulation part 3203 without being directly connected to the first handle 3204.

Continuing to refer to the drawings, in the surgical instrument 3000 according to the second embodiment of the present disclosure, the pitch manipulation part 3201 and the end tool 3100 may be formed on the same or parallel axis (X-axis). That is, the pitch rotation shaft (not shown) of the pitch manipulation part 3201 is formed at one end portion of the bent part 402 of the connection part 400, and the end tool 3100 is formed at the other end portion of the connection part 400.

In addition, one or more relay pulleys configured to change or guide paths of the wires may be disposed at some places along the connection part 400, particularly in the bent part 402. As at least some of the wires are wound around the relay pulleys to guide the paths of the wires, these wires may be disposed along a bent shape of the bent part 402.

Here, in the drawings, it is illustrated that the connection part 400 is formed to be curved with a predetermined curvature by having the bent part 402, but the concept of the present disclosure is not limited thereto, and the connection part 400 may be formed linearly or to be bent one or more times as necessary, and even in this case, it may be said that the pitch manipulation part 3201 and the end tool 3100 are formed on substantially the same axis or parallel axes. In addition, although FIG. 114 illustrates that each of the pitch manipulation part 3201 and the end tool 3100 is formed on an axis parallel to the X-axis, the concept of the present disclosure is not limited thereto, and the pitch manipulation part 3201 and the end tool 3100 may be formed on different axes.

The staple manipulation part 3260 is connected to the first staple pulley 3181 of the end tool 3100 by the wires 3307 and 3308, which are first staple wires, and serves to alternately rotate the first staple pulley 3181 in the clockwise or counterclockwise direction. In addition, the staple manipulation part 3260 is connected to the second staple pulley 3191 of the end tool 3100 by the wires 3309 and 3310, which are second staple wires, and serves to alternately rotate the second staple pulley 3191 in the counterclockwise or clockwise direction.

To this end, although not shown in the drawings, the staple manipulation part 3260 may include a motor (not shown). That is, the motor (not shown) is driven while the user presses the staple manipulation part 3260 formed in the form of a button to alternately rotate the manipulation part staple pulley (not shown) in the clockwise or counterclockwise direction. In addition, due thereto, the first staple pulley 3181 and the second staple pulley 3191 of the end tool 3100 may be rotated alternately in the clockwise and counterclockwise directions.

(End Tool-Overall Configuration)

Hereinafter, the end tool 3100 of the surgical instrument 3000 of FIG. 114 will be described in more detail.

FIGS. 116 to 119 are perspective views illustrating the end tool of the surgical instrument of FIG. 114, and FIGS. 120 and 121 are plan views illustrating the end tool of the surgical instrument of FIG. 114.

Figure 116:
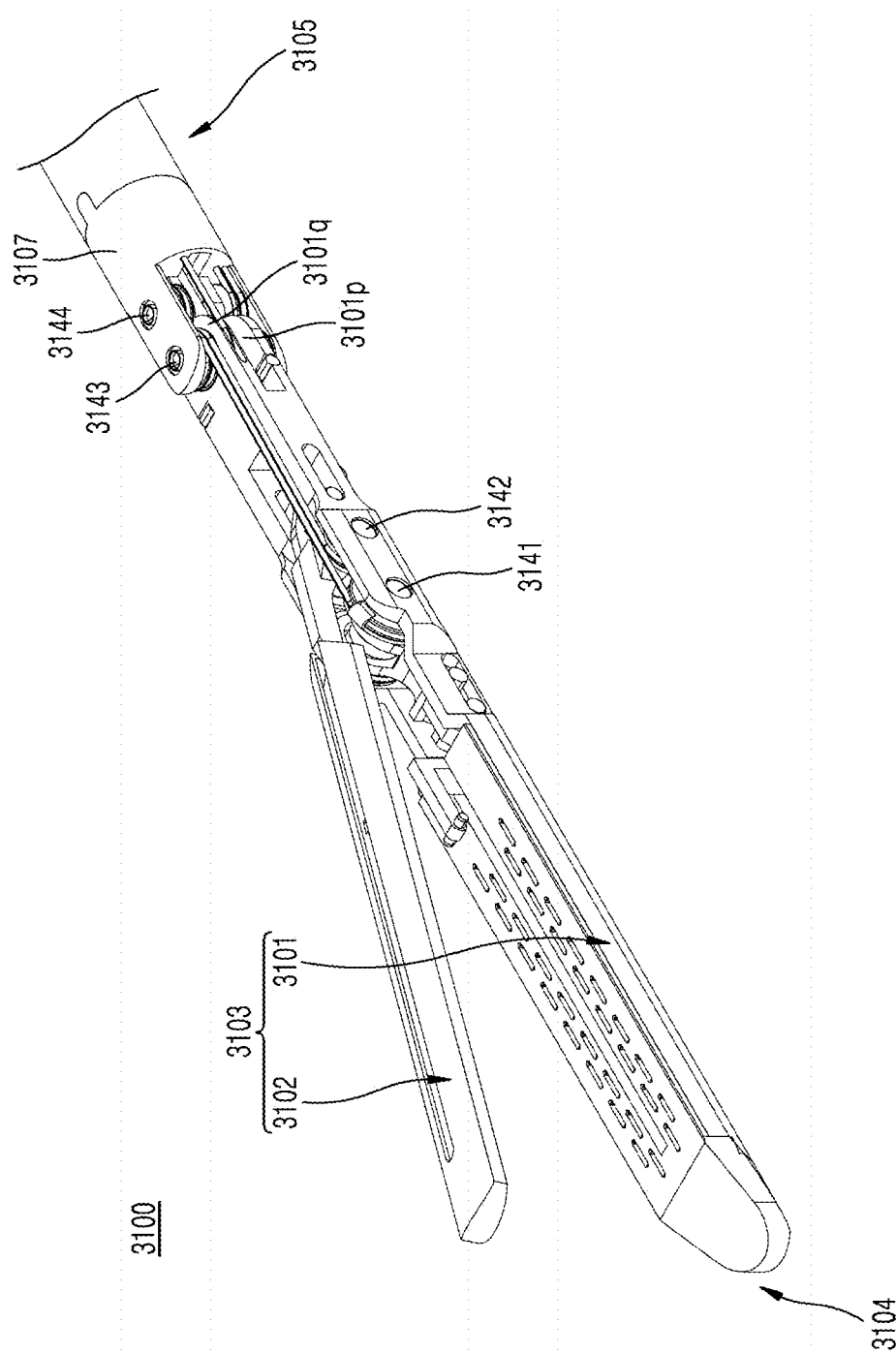
FIGS. 116 to 119 are perspective views illustrating an end tool of the surgical instrument of FIG. 114.
Figure 117:
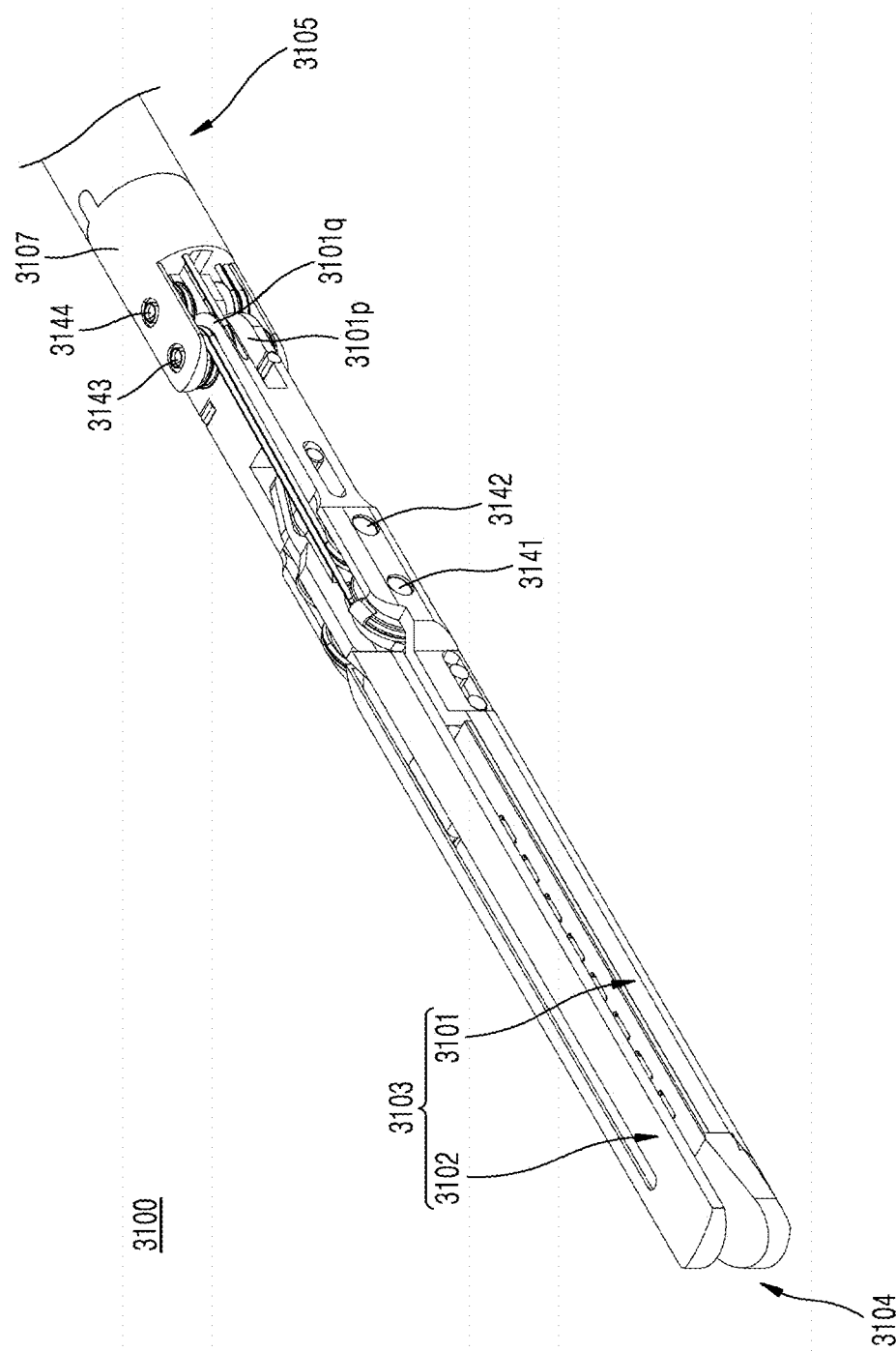

Here, FIG. 116 illustrates a state in which the jaws are opened, and FIG. 117 illustrates a state in which the jaws are closed. In addition, FIG. 118 is a magnified view of FIG. 117, and FIG. 119 illustrates a state in which the first jaw is omitted from FIG. 118.

Referring to FIGS. 116 to 121 and the like, the end tool 3100 of the second embodiment of the present disclosure includes a pair of jaws for performing a grip motion, that is, the first jaw 3101 and a second jaw 3102. Here, each of the first jaw 3101 and the second jaw 3102, or a component encompassing the first jaw 3101 and the second jaw 3102 may be referred to as the jaw 3103. The configuration of the first jaw 3101 and the second jaw 3102 will be described in more detail later.

Meanwhile, the end tool 3100 of the second embodiment of the present disclosure may include a pitch hub 3107. A rotation shaft 3143 and a rotation shaft 3144, which will be described later, may be inserted through the pitch hub 3107, and the pitch hub 3107 may be axially coupled to the first jaw 3101 by the rotation shaft 3143. Accordingly, the first jaw 3101 may be formed to be rotatable around the rotation shaft 3143 with respect to the pitch hub 3107.

Further, the pitch hub 3107 may internally accommodate at least some of a pulley 3183, a pulley 3184, a pulley 3193, and a pulley 3194 that are axially coupled to the rotation shaft 3143. In addition, the pitch hub 3107 may internally accommodate at least some of a pulley 3185, a pulley 3186, a pulley 3195, and a pulley 3196 that are axially coupled to the rotation shaft 3144.

Meanwhile, the end tool 3100 of the second embodiment of the present disclosure may include a rotation shaft 3141, a rotation shaft 3142, the rotation shaft 3143, and the rotation shaft 3144. As described above, the rotation shaft 3141 and the rotation shaft 3142 may be inserted through the first jaw 3101, and the rotation shaft 3143 and the rotation shaft 3144 may be inserted through the pitch hub 3107.

The rotation shaft 3141, the rotation shaft 3142, the rotation shaft 3143, and the rotation shaft 3144 may be arranged sequentially from the distal end 3104 of the end tool 3100 toward the proximal end 3105. Accordingly, starting from the distal end 3104, the rotation shaft 3141 may be referred to as a first pin, the rotation shaft 3142 may be referred to as a second pin, the rotation shaft 3143 may be referred to as a third pin, and the rotation shaft 3144 may be referred to as a fourth pin.

Here, the rotation shaft 3141 may function as an end tool staple pulley rotation shaft, the rotation shaft 3142 may function as an end tool staple auxiliary pulley rotation shaft while also functioning as an end tool jaw rotation shaft, the rotation shaft 3143 may function as an end tool pitch rotation shaft, and the rotation shaft 3144 may function as an end tool pitch auxiliary rotation shaft of the end tool 3100.

Each of the rotation shafts 3141, 3142, 3143, and 3144 may be fitted into one or more pulleys, which will be described in detail below.

(First and Second Jaws and Actuation Motion)

Hereinafter, a coupling structure of the first jaw 3101 and the second jaw 3102 of the end tool 3100 of the surgical instrument 3000 of FIG. 114 will be described in more detail.

Figure 123:
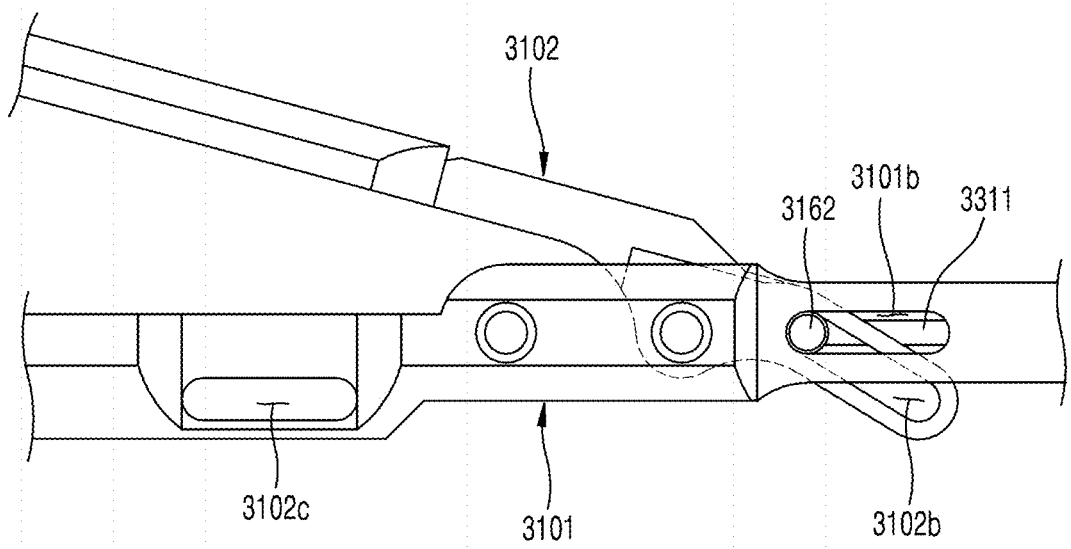
FIGS. 123 to 126 are plan views illustrating opening and closing motions of a first jaw and a second jaw of the surgical instrument of FIG. 114.
Figure 124:
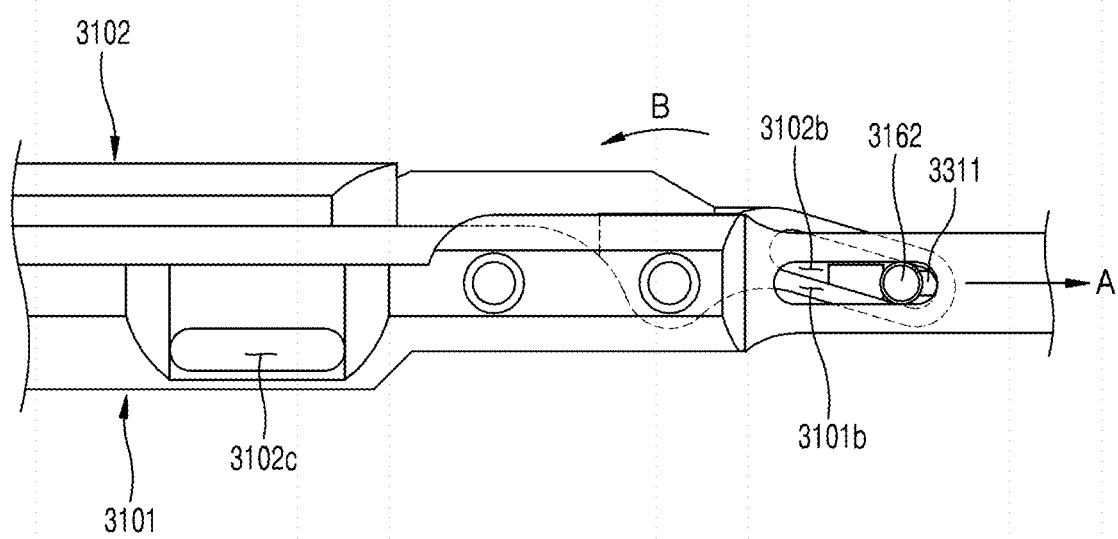
Figure 125:
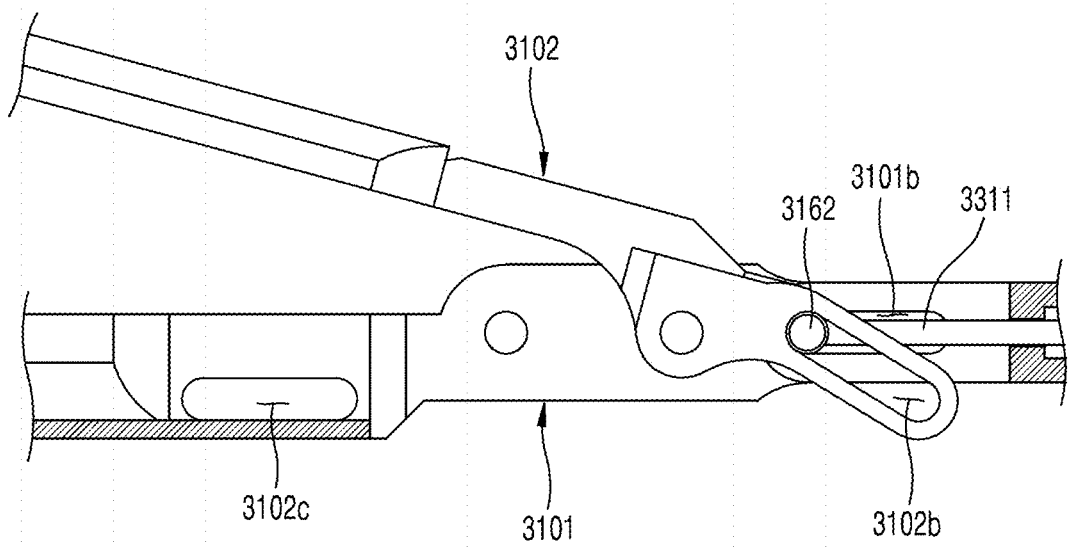
Figure 126:
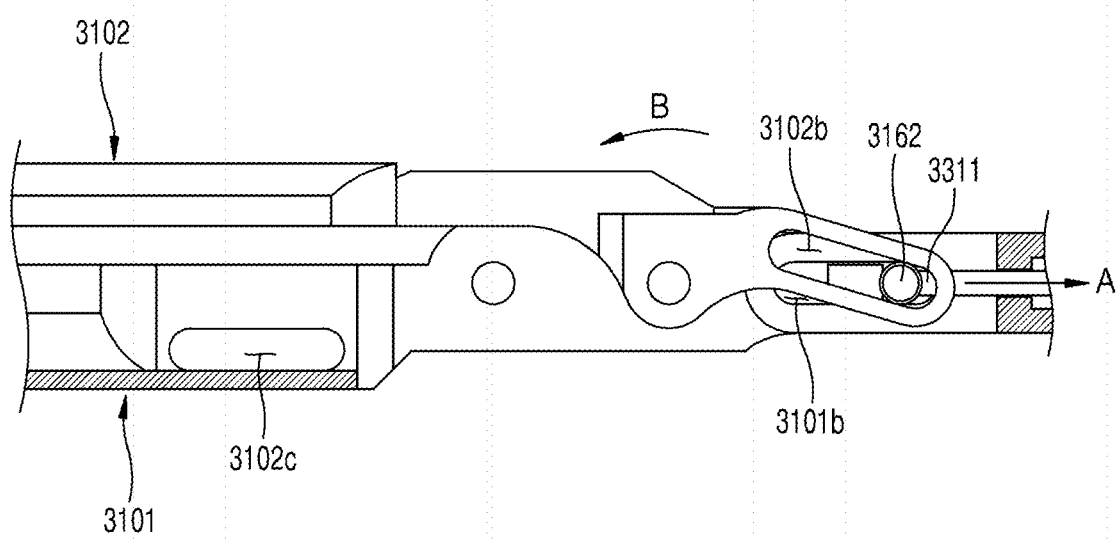

FIG. 122 is an exploded perspective view of the end tool of the surgical instrument of FIG. 114, and FIGS. 123 to 126 are plan views illustrating opening and closing motions of the first jaw and the second jaw of the surgical instrument of FIG. 114. Here, FIGS. 123 and 124 are perspective views of the first jaw 3101 and the second jaw 3102, and FIGS. 125 and 126 are cross-sectional views of the first jaw 3101 and the second jaw 3102.

Referring to FIGS. 114 to 126 and the like, the first jaw 3101 includes a cartridge accommodation part 3101*a*, a staple assembly accommodation part 3101*b*, a link guide groove 3101*c*, a pin guide groove 3101*d*, the first pitch pulley part 3101*p*, the second pitch pulley part 3101*q*, and a pitch slit 3101*s*.

The first jaw 3101 is formed in the shape of an elongated bar as a whole, and a cartridge (see 500 in FIG. 134) is accommodated in the first jaw 3101 at a distal end 3101*f* side. In other words, the first jaw 3101 may be formed entirely in the form of a hollow box with one surface (upper surface) thereof is removed, such that the cartridge accommodation part 3101*a* capable of accommodating the cartridge (see 500 in FIG. 134) may be formed inside the first jaw 3101. That is, the first jaw 3101 may be formed in an approximately "U" shape in cross section.

In addition, the first pitch pulley part 3101*p* and the second pitch pulley part 3101*q*, which serve as end tool pitch pulleys, are formed on a proximal end 3101*g* of the first jaw 3101, so that the first jaw 3101 is formed to be rotatable around the rotation shaft 3143.

Here, the first pitch pulley part 3101*p* and the second pitch pulley part 3101*q* may be formed to face each other. Here, the first pitch pulley part 3101*p* and the second pitch pulley part 3101*q* may be formed to be approximately parallel to a plane perpendicular to the third rotation shaft 3143 which is a pitch rotation shaft.

In detail, the first pitch pulley part 3101*p* and the second pitch pulley part 3101*q*, each of which is formed in the shape of a disk such as the pulley and has an outer circumferential surface in which a groove around which the wire may be wound is formed, may be formed in one end portion of the first jaw 3101. The wire 3303 and the wire 3304 described above are respectively coupled to the first pitch pulley part 3101*p* and the second pitch pulley part 3101*q* that serve as end tool pitch pulleys, and the first jaw 3101 performs a pitch motion while rotating around the third rotation shaft 3143.

Meanwhile, in the drawings, the first pitch pulley part 3101*p* and the second pitch pulley part 3101*q* are illustrated as being integrally formed with the first jaw 3101, but may be formed as separate members from the first jaw 3101 and may be coupled to the first jaw 3101.

Meanwhile, a through hole is formed in the first pitch pulley part 3101*p* so that the third rotation shaft 3143 may pass through the first pitch pulley part 3101*p*. In addition, a through hole is formed in the second pitch pulley part 3101*q* so that the third rotation shaft 3143 may pass through the second pitch pulley part 3101*q*.

Here, the third rotation shaft 3143, which is a pitch rotation shaft, may be formed by being divided into two parts that are a first sub-shaft 3143*a* and a second sub-shaft 3143*b*, and the guide tube 3160 or the actuation wire 3311 may pass between the first sub-shaft 3143*a* and the second sub-shaft 3143*b* of the third rotation shaft 3143.

Meanwhile, it is illustrated in the drawings that the third rotation shaft 3143 is formed by being divided into two parts, but the concept of the present disclosure is not limited thereto. That is, it would be possible for the third rotation shaft 3143 to be formed to bend in the middle such that an escape path for the guide tube 3160 is formed.

The pitch slit 3101*s* may be formed between the first pitch pulley part 3101*p* and the second pitch pulley part 3101*q*. As such, since the pitch slit 3101*s* is formed in the first jaw 3101, the guide tube 3160 or the actuation wire 3311 may pass through the inside of the first jaw 3101.

From another perspective, the third rotation shaft 3143 may be separated into left and right halves without passing through the first jaw 3101, and the pitch slit 3101*s* may be formed near the third rotation shaft 3143 on a plane perpendicular to the third rotation shaft 3143. Accordingly, the guide tube 3160 or the actuation wire 3311 may move (i.e., move up and down) in the pitch slit 3101*s* while passing through near the third rotation shaft 3143.

Meanwhile, the staple assembly accommodation part 3101*b* configured to accommodate a staple drive assembly 3150 including a staple link assembly 3170 and the staple pulley assembly 3180 may be formed at one side of the cartridge accommodation part 3101*a* of the first jaw 3101, for example, at the proximal end 3101*g* side. The staple assembly accommodation part 3101*b* may serve as a kind of end tool hub.

In detail, shaft pass-through parts may be formed in the staple assembly accommodation part 3101*b* so that the rotation shaft 3141 and the rotation shaft 3142 may be inserted therethrough. In addition, a link member 3171 of the staple link assembly 3170 may be disposed in the staple assembly accommodation part 3101*b*. In addition, the first and second staple pulleys 3181 and 3191 of the staple pulley assembly 3180 may be disposed in the staple assembly accommodation part 3101*b*. In addition, a first staple auxiliary pulley 3182 and a second staple auxiliary pulley 3192 of the staple pulley assembly 3180 may be disposed in the staple assembly accommodation part 3101*b*.

The link guide groove 3101*c* configured to guide the movement of the staple link assembly 3170 may be formed in a side surface of the first jaw 3101 at the distal end 3101*f* side in a region in which the staple assembly accommodation part 3101*b* is formed. The link guide groove 3101*c* may be formed in the shape of a groove formed along a moving path of the staple link assembly 3170. In addition, as a first protrusion 3171*a* and a second protrusion 3171*b* of the link member 3171, which are formed in a protruding shape, are moved along the link guide groove 3101*c* in a state in which the first protrusion 3171*a* and the second protrusion 3171*b* are fitted into the groove-shaped link guide groove 3101*c*, the staple link assembly 3170 is moved with respect to the first jaw 3101 (and the cartridge 500 therein). That is, the staple link assembly 3170 may be moved along the link guide groove 3101*c* of the first jaw 3101.

The pin guide groove 3101*d* configured to guide the movement of the guide pin 3162 may be formed at one side of the staple assembly accommodation part 3101*b*, for example, at the proximal end 3101*g* side in the first jaw 3101. The pin guide groove 3101*d* may be formed in the shape of a groove formed along a moving path of the guide pin 3162. In addition, as the guide pin 3162 is moved along the pin guide groove 3101*d* in a state in which the protruding-shaped guide pin 3162 is fitted into the groove-shaped pin guide groove 3101*d*, the second jaw 3102 is rotated around the rotation shaft 3142 with respect to the first jaw 3101 to perform an actuation motion.

The second jaw 3102 includes an anvil 3102*a*, a pin guide groove 3102*b*, and a shaft pass-through part 3102*c*.

The second jaw 3102 is formed in the shape of an elongated bar as a whole, the anvil 3102*a* is formed at a distal end 3102*f* side, and the rotation shaft 3142 is inserted through a proximal end 3102*g*, so that the second jaw 3102 is formed to be rotatable around the rotation shaft 3142.

In detail, the anvil 3102*a* is formed in the form of a flat plane, on one surface of which shapes corresponding to the shapes of staples 530 to be described later may be formed. The above-described anvil 3102*a* may serve as a support for supporting the staple 530 at the opposite side of an operation member 540 when the operation member 540 pushes and raises the staple 530 during a stapling motion, so that the staple 530 is bent.

Meanwhile, a pin guide groove 3102*b* configured to guide the movement of the guide pin 3162 may be formed at the proximal end side of the second jaw 3102. The pin guide groove 3102*b* may be formed in the shape of a groove formed along the moving path of the guide pin 3162. In addition, as the guide pin 3162 is moved along the pin guide groove 3102*b* in a state in which the protruding-shaped guide pin 3162 is fitted into the groove-shaped pin guide groove 3102*b*, the second jaw 3102 is rotated around the rotation shaft 3142 with respect to the first jaw 3101 to perform an actuation motion.

Meanwhile, the shaft pass-through part 3102*e* may be formed in the form of a hole, and the rotation shaft 3142, which is a jaw rotation shaft, may be inserted through the shaft pass-through part 3102*c*.

Hereinafter, the Actuation Wire 3311 and the Guide Tube 3160 of Present Disclosure Will be Described in More Detail.

The guide tube 3160 according to the present disclosure is formed to surround the actuation wire 3311 in a predetermined section, and in this case, the actuation wire 3311 is movable in the guide tube 3160. In other words, in a state in which the actuation wire 3311 is inserted into the guide tube 3160, the actuation wire 3311 may be moved relative to the guide tube 3160.

Here, the guide tube 3160 serves to guide the path of the actuation wire 3311 by preventing the actuation wire 3311 from being bent in an unintended direction when the actuation wire 3311 is pushed or pulled. An actuation motion may be smoothly performed by the guide tube 3160.

Meanwhile, the guide pin 3162 may be coupled to one end portion of the actuation wire 3311, and a fixing member 3163 may be further coupled to the end portion of the actuation wire 3311 to prevent the guide pin 3162 from being separated from the actuation wire 3311.

Meanwhile, the guide tube 3160 according to the present disclosure may be formed of a flexible material so as to be bent. Accordingly, when the end tool 3100 performs a pitch motion around the third rotation shaft 3143, the guide tube 3160 may be bent while being deformed in shape in response thereto. In addition, when the guide tube 3160 is bent, the actuation wire 3311 therein is also bent.

Here, a space is required in which the guide tube 3160 is moved as the end tool 3100 is pitch-rotated. To this end, the pitch slit 3101*s* is formed in the first jaw 3101 to form the space in which the guide tube 3160 can move.

Meanwhile, as described above, the actuation wire 3311 is inserted through the guide tube 3160, and the actuation wire 3311 is movable in the guide tube 3160 relative to the guide tube 3160. That is, in a state in which the guide tube 3160 is fixed, when the actuation wire 3311 is pulled, the guide pin 3162 connected to the actuation wire 3311 is moved toward the proximal end 3105, and when the actuation wire 3311 is pushed, the guide pin 3162 connected to the actuation wire 3311 is moved toward the distal end 3104.

This will be described below in more detail.

In order to securely perform an actuation motion using the guide pin 3162, it is most obvious that the guide pin 3162 is pushed and pulled by the actuation wire 3311. In addition, in order for the actuation wire 3311 to push and pull the guide pin 3162, the guide tube 3160 capable of guiding the path of the actuation wire 3311 should be provided. When the guide tube 3160 does not guide the path of the actuation wire 3311 (i.e., does not hold the actuation wire 3311), the actuation motion may not be performed even when the actuation wire 3311 is pushed, and a phenomenon in which a middle portion of the actuation wire 3311 is bent may occur. Accordingly, in order to securely perform the actuation motion using the guide pin 3162, the actuation wire 3311 and the guide tube 3160 are necessarily included.

However, when the actuation motion is driven by using the actuation wire 3311, the actuation wire 3311 should be pushed, and thus, a relatively stiff (i.e., non-bendable) wire should be used as the actuation wire 3311 so that the actuation wire 3311 can receive a force when the actuation wire 3311 is pushed. However, the stiff (i.e., non-bendable) wire may have a small bending range and may be permanently deformed when a force equal to or greater than a certain extent is applied.

From another perspective, in the case of a stiff (i.e., non-bendable) wire, there is a minimum radius of curvature that may be bent and spread without permanent deformation. In other words, when the wire or the guide tube is bent below a specific radius of curvature, both the wire and the guide tube may be permanently deformed while being bent, and thus it becomes impossible to perform cutting while moving backward and forward. Accordingly, the actuation wire 3311 needs to be bent while having a gentle curvature.

Accordingly, in order to prevent the actuation wire 3311 from being rapidly bent while passing through the pulleys, a space in which the actuation wire 3311 may be gently bent is required between the jaw 103 and the pitch hub 3107.

To this end, in the present disclosure, a space in which the actuation wire 3311 and the guide tube 3160 may be gently bent is formed by separating the rotation shaft 3142 from the rotation shaft 3143 by a certain extent.

In addition, since the actuation wire 3311 and the guide tube 3160 need to be connected to the guide pin 3162 through the first jaw 3101, and there is a need for a space in which the actuation wire 3311 and the guide tube 3160 may be bent in the first jaw 3101, 1) a space, through which the actuation wire 3311 and/or the guide tube 3160 pass and which is bendable, i.e., the pitch slit 3101s, should be formed in the first jaw 3101, and 2) each rotation shaft should be formed by being divided into two parts.

From another perspective, when one end portion of the guide tube 3160 is fixed in the connection part 400, and the other end portion thereof is moved while performing a pitch motion, the guide tube 3160 is bent in a direction that achieves the most gentle curvature (hereinafter, referred to as a "maximum gentle curvature") according to a change in a distance between the both end portions. As such, by achieving the natural maximum gentle curvature, the motion of the actuation wire 3311 is smooth and the permanent deformation does not occur.

Accordingly, in order to secure the maximum gentle curvature, the pitch slit 3161s may be formed on the path of the guide tube 3160. Accordingly, the guide tube 3160 has a shape that is as close as possible to the maximum gentle curvature (although not the maximum gentle curvature).

The coupling relationship between the components described above is as follows.

The rotation shaft 3141, which is an end tool staple pulley rotation shaft, is sequentially inserted through the first jaw 3101, a shaft pass-through part 3181c of the first staple pulley 3181, a first slot 3171d and a second slot 3171e of the link member 3171, a shaft pass-through part 3191c of the second staple pulley 3191, and the first jaw 3101.

The rotation shaft 3142, which is a jaw rotation shaft, is sequentially inserted through the first jaw 3101, the first staple auxiliary pulley 3182, the shaft pass-through part 3102e of the second jaw 3102, the second staple auxiliary pulley 3192, and the first jaw 3101.

Here, the second jaw 3102 is rotated around the rotation shaft 3142, which is a jaw rotation shaft, with respect to the first jaw 3101. In detail, the guide pin 3162 is inserted through the pin guide groove 3101d of the first jaw 3101 and the pin guide groove 3102b of the second jaw 3102. The guide pin 3162 is linearly moved along the pin guide groove 3101d of the first jaw 3101 to push the pin guide groove 3102b of the second jaw 3102, which causes the second jaw 3102 to be rotated around the rotation shaft 3142, which is a jaw rotation shaft, with respect to the first jaw 3101, thereby performing opening and closing motions of the jaw, that is, an actuation motion.

In detail, in the state as shown in FIG. 123, when an actuation wire 3161 is pulled in the direction of an arrow A of FIG. 124, the guide pin 3162 coupled to the actuation wire 3161 is also moved in the direction of the arrow A. Then, the guide pin 3162 pushes (or pulls) the pin guide groove 3102b of the second jaw 3102 while being linearly moved along the pin guide groove 3101d of the first jaw 3101, which causes the second jaw 3102 to be rotated in the direction of an arrow B of FIG. 124 around the rotation shaft 3142, which is jaw rotation shaft, with respect to the first jaw 3101, so that the jaws are closed.

In contrast, when the actuation wire 3161 is pushed in the opposite direction of the arrow A of FIG. 124, the guide pin 3162 coupled to the actuation wire 3161 is also moved in the opposite direction of the arrow A. Then, the guide pin 3162 pushes the pin guide groove 3102b of the second jaw 3102 while being linearly moved along the pin guide groove 3101d of the first jaw 3101, which causes the second jaw 3102 to be rotated in the opposite direction of the arrow B of FIG. 124 around the rotation shaft 3142, which is jaw rotation shaft, with respect to the first jaw 3101, so that the jaws are opened.

(Pitch Motion)

Hereinafter, a pitch motion of the present disclosure will be described in more detail. FIGS. 120 and 121 are plan views illustrating the end tool of the surgical instrument of FIG. 114.

Figure 169:
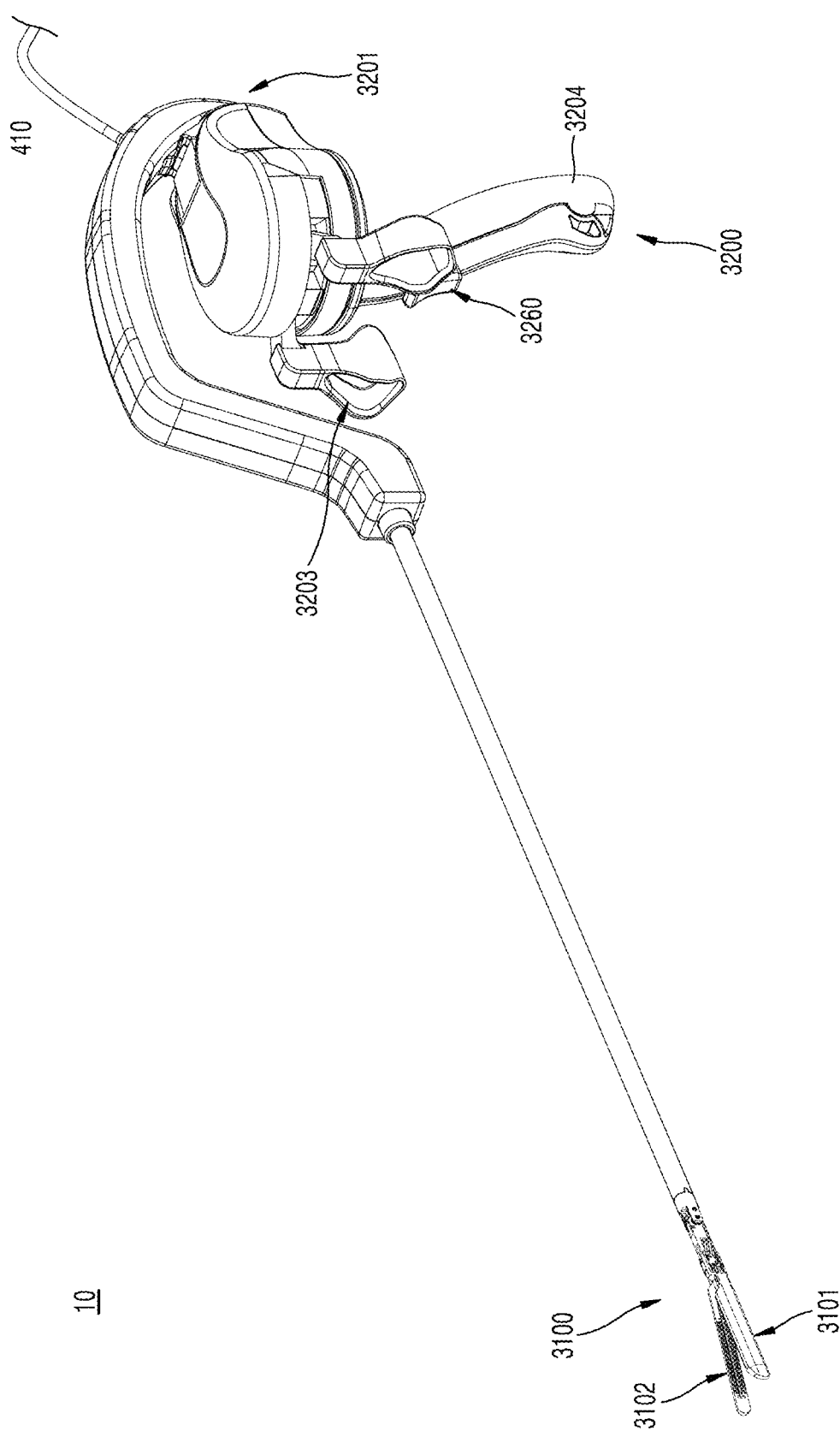
FIGS. 169 and 170 are perspective views illustrating an actuation motion of the surgical instrument of FIG. 114, and are views illustrating a process in which the jaws perform an actuation motion in a neutral state.

Referring to FIGS. 120 and 121 and the like, when the wire 3307 is pulled toward an arrow 3307 of FIG. 120, and simultaneously, the wire 3308 is pulled toward an arrow 3308 of FIG. 120 (i.e., when both strands of the first staple wire are pulled), as shown in FIG. 169, since the wires 3307 and 3308 wound around upper portions of the pulleys 3183 and 3184 rotatable around the rotation shaft 3143, which is an end tool pitch rotation shaft, the first staple pulley 3181 to which the wires 3307 and 3308 are fixedly coupled and the first jaw 3101 to which first staple pulley 3181 is coupled are rotated as a whole in the clockwise direction around the rotation shaft 3143, so that the end tool 3100 performs a pitch motion while rotating upward. In this case, since the second staple pulley 3191 and the wires 3309 and 3310 fixedly coupled thereto are wound around lower portions of the pulleys 3193 and 3194 rotatable around the rotation shaft 3143, the wire 3309 and the wire 3310 are unwound in the opposite directions of arrows 3309 and 3310, respectively.

Figure 171:
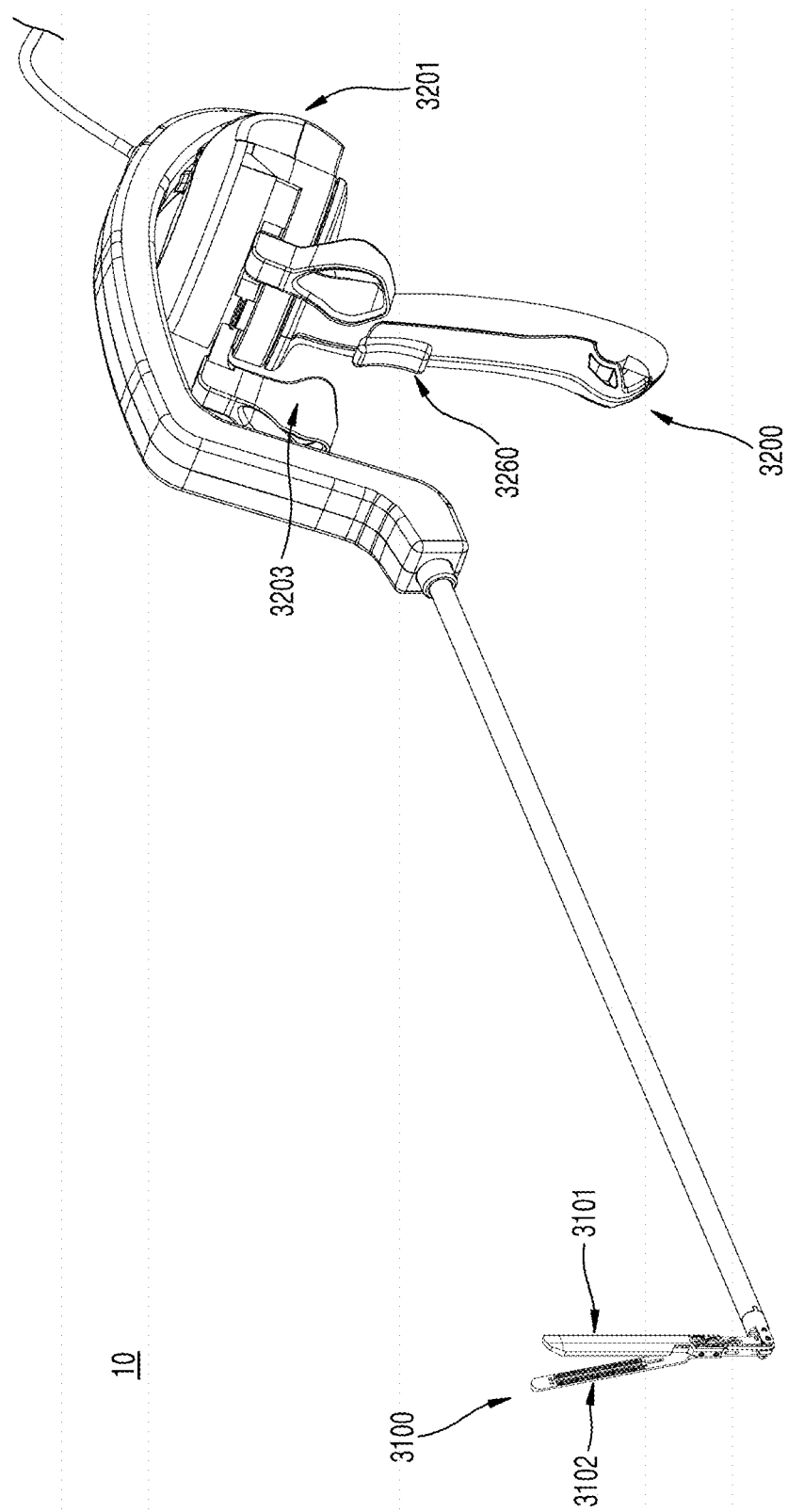
FIGS. 171 and 172 are perspective views illustrating an actuation motion of the surgical instrument of FIG. 114, and are views illustrating a process of performing an actuation motion in a state in which the jaws are pitch-rotated by −90°.

In contrast, when the wire 3309 is pulled toward the arrow 3309 of FIG. 120 and the wire 3310 is pulled toward the arrow 3310 of FIG. 120, as shown in FIG. 171, since the wires 3309 and 3310 are wound around lower portions of the pulleys 3193 and 3194 rotatable around the rotation shaft 3143, which is an end tool pitch rotation shaft, the second staple pulley 3191 to which the wires 3309 and 3310 are fixedly coupled and the first jaw 3101 to which second staple pulley 3191 is coupled are rotated as a whole in the counterclockwise direction around the rotation shaft 3143, so that the end tool 3100 performs a pitch motion while rotating downward. In this case, since the first staple pulley 3181 and the wire 3307 and the wire 3308 fixedly coupled thereto are wound around upper portions of the pulleys 3183 and 3184 rotatable around the rotation shaft 3143, the wire 3307 and the wire 3308 are moved in the opposite directions of arrows 3307 and 3318, respectively.

Meanwhile, the end tool 3100 of the surgical instrument 3000 of the present disclosure may further include the first pitch pulley part 3101p and the second pitch pulley part 3101q, which are end tool pitch pulleys, the manipulation part 3200 may further include a manipulation part pitch pulley (not shown), and the power transmission part 3300 may further include the wire 3303 and the wire 3304, which are pitch wires. In detail, the first and second pitch pulley parts 3101p and 3101q of the end tool 3100 may be rotatable around the rotation shaft 3143 that is an end tool pitch rotation shaft, and may be integrally formed with the first jaw 3101 (or formed to be fixedly coupled to the first jaw 3101). In addition, the wire 3303 and the wire 3304 may serve to connect the first and second pitch pulley parts 3101p and 3101q of the end tool 3100 to the manipulation part pitch pulley (not shown) of the manipulation part 3200.

Accordingly, when the manipulation part pitch pulley (not shown) of the manipulation part 3200 is rotated, the rotation of the manipulation part pitch pulley (not shown) is transmitted to the first and second pitch pulley parts 3101p and 3101q of the end tool 3100 through the wires 3303 and 3304, so that the first jaw 3101 integrally formed with the first and second pitch pulley parts 3101p and 3101q and the second jaw 3102 coupled to the first jaw 3101 are rotated together, and as a result, the end tool 3100 performs a pitch motion while rotating.

That is, as the surgical instrument 3000 according to the second embodiment of the present disclosure includes the first and second pitch pulley parts 3101p and 3101q of the end tool 3100, the manipulation part pitch pulley (not shown) of the manipulation part 3200, and the wires 3303 and 3304 of the power transmission part 3300 in order to transmit a driving force for a pitch motion, the driving force for the pitch motion of the manipulation part 3200 is more completely transmitted to the end tool 3100, thereby improving operation reliability.

(Components Related to Staple Pulley)

Hereinafter, the first and second staple pulleys 3181 and 3191 of the staple pulley assembly 3180 of the end tool 3100 of the surgical instrument 3000 of FIG. 114 will be described in more detail.

FIGS. 127 and 128 are exploded perspective views illustrating the staple pulley and the staple link of the surgical instrument of FIG. 114. FIG. 129 is a front view illustrating the staple pulley and the staple link of the surgical instrument of FIG. 114. FIGS. 130A to 131C are side views illustrating operating states of the staple pulley in the end tool of the surgical instrument of FIG. 114. FIGS. 132 and 133 are perspective views illustrating operating states of the staple pulley in the end tool of the surgical instrument of FIG. 114.

Referring to FIGS. 114 to 133 and the like, the end tool 3100 of the second embodiment of the present disclosure may include the first staple pulley 3181, the first staple auxiliary pulley 3182, the pulley 3183, the pulley 3184, the pulley 3185, and the pulley 3186 that are related to a linear motion/rotational motion of respective pulleys and links for stapling and cutting.

In addition, the end tool 3100 of the second embodiment of the present disclosure may include the second staple pulley 3191, the second staple auxiliary pulley 3192, the pulley 3193, the pulley 3194, the pulley 3195, and the pulley 3196 that are related to a linear motion/rotational motion of respective pulleys and links for stapling and cutting.

The first staple pulley 3181 and the second staple pulley 3191 are formed to be rotatable independently of each other around the rotation shaft 3141, which is an end tool staple pulley rotation shaft.

Here, in the present disclosure, the first staple pulley 3181 and the second staple pulley 3191 are formed to rotate around substantially the same shaft. As such, by forming the first staple pulley 3181 and the second staple pulley 3191 to rotate around the same shaft, it is possible to perform a pitch motion/actuation motion while also performing stapling and cutting motions. This will be described in more detail later. However, here, although the first staple pulley 3181 and the second staple pulley 3191 are illustrated in the drawings as being formed to rotate around one rotation shaft 3141, it is of course possible that each pulley may be formed to be rotatable around a separate shaft that is concentric therewith.

The first staple auxiliary pulley 3182 may be further provided on one side of the first staple pulley 3181, in other words, the first staple auxiliary pulley 3182 may be disposed between the first staple pulley 3181 and the pulley 3183/pulley 3184. The first staple auxiliary pulley 3182 may be formed to be rotatable independently of the pulley 3112 and the pulley 3122 around the rotation shaft 3142.

Meanwhile, the pulleys 3183 and 3184 may function as first pitch main pulleys, and the pulleys 3185 and 3186 may function as second pitch sub-pulleys.

The second staple auxiliary pulley 3192 may be further provided on one side of the second staple pulley 3191, in other words, the second staple auxiliary pulley 3192 may be disposed between the second staple pulley 3191 and the pulley 3193/pulley 3194. The second staple auxiliary pulley 3192 may be formed to be rotatable independently of the pulley 3112 and the pulley 3122 around the rotation shaft 3142.

Here, the first staple auxiliary pulley 3182 and the second staple auxiliary pulley 3192 are illustrated in the drawings as being formed to rotate around one rotation shaft 3142, but it is of course possible that each of the first staple auxiliary pulley 3182 and the second staple auxiliary pulley 3192 may be formed to be rotatable around a separate shaft that is concentric therewith. Such staple auxiliary pulleys will be described in more detail below.

Meanwhile, the pulley 3193 and the pulley 3194 may function as second pitch main pulleys, and the pulley 3195 and the pulley 3196 may function as second pitch sub-pulleys. Hereinafter, the first staple auxiliary pulley 3182 will be described in more detail.

The first staple auxiliary pulley 3182 may serve to increase a rotation angle of the first staple pulley 3181 by coming into contact with the wire 3308, which is a first staple wire, to change an arrangement path of the wire 3308 to a certain extent.

That is, when the staple auxiliary pulley is not disposed, the staple pulley may be rotated only up to a right angle, but in an embodiment of the present disclosure, by additionally providing the first staple auxiliary pulley 3182, which is an auxiliary pulley, the maximum rotation angle may be increased by 0. This allows the first staple pulley 3181 to rotate for stapling and cutting motions while two jaws of the end tool 3100 are yaw-rotated together by 90°, thus enabling a linear motion of the operation member 540 to be described later. In other words, a feature of increasing the range of yaw rotation in which stapling and cutting motions are possible may be obtained through the first staple auxiliary pulley 3182.

This will be described below in more detail.

In the case of the surgical instrument 3000 of the present disclosure, the first staple auxiliary pulley 3182 is further disposed on one side of the first staple pulley 3181. By changing the arrangement path of the wire 3308, which is a first staple wire, to a certain extent by disposing the first staple auxiliary pulley 3182 as described above, a tangential direction of the wire 3308 is changed, and thus the rotation angle of the coupling member 3323 that are couple the wire 3308 to the first staple pulley 3181 is increased. That is, the coupling member 33293, which is a coupling part of the wire 3308 and the first staple pulley 3181, is rotatable until the coupling member 33293 is located on the common internal tangent of the first staple auxiliary pulley 3182 and the staple auxiliary pulley 3122.

In other words, the wire 3308 is located on the internal tangent of the first staple pulley 3181 and the first staple auxiliary pulley 3182, and the rotation angle of the first staple pulley 3181 is increased by the first staple auxiliary pulley 3182.

According to the present disclosure, as a rotation radius of the first staple pulley 3181 increases, a yaw motion range in which normal stapling and cutting motions are performed may be increased Hereinafter, components related to the rotation of the first staple pulley 3181 will be described.

The pulleys 3183 and 3184 function as the first pitch main pulleys. Here, the wire 3307, which is a first staple wire, is wound around the pulley 3183, and the wire 3308, which is a first staple wire, is wound around the pulley 3184.

The pulleys 3185 and 3186 function as first pitch sub-pulleys. Here, the wire 3307, which is a first staple wire, is wound around the pulley 3185, and the wire 3308, which is a first staple wire, is wound around the pulley 3186.

Here, the pulley 3183 and the pulley 3184 are disposed to face each other on one side of the first staple pulley 3181 and the first staple auxiliary pulley 3182. Here, the pulley 3183 and the pulley 3184 are formed to be rotatable independently of each other around the rotation shaft 3143 that is an end tool pitch rotation shaft. In addition, the pulley 3185 and the pulley 3186 are disposed on one side of the pulley 3183 and one side of the pulley 3184, respectively, to face each other. Here, the pulley 3185 and the pulley 3186 are formed to be rotatable independently of each other around the rotation shaft 3144 that is an end tool pitch auxiliary rotation shaft. Here, in the drawings, it is illustrated that the pulley 3183, the pulley 3185, the pulley 3184, and the pulley 3186 are all formed to be rotatable around the Y-axis direction, but the concept of the present disclosure is not limited thereto, and the rotation shafts of the respective pulleys may be formed in various directions according to configurations thereof.

As described above, the rotation shaft 3141, the rotation shaft 3142, the rotation shaft 3143, and the rotation shaft 3144 may be disposed sequentially from the distal end 3104 of the end tool 3100 toward the proximal end 3105. Accordingly, the first staple pulley 3181, the first staple auxiliary pulley 3182, the pulley 3183/pulley 3184, and the pulley 3185/pulley 3186 may be disposed sequentially from the distal end 3104 of the end tool 3100 toward the proximal end 3105.

The wire 3307, which is a first staple wire, is sequentially wound to make contact with at least portions of the pulley 3185, the pulley 3183, and the first staple pulley 3181. In addition, the wire 3308 connected to the wire 3307 by the coupling member 3323 is sequentially wound to make contact with at least portions of the first staple pulley 3181, the first staple auxiliary pulley 3182, the pulley 3184, and the pulley 3186.

From another perspective, the wires 3307 and 3308, which are first staple wires, are sequentially wound to make contact with at least portions of the pulley 3185, the pulley 3183, the first staple pulley 3181, the first staple auxiliary pulley 3182, the pulley 3184, and the pulley 3186, and are formed to move along the above pulleys while rotating the above pulleys.

Accordingly, when the wire 3307 is pulled, the coupling member 3323, to which the wire 3307 is coupled, and the first staple pulley 3181 coupled to the coupling member 3323 are rotated in one direction. In contrast, when the wire 3308 is pulled, the coupling member 3323, to which the wire 3308 is coupled, and the first staple pulley 3181 coupled to the coupling member 3323 are rotated in a direction opposite to the one direction.

Meanwhile, the second staple pulley 3191, the second staple auxiliary pulley 3192, and the components related thereto, such as the pulley 3193, the pulley 3194, the pulley 3195, the pulley 3196, the wire 3309, the wire 3310, and the like, may have the same or similar configurations as the components related to the first staple pulley 3181 described above.

In detail, the pulleys 3193 and 3194 function as second pitch main pulleys. Here, the wire 3310, which is a second staple wire, is wound around the pulley 3193, and the wire 3309, which is a second staple wire, is wound around the pulley 3194.

The pulleys 3195 and 3196 function as second pitch sub-pulleys. Here, the wire 3310, which is a second staple wire, is wound around the pulley 3195, and the wire 3309, which is a second staple wire, is wound around the pulley 3196.

Here, the pulley 3193 and the pulley 3194 are disposed on one side of the second staple pulley 3191 and the second staple auxiliary pulley 3192 to face each other. Here, the pulley 3193 and the pulley 3194 are formed to be rotatable independently of each other around the rotation shaft 3143 that is an end tool pitch rotation shaft. In addition, the pulley 3195 and the pulley 3196 are disposed on one side of the pulley 3193 and one side of the pulley 3194, respectively, to face each other. Here, the pulley 3195 and the pulley 3196 are formed to be rotatable independently of each other around the rotation shaft 3144 that is an end tool pitch auxiliary rotation shaft. Here, in the drawings, it is illustrated that the pulley 3193, the pulley 3195, the pulley 3194, and the pulley 3196 are all formed to be rotatable around the Y-axis direction, but the concept of the present disclosure is not limited thereto, and the rotation shafts of the respective pulleys may be formed in various directions according to configurations thereof.

As described above, the rotation shaft 3141, the rotation shaft 3142, the rotation shaft 3143, and the rotation shaft 3144 may be disposed sequentially from the distal end 3104 of the end tool 3100 toward the proximal end 3105. Accordingly, the second staple pulley 3191, the second staple auxiliary pulley 3192, the pulley 3193/pulley 3194, and the pulley 3195/pulley 3196 may be disposed sequentially from the distal end 3104 of the end tool 3100 toward the proximal end 3105.

The wire 3309, which is a second staple wire, is sequentially wound to make contact with at least portions of the pulley 3195, the pulley 3193, and the second staple pulley 3191. In addition, the wire 3310 connected to the wire 3309 by the coupling member 3324 is sequentially wound to make contact with at least portions of the second staple pulley 3191, the second staple auxiliary pulley 3192, the pulley 3194, and the pulley 3196.

From another perspective, the wires 3309 and 3310, which are second staple wires, are sequentially wound to make contact with at least portions of the pulley 3195, the pulley 3193, the second staple pulley 3191, the second staple auxiliary pulley 3192, the pulley 3194, and the pulley 3196, and are formed to move along the above pulleys while rotating the above pulleys.

Accordingly, when the wire 3309 is pulled, the coupling member 3324, to which the wire 3309 is coupled, and the second staple pulley 3191 coupled to the coupling member 3324 are rotated in one direction. In contrast, when the wire 3310 is pulled, the coupling member 3324 to which the wire 3310 is coupled and the second staple pulley 3191 coupled to the coupling member 3324 are rotated in a direction opposite to the one direction.

(Staple Drive Assembly)

Hereinafter, the staple drive assembly 3150 will be described in more detail.

Continuing to refer to FIGS. 127 to 133 and the like, the staple drive assembly 3150 may include the staple pulley assembly 3180 and the staple link assembly 3170. Here, the staple drive assembly 3150 is connected to a reciprocating assembly 550 of the cartridge 500, which will be described later, and converts a rotational motion of the staple pulley assembly 3180 into a linear motion of the reciprocating assembly 550. In other embodiments of the present disclosure, which will be described later, the staple drive assembly may be understood as a concept including the staple pulley assembly and the staple link assembly.

The staple pulley assembly 3180 may include one or more staple pulleys. The staple pulley assembly 3180 may be formed in the staple assembly accommodation part 3101*b* of the first jaw 3101. In the present embodiment, it is assumed that the staple pulley assembly 3180 includes two staple pulleys that are the first staple pulley 3181 and the second staple pulley 3191.

The staple link assembly 3170 may include one or more link members 3171. In addition, the link member 3171 may include one or more links. In the second embodiment of the present disclosure, it is assumed that the staple link assembly 3170 includes one link member 3171, and the link member 3171 includes one link.

In the end tool 3100 of the surgical instrument according to the present disclosure, the staple pulley assembly 3180 and the staple link assembly 3170 form a cam-slot structure. In addition, with such a structure, a force for moving the reciprocating assembly 550 forward may be amplified.

In detail, the staple pulley assembly 3180 may include the first staple pulley 3181 and the second staple pulley 3191.

The first staple pulley 3181 may include a body 3181*a*, a protruding member 3181*b*, and the shaft pass-through part 3181*c*.

The body 3181*a* is formed in the shape of a disk.

The shaft pass-through part 3181*c* may be formed in a center portion of the body 3181*a*. The shaft pass-through part 3181*c* may be formed in the form of a hole, and the rotation shaft 3141, which is an end tool staple pulley rotation shaft, may be inserted through the shaft pass-through part 3181*c*.

In addition, the protruding member 3181*b* may be formed on the body 3181*a* of the first staple pulley 3181. The protruding member 3181*b* may be coupled to the link member 3171 of the staple link assembly 3170. Here, the center of the protruding member 3181*b* may not coincide with the center of the first staple pulley 3181, and the protruding member 3181*b* may be formed to be eccentric to a certain extent with respect to the first staple pulley 3181. The protruding member 3181*b* may be fitted into the first slot 3171*d* of the link member 3171, which will be described later.

The second staple pulley 3191 may include a body 3191*a*, a protruding member 3191*b*, and the shaft pass-through part 3191*c*.

The body 3191*a* is formed in the shape of a disk.

The shaft pass-through part 3191*c* may be formed in a center portion of the body 3191*a*. The shaft pass-through part 3191*c* may be formed in the form of a hole, and the rotation shaft 3141, which is an end tool staple pulley rotation shaft, may be inserted through the shaft pass-through part 3191*c*.

In addition, the protruding member 3191*b* may be formed on the body 3191*a* of the second staple pulley 3191. The protruding member 3191*b* may be coupled to the link member 3171 of the staple link assembly 3170. Here, the center of the protruding member 3191*b* may not coincide with the center of the second staple pulley 3191, and the protruding member 3191*b* may be formed to be eccentric to a certain extent with respect to the second staple pulley 3191. The protruding member 3191*b* may be fitted into the second slot 3171*e* of the link member 3171, which will be described later.

Meanwhile, the end tool 3100 of the present disclosure may further include the staple link assembly 3170 connected to the staple pulley assembly 3180, and the staple link assembly 3170 may include the link member 3171. Here, the staple link assembly 3170 may serve to connect the staple pulley assembly 3180 to the reciprocating assembly 550 of the cartridge 500, which will be described later.

In the present embodiment, the staple link assembly 3170 includes one link member 3171, and the link member 3171 includes only one link. That is, by coupling the staple pulley assembly 3180 and the staple link assembly 3170 by a cam-slot structure, it is possible to convert a rotational motion of the staple pulley assembly 3180 into a linear motion of the staple link assembly 3170, even when the staple link assembly 3170 includes only one link.

In detail, the link member 3171 may be formed as a single link.

The link member 3171 is formed in a shape in which an elongated bar and an elliptical-shaped flat plate are coupled, and may be formed in an approximately "L" shape. Here, the link member 3171 may include the first protrusion 3171a, the second protrusion 3171b, a coupling part 3171c, the first slot 3171d, and the second slot 3171e.

The first protrusion 3171a and the second protrusion 3171b may be formed in one region of a central portion of the link member 3171. The first protrusion 3171a and the second protrusion 3171b may be fitted into the link guide groove 3101c of the first jaw 3101.

As such, as the first protrusion 3171a and the second protrusion 3171b of the link member 3171, which are formed in a protruding shape, are moved along the link guide groove 3101c in a state in which the first protrusion 3171a and the second protrusion 3171b are fitted into the groove-shaped link guide groove 3101c, the link member 3171 is moved with respect to the first jaw 3101 (and the cartridge 500 therein). This will be described in more detail later.

Meanwhile, the coupling part 3171c may be formed at one end portion of the link member 3171. The coupling part 3171c may be coupled to a coupling part 551a of a reciprocating member 551 of the cartridge 500.

Meanwhile, the first slot 3171d and the second slot 3171e may be formed at an end portion of the link member 3171 opposite to the one end portion at which the coupling part 3171c is formed.

In detail, a first slot 3171d may be formed in a surface of the link member 3171 facing the first staple pulley 3181. Here, the first slot 3171d is formed in the form of an eccentric hole, into which the protruding member 3181b of the first staple pulley 3181 may be fitted. The first slot 3171d is formed to have a predetermined curvature, and may be formed in an approximately elliptical shape. At this time, the first slot 3171d may be formed to be larger than the protruding member 3181b by a certain extent. Thus, the protruding member 3181b is formed to be movable in the first slot 3171d by a certain extent in a state in which the protruding member 3181b of the first staple pulley 3181 is fitted into the first slot 3171d of the link member 3171.

As described above, the protruding member 3181b may be formed to be eccentric to a certain extent with respect to the center of the first staple pulley 3181. Thus, when the first staple pulley 3181 is rotated, the protruding member 3181b, while in contact with the first slot 3171d, may push the first slot 3171d to move the link member 3171. That is, when the first staple pulley 3181 is rotated, the protruding member 3181b, while in contact with the first slot 3171d, is moved in the first slot 3171d, which causes the link member 3171 to be linearly moved along the link guide groove 3101c of the first jaw 3101.

Here, the first slot 3171d may be formed not to pass through the entire thickness of the link member 3171 but to pass through only a portion of the entire thickness of the link member 3171. From another perspective, it may be expressed that the first slot 3171d is formed in the form of a kind of a ring. In this case, the first slot 3171d may be formed to have a thickness substantially the same as a thickness of the protruding member 3181b of the first staple pulley 3181.

Meanwhile, the second slot 3171e may be formed in the link member 3171. In detail, the second slot 3171e may be formed in a surface of the link member 3171 facing the second staple pulley 3191. Here, the second slot 3171e is formed in the form of an eccentric hole, into which the protruding member 3191b of the second staple pulley 3191 may be fitted. The second slot 3171e is formed to have a predetermined curvature, and may be formed in an approximately elliptical shape. At this time, the second slot 3171e may be formed to be larger than the protruding member 3191b by a certain extent. Thus, the protruding member 3191b is formed to be movable in the second slot 3171e by a certain extent in a state in which the protruding member 3191b of the second staple pulley 3191 is fitted into the second slot 3171e of the link member 3171.

As described above, the protruding member 3191b may be formed to be eccentric to a certain extent with respect to the center of the second staple pulley 3191. Thus, when the second staple pulley 3191 is rotated, the protruding member 3191b, while in contact with the second slot 3171e, may push the second slot 3171e to move the link member 3171. That is, when the second staple pulley 3191 is rotated, the protruding member 3191b, while in contact with the second slot 3171e, is moved in the second slot 3171e, which causes the link member 3171 to be linearly moved along the link guide groove 3101c of the first jaw 3101.

Here, the second slot 3171e may be formed not to pass through the entire thickness of the link member 3171 but to pass through only a portion of the entire thickness of the link member 3171. From another perspective, it may be expressed that the second slot 3171e is formed in the form of a kind of a ring. In this case, the second slot 3171e may be formed to have a thickness substantially the same as a thickness of the protruding member 3191b of the second staple pulley 3191.

Here, the first slot 3171d and the second slot 3171e may be formed to at least partially overlap.

In addition, the first slot 3171d and the second slot 3171e may be formed to be vertically symmetrical with respect to the rotation shaft 3141. As such, since the first slot 3171d and the second slot 3171e are formed to be vertically symmetrical with respect to the rotation shaft 3141, the protruding member 3181b of the first staple pulley 3181 coupled to the link member 3171 and the protruding member 3191b of the second staple pulley 3191 may be disposed to be symmetrical to each other. This will be described in more detail later.

Meanwhile, the first slot 3171d and the second slot 3171e are formed to be spaced apart from each other by a certain extent, and a jaw accommodation part 3171f may be formed therebetween. In addition, at least a portion of the second jaw 3102 may be disposed in the jaw accommodation part 3171f. In other words, the second jaw 3102 performs an actuation motion while rotating around the rotation shaft 3142, and at this time, the jaw accommodation part 3171f is formed between the first slot 3171d and the second slot 3171e of the link member 3171 to prevent interference between the second jaw 3102 and the link member 3171.

(Displacement and Motion of Staple Link Assembly According to Rotation of Staple Pulley)

Hereinafter, the displacement of the staple link assembly 3170 according to the rotation of the first staple pulley 3181 and the second staple pulley 3191 will be described.

Figures 130A, 130B, 130C:
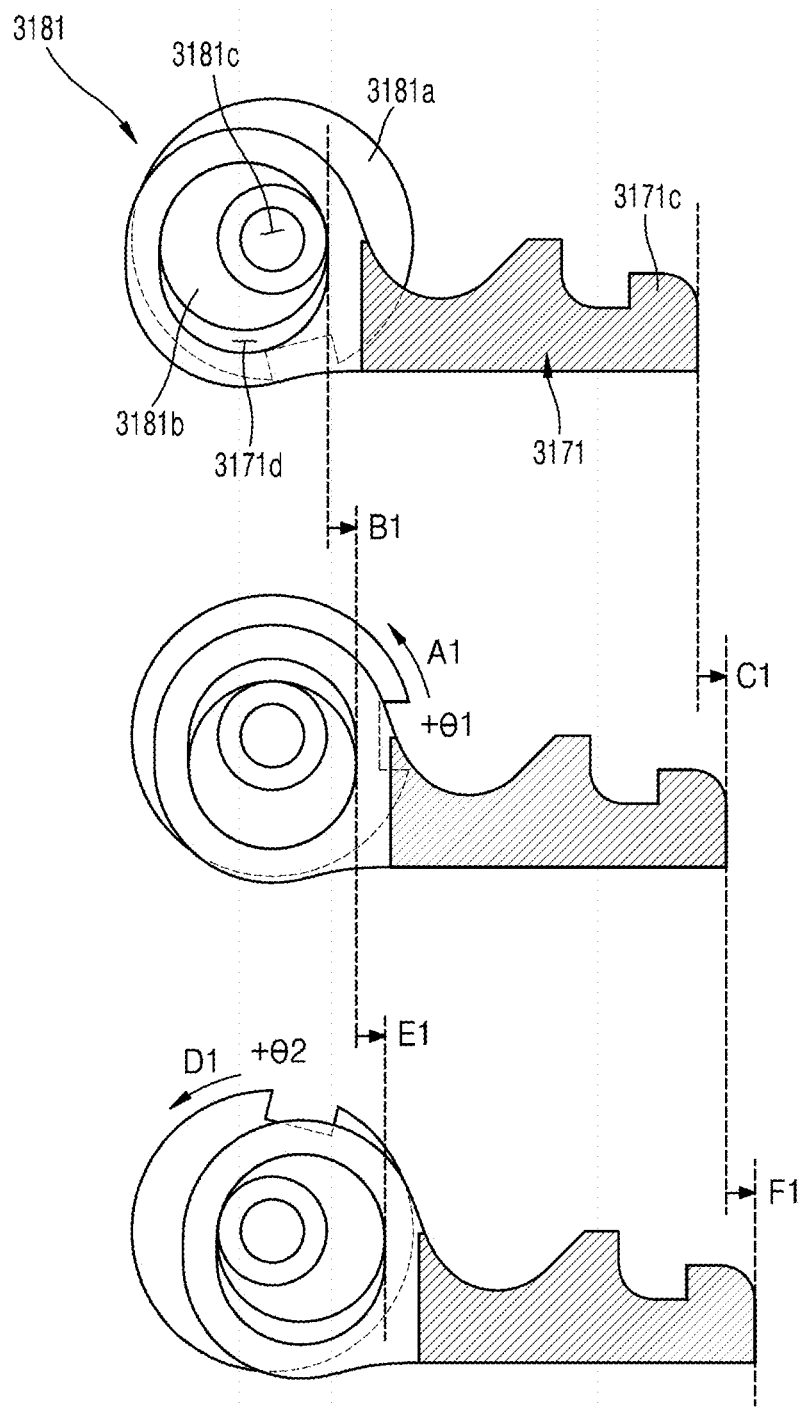

Referring to FIGS. 130A to 130C, in the second embodiment of the present disclosure, the first staple pulley 3181 and the staple link assembly 3170 are coupled in the form of a cam-slot. That is, the cam-shaped protruding member 3181b formed on the first staple pulley 3181 is coupled to the first slot 3171d formed in the link member 3171. Thus, as shown in FIG. 130B, when the first staple pulley 3181 is rotated in the direction of an arrow A1, a displacement of the protruding member 3181b of the first staple pulley 3181 in the X-axis direction becomes B1. In addition, a displacement of the staple link assembly 3170 in the X-axis direction becomes C1. Here, as shown in FIG. 130C, when the first staple pulley 3181 is further rotated in the direction of an arrow D1, the displacement of the protruding member 3181b of the first staple pulley 3181 in the X-axis direction becomes E1. In addition, the displacement of the staple link assembly 3170 in the X-axis direction becomes F1.

Figures 131A, 131B, 131C:
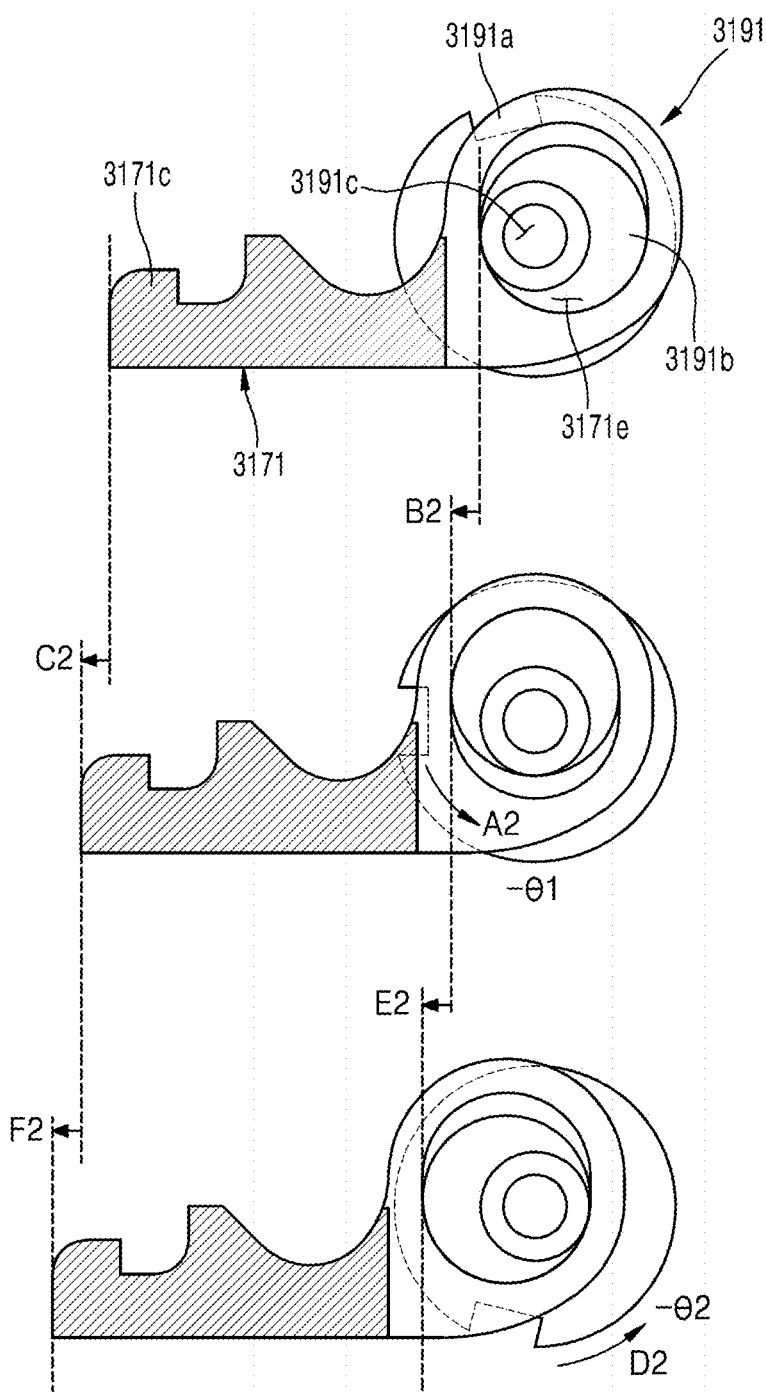

Similarly, referring to FIGS. 131A to 131C, in the second embodiment of the present disclosure, the second staple pulley 3191 and the staple link assembly 3170 are coupled in the form of a cam-slot. That is, the cam-shaped protruding member 3191b formed on the second staple pulley 3191 is coupled to the second slot 3171e formed in the link member 3171. Thus, as shown in FIG. 131B, when the second staple pulley 3191 is rotated in the direction of an arrow A2, a displacement of the protruding member 3191b of the second staple pulley 3191 in the X-axis direction becomes B2. In addition, a displacement of the staple link assembly 3170 in the X-axis direction becomes C2. Here, as shown in FIG. 131C, when the second staple pulley 3191 is further rotated in the direction of an arrow D2, the displacement of the protruding member 3191b of the second staple pulley 3191 in the X-axis direction becomes E2. In addition, the displacement of the staple link assembly 3170 in the X-axis direction becomes F2.

When the staple pulley and the staple link assembly are coupled in a link-shaft manner rather than a cam-slot manner as compared with the above case, the displacement of the staple link assembly in the X-axis direction is much longer than that in the second embodiment of the present disclosure.

In other words, as compared to the case in which the staple pulley and the staple link assembly are axially coupled, when the staple pulley and the staple link assembly are cam-slot coupled as in the present embodiment, the displacement of the staple link assembly in the X-axis direction is reduced even when the staple pulley is rotated by the same amount.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the second embodiment of the present disclosure, each of the first staple pulley 3181 and the second staple pulley 3191 is coupled in the form of a cam-slot to the staple link assembly 3170, and the displacement of the staple link assembly 3170 in the X-axis direction caused by the rotation of the first staple pulley 3181 and the second staple pulley 3191 is relatively reduced as compared to other embodiments, and thus the force received by the staple link assembly 3170 in the X-axis direction is increased relative to a simple link structure.

According to the second embodiment of the present disclosure described above, a force for moving the staple link assembly 3170 and the reciprocating assembly 550 connected thereto forward is amplified, and thus a stapling motion may be performed more robustly.

In particular, in the second embodiment of the present disclosure, since two staple pulleys (i.e., the first staple pulley 3181 and the second staple pulley 3191) that are symmetrical to each other are provided, a force with which the staple pulley assembly 3180 pushes the staple link assembly 3170 may be amplified approximately twice as compared to when only one staple pulley is provided.

In addition, the first staple pulley 3181 and the second staple pulley 3191 are symmetrically disposed in a left and right direction with respect to the XZ plane, and thus balanced in the left and right direction in performing a stapling motion, so that the end tool 3100 stably performs motions with respect to the rotation shaft 3141, which is a yaw rotation shaft, without moving in the left and right direction as a whole. In addition, by making winding directions of the wire 3307/wire 3308, which are first staple wires, and the second staple wire 3309/wire 3310 around the rotation shaft 3143, which is a pitch rotation shaft, to be opposite to each other, movements with respect to the rotation shaft 3143 may also be mutually canceled.

Hereinafter, rotation directions of the first staple pulley 3181 and the second staple pulley 3191 will be described.

Referring to FIGS. 130A to 133 and the like, the first staple pulley 3181 moves the staple link assembly 3170 forward when rotated in the direction of an arrow A1 (i.e., in the clockwise direction) of FIG. 133, and the second staple pulley 3191 moves the staple link assembly 3170 forward when rotated in the direction of an arrow A2 (i.e., in the counterclockwise direction) of FIG. 133.

In contrast, the first staple pulley 3181 moves the staple link assembly 3170 backward when rotated in the counterclockwise direction, and the second staple pulley 3191 moves the staple link assembly 3170 backward when rotated in the clockwise direction.

That is, when the first staple pulley 3181 and the second staple pulley 3191 are rotated in opposite directions, the staple link assembly 3170 is moved (forward or backward). In contrast, when the first staple pulley 3181 and the second staple pulley 3191 are rotated in the same direction, the rotations of the two pulleys are canceled out and thus the staple link assembly 3170 is not moved.

As a result, in the state as shown in FIG. 132, when the first staple pulley 3181 is rotated in the clockwise direction while the second staple pulley 3191 is rotated in the counterclockwise direction, the link member 3171 connected to the first staple pulley 3181 and the second staple pulley 3191 may be moved as a whole toward the distal end (see 3104 of FIG. 116) of the first jaw 3101.

In contrast, when the first staple pulley 3181 is rotated in the counterclockwise direction while the second staple pulley 3191 is rotated in the clockwise direction, the link member 3171 connected to the first staple pulley 3181 and the second staple pulley 3191 may be moved as a whole toward the proximal end (see 3105 of FIG. 116) of the first jaw 3101.

Thus, a bidirectional rotational motion of the staple pulley assembly 3180 causes a reciprocating linear motion of the reciprocating assembly 550 of the cartridge 500 through the staple link assembly 3170. This will be described in more detail later.

(Cartridge)

Hereinafter, the cartridge 500 of the surgical instrument 3000 of FIG. 114 will be described in more detail.

Figure 134:
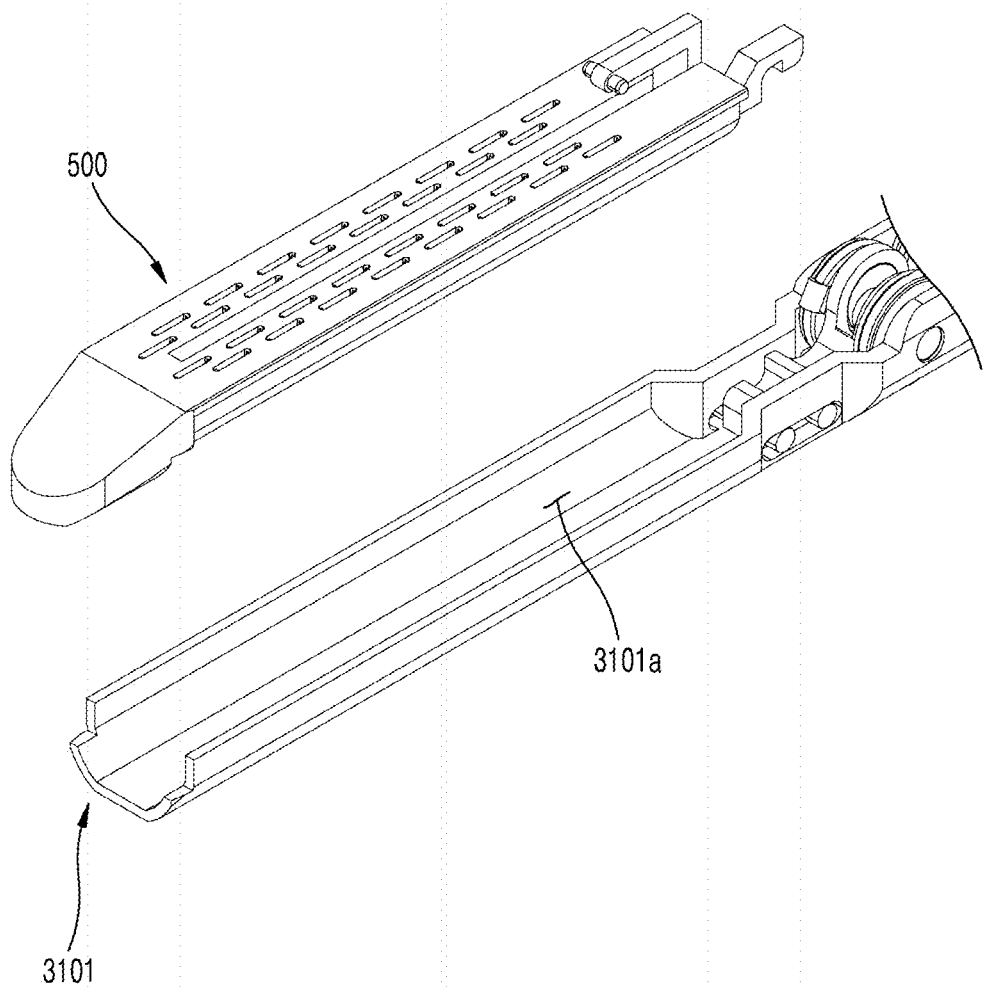
FIG. 134 is a perspective view illustrating the first jaw and a cartridge of the surgical instrument of FIG. 114.
Figure 135:
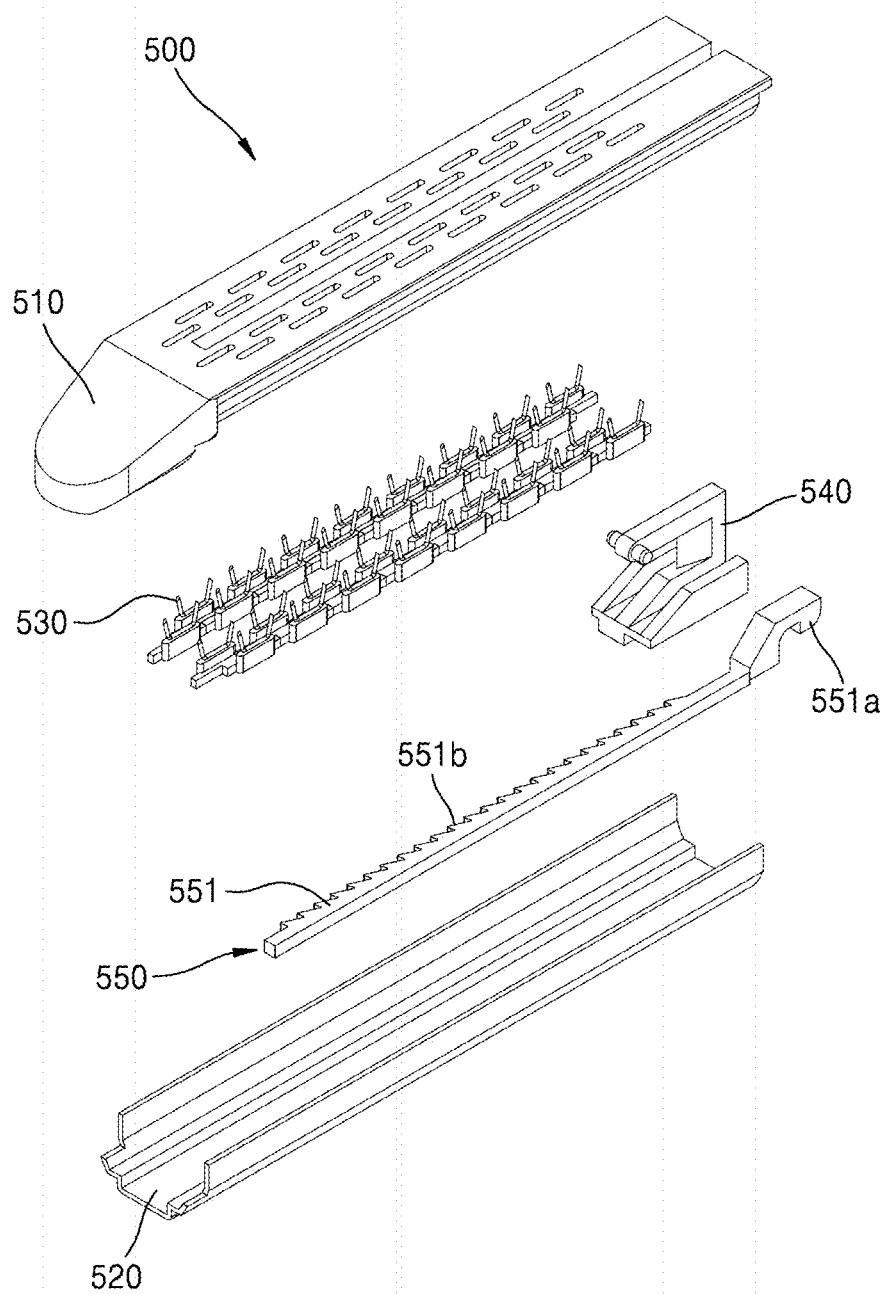
FIG. 135 is an exploded perspective view illustrating the cartridge of FIG. 134.
Figure 136:
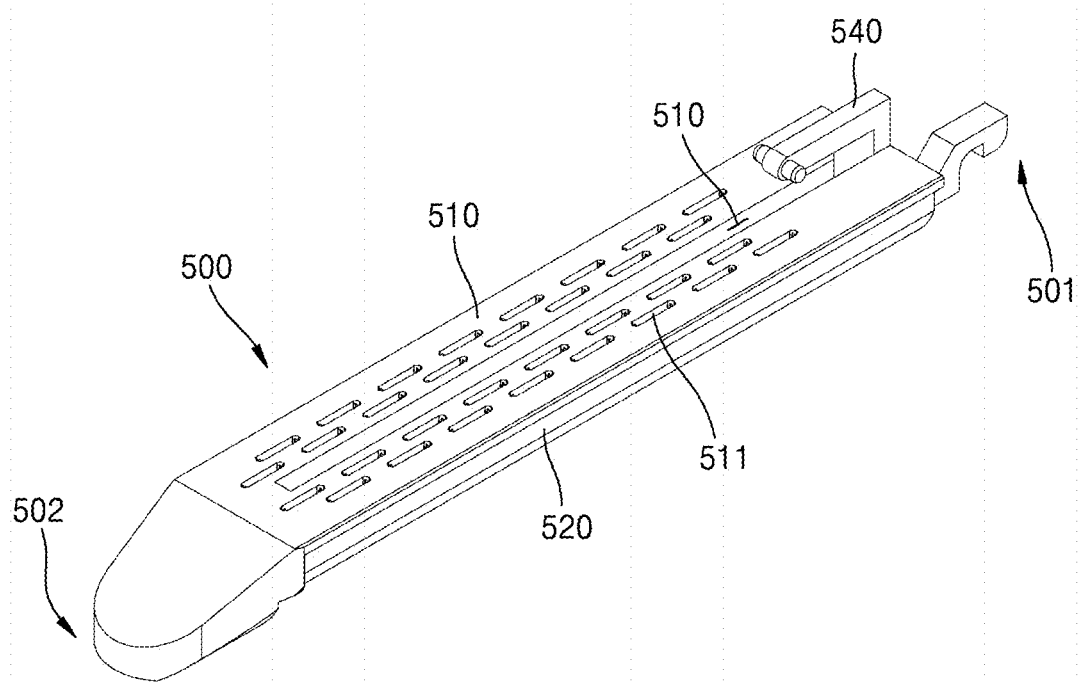
FIG. 136 is an assembled perspective view illustrating the cartridge of FIG. 134.
Figure 137:
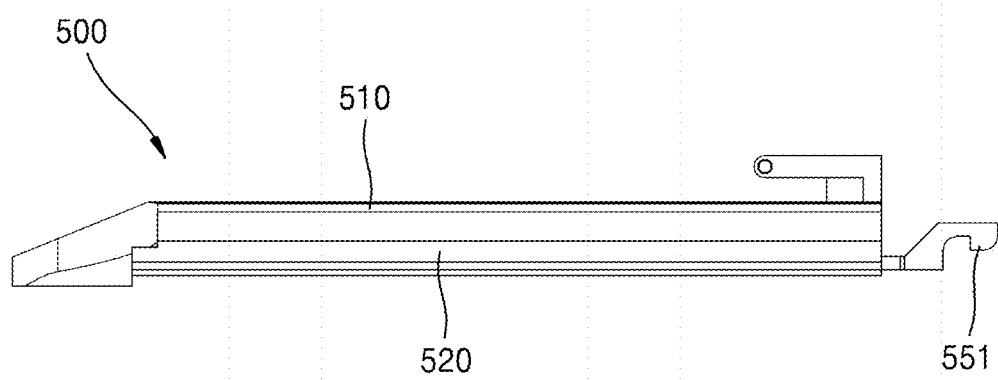
FIG. 137 is a side view illustrating the cartridge of FIG. 134.
Figure 138:
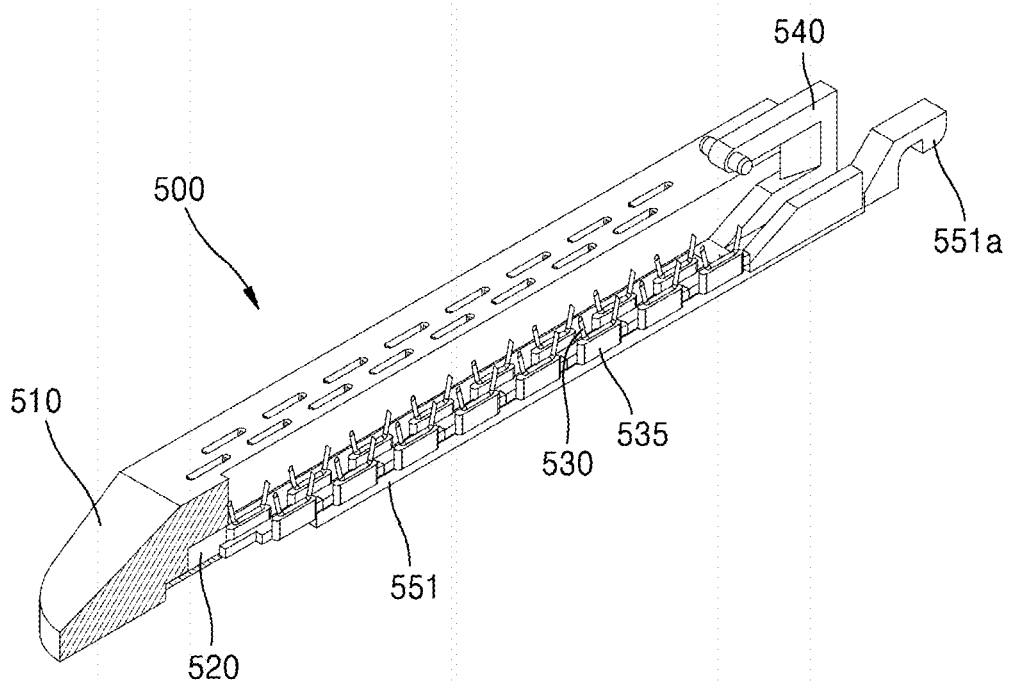
FIG. 138 is a perspective cross-sectional view illustrating the cartridge of FIG. 134.
Figure 139:
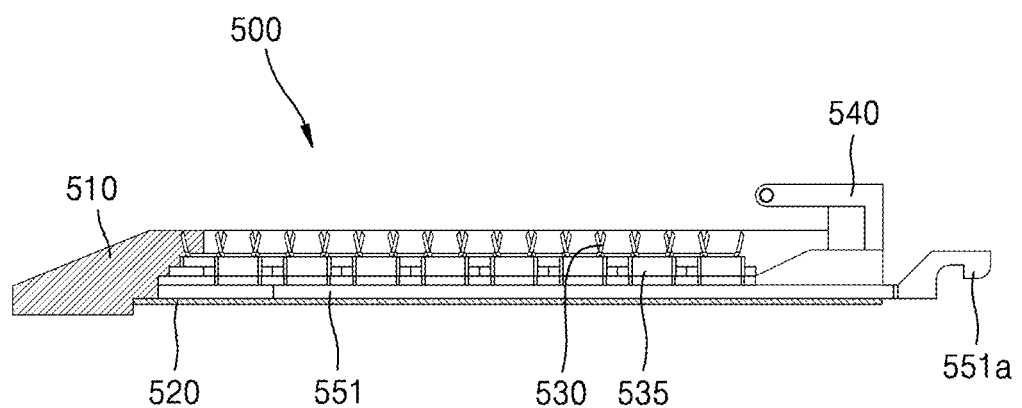
FIG. 139 is a side cross-sectional view illustrating the cartridge of FIG. 134.
Figure 140:
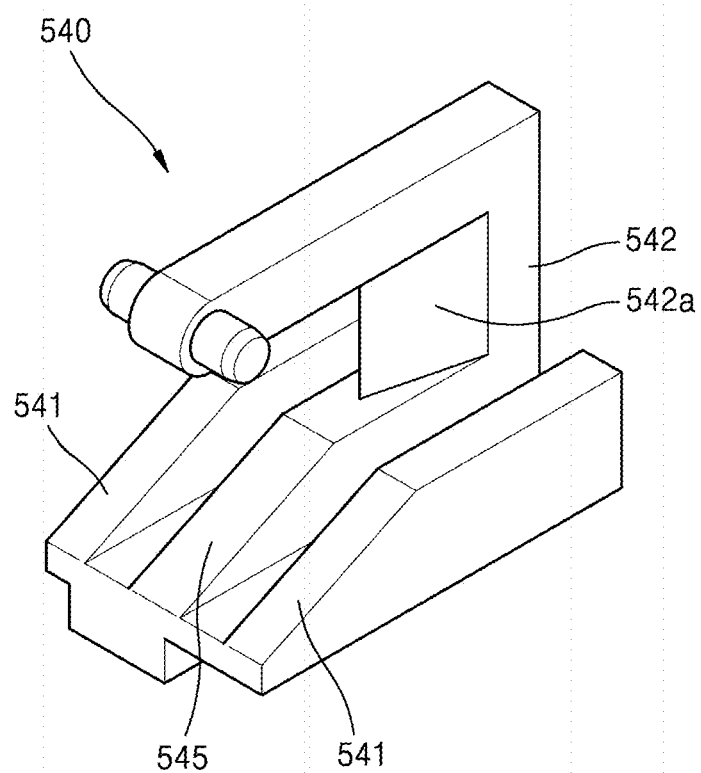
FIGS. 140 to 143 are perspective views illustrating an operation member of the cartridge of FIG. 134.
Figure 141:
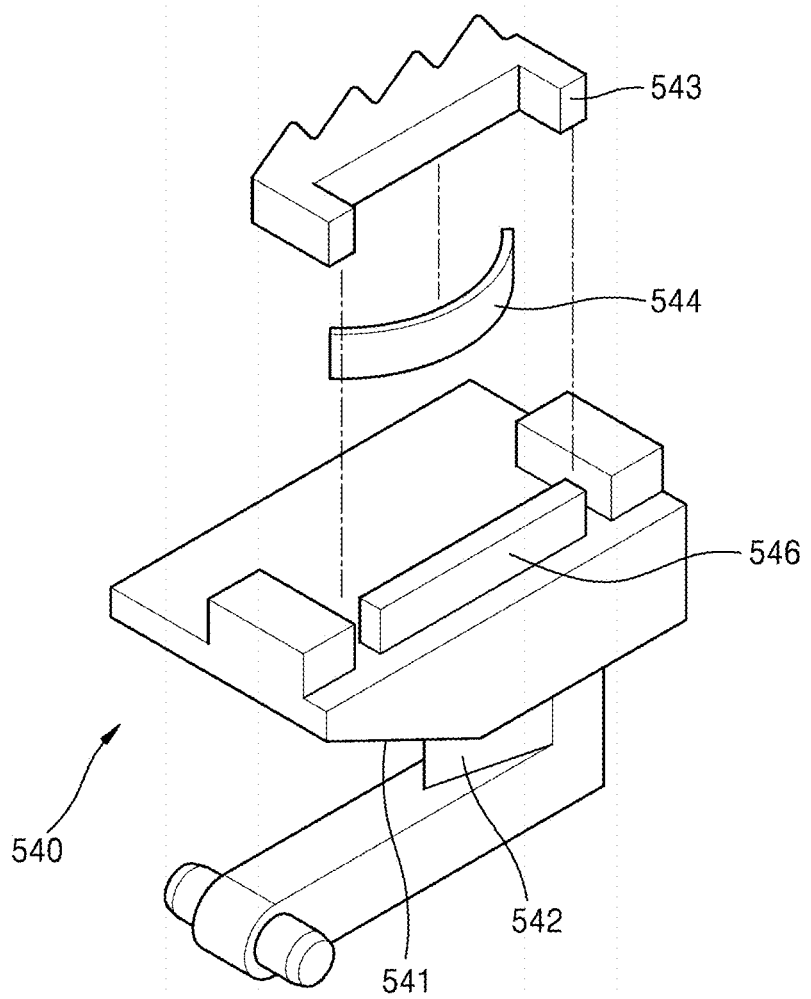
Figure 142:
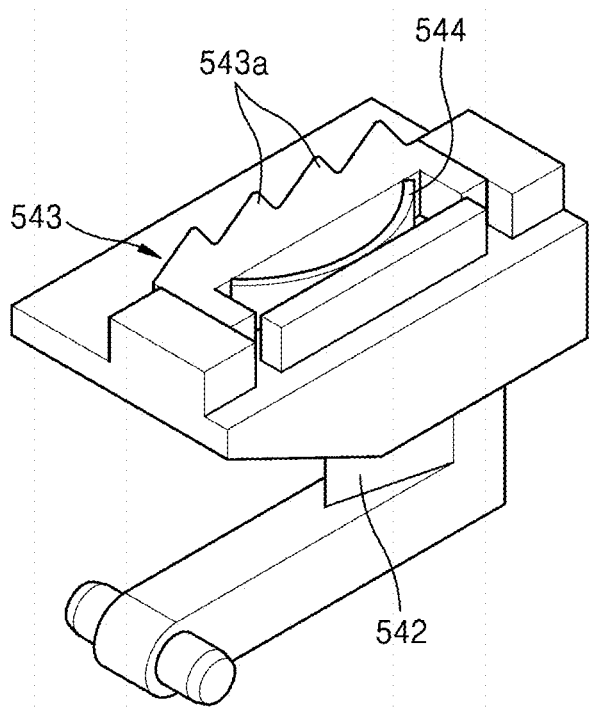
Figure 143:
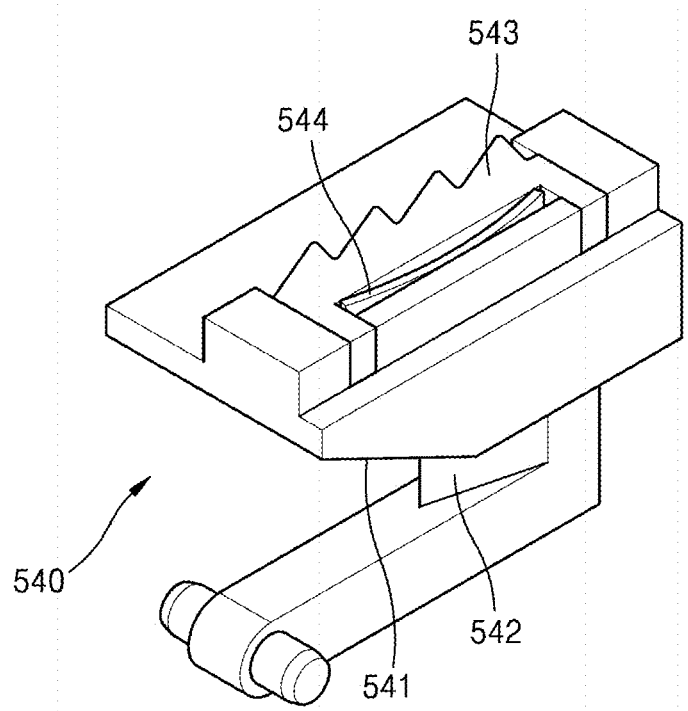
Figure 144:
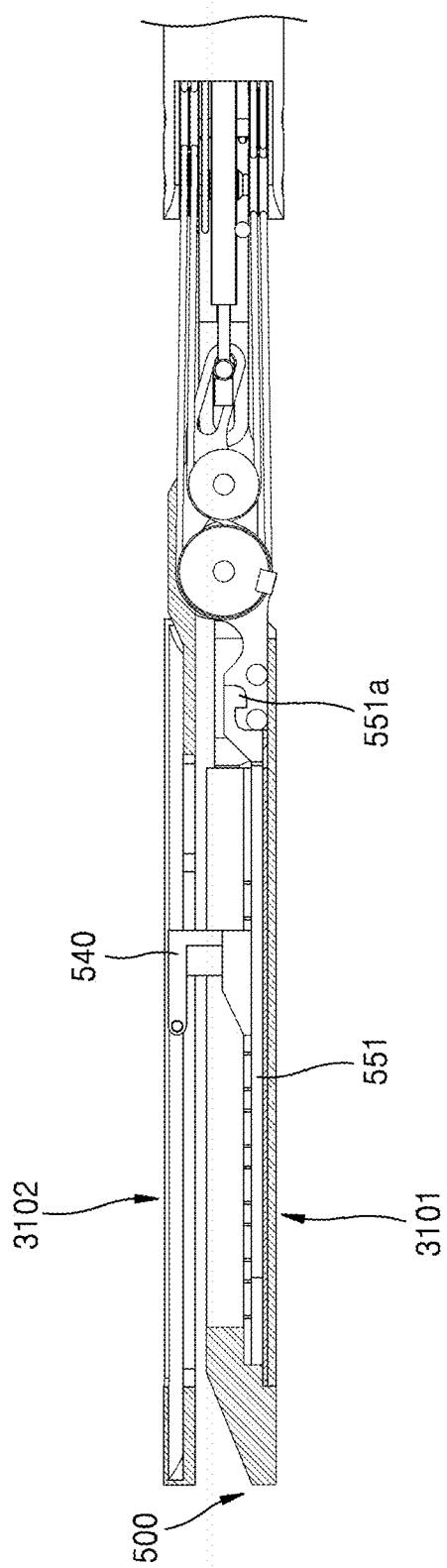
FIG. 144 is a side cross-sectional view illustrating a stapling-related structure of the end tool of the surgical instrument of FIG. 114.
Figure 145:
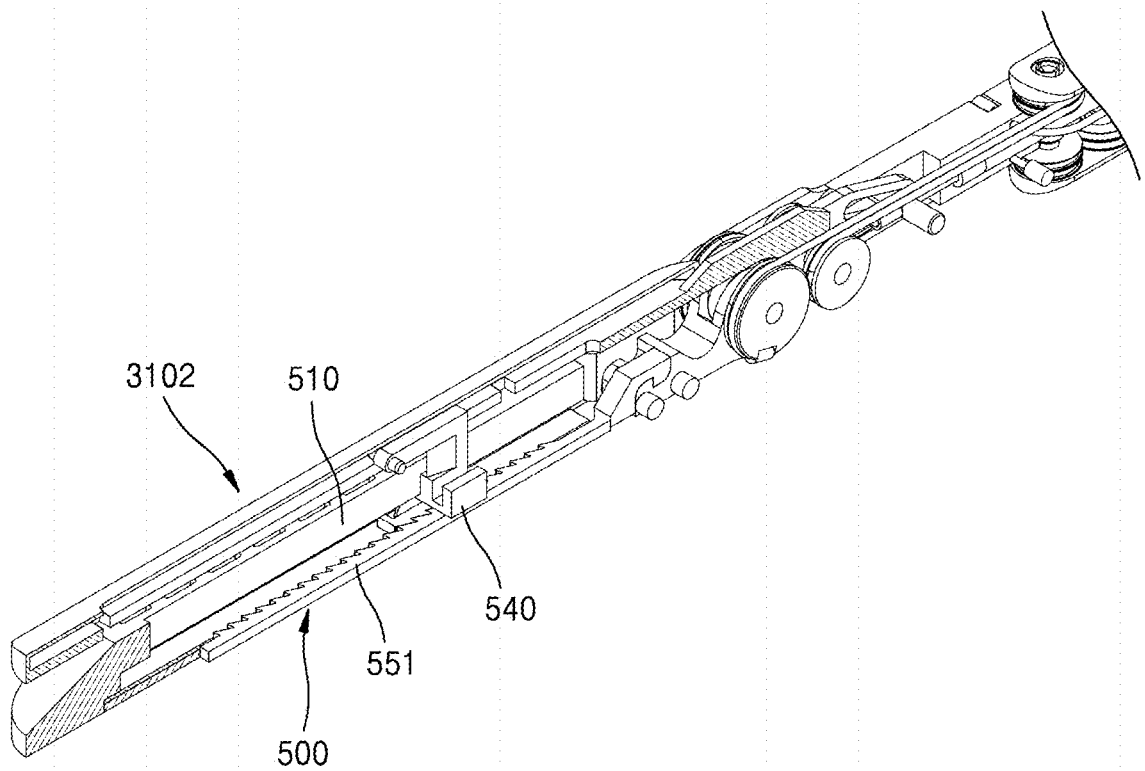
FIGS. 145 and 146 are perspective cross-sectional views illustrating a stapling structure of the end tool of the surgical instrument of FIG. 114.
Figure 146:
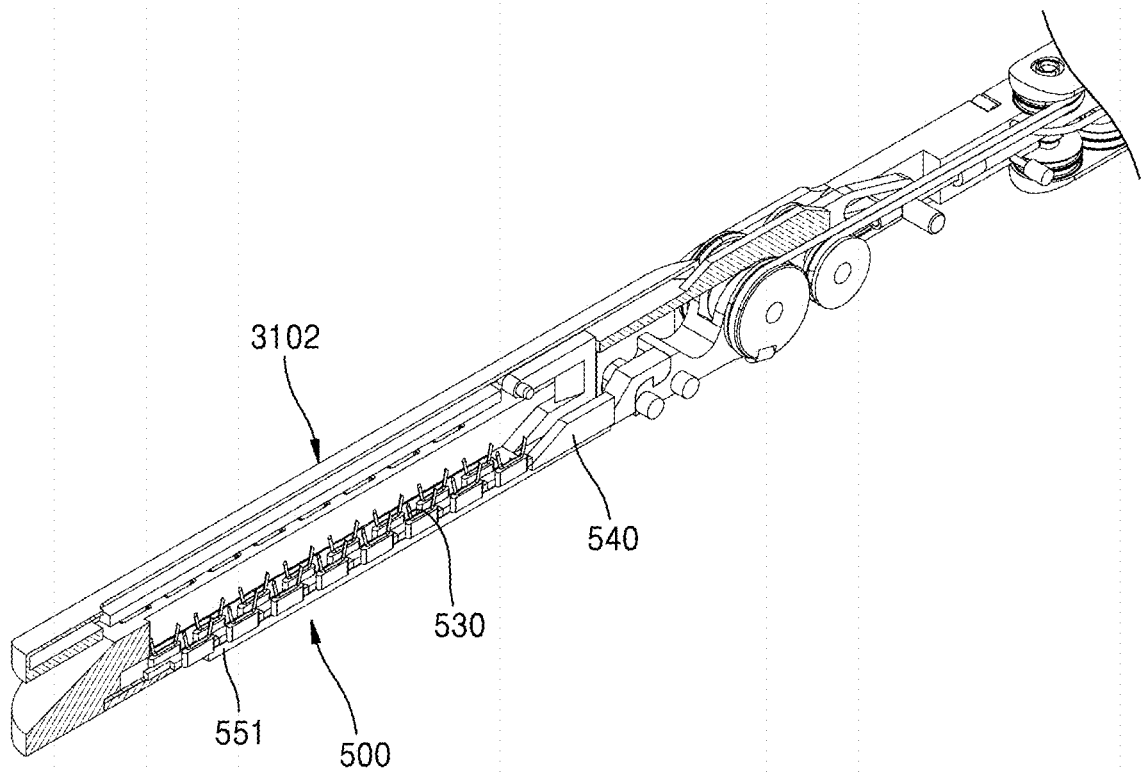
Figure 147:
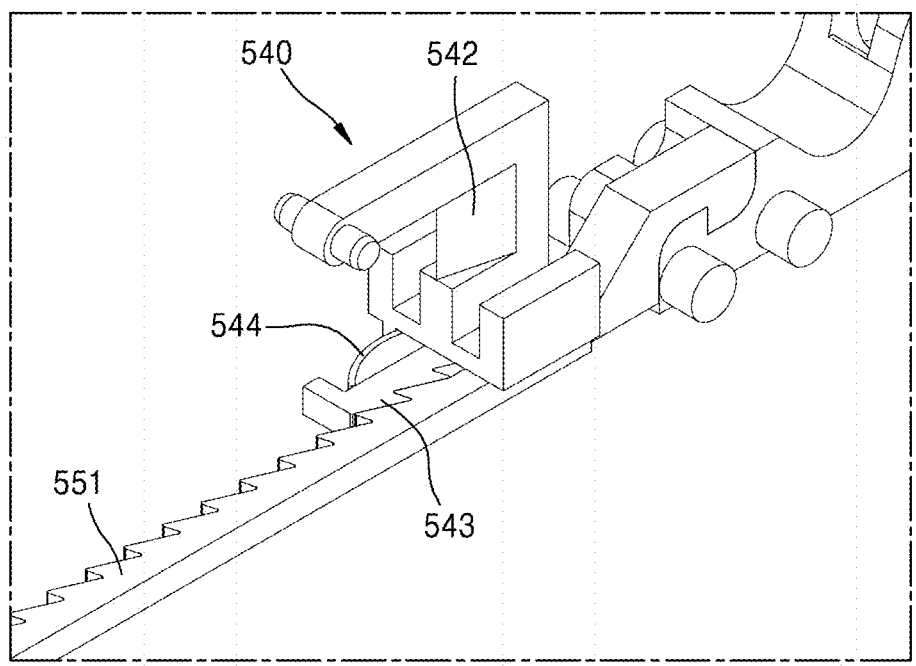
FIGS. 147 and 148 are perspective views illustrating a ratchet drive operation of the end tool of FIG. 137.
Figure 148:
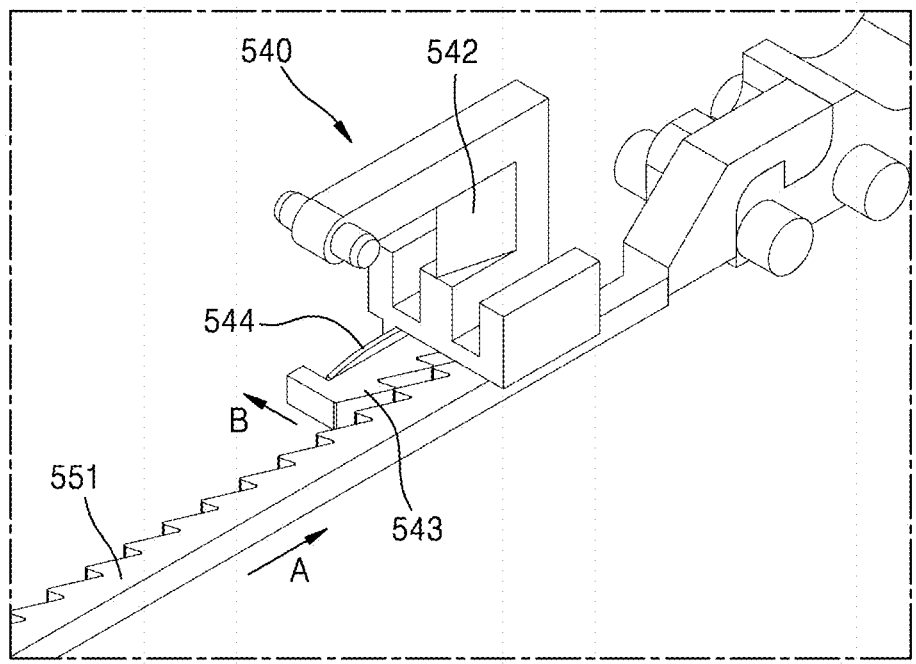

FIG. 134 is a perspective view illustrating the first jaw and the cartridge of the surgical instrument of FIG. 114. FIG. 135 is an exploded perspective view illustrating the cartridge of FIG. 134. FIG. 136 is an assembled perspective view illustrating the cartridge of FIG. 134. FIG. 137 is a side view illustrating the cartridge of FIG. 134. FIG. 138 is a perspective cross-sectional view illustrating the cartridge of FIG. 134. FIG. 139 is a side cross-sectional view illustrating the cartridge of FIG. 134. FIGS. 140 to 143 are perspective views illustrating the operation member of the cartridge of FIG. 134. FIG. 144 is a side cross-sectional view illustrating a stapling-related structure of the end tool of the surgical instrument of FIG. 114. FIGS. 145 and 146 are perspective cross-sectional views illustrating a stapling structure of the end tool of the surgical instrument of FIG. 114. FIGS. 147 and 148 are perspective views illustrating a ratchet drive operation of the end tool of FIG. 137. FIGS. 149A to 149D are plan views illustrating a ratchet drive operation of the end tool of FIG. 145. FIGS. 150A to 150D are perspective views illustrating an entire stapling motion of the end tool of FIG. 145.

Referring to FIGS. 134 to 150 and the like, the cartridge 500 is formed to be mountable to and dismountable from the first jaw 3101, and includes a plurality of staples 530 and a blade 542 therein to perform suturing and cutting of tissue. Here, the cartridge 500 may include a cover 510, a housing 520, the staples 530, withdrawal members 535, the operation member 540, and the reciprocating assembly 550.

The housing 520 forms an outer shape of the cartridge 500, and may be formed entirely in the form of a hollow box with one surface (upper surface) thereof is removed to accommodate the reciprocating assembly 550, the operation member 540, and the staple 530 therein. Here, the housing 520 may be formed in an approximately "U" shape in cross section.

The cover 510 is formed to cover an upper portion of the housing 520. Staple holes 511 through which the plurality of staples 530 may be ejected to the outside may be formed in the cover 510. As the staples 530, which are accommodated inside the housing 520 before a stapling operation, are pushed and raised upward by the operation member 540 during a stapling motion, and pass through the staple holes 511 of the cover 510 to be withdrawn to the outside of the cartridge 500, stapling is performed.

Meanwhile, a slit 512 may be formed in the cover 510 along a length direction of the cover 510. The blade 542 of the operation member 540 may protrude out of the cartridge 500 through the slit 512. As the blade 542 of the operation member 540 passes along the slit 512, staple-completed tissue may be cut.

The plurality of staples 530 may be disposed inside the housing 520. As the operation member 540, which will be described later, is linearly moved in one direction, the plurality of staples 530 are sequentially pushed and raised from the inside of the housing 520 to the outside, thereby performing suturing, that is, stapling. Here, the staples 530 may be made of a material that may include titanium, stainless steel, or the like.

Meanwhile, the withdrawal member 535 may be further disposed between the housing 520 and the staple 530. In other words, it may be said that the staple 530 is disposed above the withdrawal member 535. In this case, the operation member 540 is linearly moved in one direction to push and raise the withdrawal member 535, and the withdrawal member 535 may push and raise the staple 530.

As such, the operation member 540 may be described as pushing and raising the staples 530 in both the case in which the operation member 540 directly pushes and raises the staples 530 and the case in which the operation member 540 pushes and raises the withdrawal members 535 and the withdrawal members 535 pushes and raises the staples 530 (i.e., the operation member 540 indirectly pushes and raises the staples 530).

The reciprocating assembly 550 may be disposed at an inner lower side of the housing 520. The reciprocating assembly 550 may include one or more reciprocating members 551. In the present embodiment, it is illustrated that one reciprocating member 551 is provided, but in other embodiments, a plurality of reciprocating members 551 may be provided.

In the present embodiment, the reciprocating member 551 may be a rack. The reciprocating member 551 may include recesses 551b and the coupling part 551a. In detail, the reciprocating member 551 may be formed in the form of an elongated bar, and a plurality of recesses 551b having a sawtooth shape may be formed on one surface thereof. The recess 551b may be formed to be in contact with the operation member 540 to be described later, in particular, a ratchet member 543 of the operation member 540. In other words, the reciprocating member 551 may include the plurality of recesses 551b shaped to engage with ratchets 543a of the ratchet member 543.

Meanwhile, although not shown in the drawings, in addition to a rack shape, the reciprocating member 551 may be provided as various shapes of members, which are directly or indirectly connected to the staple pulley assembly 3180 and may perform a linear reciprocating motion according to a rotational motion of the staple pulley assembly 3180. For example, the reciprocating member 551 may be in the form of a clutch in which recesses are not present.

Here, the reciprocating member 551 is not fixedly coupled to the other components of the cartridge 500, and may be formed to be movable relatively to the other components of the cartridge 500. That is, the reciprocating member 551 may perform a reciprocating linear motion with respect to the housing 520 and the cover 510 coupled to the housing 520.

Meanwhile, in the reciprocating member 551, the coupling part 551a may be formed at a proximal end 501 side adjacent to the pulley 3111, and the coupling part 551a may be fastened and coupled to the staple link assembly 3170 of the end tool 3100. Thus, when the staple link assembly 3170 performs a reciprocating linear motion in the extension direction (i.e., the Y-axis direction) of the connection part 400, the reciprocating member 551 coupled thereto may also perform a reciprocating linear motion in the extension direction (i.e., the Y-axis direction) of the connection part 400. This will be described in more detail later.

The operation member 540 may be disposed inside the housing 520. The operation member 540 is formed to be in contact with the reciprocating member 551, and may be formed to linearly move in one direction according to the reciprocating linear motion of the reciprocating member 551. In other words, the operation member 540 interacts with the reciprocating member 551 to perform stapling and cutting motions while moving in the extension direction of the connection part 400.

The operation member 540 may include a wedge 541, the blade 542, the ratchet member 543, an elastic member 544, and a body 545.

The body 545 may be formed in the shape of an elongated square column, and forms a base of the operation member 540.

A support 546 may be formed to protrude from one surface of the body 545, for example, a lower surface of the body 545. Here, the support 546 may be formed in the form of an elongated bar, and the elastic member 544 may be accommodated in a space between the support 546 and the ratchet member 543. Accordingly, the elastic member 544 may be formed such that a central portion is in contact with the support 546 and both end portions are in contact with the ratchet member 543.

The wedge 541 is formed on at least one side of the body 545, and may be formed to have a predetermined inclined surface. That is, the wedge 541 may be formed to be inclined to a certain extent in the extension direction of the connection part 400. In other words, the wedge 541 may be formed to have a greater height at a proximal end 501 side of the cartridge 500 than a distal end 502 side of the cartridge 500. In the drawing, it is illustrated that two wedges 541 are formed on each side of the body 545 in the left and right direction, but the concept of the present disclosure is not limited thereto, and the wedge 541 may be formed in various numbers and shapes depending on the shape of the staple 530 or the withdrawal member 535 that is in contact with the wedge 541.

Figure 151A:
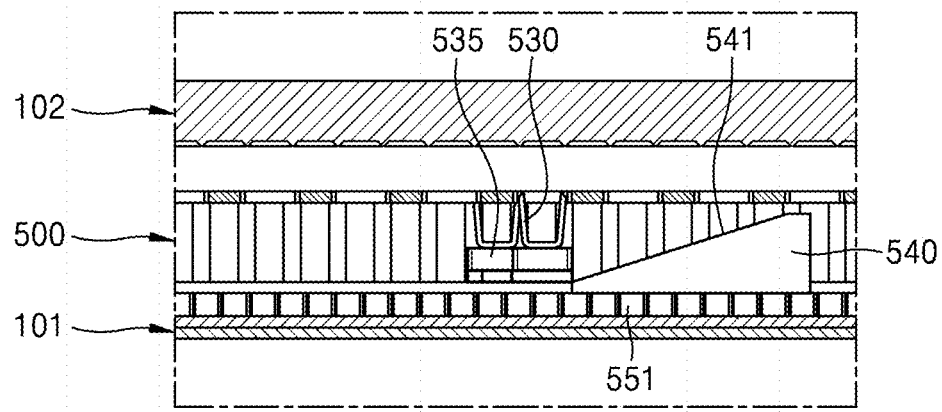
FIGS. 151A to 152 are perspective views illustrating an entire stapling motion of the end tool of FIG. 145.
Figure 151B:
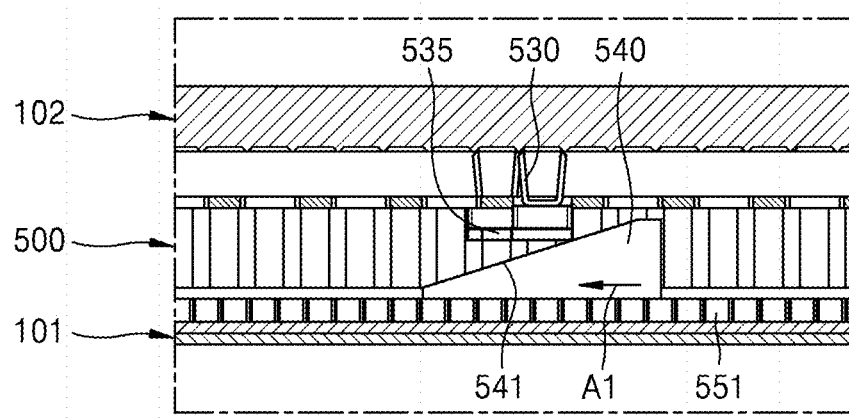
Figure 151C:
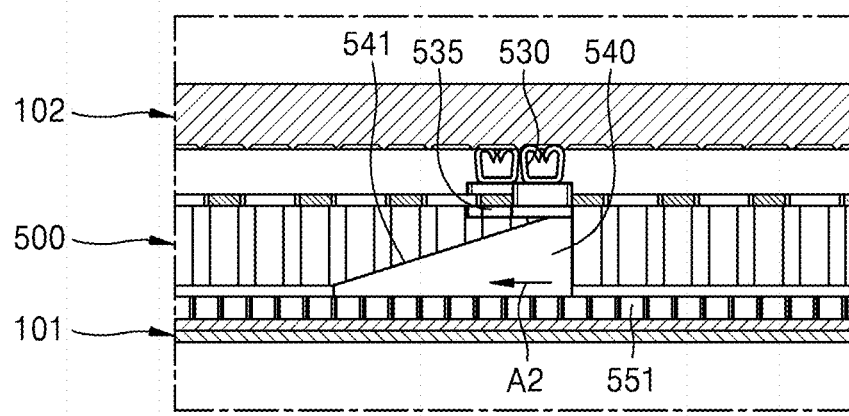

The wedge 541 may be formed to be in contact with the withdrawal members 535 or the plurality of staples 530 in turn and may serve to sequentially push and raise the staples 530. As shown in FIGS. 151A to 151C to be described later and elsewhere herein, the operation member 540 may serve to withdraw the staples 530 to the outside of the cartridge 500 by sequentially pushing and raising the staples 530 while moving toward the distal end 502

The blade 542 may be formed at one side of the wedge 541, more specifically, at one side of the wedge 541 at the proximal end 501 side. An edge 542a formed to be sharp to cut tissue is formed in one region of the blade 542. As at least a portion of the edge 542a is withdrawn to the outside of the first jaw 3101 and the cartridge 500, tissue disposed between the first jaw 3101 and the second jaw 3102 may be cut. The edge 542a of the blade 542 may be always withdrawn to the outside of the first jaw 3101. Alternatively, the edge 542a of the blade 542 may normally be accommodated inside the first jaw 3101 or inside the cartridge 500, and may be withdrawn to the outside of the first jaw 3101 only when the operation member 540 is moved in a length direction.

The ratchet member 543 is disposed under the body 545, and may be formed to face the reciprocating member 551. The ratchet member 543 may be formed in the form of a bar and may include a plurality of ratchets 543a on one surface. The operation member 540 is moved only in one direction (i.e., toward the distal end) with respect to the reciprocating member 551 by the ratchet member 543. The ratchets 543a of the ratchet member 543 may be formed to be in contact with the recess 551b of the reciprocating member 551 described above. The elastic member 544 is formed between the body 545 and the ratchet member 543 and serves to apply a predetermined elastic force to the ratchet member 543. In an example, the elastic member 544 may be formed such that one region is in contact with the body 545, and another region is in contact with the ratchet member 543. Here, the elastic member 544 may apply an elastic force in a direction in which the ratchet member 543 comes into close contact with the reciprocating member 551. To this end, the elastic member 544 may be formed in the form of a leaf spring, and may be provided in various forms capable of providing a predetermined elastic force to the ratchet member 543, such as a coil spring, a dish spring, and the like.

Here, the ratchet member 543 and the body 545 are illustrated in the drawings as being formed as separate members, but the concept of the present disclosure is not limited thereto, and the ratchet member 543 and the body 545 may be integrally formed as one body.

Here, the ratchet 543a of the ratchet member 543 may be formed such that a first surface 543a1 (specifically, at the distal end 502 side) is formed to have a gentle slope with a predetermined angle, and a second surface 543a2 (specifically, at the proximal end 501 side) is formed to be vertical or near vertical.

In addition, in order to be engaged with the ratchet 543a of the ratchet member 543, the recess 551b of the reciprocating member 551 may also be formed such that a first surface 551b1 (specifically, at the distal end 502 side) is formed to have a gentle slope with a predetermined angle, and a second surface 551b2 (specifically, at the proximal end 501 side) is formed to be vertical or near vertical.

In a state in which the reciprocating member 551 and the ratchet member 543 are coupled to each other (or engaged or in close contact with each other), the inclined first surface 543a1 of the ratchet 543a and the inclined first surface 551b1 of the recess 551b may be formed to face each other (that is, in contact with each other). In addition, the vertically formed second surface 543a2 of the ratchet 543a and the vertically formed second surface 551b2 of the recess 551b may be disposed to face each other (i.e., in contact with each other).

With this configuration, in a state in which the ratchet 543a and the recess 551b are coupled to (or engaged with) each other, the ratchet 543a and the recess 551b may be allowed to move only in one direction, acting as a kind of ratchet.

In an example, when it is assumed that the reciprocating member 551 is in a fixed state, the operation member 540 is movable in a direction in which the second surface 543a2 and the second surface 551b2, which are vertically formed, are away from each other, but when the second surface 543a2 and the second surface 551b2 are in contact with each other, the operation member 540 is not movable in a direction in which the second surface 543a2 and the second surface 551b2 are closer to each other.

From another perspective, when the reciprocating member 551 is moved toward the distal end 502 in a state in which the reciprocating member 551 and the ratchet member 543 are coupled to each other (or engaged or in close contact with each other), the ratchet member 543 is moved together toward the distal end 502 by the reciprocating member 551. That is, the vertically formed second surface 551b2 of the reciprocating member 551 pushes the vertically formed second surface 543a2 of the operation member 540 such that the ratchet member 543 is moved together toward the distal end 502 by the reciprocating member 551.

In contrast, when the reciprocating member 551 is moved toward the proximal end 501 in a state in which the reciprocating member 551 and the ratchet member 543 are coupled to each other (or engaged or in close contact with each other), only the reciprocating member 551 is moved alone toward the proximal end 501 while the ratchet member 543 a fixed. That is, the inclined first surface 551b1 of the reciprocating member 551 is moved along the inclined first surface 543a1 of the operation member 540 in a state in which the operation member 540 is fixed, so that only the reciprocating member 551 is moved alone toward the proximal end 501.

Referring to FIGS. 147 to 149D and the like, when the reciprocating member 551 is moved toward (in the direction of an arrow A of FIG. 148) the proximal end 501 in the state as shown in FIG. 147, as the inclined first surface 551b1 of the reciprocating member 551 is moved along the inclined first surface 543a1 of the operation member 540, the ratchet member 543 is pressed and pushed as a whole in the direction of an arrow B of FIG. 148. In addition, at this time, the clastic member 544 is elastically deformed to a certain extent.

In this state, when the reciprocating member 551 is further moved toward the proximal end 501, and the inclined first surface 551b1 of the reciprocating member 551 is moved beyond an end of the inclined first surface 543a1 of the operation member 540, the recess 551b of the reciprocating member 551 meets the next ratchet 543a of the ratchet member 543. In this case, since the clastic member 544 applies an clastic force in a direction in which the ratchet member 543 comes into close contact with the reciprocating member 551, front surfaces of the reciprocating member 551 and the ratchet member 543 are brought into close contact with each other again.

As a result, the cartridge 500 is accommodated in the cartridge accommodation part 3101a of the first jaw 3101, and in this case, the reciprocating member 551 of the cartridge 500 is coupled to the staple link assembly 3170 of the end tool 3100. Accordingly, the rotational motion of the first staple pulley 3181 of the end tool 3100 is converted into a linear motion of the reciprocating member 551 through the staple link assembly 3170.

In this case, when the coupling part 551a of the reciprocating member 551 is connected to the staple pulley assembly 3180 through the staple link assembly 3170, and the first staple pulley 3181 and the second staple pulley 3191 of the staple pulley assembly 3180 are alternately rotated in the clockwise/counterclockwise directions, the reciprocating member 551 may be repeatedly moved forward and backward. In addition, when the reciprocating member 551 is moved forward, the operation member 540 may be moved forward together with the reciprocating member 551, and when the reciprocating member 551 is moved backward, only the reciprocating member 551 may be moved backward and the operation member 540 may remain stationary in place. As the operation member 540 is moved forward while repeating this process, the staple 530 may be stapled by the wedge 541 while the blade 542 cuts stapled tissue. This will be described in more detail as follows.

(Stapling and Cutting Motions)

Referring to FIGS. 150A to 150D, a method of driving the surgical instrument according to an embodiment of the present disclosure is described as follows.

First, when the first staple pulley 3181 is rotated in the clockwise direction and the second staple pulley 3191 is rotated in the counterclockwise direction, the staple link assembly 3170 connected to the staple pulley assembly 3180 and the reciprocating assembly 550 of the cartridge 500 connected to the staple link assembly 3170 are moved toward the distal end 502 of the cartridge 500.

In addition, when the reciprocating assembly 550 is moved toward the distal end 502 of the cartridge 500, the operation member 540 in contact with the reciprocating assembly 550 is moved toward the distal end 502 of the cartridge 500 together with the reciprocating assembly 550.

In addition, as the operation member 540 is moved toward the distal end 502 of the cartridge 500, the blade 542 of the operation member 540 is moved toward the distal end 502 of the cartridge 500 while the operation member 540 ejects the staples 530 out of the cartridge 500.

Meanwhile, when the first staple pulley 3181 is rotated in the counterclockwise direction and the second staple pulley 3191 is rotated in the clockwise direction, the reciprocating assembly 550 of the staple link assembly 3170 connected to the staple pulley assembly 3180 and the cartridge 500 connected to the staple link assembly 3170 are moved toward the proximal end 501 of the cartridge 500, and at this time, the operation member 540 remains stationary.

In addition, as the above operations are repeatedly performed, a stapling motion by the wedge 541 and a cutting motion by the blade 542 are simultaneously performed.

This will be described in more detail as follows.

First, in the state as shown in FIG. 150A, as shown in FIG. 150B, when the first staple pulley 3181 is rotated in the direction of an arrow A1 (i.e., in the clockwise direction) and the second staple pulley 3191 is rotated in the opposite direction of the arrow A1 (i.e., in the counterclockwise direction), the staple link assembly 3170 connected to the first and second staple pulleys 3181 and 3191 and the reciprocating member 551 coupled to the staple link assembly 3170 are moved in the direction of an arrow B1 (i.e., toward the distal end). In this state, since the reciprocating member 551 and the operation member 540 are in close contact with each other by the clastic member (see 544 of FIGS. 149A to 149D), when the reciprocating member 551 is moved in the direction of the arrow B1, the operation member 540 is also moved in the direction of the arrow B1 together with the reciprocating member 551.

On the other hand, as shown in FIG. 150C, when the first staple pulley 3181 is rotated in the direction of an arrow A2 (i.e., in the counterclockwise direction) and the second staple pulley 3191 is rotated in the opposite direction of the arrow A2 (i.e., in the clockwise direction), the staple link assembly 3170 connected to the first and second staple pulleys 3181 and 3191 and the reciprocating member 551 coupled to the staple link assembly 3170 are moved in the direction of an arrow B2 (i.e., toward the proximal end). In this state, due to the coupling structure of the ratchet member 543 and the reciprocating member 551, even when the reciprocating member 551 is moved in the direction of the arrow B2, in a state in which the overall position of the operation member 540 remains unchanged, only the ratchet member 543 is spaced apart from the reciprocating member 551 by a certain extent while the clastic member 544 is elastically deformed in the direction of an arrow C2 (referring to FIGS. 149A to 149D). That is, even when the reciprocating member 551 is moved in the direction of the arrow B2, the operation member 540 remains stationary in place when viewed in the X-axis direction.

Meanwhile, as shown in FIG. 150D, when the first staple pulley 3181 is further rotated in the direction of an arrow A3, and the second staple pulley 3191 is further rotated in the opposite direction of the arrow A3, only the staple link assembly 3170 and the reciprocating member 551 connected thereto are further moved in the direction of an arrow B3. At this time, when the recess of the reciprocating member 551 is moved over the end of one ratchet 543a of the ratchet member 543 of the operation member 540, the elastic member 544 is elastically restored in the direction of an arrow C3 and the ratchet member 543 is brought into contact with the reciprocating member 551 again. At this time, the recess of the reciprocating member 551 meets the next ratchet 543a of the ratchet member 543.

In this state, when the first staple pulley 3181 stops rotating, as shown in FIG. 150A, the staple link assembly 3170, the reciprocating member 551, and the operation member 540 also stop moving.

When the first staple pulley 3181 and the second staple pulley 3191 are alternately rotated in the clockwise and counterclockwise directions while repeating the above process, the reciprocating member 551 is repeatedly moved forward and backward, and the operation member 540 repeats moving forward and stopping, and as a result, the operation member 540 is moved toward the distal end 502. In addition, as the operation member 540 is moved toward the distal end 502, a stapling motion by the wedge 541 and a cutting motion by the blade 542 are simultaneously performed.

Hereinafter, a stapling motion of the surgical instrument according to an embodiment of the present disclosure will be described.

Figure 152:
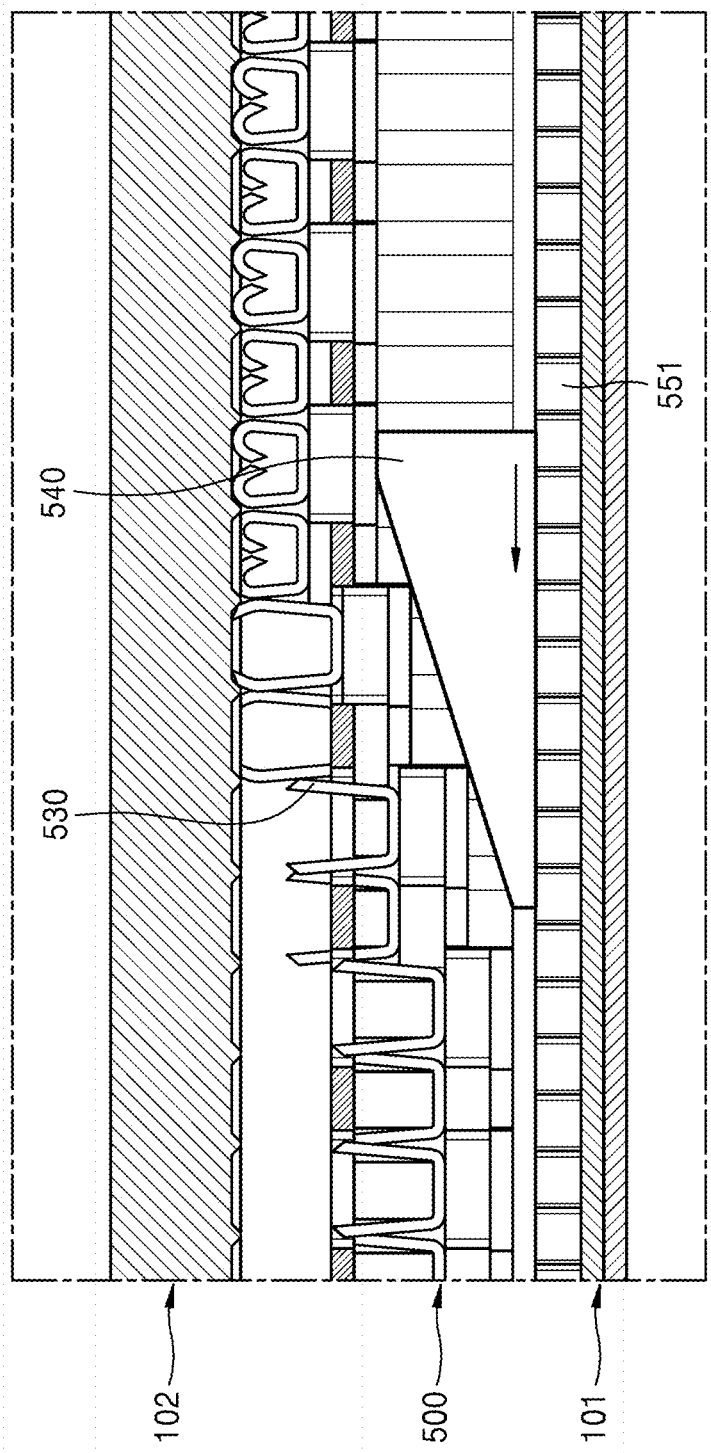

FIGS. 151A to 151C are perspective views illustrating a stapling motion of the end tool of FIG. 145 for each section, and FIG. 152 is a perspective view illustrating an entire stapling motion of the end tool of FIG. 145.

Referring to FIGS. 151A to 152, in the state as shown in FIG. 151A, as the operation member 540 is moved in the direction of an arrow A1 of FIG. 151B, the wedge 541 of the operation member 540 pushes and raises the withdrawal member 535, and the withdrawal member 535 pushes and raises one side of a lower portion of the staple 530. In addition, due thereto, the staple 530 is ejected to the outside of the first jaw 3101 and the cartridge 500.

In this state, when the operation member 540 is further moved in the direction of an arrow A2 of FIG. 151C, the ejected staple 530 is continuously pushed and raised by the operation member 540 while in contact with the anvil 3102a of the second jaw 3102, so that stapling is performed while both end portions of the staple 530 are bent.

As such motions are continuously performed, stapling is sequentially performed from the staple 530 at the proximal end 501 side to the staple 530 at the distal end 502 side among the plurality of staples 530, as illustrated in FIG. 152.

(Actuation and Pitch Motions)

Figure 153:
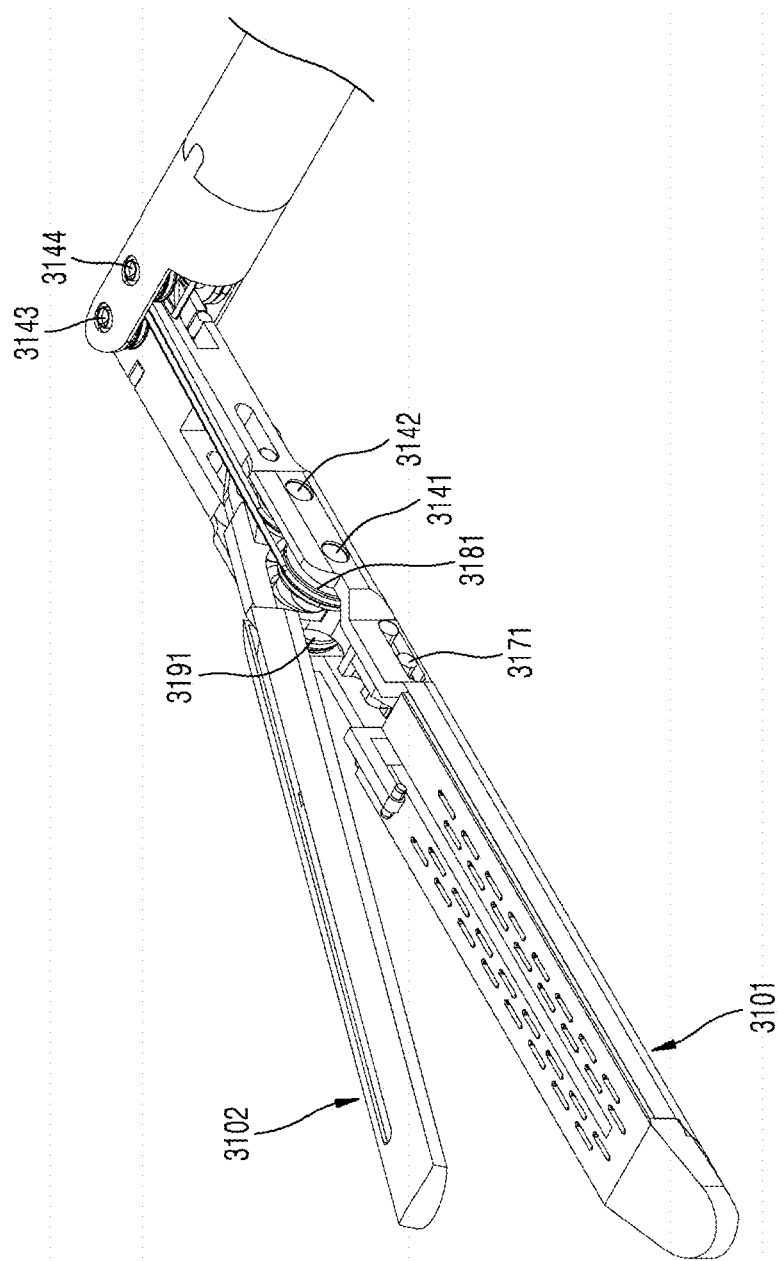
FIG. 153 is a perspective view illustrating a state in which jaws in the end tool of FIG. 114 are pitch-rotated by +90°.
Figure 154:
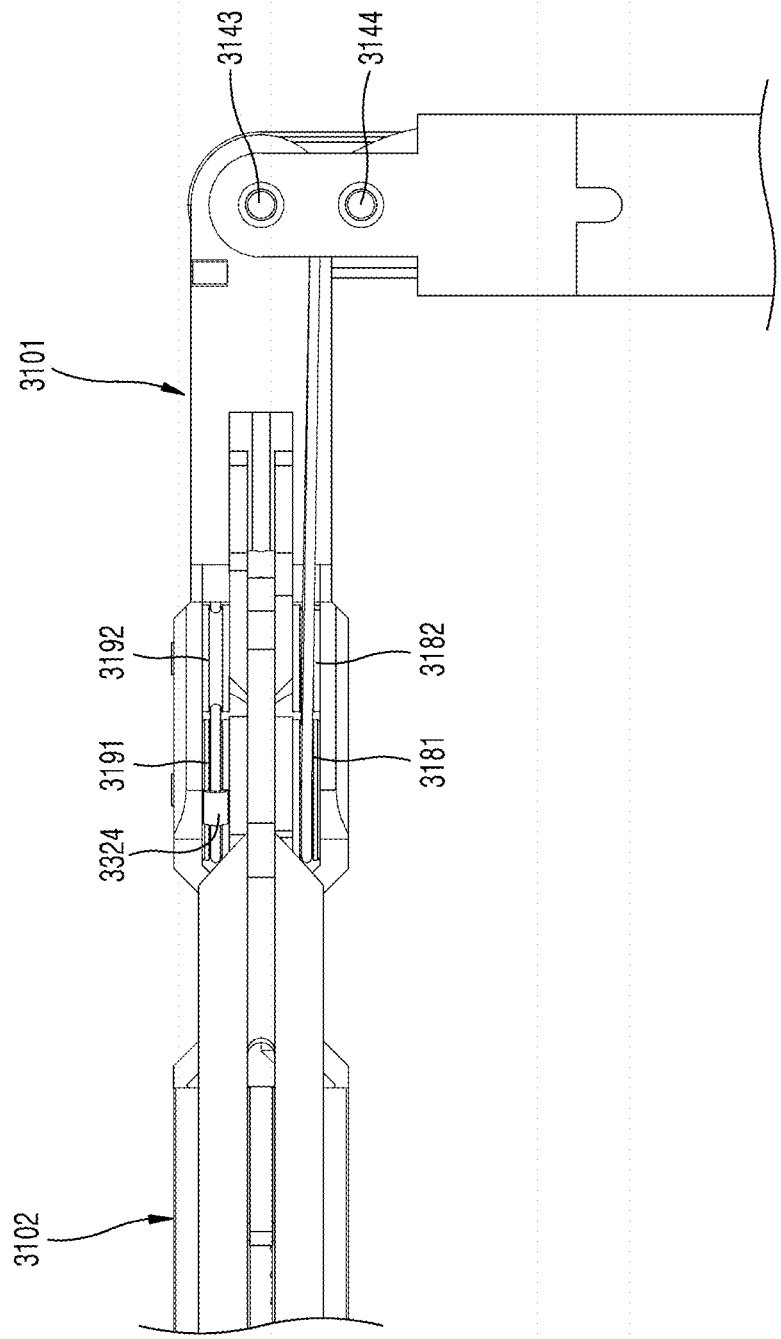
FIGS. 154 to 156 are side views of the end tool of FIG. 153, with some components are omitted from each drawing.
Figure 155:
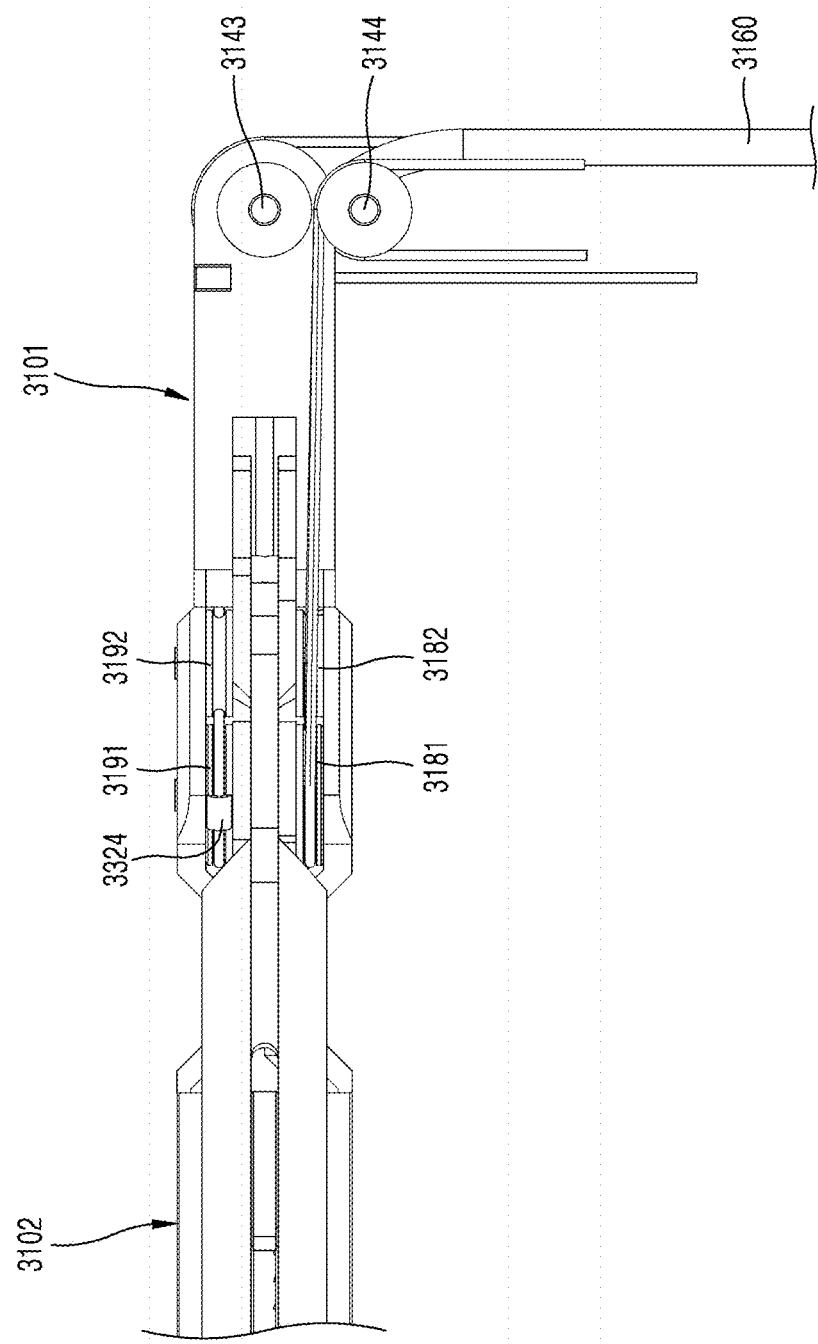
Figure 156:
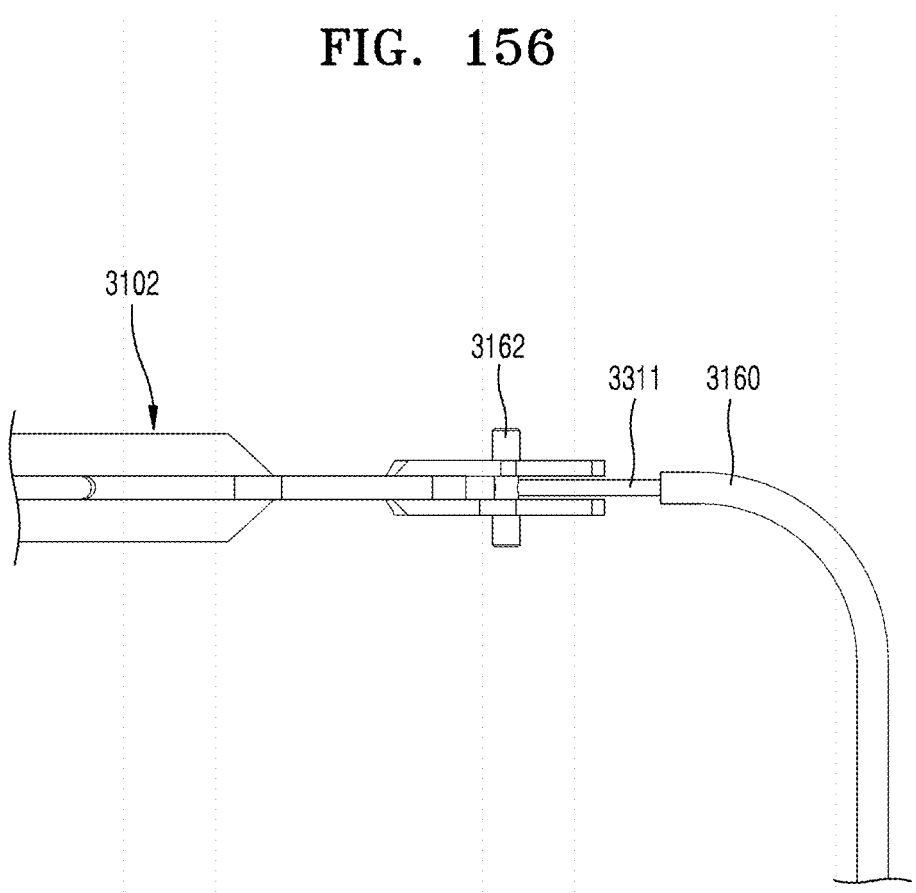
Figure 157:
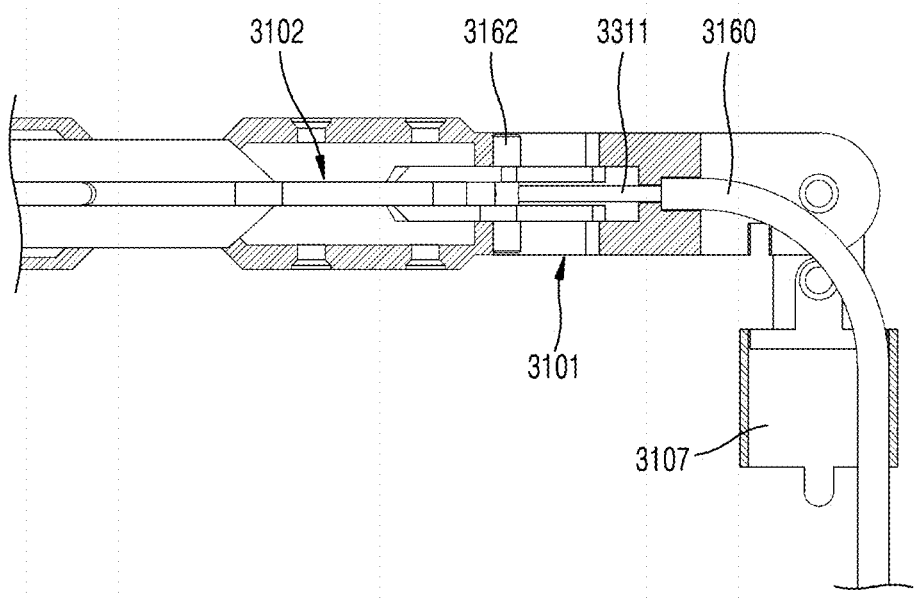
FIG. 157 is a side cross-sectional view of the end tool of FIG. 153.
Figure 158:
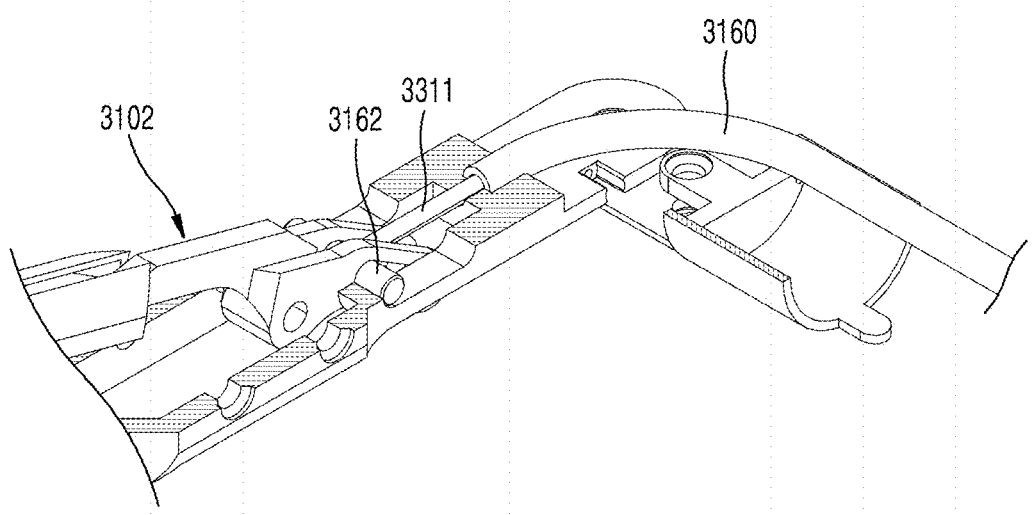
FIG. 158 is a perspective cross-sectional view of the end tool of FIG. 153.
Figure 159:
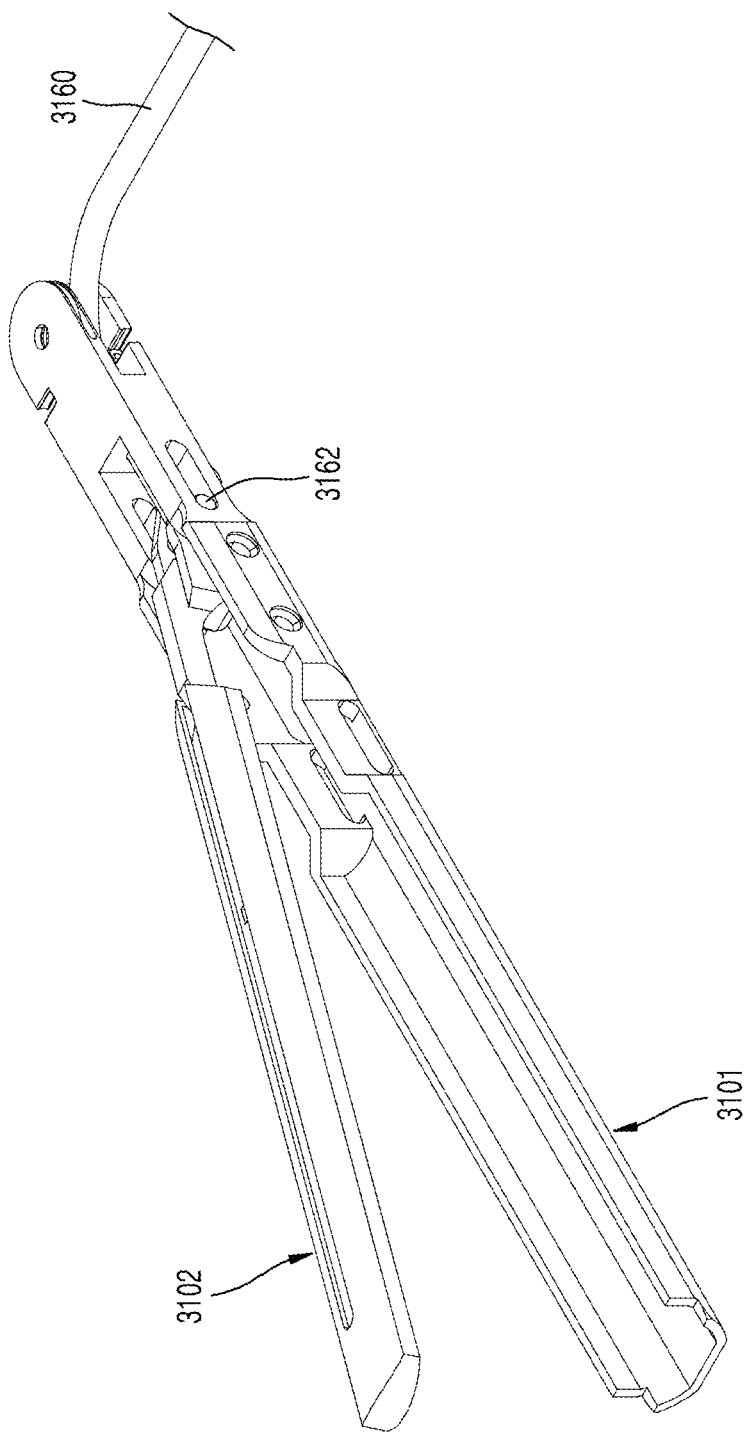
FIGS. 159 and 160 are perspective views illustrating an actuation motion of the end tool of FIG. 153, and are views illustrating a process of performing an actuation motion in a state in which the jaws are pitch-rotated by +90°.
Figure 160:
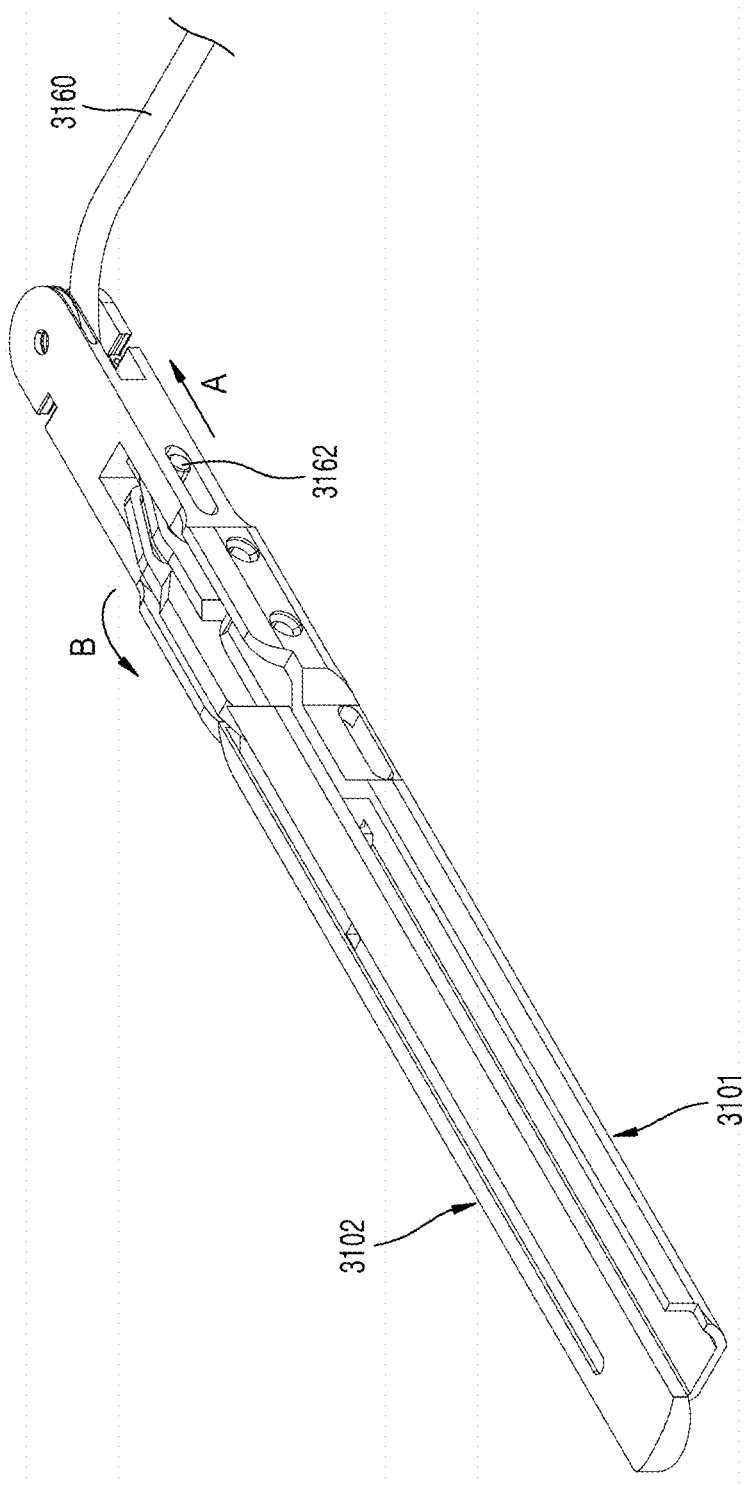

FIG. 153 is a perspective view illustrating a state in which the jaws in the end tool of FIG. 114 are pitch-rotated by +90°. FIGS. 154 to 156 are side views of the end tool of FIG. 153, with some components are omitted from each drawing. FIG. 157 is a side cross-sectional view of the end tool of FIG. 153. FIG. 158 is a perspective cross-sectional view of the end tool of FIG. 153. FIGS. 159 and 160 are perspective views illustrating an actuation motion of the end tool of FIG. 153, and are views illustrating a process of performing an actuation motion in a state in which the jaws are pitch-rotated by +90°.

As shown in FIGS. 153 to 160, the end tool of the surgical instrument according to the second embodiment of the present disclosure is formed to normally perform an actuation motion even when the jaws are pitch-rotated by +90°.

Figure 161:
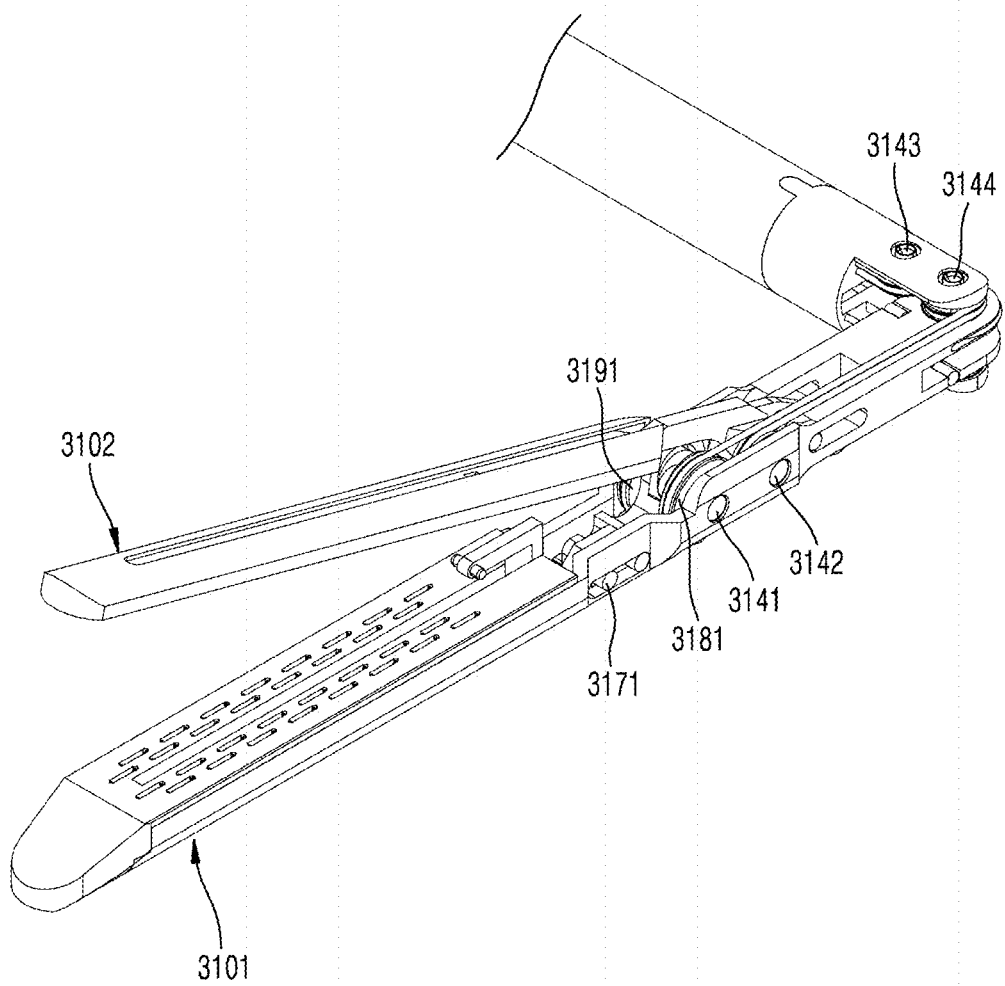
FIG. 161 is a perspective view illustrating a state in which the jaws in the end tool of FIG. 114 are pitch-rotated by −90°.
Figure 162:
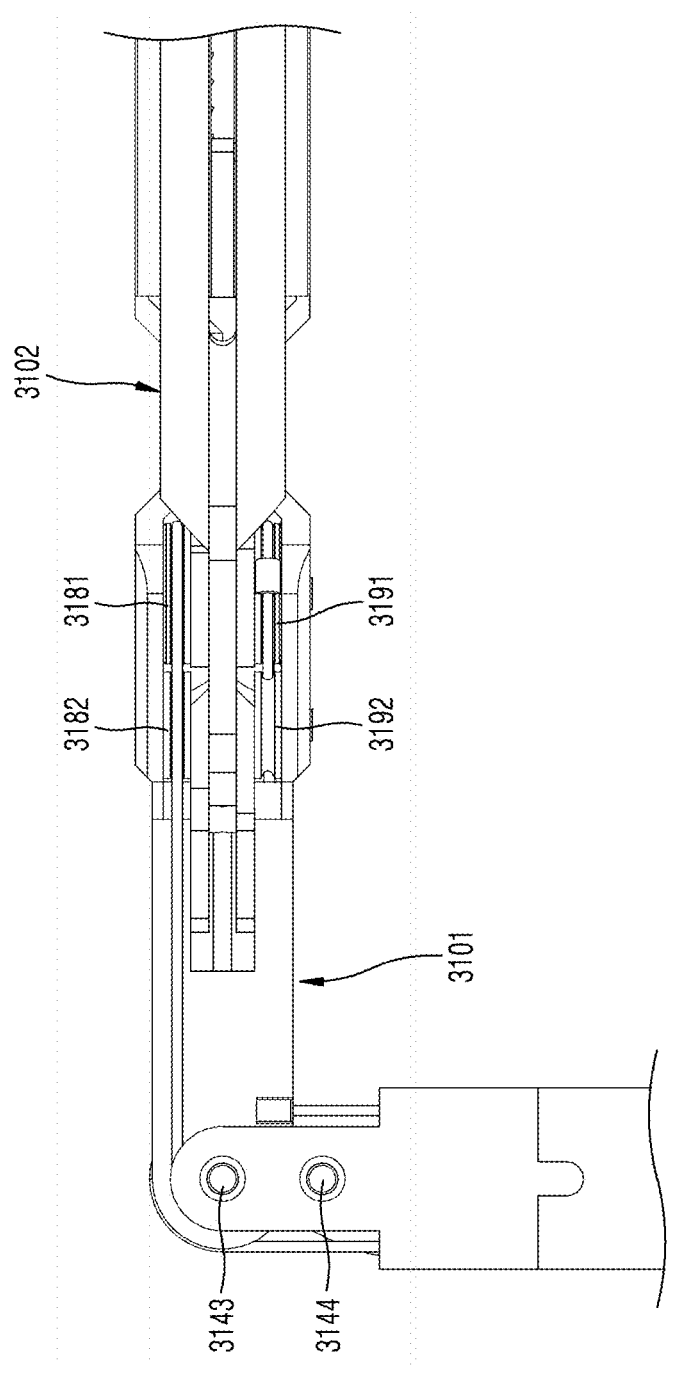
FIGS. 162 to 164 are side views of the end tool of FIG. 161, with some components are omitted from each drawing.
Figure 163:
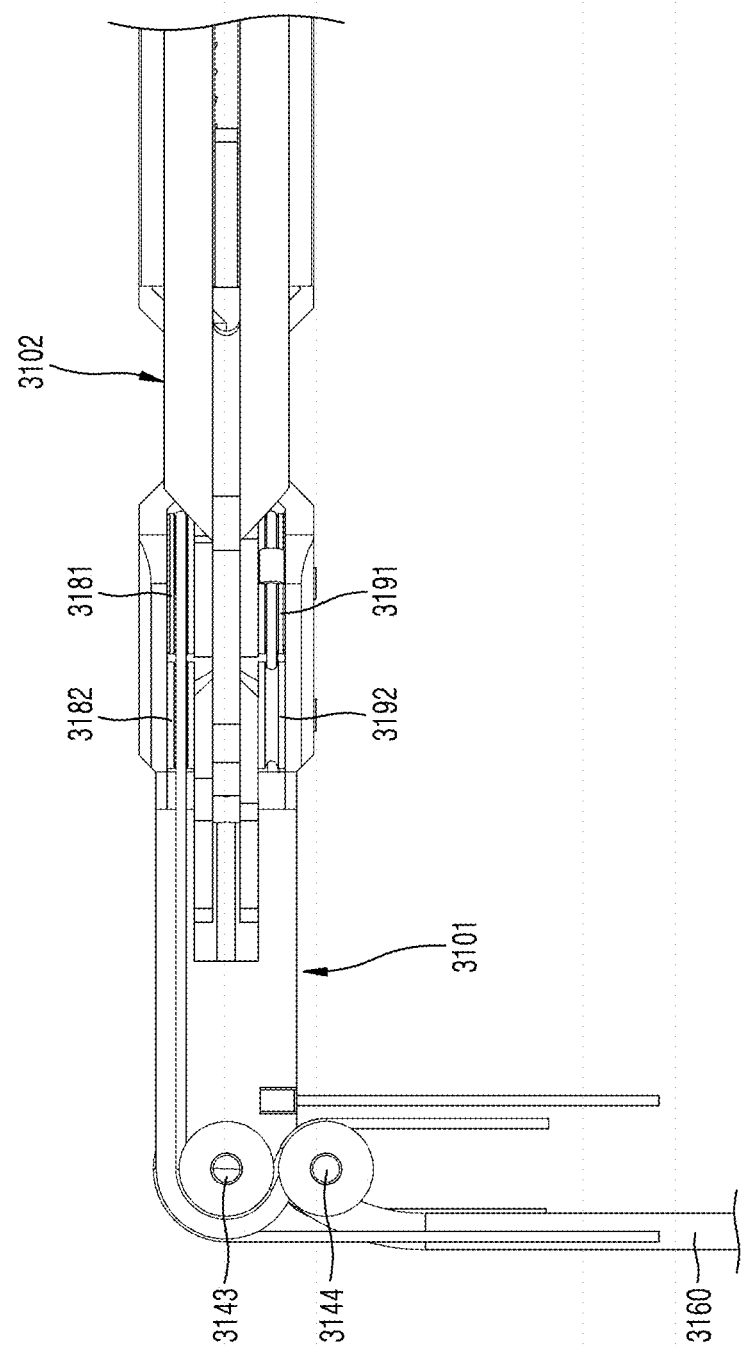
Figure 164:
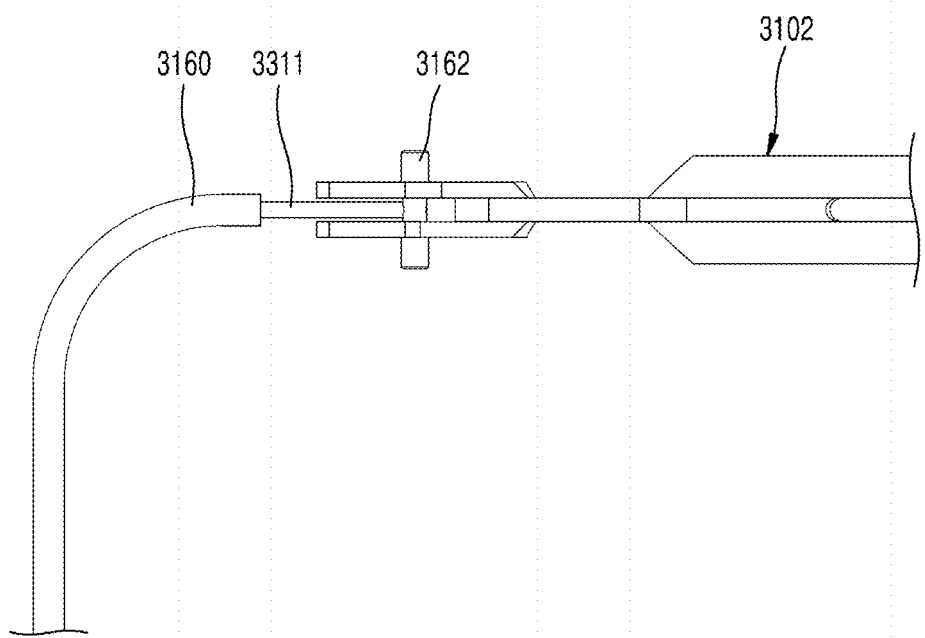
Figure 165:
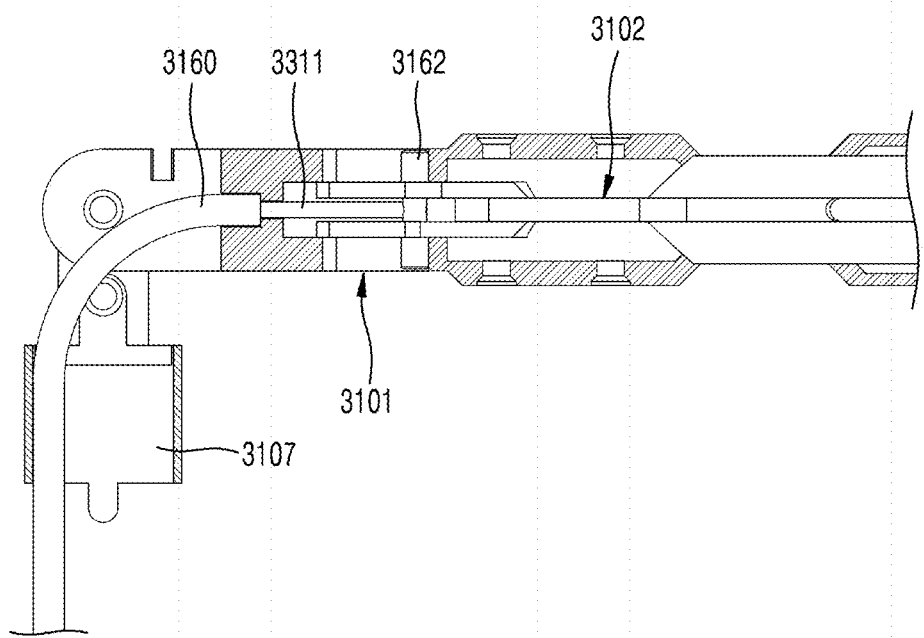
FIG. 165 is a side cross-sectional view of the end tool of FIG. 161.
Figure 166:
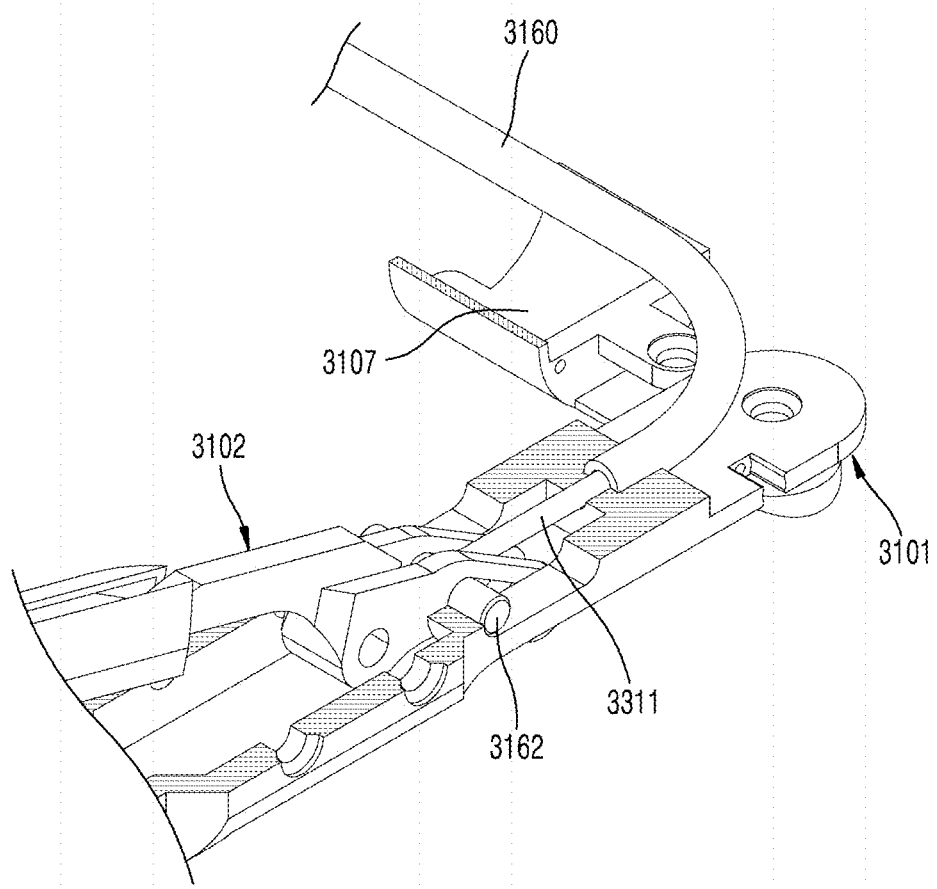
FIG. 166 is a perspective cross-sectional view of the end tool of FIG. 161.
Figure 167:
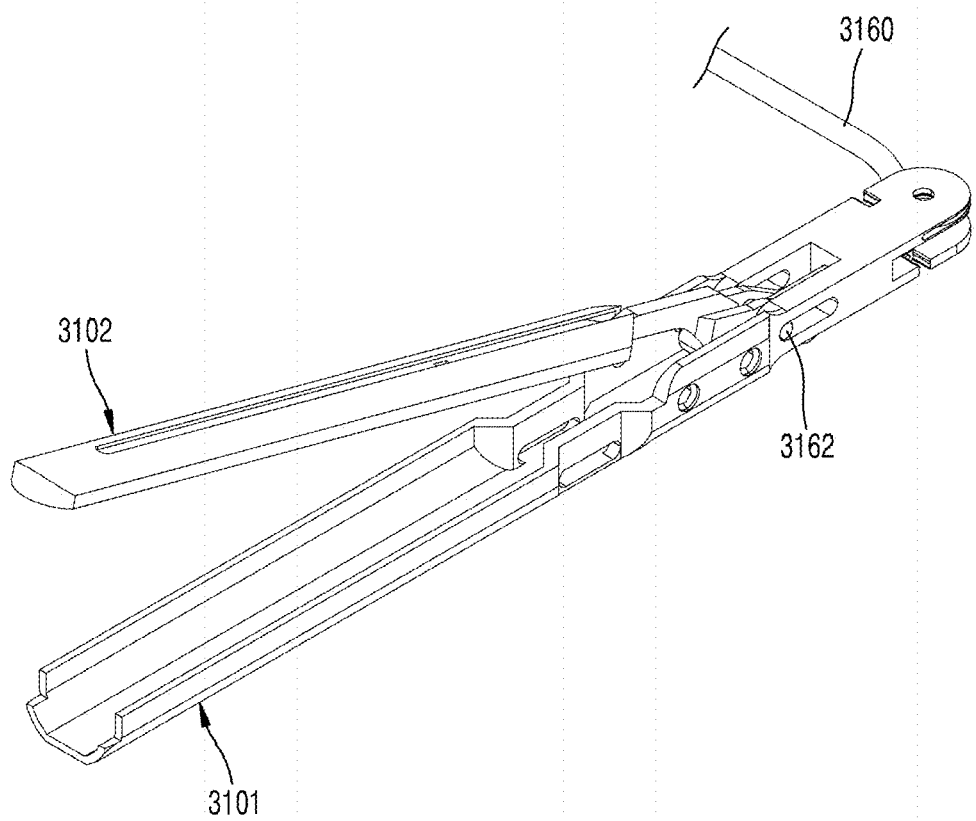
FIGS. 167 and 168 are perspective views illustrating an actuation motion of the end tool of FIG. 161, and are views illustrating a process of performing an actuation motion in a state in which the jaws are pitch-rotated by +90°.
Figure 168:
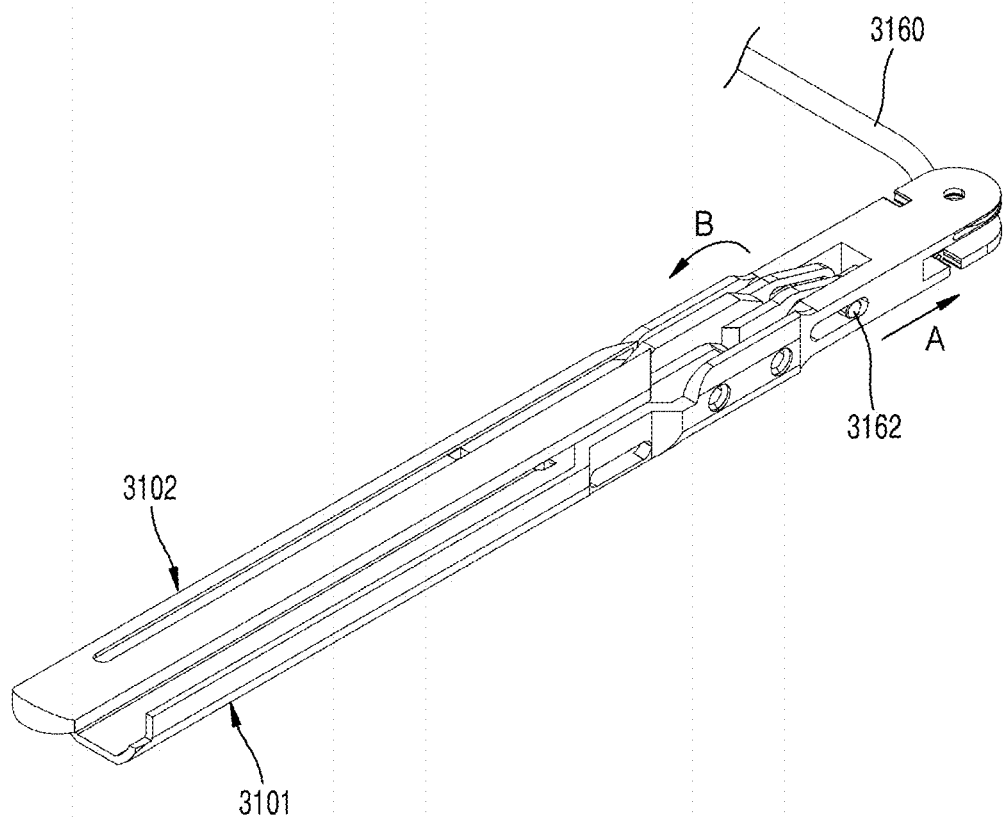

FIG. 161 is a perspective view illustrating a state in which the jaws in the end tool of FIG. 114 are pitch-rotated by −90°. FIGS. 162 to 164 are side views of the end tool of FIG. 161, with some components are omitted from each drawing. FIG. 165 is a side cross-sectional view of the end tool of FIG. 161. FIG. 166 is a perspective cross-sectional view of the end tool of FIG. 161. FIGS. 167 and 168 are perspective views illustrating an actuation motion of the end tool of FIG. 161, and are views illustrating a process of performing an actuation motion in a state in which the jaws are pitch-rotated by +90°.

As shown in FIGS. 161 to 166, the end tool of the surgical instrument according to the second embodiment of the present disclosure is formed to normally perform an actuation motion even when the jaws are pitch-rotated by −90°.

Figure 170:
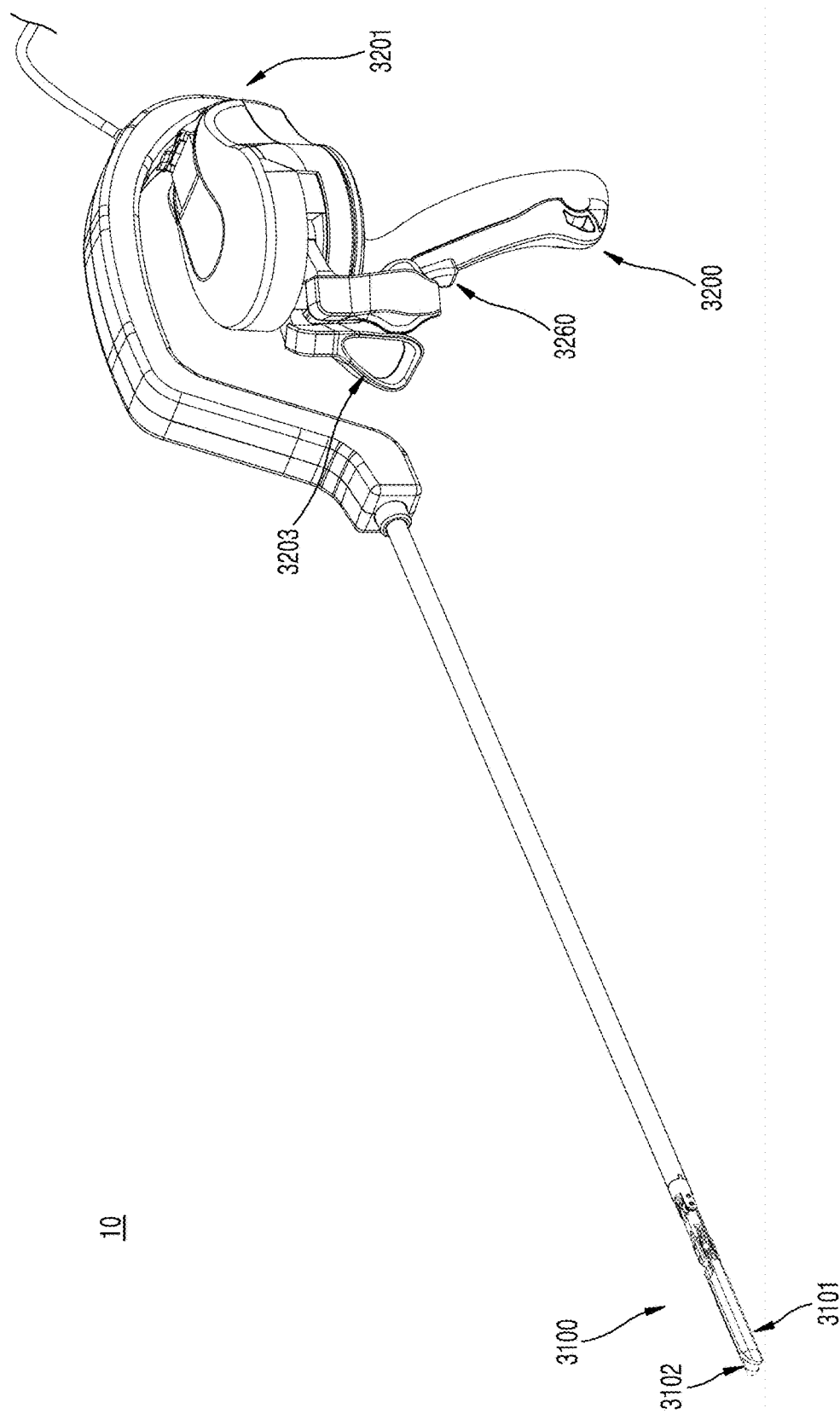
Figure 172:
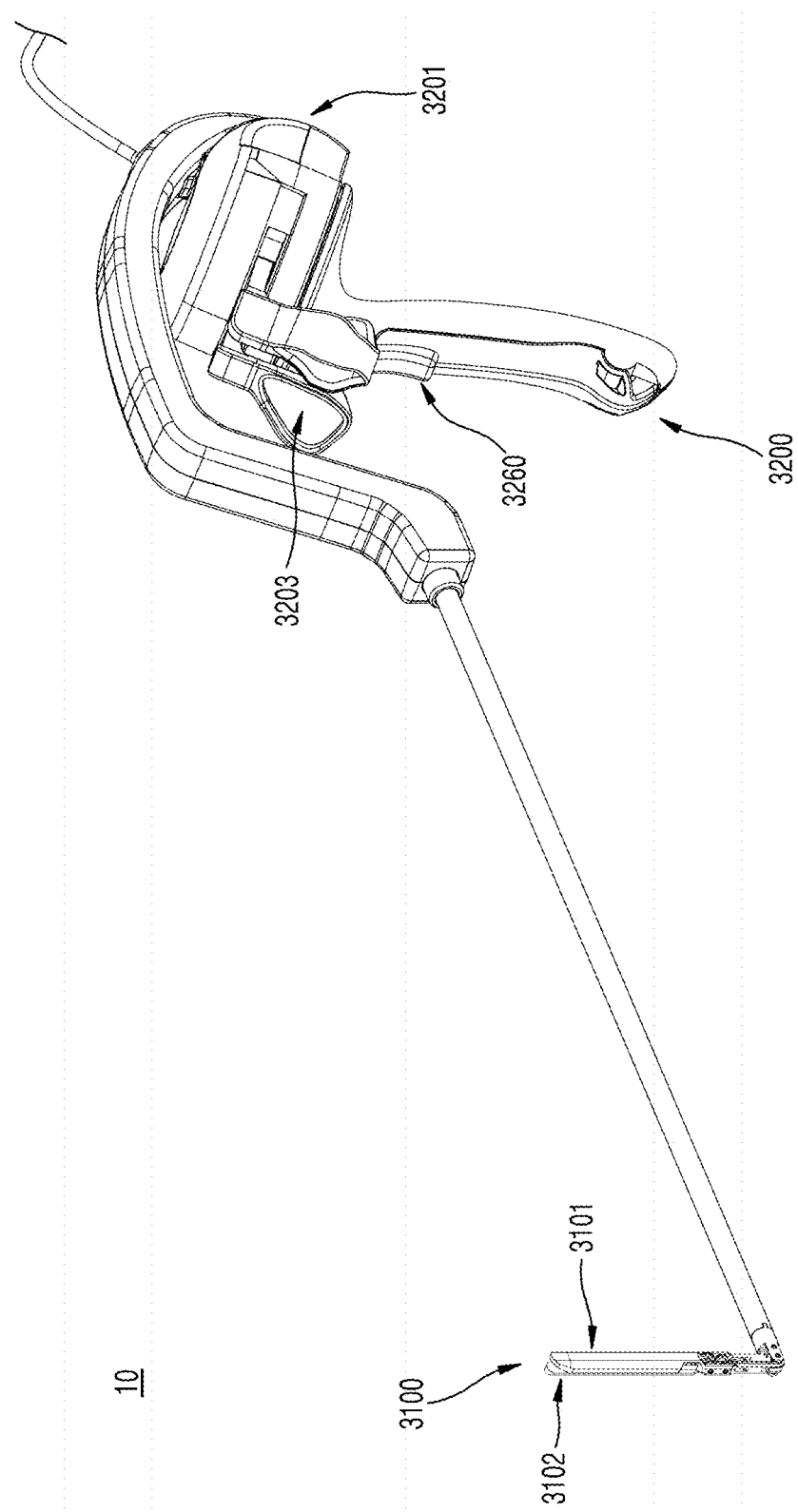
Figure 173:
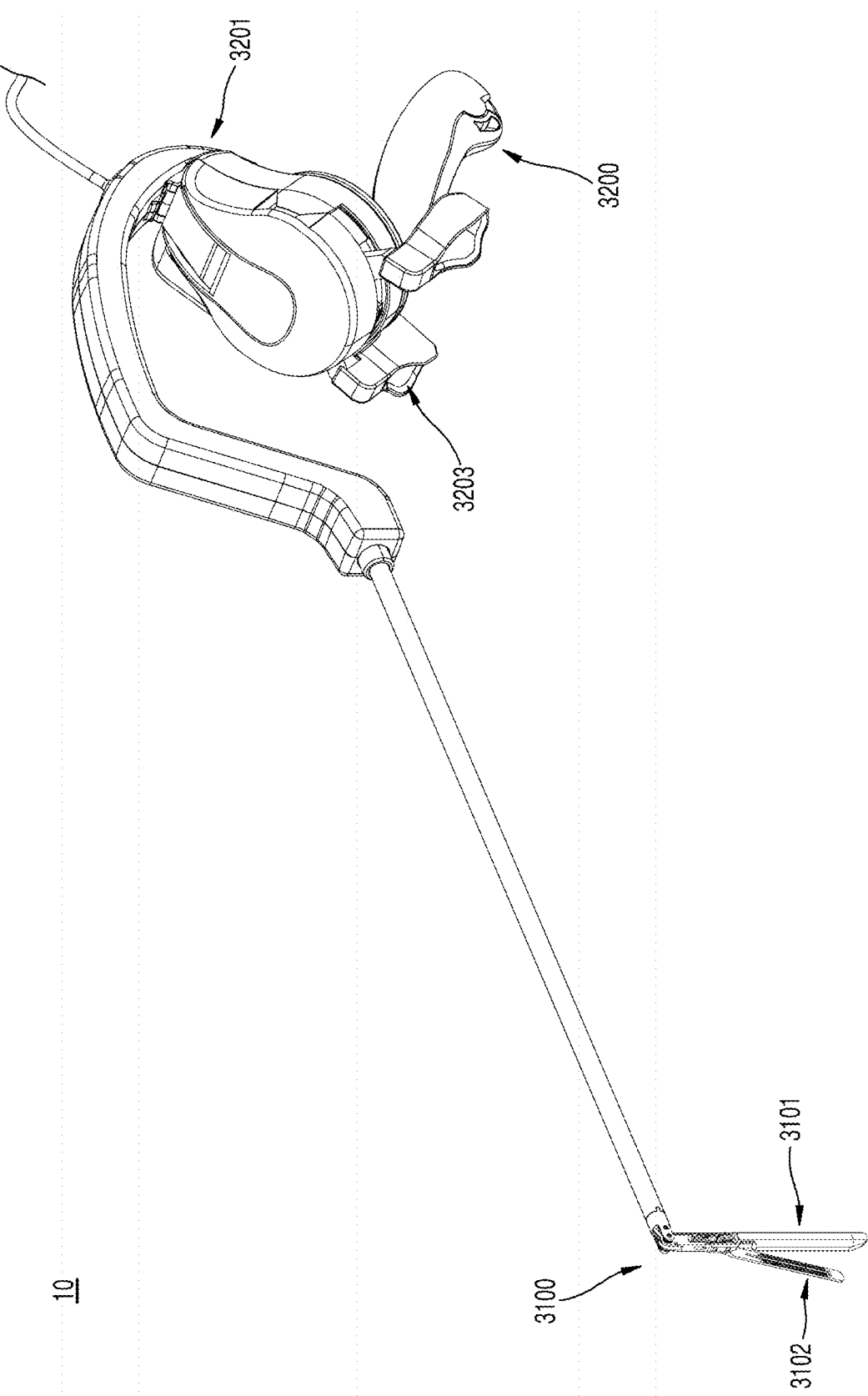
FIGS. 173 and 174 are perspective views illustrating an actuation motion of the surgical instrument of FIG. 114, and are views illustrating a process of performing an actuation motion in a state in which the jaws are pitch-rotated by −90°.
Figure 174:
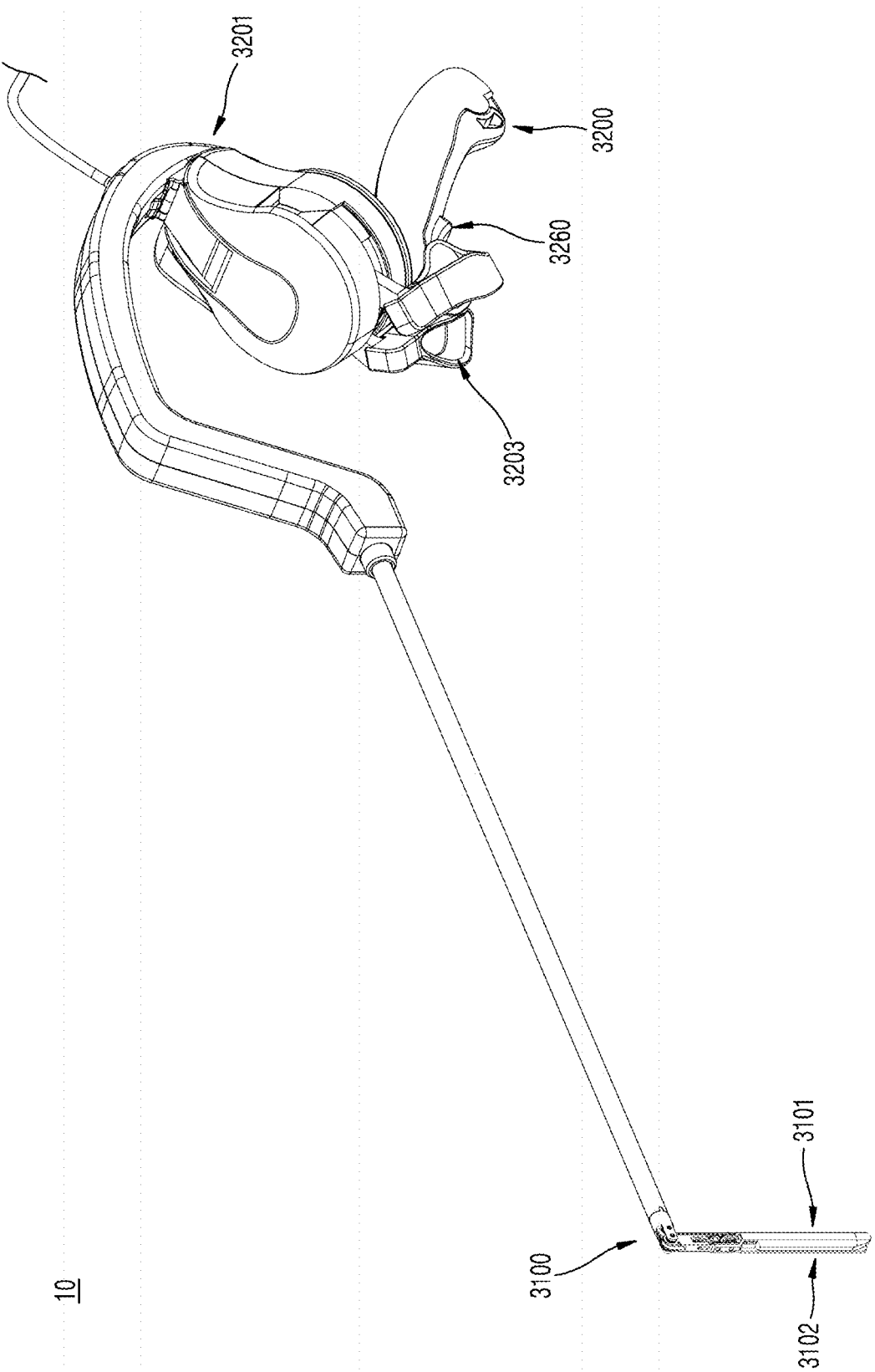

FIGS. 169 and 170 are perspective views illustrating an actuation motion of the surgical instrument of FIG. 114, and are views illustrating a process in which the jaws perform an actuation motion in a neutral state. FIGS. 171 and 172 are perspective views illustrating an actuation motion of the surgical instrument of FIG. 114, and are views illustrating a process of performing an actuation motion in a state in which the jaws are pitch-rotated by −90°. FIGS. 173 and 174 are perspective views illustrating an actuation motion of the surgical instrument of FIG. 114, and are views illustrating a process of performing an actuation motion in a state in which the jaws are pitch-rotated by −90°.

Referring to FIGS. 169 to 174, it can be seen that, in performing a pitch motion, the motions of the manipulation part 3200 and the end tool 3100 are intuitively matched. That is, when the manipulation part 3200 is rotated in a positive (+) direction with respect to the pitch rotation shaft (Y-axis), the end tool 3100 is also rotated in the positive (+) direction with respect to the pitch rotation shaft (Y-axis). In addition, when the manipulation part 3200 is rotated in a negative (−) direction with respect to the pitch rotation shaft (Y-axis), the end tool 3100 is also rotated in the negative (−) direction with respect to the pitch rotation shaft (Y-axis). Here, the rotation angle of the manipulation part 3200 and the rotation angle of the end tool 3100 may be variously set according to the ratio of the pulleys.

In summary, in the surgical instrument 3000 according to an embodiment of the present disclosure, the pulleys are formed on respective joint points (an actuation joint and a pitch joint), the wires (the first staple wire or the second staple wire) are wound around the pulleys, the rotational manipulations (an actuation rotation and a pitch rotation) of the manipulation part cause the movement of each wire, which in turn induces the desired motion of the end tool 3100. Furthermore, the auxiliary pulley may be formed at one side of each of the pulleys, and the wire may not be wound several times around one pulley due to the auxiliary pulley.

First Modified Example of Second Embodiment

Hereinafter, an end tool 3600 of a surgical instrument according to a first modified example of the second embodiment of the present disclosure will be described. Here, the end tool 3600 of the surgical instrument according to the first modified example of the second embodiment of the present disclosure is different from the end tool (see 3100 of FIG. 114 or the like) of the surgical instrument according to the second embodiment of the present disclosure described above in that the configuration of a staple pulley assembly 3680 and a staple link assembly 3670 is different. Hereinafter, the configuration that is different from that of the second embodiment will be described in detail.

Figure 175:
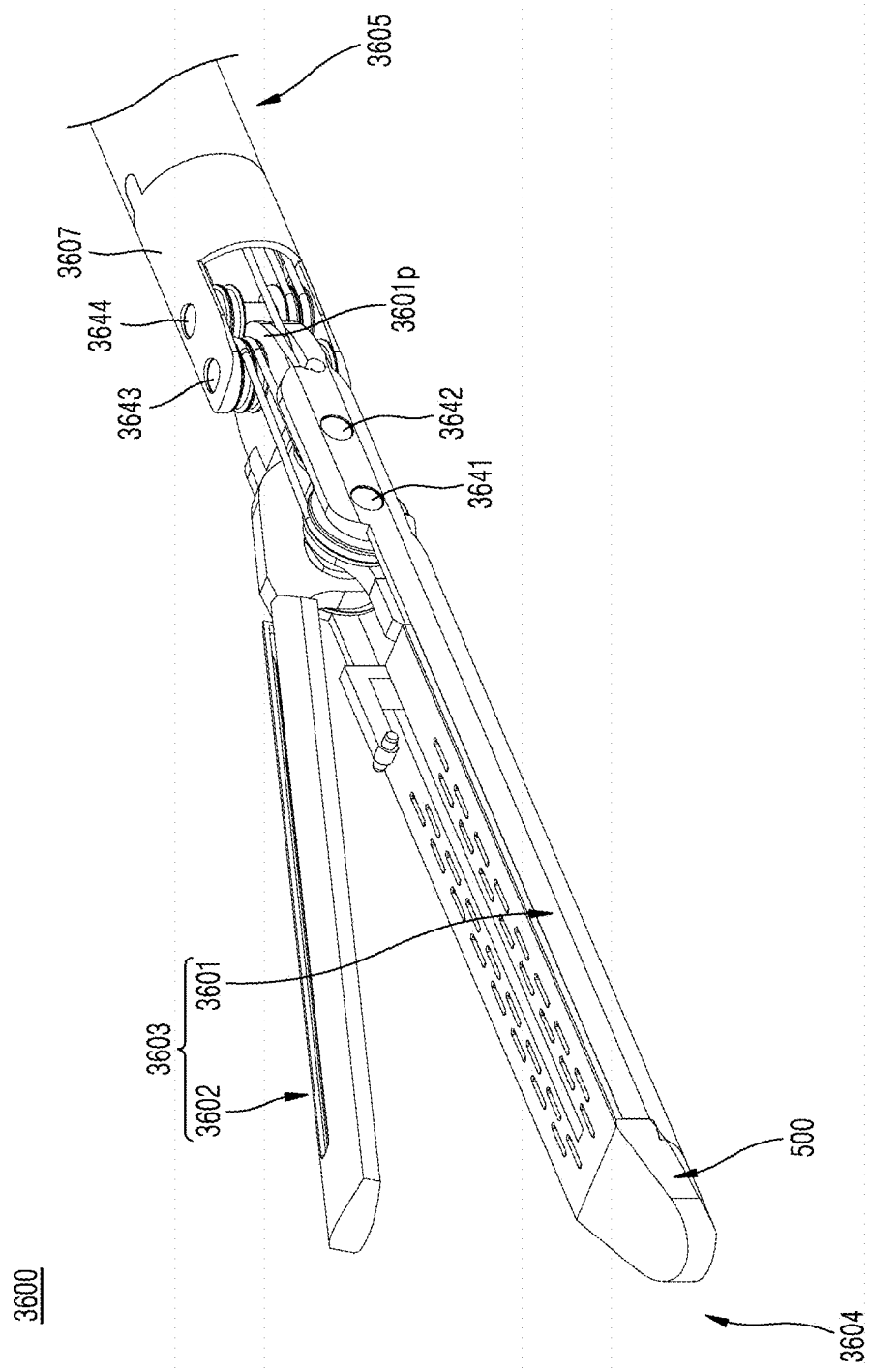
FIGS. 175 and 176 are perspective views illustrating an end tool of a surgical instrument according to a first modified example of the second embodiment of the present disclosure.
Figure 176:
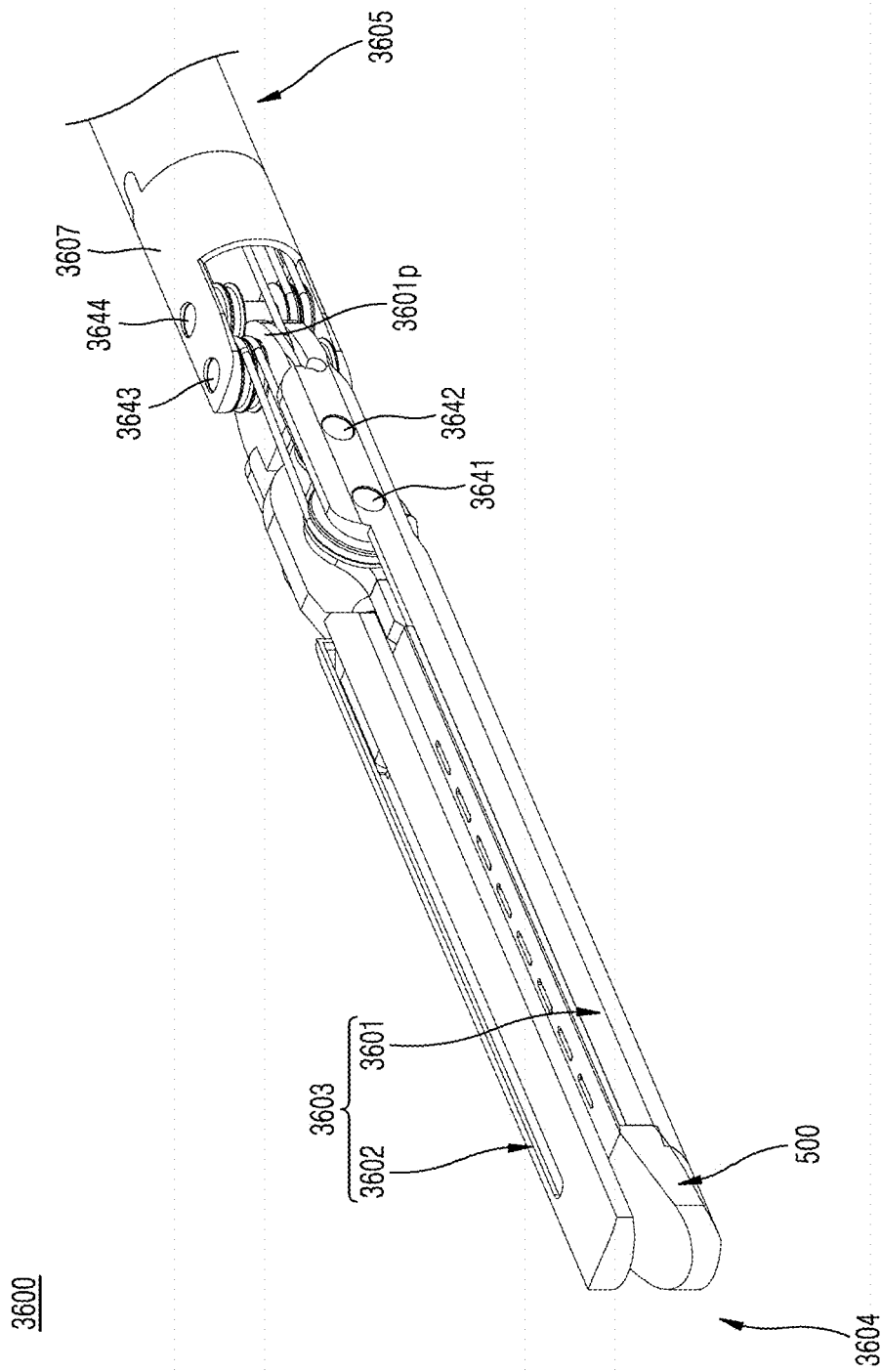
Figure 177:
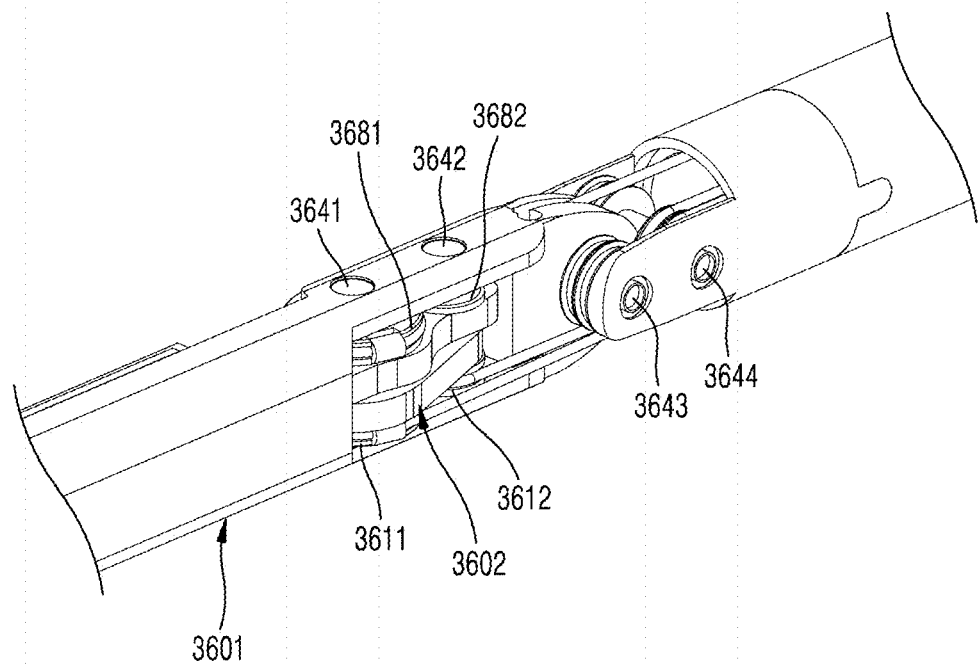
FIGS. 177 and 178 are detailed perspective views illustrating the end tool of FIG. 175.
Figure 178:
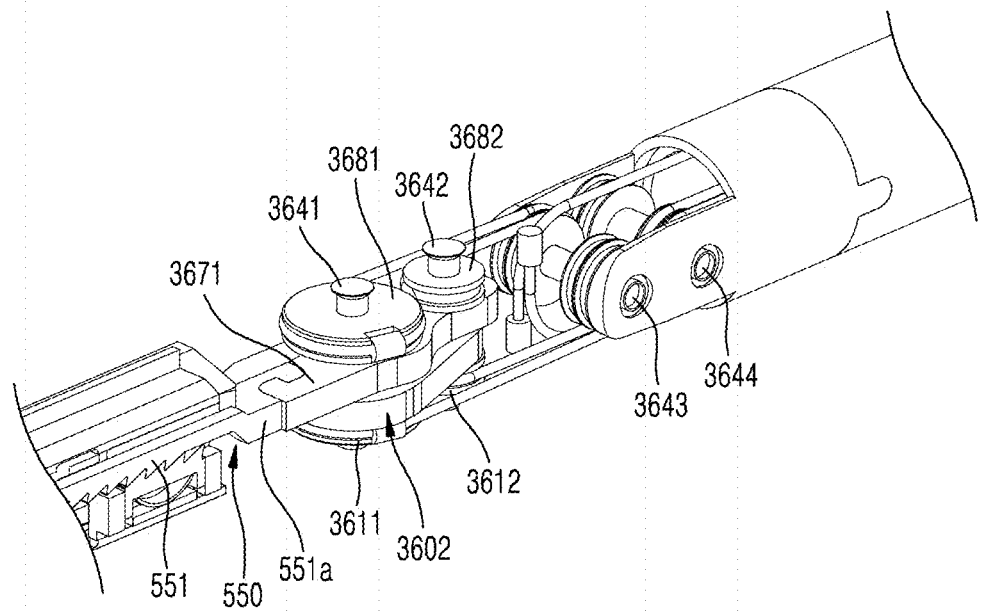
Figure 179:
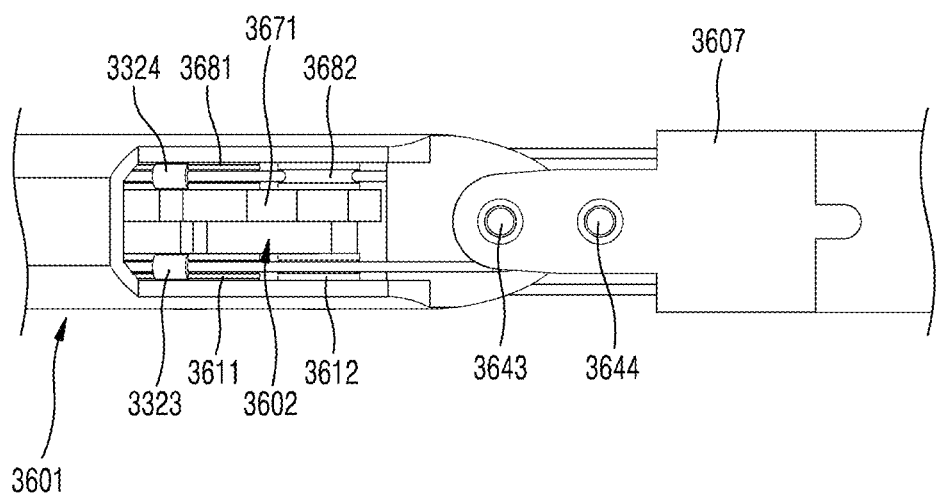
FIG. 179 is a side view illustrating the end tool of FIG. 175.
Figure 180:
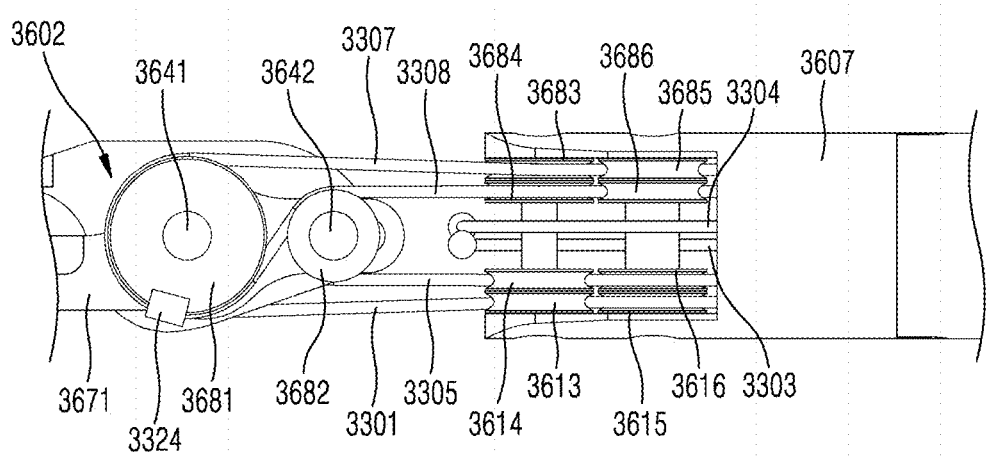
FIG. 180 is a plan view illustrating the end tool of FIG. 175.
Figure 181:
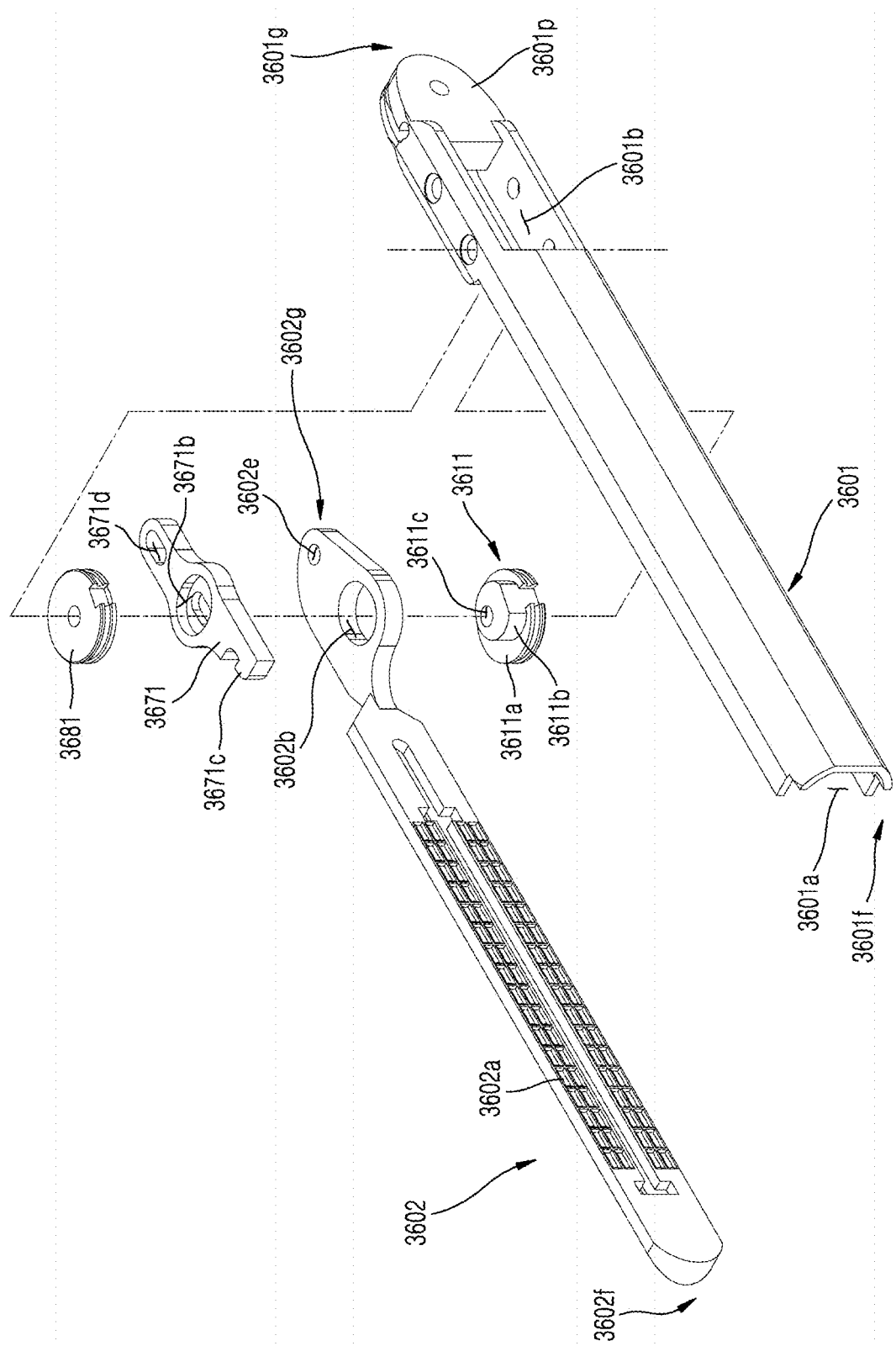
FIG. 181 is an exploded perspective view of the end tool of FIG. 175.
Figure 182:
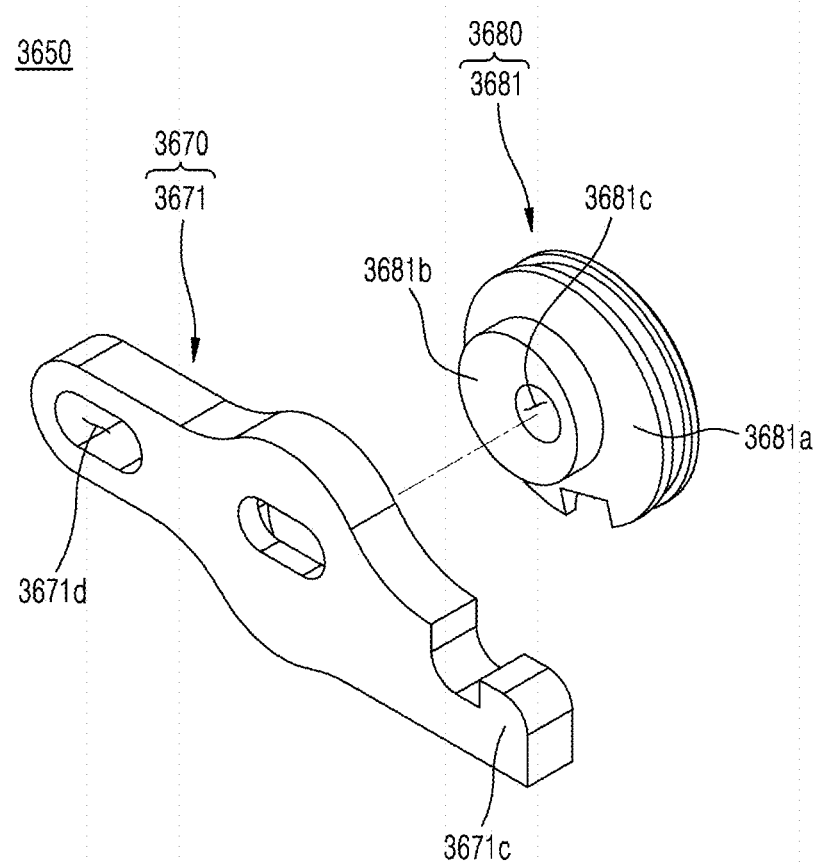
FIG. 182 is an exploded perspective view of a staple pulley and a link member of the end tool of FIG. 181.
Figure 183A:
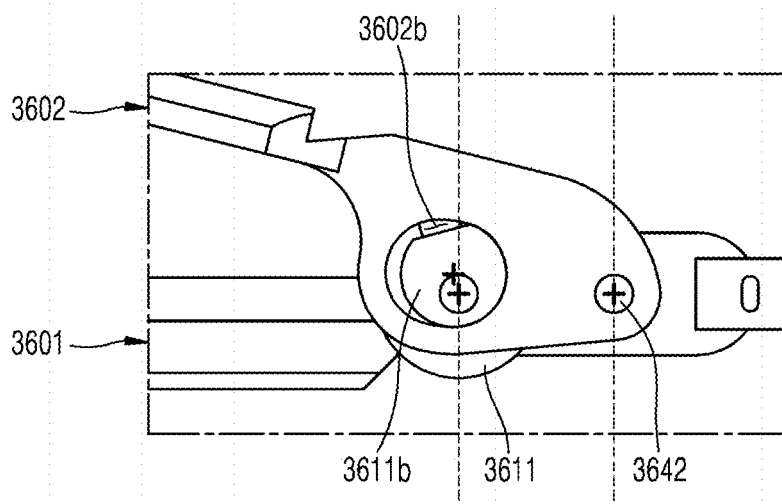
FIGS. 183A to 183C are plan views illustrating motions of a jaw pulley of the end tool of FIG. 175.
Figure 183B:
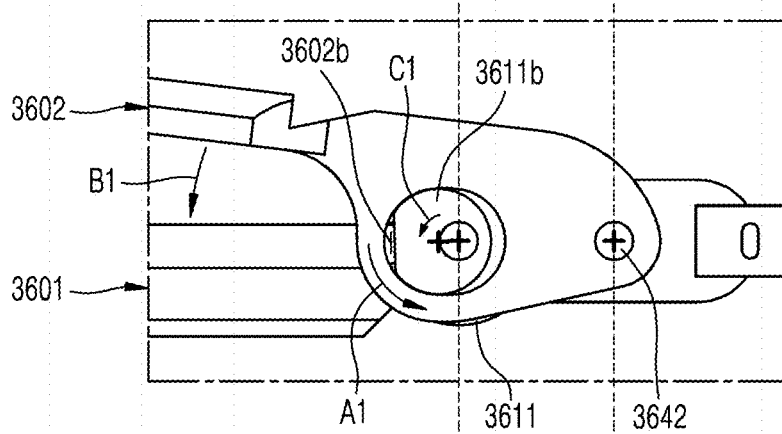
Figure 183C:
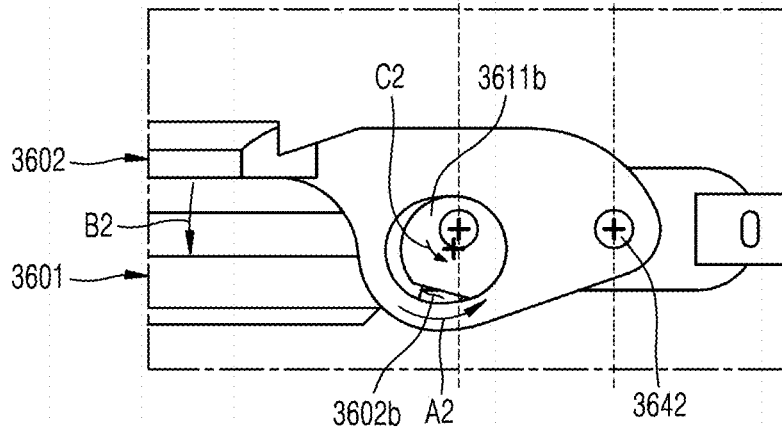
Figure 184A:
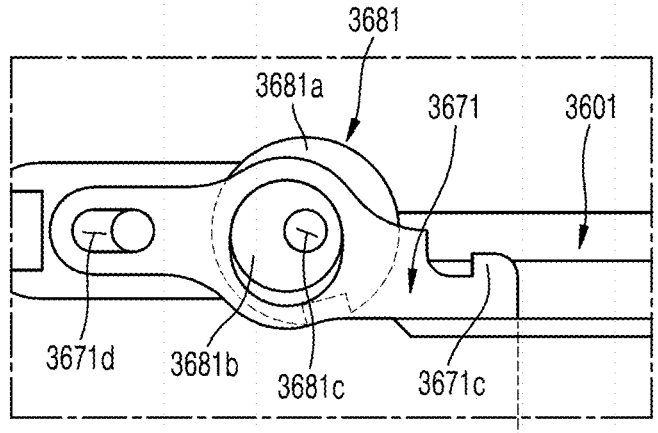
FIGS. 184A to 184C are plan views illustrating motions of the staple pulley of the end tool of FIG. 175.

FIGS. 175 and 176 are perspective views illustrating the end tool of the surgical instrument according to the first modified example of the second embodiment of the present disclosure. FIGS. 177 and 178 are detailed perspective views illustrating the end tool of FIG. 175. FIG. 179 is a side view illustrating the end tool of FIG. 175. FIG. 180 is a plan view illustrating the end tool of FIG. 175. FIG. 181 is an exploded perspective view of the end tool of FIG. 175. FIG. 182 is an exploded perspective view of a staple pulley and a link member of the end tool of FIG. 181. FIGS. 183A to 183C are plan views illustrating motions of a jaw pulley of the end tool of FIG. 175. FIGS. 184A to 183C are plan views illustrating motions of the staple pulley of the end tool of FIG. 175.

Referring to FIGS. 175 to 184C, the surgical instrument according to the first modified example of the second embodiment of the present disclosure includes the end tool 3600, a manipulation part (see 3200 of FIG. 114), a power transmission part (see 3300 of FIG. 120), and a connection part (see 400 of FIG. 114).

Here, the other components except for the end tool 3600 and the power transmission part (see 3300 of FIG. 120) are the same as or similar to those in the second embodiment of the present disclosure described with reference to FIG. 114 or the like, and thus detailed descriptions thereof will be omitted herein.

(Power Transmission Part)

Hereinafter, the power transmission part 3300 of the surgical instrument of FIG. 175 will be described in more detail.

Referring to FIG. 180 or the like, the power transmission part (see 3300 of FIG. 120) of the surgical instrument according to the first modified example of the second embodiment of the present disclosure may include a wire 3303, a wire 3304, a wire 3301, a wire 3305, a wire 3307, and a wire 3308.

Here, the wire 3303 and the wire 3304 may be paired to serve as pitch wires. In addition, the wire 3301 and the wire 3305 may be paired to serve as jaw wires. In addition, the wire 3307 and the wire 33080 may be paired to serve as staple wires.

In addition, the power transmission part 3300 of the surgical instrument 3000 according to an embodiment of the present disclosure may include a coupling member 3321, a coupling member 3322, a coupling member 3323, and a coupling member 3324 that are coupled to respective end portions of the wires to respectively couple the wires and the pulleys. Here, each of the coupling members may have various shapes as necessary, such as a ball shape, a tube shape, and the like.

The coupling relationship between the wires and the coupling members is similar to that in the second embodiment of FIG. 114 described above, and thus detailed descriptions thereof will be omitted herein.

(End Tool-Overall Configuration)

Hereinafter, the end tool 3600 of the surgical instrument of FIG. 175 will be described in more detail.

FIGS. 175 and 176 are perspective views illustrating the end tool of the surgical instrument according to the first modified example of the second embodiment of the present disclosure. FIGS. 177 and 178 are detailed perspective views illustrating the end tool of FIG. 175. FIG. 179 is a side view illustrating the end tool of FIG. 175. FIG. 180 is a plan view illustrating the end tool of FIG. 175.

Here, FIG. 176 illustrates a state in which jaws are closed, and FIG. 175 illustrates a state in which the jaws are opened. In addition, FIG. 177 is a magnified view of FIG. 176, and FIG. 178 illustrates a state in which a first jaw is omitted from FIG. 177.

The end tool 3600 of the first modified example of the second embodiment of the present disclosure includes a pair of jaws 3603 for performing a grip motion, that is, a first jaw 3601 and a second jaw 3602. Here, each of the first jaw 3601 and the second jaw 3602, or a component encompassing the first jaw 3601 and the second jaw 3602 may be referred to as the jaw.

Meanwhile, the end tool 3600 of the first modified example of the second embodiment of the present disclosure may include a pitch hub 3607. A rotation shaft 3643 and a rotation shaft 3644, which will be described later, may be inserted through the pitch hub 3607, and the pitch hub 3607 may be axially coupled to the first jaw 3601 by the rotation shaft 3643. Accordingly, the first jaw 3601 may be formed to be rotatable around the rotation shaft 3643 with respect to the pitch hub 3607.

Further, the pitch hub 3607 may internally accommodate at least some of a pulley 3613, a pulley 3614, a pulley 3683, and a pulley 3684 that are axially coupled to the rotation shaft 3643. In addition, the pitch hub 3607 may internally accommodate at least some of a pulley 3615, a pulley 3616, a pulley 3685, and a pulley 3686 that are axially coupled to the rotation shaft 3644.

Meanwhile, the end tool 3600 of the first modified example of the second embodiment of the present disclosure may include a rotation shaft 3641, a rotation shaft 3642, a rotation shaft 3643, and a rotation shaft 3644. As described above, the rotation shaft 3641 and the rotation shaft 3642 may be inserted through the first jaw 3601, and the rotation shaft 3643 and the rotation shaft 3644 may be inserted through the pitch hub 3607.

The rotation shaft 3641, the rotation shaft 3642, the rotation shaft 3643, and the rotation shaft 3644 may be sequentially disposed from a distal end 3604 of the end tool 3600 toward the proximal end 3605. Accordingly, starting from the distal end 3604, the rotation shaft 3641 may be referred to as a first pin, the rotation shaft 3642 may be referred to as a second pin, the rotation shaft 3643 may be referred to as a third pin, and the rotation shaft 3644 may be referred to as a fourth pin.

Here, the rotation shaft 3641 may function as an end tool pulley rotation shaft, the rotation shaft 3642 may function as an end tool auxiliary pulley rotation shaft, the rotation shaft 3643 may function as an end tool pitch rotation shaft, and the rotation shaft 3644 may function as an end tool pitch auxiliary rotation shaft of the end tool 3600.

Each of the rotation shafts 3641, 3642, 3643, and 3644 may be fitted into one or more pulleys, which will be described in detail below.

(Components Related to Pulley)

Hereinafter, a jaw pulley 3611 and a staple pulley 3681 of the end tool 3600 of the surgical instrument of FIG. 175 will be described in more detail.

Continuing to refer to FIGS. 175 to 180 and the like, the end tool 3600 of the first modified example of the second embodiment of the present disclosure may include the jaw pulley 3611, a jaw auxiliary pulley 3612, the pulley 3613, the pulley 3614, the pulley 3615, and the pulley 3616 related to a rotational motion of the jaw 3603.

In addition, the end tool 3600 of the first modified example of the second embodiment of the present disclosure may include the staple pulley 3681, a staple auxiliary pulley 3682, the pulley 3683, the pulley 3684, the pulley 3685, and the pulley 3686 related to a linear motion/rotational motion of the respective pulleys and links for stapling and cutting.

The jaw pulley 3611 and the staple pulley 3681 are formed to be rotatable independently of each other around the rotation shaft 3641 that is an end tool pulley rotation shaft.

Here, in the present disclosure, the jaw pulley 3611 and the staple pulley 3681 are formed to rotate around substantially the same shaft. As such, by forming the jaw pulley 3611 and the staple pulley 3681 to rotate around the same shaft, it is possible to perform a pitch motion/actuation motion while also performing stapling and cutting motions. This will be described in more detail later. However, here, although the jaw pulley 3611 and the staple pulley 3681 are illustrated in the drawings as being formed to rotate around one rotation shaft 3641. it is of course possible that each pulley may be formed to be rotatable around a separate shaft that is concentric therewith.

The jaw auxiliary pulley 3612 may be further provided on one side of the jaw pulley 3611, in other words, the jaw auxiliary pulley 3612 may be disposed between the jaw pulley 3611 and the pulley 3613/pulley 3614. The jaw auxiliary pulley 3612 may be formed to be rotatable around the rotation shaft 3642.

Meanwhile, the pulleys 3613 and 3614 may function as first pitch main pulleys, and the pulleys 3615 and 3616 may function as second pitch sub-pulleys.

The staple auxiliary pulley 3682 may be further provided on one side of the staple pulley 3681. In other words, the staple auxiliary pulley 3682 may be disposed between the staple pulley 3681 and the pulley 3683/pulley 3684. The staple auxiliary pulley 3682 may be formed to be rotatable independently of the jaw auxiliary pulley 3612 around the rotation shaft 3642.

Here, the jaw auxiliary pulley 3612 and the staple auxiliary pulley 3682 are illustrated in the drawings as being formed to rotate around one rotation shaft 3642, but each of the jaw auxiliary pulley 3612 and the staple auxiliary pulley 3682 may be formed to be rotatable around a separate shaft. Such a staple auxiliary pulley will be described in more detail below.

Meanwhile, the pulleys 3683 and 3684 may function as first pitch main pulleys, and the pulleys 3685 and 3686 may function as second pitch sub-pulleys.

Hereinafter, the jaw auxiliary pulley 3612 will be described in more detail.

The jaw auxiliary pulley 3612 may serve to increase a rotation angle of the jaw pulley 3611 by being in contact with the wire 3305, which is a jaw wire, to change an arrangement path of the wire 3305 to a certain extent.

In detail, in the case of the end tool 3600 of the surgical instrument of the present disclosure, the jaw auxiliary pulley 3612 is additionally disposed on one side of the jaw pulley 3611. As such, by changing the arrangement path of the wire 3305, which is a jaw wire, to a certain extent by disposing the jaw auxiliary pulley 3612, a tangential direction of the wire 3305 is changed, so that the rotation angle of the coupling member 3323 configured to couple the wire 3305 to the jaw pulley 3611 is increased. That is, the coupling member 3323, which is a coupling part of the wire 3305 and the jaw pulley 3611, is rotatable until the coupling member 3323 is located on a common internal tangent of the jaw pulley 3611 and the jaw auxiliary pulley 3612.

In other words, the wire 3305 is located on the internal tangent of the jaw pulley 3611 and the jaw auxiliary pulley 3612, and the rotation angle of the jaw pulley 3611 is increased by the jaw auxiliary pulley 3612.

According to the present disclosure, as a rotation radius of the jaw pulley 3611 increases, a yaw motion range in which normal stapling and cutting motions are performed may be increased Hereinafter, components related to the rotation of the jaw pulley 3611 will be described. The pulleys 3613 and 3614 function as first pitch main pulleys. Here, the wire 3301, which is a jaw wire, is wound around the pulley 3613, and the wire 3305, which is a jaw wire, is wound around the pulley 3614.

The pulleys 3615 and 3616 function as first pitch sub-pulleys. Here, the wire 3301, which is a jaw wire, is wound around the pulley 3615, and the wire 3305, which is a jaw wire, is wound around the pulley 3616.

Here, the pulley 3613 and the pulley 3614 are disposed on one side of the jaw pulley 3611 and the jaw auxiliary pulley 3612 to face each other. Here, the pulley 3613 and the pulley 3614 are formed to be rotatable independently of each other around the rotation shaft 3643 that is an end tool pitch rotation shaft. In addition, the pulley 3615 and the pulley 3616 are disposed on one side of the pulley 3613 and one side of the pulley 3614, respectively, to face each other. Here, the pulley 3615 and the pulley 3616 are formed to be rotatable independently of each other around the rotation shaft 3644 that is an end tool pitch auxiliary rotation shaft. Here, in the drawings, it is illustrated that the pulley 3613, the pulley 3615, the pulley 3614, and the pulley 3616 are all formed to be rotatable around the Y-axis direction, but the concept of the present disclosure is not limited thereto, and the rotation shafts of the respective pulleys may be formed in various directions according to configurations thereof.

As described above, the rotation shaft 3641, the rotation shaft 3642, the rotation shaft 3643, and the rotation shaft 3644 may be sequentially disposed from the distal end 3604 of the end tool 3600 toward the proximal end 3605. Accordingly, the jaw pulley 3611, the jaw auxiliary pulley 3612, the pulley 3613/pulley 3614, and the pulley 3615/pulley 3616 may be sequentially disposed from the distal end 3604 of the end tool 3600 toward the proximal end 3605.

The wire 3301, which is a jaw wire, is sequentially wound to make contact with at least portions of the pulley 3615, the pulley 3613, and the jaw pulley 3611. In addition, the wire 3305 connected to the wire 3301 by the coupling member 3323 is sequentially wound to make contact with at least portions of the jaw pulley 3611, the jaw auxiliary pulley 3612, the pulley 3614, and the pulley 3616.

From another perspective, the wires 3301 and 3305, which are jaw wires, are sequentially wound to make contact with at least portions of the pulley 3615, the pulley 3613, the jaw pulley 3611, the jaw auxiliary pulley 3612, the pulley 3614, and the pulley 3616, and are formed to move along the above pulleys while rotating the above pulleys.

Accordingly, when the wire 3301 is pulled, the coupling member 3323 to which the wire 3301 is coupled and the jaw pulley 3611 coupled coupling member 3323 are rotated in one direction. In contrast, when the wire 3305 is pulled, the coupling member 3323 to which the wire 3305 is coupled and the jaw pulley 3611 coupled to the coupling member 3323 are rotated in a direction opposite to the one direction.

Meanwhile, the staple pulley 3681, the staple auxiliary pulley 3682, and the components related thereto, such as the pulley 3683, the pulley 3684, the pulley 3685, the pulley 3686, the wire 3307, the wire 3308, and the like, may have the same or similar configurations as the components related to the jaw pulley 3611 described above.

In detail, the pulleys 3683 and 3684 function as second pitch main pulleys. Here, the wire 3307, which is a staple wire, is wound around the pulley 3683, and the wire 3308, which is the staple wire, is wound around the pulley 3684.

The pulleys 3685 and 3686 function as second pitch sub-pulleys. Here, the wire 3307, which is a staple wire, is wound around the pulley 3685, and the wire 3308, which is a staple wire, is wound around the pulley 3686.

Here, the pulley 3683 and the pulley 3684 are disposed on one side of the staple pulley 3681 and the staple auxiliary pulley 3682 to face each other. Here, the pulley 3683 and the pulley 3684 are formed to be rotatable independently of each other around the rotation shaft 3643 that is an end tool pitch rotation shaft. In addition, the pulley 3685 and the pulley 3686 are disposed on one side of the pulley 3683 and one side of the pulley 3684, respectively, to face each other. Here, the pulley 3685 and the pulley 3686 are formed to be rotatable independently of each other around the rotation shaft 3644 that is an end tool pitch auxiliary rotation shaft. Here, in the drawings, it is illustrated that the pulley 3683, the pulley 3685, the pulley 3684, and the pulley 3686 are all formed to be rotatable around the Y-axis direction, but the concept of the present disclosure is not limited thereto, and the rotation shafts of the respective pulleys may be formed in various directions according to configurations thereof.

As described above, the rotation shaft 3641, the rotation shaft 3642, the rotation shaft 3643, and the rotation shaft 3644 may be sequentially disposed from the distal end 3604 of the end tool 3600 toward the proximal end 3605. Accordingly, the staple pulley 3681, the staple auxiliary pulley 3682, the pulley 3683/pulley 3684, and the pulley 3685/pulley 3686 may be sequentially disposed from the distal end 3604 of the end tool 3600 toward the proximal end 3605.

The wire 3307, which is a staple wire, is sequentially wound to make contact with at least portions of the pulley 3685, the pulley 3683, and the staple pulley 3681. In addition, the wire 3308 connected to the wire 3307 by the coupling member 3324 is sequentially wound to make contact with at least portions of the first staple pulley 3681, the staple auxiliary pulley 3682, the pulley 3684, and the pulley 3686.

From another perspective, the wires 3307 and 3308, which are first staple wires, are sequentially wound to make contact with at least portions of the pulley 3685, the pulley 3683, the first staple pulley 3681, the staple auxiliary pulley 3682, the pulley 3684, and the pulley 3686, and are formed to move along the above pulleys while rotating the above pulleys.

Accordingly, when the wire 3308 is pulled, the coupling member 3324, to which the wire 3308 is coupled, and the staple pulley 3681 coupled to the coupling member 3324 are rotated in one direction. In contrast, when the wire 3307 is pulled, the coupling member 3324, to which the wire 3307 is coupled, and the staple pulley 3681 coupled to the coupling member 3324 are rotated in a direction opposite to the one direction.

(First and Second Jaws and Actuation Motion)

Hereinafter, a coupling structure of the first jaw 3601 and the second jaw 3602 of the end tool 3600 of the surgical instrument of FIG. 175 will be described in more detail.

FIG. 181 is an exploded perspective view of the end tool of FIG. 175. FIG. 182 is an exploded perspective view of the staple pulley and the link member of the end tool of FIG. 181. FIGS. 183A to 183C are plan views illustrating motions of the jaw pulley of the end tool of FIG. 175.

Referring to FIGS. 181 to 183C and the like, the jaw pulley 3611 may include a body 3611a, a protruding member 3611b, and a shaft pass-through part 3611c.

In detail, the body 3611a is formed in the shape of a disk. The shaft pass-through part 3611c may be formed in a center portion of the body 3611a. The shaft pass-through part 3611c is formed in the form of a hole, and the rotation shaft 3641, which is an end tool pulley rotation shaft, may be inserted through the shaft pass-through part 3611c.

In addition, the protruding member 3611b may be formed in the body 3611a of the jaw pulley 3611. The protruding member 3611b may be coupled to a jaw pulley coupling hole 3602b of the second jaw 3602. Here, the center of the protruding member 3611b may not coincide with the center of the jaw pulley 3611, and the protruding member 3611b may be formed to be eccentric to a certain extent with respect to the jaw pulley 3611.

The first jaw 3601 includes a cartridge accommodation part 3601a, a staple assembly accommodation part 3601b, and a pitch pulley part 3601p.

The first jaw 3601 is formed in the shape of an elongated bar as a whole, and a cartridge 500 is accommodated in the first jaw 3601 at a distal end 3601f side. In other words, the first jaw 3601 may be formed entirely in the form of a hollow box with one surface (upper surface) thereof is removed, such that the cartridge accommodation part 3601a capable of accommodating the cartridge 500 may be formed inside the first jaw 3601. That is, the first jaw 3601 may be formed in an approximately "U" shape in cross section.

In addition, the first pitch pulley part 3601p, which serves as an end tool pitch pulley, is formed on a proximal end 3601g of the first jaw 3601, so that the first jaw 3601 is formed to be rotatable around the rotation shaft 3643. Here, the pitch pulley part 3601p may be formed to be approximately parallel to a plane perpendicular to the third rotation shaft 3643 which is a pitch rotation shaft.

In detail, the pitch pulley part 3601p, which is formed in the shape of a disk such as the pulley and has an outer circumferential surface in which a groove around which the wire may be wound is formed, may be formed in one end portion of the first jaw 3601. The wires 3303 and 3304 described above are coupled to the pitch pulley part 3601p serving as an end tool pitch pulley, and a pitch motion is performed as the first jaw 3601 is rotated around the third rotation shaft 3643.

Meanwhile, although it is illustrated in the drawing that the pitch pulley part 3601p is integrally formed with the first jaw 3601 as one body, the pitch pulley part may be formed as a separate member from the first jaw 3601 and coupled to the first jaw 3601.

Meanwhile, a through hole is formed in the pitch pulley part 3601p to allow the third rotation shaft 3643 to pass through the pitch pulley part 3601p.

Meanwhile, the staple assembly accommodation part 3601b configured to accommodate a staple drive assembly 3650 including the staple link assembly 3670 and the staple pulley assembly 3680 may be formed at one side of the cartridge accommodation part 3601a of the first jaw 3601, for example, at the proximal end 3601g side. The staple assembly accommodation part 3601b may serve as a kind of end tool hub.

In detail, shaft pass-through parts may be formed in the staple assembly accommodation part 3601b so that the rotation shaft 3641 and the rotation shaft 3642 may be inserted therethrough. In addition, a link member 3671 of the staple link assembly 3670 may be disposed in the staple assembly accommodation part 3601b. In addition, the staple pulley 3681 of the staple pulley assembly 3680 may be disposed in the staple assembly accommodation part 3601b. In addition, the staple auxiliary pulley 3682 of the staple pulley assembly 3680 may be disposed in the staple assembly accommodation part 3601b.

The second jaw 3602 includes an anvil 3602a, the jaw pulley coupling hole 3602b, and a shaft pass-through part 3602c.

The second jaw 3602 is formed in the shape of an elongated bar as a whole, the anvil 3602a is formed at a distal end 3602f side, and the rotation shaft 3642 is inserted through a proximal end 3602g, so that the second jaw 3602 is formed to be rotatable around the rotation shaft 3642.

In detail, the anvil 3602a is formed in the form of a flat plane, on one surface of which shapes corresponding to the shapes of staples (see 530 of FIG. 135) may be formed. The anvil 3602a may serve as a support for supporting the staple (see 530 of FIG. 135) at an opposite side of an operation member 540 when the operation member (see 540 of FIG. 135) pushes and raises the staple (see 530 of FIG. 135) during a stapling motion, so that the staple (see 530 of FIG. 135) is bent.

Meanwhile, the jaw pulley coupling hole 3602b is formed in a region adjacent to the proximal end 3602g of the second jaw 3602. Here, the jaw pulley coupling hole 3602b is formed in the form of an eccentric hole, into which the protruding member 3611b of the jaw pulley 3611 may be fitted. The jaw pulley coupling hole 3602b is formed to have a predetermined curvature and may be formed in an approximately elliptical shape. At this time, the jaw pulley coupling hole 3602b may be formed to be larger than the protruding member 3611b by a certain extent. Thus, the jaw pulley coupling hole 3602b is formed so that the protruding member 3611b is movable to a certain extent in the jaw pulley coupling hole 3602b in a state in which the protruding member 3611b of the jaw pulley 3611 is fitted into the jaw pulley coupling hole 3602b of the second jaw 3602.

As described above, the protruding member 3611b may be formed to be eccentric to a certain extent with respect to the center of the jaw pulley 3611. Thus, when the jaw pulley 3611 is rotated, the protruding member 3611b, while in contact with the jaw pulley coupling hole 3602b, may push the jaw pulley coupling hole 3602b to rotate the second jaw 3602. That is, when the jaw pulley 3611 is rotated, the protruding member 3611b, while in contact with the jaw pulley coupling hole 3602b, may be moved in the jaw pulley coupling hole 3602b, which causes the second jaw 3602 is rotated around the rotation shaft 3642.

Meanwhile, the shaft pass-through part 3602e may be formed in the form of a hole at one side of the jaw pulley coupling hole 3602b, and the rotation shaft 3642, which is a jaw rotation shaft, may be inserted through the shaft pass-through part 3602c.

The coupling relationship between the components described above is as follows.

The rotation shaft 3641, which is an end tool pulley rotation shaft, is sequentially inserted through the first jaw 3601, a shaft pass-through part 3681c of the staple pulley 3681, a slot 3671b of the link member 3671, the shaft pass-through part 3611c of the jaw pulley 3611 coupled to the jaw pulley coupling hole 3602b of the second jaw 3602, and the first jaw 3601.

The rotation shaft 3642, which is a jaw rotation shaft, is sequentially inserted through the first jaw 3601, the staple auxiliary pulley 3682, a guide groove 3671d of the link member 3671, the shaft pass-through part 3602e of the second jaw 3602, the jaw auxiliary pulley 3612, and the first jaw 3601.

Hereinafter, the rotation of the second jaw 3602 according to the rotation of the jaw pulley 3611 will be described.

Referring to FIGS. 183A to 183C and the like, in the first modified example of the second embodiment of the present disclosure, the jaw pulley 3611 and the second jaw 3602 are coupled to each other in the form of a cam-slot. That is, the cam-shaped protruding member 3611b formed on the jaw pulley 3611 is coupled to the slot-shaped jaw pulley coupling hole 3602b formed in the second jaw 3602. Thus, as shown in FIG. 183B, when the jaw pulley 3611 is rotated in the direction of an arrow A1, the second jaw 3602 is rotated in the direction of an arrow B1 around the rotation shaft 3642. Here, as shown in FIG. 184C, when the jaw pulley 3611 is further rotated in the direction of an arrow A2, an actuation motion or a grip motion is performed as the second jaw 3602 is further rotated in the direction of an arrow B2 around the rotation shaft 3642.

Here, in the end tool 3600 according to the first modified example of the second embodiment of the present disclosure, when the first jaw 3601 and the second jaw 3602 are rotated in directions close to each other (i.e., when the first jaw 3601 and the second jaw 3602 are closed), a grip force in a direction in which the first jaw 3601 and the second jaw 3602 are closed is further increased.

That is, when the jaw pulley 3611 is rotated in a state in which the rotation shaft 3641 and the rotation shaft 3642 are fixed in position, a central axis of the cam-shaped eccentric protruding member 3611b formed on the jaw pulley 3611 sequentially moves in the directions of arrows C1 and C2, and thus the grip force in the direction in which the second jaw 3602 is closed is further increased.

With this configuration, the grip force becomes greater when the second jaw 3602 is closed with respect to the first jaw 3601, thereby enabling a surgical operator to perform the actuation motion powerfully even with a small force.

(Staple Drive Assembly and Stapling Motion)

Hereinafter, the staple drive assembly 3650 will be described in more detail.

Continuing to refer to FIGS. 175 to 184 and the like, the staple drive assembly 3650 may include the staple pulley assembly 3680 and the staple link assembly 3670. Here, the staple drive assembly 3650 is connected to a reciprocating assembly 550 of the cartridge 500, and converts a rotational motion of the staple pulley assembly 3680 into a linear motion of the reciprocating assembly 550. In other embodiments of the present disclosure, which will be described later, the staple drive assembly may be understood as a concept including the staple pulley assembly and the staple link assembly.

The staple pulley assembly 3680 may include one or more staple pulleys. The staple pulley assembly 3680 may be formed in the staple assembly accommodation part 3601b of the first jaw 3601. In the present embodiment, it is assumed that the staple pulley assembly 3680 includes one staple pulley 3681.

The staple link assembly 3670 may include one or more link members 3671. In addition, the link member 3671 may include one or more links. In the first modified example of the second embodiment of the present disclosure, it is assumed that the staple link assembly 3670 includes one link member 3671, and the link member 3671 includes one link.

Here, in the end tool 3600 of the surgical instrument according to the present disclosure, the staple pulley assembly 3680 and the staple link assembly 3670 form a cam-slot structure. In addition, with such a structure, a force for moving the reciprocating assembly 550 forward may be amplified.

In detail, the staple pulley assembly 3680 may include the staple pulley 3681.

The staple pulley 3681 may include a body 3681a, the protruding member 3681b, and the shaft pass-through part 3681c.

The body 3681a is formed in the shape of a disk.

The shaft pass-through part 3681c may be formed in a center portion of the body 3681a. The shaft pass-through part 3681c may be formed in the form of a hole, and the rotation shaft 3641, which is an end tool pulley rotation shaft, may be inserted through the shaft pass-through part 3681c.

In addition, the protruding member 3681b may be formed in the body 3681a of the staple pulley 3681. The protruding member 3681b may be coupled to the link member 3671 of the staple link assembly 3670. Here, the center of the protruding member 3681b may not coincide with the center of the staple pulley 3681, and the protruding member 3681b may be formed to be eccentric to a certain extent with respect to the staple pulley 3681. The protruding member 3681b may be fitted into the slot 3671b of the link member 3671 to be described later.

Meanwhile, the end tool 3600 of the present disclosure may further include the staple link assembly 3670 connected to the staple pulley assembly 3680, and the staple link assembly 3670 may include the link member 3671. Here, the staple link assembly 3670 may serve to connect the staple pulley assembly 3680 to the reciprocating assembly 550 of the cartridge 500.

In the present embodiment, the staple link assembly 3670 includes one link member 3671, and the link member 3671 includes only one link. That is, by coupling the staple pulley assembly 3680 and the staple link assembly 3670 by a cam-slot structure, it is possible to convert a rotational motion of the staple pulley assembly 3680 into a linear motion of the staple link assembly 3670 even when the staple link assembly 3670 includes only one link.

In detail, the link member 3671 may be formed as a single link.

The link member 3671 may be formed in the form of an elongated bar. Here, the link member 3671 may include the guide groove 3671d, the slot 3671b, and a coupling part 3671c.

In detail, the coupling part 3671c may be formed at one end portion of the link member 3671. The coupling part 3671c may be coupled to a coupling part 551a of a reciprocating member 551 of the cartridge 500.

Meanwhile, the guide groove 3671d may be formed at an end portion of the link member 3671 opposite to the one end portion at which the coupling part 3671c is formed. The rotation shaft 3642 may be inserted through the guide groove 3671d, and when the staple pulley 3681 is rotated, the link member 3671 may be linearly moved along the guide groove 3671d. This will be described in more detail later.

Meanwhile, the slot 3671b may be formed in one region of a central portion of the link member 3671.

In detail, the slot 3671b may be formed in a surface of the link member 3671 facing the staple pulley 3681. Here, the slot 3671b is formed in the form of an eccentric hole, into which the protruding member 3681b of the staple pulley 3681 may be fitted. The slot 3671b is formed to have a predetermined curvature and may be formed in an approximately elliptical shape. Here, the slot 3671b may be formed to be larger than the protruding member 3681b by a certain extent. Thus, the protruding member 3681b is formed to be movable to a certain extent in the slot 3671b in a state in which the protruding member 3681b of the staple pulley 3681 is fitted into the slot 3671b of the link member 3671.

As described above, the protruding member 3681b may be formed to be eccentric to a certain extent with respect to the center of the staple pulley 3681. Thus, when the staple pulley 3681 is rotated, the link member 3671, while in contact with the slot 3671b, may push the slot 3671b to move the link member 3671. That is, when the staple pulley 3681 is rotated, the protruding member 3681b, while in contact with the slot 3671b, is moved in the slot 3671b, which causes the link member 3671 to be linearly moved along a link guide groove 3601c of the first jaw 3601.

Here, the slot 3671b may be formed to not pass through the entire thickness of the link member 3671 but to pass through only a portion of the entire thickness of the link member 3671. In this case, the slot 3671b may be formed to have a thickness substantially the same as a thickness of the protruding member 3681b of the staple pulley 3681.

Hereinafter, the motion and displacement of the staple link assembly 3670 according to the rotation of the staple pulley 3681 will be described.

Figure 184B:
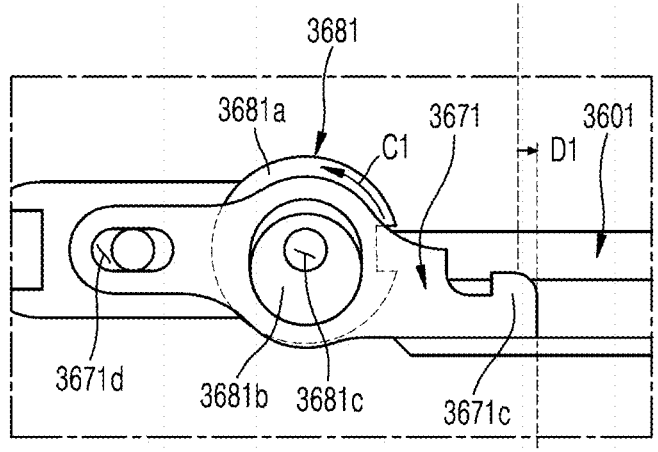
Figure 184C:
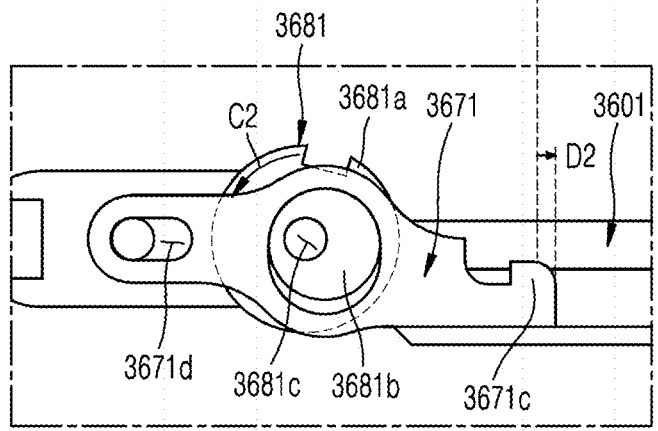

Referring to FIGS. 184A to 184C or the like, in the first modified example of the second embodiment of the present disclosure, the staple pulley 3681 and the staple link assembly 3670 are coupled in the form of a cam-slot. That is, the cam-shaped protruding member 3681b formed on the staple pulley 3681 is coupled to the slot 3671b formed in the link member 3671. Thus, as shown in FIG. 184B, when the staple pulley 3681 is rotated in the direction of an arrow C1, a displacement of the staple link assembly 3670 in the X-axis direction becomes D1. Here, as shown in FIG. 184C, when the staple pulley 3681 is further rotated in the direction of an arrow C2, the displacement of the staple link assembly 3670 in the X-axis direction becomes D2.

When the staple pulley and the staple link assembly are coupled in a link-shaft manner rather than a cam-slot manner as compared with the above case, the displacement of the staple link assembly in the X-axis direction is much longer than that in the first modified example of the second embodiment of the present disclosure.

In other words, as compared to the case in which the staple pulley and the staple link assembly are axially coupled, when the staple pulley and the staple link assembly are cam-slot coupled as in the present embodiment, the displacement of the staple link assembly in the X-axis direction is reduced even when the staple pulley is rotated by the same amount.

Meanwhile, since work is the product of force and displacement, assuming that the work for rotating the staple pulley is the same, the displacement and the force are inversely proportional to each other. Accordingly, when the displacement is reduced, the force is increased in inverse proportion to the displacement.

As a result, in the first modified example of the second embodiment of the present disclosure, the staple pulley 3681 and the staple link assembly 3670 are coupled in the form of a cam-slot, and the displacement of the staple link assembly 3670 in the X-axis direction caused by the rotation of the staple pulley 3681 is relatively reduced compared to the other embodiments, and thus the force received by the staple link assembly 3670 in the X-axis direction is relatively increased compared to a simple link structure.

According to the first modified example of the second embodiment of the present disclosure described above, a force for moving the staple link assembly 3670 and the reciprocating assembly 550 connected thereto forward is amplified, and thus a stapling motion may be performed more robustly.

(Actuation and Pitch Motions)

Figure 185:
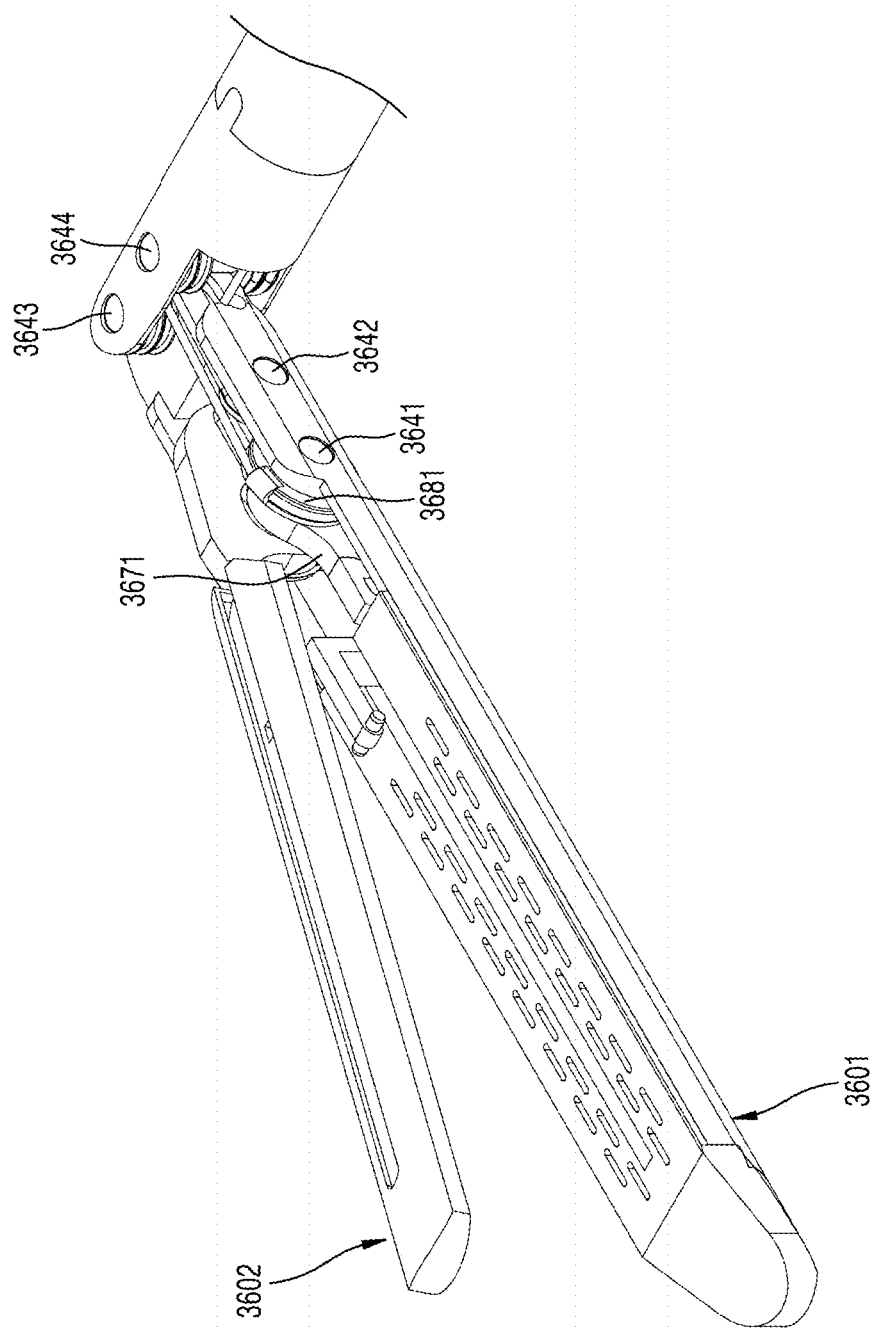
FIGS. 185 and 186 are perspective views illustrating an actuation motion of the end tool of FIG. 175, and are views illustrating a process of performing an actuation motion in a state in which jaws are pitch-rotated by +90°.
Figure 186:
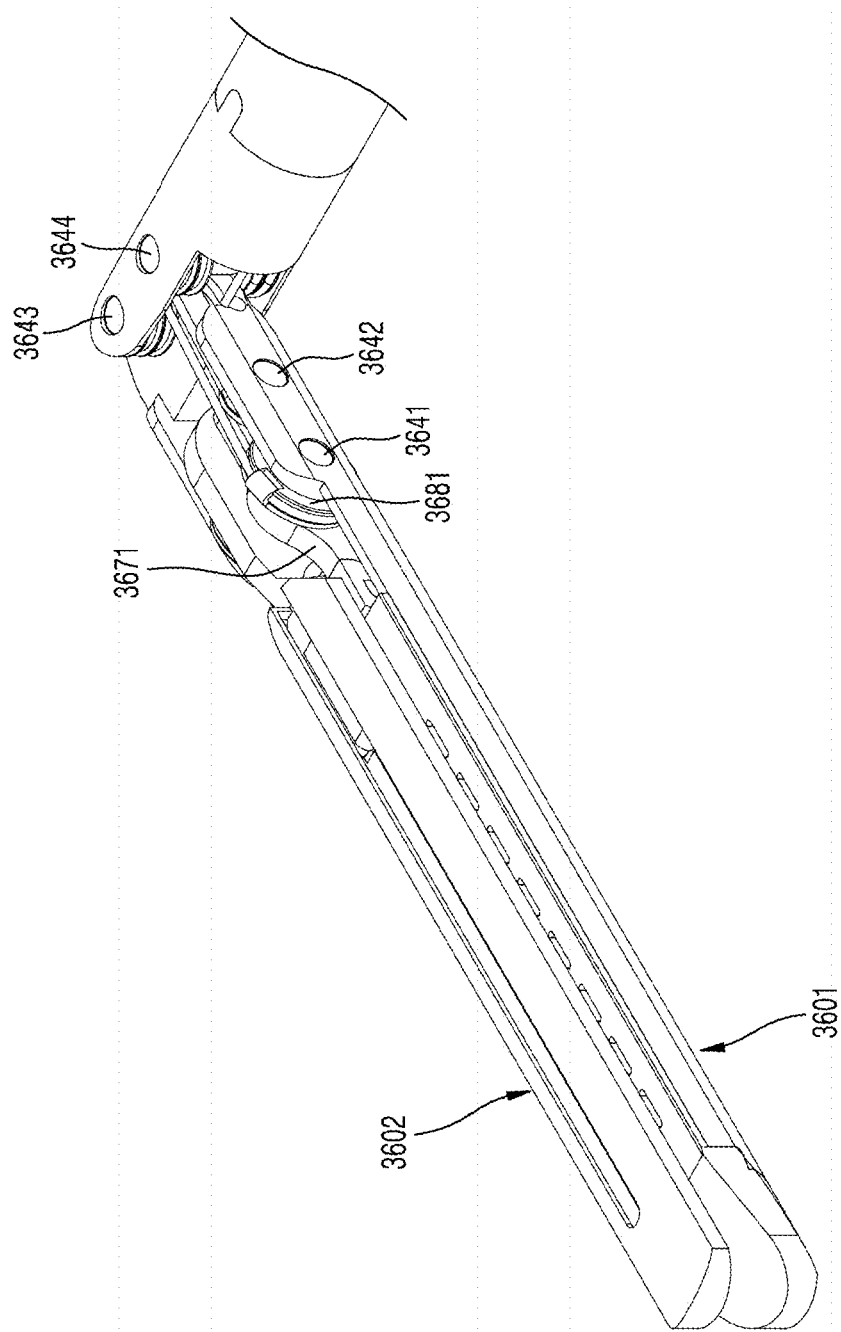
Figure 187:
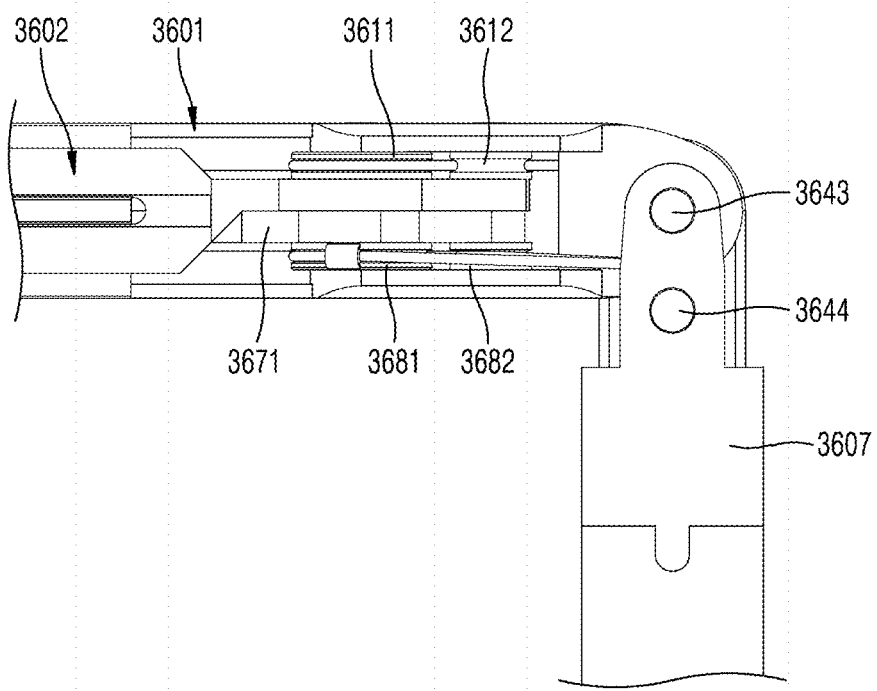
FIG. 187 is a side view of the end tool of FIG. 186.
Figure 188:
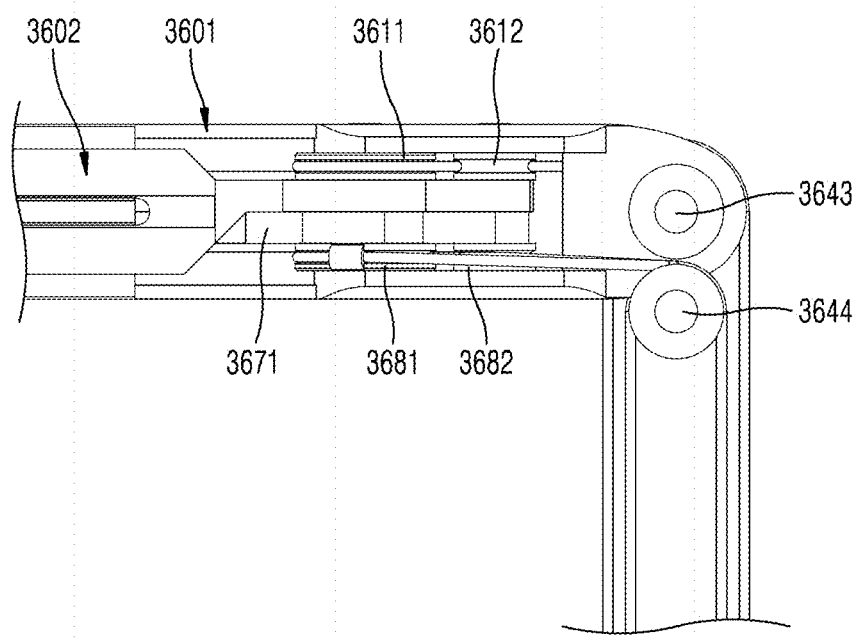
FIG. 188 is a side cross-sectional view of the end tool of FIG. 186.

FIGS. 185 and 186 are perspective views illustrating an actuation motion of the end tool of FIG. 175, and are views illustrating a process of performing an actuation motion in a state in which the jaws are pitch-rotated by +90°. FIG. 187 is a side view of the end tool of FIG. 186. FIG. 188 is a side cross-sectional view of the end tool of FIG. 186.

As shown in FIGS. 185 to 188, the end tool of the surgical instrument according to the first modified example of the second embodiment of the present disclosure is formed to normally perform an actuation motion even when the jaws are pitch-rotated by +90°.

Figure 189:
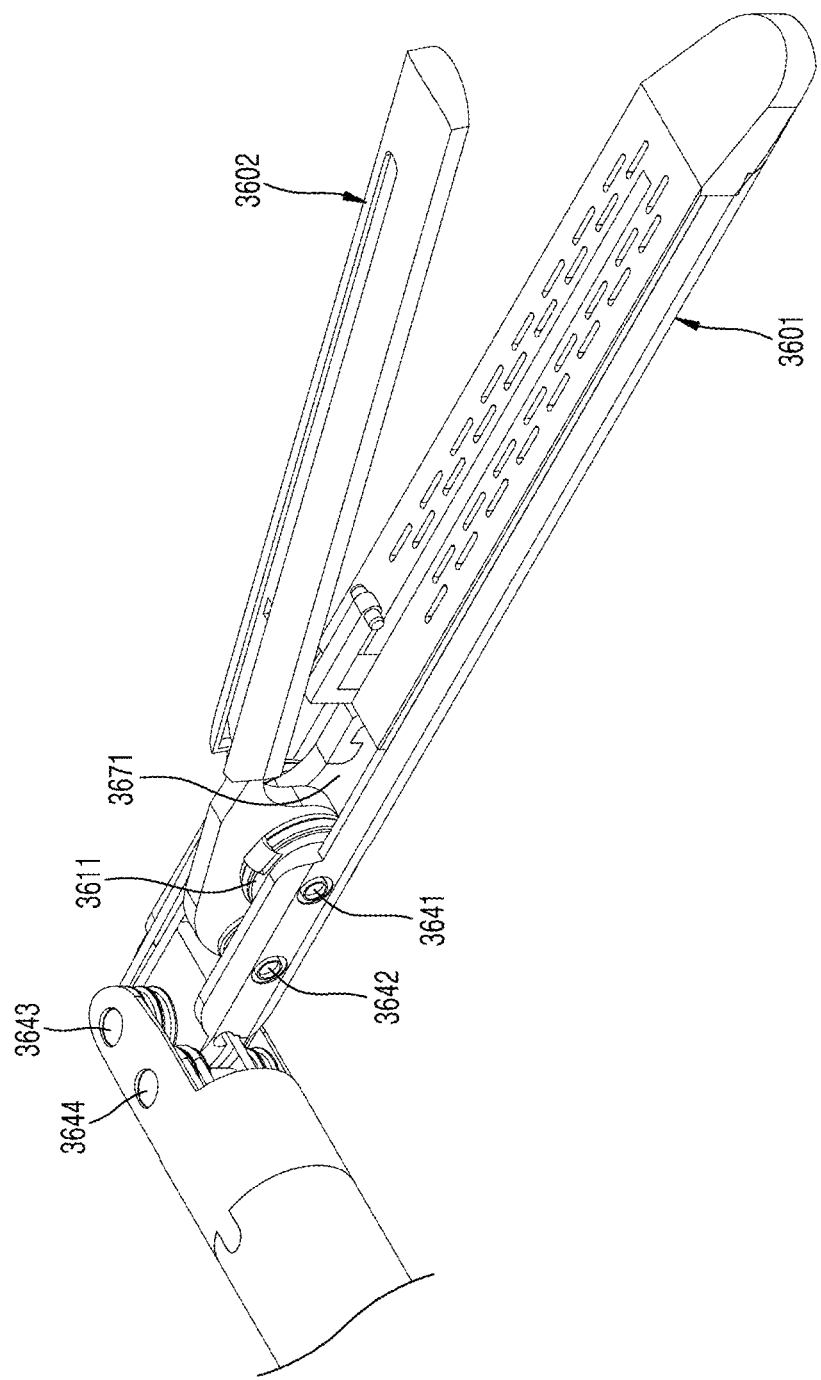
FIGS. 189 and 190 are perspective views illustrating an actuation motion of the end tool of FIG. 175, and are views illustrating a process of performing an actuation motion in a state in which the jaws are pitch-rotated by −90°.
Figure 190:
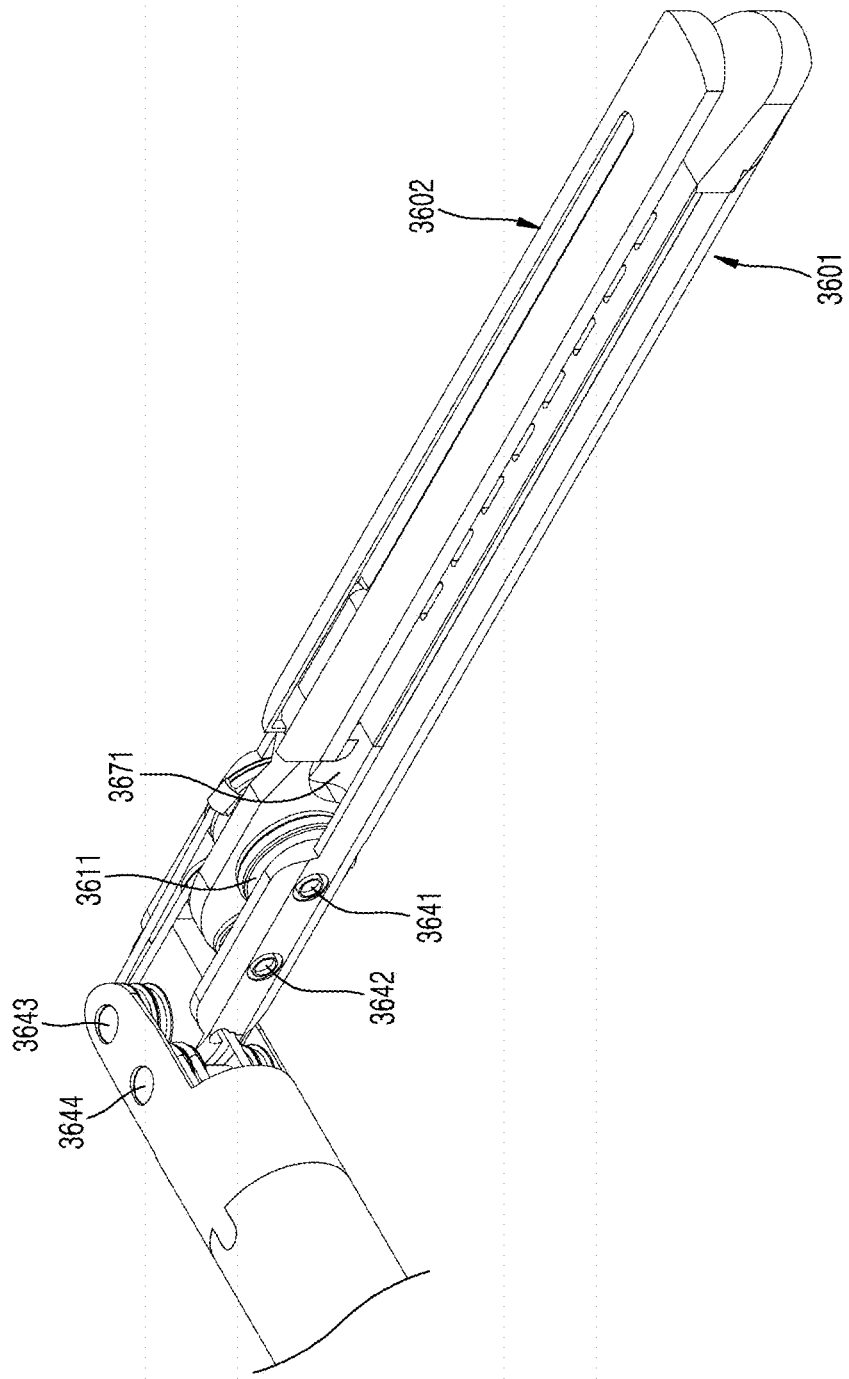
Figure 191:
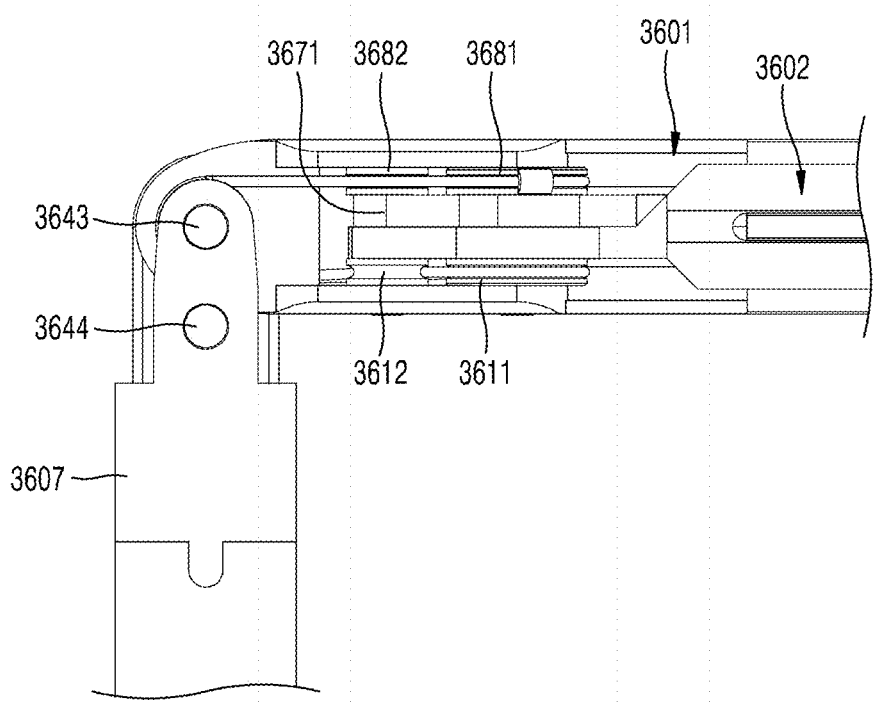
FIG. 191 is a side view of the end tool of FIG. 190.
Figure 192:
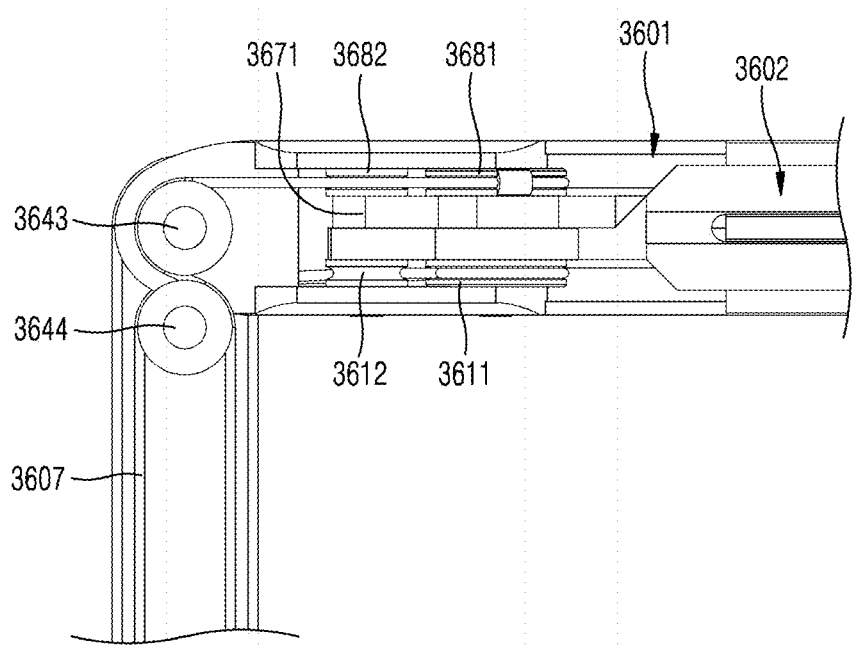
FIG. 192 is a side cross-sectional view of the end tool of FIG. 190.

FIGS. 189 and 190 are perspective views illustrating an actuation motion of the end tool of FIG. 175, and are views illustrating a process of performing an actuation motion in a state in which the jaws are pitch-rotated by −90°. FIG. 191 is a side view of the end tool of FIG. 190. FIG. 192 is a side cross-sectional view of the end tool of FIG. 190.

As shown in FIGS. 189 to 192, the end tool of the surgical instrument according to the first modified example of the second embodiment of the present disclosure is formed to normally perform an actuation motion even when the jaws are pitch-rotated by −90°.

Second Modified Example of Second Embodiment

Hereinafter, an end tool 3700 of a surgical instrument according to a second modified example of the second embodiment of the present disclosure will be described. Here, the end tool 3700 of the surgical instrument according to the second modified example of the second embodiment of the present disclosure is different from the end tool (see 3600 of FIG. 175 or the like) of the surgical instrument according to the first modified example of the second embodiment of the present disclosure described above in that the configuration and connection relationship of a second jaw 3702 and a jaw pulley 3711. Hereinafter, the configuration that is different from that of the first modified example of the second embodiment will be described in detail.

Figure 193:
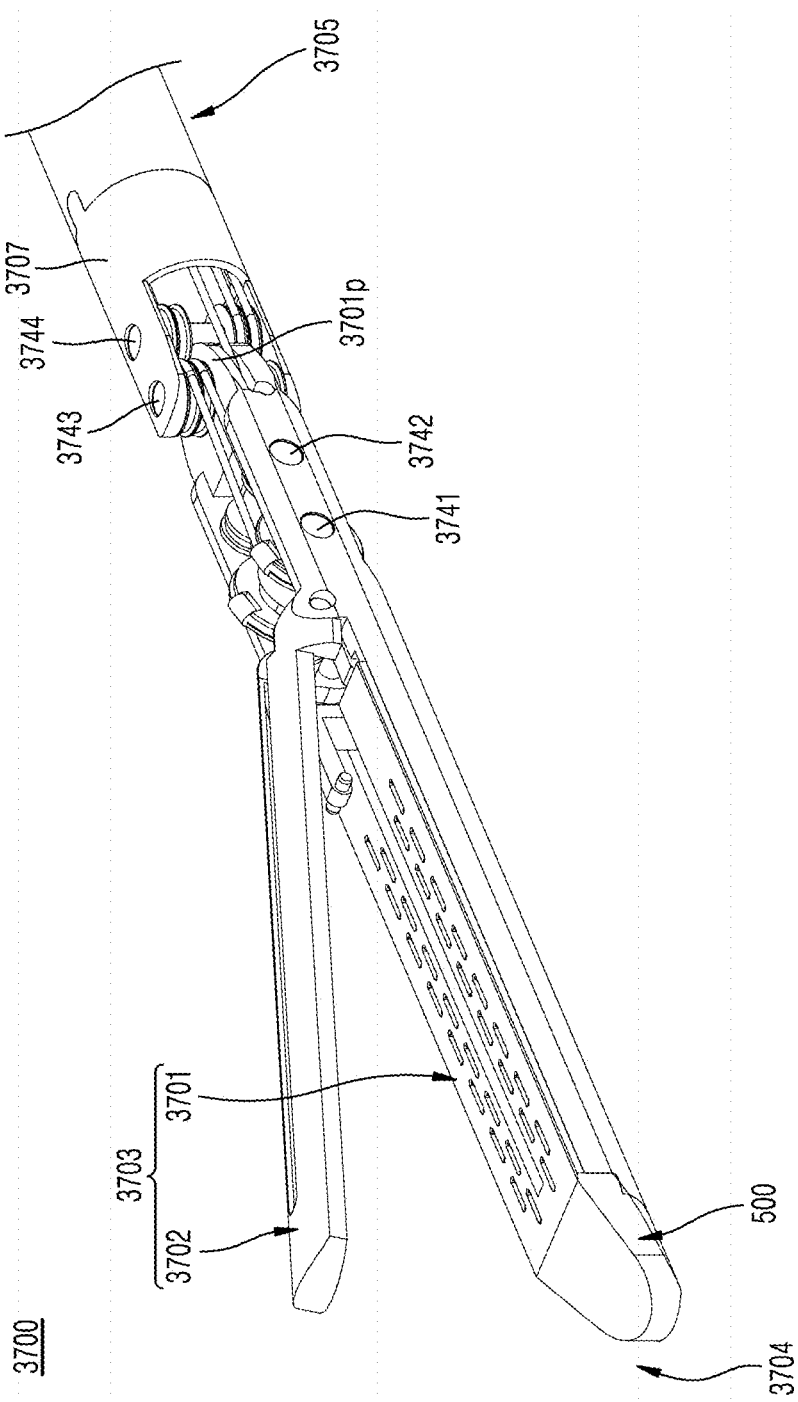
FIGS. 193 and 194 are perspective views illustrating an end tool of a surgical instrument according to a second modified example of the second embodiment of the present disclosure.
Figure 194:
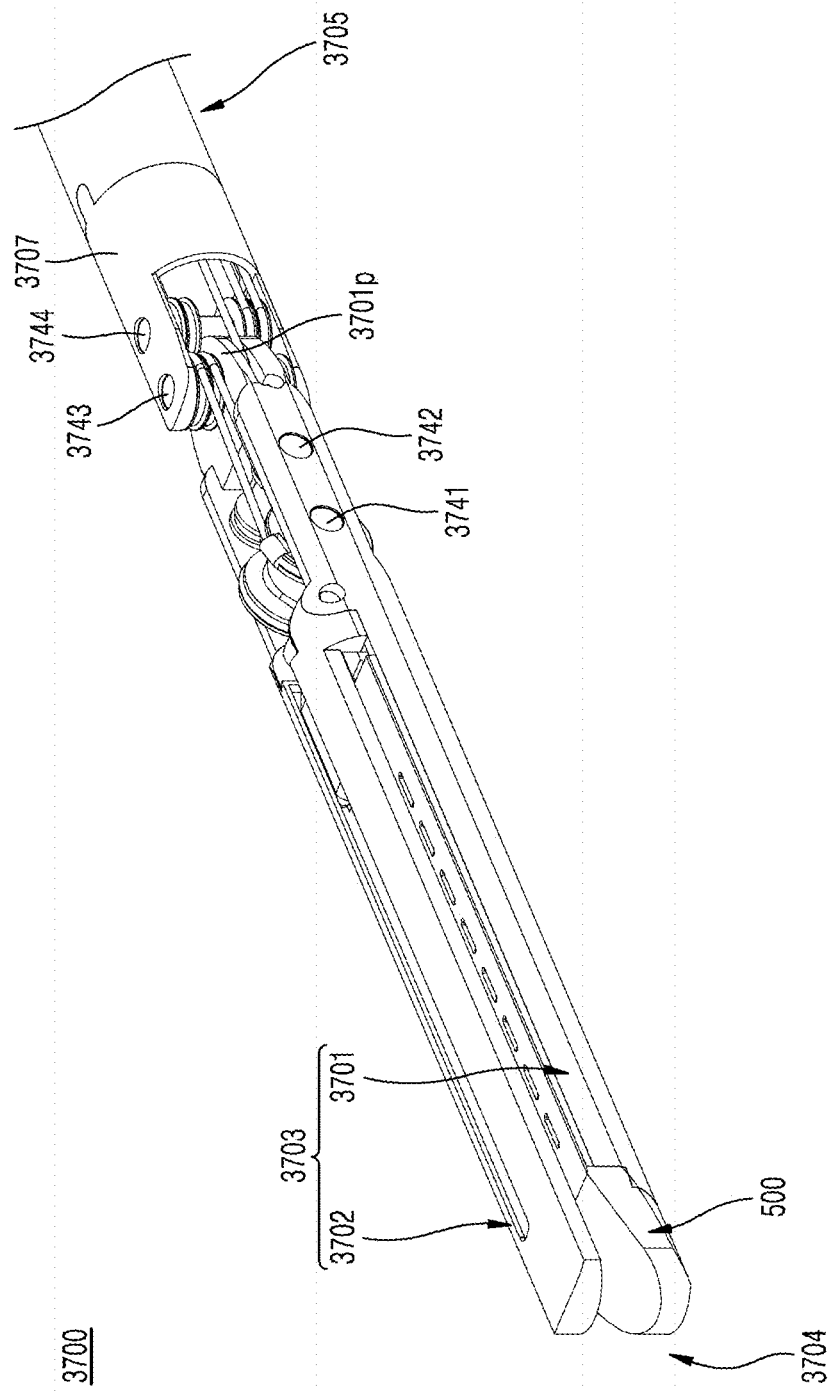
Figure 195:
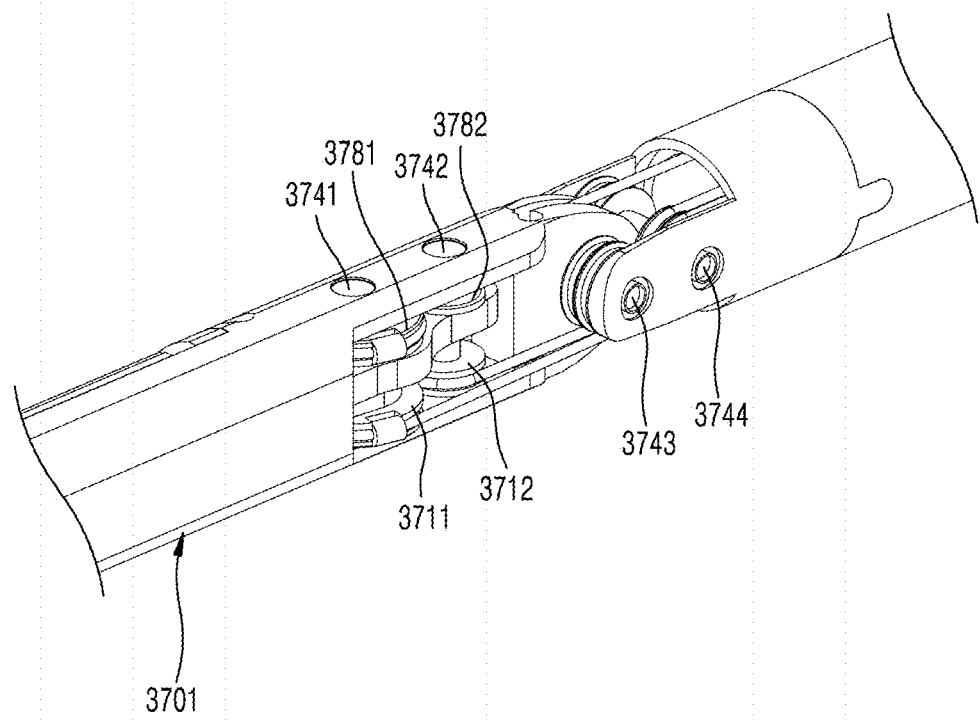
FIGS. 195 and 196 are detailed perspective views illustrating the end tool of FIG. 193.
Figure 196:
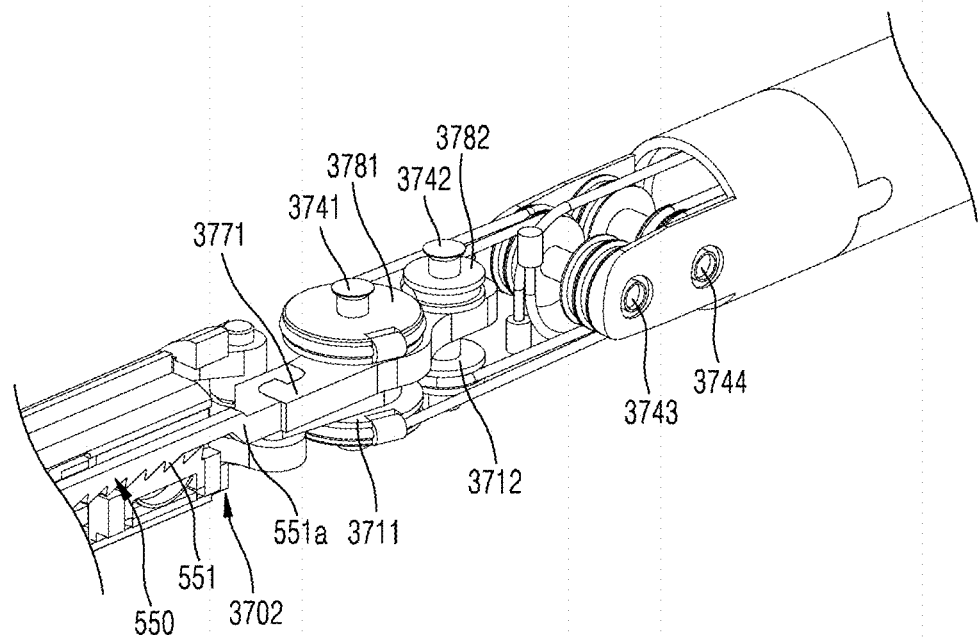
Figure 197:
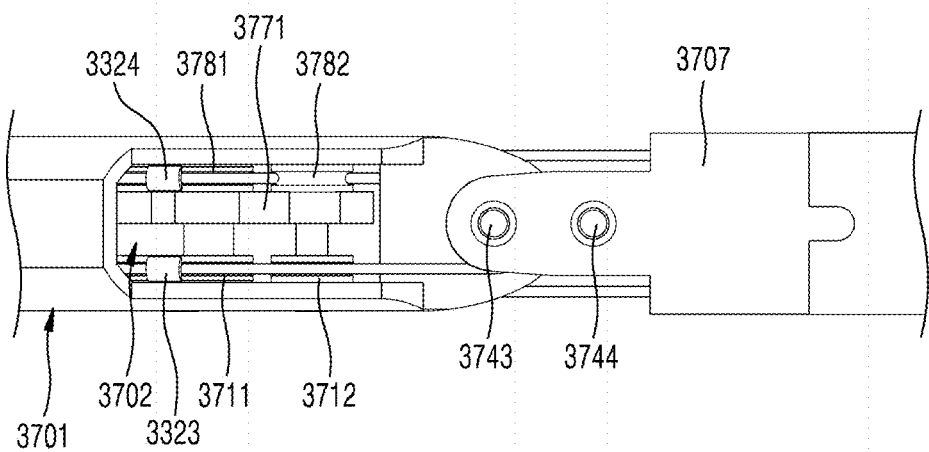
FIG. 197 is a side view illustrating the end tool of FIG. 193.
Figure 198:
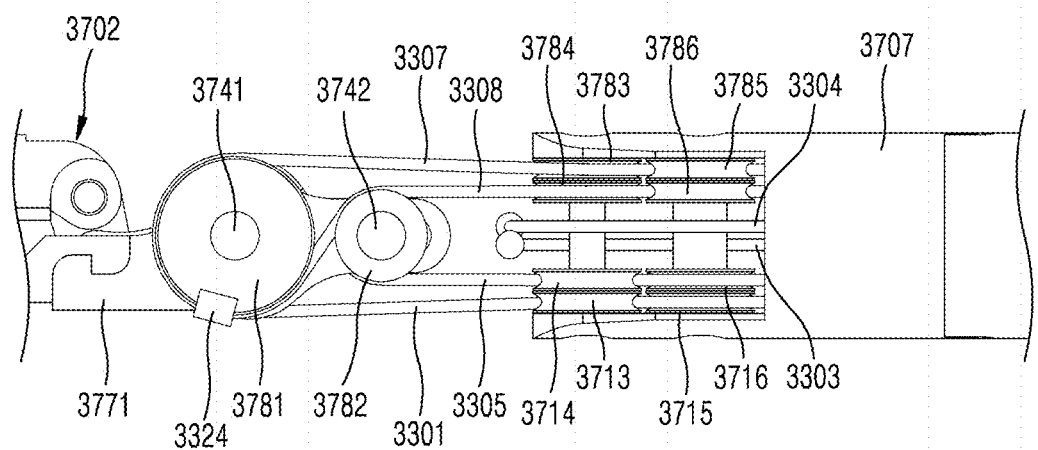
FIG. 198 is a plan view illustrating the end tool of FIG. 193.
Figure 199:
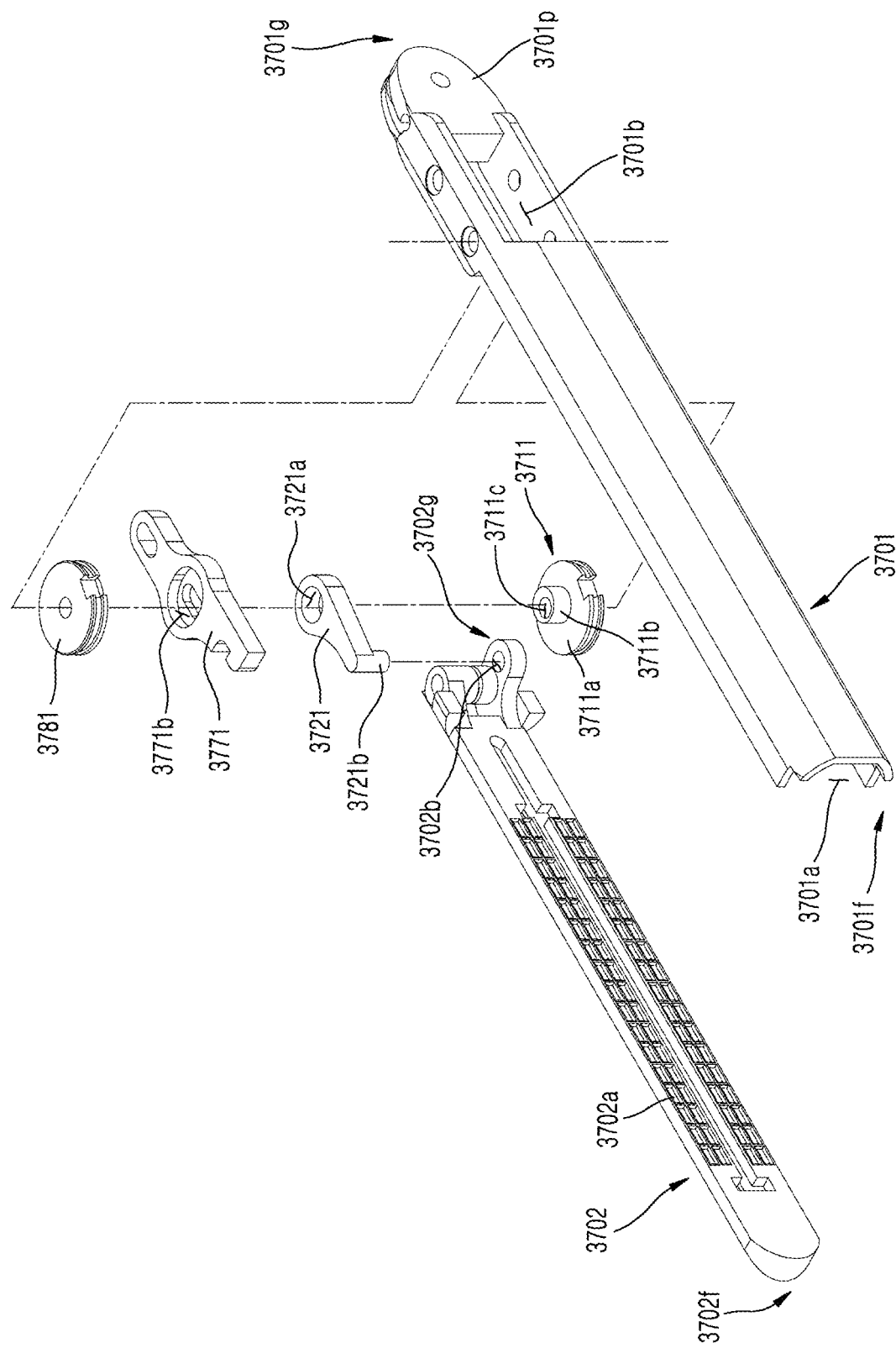
FIG. 199 is an exploded perspective view of the end tool of FIG. 193.
Figure 200:
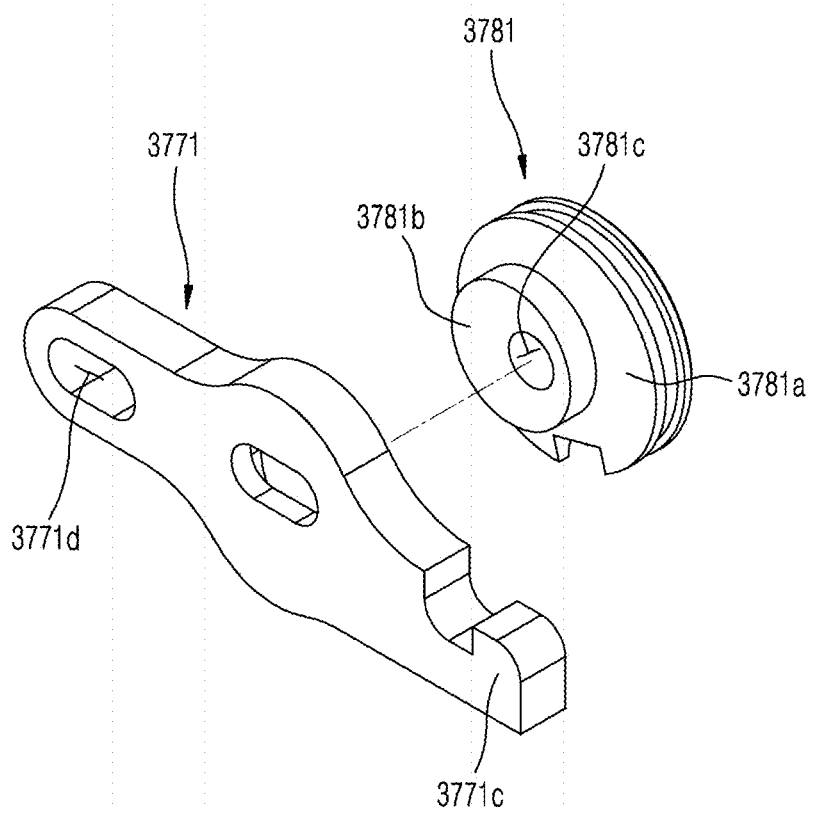
FIG. 200 is an exploded perspective view of a staple pulley and a link member of the end tool of FIG. 199.

FIGS. 193 and 194 are perspective views illustrating the end tool of the surgical instrument according to the second modified example of the second embodiment of the present disclosure. FIGS. 195 and 196 are detailed perspective views illustrating the end tool of FIG. 193. FIG. 197 is a side view illustrating the end tool of FIG. 193. FIG. 198 is a plan view illustrating the end tool of FIG. 193. FIG. 199 is an exploded perspective view of the end tool of FIG. 193. FIG. 200 is an exploded perspective view of a staple pulley and a link member of the end tool of FIG. 199. FIGS. 201 to 201C are plan views illustrating motions of a jaw pulley of the end tool of FIG. 193.

Referring to FIGS. 193 to 201, the surgical instrument according to the second modified example of the second embodiment of the present disclosure includes an end tool 3700, a manipulation part (see 3200 of FIG. 114), a power transmission part (see 3300 of FIG. 120), and a connection part (see 400 of FIG. 114).

Here, the remaining components except for the end tool 3700 are the same as or similar to those in the first modified example of the second embodiment of the present disclosure described in FIG. 175 or the like, and thus detailed descriptions thereof will be omitted herein.

(End Tool-Overall Configuration)

Hereinafter, the end tool 3700 of the surgical instrument of FIG. 193 will be described in more detail.

The end tool 3700 of the second modified example of the second embodiment of the present disclosure includes a pair of jaws 3703 for performing a grip motion, that is, a first jaw 3701 and the second jaw 3702. Herein, each of the first jaw 3701 and the second jaw 3702, or a component comprising the first jaw 3701 and the second jaw 3702, may be referred to as the jaw.

Meanwhile, the end tool 3700 of the second modified example of the second embodiment of the present disclosure may include a pitch hub 3707. A rotation shaft 3743 and a rotation shaft 3744, which will be described later, may be inserted through the pitch hub 3707, and the pitch hub 3707 may be axially coupled to the first jaw 3701 by the rotation shaft 3743. Accordingly, the first jaw 3701 may be formed to be rotatable around the rotation shaft 3743 with respect to the pitch hub 3707.

Further, the pitch hub 3707 may internally accommodate at least some of a pulley 3713, a pulley 3714, a pulley 3783, and a pulley 3784 that are axially coupled to the rotation shaft 3743. In addition, the pitch hub 3707 may internally accommodate at least some of a pulley 3715, a pulley 3716, a pulley 3785, and a pulley 3786 that are axially coupled to the rotation shaft 3744.

Meanwhile, the end tool 3700 of the second modified example of the second embodiment of the present disclosure may include a rotation shaft 3741, a rotation shaft 3742, the rotation shaft 3743, and the rotation shaft 3744. As described above, the rotation shaft 3741 and the rotation shaft 3742 may be inserted through the first jaw 3701, and the rotation shaft 3743 and the rotation shaft 3744 may be inserted through the pitch hub 3707.

The rotation shaft 3741, the rotation shaft 3742, the rotation shaft 3743, and the rotation shaft 3744 may be sequentially disposed from a distal end 3704 of the end tool 3700 toward a proximal end 3705. Accordingly, starting from the distal end 3704, the rotation shaft 3741 may be referred to as a first pin, the rotation shaft 3742 may be referred to as a second pin, the rotation shaft 3743 may be referred to as a third pin, and the rotation shaft 3744 may be referred to as a fourth pin.

Here, the rotation shaft 3741 may function as an end tool pulley rotation shaft, the rotation shaft 3742 may function as an end tool auxiliary pulley rotation shaft, the rotation shaft 3743 may function as an end tool pitch rotation shaft, and the rotation shaft 3744 may function as an end tool pitch auxiliary rotation shaft of the end tool 3700.

Each of the rotation shafts 3741, 3742, 3743, and 3744 may be fitted into one or more pulleys, which will be described in detail below.

(Components Related to Pulley)

Hereinafter, the jaw pulley 3711 and a staple pulley 3781 of the end tool 3700 of the surgical instrument of FIG. 193 will be described.

Continuing to refer to FIGS. 193 to 201 and the like, the end tool 3700 of the second modified example of the second embodiment of the present disclosure may include the jaw pulley 3711, a jaw auxiliary pulley 3712, the pulley 3713, the pulley 3714, the pulley 3715, and the pulley 3716 related to a rotational motion of the jaw 3703.

In addition, the end tool 3700 of the second modified example of the second embodiment of the present disclosure may include the staple pulley 3781, a staple auxiliary pulley 3782, the pulley 3783, the pulley 3784, the pulley 3785, and the pulley 3786 related to a linear motion/rotational motion of the respective pulleys and links for stapling and cutting. The jaw pulley 3711 and the staple pulley 3781 are formed to be rotatable independently of each other around the rotation shaft 3741 that is an end tool pulley rotation shaft.

Here, the configuration of pulleys including the jaw pulley 3711 and the staple pulley 3781 is the same as or similar to that in the first modified example of the second embodiment of the present disclosure described in FIG. 175 or the like, and thus detailed descriptions thereof will be omitted herein.

(First and Second Jaws and Actuation Motion)

Hereinafter, a coupling structure of the first jaw 3701 and the second jaw 3702 of the end tool 3700 of the surgical instrument of FIG. 193 will be described in more detail.

Continuing to refer to FIGS. 199 to 201 and the like, the jaw pulley 3711 may include a body 3711a, a protruding member 3711b, and a shaft pass-through part 3711c.

In detail, the body 3711a is formed in the shape of a disk. The shaft pass-through part 3711c may be formed in a center portion of the body 3711a. The shaft pass-through part 3711c is formed in the form of a hole, and the rotation shaft 3741, which is an end tool pulley rotation shaft, may be inserted through the shaft pass-through part 3711c.

In addition, the protruding member 3711b may be formed in the body 3711a of the jaw pulley 3711. The protruding member 3711b may be coupled to a pulley coupling part 3721a of a jaw-pulley connection link 3720 to be described later. Here, the center of the protruding member 3711b may not coincide with the center of the jaw pulley 3711, and the protruding member 3711b may be formed to be eccentric to a certain extent with respect to the jaw pulley 3711.

The first jaw 3701 includes a cartridge accommodation part 3701a, a staple assembly accommodation part 3701b, and a pitch pulley part 3701p. Here, since the configuration of the first jaw 3701 is the same as or similar to that in first modified example of the second embodiment of the present disclosure described in FIG. 175 or the like, detailed descriptions thereof will be omitted herein.

The second jaw 3702 includes an anvil 3702a and a jaw pulley coupling part 3702b.

The second jaw 3702 is formed in the shape of an elongated bar as a whole, the anvil 3702a is formed at a distal end 3702f side, the jaw pulley coupling part 3702b is formed on a proximal end 3702g, and a jaw-pulley connection link 3721 is coupled to the jaw pulley coupling part 3702b.

The jaw-pulley connection link 3720 serves as a link connecting the jaw pulley 3711 and the second jaw 3702.

The jaw-pulley connection link 3720 is formed in the form of an elongated bar, and includes one end portion at which the pulley coupling part 3721a, to which the jaw pulley 3711 may be coupled, is formed. The pulley coupling part 3721a is formed in the form of a through hole so that the protrusion member 3711b of the jaw pulley 3711 is fitted into the pulley coupling part 3721a.

A jaw coupling part 3721b, to which the second jaw 3702 may be coupled, is formed at the other end portion of the jaw-pulley connection link 3720. The jaw coupling part 3721b is formed to protrude in one direction and is fitted into the jaw pulley coupling part 3702b of the second jaw 3702. Alternatively, although not shown in the drawings, the jaw coupling part of the jaw-pulley connection link 3720 may be formed in the shape of a through hole, and the jaw pulley coupling part of the second jaw 3702 may be formed the shape of a protrusion, so that the jaw pulley coupling part of the second jaw 3702 may be fitted into the jaw coupling part of the jaw-pulley connection link 3720.

As described above, the protruding member 3711b may be formed to be eccentric to a certain extent with respect to the center of the jaw pulley 3711. Accordingly, when the jaw pulley 3711 is rotated, the protruding member 3711b may rotate the jaw-pulley connection link 3720 by pushing the pulley coupling part 3721a in a state in which the protruding member 3711b is in contact with the pulley coupling part 3721a of the jaw-pulley connection link 3720. In addition, when the jaw-pulley connection link 3720 is rotated, the second jaw 3702 coupled thereto is also rotated together. That is, when the jaw pulley 3711 is rotated, the protruding member 3711b pushes the jaw-pulley connection link 3720, and the jaw-pulley connection link 3720 again pushes the second jaw 3702, which causes the second jaw 3702 to be rotated. In other words, the jaw-pulley connection link 3720 serves to connect the jaw pulley 3711 and the second jaw 3702 and transmit the rotation of the jaw pulley 3711 to the second jaw 3702.

The coupling relationship between the components described above is as follows.

The rotation shaft 3741, which is an end tool pulley rotation shaft, is sequentially inserted through the first jaw 3701, a shaft pass-through part 3781c of the staple pulley 3781, a slot 3771b of a link member 3771, the shaft pass-through part 3781c of the jaw pulley 3711 into which the jaw-pulley connection link 3720 is inserted, and the first jaw 3701.

Hereinafter, the rotation of the second jaw 3702 according to the rotation of the jaw pulley 3711 will be described.

Figure 201A:
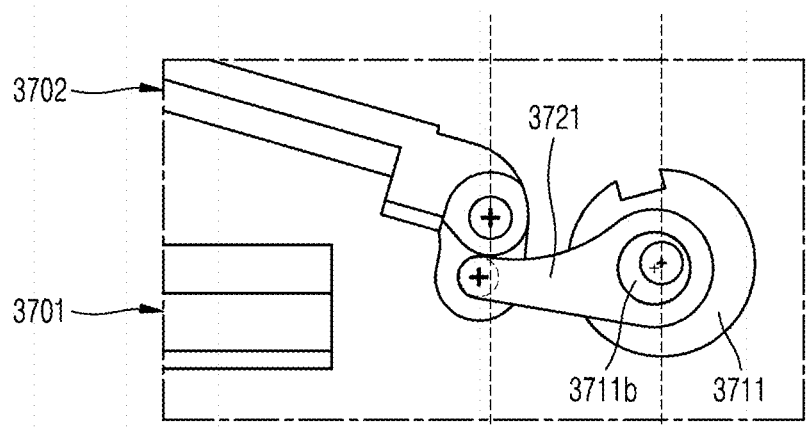
FIGS. 201A to 201C are plan views illustrating motions of a jaw pulley of the end tool of FIG. 193.
Figure 201B:
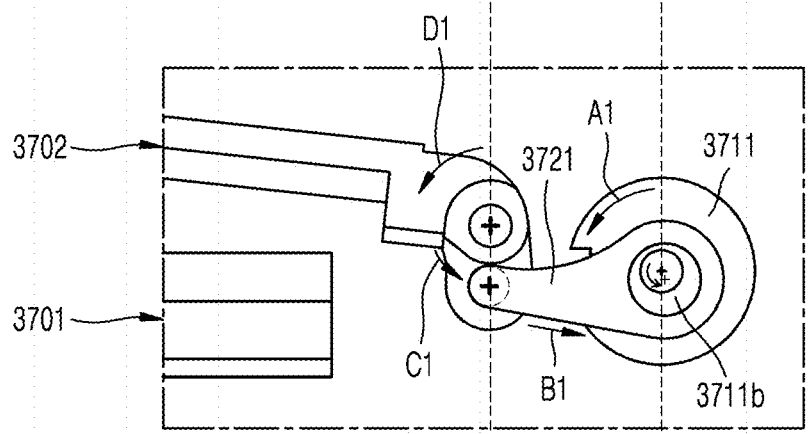
Figure 201C:
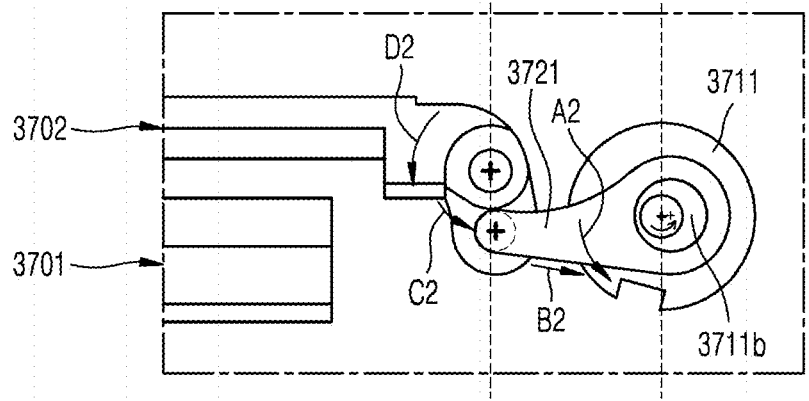

Referring to FIGS. 201A to 201C and the like, in the second modified example of the second embodiment of the present disclosure, the jaw pulley 3711 and the second jaw 3702 are coupled in the form of a four-section link. That is, the cam-shaped protruding member 3711b formed on the jaw pulley 3711 is coupled to the pulley coupling part 3721a formed at one end portion of the jaw-pulley connection link 3720, and the jaw coupling part 3721b formed at the other end portion of the jaw-pulley connection link 3720 is coupled to the jaw pulley coupling part 3702b of the second jaw 3702.

Thus, as shown in FIG. 201B, when the jaw pulley 3711 is rotated in the direction of an arrow A1, the jaw-pulley connection link 3720 is moved in the direction of an arrow B1, which causes the jaw coupling part 3721b of the jaw-pulley connection link 3720 and the jaw pulley coupling part 3702b of the second jaw 3702 coupled thereto to be moved in the direction of an arrow C1. In addition, due thereto, the second jaw 3702 as a whole is rotated in the direction of an arrow D1.

Here, as shown in FIG. 201C, when the jaw pulley 3711 is further rotated in the direction of an arrow A2, the jaw-pulley connection link 3720 is further moved in the direction of an arrow B2, which causes the jaw coupling part 3721b of the jaw-pulley connection link 3720 and the jaw pulley coupling part 3702b of the second jaw 3702 coupled thereto to be further moved in the direction of the arrow C1. In addition, due thereto, the second jaw 3702 as a whole is further rotated in the direction of an arrow D2 to perform an actuation motion or a grip motion.

(Staple Drive Assembly and Stapling Motion)

Meanwhile, a staple drive assembly 3750 may include a staple pulley assembly 3780 and a staple link assembly 3770.

The staple pulley assembly 3780 may include one or more staple pulleys. In the present embodiment, it is assumed that the staple pulley assembly 3780 includes one staple pulley 3781.

The staple link assembly 3770 may include one or more link members 3771. In addition, the link member 3771 may include one or more links.

In the end tool 3700 of the surgical instrument according to the present disclosure, the staple pulley assembly 3780 and the staple link assembly 3770 form a cam-slot structure. In addition, with such a structure, a force for moving the reciprocating assembly 550 forward may be amplified.

Here, the configuration and motion of the staple drive assembly 3750 are the same as or similar to those in the first modified example of the second embodiment of the present disclosure described in FIG. 175 or the like, and thus detailed descriptions thereof will be omitted herein.

Third Modified Example of Second Embodiment

Hereinafter, an end tool 3800 of a surgical instrument according to a third modified example of the second embodiment of the present disclosure will be described. Here, the end tool 3800 of the surgical instrument according to the third modified example of the second embodiment of the present disclosure is different from the end tool (see 3600 of FIG. 175 or the like) of the surgical instrument according to the first modified example of the second embodiment of the present disclosure described above in that the configuration and connection relationship of a second jaw 3802 and a jaw pulley 3811. Hereinafter, the configuration that is different from that of the first modified example of the second embodiment will be described in detail.

Figure 202:
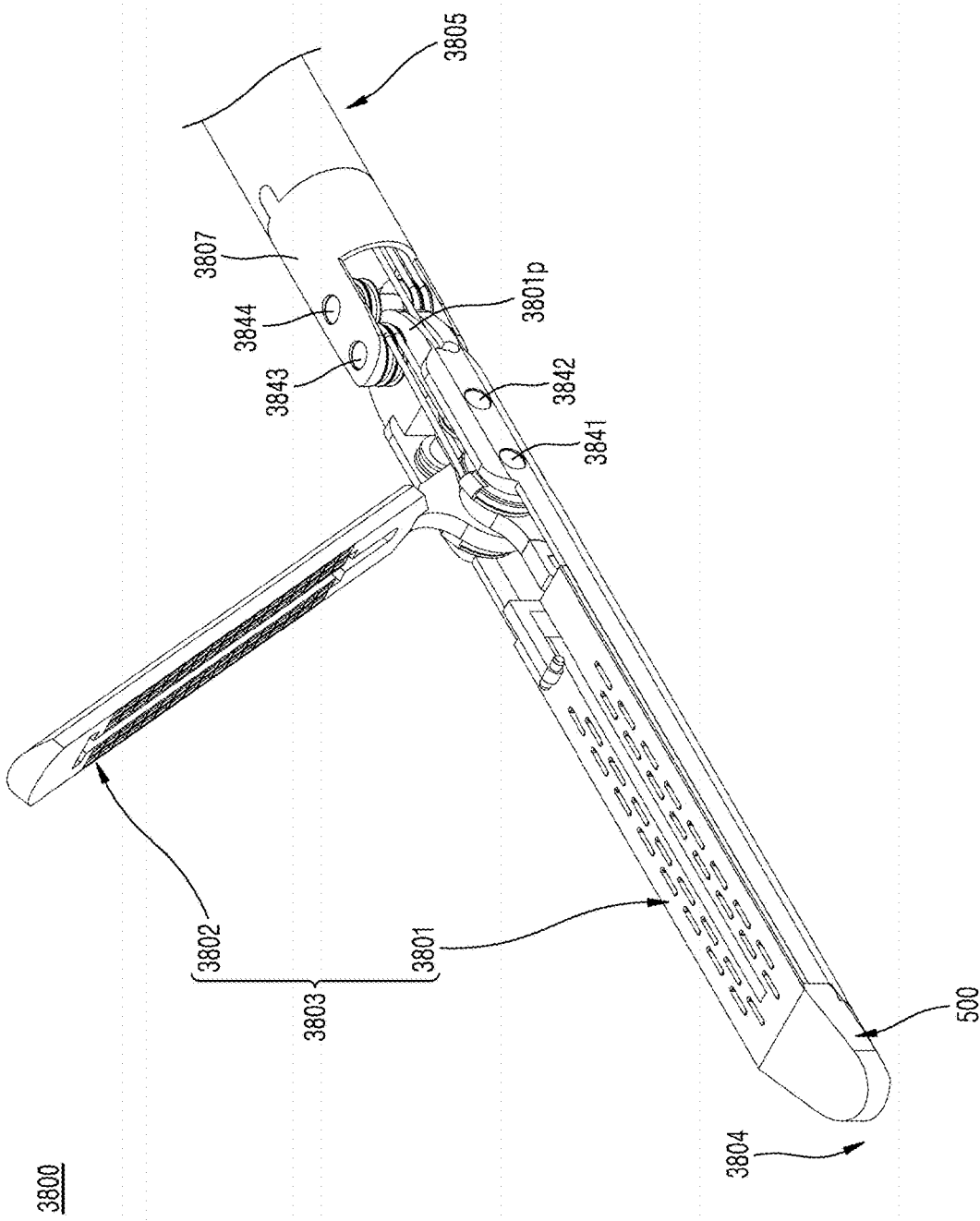
FIGS. 202 and 203 are perspective views illustrating an end tool of a surgical instrument according to a third modified example of the second embodiment of the present disclosure.
Figure 203:
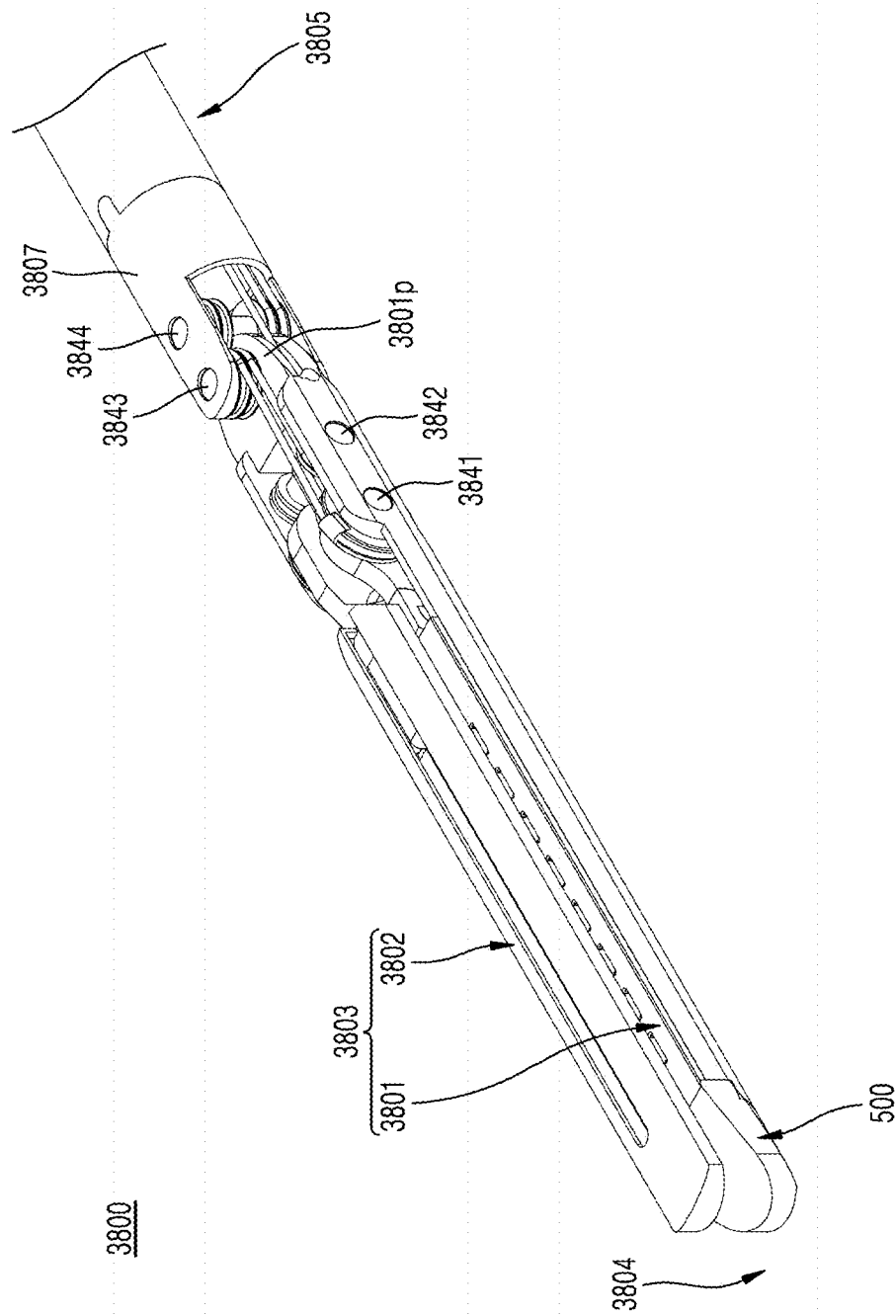
Figure 204:
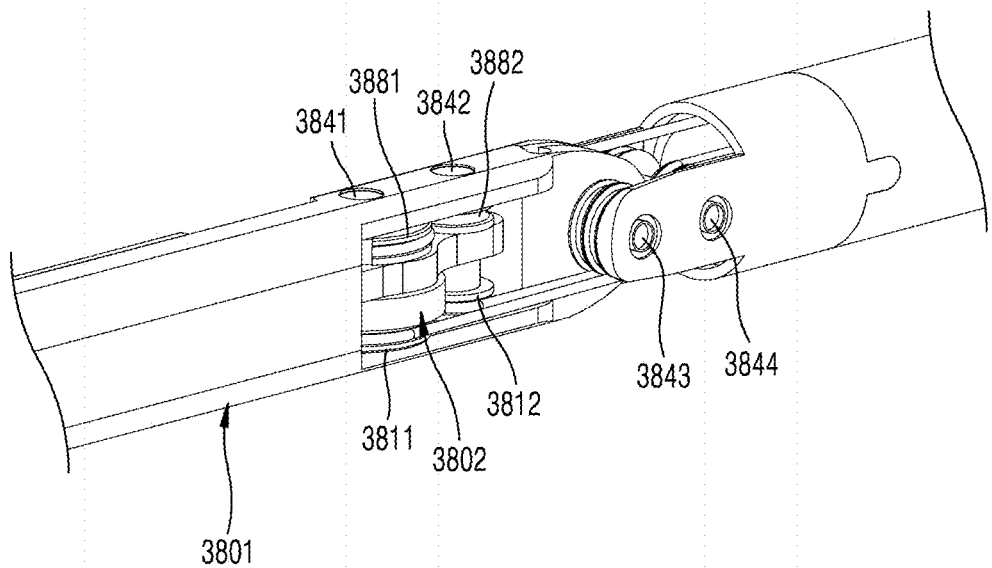
FIGS. 204 and 205 are detailed perspective views illustrating the end tool of FIG. 202.
Figure 205:
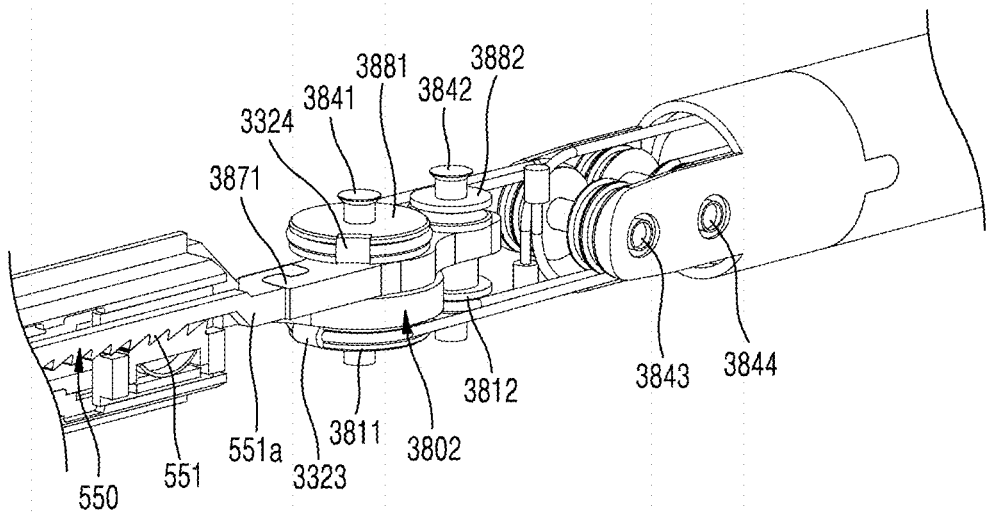
Figure 206:
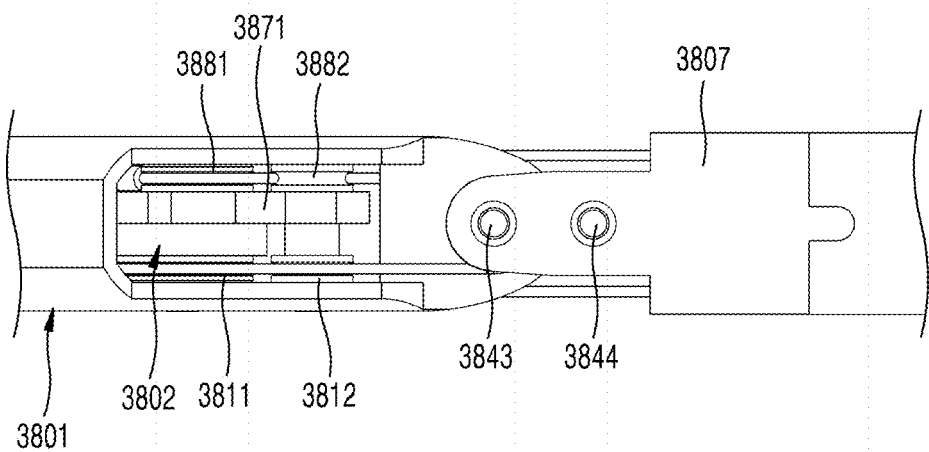
Figure 207:
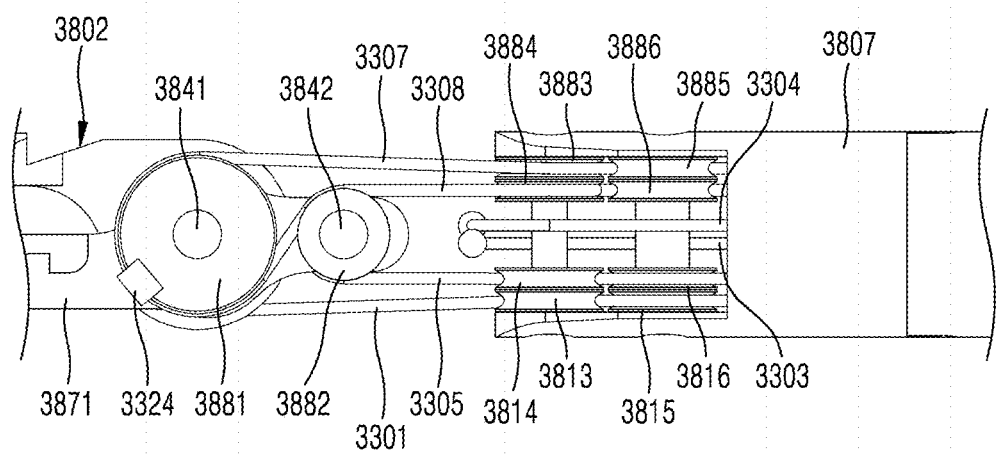
Figure 208:
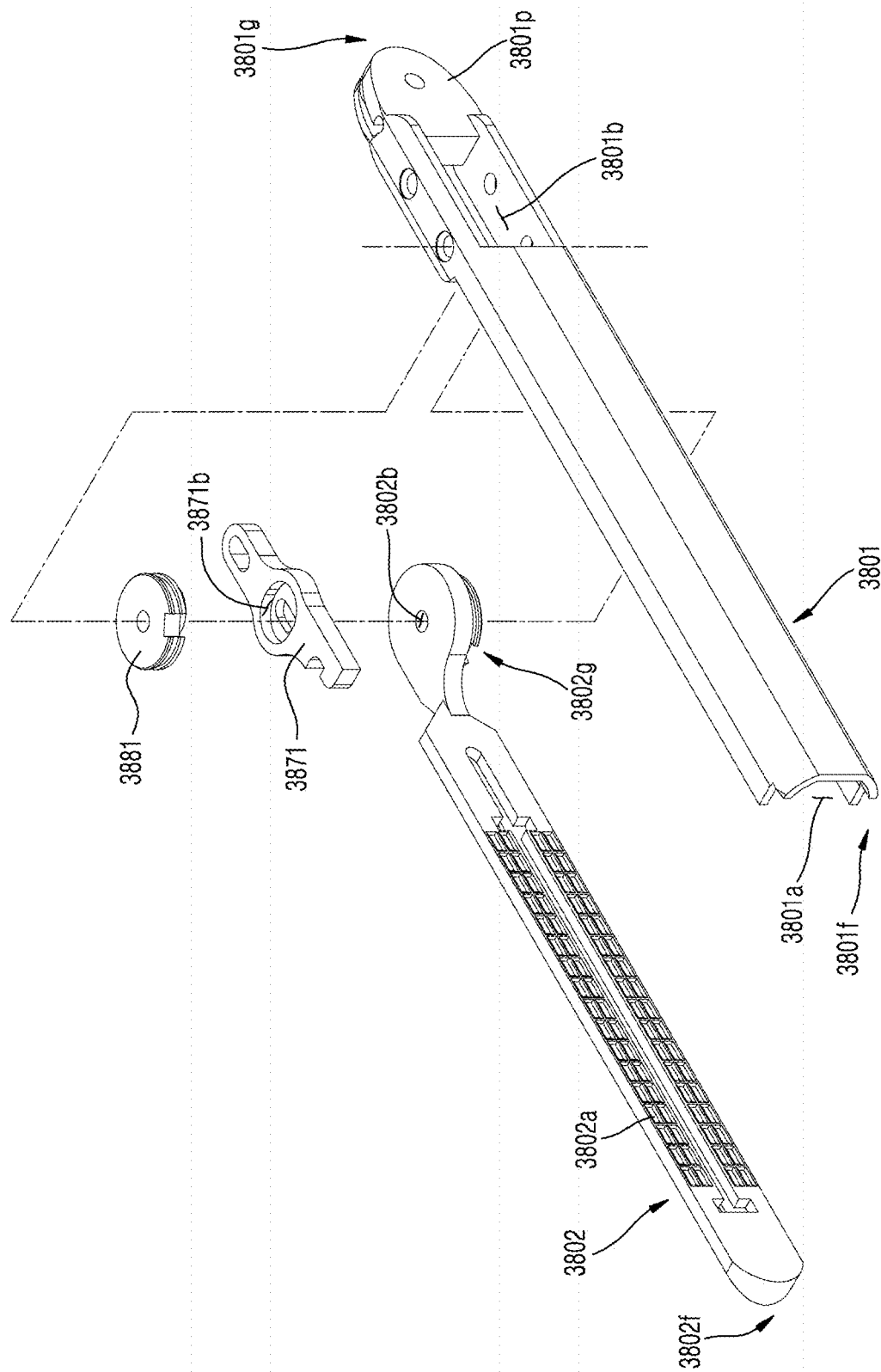
Figure 209:
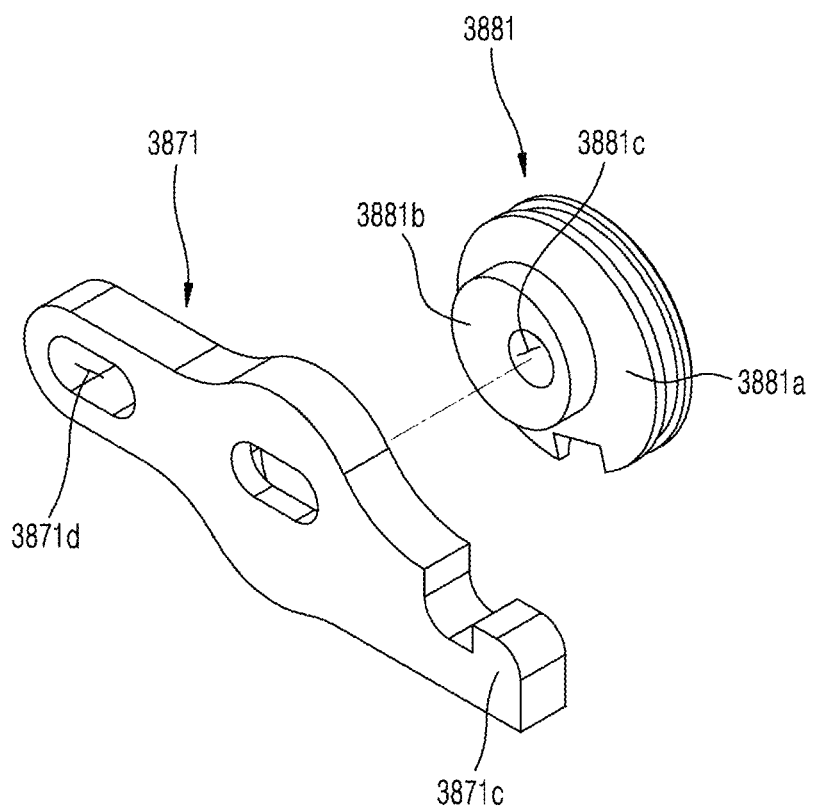
Figure 210:
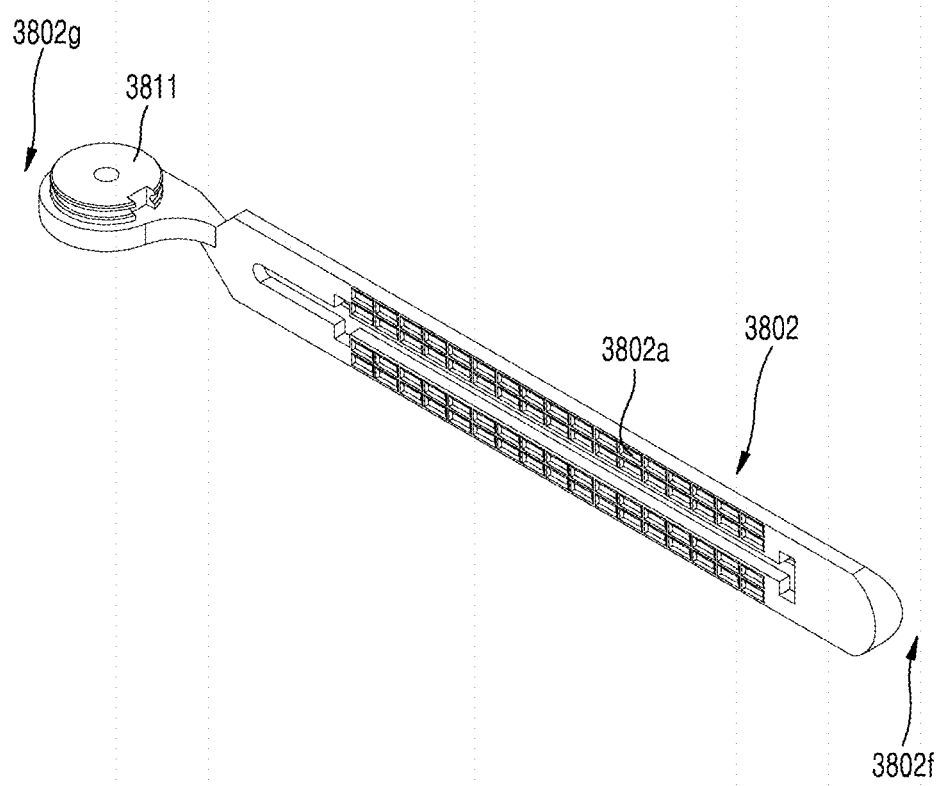
Figure 211:
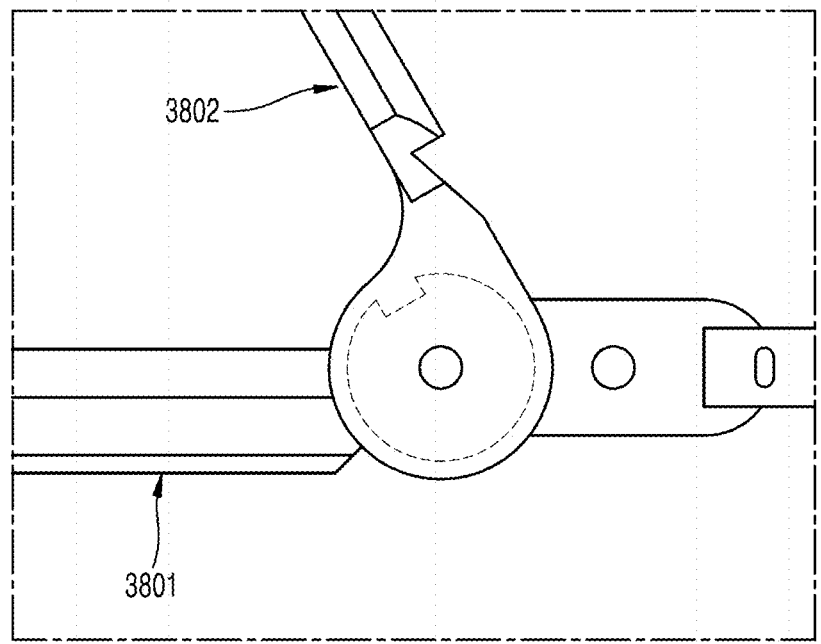
Figure 212:
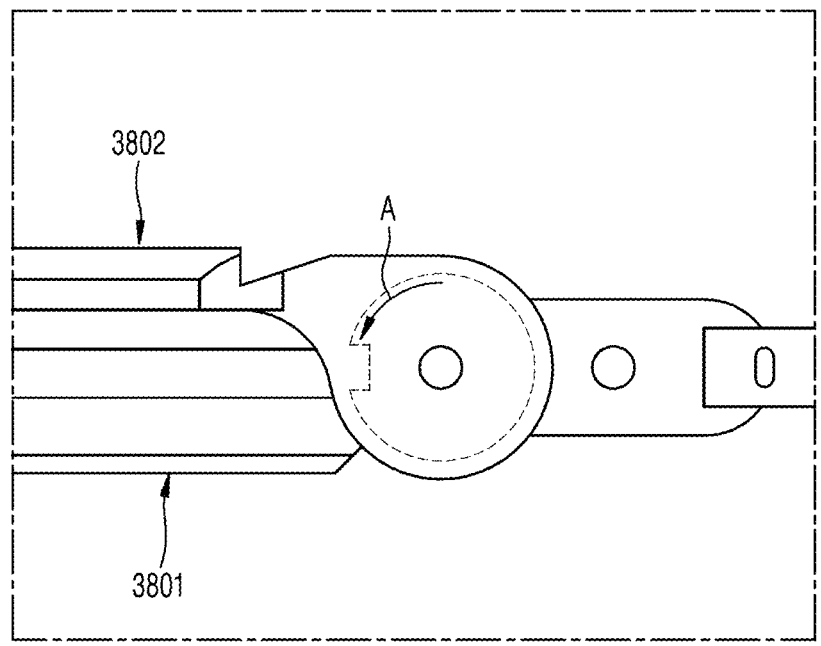

FIGS. 202 and 203 are perspective views illustrating the end tool of the surgical instrument according to the third modified example of the second embodiment of the present disclosure. FIGS. 204 and 205 are detailed perspective views illustrating the end tool of FIG. 202. FIG. 206 is a side view illustrating the end tool of FIG. 202. FIG. 207 is a plan view illustrating the end tool of FIG. 202. FIG. 208 is an exploded perspective view of the end tool of FIG. 202. FIG. 209 is an exploded perspective view of a staple pulley and a link member of the end tool of FIG. 199. FIG. 210 is a perspective view of a second jaw of the end tool of FIG. 199. FIGS. 211 and 212 are plan views illustrating motions of a jaw pulley of the end tool of FIG. 202.

Referring to FIGS. 202 to 212, the surgical instrument according to the third modified example of the second embodiment of the present disclosure includes an end tool 3800, a manipulation part (see 3200 of FIG. 114), a power transmission part (see 3300 of FIG. 120), and a connection part (see 400 of FIG. 114).

Here, the remaining components except for the end tool 3800 are the same as or similar to those in the first modified example of the second embodiment of the present disclosure described in FIG. 175 or the like, and thus detailed descriptions thereof will be omitted herein.

(End Tool-Overall Configuration)

Hereinafter, the end tool 3800 of the surgical instrument of FIG. 202 will be described in more detail.

The end tool 3800 of the third modified example of the second embodiment of the present disclosure includes a pair of jaws 3803 for performing a grip motion, that is, a first jaw 3801 and the second jaw 3802. Here, each of the first jaw 3801 and the second jaw 3802, or a component encompassing the first jaw 3801 and the second jaw 3802 may be referred to as the jaw.

Meanwhile, the end tool 3800 of the third modified example of the second embodiment of the present disclosure may include a pitch hub 3807. A rotation shaft 3843 and a rotation shaft 3844, which will be described later, may be inserted through the pitch hub 3807, and the pitch hub 3807 may be axially coupled to the first jaw 3801 by the rotation shaft 3843. Accordingly, the first jaw 3801 may be formed to be rotatable around the rotation shaft 3843 with respect to the pitch hub 3807.

Further, the pitch hub 3807 may internally accommodate at least some of a pulley 3813, a pulley 3814, a pulley 3883, and a pulley 3884 that are axially coupled to the rotation shaft 3843. In addition, the pitch hub 3807 may internally accommodate at least some of a pulley 3815, a pulley 3816, a pulley 3885, and a pulley 3886 that are axially coupled to the rotation shaft 3844.

Meanwhile, the end tool 3800 of the third modified example of the second embodiment of the present disclosure may include a rotation shaft 3841, a rotation shaft 3842, the rotation shaft 3843, and the rotation shaft 3844. As described above, the rotation shaft 3841 and the rotation shaft 3842 may be inserted through the first jaw 3801, and the rotation shaft 3843 and the rotation shaft 3844 may be inserted through the pitch hub 3807.

The rotation shaft 3841, the rotation shaft 3842, the rotation shaft 3843, and the rotation shaft 3844 may be sequentially disposed from a distal end 3804 of the end tool 3800 toward a proximal end 3805. Accordingly, starting from the distal end 3804, the rotation shaft 3841 may be referred to as a first pin, the rotation shaft 3842 may be referred to as a second pin, the rotation shaft 3843 may be referred to as a third pin, and the rotation shaft 3844 may be referred to as a fourth pin.

Here, the rotation shaft 3841 may function as an end tool pulley rotation shaft, the rotation shaft 3842 may function as an end tool auxiliary pulley rotation shaft, the rotation shaft 3843 may function as an end tool pitch rotation shaft, and the rotation shaft 3844 may function as an end tool pitch auxiliary rotation shaft of the end tool 3800.

Each of the rotation shafts 3841, 3842, 3843, and 3844 may be fitted into one or more pulleys, which will be described in detail below.

(Components Related to Pulley)

Hereinafter, the jaw pulley 3811 and a staple pulley 3881 of the end tool 3800 of the surgical instrument of FIG. 202 will be described.

Continuing to refer to FIGS. 193 to 201C and the like, the end tool 3800 of the third modified example of the second embodiment of the present disclosure may include the jaw pulley 3811, a jaw auxiliary pulley 3812, the pulley 3813, the pulley 3814, the pulley 3815, and the pulley 3816 related to a rotational motion of the jaw 3803.

In addition, the end tool 3800 of the third modified example of the second embodiment of the present disclosure may include the staple pulley 3881, a staple auxiliary pulley 3882, the pulley 3883, the pulley 3884, the pulley 3885, and the pulley 3886 related to a linear motion/rotational motion of the respective pulleys and links for stapling and cutting.

The jaw pulley 3811 and the staple pulley 3881 are formed to be rotatable independently of each other around the rotation shaft 3841 that is an end tool pulley rotation shaft.

Here, the configuration of pulleys including the jaw pulley 3811 and the staple pulley 3881 is the same as or similar to that in the first modified example of the second embodiment of the present disclosure described in FIG. 175 or the like, and thus detailed descriptions thereof will be omitted herein.

(First and Second Jaws and Actuation Motion)

Hereinafter, a coupling structure of the first jaw 3801 and the second jaw 3802 of the end tool 3800 of the surgical instrument of FIG. 202 will be described in more detail.

Continuing to refer to FIGS. 208 to 210 and the like, the first jaw 3801 includes a cartridge accommodation part 3801*a*, a staple assembly accommodation part 3801*b*, and a pitch pulley part 3801*p*. Here, since the configuration of the first jaw 3801 is the same as or similar to that in first modified example of the second embodiment of the present disclosure described in FIG. 175 or the like, detailed descriptions thereof will be omitted herein.

The second jaw 3802 is formed in the shape of an elongated bar as a whole, and an anvil 3802*a* is formed in the second jaw 3802 at a distal end 3802*f* side, and a shaft coupling part 3802*b* is formed on a proximal end 3802*g*. In addition, the second jaw 3802 further includes the jaw pulley 3811. That is, in the present modified example, the second jaw 3802 and the jaw pulley 3811 are integrally formed as one body.

In addition, a coupling member 3323 for connecting a wire 3301 and a wire 3305, which are jaw wires, is coupled to the jaw pulley 3811.

Accordingly, when either the wire 3301 or the wire 3305 is pulled, an actuation motion is performed while the jaw pulley 3811 and the second jaw 3802 coupled thereto are rotated.

The coupling relationship between the components described above is as follows. The rotation shaft 3841, which is an end tool pulley rotation shaft, is sequentially inserted through the first jaw 3801, a shaft pass-through part 3881*c* of the staple pulley 3881, a slot 3871*b* of a link member 3871, the jaw pulley 3811 integrally formed with the second jaw 3802, and the first jaw 3801.

Hereinafter, the rotation of the second jaw 3802 according to the rotation of the jaw pulley 3811 will be described. Referring to FIGS. 201A to 201C or the like, in the third modified example of the second embodiment of the present disclosure, the jaw pulley 3811 and the second jaw 3802 are integrally formed as one body, and thus, when the jaw pulley 3811 is rotated, the second jaw 3802 is rotated together therewith. That is, as shown in FIG. 212, when the jaw pulley 3811 is rotated in the direction of an arrow A, the second jaw 3802 formed integrally therewith is rotated in the direction of the arrow A to perform an actuation motion or a grip motion.

From another perspective, it may be expressed that no separate jaw pulley is formed and the jaw wire is directly connected to the second jaw 3802. As such, the second jaw 3802 is directly connected to the jaw wire, so that the second jaw 3802 is rotated around the rotation shaft 3841 in response to pushing and pulling of the jaw wire.

(Staple Drive Assembly and Stapling Motion)

Meanwhile, a staple drive assembly 3850 may include a staple pulley assembly 3880 and a staple link assembly 3870.

The staple pulley assembly 3880 may include one or more staple pulleys. In the present embodiment, it is assumed that the staple pulley assembly 3880 includes one staple pulley 3881.

The staple link assembly 3870 may include one or more link members 3871. In addition, the link member 3871 may include one or more links.

In the end tool 3800 of the surgical instrument according to the present disclosure, the staple pulley assembly 3880 and the staple link assembly 3870 form a cam-slot structure. In addition, with such a structure, a force for moving the reciprocating assembly 550 forward may be amplified.

Here, the configuration and motion of the staple drive assembly 3850 are the same as or similar to those in the first modified example of the second embodiment of the present disclosure described in FIG. 175, and thus detailed descriptions thereof will be omitted herein.

As such, the present disclosure has been described with reference to an embodiment shown in the drawings, but it will be understood that this is merely exemplary, and those of ordinary skill in the art will understand that various modifications and variations of the embodiments are possible therefrom. Accordingly, the true technical protection scope of the present disclosure should be defined by the technical spirit of the appended claims.

INDUSTRIAL USABILITY

The present disclosure relates to an end tool of a surgical instrument and a surgical instrument including the same, and more particularly, may be used to an end tool of a surgical instrument that may be mounted on a robotic arm or operable manually to be used in laparoscopic surgery or other various surgeries, wherein the end tool is rotatable in two or more directions and is moved in a way that intuitively matches a motion of a manipulation part, and a surgical instrument including the same.

The invention claimed is:

1. A surgical instrument comprising:
an end tool including:
a first jaw;
a second jaw formed to face the first jaw;
a first jaw pulley coupled to the first jaw and formed to be rotatable around a first shaft;
a second jaw pulley coupled to the second jaw, formed to be rotatable around a shaft the same as or parallel to the first shaft, and formed to be spaced apart from the first jaw pulley by a certain extent; and
a staple drive assembly including one or more staple pulleys at least partially formed between the first jaw pulley and the second jaw pulley; and
a cartridge including:
a reciprocating member that is connected to the staple drive assembly, and linearly moved when the staple pulley is rotationally moved; and
an operation member including a contact member formed to be in contact with the reciprocating member, and configured to move in one direction together with the reciprocating member when the reciprocating member is moved in the one direction,
wherein, when the reciprocating member is moved toward a distal end of the cartridge, a relative movement between the operation member and the reciprocating member is restricted by the contact member, so that the reciprocating member and the operation member are moved together, and
when the reciprocating member is moved toward a proximal end of the cartridge, the relative movement between the operation member and the reciprocating member is possible, so that only the reciprocating member is moved.

2. The surgical instrument of claim 1, wherein
when the reciprocating member is moved toward the distal end of the cartridge, the contact member and the reciprocating member are in a fitted state, so that the relative movement between the operation member and the reciprocating member is restricted, and
when the reciprocating member is moved toward the proximal end of the cartridge, the fitted state between the contact member and the reciprocating member is released, so that the relative movement between the operation member and the reciprocating member is possible.

3. The surgical instrument of claim 1, wherein
when the staple pulley is rotated,
the reciprocating member connected to the staple drive assembly is moved toward the distal end or the proximal end of the cartridge.

4. The surgical instrument of claim 3, wherein
when the staple pulley is alternately rotated in a clockwise direction and a counterclockwise direction,
the reciprocating member connected to the staple drive assembly is alternately moved toward the distal end and the proximal end of the cartridge.

5. The surgical instrument of claim 4, wherein,
when the reciprocating member is moved toward the distal end of the cartridge,
the operation member is moved toward the distal end of the cartridge by the reciprocating member.

6. The surgical instrument of claim 1, wherein a bidirectional rotational motion of the staple pulley is converted into a reciprocating linear motion of the reciprocating member, which is connected to the staple drive assembly, by the staple drive assembly.

7. The surgical instrument of claim 1, wherein
as the operation member is moved in the one direction,
a wedge of the operation member sequentially pushes and raises a plurality of staples in the cartridge to perform a stapling motion, and simultaneously a blade formed at one side of the wedge of the operation member is moved in the one direction to perform a cutting motion.

8. The surgical instrument of claim 1, wherein
when the reciprocating member is moved toward the distal end of the cartridge,
the contact member and the reciprocating member are in a fitted state to allow the reciprocating member to push the operation member including the contact member, so that the operation member is moved toward the distal end of the cartridge.

9. The surgical instrument of claim 1, wherein
when the reciprocating member is moved toward the proximal end of the cartridge,
the operation member remains stationary with respect to the one direction.

10. The surgical instrument of claim 1, wherein the contact member is formed to be spaced apart from the reciprocating member by a certain extent when the reciprocating member is moved toward the proximal end of the cartridge.

11. The surgical instrument of claim 1, wherein the staple drive assembly includes a link member configured to connect the staple pulley and the reciprocating member.

12. The surgical instrument of claim 11, wherein
when the staple pulley is rotated in a first direction between a clockwise direction and a counterclockwise direction,
the link member connected to the staple pulley,
the reciprocating member connected to the link member, and
the operation member in contact with the reciprocating member are moved toward the distal end of the cartridge.

13. The surgical instrument of claim 12, wherein
when the staple pulley is rotated in a direction opposite to the first direction between the clockwise and counterclockwise directions,
the link member connected to the staple pulley and the reciprocating member connected to the link member are moved toward a proximal end of the end tool, and
the operation member remains stationary with respect to the one direction.

14. The surgical instrument of claim 1, wherein
the operation member of the cartridge includes:
a body;
one or more wedges formed at one side of the body and each including an inclined surface formed to have a greater height at a proximal end side of the cartridge than a distal end side of the cartridge; and
a blade formed at one side of the wedge and including an edge formed to be sharp,
wherein the contact member is disposed in an accommodation part formed on one surface of the body.

15. The surgical instrument of claim 14, wherein
an inclined part is formed on a surface of the accommodation part, which is formed on the body, facing the reciprocating member, and
a width of the accommodation part becomes narrower toward the distal end of the cartridge.

16. The surgical instrument of claim 15, wherein
a spacing between the inclined part and the reciprocating member decreases toward the distal end of the cartridge.

17. The surgical instrument of claim 16, wherein
when the contact member is pressed in a direction in which the spacing between the inclined part and the reciprocating member decreases,
the contact member and the reciprocating member are in a fitted state, so that the relative movement between the reciprocating member and the operation member is blocked.

18. The surgical instrument of claim 14, wherein the contact member is formed such that a center distance is different for each region,
wherein the center distance is a distance from a center of rotation of the contact member to an end portion of the contact member.

19. The surgical instrument of claim 18, wherein
when a region of the contact member, in which the center distance is relatively large, is in contact with the reciprocating member, the contact member and the reciprocating member are in a fitted state, so that the relative movement between the operation member and the reciprocating member is restricted, and
when a region of the contact member, in which the center distance is relatively small, is in contact with the reciprocating member, the fitted state between the contact member and the reciprocating member is released, so that the relative movement between the operation member and the reciprocating member is possible.

20. The surgical instrument of claim 1, further comprising a staple wire coupled to the staple pulley and configured to rotate the staple pulley.

21. The surgical instrument of claim 1, further comprising:
a pair of end tool first jaw pitch main pulleys formed at one side of the first jaw pulley, and formed to be rotatable around a second shaft forming a predetermined angle with the first shaft; and
a pair of end tool second jaw pitch main pulleys formed at one side of the second jaw pulley, and formed to be rotatable around a shaft that is the same as or parallel to the second shaft.

22. The surgical instrument of claim 21, wherein the end tool is formed to be yaw-rotatable around the first shaft and simultaneously pitch-rotatable around the second shaft.

23. The surgical instrument of claim 1, wherein the first jaw pulley, the one or more staple pulleys, and the second jaw pulley are sequentially stacked.

* * * * *